(12) United States Patent
Malleron et al.

(10) Patent No.: US 6,403,610 B1
(45) Date of Patent: Jun. 11, 2002

(54) QUINOLYLPROPYLPIPERIDINE DERIVATIVES, THEIR PREPARATION AND THE COMPOSITIONS WHICH COMPRISE THEM

(75) Inventors: Jean-Luc Malleron, Marcoussis; Michel Tabart, La Norville; Jean-Christophe Carry, Saint Maur; Michel Evers, La Queue en Brie; Youssef El Ahmad, Creteil; Serge Mignani, Chatenay-Malabry; Fabrice Viviani, Louvres; Michel Cheve, Soisy sur Seine, all of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/664,959

(22) Filed: Sep. 18, 2000

Related U.S. Application Data
(60) Provisional application No. 60/162,225, filed on Oct. 29, 1999.

(30) Foreign Application Priority Data

Sep. 17, 1999 (FR) ............................................. 99 11679

(51) Int. Cl.$^7$ ...................... A61K 31/47; C07D 215/12; C07D 215/14
(52) U.S. Cl. ........................ 514/314; 546/174; 546/177; 546/178
(58) Field of Search .......................... 514/314; 546/174, 546/177, 178

(56) References Cited

FOREIGN PATENT DOCUMENTS

| WO | WO 99/37635 | | 7/1999 |
|---|---|---|---|
| WO | 99-37635 | * | 7/1999 |
| WO | WO 00/43383 | | 7/2000 |
| WO | 00-43383 | * | 7/2000 |

* cited by examiner

*Primary Examiner*—D. Margaret Seaman
(74) *Attorney, Agent, or Firm*—Finnegan, Henderson, Farabow, Garrett & Dunner LLP

(57) ABSTRACT

Quinolylpropylpiperidine derivatives of formula (I)

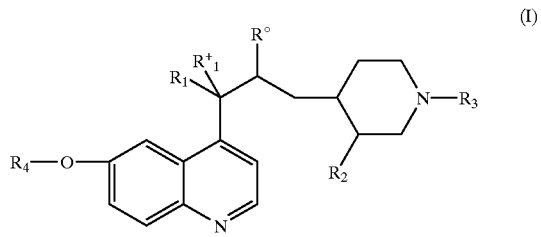

which are particularly advantageous antimicrobial agents, their compositions, and their use.

27 Claims, No Drawings

QUINOLYLPROPYLPIPERIDINE DERIVATIVES, THEIR PREPARATION AND THE COMPOSITIONS WHICH COMPRISE THEM

This application claims benefit of provisional application 60/162,225 filed Oct. 29, 1999.

The present invention relates to quinolylpropylpiperidine derivatives of formula:

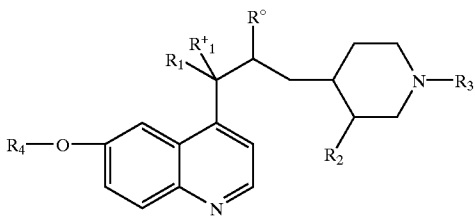

which are active as antimicrobials. The invention also relates to their preparation, to their use, and to compositions comprising them.

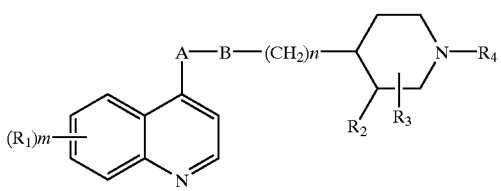

in which the $R_1$ radical can be (C1–C6)alkoxy, $R_2$ is hydrogen, $R_3$ is in the 2- or 3-position and represents (C1–C6)alkyl which can optionally be substituted by 1 to 3 substituents chosen from thiol, halogen, alkylthio, trifluoromethyl, alkyloxycarbonyl, alkylcarbonyl, alkenyloxycarbonyl, alkenylcarbonyl, hydroxyl optionally substituted by alkyl, and the like, $R_4$ is a —$CH_2$—$R_5$ group in which $R_5$ is selected from alkyl, hydroxyalkyl, alkenyl, alkynyl, tetrahydrofuryl, optionally substituted phenylalkyl, optionally substituted phenylalkenyl, optionally substituted heteroarylalkyl, optionally substituted heteroaryl, and the like, n is 0 to 2, m is 1 or 2, and A and B are in particular oxygen, sulfur, sulfinyl, sulfonyl, or $CR_6R_7$ in which $R_6$ and $R_7$ represent H, thiol, alkylthio, halo, trifluoromethyl, alkenyl, alkenylcarbonyl, hydroxyl, amino, and the like.

European Patent Application EP30044 discloses quinoline derivatives, for use as cardiovasculars, corresponding to the formula:

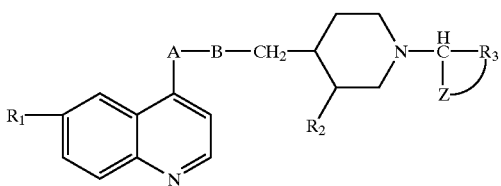

in which $R_1$ can be alkyloxy, A-B is —$CH_2$—$CH_2$—, —CHOH—$CH_2$—, —$CH_2$—CHOH—, —$CH_2$CO—, or —CO—$CH_2$—, $R_1$ is H, OH or alkyloxy, $R_2$ is ethyl or vinyl, $R_3$ can be alkyl, hydroxyalkyl, cycloalkyl, hydroxyl, alkenyl, alkynyl, tetrahydrofuryl, phenylalkyl, optionally substituted diphenylalkyl, optionally substituted phenylalkenyl, optionally substituted benzoyl or benzoylalkyl, or optionally substituted heteroaryl or heteroarylalkyl, and Z is H or alkyl or forms, with $R_3$, a cycloalkyl radical.

It has now been found, and it is this which forms the subject of the present invention, that the products of formula (I) in which:

$R_1$ is a hydrogen atom, a halogen atom, or a hydroxyl radical;

$R'_1$ is a hydrogen atom or can represent halogen when $R_1$ is a halogen atom; and $R°$ is a hydrogen atom; or $R_1$ and $R°$ together form a bond; and $R'_1$ is a hydrogen atom;

$R_2$ represents a carboxyl, carboxymethyl, or 2-carboxyethyl radical; and $R_3$ represents an alkyl radical having 1 to 6 carbon atoms substituted by 1 to 3 substituents chosen from hydroxyl, halogen, oxo, carboxyl, alkyloxycarbonyl, alkyloxy, and alkylthio;

or from phenyl, phenylthio, or phenylalkylthio radicals, which radicals are unsubstituted or substituted by 1 to 4 substituents chosen from halogen, hydroxyl, alkyl, alkyloxy, trifluoromethyl, trifluoromethoxy, carboxyl, alkyloxycarbonyl, cyano, acetamido having 1 to 4 carbon atoms, and amino;

or from cycloalkyl or cycloalkylthio radicals, the cyclic part of which comprises 3 to 7 members;

or from 5- to 6-membered aromatic heterocyclyl or heterocyclylthio radicals comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents a propargyl radical substituted by a phenyl radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or the propargyl radical is substituted by a cycloalkyl radical comprising 3 to 7 members;

or the propargyl radicals is substituted by a 5- to 6-membered aromatic heterocyclyl radical comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents cinnamyl or 4-phenylbuten-3-yl;

or $R_2$ represents a hydroxymethyl, alkyloxycarbonyl, alkyloxycarbonylmethyl, or 2-(alkyloxycarbonyl)ethyl radical, wherein the alkyl parts of the radicals comprise 1 to 6 carbon atoms; and $R_3$ represents an alkyl radical having 1 to 6 carbon atoms substituted by a phenylthio radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or the alkyl radical is substituted by a cycloalkylthio radical, the cyclic part of which comprises 3 to 7 members;

or the alkyl radical is substituted by a 5- to 6-membered aromatic heterocyclylthio radical comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents a propargyl radical substituted by a phenyl radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or the propargyl radical is substituted by a cycloalkyl radical comprising 3 to 7 members;

or the propargyl radical is substituted by a 5- to 6-membered aromatic heterocyclyl radical comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino;

and $R_4$ represents an alkyl radical comprising 1 to 6 carbon atoms, or an alkenyl-$CH_2$— or an alkynyl-$CH_2$— radical, the alkenyl or alkynyl parts of which comprise 2 to 6 carbon atoms;

it being understood that the alkyl radicals and alkyl portions of radicals are straight- or branched-chain radicals and portions of radicals and comprise, except when specifically mentioned, 1 to 4 carbon atoms;

the diastereoisomers thereof, the mixtures of diastereoisomers thereof, and the salts thereof;

are powerful antibacterial agents.

It is understood that the alkyl radicals and portions of radicals are straight- or branched-chain radicals and portions and comprise, except when specifically mentioned, 1 to 4 carbon atoms and that, in the alternative where $R_1$ or $R'_1$ represent a halogen atom or when $R_3$ carries a halogen substituent, the latter can be chosen from fluorine, chlorine, bromine, or iodine, and is typically fluorine.

In the above formula (I), when $R_3$ carries an aromatic heterocyclyl substituent, the latter can be chosen, without implied limitation, from thienyl, furyl, pyrrolyl, imidazolyl, thiazolyl, oxazolyl, thiadiazolyl, oxadiazolyl, tetrazolyl, pyridyl, pyridazinyl, pyrazinyl, or pyrimidinyl. It is also understood that, in the definition of $R_3$, the substituted alkyl radical only simultaneously carries a single cyclic radical.

According to the invention, the products of formula (I) can be obtained by condensation of an $R_3$ chain onto a quinolylpropylpiperidine derivative of formula:

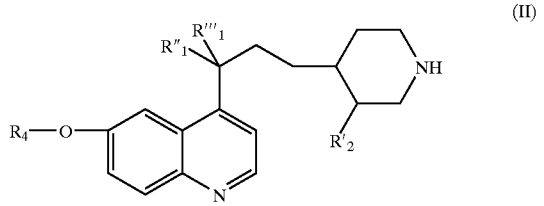

(II)

in which $R_4$ is defined as above, $R''_1$ and $R'''_1$ represent hydrogen atoms or together form an oxo radical, and $R'_2$ represents a protected carboxyl, carboxymethyl, or 2-carboxyethyl radical, or an alkyloxycarbonyl, alkyloxycarbonylmethyl, or 2-(alkyloxycarbonyl)ethyl radical, in order to obtain a quinolylpropylpiperidine derivative of formula:

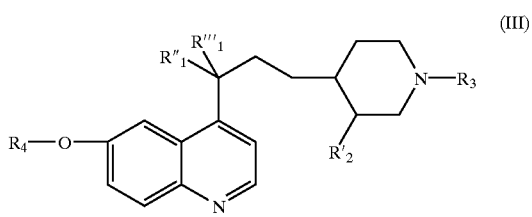

(III)

in which $R''_1$, $R'''_1$, $R'_2$, and $R_4$ are defined as above and $R_3$ is also defined as above, followed, if appropriate, by the removal of the acid-protecting radical, then, if appropriate, followed by the reduction of the oxo radical represented by $R''_1$ and $R'''_1$ to an alcohol in which $R_1$ represents hydroxyl, then, optionally, by halogenation, if it is desired to obtain a quinolylpropylpiperidine derivative in which $R_1$ is a halogen atom, and, optionally, by dehydrohalogenation of the corresponding halogenated derivative, in order to obtain a quinolylpropylpiperidine derivative in which $R_1$ and $R°$ together form a bond, or else by dihalogenation of the product of formula (III) in which $R''_1$ and $R'''_1$ together form an oxo radical, in order to obtain a quinolylpropylpiperidine derivative in which $R_1$ and $R'_1$ are halogen atoms, and/or, if appropriate, followed by the reduction of the acid, protected in the form of an $R'_2$ radical, in the 3-position of the piperidine to a hydroxymethyl radical and optionally by the conversion to a carboxymethyl or 2-carboxyethyl radical according to the usual methods, then, optionally, followed by the removal of the acid-protecting radical, and optionally by the conversion of the product obtained to a salt.

The condensation of the $R_3$ chain onto the piperidine is advantageously carried out by the action of a derivative of formula:

$$R_3-X \quad (IV)$$

in which $R_3$ is defined as above and X represents a halogen atom, a methylsulfonyloxy radical, a trifluoromethylsulfonyloxy radical, or a p-toluenesulfonyloxy radical, the reaction being carried out in an anhydrous environment, typically an inert environment (nitrogen or argon, for example), in an organic solvent, such as an amide (dimethylformamide, for example), a ketone (acetone, for example), or a nitrile (acetonitrile, for example), in the presence of a base, such as, a nitrogenous organic base (for example, triethylamine) or an inorganic base (alkali metal carbonate: potassium carbonate, for example), at a temperature of between 20° C. and the reflux temperature of the solvent.

Typically, the reaction is carried out with a derivative in which X is a bromine or iodine atom.

When $R_3$ represents a propargyl radical substituted by phenyl, cycloalkyl, or heterocyclyl, it is possible to condense a propargyl halide and then to substitute the chain with a phenyl, cycloalkyl, or heterocyclyl radical.

In this alternative, the addition of the propargyl chain is carried out by means of propargyl bromide, under the conditions set out above for $R_3$, in the presence or absence of an alkali metal iodide, such as, for example, potassium iodide or sodium iodide.

When it is a matter of the substitution by a phenyl or heterocyclyl radical, the reaction is carried out by the action of a halide derived from the cyclic radical to be substituted, in the presence of triethylamine, in an anhydrous environment in a solvent, such as an amide (dimethylformamide, for example), or a nitrile (acetonitrile, for example), and in the presence of a palladium salt, such as, for example, tetrakis (triphenylphosphine)palladium, and of cuprous iodide, at a temperature of between 20° C. and the reflux temperature of the solvent.

When it is a matter of the substitution by a cycloalkyl group, the reaction is carried out by the action of an organolithium compound, such as n-butyllithium or tert-butyllithium, on the propargyl derivative obtained above, in an anhydrous environment in an ether, such as, for example, tetrahydrofuran, at a temperature of between −78 and 0° C., and then the action of a cycloalkanone, followed by the deoxygenation of the intermediate alcohol according to conventional methods.

It is understood that, when the alkyl radicals represented by $R_3$ carry carboxyl or amino substituents, the latter are protected beforehand and then released after the reaction. These operations are carried out according to the usual methods which do not detrimentally affect the remainder of the molecule, in particular according to the methods described by T. W. Greene and P. G. M. Wuts, Protective Groups in Organic Synthesis (2nd ed.), A. Wiley-Interscience Publication (1991), or by McOmie, Protective Groups in Organic Chemistry, Plenum Press (1973), the disclosures of which are specifically incorporated by reference herein.

The protected carboxyl radical represented by $R'_2$ can be chosen from easily hydrolyzable esters. Mention may be made, by way of example, of methyl, benzyl, or tert-butyl esters, or alternatively, phenylpropyl or propargyl esters. The protecting of the carboxyl radical is optionally carried out simultaneously with the reaction. In this case, the derivative of formula (II) employed carries an $R'_2$ radical which is the carboxyl radical.

The reduction of the oxo radical to an alcohol is carried out according to the usual methods which do not detrimentally affect the remainder of the molecule, typically by the action of a reduction agent, such as, for example, a hydride (alkaline borohydride: sodium borohydride, potassium borohydride, sodium triacetoxyborohydride, or sodium cyanoborohydride, for example, lithium aluminum hydride or diisobutylaluminum hydride), the reaction typically being carried out in an inert atmosphere, in an organic solvent, such as an alcohol (methanol, ethanol, or isopropanol, for example), or an ether (for example, tetrahydrofuran), or a chlorinated solvent (for example, dichloromethane), at a temperature of between 20° C. and the reflux temperature of the solvent.

The halogenation intended to produce a quinolylpropylquinoline derivative in which $R'_1$ is a halogen atom from the derivative in which $R'_1$ is hydroxyl can be carried out in the presence of an aminosulfur trifluoride (diethylaminosulfur trifluoride, bis(2-methoxyethyl)aminosulfur trifluoride (Deoxofluor®), or morpholinosulfur trifluoride, for example), or alternatively in the presence of sulfur tetrafluoride, by means of a reagent, such as a tetraalkylammonium, trialkylbenzylammonium, or trialkylphenylammonium halide, or by means of an alkali metal halide, optionally with a crown ether added. The fluorination reaction can also be carried out by the action of a fluorinating agent such as a sulfur fluoride [for example, morpholinosulfur trifluoride, sulfur tetrafluoride (J. Org. Chem., 40, 3808 (1975)), diethylaminosulfur trifluoride (Tetrahedron, 44, 2875 (1988)), or bis(2-methoxyethyl)aminosulfur trifluoride (Deoxofluor®)]. Alternatively, the fluorination reaction can also be carried out by means of a fluorinating agent such as hexafluoropropyldiethylamine (JP 2 039 546) or N-(2-chloro-1,1,2-trifluoroethyl)diethylamine.

When a tetraalkylammonium halide is employed, the latter can be chosen, by way of example, from tetramethylammonium, tetraethylammonium, tetrapropylammonium, tetrabutylammonium (tetra(n-butyl) ammonium, for example), tetrapentylammonium, tetracyclohexylammonium, triethylmethylammonium, tributylmethylammonium, or trimethylpropylammonium halides.

The reaction is carried out in an organic solvent, such as a chlorinated solvent (for example, dichloromethane, dichloroethane, or chloroform) or in an ether (tetrahydrofuran or dioxane, for example), at a temperature of between −78 and 40° C.; typically between 0 and 30° C. It is advantageous to carry out the reaction in an inert environment (for example, argon or nitrogen).

It is also possible to carry out the reaction by treatment with a halogenating agent, such as thionyl chloride or phosphorus trichloride, in an organic solvent, such as a chlorinated solvent (dichloromethane or chloroform, for example), at a temperature of between 0° C. and the reflux temperature of the reaction mixture.

The dihalogenation of the product of formula (III) in which $R''_1$ and $R'''_1$ together form an oxo radical, in order to produce a quinolylpropylpiperidine derivative in which $R_1$ and $R'_1$ are halogen atoms, can be carried out under conditions analogous to those of the above halogenation.

The dehydrohalogenation of the halogenated derivative obtained from the derivative in which $R_1$ is hydroxyl can be carried out by treatment with diazabicyclo[5,4,0]undec-7-ene in an aromatic organic solvent (toluene, for example) at a temperature of between 20° C. and the reflux temperature of the reaction mixture.

The reduction of the acid, protected in the form of an $R'_2$ radical, in the 3-position of the piperidine to a hydroxymethyl radical is carried out according to the usual methods which do not detrimentally affect the remainder of the molecule, typically, the reduction is carried out by the action of a hydride (lithium aluminum hydride or diisobutylaluminum hydride, for example) in a solvent, such as an ether (tetrahydrofuran, for example), at a temperature of between 20 and 60° C.

The conversion of the hydroxymethyl radical in the 3-position of the piperidine to a carboxymethyl radical is carried out according to the usual methods which do not detrimentally affect the remainder of the molecule, for example, it can be carried out by the action of a halogenating agent, such as, for example, thionyl chloride or phosphorus trichloride or phosphorus tribromide, and then of an alkaline cyanide (potassium cyanide or sodium cyanide, for example), in order to prepare the corresponding cyanomethyl derivative, followed by the hydrolysis of the nitrile.

The halogenation can be carried out in a chlorinated solvent (dichloromethane or chloroform, for example) at a temperature of between 0° C. and the reflux temperature of the solvent.

The reaction of the alkaline cyanide can be carried out in a solvent, such as dimethyl sulfoxide, an amide (dimethylformamide, for example), a ketone (acetone, for example), an ether, such as, for example, tetrahydrofuran, or an alcohol, such as, for example, methanol or ethanol, at a temperature of between 20° C. and the reflux temperature of the reaction mixture.

The hydrolysis of the nitrile is carried out according to conventional methods which do not detrimentally affect the remainder of the molecule, typically, by the action of hydrochloric acid in methanolic medium, at a temperature of between 20 and 70° C., followed by the saponification of the ester obtained, for example, by sodium hydroxide in a mixture of dioxane and water, or else, directly by the action of aqueous sulfuric acid at a temperature of between 50 and 80° C.

The conversion of the hydroxymethyl radical in the 3-position of the piperidine to a 2-carboxyethyl radical is carried out, for example, from the halogenated derivative prepared as described above by condensation of the sodium salt of diethyl malonate, followed by acid hydrolysis in aqueous medium of the product obtained.

The removal, if appropriate, of the acid-protecting radical, in order to obtain a quinolylpropylpiperidine derivative in which $R_2$ is a carboxyl radical, is carried out according to the usual methods, in particular by acid hydrolysis or saponification of the $R'_2$ ester. Typically, sodium hydroxide is reacted in aqueous/organic medium, for example in an alcohol, such as methanol, or an ether, such as dioxane, at a temperature of between 20° C. and the reflux temperature of the reaction mixture. The hydrolysis can also be carried out in aqueous hydrochloric medium at a temperature of between 20 and 100° C.

The quinolylpropylpiperidine derivative of formula (II) or the corresponding acid in which $R'_2$ represents a carboxyl radical can be prepared according to or by analogy with the methods described hereinbelow in the examples or according to or by analogy with the methods disclosed in European Patent Application EP 30044 or in International Application WO 99/37635, the disclosures of which are specifically incorporated by reference herein. The intermediates of the quinolylpropylpiperidine derivatives in which $R_4$ represents alkenyl-$CH_2O$— or alkynyl-$CH_2O$— can be obtained, by analogy with the preparation of the intermediates in which $R_4$ is alkyloxy, by the action of the corresponding halogenated derivative on the quinoline derivative hydroxylated in the 6-position.

The protected 2-carboxyethyl derivative of formula (II) can be obtained according to or by analogy with the method disclosed in International Application WO 99/37635, the disclosure of which is specifically incorporated by reference herein, followed by the hydrolysis of the nitrile and by the esterification of the acid thus obtained, or can be prepared according to or by analogy with the methods described hereinbelow in the examples.

It is understood that the derivatives of formula (I), (II), or (III), or their starting intermediates, can exist in the cis or trans form with regard to the substituents in the 3- and 4-position of the piperidine. The derivatives with the trans configuration can be obtained from the derivatives with the cis configuration according to or by analogy with the method disclosed in International Application WO 99/37635, the disclosure of which is specifically incorporated by reference herein.

The quinolylpropylpiperidine derivatives of formula (I) can be purified, if appropriate, by physical methods, such as crystallization or chromatography.

Furthermore, it is understood that, when $R'_1$ is a hydrogen atom and $R_1$ is hydroxyl or halogen, diastereoisomeric forms exist and that the diastereoisomeric forms and their mixtures also come within the scope of the present invention. The latter can be separated, for example, by silica chromatography or by High Performance Liquid Chromatography (HPLC).

The quinolylpropylpiperidine derivatives of formula (I) can be converted to addition salts with acids by known methods. It is understood that these salts also come within the scope of the present invention.

Mention may be made, as examples of addition salts with pharmaceutically acceptable acids, of the salts formed with inorganic acids (hydrochlorides, hydrobromides, sulfates, nitrates, or phosphates) or with organic acids (succinates, fumarates, tartrates, acetates, propionates, maleates, citrates, methanesulfonates, ethanesulfonates, benzenesulfonates, p-toluenesulfonates, isethionates, naphthalenesulfonates, or camphorsulfonates, or with substituted derivatives of these compounds).

Some of the quinolylpropylpiperidine derivatives of formula (I) carrying a carboxyl radical can be converted to the form of metal salts or to addition salts with nitrogenous bases according to methods known per se. These salts also come within the scope of the present invention. The salts can be obtained by the action of a metal base (for example, an alkali metal or alkaline earth metal base), of ammonia or an amine on a product according to the invention in an appropriate solvent, such as an alcohol, an ether, or water, or by an exchange reaction with a salt of an organic acid. The salt formed precipitates, after optional concentration of the solution, and it is separated by filtration, settling, or lyophilization.

Mention may be made, as examples of pharmaceutically acceptable salts, of the salts with alkali metals (sodium, potassium, or lithium) or with alkaline earth metals (magnesium or calcium), and of the ammonium salt or the salts of nitrogenous bases (ethanolamine, diethanolamine, trimethylamine, triethylamine, methylamine, propylamine, diisopropylamine, NN-dimethylethanolamine, benzylamine, dicyclohexyl-amine,. N-benzyl-β-phenethylamine, NN'-dibenzylethylenediamine, diphenylenediamine, benzhydrylamine, quinine, choline, arginine, lysine, leucine, or dibenzylamine).

The quinolylpropylpiperidine derivatives according to the invention are particularly advantageous antibacterial agents.

In vitro, with regard to gram-positive microorganisms, the quinolylpropylpiperidine derivatives according to the invention have proved to be active at concentrations of between 0.015 and 4 μg/ml with regard to methicillin-resistant *Staphylococcus aureus* AS5155. Most of them at concentrations of between 0.06 and 8 μg/ml with regard to *Streptococcus pneumoniae* IP53146; and at concentrations of between 0.12 and 64 μg/ml with regard to *Enterococcus faecium* ATCC19434 or H983401. With regard to gram-negative microorganisms, they have proved to be active at concentrations of between 0.12 and 32 μg/ml with regard to *Moraxella catharrhalis* IPA152; in vivo, they have proved to be active with regard to experimental infections of mice with *Staphylococcus aureus* IP8203 at doses of between 10 and 150 mg/kg subcutaneously ($CD_{50}$) and, for some of them, at doses of between 20 and 150 mg/kg orally.

Finally, the products according to the invention are particularly advantageous because of their low toxicity. None of the products displayed toxicity at a dose of 100 mg/kg subcutaneously in mice (2 administrations).

Another aspect, among the products according to the invention, are the quinolylpropylquinoline derivatives of formula (I) in which:

$R_1$ is a hydrogen atom, a halogen atom, or a hydroxy radical;

$R'_1$ is a hydrogen atom or can represent a halogen atom when $R_1$ is a halogen atom; and $R°$ is a hydrogen atom; or $R_1$ and $R°$ together form a bond; and $R'_1$ is a hydrogen atom;

$R_2$ represents a carboxyl, carboxymethyl, or carboxy-2-ethyl radical; and $R_3$ represents an alkyl radical having 1 to 6 carbon atoms substituted by 1 to 3 substituents chosen from halogen, oxo, carboxyl, alkyloxycarbonyl, and alkylthio;

or from phenylthio and phenylalkylthio radicals, which are unsubstituted or substituted by 1 to 4 substituents chosen from halogen, hydroxyl, alkyl, alkyloxy, trifluoromethyl, trifluoromethoxy, carboxyl, alkyloxycarbonyl, cyano, acetamido having 1 to 4 carbon atoms, and amino;

or from a cycloalkylthio radical, the cyclic part of which comprises 3 to 7 members;

or from a 5- to 6-membered aromatic heterocyclylthio radical comprising 1 to 4 heteroatoms chosen from nitrogen, oxygen, and sulfur, and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents an alkyl radical having 1 to 6 carbon atoms, and being substituted by 2 or 3 substituents chosen from hydroxy and alkyloxy;

or from phenylthio and phenylalkylthio radicals, which are unsubstituted or substituted by 1 to 4 substituents chosen from halogen, hydroxyl, alkyl, alkyloxy, trifluoromethyl, trifluoromethoxy, carboxyl, alkyloxycarbonyl, cyano, acetamido having 1 to 4 carbon atoms, and amino;

or from a cycloalkylthio radical, the cyclic part of which comprises 3 to 7 members;

or from a 5- to 6-membered aromatic heterocyclylthio radical comprising 1 to 4 heteroatoms chosen from nitrogen, oxygen, and sulfur, and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents a propargyl radical substituted by a phenyl radical which is unsubstituted or substituted by 1 to 4 substituents chosen from halogen, hydroxy, alkyl, alkyloxy, trifluoromethyl, trifluoromethoxy, carboxy, alkyloxycarbonyl, cyano, and amino;

or the propargyl radical is substituted by a cycloalkyl radical comprising 3 to 7 members;

or the propargyl radical is substituted by a 5- to 6-membered aromatic heterocyclyl radical comprising 1 to 4 heteroatoms chosen from nitrogen, oxygen, and sulfur, and being unsubstituted or substituted by halogen, hydroxyl, alkyl, alkyloxy, trifluoromethyl, trifluoromethoxy, oxo, carboxyl, alkyloxycarbonyl, cyano or amino;

or $R_2$ represents a hydroxymethyl, alkyloxycarbonyl, alkyloxycarbonylmethyl, or alkyloxycarbonyl-2-ethyl radical, wherein the alkyl parts of which comprise 1 to 6 carbon atoms; and $R_3$ represents an alkyl radical having 1 to 6 carbon atoms substituted by a phenylthio radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or the alkyl radical is substituted by a cycloalkylthio radical, the cyclic part of which comprises 3 to 7 members;

or the alkyl radical is substituted by a 5- to 6-membered aromatic heterocyclylthio radical comprising 1 to 4 heteroatoms chosen from nitrogen, oxygen, and sulfur, and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents a propargyl radical substituted by a phenyl radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or the propargyl radical is substituted by a cycloalkyl radical comprising 3 to 7 members;

or the propargyl radical is substituted by a 5- to 6-membered aromatic heterocyclyl radical comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino; and $R_4$ represents an alkyl radical comprising 1 to 6 carbon atoms, or an alkenyl-$CH_2$— or alkynyl-$CH_2$— radical, the alkenyl or alkynyl parts of which comprise 2 to 6 carbon atoms;

it being understood that the alkyl radicals and alkyl portions of radicals are straight- or branched-chain radicals and portions of radicals and comprise, except when specifically mentioned, 1 to 4 carbon atoms;

diastereoisomers thereof, mixtures of diastereoisomers thereof, and salts thereof; which are powerful antibacterial agents.

A further aspect, among the products according to the invention, are the quinolylpropylquinoline derivatives of formula (I) in which:

$R_1$ is a hydrogen atom, a halogen atom, or a hydroxyl radical;

$R'_1$ is a hydrogen atom; and $R°$ is a hydrogen atom; or $R_1$ and $R°$ together form a bond; and $R'_1$ is a hydrogen atom;

$R_2$ represents a carboxyl or carboxymethyl radical; and $R_3$ represents an alkyl radical having 1 to 6 carbon atoms substituted by 1 to 3 substituents chosen from halogen, oxo, alkyloxy, and alkylthio;

or from phenyl and phenylthio radicals, which are unsubstituted or substituted by 1 to 4 halogen atoms;

or from cycloalkyl. and cycloalkylthio radicals, the cyclic part of which comprises 3 to 7 members;

or from 5- to 6-membered aromatic heterocyclyl and heterocyclylthio radicals comprising 1 to 4 heteroatoms chosen from nitrogen, oxygen, and sulfur and being unsubstituted or substituted by halogen;

or $R_3$ represents a propargyl radical substituted by a phenyl radical which is unsubstituted or substituted by 1 to 3 halogen substituents;

or the propargyl radical is substituted by a 5- to 6-membered aromatic heterocyclyl radical comprising 1 to 4 heteroatoms chosen from nitrogen, oxygen, and sulfur;

or $R_3$ represents cinnamyl;

or $R_2$ represents a hydroxymethyl, alkyloxycarbonyl, or alkyloxycarbonylmethyl radical, the alkyl portions of said radicals comprising 1 to 6 carbon atoms; and $R_3$ represents an alkyl radical having 1 to 6 carbon atoms substituted by a 5- to 6-membered aromatic heterocyclylthio radical comprising 1 to 4 heteroatoms chosen from nitrogen, oxygen, and sulfur;

or R₃ represents a propargyl radical substituted by a 5- to 6-membered aromatic heterocyclyl radical comprising 1 to 4 heteroatoms chosen from nitrogen, oxygen, and sulfur; and $R_4$ represents an alkyl radical comprising 1 to 6 carbon atoms;

it being understood that the alkyl radicals and alkyl portions of radicals are straight- or branched-chain radicals and portions of radicals;

diastereoisomers thereof, mixtures of diastereoisomers thereof, and salts thereof; which are powerful antibacterial agents.

Notable, among the products of the invention, are the following products:

(3R,4R)-4-[3-Hydroxy-3-(6-methoxyquinolin-4-yl)propyl]-1-[2-(2-thienylthio)ethyl]piperidine-3-acetic acid;

(3R,4R)-4-[3-(6-Methoxyquinolin-4-yl)propyl]-1-[2-(2-thienylthio)ethyl]piperidine-3-acetic acid;

(3R,4R)-4-[3-Fluoro-3-(6-methoxyquinolin-4-yl)propyl]-1-[2-(2-thienylsulfanyl)ethyl]piperidine-3-acetic acid;

(3R,4R)-1-[2-(3-Fluorophenylthio)ethyl]-4-[3-hydroxy-3-(6-methoxyquinolin-4-yl)propyl]piperidine-3-acetic acid; and (3R,4R)-4-[3-Hydroxy-3-(6-methoxyquinolin-4-yl)propyl]-1-[3-(2,3,5-trifluorophenyl)prop-2-ynyl]piperidine-3-carboxylic acid; as well as their diastereoisomers and salts, when they exist.

The products cited in the examples are also notable, advantageous products; as are the quinolylpropylpiperidine derivatives hereinbelow:

(3R,4R)-4-[3-(6-Methoxyquinolin-4-yl)propyl]-1-[4-phenylbutyl]piperidine-3-carboxylic acid (3R,4R)-4-[3-(6-Methoxyquinolin-4-yl)propyl]-1-[4-(2-fluorophenyl)butyl]piperidine-3-carboxylic acid (3R,4R)-4-[3-(6-Methoxyquinolin-4-yl)propyl]-1-[4-(3-fluorophenyl)butyl]piperidine-3-carboxylic acid (3R,4R)-4-[3-(6-Methoxyquinolin-4-yl)propyl]-1-[3-(4-fluorophenyl)propyl]piperidine-3-carboxylic acid (3R,4R)-4-[3-(6-Methoxyquinolin-4-yl)propyl]-1-[4-(4-fluorophenyl)butyl]piperidine-3-carboxylic acid (3R,4R)-4-[3-(6-Methoxyquinolin-4-yl)propyl]-1-[3-(2,3-difluorophenyl)propyl]piperidine-3-carboxylic acid (3R,4R)-4-[3-(6-Methoxyquinolin-4-yl)propyl]-1-[4-(2,3-difluorophenyl)butyl]piperidine-3-carboxylic acid (3R,4R)-4-[3-(6-Methoxyquinolin-4-yl)propyl]-1-[3-(2,6-difluorophenyl)propyl]piperidine-3-carboxylic acid (3R,4R)-4-[3-(6-Methoxyquinolin-4-yl)propyl]-1-[4-(2,6-difluorophenyl)butyl]piperidine-3-carboxylic acid (3R,4R)-4-[3-(6-Methoxyquinolin-4-yl)propyl]-1-[3-(2-chlorophenyl)propyl]piperidine-3-carboxylic acid (3R,4R)-4-[3-(6-Methoxyquinolin-4-yl)propyl]-1-[4-(2-chlorophenyl)butyl]piperidine-3-carboxylic acid (3R,4R)-4-[3-(6-Methoxyquinolin-4-yl)propyl]-1-[3-(3-chlorophenyl)propyl]piperidine-3-carboxylic acid (3R,4R)-4-[3-(6-Methoxyquinolin-4-yl)propyl]-1-[4-(3-chlorophenyl)butyl]piperidine-3-carboxylic acid (3R,4R)-4-[3-(6-Methoxyquinolin-4-yl)propyl)-1-[3-(4-chlorophenyl)propyl]piperidine-3-carboxylic acid (3R,4R)-4-[3-(6-Methoxyquinolin-4-yl)propyl]-1-[4-(4-chlorophenyl)butyl]piperidine-3-carboxylic acid (3R,4R)-4-[3-(6-Methoxyquinolin-4-yl)propyl]-1-[3-(2,3-dichlorophenyl)propyl]piperidine-3-carboxylic acid (3R,4R)-4-[3-(6-Methoxyquinolin-4-yl)propyl]-1-[4-(2,3-dichlorophenyl)butyl]piperidine-3-carboxylic acid (3R,4R)-4-[3-(6-Methoxyquinolin-4-yl)propyl]-1-[3-(2,6-dichlorophenyl)propyl]piperidine-3-carboxylic acid (3R,4R)-4-[3-(6-Methoxyquinolin-4-yl)propyl]-1-[4-(2,6-dichlorophenyl)butyl]piperidine-3-carboxylic acid (3R,4R)-4-[3-(6-Methoxyquinolin-4-yl)propyl]-1-[3-(2-methylphenyl)propyl]piperidine-3-carboxylic acid (3R,4R)-4-[3-(6-Methoxyquinolin-4-yl)propyl]-1-[4-(2-methylphenyl)butyl]piperidine-3-carboxylic acid (3R,4R)-4-[3-(6-Methoxyquinolin-4-yl)propyl]-1-[5-(2-methylphenyl)pentyl]piperidine-3-carboxylic acid (3R,4R)-4-[3-(6-Methoxyquinolin-4-yl)propyl]-1-[3-(3-methylphenyl)propyl]piperidine-3-carboxylic acid (3R,4R)-4-[3-(6-Methoxyquinolin-4-yl)propyl]-1-[4-(3-methylphenyl)butyl]piperidine-3-carboxylic acid (3R,4R)-4-[3-(6-Methoxyquinolin-4-yl)propyl]-1-[3-(4-methylphenyl)propyl]piperidine-3-carboxylic acid (3R,4R)-4-[3-(6-Methoxyquinolin-4-yl)propyl]-1-[4-(4-methylphenyl)butyl]piperidine-3-carboxylic acid (3R,4R)-4-[3-(6-Methoxyquinolin-4-yl)propyl]-1-[3-(2-methoxyphenyl)propyl]piperidine-3-carboxylic acid (3R,4R)-4-[3-(6-Methoxyquinolin-4-yl)propyl]-1-[4-(2-methoxyphenyl)butyl]piperidine-3-carboxylic acid (3R,4R)-4-[3-(6-Methoxyquinolin-4-yl)propyl]-1-[3-(3-methoxyphenyl)propyl]piperidine-3-carboxylic acid (3R,4R)-4-[3-(6-Methoxyquinolin-4-yl)propyl]-1-[4-(3-methoxyphenyl)butyl]piperidine-3-carboxylic acid (3R,4R)-4-[3-(6-Methoxyquinolin-4-yl)propyl]-1-[3-(4-methoxyphenyl)propyl]piperidine-3-carboxylic acid (3R,4R)-4-[3-(6-Methoxyquinolin-4-yl)propyl]-1-[4-(4-methoxyphenyl)butyl]piperidine-3-carboxylic acid (3R,4R)-4-[3-(6-Methoxyquinolin-4-yl)propyl]-1-[3-(2-trifluoromethylphenyl)propyl]piperidine-3-carboxylic acid (3R,4R)-4-[3-(6-Methoxyquinolin-4-yl)propyl]-1-(4-(2-trifluoromethylphenyl)butyl]piperidine-3-carboxylic acid (3R,4R)-4-[3-(6-Methoxyquinolin-4-yl)propyl]-1-[3-(3-trifluoromethylphenyl)propyl]piperidine-3-carboxylic acid (3R,4R)-4-[3-(6-Methoxyquinolin-4-yl)propyl]-1-[4-(3-trifluoromethylphenyl)butyl]piperidine-3-carboxylic acid (3R,4R)-4-[3-(6-Methoxyquinolin-4-yl)propyl]-1-[3-(4-trifluoromethylphenyl)propyl]piperidine-3-carboxylic acid (3R,4R)-4-[3-(6-Methoxyquinolin-4-yl)propyl]-1-[4-(4-trifluoromethylphenyl)butyl]piperidine-3-carboxylic acid (3R,4R)-4-[3-(6-Methoxyquinolin-4-yl)propyl]-1-[3-phenylthiopropyl]piperidine-3-carboxylic acid (3R,4R)-4-[3-(6-Methoxyquinolin-4-yl)propyl]-1-[3-(2-fluorophenylthio)propyl]piperidine-3-carboxylic acid (3R,4R)-4-[3-(6-Methoxyquinolin-4-yl)propyl]-1-[3-(3-fluorophenylthio)propyl]piperidine-3-carboxylic acid (3R,4R)-4-[3-(6-Methoxyquinolin-4-yl)propyl]-1-[2-(4-fluorophenylthio)ethyl]piperidine-3-carboxylic acid (3R,4R)-4-[3-(6-Methoxyquinolin-4-yl)propyl]-1-[3-(4-fluorophenylthio)propyl]piperidine-3-carboxylic acid (3R,4R)-4-[3-(6-Methoxyquinolin-4-yl)propyl]-1-[2-(2,3-difluorophenylthio)ethyl]piperidine-3-carboxylic acid (3R,4R)-4-[3-(6-Methoxyquinolin-4-yl)propyl]-1-[3-(2,3-difluorophenylthio)propyl]piperidine-3-carboxylic acid (3R,4R)-4-[3-(6-Methoxyquinolin-4-yl)propyl]-1-[2-(2,6-difluorophenylthio)ethyl]piperidine-3-carboxylic acid (3R,4R)-4-[3-(6-Methoxyquinolin-4-yl)propyl]-1-[3-(2,6-difluorophenylthio)propyl]piperidine-3-carboxylic acid (3R,4R)-4-[3-(6-Methoxyquinolin-4-yl)propyl]-1-[2-(2-chlorophenylthio)ethyl]piperidine-3-carboxylic acid (3R,4R)-4-[3-(6-Methoxyquinolin-4-yl)propyl]-1-[3-(2-chlorophenylthio)propyl]piperidine-3-carboxylic acid (3R,4R)-4-[3-(6-Methoxyquinolin-4-yl)propyl]-1-[2-(3-chlorophenylthio)ethyl]piperidine-3-carboxylic acid (3R,4R)-4-[3-(6-Methoxyquinolin-4-yl)propyl]-1-[3-(3-chlorophenylthio)propyl]piperidine-3-carboxylic acid
(3R,4R)-4-[3-(6-Methoxyquinolin-4-yl)propyl]-1-[2-(4-chlorophenylthio)ethyl]piperidine-3-carboxylic acid
(3R,4R)-4-[3-(6-Methoxyquinolin-4-yl)propyl]-1-[3-(4-chlorophenylthio)propyl]piperidine-3-carboxylic acid
(3R,4R)-4-[3-(6-Methoxyquinolin-4-yl)propyl]-1-[2-(2,3-dichlorophenylthio)ethyl]piperidine-3-carboxylic acid
(3R,4R)-4-[3-(6-Methoxyquinolin-4-yl)propyl]-1-[3-(2,3-dichlorophenylthio)propyl]piperidine-3-carboxylic acid
(3R,4R)-4-[3-(6-Methoxyquinolin-4-yl)propyl]-1-[2-(2,6-dichlorophenylthio)ethyl]piperidine-3-carboxylic acid
(3R,4R)-4-[3-(6-Methoxyquinolin-4-yl)propyl]-1-[3-(2,6-dichlorophenylthio)propyl]piperidine-3-carboxylic acid
(3R,4R)-4-[3-(6-Methoxyquinolin-4-yl)propyl]-1-[2-(2-methylphenylthio)ethyl]piperidine-3-carboxylic acid
(3R,4R)-4-[3-(6-Methoxyquinolin-4-yl)propyl]-1-[3-(2-methylphenylthio)propyl]piperidine-3-carboxylic acid
(3R,4R)-4-[3-(6-Methoxyquinolin-4-yl)propyl]-1-[2-(3-methylphenylthio)ethyl]piperidine-3-carboxylic acid
(3R,4R)-4-[3-(6-Methoxyquinolin-4-yl)propyl]-1-[3-(3-methylphenylthio)propyl]piperidine-3-carboxylic acid
(3R,4R)-4-[3-(6-Methoxyquinolin-4-yl)propyl]-1-[2-(4-methylphenylthio)ethyl]piperidine-3-carboxylic acid
(3R,4R)-4-[3-(6-Methoxyquinolin-4-yl)propyl]-1-[3-(4-methylphenylthio)propyl]piperidine-3-carboxylic acid
(3R,4R)-4-[3-(6-Methoxyquinolin-4-yl)propyl]-1-[2-(2-trifluoromethylphenylthio)ethyl]piperidine-3-carboxylic acid
(3R,4R)-4-[3-(6-Methoxyquinolin-4-yl)propyl]-1-[3-(2-trifluoromethylphenylthio)propyl]piperidine-3-carboxylic acid
(3R,4R)-4-[3-(6-Methoxyquinolin-4-yl)propyl]-1-[2-(3-trifluoromethylphenylthio)ethyl]piperidine-3-carboxylic acid
(3R,4R)-4-[3-(6-Methoxyquinolin-4-yl)propyl]-1-[3-(3-trifluoromethylphenylthio)phenylthio)propyl]piperidine-3-carboxylic acid
(3R,4R)-4-[3-(6-Methoxyquinolin-4-yl)propyl]-1-[2-(4-trifluoromethylphenylthio)ethyl]piperidine-3-carboxylic acid
(3R,4R)-4-[3-(6-Methoxyquinolin-4-yl)propyl]-1-[3-(4-trifluoromethylphenylthio)propyl]piperidine-3-carboxylic acid
(3R,4R)-4-(3-(6-Methoxyquinolin-4-yl)propyl]-1-[2-(2-methoxyphenylthio)ethyl]piperidine-3-carboxylic acid
(3R,4R)-4-[3-(6-Methoxyquinolin-4-yl)propyl]-1-[3-(2-methoxyphenylthio)propyl]piperidine-3-carboxylic acid
(3R,4R)-4-[3-(6-Methoxyquinolin-4-yl)propyl]-1-[2-(3-methoxyphenylthio)ethyl]piperidine-3-carboxylic acid
(3R,4R)-4-[3-(6-Methoxyquinolin-4-yl)propyl]-1-[3-(3-methoxyphenylthio)propyl]piperidine-3-carboxylic acid
(3R,4R)-4-[3-(6-Methoxyquinolin-4-yl)propyl]-1-[2-(4-methoxyphenylthio)ethyl]piperidine-3-carboxylic acid
(3R,4R)-4-[3-(6-Methoxyquinolin-4-yl)propyl]-1-[3-(4-methoxyphenylthio)propyl]piperidine-3-carboxylic acid
(3R,4R)-4-[3-(6-Methoxyquinolin-4-yl)propyl]-1-[cyclopropylmethyl]piperidine-3-carboxylic acid
(3R,4R)-4-[3-(6-Methoxyquinolin-4-yl)propyl]-1-[2-(cyclopropyl)ethyl]piperidine-3-carboxylic acid
(3R,4R)-4-[3-(6-Methoxyquinolin-4-yl)propyl]-1-[cyclobutylmethyl]piperidine-3-carboxylic acid
(3R,4R)-4-[3-(6-Methoxyquinolin-4-yl)propyl]-1-[2-(cyclobutyl)ethyl]piperidine-3-carboxylic acid
(3R,4R)-4-[3-(6-Methoxyquinolin-4-yl)propyl]-1-[cyclopentylmethyl]piperidine-3-carboxylic acid
(3R,4R)-4-[3-(6-Methoxyquinolin-4-yl)propyl]-1-[2-(cyclopentyl)ethyl]piperidine-3-carboxylic acid
(3R,4R)-4-[3-(6-Methoxyquinolin-4-yl)propyl]-1-[cyclohexylmethyl]piperidine-3-carboxylic acid
(3R,4R)-4-[3-(6-Methoxyquinolin-4-yl)propyl]-1-[2-(cyclohexyl)ethyl]piperidine-3-carboxylic acid
(3R,4R)-4-[3-(6-Methoxyquinolin-4-yl)propyl]-1-[2-(cyclopropylthio)ethyl]piperidine-3-carboxylic acid
(3R,4R)-4-[3-(6-Methoxyquinolin-4-yl)propyl]-1-[3-(cyclopropylthio)propyl]piperidine-3-carboxylic acid
(3R,4R)-4-[3-(6-Methoxyquinolin-4-yl)propyl]-1-[2-(cyclobutylthio)ethyl]piperidine-3-carboxylic acid
(3R,4R)-4-[3-(6-Methoxyquinolin-4-yl)propyl]-1-[3-(cyclobutylthio)propyl]piperidine-3-carboxylic acid
(3R,4R)-4-[3-(6-Methoxyquinolin-4-yl)propyl]-1-[2-(cyclopentylthio)ethyl]piperidine-3-carboxylic acid
(3R,4R)-4-[3-(6-Methoxyquinolin-4-yl)propyl]-1-[3-(cyclopentylthio)propyl]piperidine-3-carboxylic acid
(3R,4R)-4-[3-(6-Methoxyquinolin-4-yl)propyl]-1-[3-(cyclohexylthio)propyl]piperidine-3-carboxylic acid
(3R,4R)-4-[3-(6-Methoxyquinolin-4-yl)propyl]-1-[2-methylthioethyl]piperidine-3-carboxylic acid
(3R,4R)-4-[3-(6-Methoxyquinolin-4-yl)propyl]-1-[3-methylthiopropyl]piperidine-3-carboxylic acid
(3R,4R)-4-[3-(6-Methoxyquinolin-4-yl)propyl]-1-[2-ethylthioethyl]piperidine-3-carboxylic acid
(3R,4R)-4-[3-(6-Methoxyquinolin-4-yl)propyl]-1-[3-ethylthiopropyl]piperidine-3-carboxylic acid
(3R,4R)-4-[3-(6-Methoxyquinolin-4-yl)propyl]-1-[2-(n-propylthio)ethyl]piperidine-3-carboxylic acid
(3R,4R)-4-[3-(6-Methoxyquinolin-4-yl)propyl]-1-[3-(n-propylthio)propyl]piperidine-3-carboxylic acid
(3R,4R)-4-[3-(6-Methoxyquinolin-4-yl)propyl]-1-[2-(n-butylthio)ethyl]piperidine-3-carboxylic acid
(3R,4R)-4-[3-(6-Methoxyquinolin-4-yl)propyl]-1-[3-(n-butylthio)propyl]piperidine-3-carboxylic acid
(3R,4R)-4-[3-(6-Methoxyquinolin-4-yl)propyl]-1-[4-(thien-2-yl)butyl]piperidine-3-carboxylic acid
(3R,4R)-4-[3-(6-Methoxyquinolin-4-yl)propyl]-1-[3-(thien-2-yl)thiopropyl]piperidine-3-carboxylic acid
(3R,4R)-4-[3-(6-Methoxyquinolin-4-yl)propyl]-1-[3-(5-chlorothien-2-yl)propyl]piperidine-3-carboxylic acid
(3R,4R)-4-[3-(6-Methoxyquinolin-4-yl)propyl]-1-[4-(5-chlorothien-2-yl)butyl]piperidine-3-carboxylic acid
(3R,4R)-4-[3-(6-Methoxyquinolin-4-yl)propyl]-1-[2-(5-chlorothien-2-yl)thioethyl]piperidine-3-carboxylic acid
(3R,4R)-4-[3-(6-Methoxyquinolin-4-yl)propyl]-1-[3-(5-chlorothien-2-yl)thiopropyl]piperidine-3-carboxylic acid
(3R,4R)-4-[3-(6-Methoxyquinolin-4-yl)propyl]-1-[3-(3-chlorothien-2-yl)propyl]piperidine-3-carboxylic acid
(3R,4R)-4-[3-(6-Methoxyquinolin-4-yl)propyl]-1-[4-(3-chlorothien-2-yl)butyl]piperidine-3-carboxylic acid
(3R,4R)-4-[3-(6-Methoxyquinolin-4-yl)propyl]-1-[2-(3-chlorothien-2-yl)thioethyl]piperidine-3-carboxylic acid
(3R,4R)-4-[3-(6-Methoxyquinolin-4-yl)propyl]-1-[3-(3-chlorothien-2-yl)thiopropyl]piperidine-3-carboxylic acid
(3R,4R)-4-[3-(6-Methoxyquinolin-4-yl)propyl]-1-[3-(5-methylthien-2-yl)propyl]piperidine-3-carboxylic acid
(3R,4R)-4-[3-(6-Methoxyquinolin-4-yl)propyl]-1-[4-(5-methylthien-2-yl)butyl]piperidine-3-carboxylic acid
(3R,4R)-4-[3-(6-Methoxyquinolin-4-yl)propyl]-1-[2-(5-methylthien-2-yl)thioethyl]piperidine-3-carboxylic acid
(3R,4R)-4-[3-(6-Methoxyquinolin-4-yl)propyl]-1-[3-(5-methylthien-2-yl)thiopropyl]piperidine-3-carboxylic acid
(3R,4R)-4-[3-(6-Methoxyquinolin-4-yl)propyl]-1-[3-(3-methylthien-2-yl)propyl]piperidine-3-carboxylic acid
(3R,4R)-4-[3-(6-Methoxyquinolin-4-yl)propyl]-1-[4-(3-methylthien-2-yl)butyl]piperidine-3-carboxylic acid
(3R,4R)-4-[3-(6-Methoxyquinolin-4-yl)propyl]-1-[2-(3-methylthien-2-yl)thioethyl]piperidine-3-carboxylic acid (3R,4R)-4-[3-(6-Methoxyquinolin-4-yl)propyl]-1-[3-(3-methylthien-2-yl)thiopropyl]piperidine-3-carboxylic acid
(3R,4R)-4-[3-(6-Methoxyquinolin-4-yl)propyl]-1-[3-(thien-3-yl)propyl]piperidine-3-carboxylic acid
(3R,4R)-4-[3-(6-Methoxyquinolin-4-yl)propyl]-1-[4-(thien-3-yl)butyl]piperidine-3-carboxylic acid
(3R,4R)-4-[3-(6-Methoxyquinolin-4-yl)propyl]-1-[2-(thien-3-yl)thioethyl]piperidine-3-carboxylic acid
(3R,4R)-4-[3-(6-Methoxyquinolin-4-yl)propyl]-1-[3-(thien-3-yl)thiopropyl]piperidine-3-carboxylic acid
(3R,4R)-4-[3-(6-Methoxyquinolin-4-yl)propyl]-1-[3-(fur-2-yl)propyl]piperidine-3-carboxylic acid
(3R,4R)-4-[3-(6-Methoxyquinolin-4-yl)propyl]-1-[4-(fur-2-yl)butyl]piperidine-3-carboxylic acid
(3R,4R)-4-[3-(6-Methoxyquinolin-4-yl)propyl]-1-[2-(fur-2-yl)thioethyl]piperidine-3-carboxylic acid
(3R,4R)-4-[3-(6-Methoxyquinolin-4-yl)propyl]-1-[3-(fur-2-yl)thiopropyl]piperidine-3-carboxylic acid
(3R,4R)-4-[3-(6-Methoxyquinolin-4-yl)propyl]-1-[3-(fur-3-yl)propyl]piperidine-3-carboxylic acid
(3R,4R)-4-[3-(6-Methoxyquinolin-4-yl)propyl]-1-[4-(fur-3-yl)butyl]piperidine-3carboxylic acid
(3R,4R)-4-[3-(6-Methoxyquinolin-4-yl)propyl]-1-[2-(fur-3-yl)thioethyl]piperidine-3-carboxylic acid
(3R,4R)-4-[3-(6-Methoxyquinolin-4-yl)propyl]-1-[3-(fur-3-yl)thiopropyl]piperidine-3-carboxylic acid
(3R,4R)-4-[3-(6-Methoxyquinolin-4-yl)propyl]-1-[3-(1-methylpyrrol-2-yl)propyl]piperidine-3-carboxylic acid
(3R,4R)-4-[3-(6-Methoxyquinolin-4-yl)propyl]-1-[4-(1-methylpyrrol-2-yl)butyl]piperidine-3-carboxylic acid
(3R,4R)-4-[3-(6-Methoxyquinolin-4-yl)propyl]-1-[2-(1-methylpyrrol-2-yl)thioethyl]piperidine-3-carboxylic acid
(3R,4R)-4-[3-(6-Methoxyquinolin-4-yl)propyl]-1-[3-(1-methylpyrrol-2-yl)thiopropyl]piperidine-3-carboxylic acid
(3R,4R)-4-[3-(6-Methoxyquinolin-4-yl)propyl]-1-[3-(1-methylpyrrol-2-yl)propyl]piperidine-3-carboxylic acid
(3R,4R)-4-[3-(6-Methoxyquinolin-4-yl)propyl]-1-[4-(1-methylpyrrol-3-yl)butyl]piperidine-3-carboxylic acid
(3R,4R)-4-[3-(6-Methoxyquinolin-4-yl)propyl]-1-[2-(1-methylpyrrol-3-yl)thioethyl]piperidine-3-carboxylic acid
(3R,4R)-4-[3-(6-Methoxyquinolin-4-yl)propyl]-1-[3-(1-methylpyrrol-3-yl)thiopropyl]piperidine-3-carboxylic acid
(3R,4R)-4-[3-(6-Methoxyquinolin-4-yl)propyl]-1-[3-(1,3-thiazol-2-yl)propyl]piperidine-3-carboxylic acid
(3R,4R)-4-[3-(6-Methoxyquinolin-4-yl)propyl]-1-[4-(1,3-thiazol-2-yl)butyl]piperidine-3-carboxylic acid
(3R,4R)-4-[3-(6-Methoxyquinolin-4-yl)propyl]-1-[3-(1,3-thiazol-2-yl)thiopropyl]piperidine-3-carboxylic acid
(3R,4R)-4-[3-(6-Methoxyquinolin-4-yl)propyl]-1-[3-(1-methylimidazol-2-yl)propyl]piperidine-3-carboxylic acid
(3R,4R)-4-[3-(6-Methoxyquinolin-4-yl)propyl]-1-[4-(1-methylimidazol-2-yl)butyl]piperidine-3-carboxylic acid
(3R,4R)-4-[3-(6-Methoxyquinolin-4-yl)propyl]-1-[2-(1-methylimidazol-2-yl)thioethyl]piperidine-3-carboxylic acid
(3R,4R)-4-[3-(6-Methoxyquinolin-4-yl)propyl]-1-[3-(1-methylimidazol-2-yl)thiopropyl]piperidine-3-carboxylic acid
(3R,4R)-4-[3-(6-Methoxyquinolin-4-yl)propyl]-1-[3-(3-methylimidazol-4-yl)propyl]piperidine-3-carboxylic acid
(3R,4R)-4-[3-(6-Methoxyquinolin-4-yl)propyl]-1-[4-(3-methylimidazol-4-yl)butyl]piperidine-3-carboxylic acid
(3R,4R)-4-[3-(6-Methoxyquinolin-4-yl)propyl]-1-[2-(3-methylimidazol-4-yl)thioethyl]piperidine-3-carboxylic acid
(3R,4R)-4-[3-(6-Methoxyquinolin-4-yl)propyl]-1-[3-(3-methylimidazol-4-yl)thiopropyl]piperidine-3-carboxylic acid
(3R,4R)-4-[3-(6-Methoxyquinolin-4-yl)propyl]-1-[3-(3-methylpyrazol-4-yl)propyl]piperidine-3-carboxylic acid
(3R,4R)-4-[3-(6-Methoxyquinolin-4-yl)propyl]-1-[4-(3-methylpyrazol-4-yl)butyl]piperidine-3-carboxylic acid
(3R,4R)-4-[3-(6-Methoxyquinolin-4-yl)propyl]-1-[2-(3-methylpyrazol-4-yl)thioethyl]piperidine-3-carboxylic acid
(3R,4R)-4-[3-(6-Methoxyquinolin-4-yl)propyl]-1-[3-(3-methylpyrazol-4-yl)thiopropyl]piperidine-3-carboxylic acid
(3R,4R)-4-[3-(6-Methoxyquinolin-4-yl)propyl]-1-[3-(oxazol-2-yl)propyl]piperidine-3-carboxylic acid
(3R,4R)-4-[3-(6-Methoxyquinolin-4-yl)propyl]-1-[4-(oxazol-2-yl)butyl]piperidine-3-carboxylic acid
(3R,4R)-4-[3-(6-Methoxyquinolin-4-yl)propyl]-1-[2-(oxazol-2-yl)thioethyl]piperidine-3-carboxylic acid
(3R,4R)-4-[3-(6-Methoxyquinolin-4-yl)propyl]-1-[3-(oxazol-2-yl)thiopropyl]piperidine-3-carboxylic acid
(3R,4R)-4-[3-(6-Methoxyquinolin-4-yl)propyl]-1-[3-(pyridin-2-yl)propyl]piperidine-3-carboxylic acid
(3R,4R)-4-[3-(6-Methoxyquinolin-4-yl)propyl]-1-[4-(pyridin-2-yl)butyl]piperidine-3-carboxylic acid
(3R,4R)-4-[3-(6-Methoxyquinolin-4-yl)propyl]-1-[3-(pyridin-2-yl)thiopropyl]piperidine-3-carboxylic acid
(3R,4R)-4-[3-(6-Methoxyquinolin-4-yl)propyl]-1-[3-(pyridin-3-yl)propyl]piperidine-3-carboxylic acid
(3R,4R)-4-[3-(6-Methoxyquinolin-4-yl)propyl]-1-[4-(pyridin-3-yl)butyl]piperidine-3-carboxylic acid
(3R,4R)-4-[3-(6-Methoxyquinolin-4-yl)propyl]-1-[2-(pyridin-3-yl)thioethyl]piperidine-3-carboxylic acid
(3R,4R)-4-[3-(6-Methoxyquinolin-4-yl)propyl]-1-[3-(pyridin-3-yl)thiopropyl]piperidine-3-carboxylic acid
(3R,4R)-4-[3-(6-Methoxyquinolin-4-yl)propyl]-1-[3-(pyridin-4-yl)propyl]piperidine-3-carboxylic acid
(3R,4R)-4-[3-(6-Methoxyquinolin-4-yl)propyl]-1-[4-(pyridin-4-yl)butyl]piperidine-3-carboxylic acid
(3R,4R)-4-[3-(6-Methoxyquinolin-4-yl)propyl]-1-[5-(pyridin-4-yl)pentyl]piperidine-3-carboxylic acid
(3R,4R)-4-[3-(6-Methoxyquinolin-4-yl)propyl]-1-[2-(pyridin-4-yl)thioethyl]piperidine-3-carboxylic acid
(3R,4R)-4-[3-(6-Methoxyquinolin-4-yl)propyl]-1-[3-(pyridin-4-yl)thiopropyl]piperidine-3-carboxylic acid
(3R,4R)-4-[3-(6-Methoxyquinolin-4-yl)propyl]-1-[3-(pyrimidin-2-yl)propyl]piperidine-3-carboxylic acid
(3R,4R)-4-[3-(6-Methoxyquinolin-4-yl)propyl]-1-[4-(pyrimidin-2-yl)butyl]piperidine-3-carboxylic acid
(3R,4R)-4-[3-(6-Methoxyquinolin-4-yl)propyl]-1-[2-(pyrimidin-2-yl)thioethyl]piperidine-3-carboxylic acid
(3R,4R)-4-[3-(6-Methoxyquinolin-4-yl)propyl]-1-[3-(pyrimidin-2-yl)thiopropyl]piperidine-3-carboxylic acid
(3R,4R)-4-[3-(6-Methoxyquinolin-4-yl)propyl]-1-[3-(pyrimidin-4-yl)propyl]piperidine-3-carboxylic acid
(3R,4R)-4-[3-(6-Methoxyquinolin-4-yl)propyl]-1-[4-(pyrimidin-4-yl)butyl]piperidine-3-carboxylic acid
(3R,4R)-4-[3-(6-Methoxyquinolin-4-yl)propyl]-1-[2-(pyrimidin-4-yl)thioethyl]piperidine-3-carboxylic acid
(3R,4R)-4-[3-(6-Methoxyquinolin-4-yl)propyl]-1-[3-(pyrimidin-4-yl)thiopropyl]piperidine-3-carboxylic acid
(3R,4R)-4-[3-(6-Methoxyquinolin-4-yl)propyl]-1-[3-(pyrimidin-5-yl)propyl]piperidine-3-carboxylic acid
(3R,4R)-4-[3-(6-Methoxyquinolin-4-yl)propyl]-1-[4-(pyrimidin-5-yl)butyl]piperidine-3-carboxylic acid
(3R,4R)-4-[3-(6-Methoxyquinolin-4-yl)propyl]-1-[2-(pyrimidin-5-yl)thioethyl]piperidine-3-carboxylic acid (3R,4R)-4-[3-(6-Methoxyquinolin-4-yl)propyl]-1-[3-(pyrimidin-5-yl)thiopropyl]piperidine-3-carboxylic acid
(3R,4R)-4-[3-(6-Methoxyquinolin-4-yl)propyl]-1-[3-(pyrazin-2-yl)propyl]piperidine-3-carboxylic acid
(3R,4R)-4-[3-(6-Methoxyquinolin-4-yl)propyl]-1-[4-(pyrazin-2-yl)butyl]piperidine-3-carboxylic acid
(3R,4R)-4-[3-(6-Methoxyquinolin-4-yl)propyl]-1-[2-(pyrazin-2-yl)thioethyl]piperidine-3-carboxylic acid
(3R,4R)-4-[3-(6-Methoxyquinolin-4-yl)propyl]-1-[3-(pyrazin-2-yl)thiopropyl]piperidine-3-carboxylic acid
(3R,4R)-4-[3-(6-Methoxyquinolin-4-yl)propyl]-1-[3-(pyridazin-3-yl)propyl]piperidine-3-carboxylic acid
(3R,4R)-4-[3-(6-Methoxyquinolin-4-yl)propyl]-1-[4-(pyridazin-3-yl)butyl]piperidine-3-carboxylic acid
(3R,4R)-4-[3-(6-Methoxyquinolin-4-yl)propyl]-1-[2-(pyridazin-3-yl)thioethyl]piperidine-3-carboxylic acid
(3R,4R)-4-[3-(6-Methoxyquinolin-4-yl)propyl]-1-[3-(pyridazin-3-yl)thiopropyl]piperidine-3-carboxylic acid
(3R,4R)-4-[3-(6-Methoxyquinolin-4-yl)propyl]-1-[3-(pyridazin-4-yl)propyl]piperidine-3-carboxylic acid
(3R,4R)-4-[3-(6-Methoxyquinolin-4-yl)propyl]-1-[4-(pyridazin-4-yl)butyl]piperidine-3-carboxylic acid
(3R,4R)-4-[3-(6-Methoxyquinolin-4-yl)propyl]-1-[2-(pyridazin-4-yl)thioethyl]piperidine-3-carboxylic acid
(3R,4R)-4-[3-(6-Methoxyquinolin-4-yl)propyl]-1-[3-(pyridazin-4-yl)thiopropyl]piperidine-3-carboxylic acid
(3R,4R)-4-[3-(6-Methoxyquinolin-4-yl)propyl]-1-[3-(4-fluorophenyl)prop-2-ynyl]piperidine-3-carboxylic acid
(3R,4R)-4-[3-(6-Methoxyquinolin-4-yl)propyl]-1-[3-(2-chlorophenyl)prop-2-ynyl]piperidine-3-carboxylic acid
(3R,4R)-4-[3-(6-Methoxyquinolin-4-yl)propyl]-1-[3-(3-chlorophenyl)prop-2-ynyl]piperidine-3-carboxylic acid
(3R,4R)-4-[3-(6-Methoxyquinolin-4-yl)propyl]-1-[3-(4-chlorophenyl)prop-2-ynyl]piperidine-3-carboxylic acid
(3R,4R)-4-[3-(6-Methoxyquinolin-4-yl)propyl]-1-[3-(2-methylphenyl)prop-2-ynyl]piperidine-3-carboxylic acid
(3R,4R)-4-[3-(6-Methoxyquinolin-4-yl)propyl]-1-[3-(3-methylphenyl)prop-2-ynyl]piperidine-3-carboxylic acid
(3R,4R)-4-[3-(6-Methoxyquinolin-4-yl)propyl]-1-[3-(4-methylphenyl)prop-2-ynyl]piperidine-3-carboxylic acid
(3R,4R)-4-[3-(6-Methoxyquinolin-4-yl)propyl]-1-[3-(2-(trifluoromethyl)phenyl)prop-2-ynyl]-piperidine-3-carboxylic acid
(3R,4R)-4-[3-(6-Methoxyquinolin-4-yl)propyl]-1-[3-(3-(trifluoromethyl)phenyl)prop-2-ynyl]-piperidine-3-carboxylic acid
(3R,4R)-4-[3-(6-Methoxyquinolin-4-yl)propyl]-1-[3-(4-(trifluoromethyl)phenyl)prop-2-ynyl]-piperidine-3-carboxylic acid
(3R,4R)-4-[3-(6-Methoxyquinolin-4-yl)propyl]-1-[3-(2-Methoxyphenyl)prop-2-ynyl]piperidine-3-carboxylic acid
(3R,4R)-4-[3-(6-Methoxyquinolin-4-yl)propyl]-1-[3-(3-methoxyphenyl)prop-2-ynyl]piperidine-3-carboxylic acid
(3R,4R)-4-[3-(6-Methoxyquinolin-4-yl)propyl]-1-[3-(4-methoxyphenyl)prop-2-ynyl]piperidine-3-carboxylic acid
(3R,4R)-4-[3-(6-Methoxyquinolin-4-yl)propyl]-1-[3-(3,4-difluorophenyl)prop-2-ynyl]piperidine-3-carboxylic acid
(3R,4R)-4-[3-(6-Methoxyquinolin-4-yl)propyl]-1-[3-(2,4-difluorophenyl)prop-2-ynyl]piperidine-3-carboxylic acid
(3R,4R)-4-[3-(6-Methoxyquinolin-4-yl)propyl]-1-[3-(3,4-dichlorophenyl)prop-2-ynyl]piperidine-3-carboxylic acid
(3R,4R)-4-[3-(6-Methoxyquinolin-4-yl)propyl]-1-[3-(2,3-dichlorophenyl)prop-2-ynyl]piperidine-3-carboxylic acid
(3R,4R)-4-[3-(6-Methoxyquinolin-4-yl)propyl]-1-[3-(2,4-dichlorophenyl)prop-2-ynyl]piperidine-3-carboxylic acid
(3R,4R)-4-[3-(6-Methoxyquinolin-4-yl)propyl]-1-[3-(2,4,6-trichlorophenyl)prop-2-ynyl]piperidine-3-carboxylic acid
(3R,4R)-4-[3-(6-Methoxyquinolin-4-yl)propyl]-1-[3-(3,5-dichlorophenyl)prop-2-ynyl]piperidine-3-carboxylic acid
(3R,4R)-4-[3-(6-Methoxyquinolin-4-yl)propyl]-1-[3-(4-chloro-3-fluorophenyl)prop-2-ynyl]piperidine-3-carboxylic acid
(3R,4R)-4-[3-(6-Methoxyquinolin-4-yl)propyl]-1-[3-(3-chloro-4-fluorophenyl)prop-2-ynyl]piperidine-3-carboxylic acid
(3R,4R)-4-[3-(6-Methoxyquinolin-4-yl)propyl]-1-[3-(2-chloro-4-fluorophenyl)prop-2-ynyl]piperidine-3-carboxylic acid
(3R,4R)-4-[3-(6-Methoxyquinolin-4-yl)propyl]-1-[3-(3-chloro-5-fluorophenyl)prop-2-ynyl]piperidine-3-carboxylic acid
(3R,4R)-4-[3-(6-Methoxyquinolin-4-yl)propyl]-1-[3-(4-chloro-2-fluorophenyl)prop-2-ynyl]piperidine-3-carboxylic acid
(3R,4R)-4-[3-(6-Methoxyquinolin-4-yl)propyl]-1-[3-(3-fluoro-4-methylphenyl)prop-2-ynyl]piperidine-3-carboxylic acid
(3R,4R)-4-[3-(6-Methoxyquinolin-4-yl)propyl]-1-[3-(4-chloro-3-(trifluoromethyl)phenyl)prop-2-ynyl]piperidine-3-carboxylic acid
(3R,4R)-4-[3-(6-Methoxyquinolin-4-yl)propyl]-1-[3-(2-chloro4-(trifluoromethyl)phenyl)prop-2-ynyl]piperidine-3-carboxylic acid
(3R,4R)-4-[3-(6-Methoxyquinolin-4-yl)propyl]-1-[3-(2-chloro-5-(trifluoromethyl)phenyl)prop-2-ynyl]piperidine-3-carboxylic acid
(3R,4R)-4-[3-(6-Methoxyquinolin-4-yl)propyl]-1-[3-(5-chloro-2-methoxyphenyl)prop-2-ynyl]piperidine-3-carboxylic acid
(3R,4R)-4-[3-(6-Methoxyquinolin-4-yl)propyl]-1-[3-(3,5-bis(trifluoromethyl)phenyl)prop-2-ynyl]-piperidine-3-carboxylic acid
(3R,4R)-4-[3-(6-Methoxyquinolin-4-yl)propyl]-1-[3-(3,5-dimethylphenyl)prop-2-ynyl)piperidine-3-carboxylic acid
(3R,4R)-4-[3-(6-Methoxyquinolin-4-yl)propyl]-1-[3-(2,4-dichloro-6-methylphenyl)prop-2-ynyl]piperidine-3-carboxylic acid
(3R,4R)-4-[3-(6-Methoxyquinolin-4-yl)propyl]-1-[3-(5-chlorothien-2-yl)prop-2-ynyl]piperidine-3-carboxylic acid
(3R,4R)-4-[3-(6-Methoxyquinolin-4-yl)propyl]-1-[3-(3-chlorothien-2-yl)prop-2-ynyl]piperidine-3-carboxylic acid
(3R,4R)-4-[3-(6-Methoxyquinolin-4-yl)propyl]-1-[3-(5-methylthien-2-yl)prop-2-ynyl]piperidine-3-carboxylic acid
(3R,4R)-4-[3-(6-Methoxyquinolin-4-yl)propyl]-1-[3-(3-methylthien-2-yl)prop-2-ynyl]piperidine-3-carboxylic acid
(3R,4R)-4-[3-(6-Methoxyquinolin-4-yl)propyl]-1-[3-(thien-3-yl)prop-2-ynyl]piperidine-3-carboxylic acid
(3R,4R)-4-[3-(6-Methoxyquinolin-4-yl)propyl]-1-[3-(1-methylpyrrol-2-yl)prop-2-ynyl]piperidine-3-carboxylic acid
(3R,4R)-4-[3-(6-Methoxyquinolin-4-yl)propyl]-1-[3-(1-methylpyrrol-3-yl)prop-2-ynyl]piperidine-3-carboxylic acid
(3R,4R)-4-[3-(6-Methoxyquinolin-4-yl)propyl]-1-[3-(1,3-thiazol-2-yl)prop-2-ynyl]piperidine-3-carboxylic acid
(3R,4R)-4-[3-(6-Methoxyquinolin-4-yl)propyl]-1-[3-(1,3-thiazol-4-yl)prop-2-ynyl]piperidine-3-carboxylic acid
(3R,4R)-4-[3-(6-Methoxyquinolin-4-yl)propyl]-1-[3-(1,3-thiazol-5-yl)prop-2-ynyl]piperidine-3-carboxylic acid (3R,4R)-4-[3-(6-Methoxyquinolin-4-yl)propyl]-1-[3-(1-methylimidazol-2-yl)prop-2-ynyl]piperidine-3-carboxylic acid (3R,4R)-4-[3-(6-Methoxyquinolin-4-yl)propyl]-1-[3-(3-methylimidazol-4-yl)prop-2-ynyl]piperidine-3-carboxylic acid (3R,4R)-4-[3-(6-Methoxyquinolin-4-yl)propyl]-1-[3-(3-methylpyrazol-4-yl)prop-2-ynyl]piperidine-3-carboxylic acid (3R,4R)-4-[3-(6-Methoxyquinolin-4-yl)propyl]-1-[3-(oxazol-2-yl)prop-2-ynyl]piperidine-3-carboxylic acid (3R,4R)-4-[3-(6-Methoxyquinolin-4-yl)propyl]-1-[3-(oxazol-4-yl)prop-2-ynyl]piperidine-3-carboxylic acid (3R,4R)-4-[3-(6-Methoxyquinolin-4-yl)propyl]-1-[3-(oxazol-5-yl)prop-2-ynyl]piperidine-3-carboxylic acid (3R,4R)-4-[3-(6-Methoxyquinolin-4-yl)propyl]-1-[3-(pyridin-2-yl)prop-2-ynyl]piperidine-3-carboxylic acid (3R,4R)-4-[3-(6-Methoxyquinolin-4-yl)propyl]-1-[3-(pyridin-3-yl)prop-2-ynyl]piperidine-3-carboxylic acid (3R,4R)-4-[3-(6-Methoxyquinolin-4-yl)propyl]-1-[3-(pyridin-4-yl)prop-2-ynyl]piperidine-3-carboxylic acid (3R,4R)-4-[3-(6-Methoxyquinolin-4-yl)propyl]-1-[3-(pyrimidin-2-yl)prop-2-ynyl]piperidine-3-carboxylic acid (3R,4R)-4-[3-(6-Methoxyquinolin-4-yl)propyl]-1-[3-(pyrimidin-4-yl)prop-2-ynyl]piperidine-3-carboxylic acid (3R,4R)-4-[3-(6-Methoxyquinolin-4-yl)propyl]-1-[3-(pyrimidin-5-yl)prop-2-ynyl]piperidine-3-carboxylic acid (3R,4R)-4-[3-(6-Methoxyquinolin-4-yl)propyl]-1-[3-(pyrazin-2-yl)prop-2-ynyl]piperidine-3-carboxylic acid (3R,4R)-4-[3-(6-Methoxyquinolin-4-yl)propyl]-1-[3-(pyridazin-3-yl)prop-2-ynyl]piperidine-3-carboxylic acid (3R,4R)-4-[3-(6-Methoxyquinolin-4-yl)propyl]-1-(3-(pyridazin-4-yl)prop-2-ynyl]piperidine-3-carboxylic acid (3R,4R)-4-[3-(6-Methoxyquinolin-4-yl)propyl]-1-[4-phenylbuten-3-yl]piperidine-3-carboxylic acid (3R,4R)-4-[3-(R,S)-Hydroxy-3-(6-methoxyquinolin-4-yl)propyl]-1-[4-phenylbutyl]piperidine-3-carboxylic acid (3R,4R)-4-[3-(R,S)-Hydroxy-3-(6-methoxyquinolin-4-yl)propyl]-1-[3-(2-fluorophenyl)propyl]piperidine-3-carboxylic acid (3R,4R)-4-[3-(R,S)-Hydroxy-3-(6-methoxyquinolin-4-yl)propyl]-1-[4-(2-fluorophenyl)butyl]piperidine-3-carboxylic acid (3R,4R)-4-[3-(R,S)-Hydroxy-3-(6-methoxyquinolin-4-yl)propyl]-1-[3-(3-fluorophenyl)propyl]piperidine-3-carboxylic acid (3R,4R)-4-[3-(R,S)-Hydroxy-3-(6-methoxyquinolin-4-yl)propyl]-1-[4-(3-fluorophenyl)butyl]piperidine-3-carboxylic acid (3R,4R)-4-[3-(R,S)-Hydroxy-3-(6-methoxyquinolin-4-yl)propyl]-1-[3-(4-fluorophenyl)propyl]piperidine-3-carboxylic acid (3R,4R)-4-[3-(R,S)-Hydroxy-3-(6-methoxyquinolin-4-yl)propyl]-1-[4-(4-fluorophenyl)butyl]piperidine-3-carboxylic acid (3R,4R)-4-[3-(R,S)-Hydroxy-3-(6-methoxyquinolin-4-yl)propyl]-1-[3-(2,3-difluorophenyl)propyl]piperidine-3-carboxylic acid (3R,4R)-4-[3-(R,S)-Hydroxy-3-(6-methoxyquinolin-4-yl)propyl]-1-[4-(2,3-difluorophenyl)butyl]piperidine-3-carboxylic acid (3R,4R)-4-[3-(R,S)-Hydroxy-3-(6-methoxyquinolin-4-yl)propyl]-1-[3-(2,6-difluorophenyl)propyl]piperidine-3-carboxylic acid (3R,4R)-4-[3-(R,S)-Hydroxy-3-(6-methoxyquinolin-4-yl)propyl]-1-[4-(2,6-difluorophenyl)butyl]piperidine-3-carboxylic acid (3R,4R)-4-[3-(R,S)-Hydroxy-3-(6-methoxyquinolin-4-yl)propyl]-1-[3-(2-chlorophenyl)propyl]piperidine-3-carboxylic acid (3R,4R)-4-[3-(R,S)-Hydroxy-3-(6-methoxyquinolin-4-yl)propyl]-1-[4-(2-chlorophenyl)butyl]piperidine-3-carboxylic acid (3R,4R)-4-[3-(R,S)-Hydroxy-3-(6-methoxyquinolin-4-yl)propyl]-1-[3-(3-chlorophenyl)propyl]piperidine-3-carboxylic acid (3R,4R)-4-[3-(R,S)-Hydroxy-3-(6-methoxyquinolin-4-yl)propyl]-1-[4-(3-chlorophenyl)butyl]piperidine-3-carboxylic acid (3R,4R)-4-[3-(R,S)-Hydroxy-3-(6-methoxyquinolin-4-yl)propyl]-[3-(4-chlorophenyl)propyl]piperidine-3-carboxylic acid (3R,4R)-4-[3-(R,S)-Hydroxy-3-(6-methoxyquinolin-4-yl)propyl]-1-[4-(4-chlorophenyl)butyl]piperidine-3-carboxylic acid (3R,4R)-4-[3-(R,S)-Hydroxy-3-(6-methoxyquinolin-4-yl)propyl]-1-[3-(2,3-dichlorophenyl)propyl]piperidine-3-carboxylic acid (3R,4R)-4-[3-(R,S)-Hydroxy-3-(6-methoxyquinolin-4-yl)propyl]-1-[4-(2,3-dichlorophenyl)butyl]piperidine-3-carboxylic acid (3R,4R)-4-[3-(R,S)-Hydroxy-3-(6-methoxyquinolin-4-yl)propyl]-1-[3-(2,6-dichlorophenyl)propyl]piperidine-3-carboxylic acid (3R,4R)-4-[3-(R,S)-Hydroxy-3-(6-methoxyquinolin-4-yl)propyl]-1-[4-(2 ,6-dichlorophenyl)butyl]piperidine-3-carboxylic acid (3R,4R)-4-[3-(R,S)-Hydroxy-3-(6-methoxyquinolin-4-yl)propyl]-1-[3-(2-methylphenyl)propyl]piperidine-3-carboxylic acid (3R,4R)-4-[3-(R,S)-Hydroxy-3-(6-methoxyquinolin-4-yl)propyl]-1-[4-(2-methylphenyl)butyl]piperidine-3-carboxylic acid (3R,4R)-4-[3-(R,S)-Hydroxy-3-(6-methoxyquinolin-4-yl)propyl]-1-[5-(2-methylphenyl)pentyl]piperidine-3-carboxylic acid (3R,4R)-4-[3-(R,S)-Hydroxy-3-(6-methoxyquinolin-4-yl)propyl]-1-[3-(3-methylphenyl)propyl]piperidine-3-carboxylic acid (3R,4R)-4-[3-(R,S)-Hydroxy-3-(6-methoxyquinolin-4-yl)propyl]-1-[4-(3-methylphenyl)butyl]piperidine-3-carboxylic acid (3R,4R)-4-[3-(R,S)-Hydroxy-3-(6-methoxyquinolin-4-yl)propyl]-1-[3-(4-methylphenyl)propyl]piperidine-3-carboxylic acid (3R,4R)-4-[3-(R,S)-Hydroxy-3-(6-methoxyquinolin-4-yl)propyl]-1-[4-(4-methylphenyl)butyl]piperidine-3-carboxylic acid (3R,4R)-4-[3-(R,S)-Hydroxy-3-(6-methoxyquinolin-4-yl)propyl]-1-[3-(2-methoxyphenyl)propyl]piperidine-3-carboxylic acid (3R,4R)-4-[3-(R,S)-Hydroxy-3-(6-methoxyquinolin-4-yl)propyl]-1-[4-(2-methoxyphenyl)butyl]piperidine-3-carboxylic acid (3R,4R)-4-[3-(R,S)-Hydroxy-3-(6-methoxyquinolin-4-yl)propyl]-1-[3-(3-methoxyphenyl)propyl]piperidine-3-carboxylic acid (3R,4R)-4-[3-(R,S)-Hydroxy-3-(6-methoxyquinolin-4-yl)propyl]-1-[4-(3-methoxyphenyl)butyl]piperidine-3-carboxylic acid (3R,4R)-4-[3-(R,S)-Hydroxy-3-(6-methoxyquinolin-4-yl)propyl]-[3-(4-methoxyphenyl)propyl]piperidine-3-carboxylic acid (3R,4R)-4-[3-(R,S)-Hydroxy-3-(6-methoxyquinolin-4-yl)propyl]-1-[4-(4-methoxyphenyl)butyl]piperidine-3-carboxylic acid (3R,4R)-4-[3-(R,S)-Hydroxy-3-(6-methoxyquinolin-4-yl)propyl]-1-[3-(2-trifluoromethylphenyl)propyl]piperidine-3-carboxylic acid (3R,4R)-4-[3-(R,S)-Hydroxy-3-(6-methoxyquinolin-4-yl)propyl]-1-[4-(2-trifluoromethylphenyl)butyl]piperidine-3-carboxylic acid (3R,4R)-4-[3-(R,S)-Hydroxy-3-(6-methoxyquinolin-4-yl)propyl]-1-[3-(3-trifluoromethylphenyl)propyl]piperidine-3-carboxylic acid (3R,4R)-4-[3-(R,S)-Hydroxy-3-(6-methoxyquinolin-4-yl)propyl]-1-[4-(3-trifluoromethylphenyl)butyl]piperidine-3-carboxylic acid (3R,4R)-4-[3-(R,S)-Hydroxy-3-(6-methoxyquinolin-4-yl)propyl]-1-[3-(4-trifluoromethylphenyl)propyl]piperidine-3-carboxylic acid (3R,4R)-4-[3-(R,S)-Hydroxy-3-(6-methoxyquinolin-4-yl)propyl]-1-[4-(4-trifluoromethylphenyl)butyl]piperidine-3-carboxylic acid (3R,4R)-4-[3-(R,S)-Hydroxy-3-(6-methoxyquinolin-4-yl)propyl]-1-[2-phenylthioethyl]piperidine3-carboxylic acid (3R,4R)-4-[3-(R,S)-Hydroxy-3-(6-methoxyquinolin-4-yl)propyl]-1-[3-phenylthiopropyl]piperidine3-carboxylic acid (3R,4R)-4-[3-(R,S)-Hydroxy-3-(6-methoxyquinolin-4-yl)propyl]-1-[3-(2-fluorophenylthio)propyl]piperidine-3-carboxylic acid (3R,4R)-4-[3-(R,S)-Hydroxy-3-(6-methoxyquinolin-4-yl)propyl]-1-[3-(3-fluorophenylthio)propyl]piperidine-3-carboxylic acid (3R,4R)-4-[3-(R,S)-Hydroxy-3-(6-methoxyquinolin-4-yl)propyl]-1-[2-(2-fluorophenylthio)ethyl]piperidine-3-carboxylic acid (3R,4R)-4-[3-(R,S)-Hydroxy-3-(6-methoxyquinolin-4-yl)propyl]-1-[2-(4-fluorophenylthio)ethyl]piperidine-3-carboxylic acid (3R,4R)-4-[3-(R,S)-Hydroxy-3-(6-methoxyquinolin-4-yl)propyl]-1-[3-(4-fluorophenylthio)propyl]piperidine-3-carboxylic acid (3R,4R)-4-[3-(R,S)-Hydroxy-3-(6-methoxyquinolin-4-yl)propyl]-1-[2-(2,3-difluorophenylthio)ethyl]piperidine-3-carboxylic acid (3R,4R)-4-[3-(R,S)-Hydroxy-3-(6-methoxyquinolin-4-yl)propyl]-1-[3-(2,3-difluorophenylthio)propyl]piperidine-3-carboxylic acid (3R,4R)-4-[3-(R,S)-Hydroxy-3-(6-methoxyquinolin-4-yl)propyl]-1-[2-(2,6-difluorophenylthio)ethyl]piperidine-3-carboxylic acid (3R,4R)-4-[3-(R,S)-Hydroxy-3-(6-methoxyquinolin-4-yl)propyl]-1-[3-(2,6-difluorophenylthio)propyl]piperidine-3-carboxylic acid (3R,4R)-4-[3-(R,S)-Hydroxy-3-(6-methoxyquinolin-4-yl)propyl]-1-[2-(2-chlorophenylthio)ethyl]piperidine-3-carboxylic acid (3R,4R)-4-[3-(R,S)-Hydroxy-3-(6-methoxyquinolin-4-yl)propyl]-1-[3-(2-chlorophenylthio)propyl]piperidine-3-carboxylic acid (3R,4R)-4-[3-(R,S)-Hydroxy-3-(6-methoxyquinolin-4-yl)propyl]-1-[2-(3-chlorophenylthio)ethyl]piperidine-3-carboxylic acid (3R,4R)-4-[3-(R,S)-Hydroxy-3-(6-methoxyquinolin-4-yl)propyl]-1-[3-(3-chlorophenylthio)-propyl]piperidine-3-carboxylic acid (3R,4R)-4-[3-(R,S)-Hydroxy-3-(6-methoxyquinolin-4-yl)propyl]-1-[2-(4-chlorophenylthio)ethyl]piperidine-3-carboxylic acid (3R,4R)-4-[3-(R,S)-Hydroxy-3-(6-methoxyquinolin-4-yl)propyl]-1-[3-(4-chlorophenylthio)propyl]piperidine-3-carboxylic acid (3R,4R)-4-[3-(R,S)-Hydroxy-3-(6-methoxyquinolin-4-yl)propyl]-1-[2-(2,3-dichlorophenylthio)ethyl]piperidine-3-carboxylic acid (3R,4R)-4-[3-(R,S)-Hydroxy-3-(6-methoxyquinolin-4-yl)propyl]-1-[3-(2,3-dichlorophenylthio)propyl]piperidine-3-carboxylic acid (3R,4R)-4-[3-(R,S)-Hydroxy-3-(6-methoxyquinolin-4-yl)propyl]-1-[2-(2,6-dichlorophenylthio)ethyl]piperidine-3-carboxylic acid (3R,4R)-4-[3-(R,S)-Hydroxy-3-(6-methoxyquinolin-4-yl)propyl]-1-[3-(2,6-dichlorophenylthio)propyl]piperidine-3-carboxylic acid (3R,4R)-4-[3-(R,S)-Hydroxy-3-(6-methoxyquinolin-4-yl)propyl]-1-[2-(2-methylphenylthio)ethyl]piperidine-3-carboxylic acid (3R,4R)-4-[3-(R,S)-Hydroxy-3-(6-methoxyquinolin-4-yl)propyl]-1-[3-(2-methylphenylthio)propyl]piperidine-3-carboxylic acid (3R,4R)-4-[3-(R,S)-Hydroxy-3-(6-methoxyquinolin-4-yl)propyl]-1-[2-(3-methylphenylthio)ethyl]piperidine-3-carboxylic acid (3R,4R)-4-[3-(R,S)-Hydroxy-3-(6-methoxyquinolin-4-yl)propyl]-1-[3-(3-methylphenylthio)propyl]piperidine-3-carboxylic acid (3R,4R)-4-[3-(R,S)-Hydroxy-3-(6-methoxyquinolin-4-yl)propyl]-1-[2-(4-methylphenylthio)ethyl]piperidine-3-carboxylic acid (3R,4R)-4-[3-(R,S)-Hydroxy-3-(6-methoxyquinolin-4-yl)propyl]-1-[3-(4-methylphenylthio)propyl]piperidine-3-carboxylic acid (3R,4R)-4-[3-(R,S)-Hydroxy-3-(6-methoxyquinolin-4-yl)propyl]-1-[2-(2-trifluoromethylphenylthio)ethyl]piperidine-3-carboxylic acid (3R,4R)-4-[3-(R,S)-Hydroxy-3-(6-methoxyquinolin-4-yl)propyl]-1-[3-(2-trifluoromethylphenylthio)propyl]piperidine-3-carboxylic acid (3R,4R)-4-[3-(R,S)-Hydroxy-3-(6-methoxyquinolin-4-yl)propyl]-1-[2-(3-trifluoromethylphenylthio)ethyl]piperidine-3-carboxylic acid (3R,4R)-4-[3-(R,S)-Hydroxy-3-(6-methoxyquinolin-4-yl)propyl]-1-[3-(3-trifluoromethylphenylthio)propyl]piperidine-3-carboxylic acid (3R,4R)-4-[3-(R,S)-Hydroxy-3-(6-methoxyquinolin-4-yl)propyl]-1-[2-(4-trifluoromethylphenylthio)ethyl]piperidine-3-carboxylic acid (3R,4R)-4-[3-(R,S)-Hydroxy-3-(6-methoxyquinolin-4-yl)propyl]-1-[3-(4-trifluoromethylphenylthio)propyl]piperidine-3-carboxylic acid (3R,4R)-4-[3-(R,S)-Hydroxy-3-(6-methoxyquinolin-4-yl)propyl]-1-[2-(2-methoxyphenylthio)ethyl]piperidine-3-carboxylic acid (3R,4R)-4-[3-(R,S)-Hydroxy-3-(6-methoxyquinolin-4-yl)propyl]-1-[3-(2-methoxyphenylthio)propyl]piperidine-3-carboxylic acid (3R,4R)-4-[3-(R,S)-Hydroxy-3-(6-methoxyquinolin-4-yl)propyl]-1-[2-(3-methoxyphenylthio)ethyl]piperidine-3-carboxylic acid (3R,4R)-4-[3-(R,S)-Hydroxy-3-(6-methoxyquinolin-4-yl)propyl]-1-[3-(3-methoxyphenylthio)propyl]piperidine-3-carboxylic acid (3R,4R)-4-[3-(R,S)-Hydroxy-3-(6-methoxyquinolin-4-yl)propyl]-1-[2-(4-methoxyphenylthio)ethyl]piperidine-3-carboxylic acid (3R,4R)-4-[3-(R,S)-Hydroxy-3-(6-methoxyquinolin-4-yl)propyl]-1-[3-(4-methoxyphenylthio)propyl]piperidine-3-carboxylic acid (3R,4R)-4-[3-(R,S)-Hydroxy-3-(6-methoxyquinolin-4-yl)propyl]-1-[cyclopropylmethyl]piperidine3-carboxylic acid (3R,4R)-4-[3-(R,S)-Hydroxy-3-(6-methoxyquinolin-4-yl)propyl]-1-[2-(cyclopropyl)ethyl]piperidine3-carboxylic acid
(3R,4R)-4-[3-(RS)-Hydroxy-3-(6-methoxyquinolin-4-yl)propyl]-1-[cyclobutylmethyl]piperidine-3-carboxylic acid
(3R,4R)-4-[3-(R,S)-Hydroxy-3-(6-methoxyquinolin-4-yl)propyl]-1-[2-(cyclobutyl)ethyl]piperidine-3-carboxylic acid
(3R,4R)-4-[3-(R,S)-Hydroxy-3-(6-methoxyquinolin-4-yl)propyl]-1-[cyclopentylmethyl]piperidine-3-carboxylic acid
(3R,4R)-4-[3-(R,S)-Hydroxy-3-(6-methoxyquinolin-4-yl)propyl]-1-[2-(cyclopentyl)ethyl]piperidine-3-carboxylic acid
(3R,4R)-4-[3-(R,S)-Hydroxy-3-(6-methoxyquinolin-4-yl)propyl]-1-[cyclohexylmethyl]piperidine-3-carboxylic acid
(3R,4R)-4-[3-(R,S)-Hydroxy-3-(6-methoxyquinolin-4-yl)propyl]-1-[2-(cyclohexyl)ethyl]piperidine-3-carboxylic acid
(3R,4R)-4-[3-(R,S)-Hydroxy-3-(6-methoxyquinolin-4-yl)propyl]-1-[2-(cyclopropylthio)ethyl]piperidine-3-carboxylic acid
(3R,4R)-4-[3-(R,S)-Hydroxy-3-(6-methoxyquinolin-4-yl)propyl]-1-[3-(cyclopropylthio)propyl]piperidine-3-carboxylic acid
(3R,4R)-4-[3-(R,S)-Hydroxy-3-(6-methoxyquinolin-4-yl)propyl]-1-[2-(cyclobutylthio)ethyl]piperidine-3-carboxylic acid
(3R,4R)-4-[3-(R,S)-Hydroxy-3-(6-methoxyquinolin-4-yl)propyl]-1-[3-(cyclobutylthio)propyl]piperidine-3-carboxylic acid
(3R,4R)-4-[3-(R,S)-Hydroxy-3-(6-methoxyquinolin-4-yl)propyl]-1-[3-(cyclopentylthio)propyl]piperidine-3-carboxylic acid
(3R,4R)-4-[3-(R,S)-Hydroxy-3-(6-methoxyquinolin-4-yl)propyl]-1-[3-(cyclohexylthio)propyl]piperidine-3-carboxylic acid
(3R,4R)-4-[3-(R,S)-Hydroxy-3-(6-methoxyquinolin-4-yl)propyl]-1-[2-methylthioethyl]piperidine-3-carboxylic acid
(3R,4R)-4-[3-(R,S)-Hydroxy-3-(6-methoxyquinolin-4-yl)propyl]-1-[3-methylthiopropyl]piperidine-3-carboxylic acid
(3R,4R)-4-[3-(R,S)-Hydroxy-3-(6-methoxyquinolin-4-yl)propyl]-1-[2-ethylthioethyl]piperidine-3-carboxylic acid
(3R,4R)-4-[3-(R,S)-Hydroxy-3-(6-methoxyquinolin-4-yl)propyl]-1-[3-ethylthiopropyl]piperidine-3-carboxylic acid
(3R,4R)-4-[3-(R,S)-Hydroxy-3-(6-methoxyquinolin-4-yl)propyl]-1-[2-(n-propylthio)ethyl]piperidine-3-carboxylic acid
(3R,4R)-4-[3-(R,S)-Hydroxy-3-(6-methoxyquinolin-4-yl)propyl]-1-[3-(n-propylthio)propyl]piperidine-3-carboxylic acid
(3R,4R)-4-[3-(R,S)-Hydroxy-3-(6-methoxyquinolin-4-yl)propyl]-1-[2-(n-butylthio)ethyl]piperidine-3-carboxylic acid
(3R,4R)-4-[3-(R,S)-Hydroxy-3-(6-methoxyquinolin-4-yl)propyl]-1-[3-(n-butylthio)propyl]piperidine-3-carboxylic acid
(3R,4R)-4-[3-(R,S)-Hydroxy-3-(6-methoxyquinolin-4-yl)propyl]-1-[3-(thien-2-yl)propyl]piperidine-3-carboxylic acid
(3R,4R)-4-[3-(R,S)-Hydroxy-3-(6-methoxyquinolin-4-yl)propyl]-1-[4-(thien-2-yl)butyl]piperidine-3-carboxylic acid
(3R,4R)-4-[3-(R,S)-Hydroxy-3-(6-methoxyquinolin-4-yl)propyl]-1-[3-(thien-2-yl)thiopropyl]piperidine-3-carboxylic acid
(3R,4R)-4-[3-(R,S)-Hydroxy-3-(6-methoxyquinolin-4-yl)propyl]-1-[3-(5-chlorothien-2-yl)propyl]piperidine-3-carboxylic acid
(3R,4R)-4-[3-(R,S)-Hydroxy-3-(6-methoxyquinolin-4-yl)propyl]-1-[4-(5-chlorothien-2-yl)butyl]piperidine-3-carboxylic acid
(3R,4R)-4-[3-(R,S)-Hydroxy-3-(6-methoxyquinolin-4-yl)propyl]-1-[3-(5-chlorothien-2-yl)thiopropyl]piperidine-3-carboxylic acid
(3R,4R)-4-[3-(R,S)-Hydroxy-3-(6-methoxyquinolin-4-yl)propyl]-1-[3-(3-chlorothien-2-yl)propyl]piperidine-3-carboxylic acid
(3R,4R)-4-[3-(R,S)-Hydroxy-3-(6-methoxyquinolin-4-yl)propyl]-1-[4-(3-chlorothien-2-yl)butyl]piperidine-3-carboxylic acid
(3R,4R)-4-[3-(R,S)-Hydroxy-3-(6-methoxyquinolin-4-yl)propyl]-1-[2-(3-chlorothien-2-yl)thioethyl]piperidine-3-carboxylic acid
(3R,4R)-4-[3-(R,S)-Hydroxy-3-(6-methoxyquinolin-4-yl)propyl]-1-[3-(3-chlorothien-2-yl)thiopropyl]piperidine-3-carboxylic acid
(3R,4R)-4-[3-(R,S)-Hydroxy-3-(6-methoxyquinolin-4-yl)propyl]-1-[3-(5-methylthien-2-yl)propyl]piperidine-3-carboxylic acid
(3R,4R)-4-[3-(R,S)-Hydroxy-3-(6-methoxyquinolin-4-yl)propyl]-1-[4-(5-methylthien-2-yl)butyl]piperidine-3-carboxylic acid
(3R,4R)-4-[3-(R,S)-Hydroxy-3-(6-methoxyquinolin-4-yl)propyl]-1-[2-(5-methylthien-2-yl)thioethyl]piperidine-3-carboxylic acid
(3R,4R)-4-[3-(R,S)-Hydroxy-3-(6-methoxyquinolin-4-yl)propyl]-1-[3-(5-methylthien-2-yl)thiopropyl]piperidine-3-carboxylic acid
(3R,4R)-4-[3-(R,S)-Hydroxy-3-(6-methoxyquinolin-4-yl)propyl]-1-[3-(3-methylthien-2-yl)propyl]piperidine-3-carboxylic acid
(3R,4R)-4-[3-(R,S)-Hydroxy-3-(6-methoxyquinolin-4-yl)propyl]-1-[4-(3-methylthien-2-yl)butyl]piperidine-3-carboxylic acid
(3R,4R)-4-[3-(R,S)-Hydroxy-3-(6-methoxyquinolin-4-y))propyl]-1-[2-(3-methylthien-2-yl)thioethyl]piperidine-3-carboxylic acid
(3R,4R)-4-[3-(R,S)-Hydroxy-3-(6-methoxyquinolin-4-yl)propyl]-1-[3-(3-methylthien-2-yl)thiopropyl]piperidine-3-carboxylic acid
(3R,4R)-4-[3-(R,S)-Hydroxy-3-(6-methoxyquinolin-4-yl)propyl]-1-[3-(thien-3-yl)propyl]piperidine-3-carboxylic acid
(3R,4R)-4-[3-(R,S)-Hydroxy-3-(6-methoxyquinolin-4-yl)propyl]-1-[4-(thien-3-yl)butyl]piperidine-3-carboxylic acid
(3R,4R)-4-[3-(R,S)-Hydroxy-3-(6-methoxyquinolin-4-yl)propyl]-1-[2-(thien-3-yl)thioethyl]piperidine-3-carboxylic acid
(3R,4R)-4-[3-(R,S)-Hydroxy-3-(6-methoxyquinolin-4-yl)propyl]-1-[3-(thien-3-yl)thiopropyl]piperidine-3-carboxylic acid
(3R,4R)-4-[3-(R,S)-Hydroxy-3-(6-methoxyquinolin-4-yl)propyl]-1-[3-(fur-2-yl)propyl]piperidine-3-carboxylic acid
(3R,4R)-4-[3-(R,S)-Hydroxy-3-(6-methoxyquinolin-4-yl)propyl]-1-[4-(fur-2-yl)butyl]piperidine-3-carboxylic acid
(3R,4R)-4-[3-(R,S)-Hydroxy-3-(6-methoxyquinolin-4-yl)propyl]-1-[2-(fur-2-yl)thioethyl]piperidine-3-carboxylic acid (3R,4R)-4-[3-(R,S)-Hydroxy-3-(6-methoxyquinolin-4-yl) propyl]-1-[3-(fur-2-yl)thiopropyl]piperidine-3-carboxylic acid (3R,4R)-4-[3-(R,S)-Hydroxy-3-(6-methoxyquinolin-4-yl) propyl]-1-[3-(fur-3-yl)propyl]piperidine-3-carboxylic acid (3R,4R)-4-[3-(R,S)-Hydroxy-3-(6-methoxyquinolin-4-yl) propyl]-1-[4-(fur-3-yl)butyl]piperidine-3-carboxylic acid (3R,4R)-4-[3-(R,S)-Hydroxy-3-(6-methoxyquinolin-4-yl) propyl]-1-[2-(fur-3-yl)thioethyl]piperidine-3-carboxylic acid (3R,4R)-4-[3-(R,S)-Hydroxy-3-(6-methoxyquinolin-4-yl) propyl]-1-[3-(fur-3-yl)thiopropyl]piperidine-3-carboxylic acid (3R,4R)-4-[3-(R,S)-Hydroxy-3-(6-methoxyquinolin-4-yl) propyl]-1-[3-(1-methylpyrrol-2-yl)propyl]piperidine-3-carboxylic acid (3R,4R)-4-[3-(R,S)-Hydroxy-3-(6-methoxyquinolin-4-yl) propyl]-1-[4-(1-methylpyrrol-2-yl)butyl]piperidine-3-carboxylic acid (3R,4R)-4-[3-(R,S)-Hydroxy-3-(6-methoxyquinolin-4-yl) propyl]-1-[2-(1-methylpyrrol-2-yl)thioethyl]piperidine-3-carboxylic acid (3R,4R)-4-[3-(R,S)-Hydroxy-3-(6-methoxyquinolin-4-yl) propyl]-1-[3-(1-methylpyrrol-2-yl)thiopropyl]piperidine-3-carboxylic acid (3R,4R)-4-[3-(R,S)-Hydroxy-3-(6-methoxyquinolin-4-yl) propyl]-1-[3-(1-methylpyrrol-2-yl)propyl]piperidine-3-carboxylic acid (3R,4R)-4-[3-(R,S)-Hydroxy-3-(6-methoxyquinolin-4-yl) propyl]-1-[4-(1-methylpyrrol-2-yl)butyl]piperidine-3-carboxylic acid (3R,4R)-4-[3-(R,S)-Hydroxy-3-(6-methoxyquinolin-4-yl) propyl]-1-[2-(1-methylpyrrol-2-yl)thioethyl]piperidine-3-carboxylic acid (3R,4R)-4-[3-(R,S)-Hydroxy-3-(6-methoxyquinolin-4-yl) propyl]-1-[3-(1-methylpyrrol-2-yl)thiopropyl]piperidine-3-carboxylic acid (3R,4R)-4-[3-(R,S)-Hydroxy-3-(6-methoxyquinolin-4-yl) propyl]-1-[3-(1,3-thiazol-2-yl)propyl]piperidine-3-carboxylic acid (3R,4R)-4-[3-(R,S)-Hydroxy-3-(6-methoxyquinolin-4-yl) propyl]-1-[4-(1,3-thiazol-2-yl)butyl]piperidine-3-carboxylic acid (3R,4R)-4-[3-(R,S)-Hydroxy-3-(6-methoxyquinolin-4-yl) propyl]-1-[3-(1,3-thiazol-2-yl)thiopropyl]piperidine-3-carboxylic acid (3R,4R)-4-[3-(R,S)-Hydroxy-3-(6-methoxyquinolin-4-yl) propyl]-1-[3-(1-methylimidazol-2-yl)propyl]piperidine-3-carboxylic acid (3R,4R)-4-[3-(R,S)-Hydroxy-3-(6-methoxyquinolin-4-yl) propyl]-1-[4-(1-methylimidazol-2-yl)butyl]piperidine-3-carboxylic acid (3R,4R)-4-[3-(R,S)-Hydroxy-3-(6-methoxyquinolin-4-yl) propyl]-1-[2-(1-methylimidazol-2-yl)thioethyl] piperidine-3-carboxylic acid (3R,4R)-4-[3-(R,S)-Hydroxy-3-(6-methoxyquinolin-4-yl) propyl]-1-(3-[1-methylimidazol-2-yl)thiopropyl] piperidine-3-carboxylic acid (3R,4R)-4-[3-(R,S)-Hydroxy-3-(6-methoxyquinolin-4-yl) propyl]-1-[3-(3-methylimidazol-4-yl)propyl]piperidine-3-carboxylic acid (3R,4R)-4-[3-(R,S)-Hydroxy-3-(6-methoxyquinolin-4-yl) propyl]-1-[4-(3-methylimidazol-4-yl)butyl]piperidine-3-carboxylic acid (3R,4R)-4-[3-(R,S)-Hydroxy-3-(6-methoxyquinolin-4-yl) propyl]-1-[2-(3-methylimidazol-4-yl)thioethyl] piperidine-3-carboxylic acid (3R,4R)-4-[3-(R,S)-Hydroxy-3-(6-methoxyquinolin-4-yl) propyl]-1-[3-(3-methylimidazol-4-yl)thiopropyl] piperidine-3-carboxylic acid (3R,4R)-4-[3-(R,S)-Hydroxy-3-(6-methoxyquinolin-4-yl) propyl]-1-[3-(3-methylimidazol-4-yl)propyl]piperidine-3-carboxylic acid (3R,4R)-4-[3-(R,S)-Hydroxy-3-(6-methoxyquinolin-4-yl) propyl]-1-[4-(3-methylimidazol-4-yl)butyl]piperidine-3-carboxylic acid (3R,4R)-4-[3-(R,S)-Hydroxy-3-(6-methoxyquinolin-4-yl) propyl]-1-[2-(3-methylimidazol-4-yl)thioethyl] piperidine-3-carboxylic acid (3R,4R)-4-[3-(R,S)-Hydroxy-3-(6-methoxyquinolin-4-yl) propyl-1-[3-(3-methylimidazol-4-yl)thiopropyl] piperidine-3-carboxylic acid (3R,4R)-4-[3-(R,S)-Hydroxy-3-(6-methoxyquinolin-4-yl) propyl]-[3-(oxazol-2-yl)propyl]piperidine-3-carboxylic acid (3R,4R)-4-[3-(R,S)-Hydroxy-3-(6-methoxyquinolin-4-yl) propyl]-1-[4-(oxazol-2-yl)butyl]piperidine-3-carboxylic acid (3R,4R)-4-(3-(R,S)-Hydroxy-3-(6-methoxyquinolin-4-yl) propyl]-1-[2-(oxazol-2-yl)thioethyl]piperidine-3-carboxylic acid (3R,4R)-4-[3-(R,S)-Hydroxy-3-(6-methoxyquinolin-4-yl) propyl]-1-[3-(oxazol-2-yl)thiopropyl]piperidine-3-carboxylic acid (3R,4R)-4-[3-(R,S)-Hydroxy-3-(6-methoxyquinolin-4-yl) propyl]-1-[3-(pyridin-2-yl)propyl]piperidine-3-carboxylic acid (3R,4R)-4-[3-(R,S)-Hydroxy-3-(6-methoxyquinolin-4-yl) propyl]-1-[4-(pyridin-2-yl)butyl]piperidine-3-carboxylic acid (3R,4R)-4-[3-(R,S)-Hydroxy-3-(6-methoxyquinolin-4-yl) propyl]-1-[3-(pyridin-2-yl)thiopropyl]piperidine-3-carboxylic acid (3R,4R)-4-[3-(R,S)-Hydroxy-3-(6-methoxyquinolin-4-yl) propyl]-1-[3-(pyridin-3-yl)propyl]piperidine-3-carboxylic acid (3R,4R)-4-[3-(R,S)-Hydroxy-3-(6-methoxyquinolin-4-yl) propyl]-1-[4-(pyridin-3-yl)butyl]piperidine-3-carboxylic acid (3R,4R)-4-[3-(R,S)-Hydroxy-3-(6-methoxyquinolin-4-yl) propyl]-1-[2-(pyridin-3-yl)thioethyl]piperidine-3-carboxylic acid (3R,4R)-4-[3-(R,S)-Hydroxyquinolin-4-y) propyl]-1-[3-(pyridin-3-yl)thiopropyl]piperidine-3-carboxylic acid (3R,4R)-4-[3-(R,S)-Hydroxy-3-(6-methoxyquinolin-4-yl) propyl-1-[3-(pyridin-4-yl)propyl]piperidine-3-carboxylic acid (3R,4R)-4-[3-(R,S)-Hydroxy-3-(6-methoxyquinolin-4-yl) propyl]-1-[4-(pyridin-4-yl)butyl]piperidine-3-carboxylic acid (3R,4R)-4-[3-(R,S)-Hydroxy-3-(6-methoxyquinolin-4-yl) propyl]-1-[5-(pyridin-4-yl)pentyl]piperidine-3-carboxylic acid (3R,4R)-4-[3-(R,S)-Hydroxy-3-(6-methoxyquinolin-4-yl) propyl]-1-[2-(pyridin-2-yl)thioethyl]piperidine-3-carboxylic acid (3R,4R)-4-[3-(R,S)-Hydroxy-3-(6-methoxyquinolin-4-yl) propyl]-1-[2-(pyridin-4-yl)thioethyl]piperidine-3-carboxylic acid (3R,4R)-4-[3-(R,S)-Hydroxy-3-(6-methoxyquinolin-4-yl) propyl]-1-[3-(pyridin-4-yl)thiopropyl]piperidine-3-carboxylic acid (3R,4R)-4-[3-(R,S)-Hydroxy-3-(6-methoxyquinolin-4-yl) propyl]-1-[3-(pyrimidin-2-yl)propyl]piperidine-3-carboxylic acid (3R,4R)-4-[3-(R,S)-Hydroxy-3-(6-methoxyquinolin-4-yl)propyl]-1-[4-(pyrimidin-2-yl)butyl]piperidine-3-carboxylic acid
(3R,4R)-4-[3-(R,S)-Hydroxy-3-(6-methoxyquinolin-4-yl)propyl]-1-[2-(pyrimidin-2-yl)thioethyl]piperidine-3-carboxylic acid
(3R,4R)-4-[3-(R,S)-Hydroxy-3-(6-methoxyquinolin-4-yl)propyl]-1-[3-(pyrimidin-2-yl)thiopropyl]piperidine-3-carboxylic acid
(3R,4R)-4-[3-(R,S)-Hydroxy-3-(6-methoxyquinolin-4-yl)propyl]-1-[3-(pyrimidin-4-yl)propyl]piperidine-3-carboxylic acid
(3R,4R)-4-[3-(R,S)-Hydroxy-3-(6-methoxyquinolin-4-yl)propyl]-1-[4-(pyrimidin-4-yl)butyl]piperidine-3-carboxylic acid
(3R,4R)-4-[3-(R,S)-Hydroxy-3-(6-methoxyquinolin-4-yl)propyl]-1-[2-(pyrimidin-4-yl)thioethyl]piperidine-3-carboxylic acid
(3R,4R)-4-[3-(R,S)-Hydroxy-3-(6-methoxyquinolin-4-yl)propyl]-1-[3-(pyrimidin-4-yl)thiopropyl]piperidine-3-carboxylic acid
(3R,4R)-4-[3-(R,S)-Hydroxy-3-(6-methoxyquinolin-4-yl)propyl]-1-[3-(pyrimidin-5-yl)propyl]piperidine-3-carboxylic acid
(3R,4R)-4-[3-(R,S)-Hydroxy-3-(6-methoxyquinolin-4-yl)propyl]-1-[4-(pyrimidin-5-yl)butyl]piperidine-3-carboxylic acid
(3R,4R)-4-[3-(R,S)-Hydroxy-3-(6-methoxyquinolin-4-yl)propyl]-1-[2-(pyrimidin-5-yl)thioethyl]piperidine-3-carboxylic acid
(3R,4R)-4-[3-(R,S)-Hydroxy-3-(6-methoxyquinolin-4-yl)propyl]-1-[3-(pyrimidin-5-yl)thiopropyl]piperidine-3-carboxylic acid
(3R,4R)-4-[3-(R,S)-Hydroxy-3-(6-methoxyquinolin-4-yl)propyl]-1-[3-(pyrazin-2-yl)propyl]piperidine-3-carboxylic acid
(3R,4R)-4-[3-(R,S)-Hydroxy-3-(6-methoxyquinolin-4-yl)propyl]-1-[4-(pyrazin-2-yl)butyl]piperidine-3-carboxylic acid
(3R,4R)-4-[3-(R,S-Hydroxy-3-(6-methoxyquinolin-4-yl(propyl)-1-[2-(pyrazin-2-yl)thioethyl]piperidine-3-carboxylic acid
(3R,4R)-4-[3-(R,S)-Hydroxy-3-(6-methoxyquinolin-4-yl)propyl]-1-[3-(pyrazin-2-yl)thiopropyl]piperidine-3-carboxylic acid
(3R,4R)-4-[3-(R,S)-Hydroxy-3-(6-methoxyquinolin-4-yl)propyl]-1-[3-(pyridazin-3-yl)propyl]piperidine-3-carboxylic acid
(3R,4R)-4-[3-(R,S)-Hydroxy-3-(6-methoxyquinolin-4-yl)propyl]-1-[4-(pyridazin-3-yl)butyl]piperidine-3-carboxylic acid
(3R,4R)-4-[3-(R,S)-Hydroxy-3-(6-methoxyquinolin-4-yl)propyl]-1-[2-(pyridazin-3-yl)thioethyl]piperidine-3-carboxylic acid
(3R,4R)-4-[3-(R,S)-Hydroxy-3-(6-methoxyquinolin-4-yl)propyl]-1-[3-(pyridazin-3-yl)thiopropyl]piperidine-3-carboxylic acid
(3R,4R)-4-[3-(R,S)-Hydroxy-3-(6-methoxyquinolin-4-yl)propyl]-1-[3-(pyridazin-4-yl)propyl]piperidine-3-carboxylic acid
(3R,4R)-4-[3-(R,S)-Hydroxy-3-(6-methoxyquinolin-4-yl)propyl]-1-[4-(pyridazin-4-yl)butyl]piperidine-3-carboxylic acid
(3R,4R)-4-[3-(R,S)-Hydroxy-3-(6-methoxyquinolin-4-yl)propyl]-1-[2-(pyridazin-4-yl)thioethyl]piperidine-3-carboxylic acid
(3R,4R)-4-[3-(R,S)-Hydroxy-3-(6-methoxyquinolin-4-yl)propyl]-1-[3-(pyridazin-4-yl)thiopropyl]piperidine-3-carboxylic acid
(3R,4R)-4-[3-(R,S)-Hydroxy-3-(6-methoxyquinolin-4-yl)propyl]-1-[3-phenylprop-2-ynyl]piperidine-3-carboxylic acid
(3R,4R)-4-[3-(R,S)-Hydroxy-3-(6-methoxyquinolin-4-yl)propyl]-1-[3-(2-fluorophenyl)prop-2-ynyl]piperidine-3-carboxylic acid
(3R,4R)-4-[3-(R,S)-Hydroxy-3-(6-methoxyquinolin-4-yl)propyl]-1-[3-(4-fluorophenyl)prop-2-ynyl]piperidine-3-carboxylic acid
(3R,4R)-4-[3-(R,S)-Hydroxy-3-(6-methoxyquinolin-4-yl)propyl]-1-[3-(2-chlorophenyl)prop-2-ynyl]piperidine-3-carboxylic acid
(3R,4R)-4-[3-(R,S)-Hydroxy-3-(6-methoxyquinolin-4-yl)propyl]-1-[3-(3-chlorophenyl)prop-2-ynyl]piperidine-3-carboxylic acid
(3R,4R)-4-[3-(R,S)-Hydroxy-3-(6-methoxyquinolin-4-yl)propyl]-1-[3-(4-chlorophenyl)prop-2-ynyl]piperidine-3-carboxylic acid
(3R,4R)-4-[3-(R,S)-Hydroxy-3-(6-methoxyquinolin-4-yl)propyl]-1-[3-(2-methylphenyl)prop-2-ynyl]piperidine-3-carboxylic acid
(3R,4R)-4-[3-(R,S)-Hydroxy-3-(6-methoxyquinolin-4-yl)propyl]-1-[3-(3-methylphenyl)prop-2-ynyl]piperidine-3-carboxylic acid
(3R,4R)-4-[3-(R,S)-Hydroxy-3-(6-methoxyquinolin-4-yl)propyl]-1-[3-(4-methylphenyl)prop-2-ynyl]piperidine-3-carboxylic acid
(3R,4R)-4-[3-(R,S)-Hydroxy-3-(6-methoxyquinolin-4-yl)propyl-1-[3-(2-(trifluoromethyl)phenyl)prop-2-ynyl]-piperidine-3-carboxylic acid
(3R,4R)-4-[3-(R,S)-Hydroxy-3-(6-methoxyquinolin-4-yl)propyl]-1-[3-(3-(trifluoromethyl)phenyl)prop-2-ynyl]-piperidine-3-carboxylic acid
(3R,4R)-4-[3-(R,S)-Hydroxy-3-(6-methoxyquinolin-4-yl)propyl]-1-[3-(4-(trifluoromethyl)phenyl)prop-2-ynyl]-piperidine-3-carboxylic acid
(3R,4R)-4-[3-(R,S)-Hydroxy-3-(6-methoxyquinolin-4-yl)propyl]-1-[3-(2-methoxyphenyl)prop-2-ynyl]piperidine-3-carboxylic acid
(3R,4R)-4-[3-(R,S)-Hydroxy-3-(6-methoxyquinolin-4-yl)propyl]-1-[3-(3-methoxyphenyl)prop-2-ynyl]piperidine-3-carboxylic acid
(3R,4R)-4-[3-(R,S)-Hydroxy-3-(6-methoxyquinolin-4-yl)propyl]-1-[3-(4-methoxyphenyl)prop-2-ynyl]piperidine-3-carboxylic acid
(3R,4R)-4-[3-(R,S)-Hydroxy-3-(6-methoxyquinolin-4-yl)propyl]-1-(3-(3,4-difluorophenyl)prop-2-ynyl]piperidine-3-carboxylic acid
(3R,4R)-4-[3-(R,S)-Hydroxy-3-(6-methoxyquinolin-4-yl)propyl]-1-[3-(2,4-fluorophenyl)prop-2-ynyl]piperidine-3-carboxylic acid
(3R,4R)-4-[3-(R,S)-Hydroxy-3-(6-methoxyquinolin-4-yl)propyl]-1-[3-(3,4-dichlorophenyl)prop-2-ynyl]piperidine-3-carboxylic acid
(3R,4R)-4-[3-(R,S)-Hydroxy-3-(6-methoxyquinolin-4-yl)propyl]-1-[3-(2,3-dichlorophenyl)prop-2-ynyl]piperidine-3-carboxylic acid
(3R,4R)-4-[3-(R,S)-Hydroxy-3-(6-methoxyquinolin-4-yl)propyl]-1-[3-(2,4-dichlorophenyl)prop-2-ynyl]-piperidine-3-carboxylic acid
(3R,4R)-4-(3-(R,S)-Hydroxy-3-(6-methoxyquinolin-4-yl)propyl]-1-[3-(2,4,6-trichlorophenyl)prop-2-ynyl]-piperidine-3-carboxylic acid
(3R,4R)-4-[3-(R,S)-Hydroxy-3-(6-methoxyquinolin-4-yl)propyl]-1-[3-(3,5-dichlorophenyl)prop-2-ynyl]piperidine-3-carboxylic acid
(3R,4R)-4-[3-(R,S)-Hydroxy-3-(6-methoxyquinolin-4-yl)propyl]-1-[3-(4-chloro-3-fluorophenyl)prop-2-ynyl]piperidine-3-carboxylic acid (3R,4R)-4-[3-(R,S)-Hydroxy-3-(6-methoxyquinolin-4-yl)
  propyl]-1-[3-(3-chloro-4-fluorophenyl)prop-2-ynyl]
  piperidine-3-carboxylic acid
(3R,4R)-4-[3-(R,S)-Hydroxy-3-(6-methoxyquinolin-4-yl)
  propyl]-1-[3-(2-chloro-4-fluorophenyl)prop-2-ynyl]-
  piperidine-3-carboxylic acid
(3R,4R)-4-[3-(R,S)-Hydroxy-3-(6-methoxyquinolin-4-yl)
  propyl]-1-[3-(3-chloro-5-fluorophenyl)prop-2-ynyl]-
  piperidine-3-carboxylic acid
(3R,4R)-4-[3-(R,S)-Hydroxy-3-(6-methoxyquinolin-4-yl)
  propyl]-1 -[3-(4-chloro-2-fluorophenyl)prop-2-ynyl]-
  piperidine-3-carboxylic acid
(3R,4R)-4-[3-(R,S)-Hydroxy-3-(6-methoxyquinolin-4-yl)
  propyl]-1-[3-(3-fluoro-4-methylphenyl)prop-2-ynyl]
  piperidine-3-carboxylic acid
(3R,4R)-4-[3-(R,S)-Hydroxy-3-(6-methoxyquinolin-4-yl)
  propyl]-1-[3-(4-chloro-3-trifluoromethyl)phenyl)prop-2-
  ynyl]piperidine-3-carboxylic acid
(3R,4R)-4-[3-(R,S)-Hydroxy-3-(6-methoxyquinolin-4-yl)
  propyl]-1-[3-(2-chloro-4-trifluoromethyl)phenyl)prop-2-
  ynyl]piperidine-3-carboxylic acid
(3R,4R)-4-[3-(R,S)-Hydroxy-3-(6-methoxyquinolin-4-yl)
  propyl]-1-[3-(2-chloro-5-(trifluoromethyl)phenyl)prop-2-
  ynyl]piperidine-3-carboxylic acid
(3R,4R)-4-[3-(R,S)-Hydroxy-3-(6-methoxyquinolin-4-yl)
  propyl]-1-[3-(5-chloro-2-methoxyphenyl)prop-2-ynyl]
  piperidine-3-carboxylic acid
(3R,4R)-4-[3-(R,S)-Hydroxy-3-(6-methoxyquinolin-4-yl)
  propyl]-1-[3-(3,5-bis(trifluoromethyl)phenyl)prop-2-
  ynyl]piperidine-3-carboxylic acid
(3R,4R)-4-[3-(R,S)-Hydroxy-3-(6-methoxyquinolin-4-yl)
  propyl]-1-[3-(3,5-dimethylphenyl)prop-2-ynyl]
  piperidine-3-carboxylic acid
(3R,4R)-4-[3-(R,S)-Hydroxy-3-(6-methoxyquinolin-4-yl)
  propyl]-1-[3-(2,4-dichloro-6-methylphenyl)prop2-ynyl]
  piperidine-3-carboxylic acid
(3R,4R)-4-[3-(R,S)-Hydroxy-3-(6-methoxyquinolin-4-yl)
  propyl]-1-[3-(5-chlorothien-2-yl)prop-2-ynyl]piperidine-
  3-carboxylic acid
(3R,4R)-4-[3-(R,S)-Hydroxy-3-(6-methoxyquinolin-4-yl)
  propyl]-1-[3-(3-chlorothien-2-yl)prop-2-ynyl]-
  piperidine-3-carboxylic acid
(3R,4R)-4-[3-(R,S)-Hydroxy-3-(6-methoxyquinolin-4-yl)
  propyl]-1-[3-(5-methylthien-2-yl)prop-2-ynyl]piperidine-
  3-carboxylic acid
(3R,4R)-4-[3-(R,S)-Hydroxy-3-(6-methoxyquinolin-4-yl)
  propyl]-1-[3-(3-methylthien-2-yl)prop-2-ynyl]piperidine-
  3-carboxylic acid
(3R,4R)-4-[3-(R,S)-Hydroxy-3-(6-methoxyquinolin-4-yl)
  propyl]-1-[3-(1-methylpyrrol-2-yl)prop-2-ynyl]
  piperidine-3-carboxylic acid
(3R,4R)-4-[3-(R,S)-Hydroxy-3-(6-methoxyquinolin-4-yl)
  propyl]-1-[3-(1-methylpyrrol-3-yl)prop-2-ynyl]
  piperidine-3-carboxylic acid
(3R,4R)-4-[3-(R,S)-Hydroxy-3-(6-methoxyquinolin-4-yl)
  propyl]-1-[3-(1,3-thiazol-2-yl)prop-2-ynyl]piperidine-3-
  carboxylic acid
(3R,4R)-4-[3-(R,S)-Hydroxy-3-(6-methoxyquinolin-4-yl)
  propyl]-1-[3-(1,3-thiazol-4-yl)prop-2-ynyl]piperidine-3-
  carboxylic acid
(3R,4R)-4-[3-(R,S)-Hydroxy-3-(6-methoxyquinolin-4-yl)
  propyl]-1-[3-(1,3-thiazol-5-yl)prop-2-ynyl]piperidine-3-
  carboxylic acid
(3R,4R)-4-[3-(R,S)-Hydroxy-3-(6-methoxyquinolin-4-yl)
  propyl]-1-[3-(1-methylimidazol-2-yl)prop-2-ynyl]
  piperidine-3-carboxylic acid
(3R,4R)-4-[3-(R,S)-Hydroxy-3-(6-methoxyquinolin-4-yl)
  propyl]-1-[3-(3-methylimidazol-4-yl)prop-2-ynyl]
  piperidine-3-carboxylic acid
(3R,4R)-4-[3-(R,S)-Hydroxy-3-(6-methoxyquinolin-4-yl)
  propyl]-1-[3-(3-methylpyrazol-4-yl)prop-2-ynyl]
  piperidine-3-carboxylic acid
(3R,4R)-4-[3-(R,S)-Hydroxy-3-(6-methoxyquinolin-4-yl)
  propyl]-1-[3-(oxazol-2-yl)prop-2-ynyl]piperidine-3-
  carboxylic acid
(3R,4R)-4-[3-(R,S)-Hydroxy-3-(6-methoxyquinolin-4-yl)
  propyl]-1-[3-(oxazol-4-yl)prop-2-ynyl]piperidine-3-
  carboxylic acid
(3R,4R)-4-[3-(R,S)-Hydroxy-3-(6-methoxyquinolin-4-yl)
  propyl]-1-[3-(oxazol-5-yl)prop-2-ynyl]piperidine-3-
  carboxylic acid
(3R,4R)-4-[3-(R,S)-Hydroxy-3-(6-methoxyquinolin-4-yl)
  propyl]-1-[3-(pyridin-2-yl)prop-2-ynyl]piperidine-3-
  carboxylic acid
(3R,4R)-4-[3-(R,S)-Hydroxy-3-(6-methoxyquinolin-4-yl)
  propyl]-1-[3-(pyridin-3-yl)prop-2-ynyl]piperidine-3-
  carboxylic acid
(3R,4R)-4-[3-(R,S)-Hydroxy-3-(6-methoxyquinolin-4-yl)
  propyl]-1-[3-(pyridin-4-yl)prop-2-ynyl]piperidine-3-
  carboxylic acid
(3R,4R)-4-[3-(R,S)-Hydroxy-3-(6-methoxyquinolin-4-yl)
  propyl]-1-[3-(pyrimidin-2-yl)prop-2-2-ynyl]piperidine-3-
  carboxylic acid
(3R,4R)-4-[3-(R,S)-Hydroxy-3-(6-methoxyquinolin-4-yl)
  propyl]-1-[3-(pyrimidin-4-yl)prop-2-ynyl]piperidine-3-
  carboxylic acid
(3R,4R)-4-[3-(R,S)-Hydroxy-3-(6-methoxyquinolin-4-yl)
  propyl]-1-[3-(pyrimidin-5-yl)prop-2-ynyl]piperidine-3-
  carboxylic acid
(3R,4R)-4-[3-(R,S)-Hydroxy-3-(6-methoxyquinolin-4-yl)
  propyl]-1-[3-(pyrazin-2-yl)prop-2-ynyl]piperidine-3-
  carboxylic acid
(3R,4R)-4-[3-(R,S)-Hydroxy-3-(6-methoxyquinolin-4-yl)
  propyl]-1-[3-(pyridazin-3-yl)prop-2-ynyl]piperidine-3-
  carboxylic acid
(3R,4R)-4-[3-(R,S)-Hydroxy-3-(6-methoxyquinolin-4-yl)
  propyl]-1-[3-(pyridazin-4-yl)prop-2-ynyl]piperidine-3-
  carboxylic acid
(3R,4R)-4-[3-(R,S)-Hydroxy-3-(6-methoxyquinolin-4-yl)
  propyl]-1-[3-phenylpropen-2-yl]piperidine-3-carboxylic
  acid
(3R,4R)-4-[3-(R,S)-Hydroxy-3-(6-methoxyquinolin-4-yl)
  propyl]-1-[4-phenylbuten-3-yl]piperidine-3-carboxylic
  acid
(3R,4R)-4-[3-(R,S)-Fluoro-3-(6-methoxyquinolin-4-yl)
  propyl]-1-[4-phenylbutyl]piperidine-3-carboxylic acid
(3R,4R)-4-[3-(R,S)-Fluoro-3-(6-methoxyquinolin-4-yl)
  propyl]-1-[3-(2-fluorophenyl)propyl]piperidine-3-
  carboxylic acid
(3R,4R)-4-[3-(R,S)-Fluoro-3-(6-methoxyquinolin-4-yl)
  propyl]-1-[4-(2-fluorophenyl)butyl]piperidine-3-
  carboxylic acid
(3R,4R)-4-[3-(R,S)-Fluoro-3-(6-methoxyquinolin-4-yl)
  propyl]-1-[3-(3-fluorophenyl)propyl]piperidine-3-
  carboxylic acid
(3R,4R)-4-[3-(R,S)-Fluoro-3-(6-methoxyquinolin-4-yl)
  propyl]-[4-(3-fluorophenyl)butyl]piperidine-3-carboxylic
  acid
(3R,4R)-4-[3-(R,S)-Fluoro-3-(6-methoxyquinolin-4-yl)
  propyl]-1-[3-(4-fluorophenyl)propyl]piperidine-3-
  carboxylic acid
(3R,4R)-4-[3-(R,S)-Fluoro-3-(6-methoxyquinolin-4-
  ylpropyl)-1-[4-(4-fluorophenyl)butyl]piperidine-3-
  carboxylic acid
(3R,4R)-4-[3-(R,S)-Fluoro-3-(6-methoxyquinolin-4-yl)
  propyl]-1-[3-(2,3-difluorophenyl)propyl]piperidine-3-
  carboxylic acid (3R,4R)-4-[3-(R,S)-Fluoro-3-(6-methoxyquinolin-4-yl)
propyl]-1-[4-(2,3-difluorophenyl)butyl]piperidine-3-
carboxylic acid
(3R,4R)-4-[3-(R,S)-Fluoro-3-(6-methoxyquinolin-4-yl)
propyl]-1-[3-(2,6-difluorophenyl)propyl]piperidine-3-
carboxylic acid
(3R,4R)-4-[3-(R,S)-Fluoro-3-(6-methoxyquinolin-4-yl)
propyl]-1-[4-(2,6-difluorophenyl)butyl]piperidine-3-
carboxylic acid
(3R,4R)-4-[3-(R,S)-Fluoro-3-(6-methoxyquinolin-4-yl)
propyl]-1-[3-(2-chlorophenyl)propyl]piperidine-3-
carboxylic acid
(3R,4R)-4-[3-(R,S)-Fluoro-3-(6-methoxyquinolin-4-yl)
propyl]-1-[4-(2-chlorophenyl)butyl]piperidine-3-
carboxylic acid
(3R,4R)-4-[3-(R,S)-Fluoro-3-(6-methoxyquinolin-4-yl)
propyl]-1-[3-(3-chlorophenyl)propyl]piperidine-3-
carboxylic acid
(3R,4R)-4-[3-(R,S)-Fluoro-3-(6-methoxyquinolin-4-yl)
propyl]-1-[4-(3-chlorophenyl)butyl]piperidine-3-
carboxylic acid
(3R,4R)-4-[3-(R,S)-Fluoro-3-(6-methoxyquinolin-4-yl)
propyl]-1-[3-(4-chlorophenyl)propyl]piperidine-3-
carboxylic acid
(3R,4R)-4-[3-(R,S)-Fluoro-3-(6-methoxyquinolin-4yl)
propyl]-1-[4-(4-chlorophenyl)butyl]piperidine-3-
carboxylic acid
(3R,4R)-4-[3-(R,S)-Fluoro-3-(6-methoxyquinolin-4-yl)
propyl]-1-[3-(2,3-dichlorophenyl)propyl]piperidine-3-
carboxylic acid
(3R,4R)-4-[3-(R,S)-Fluoro-3-(6-methoxyquinolin-4-yl)
propyl]-1-[4-(2,3-dichlorophenyl)butyl]piperidine-3-
carboxylic acid
(3R,4R)-4-[3-(R,S)-Fluoro-3-(6-methoxyquinolin-4-yl)
propyl]-1-[3-(2,6-dichlorophenyl)propyl]piperidine-3-
carboxylic acid
(3R,4R)-4-[3-(R,S)-Fluoro-3-(6-methoxyquinolin-4-yl)
propyl]-1-[4-(2,6-dichlorophenyl)butyl]piperidine-3-
carboxylic acid
(3R,4R)-4-[3-(R,S)-Fluoro-3-(6-methoxyquinolin-4-yl)
propyl]-1-[3-(2-methylphenyl)propyl]piperidine-3-
carboxylic acid
(3R,4R)-4-[3-(R,S)-Fluoro-3-(6-methoxyquinolin-4-yl)
propyl]-1-[4-(2-methylphenyl)butyl]piperidine-3-
carboxylic acid
(3R,4R)-4-[3-(R,S)-Fluoro-3-(6-methoxyquinolin-4-yl)
propyl]-1-[5-(2-methylphenyl)pentyl]piperidine-3-
carboxylic acid
(3R,4R)-4-[3-(R,S)-Fluoro-3-(6-methoxyquinolin-4-yl)
propyl]-1-[3-(3-methylphenyl)propyl]piperidine-3-
carboxylic acid
(3R,4R)-4-[3-(R,S)-Fluoro-3-(6-methoxyquinolin-4-yl)
propyl]-1-[4-(3-methylphenyl)butyl]piperidine-3-
carboxylic acid
(3R,4R)-4-[3-(R,S)-Fluoro-3-(6-methoxyquinolin-4-yl)
propyl]-1-[3-(4-methylphenyl)propyl]piperidine-3-
carboxylic acid
(3R,4R)-4-[3-(R,S)-Fluoro-3-(6-methoxyquinolin-4-yl)
propyl]-1-[4-(4-methylphenyl)butyl]piperidine-3-
carboxylic acid
(3R,4R)-4-[3-(R,S)-Fluoro-3-(6-methoxyquinolin-4-yl)
propyl)-1-[3-(2-methoxyphenyl)propyl]piperidine-3-
carboxylic acid
(3R,4R)-4-[3-(R,S)-Fluoro-3-(6-methoxyquinolin-4-yl)
propyl]-1-[4-(2-methoxyphenyl)butyl]piperidine-3-
carboxylic acid
(3R,4R)-4-[3-(R,S)-Fluoro-3-(6-methoxyquinolin-4-yl)
propyl]-1-[3-(3-methoxyphenyl)propyl]piperidine-3-
carboxylic acid
(3R,4R)-4-[3-(R,S)-Fluoro-3-(6-methoxyquinolin-4-yl)
propyl]-1-[4-(3-methoxyphenyl)butyl]piperidine-3-
carboxylic acid
(3R,4R)-4-[3-(R,S)-Fluoro-3-(6-methoxyquinolin-4-yl)
propyl]-1-[3-(4-methoxyphenyl)propyl]piperidine-3-
carboxylic acid
(3R,4R)-4-[3-(R,S)-Fluoro-3-(6-methoxyquinolin-4-yl)
propyl]-1-[4-(4-methoxyphenyl)butyl]piperidine-3-
carboxylic acid
(3R,4R)-4-[3-(R,S)-Fluoro-3-(6-methoxyquinolin-4-yl)
propyl]-1-[3-(2-trifluoromethylphenyl)propyl]piperidine-
3-carboxylic acid
(3R,4R)-4-[3-(R,S)-Fluoro-3-(6-methoxyquinolin-4-yl)
propyl]-1-[4-(2-trifluoromethylphenyl)butyl]piperidine-
3-carboxylic acid
(3R,4R)-4-[3-(R,S)-Fluoro-3-(6-methoxyquinolin-4-yl)
propyl]-1-[3-(3-trifluoromethylphenyl)propyl]piperidine-
3-carboxylic acid
(3R,4R)-4-[3-(R,S)-Fluoro-3-(6-methoxyquinolin-4-yl)
propyl]-1-[4-(3-trifluoromethylphenyl)butyl]piperidine-
3-carboxylic acid
(3R,4R)-4-[3-(R,S)-Fluoro-3-(6-methoxyquinolin-4-yl)
propyl]-1-[3-(4-trifluoromethylphenyl)propyl]piperidine-
3-carboxylic acid
(3R,4R)-4-[3-(R,S)-Fluoro-3-(6-methoxyquinolin-4-yl)
propyl]-1-[4-(4-trifluoromethylphenyl)butyl]piperidine-
3-carboxylic acid
(3R,4R)-4-[3-(R,S)-Fluoro-3-(6-methoxyquinolin-4-yl)
propyl]-1-[2-phenylthioethyl]piperidine-3-carboxylic
acid
(3R,4R)-4-[3-(R,S)-Fluoro-3-(6-methoxyquinolin-4-yl)
propyl]-1-[3-phenylthiopropyl]piperidine-3-carboxylic
acid
(3R,4R)-4-[3-(R,S)-Fluoro-3-(6-methoxyquinolin-4-yl)
propyl]-1-[3-(2-fluorophenylthio)propyl]piperidine-3-
carboxylic acid
(3R,4R)-4-[3-(R,S)-Fluoro-3-(6-methoxyquinolin-4-yl)
propyl]-1-[3-(3-fluorophenylthio)propyl]piperidine-3-
carboxylic acid
(3R,4R)-4-[3-(R,S)-Fluoro-3-(6-methoxyquinolin-4-yl)
propyl]-1-[2-(2-fluorophenylthio)ethyl]piperidine-3-
carboxylic acid
(3R,4R)-4-[3-(R,S)-Fluoro-3-(6-methoxyquinolin-4-yl)
propyl]-1-[2-(4-fluorophenylthio)ethyl]piperidine-3-
carboxylic acid
(3R,4R)-4-[3-(R,S)-Fluoro-3-(6-methoxyquinolin-4-yl)
propyl]-1-[3-(4-fluorophenylthio)propyl]piperidine-3-
carboxylic acid
(3R,4R)-4-[3-(R,S)-Fluoro-3-(6-methoxyquinolin-4-yl)
propyl]-1-[2-(2,3-difluorophenylthio)ethyl]piperidine-3-
carboxylic acid
(3R,4R)-4-[3-(R,S)-Fluoro-3-(6-methoxyquinolin-4-yl)
propyl]-1-[3-(2,3-difluorophenylthio)propyl]piperidine-
3-carboxylic acid
(3R,4R)-4-[3-(R,S)-Fluoro-3-(6-methoxyquinolin-4-yl)
propyl]-1-[2-(2,6-difluorophenylthio)ethyl]piperidine-3-
carboxylic acid
(3R,4R)-4-[3-(R,S)-Fluoro-3-(6-methoxyquinolin-4-yl)
propyl]-1-[3-(2,6-difluorophenylthio)propyl]piperidine-
3-carboxylic acid
(3R,4R)-4-[3-(R,S)-Fluoro-3-(6-methoxyquinolin-4-yl)
propyl]-1-[2-(2-chlorophenylthio)ethyl]piperidine-3-
carboxylic acid
(3R,4R)-4-[3-(R,S)-Fluoro-3-(6-methoxyquinolin-4-yl)
propyl]-1-[3-(2-chlorophenylthio)propyl]piperidine-3-
carboxylic acid
(3R,4R)-4-[3-(R,S)-Fluoro-3-(6-methoxyquinolin-4-yl)
propyl]-1-[2-(3-chlorophenylthio)ethyl]piperidine-3-
carboxylic acid (3R,4R)-4-[3-(R,S)-Fluoro-3-(6-methoxyquinolin-4-yl)
propyl]-1-[3-(3-chlorophenylthio)propyl]piperidine-3-
carboxylic acid
(3R,4R)-4-[3-(R,S)-Fluoro-3-(6-methoxyquinolin-4-yl)
propyl]-1-[2-(4-chlorophenylthio)ethyl]piperidine-3-
carboxylic acid
(3R,4R)-4-[3-(R,S)-Fluoro-3-(6-methoxyquinolin-4-yl)
propyl]-1-[3-(4-chlorophenylthio)propyl]piperidine-3-
carboxylic acid
(3R,4R)-4-[3-(R,S)-Fluoro-3-(6-methoxyquinolin-4-yl)
propyl]-1-[2-(2,3-dichlorophenylthio)ethyl]piperidine-3-
carboxylic acid
(3R,4R)-4-[3-(R,S)-Fluoro-3-(6-methoxyquinolin-4-yl)
propyl]-1-[3-(2,3-dichlorophenylthio)propyl]piperidine-
3-carboxylic acid
(3R,4R)-4-[3-(R,S)-Fluoro-3-(6-methoxyquinolin-4-yl)
propyl]-1-[2-(2,6-dichlorophenylthio)ethyl]piperidine-3-
carboxylic acid
(3R,4R)-4-[3-(R,S)-Fluoro-3-(6-methoxyquinolin-4-yl)
propyl]-1-[3-(2,6-dichlorophenylthio)propyl]piperidine-
3-carboxylic acid
(3R,4R)-4-[3-(R,S)-Fluoro-3-(6-methoxyquinolin-4-yl)
propyl]-1-[2-(2-methylphenylthio)ethyl]piperidine-3-
carboxylic acid
(3R,4R)-4-[3-(R,S)-Fluoro-3-(6-methoxyquinolin-4-yl)
propyl]-1-[3-(2-methylphenylthio)propyl]piperidine-3-
carboxylic acid
(3R,4R)-4-[3-(R,S)-Fluoro-3-(6-methoxyquinolin-4-yl)
propyl]-1-[2-(3-methylphenylthio)ethyl]piperidine-3-
carboxylic acid
(3R,4R)-4-[3-(R,S)-Fluoro-3-(6-methoxyquinolin-4-yl)
propyl]-1-[3-(3-methylphenylthio)propyl]piperidine-3-
carboxylic acid
(3R,4R)-4-[3-(R,S)-Fluoro-3-(6-methoxyquinolin-4-yl)
propyl]-1-[2-(4-methylphenylthio)ethyl]piperidine-3-
carboxylic acid
(3R,4R)-4-[3-(R,S)-Fluoro-3-(6-methoxyquinolin-4-yl)
propyl]-1-[3-(4-methylphenylthio)propyl]piperidine-3-
carboxylic acid
(3R,4R)-4-[3-(R,S)-Fluoro-3-(6-methoxyquinolin-4-yl)
propyl]-1-[2-(2-trifluoromethylphenylthio)ethyl]
piperidine-3-carboxylic acid
(3R,4R)-4-[3-(R,S)-Fluoro-3-(6-methoxyquinolin-4-yl)
propyl]-1-[3-(2-trifluoromethylphenylthio)propyl]
piperidine-3-carboxylic acid
(3R,4R)-4-[3-(R,S)-Fluoro-3-(6-methoxyquinolin-4-yl)
propyl]-1-[2-(3-trifluoromethylphenylthio)ethyl]
piperidine-3-carboxylic acid
(3R,4R)-4-[3-(R,S)-Fluoro-3-(6-methoxyquinolin-4-yl)
propyl]-1-[3-(3-trifluoromethylphenylthio)propyl]
piperidine-3-carboxylic acid
(3R,4R)-4-[3-(R,S)-Fluoro-3-(6-methoxyquinolin-4-yl)
propyl]-1-[2-(4-trifluoromethylphenylthio)ethyl]
piperidine-3-carboxylic acid
(3R,4R)-4-[3-(R,S)-Fluoro-3-(6-methoxyquinolin-4-yl)
propyl]-1-[3-(4-trifluoromethylphenylthio)propyl]
piperidine-3-carboxylic acid
(3R,4R)-4-[3-(R,S)-Fluoro-3-(6-methoxyquinolin-4-yl)
propyl]-1-[2-(2-methoxyphenylthio)ethyl]piperidine-3-
carboxylic acid
(3R,4R)-4-[3-(R,S)-Fluoro-3-(6-methoxyquinolin-4-yl)
propyl]-1-[3-(2-methoxyphenylthio)propyl]piperidine-3-
carboxylic acid
(3R,4R)-4-[3-(R,S)-Fluoro-3-(6-methoxyquinolin-4-yl)
propyl]-1-[2-(3-methoxyphenylthio)ethyl]piperidine-3-
carboxylic acid
(3R,4R)-4-[3-(R,S)-Fluoro-3-(6-methoxyquinolin-4-yl)
propyl]-1-[3-(3-methoxyphenylthio)propyl]piperidine-3-
carboxylic acid
(3R,4R)-4-[3-(R,S)-Fluoro-3-(6-methoxyquinolin-4-yl)
propyl]-1-[2-(4-methoxyphenylthio)ethyl]piperidine-3-
carboxylic acid
(3R,4R)-4-[3-(R,S)-Fluoro-3-(6-methoxyquinolin-4-yl)
propyl]-1-[3-(4-methoxyphenylthio)propyl]piperidine-3-
carboxylic acid
(3R,4R)-4-[3-(R,S)-Fluoro-3-(6-methoxyquinolin-4-yl)
propyl]-1-[cyclopropylmethyl]piperidine-3-carboxylic
acid
(3R,4R)-4-[3-(R,S)-Fluoro-3-(6-methoxyquinolin-4-yl)
propyl]-1-[2-(cyclopropyl)ethyl]piperidine-3-carboxylic
acid
(3R,4R)-4-[3-(R,S)-Fluoro-3-(6-methoxyquinolin-4-yl)
propyl]-1-[cyclobutylmethyl]piperidine-3-carboxylic
acid
(3R,4R)-4-[3-(R,S)-Fluoro-3-(6-methoxyquinolin-4-yl)
propyl]-1-[2-(cyclobutyl)ethyl]piperidine-3-carboxylic
acid
(3R,4R)-4-[3-(R,S)-Fluoro-3-(6-methoxyquinolin-4-yl)
propyl]-1-[cyclopentylmethyl]piperidine-3-carboxylic
acid
(3R,4R)-4-[3-(R,S)-Fluoro-3-(6-methoxyquinolin-4-yl)
propyl]-1-[2-(cyclopentyl)ethyl]piperidine-3-carboxylic
acid
(3R,4R)-4-[3-(R,S)-Fluoro-3-(6-methoxyquinolin-4-yl)
propyl]-1-[cyclohexylmethyl]piperidine-3-carboxylic
acid
(3R,4R)-4-[3-(R,S)-Fluoro-3-(6-methoxyquinolin-4-yl)
propyl]-1-[2-(cyclohexyl)ethyl]piperidine-3-carboxylic
acid
(3R,4R)-4-[3-(R,S)-Fluoro-3-(6-methoxyquinolin-4-yl)
propyl]-1-[2-(cyclopropylthio)ethyl]piperidine-3-
carboxylic acid
(3R,4R)-4-[3-(R,S)-Fluoro-3-(6-methoxyquinolin-4-yl)
propyl]-1-[3-(cyclopropylthio)propyl]piperidine-3-
carboxylic acid
(3R,4R)-4-[3-(R,S)-Fluoro-3-(6-methoxyquinolin-4-yl)
propyl]-1-[2-(cyclobutylthio)ethyl]piperidine-3-
carboxylic acid
(3R,4R)-4-[3-(R,S)-Fluoro-3-(6-methoxyquinolin-4-yl)
propyl]-1-[3-(cyclobutylthio)propyl]piperidine-3-
carboxylic acid
(3R,4R)-4-[3-(R,S)-Fluoro-3-(6-methoxyquinolin-4-yl)
propyl]-1-[2-(cyclopentylthio)ethyl]piperidine-3-
carboxylic acid
(3R,4R)-4-[3-(R,S)-Fluoro-3-(6-methoxyquinolin-4-yl)
propyl]-1-[3-(cyclopentylthio)propyl]piperidine-3-
carboxylic acid
(3R,4R)-4-[3-(R,S)-Fluoro-3-(6-methoxyquinolin-4-yl)
propyl]-1-[2-(cyclohexylthio)ethyl]piperidine-3-
carboxylic acid
(3R,4R)-4-[3-(R,S)-Fluoro-3-(6-methoxyquinolin-4-yl)
propyl]-1-[3-(cyclohexylthio)propyl]piperidine-3-
carboxylic acid
(3R,4R)-4-[3-(R,S)-Fluoro-3-(6-methoxyquinolin-4-yl)
propyl]-1-[2-methylthioethyl]piperidine-3-carboxylic
acid
(3R,4R)-4-[3-(R,S)-Fluoro-3-(6-methoxyquinolin-4-yl)
propyl]-1-[3-methylthiopropyl]piperidine-3-carboxylic
acid
(3R,4R)-4-[3-(R,S)-Fluoro-3-(6-methoxyquinolin-4-yl)
propyl]-1-[2-ethylthioethyl]piperidine-3-carboxylic acid
(3R,4R)-4-[3-(R,S)-Fluoro-3-(6-methoxyquinolin-4-yl)
propyl]-1-[3-ethylthiopropyl]piperidine-3-carboxylic
acid
(3R,4R)-4-[3-(R,S)-Fluoro-3-(6-methoxyquinolin-4-yl)
propyl]-1-[2-(n-propylthio)ethyl]piperidine-3-carboxylic
acid (3R,4R)-4-[3-(R,S)-Fluoro-3-(6-methoxyquinolin-4-yl)propyl]-1-[3-(n-propylthio)propyl]piperidine-3-carboxylic acid (3R,4R)-4-[3-(R,S)-Fluoro-3-(6-methoxyquinolin-4-yl)propyl]-1-[2-(n-butylthio)ethyl]piperidine-3-carboxylic acid (3R,4R)-4-[3-(R,S)-Fluoro-3-(6-methoxyquinolin-4-yl)propyl]-1-[3-(n-butylthio)propyl]piperidine-3-carboxylic acid (3R,4R)-4-[3-(R,S)-Fluoro-3-(6-methoxyquinolin-4-yl)propyl]-1-[3-(thien-2-yl)propyl]piperidine-3-carboxylic acid (3R,4R)-4-[3-(R,S)-Fluoro-3-(6-methoxyquinolin-4-yl)propyl]-1-[4-(thien-2-yl)butyl]piperidine-3-carboxylic acid (3R,4R)-4-[3-(R,S)-Fluoro-3-(6-methoxyquinolin-4-yl)propyl]-1-[3-(thien-2-yl)thiopropyl]piperidine-3-carboxylic acid (3R,4R)-4-[3-(R,S)-Fluoro-3-(6-methoxyquinolin-4-yl)propyl]-1-[3-(5-chlorothien-2-yl)propyl]piperidine-3-carboxylic acid (3R,4R)-4-[3-(R,S)-Fluoro-3-(6-methoxyquinolin-4-yl)propyl]-1-[4-(5-chlorothien-2-yl)butyl]piperidine-3-carboxylic acid (3R,4R)-4-[3-(R,S)-Fluoro-3-(6-methoxyquinolin-4-yl)propyl]-1-[2-(5-chlorothien-2-yl)thioethyl]piperidine-3-carboxylic acid (3R,4R)-4-[3-(R,S)-Fluoro-3-(6-methoxyquinolin-4-yl)propyl]-1-[3-(5-chlorothien-2-yl)thiopropyl]piperidine-3-carboxylic acid (3R,4R)-4-[3-(R,S)-Fluoro-3-(6-methoxyquinolin-4-yl)propyl]-1-[3-(3-chlorothien-2-yl)propyl]piperidine-3-carboxylic acid (3R,4R)-4-[3-(R,S)-Fluoro-3-(6-methoxyquinolin-4-yl)propyl]-1-[4-(3-chlorothien-2-yl)butyl]piperidine-3-carboxylic acid (3R,4R)-4-[3-(R,S)-Fluoro-3-(6-methoxyquinolin-4-yl)propyl]-1-[2-(3-chlorothien-2-yl)thioethyl]piperidine-3-carboxylic acid (3R,4R)-4-[3-(R,S)-Fluoro-3-(6-methoxyquinolin-4-yl)propyl]-1-[3-(3-chlorothien-2-yl)thiopropyl]piperidine-3-carboxylic acid (3R,4R)-4-[3-(R,S)-Fluoro-3-(6-methoxyquinolin-4-yl)propyl]-1-[3-(5-methylthien-2-yl)propyl]piperidine-3-carboxylic acid (3R,4 R)-4-[3-(R,S)-Fluoro-3-(6-methoxyquinolin-4-yl)propyl]-1-[4-(5-methylthien-2-yl)butyl]piperidine-3-carboxylic acid (3R,4R)-4-[3-(R,S)-Fluoro-3-(6-methoxyquinolin-4-yl)propyl]-1-[2-(5-methylthien-2-yl)thioethyl]piperidine-3-carboxylic acid (3R,4R)-4-[3-(R,S)-Fluoro-3-(6-methoxyquinolin-4-yl)propyl]-1-[3-(5-methylthien-2-yl)thiopropyl]piperidine-3-carboxylic acid (3R,4R)-4-[3-(R,S)-Fluoro-3-(6-methoxyquinolin-4-yl)propyl]-1-[3-(3-methylthien-2-yl)propyl]piperidine-3-carboxylic acid (3R,4R)-4-[3-(R,S)-Fluoro-3-(6-methoxyquinolin-4-yl)propyl]-1-[4-(3-methylthien-2-yl)butyl]piperidine-3-carboxylic acid (3R,4R)-4-[3-(R,S)-Fluoro-3-(6-methoxyquinolin-4-yl)propyl]-1-[2-(3-methylthien-2-yl)thioethyl]piperidine-3-carboxylic acid (3R,4R)-4-[3-(R,S)-Fluoro-3-(6-methoxyquinolin-4-yl)propyl]-1-[3-(3-methylthien-2-yl)thiopropyl]piperidine-3-carboxylic acid (3R,4R)-4-[3-(R,S)-Fluoro-3-(6-methoxyquinolin-4-yl)propyl]-1-[3-(thien-3-yl)propyl]piperidine-3-carboxylic acid (3R,4R)-4-[3-(R,S)-Fluoro-3-(6-methoxyquinolin-4-yl)propyl]-1-[4-(thien-3-yl)butyl]piperidine-3-carboxylic acid (3R,4R)-4-[3-(R,S)-Fluoro-3-(6-methoxyquinolin-4-yl)propyl]-1-[2-(thien-3-yl)thioethyl]piperidine-3-carboxylic acid (3R,4R)-4-[3-(R,S)-Fluoro-3-(6-methoxyquinolin-4-yl)propyl]-1-[3-(thien-3-yl)thiopropyl]piperidine-3-carboxylic acid (3R,4R)-4-[3-(R,S)-Fluoro-3-(6-methoxyquinolin-4-yl)propyl]-1-[3-(fur-2-yl)propyl]piperidine-3-carboxylic acid (3R,4R)-4-[3-(R,S)-Fluoro-3-(6-methoxyquinolin-4-yl)propyl]-1-[4-(fur-2-yl)butyl]piperidine-3-carboxylic acid (3R,4R)-4-[3-(R,S)-Fluoro-3-(6-methoxyquinolin-4-yl)propyl]-1-[2-(fur-2-yl)thioethyl]piperidine-3-carboxylic acid (3R,4R)-4-[3-(R,S)-Fluoro-3-(6-methoxyquinolin-4-yl)propyl]-1-[3-(fur-2-yl)thiopropyl]piperidine-3-carboxylic acid (3R,4R)-4-[3-(R,S)-Fluoro-3-(6-methoxyquinolin-4-yl)propyl]-1-[3-(fur-3-yl)propyl]piperidine-3-carboxylic acid (3R,4R)-4-[3-(R,S)-Fluoro-3-(6-methoxyquinolin-4-yl)propyl]-1-[4-(fur-3-yl)butyl]piperidine-3-carboxylic acid (3R,4R)-4-[3-(R,S)-Fluoro-3-(6-methoxyquinolin-4-yl)propyl]-1-[2-(fur-3-yl)thioethyl]piperidine-3-carboxylic acid (3R,4R)-4-[3-(R,S)-Fluoro-3-(6-methoxyquinolin-4-yl)propyl]-1-[3-(fur-3-yl)thiopropyl]piperidine-3-carboxylic acid (3R,4R)-4-[3-(R,S)-Fluoro-3-(6-methoxyquinolin-4-yl)propyl]-1-[3-(1-methylpyrrol-2-yl)propyl]piperidine-3-carboxylic acid (3R,4R)-4-[3-(R,S)-Fluoro-3-(6-methoxyquinolin-4-yl)propyl]-1-[4-(1-methylpyrrol-2-yl)butyl]piperidine-3-carboxylic acid (3R,4R)-4-[3-(R,S)-Fluoro-3-(6-methoxyquinolin-4-yl)propyl]-1-[2-(1-methylpyrrol-2-yl)thioethyl]piperidine-3-carboxylic acid (3R,4R)-4-[3-(R,S)-Fluoro-3-(6-methoxyquinolin-4-yl)propyl]-1-[3-(1-methylpyrrol-2-yl)thiopropyl]piperidine-3-carboxylic acid (3R,4R)-4-[3-(R,S)-Fluoro-3-(6-methoxyquinolin-4-yl)propyl]-1-[3-(1-methylpyrrol-2-yl)propyl]piperidine-3-carboxylic acid (3R,4R)-4-[3-(R,S)-Fluoro-3-(6-methoxyquinolin-4-yl)propyl]-1-[4-(1-methylpyrrol-3-yl)butyl]piperidine-3-carboxylic acid (3R,4R)-4-[3-(R,S)-Fluoro-3-(6-methoxyquinolin-4-yl)propyl]-1-[2-(1-methylpyrrol-3-yl)thioethyl]piperidine-3-carboxylic acid (3R,4R)-4-[3-(R,S)-Fluoro-3-(6-methoxyquinolin-4-yl)propyl]-1-[3-(1-methylpyrrol-3-yl)thiopropyl]piperidine-3-carboxylic acid (3R,4R)-4-[3-(R,S)-Fluoro-3-(6-methoxyquinolin-4-yl)propyl]-1-[3-(1,3-thiazol-2-yl)propyl]piperidine-3-carboxylic acid (3R,4R)-4-[3-(R,S)-Fluoro-3-(6-methoxyquinolin-4-yl)propyl]-1-[4-(1,3-thiazol-2-yl)butyl]piperidine-3-carboxylic acid (3R,4R)-4-[3-(R,S)-Fluoro-3-(6-methoxyquinolin-4-yl)propyl]-1-[2-(1,3-thiazol-2-yl)thioethyl]piperidine-3-carboxylic acid (3R,4R)-4-[3-(R,S)-Fluoro-3-(6-methoxyquinolin-4-yl)propyl]-1-[3-(1,3-thiazol-2-yl)thiopropyl]piperidine-3-carboxylic acid (3R,4R)-4-[3-(R,S)-Fluoro-3-(6-methoxyquinolin-4-yl)propyl]-1-[3-(1-methylimidazol-2-yl)propyl]piperidine-3-carboxylic acid (3R,4R)-4-[3-(R,S)-Fluoro-3-(6-methoxyquinolin-4-yl)propyl]-1-[4-(1-methylimidazol-2-yl)butyl]piperidine-3-carboxylic acid (3R,4R)-4-[3-(R,S)-Fluoro-3-(6-methoxyquinolin-4-yl)propyl]-1-[2-(1-methylimidazol-2-yl)thioethyl]piperidine-3-carboxylic acid (3R,4R)-4-[3-(R,S)-Fluoro-3-(6-methoxyquinolin-4-yl)propyl]-1-[3-(1-methylimidazol-2-yl)thiopropyl]piperidine-3-carboxylic acid (3R,4R)-4-[3-(R,S)-Fluoro-3-(6-methoxyquinolin-4-yl)propyl]-1-[3-(3-methylimidazol-4-yl)propyl]piperidine-3-carboxylic acid (3R,4R)-4-[3-(R,S)-Fluoro-3-(6-methoxyquinolin-4-yl)propyl]-1-[4-(3-methylimidazol-4-yl)butyl]piperidine-3-carboxylic acid (3R,4R)-4-[3-(R,S)-Fluoro-3-(6-methoxyquinolin-4-yl)propyl]-1-[2-(3-methylimidazol-4-yl)thioethyl]piperidine-3-carboxylic acid (3R,4R)-4-[3-(R,S)-Fluoro-3-(6-methoxyquinolin-4-yl)propyl]-1-[3-(3-methylimidazol-4-yl)thiopropyl]piperidine-3-carboxylic acid (3R,4R)-4-[3-(R,S)-Fluoro-3-(6-methoxyquinolin-4-yl)propyl]-1-[3-(3-methylpyrazol-4-yl)propyl]piperidine-3-carboxylic acid (3R,4R)-4-[3-(R,S)-Fluoro-3-(6-methoxyquinolin-4-yl)propyl]-1-[4-(3-methylimidazol-4-yl)butyl]piperidine-3-carboxylic acid (3R,4R)-4-[3-(R,S)-Fluoro-3-(6-methoxyquinolin-4-yl)propyl]-1-[2-(3-methylimidazol-4-yl)thioethyl]piperidine-3-carboxylic acid (3R,4R)-4-[3-(R,S)-Fluoro-3-(6-methoxyquinolin-4-yl)propyl]-1-[3-(3-methylimidazol-4-yl)thiopropyl]piperidine-3-carboxylic acid (3R,4R)-4-[3-(R,S)-Fluoro-3-(6-methoxyquinolin-4-yl)propyl]-1-[3-(oxazol-2-yl)propyl]piperidine-3-carboxylic acid (3R,4R)-4-[3-(R,S)-Fluoro-3-(6-methoxyquinolin-4-yl)propyl]-1-[4-(oxazol-2-yl)butyl]piperidine-3-carboxylic acid (3R,4R)-4-[3-(R,S)-Fluoro-3-(6-methoxyquinolin-4-yl)propyl]-1-[2-(oxazol-2-yl)thioethyl]piperidine-3-carboxylic acid (3R,4R)-4-[3-(R,S)-Fluoro-3-(6-methoxyquinolin-4-yl)propyl]-1-[3-(oxazol-2-yl)thiopropyl]piperidine-3-carboxylic acid (3R,4R)-4-[3-(R,S)-Fluoro-3-(6-methoxyquinolin-4-yl)propyl]-1-[3-(pyridin-2-yl)propyl]piperidine-3-carboxylic acid (3R,4R)-4-[3-(R,S)-Fluoro-3-(6-methoxyquinolin-4-yl)propyl]-1-[4-(pyridin-2-yl)butyl]piperidine-3-carboxylic acid (3R,4R)-4-[3-(R,S)-Fluoro-3-(6-methoxyquinolin-4-yl)propyl]-1-[3-(pyridin-2-yl)thiopropyl]piperidine-3-carboxylic acid (3R,4R)-4-[3-(R,S)-Fluoro-3-(6-methoxyquinolin-4-yl)propyl]-1-[3-(pyridin-3-yl)propyl]piperidine-3-carboxylic acid (3R,4R)-4-[3-(R,S)-Fluoro-3-(6-methoxyquinolin-4-yl)propyl]-1-[4-(pyridin-3-yl)butyl]piperidine-3-carboxylic acid (3R,4R)-4-[3-(R,S)-Fluoro-3-(6-methoxyquinolin-4-yl)propyl]-1-[2-(pyridin-3-yl)thioethyl]piperidine-3-carboxylic acid (3R,4R)-4-[3-(R,S)-Fluoro-3-(6-methoxyquinolin-4-yl)propyl]-1-[3-(pyridin-3-yl)thiopropyl]piperidine-3-carboxylic acid (3R,4R)-4-[3-(R,S)-Fluoro-3-(6-methoxyquinolin-4-yl)propyl]-1-[3-(pyridin-4-yl)propyl]piperidine-3-carboxylic acid (3R,4R)-4-[3-(R,S)-Fluoro-3-(6-methoxyquinolin-4-yl)propyl]-1-[4-(pyridin-4-yl)butyl]piperidine-3-carboxylic acid (3R,4R)-4-[3-(R,S)-Fluoro-3-(6-methoxyquinolin-4-yl)propyl]-1-[5-(pyridin-4-yl)pentyl]piperidine-3-carboxylic acid (3R,4R)-4-[3-(R,S)-Fluoro-3-(6-methoxyquinolin-4-yl)propyl]-1-[2-(pyridin-2-yl)thioethyl]piperidine-3-carboxylic acid (3R,4R)-4-[3-(R,S)-Fluoro-3-(6-methoxyquinolin-4-yl)propyl]-1-[2-(pyridin-4-yl)thioethyl]piperidine-3-carboxylic acid (3R,4R)-4-[3-(R,S)-Fluoro-3-(6-methoxyquinolin-4-yl)propyl]-1-[3-(pyridin-4-yl)thiopropyl]piperidine-3-carboxylic acid (3R,4R)-4-[3-(R,S)-Fluoro-3-(6-methoxyquinolin-4-yl)propyl]-1-[3-(pyrimidin-2-yl)propyl]piperidine-3-carboxylic acid (3R,4R)-4-[3-(R,S)-Fluoro-3-(6-methoxyquinolin-4-yl)propyl]-1-[4-(pyrimidin-2-yl)butyl]piperidine-3-carboxylic acid (3R,4R)-4-[3-(R,S)-Fluoro-3-(6-methoxyquinolin-4-yl)propyl]-1-[2-(pyrimidin-2-yl)thioethyl]piperidine-3-carboxylic acid (3R,4R)-4-[3-(R,S)-Fluoro-3-(6-methoxyquinolin-4-yl)propyl]-1-[3-(pyrimidin-2-yl)thiopropyl]piperidine-3-carboxylic acid (3R,4R)-4-[3-(R,S)-Fluoro-3-(6-methoxyquinolin-4-yl)propyl]-1-[3-(pyrimidin-4-yl)propyl]piperidine-3-carboxylic acid (3R,4R)-4-[3-(R,S)-Fluoro-3-(6-methoxyquinolin-4-yl)propyl]-1-[4-(pyrimidin-4-yl)butyl]piperidine-3-carboxylic acid (3R,4R)-4-[3-(R,S)-Fluoro-3-(6-methoxyquinolin-4-yl)propyl]-1-[2-(pyrimidin-4-yl)thioethyl]piperidine-3-carboxylic acid (3R,4R)-4-[3-(R,S)-Fluoro-3-(6-methoxyquinolin-4-yl)propyl]-1-[3-(pyrimidin-4-yl)thiopropyl]piperidine-3-carboxylic acid (3R,4R)-4-[3-(R,S)-Fluoro-3-(6-methoxyquinolin-4-yl)propyl]-1-[3-(pyrimidin-5-yl)propyl]piperidine-3-carboxylic acid (3R,4R)-4-[3-(R,S)-Fluoro-3-(6-methoxyquinolin-4-yl)propyl]-1-[4-(pyrimidin-5-yl)butyl]piperidine-3-carboxylic acid (3R,4R)-4-[3-(R,S)-Fluoro-3-(6-methoxyquinolin-4-yl)propyl]-1-[2-(pyrimidin-5-yl)thioethyl]piperidine-3-carboxylic acid (3R,4R)-4-[3-(R,S)-Fluoro-3-(6-methoxyquinolin-4-yl)propyl]-1-[3-(pyrimidin-5-yl)thiopropyl]piperidine-3-carboxylic acid (3R,4R)-4-[3-(R,S)-Fluoro-3-(6-methoxyquinolin-4-yl)propyl]-1-[3-(pyrazin-2-yl)propyl]piperidine-3-carboxylic acid (3R,4R)-4-[3-(R,S)-Fluoro-3-(6-methoxyquinolin-4-yl)propyl]-1-(4-(pyrazin-2-yl)butyl]piperidine-3-carboxylic acid (3R,4R)-4-[3-(R,S)-Fluoro-3-(6-methoxyquinolin-4-yl)propyl]-1-[2-(pyrazin-2-yl)thioethyl]-piperidine-3-carboxylic acid (3R,4R)-4-[3-(R,S)-Fluoro-3-(6-methoxyquinolin-4-yl)propyl]-1-[3-(pyrazin-2-yl)thiopropyl]piperidine-3-carboxylic acid (3R,4R)-4-[3-(R,S)-Fluoro-3-(6-methoxyquinolin-4-yl)propyl]-1-[3-(pyridazin-3-yl)propyl]piperidine-3-carboxylic acid (3R,4R)-4-[3-(R,S)-Fluoro-3-(6-methoxyquinolin-4-yl)propyl]-1-[4-(pyridazin-3-yl)butyl]piperidine-3-carboxylic acid (3R,4R)-4-[3-(R,S)-Fluoro-3-(6-methoxyquinolin-4-yl)propyl]-1-[2-(pyridazin-3-yl)thioethyl]piperidine-3-carboxylic acid (3R,4R)-4-[3-(R,S)-Fluoro-3-(6-methoxyquinolin-4-yl)propyl]-1-[3-(pyridazin-3-yl)thiopropyl]piperidine-3-carboxylic acid (3R,4R)-4-[3-(R,S)-Fluoro-3-(6-methoxyquinolin-4-yl)propyl]-1-[3-(pyridazin-4-yl)propyl]piperidine-3-carboxylic acid (3R,4R)-4-[3-(R,S)-Fluoro-3-(6-methoxyquinolin-4-yl)propyl]-1-[4-(pyridazin-4-yl)butyl]piperidine-3-carboxylic acid (3R,4R)-4-[3-(R,S)-Fluoro-3-(6-methoxyquinolin-4-yl)propyl]-1-[2-(pyridazin-4-yl)thioethyl]piperidine-3-carboxylic acid (3R,4R)-4-[3-(R,S)-Fluoro-3-(6-methoxyquinolin-4-yl)propyl]-1-[3-(pyridazin-4-yl)thiopropyl]piperidine-3-carboxylic acid (3R,4R)-4-[3-(R,S)-Fluoro-3-(6-methoxyquinolin-4-yl)propyl]-1-[3-phenylprop-2-ynyl]piperidine-3-carboxylic acid (3R,4R)-4-[3-(R,S)-Fluoro-3-(6-methoxyquinolin-4-yl)propyl]-1-[3-(2-fluorophenyl)prop-2-ynyl]piperidine-3-carboxylic acid (3R,4R)-4-[3-(R,S)-Fluoro-3-(6-methoxyquinolin-4-yl)propyl]-1-[3-(4-fluorophenyl)prop-2-ynyl]piperidine-3-carboxylic acid (3R,4R)-4-[3-(R,S)-Fluoro-3-(6-methoxyquinolin-4-yl)propyl]-1-[3-(2-chlorophenyl)prop-2-ynyl]piperidine-3-carboxylic acid (3R,4R)-4-[3-(R,S)-Fluoro-3-(6-methoxyquinolin-4-yl)propyl]-1-[3-(3-chlorophenyl)prop-2-ynyl]piperidine-3-carboxylic acid (3R,4R)-4-[3-(R,S)-Fluoro-3-(6-methoxyquinolin-4-yl)propyl]-1-[3-(4-chlorophenyl)prop-2-ynyl]piperidine-3-carboxylic acid (3R,4R)-4-[3-(R,S)-Fluoro-3-(6-methoxyquinolin-4-yl)propyl]-1-[3-(2-methylphenyl)prop-2-ynyl]piperidine-3-carboxylic acid (3R,4R)-4-[3-(R,S)-Fluoro-3-(6-methoxyquinolin-4-yl)propyl]-1-[3-(3-methylphenyl)prop-2-ynyl]piperidine-3-carboxylic acid (3R,4R)-4-[3-(R,S)-Fluoro-3-(6-methoxyquinolin-4-yl)propyl]-1-[3-(4-methylphenyl)prop-2-ynyl]piperidine-3-carboxylic acid (3R,4R)-4-[3-(R,S)-Fluoro-3-(6-methoxyquinolin-4-yl)propyl]-1-[3-(2-(trifluoromethyl)phenyl)prop-2-ynyl]-piperidine-3-carboxylic acid (3R,4R)-4-[3-(R,S)-Fluoro-3-(6-methoxyquinolin-4-yl)propyl]-1-[3-(3-(trifluoromethyl)phenyl)prop-2-ynyl]-piperidine-3-carboxylic acid (3R,4R)-4-[3-(R,S)-Fluoro-3-(6-methoxyquinolin-4-yl)propyl]-1-[3-(4-(trifluoromethyl)phenyl)prop-2-ynyl]-piperidine-3-carboxylic acid (3R,4R)-4-[3-(R,S)-Fluoro-3-(6-methoxyquinolin-4-yl)propyl]-1-[3-(2-methoxyphenyl)prop-2-ynyl]piperidine-3-carboxylic acid (3R,4R)-4-[3-(R,S)-Fluoro-3-(6-methoxyquinolin-4-yl)propyl]-1-[3-(3-methoxyphenyl)prop-2-ynyl]piperidine-3-carboxylic acid (3R,4R)-4-[3-(R,S)-Fluoro-3-(6-methoxyquinolin-4-yl)propyl]-1-[3-(4-methoxyphenyl)prop-2-ynyl]piperidine-3-carboxylic acid (3R,4R)-4-[3-(R,S)-Fluoro-3-(6-methoxyquinolin-4-yl)propyl]-1-[3-(3,4-difluorophenyl)prop-2-ynyl]-piperidine-3-carboxylic acid (3R,4R)-4-[3-(R,S)-Fluoro-3-(6-methoxyquinolin-4-yl)propyl]-1-[3-(2,4-difluorophenyl)prop-2-ynyl]-piperidine-3-carboxylic acid (3R,4R)-4-[3-(R,S)-Fluoro-3-(6-methoxyquinolin-4-yl)propyl]-1-[3-(3,4-dichlorophenyl)prop-2-ynyl]-piperidine-3-carboxylic acid (3R,4R)-4-[3-(R,S)-Fluoro-3-(6-methoxyquinolin-4-yl)propyl]-1-[3-(2,3-dichlorophenyl)prop-2-ynyl]-piperidine-3-carboxylic acid (3R,4R)-4-[3-(R,S)-Fluoro-3-(6-methoxyquinolin-4-yl)propyl]-1-[3-(2,4-dichlorophenyl)prop-2-ynyl]-piperidine-3-carboxylic acid (3R,4R)-4-[3-(R,S)-Fluoro-3-(6-methoxyquinolin-4-yl)propyl]-1-[3-(2,4,6-trichlorophenyl)prop-2-ynyl]-piperidine-3-carboxylic acid (3R,4R)-4-[3-(R,S)-Fluoro-3-(6-methoxyquinolin-4-yl)propyl]-1-[3-(3,5-dichlorophenyl)prop-2-ynyl]-piperidine-3-carboxylic acid (3R,4R)-4-[3-(R,S)-Fluoro-3-(6-methoxyquinolin-4-yl)propyl]-1-[3-(4-chloro-3-fluorophenyl)prop-2-ynyl]-piperidine-3-carboxylic acid (3R,4R)-4-[3-(R,S)-Fluoro-3-(6-methoxyquinolin-4-yl)propyl]-1-[3-(3-chloro-4-fluorophenyl)prop-2-ynyl]-piperidine-3-carboxylic acid (3R,4R)-4-[3-(R,S)-Fluoro-3-(6-methoxyquinolin-4-yl)propyl]-1-[3-(2-chloro-4-fluorophenyl)prop-2-ynyl]-piperidine-3-carboxylic acid (3R,4R)-4-[3-(R,S)-Fluoro-3-(6-methoxyquinolin-4-yl)propyl]-1-[3-(3-chloro-5-fluorophenyl)prop-2-ynyl]-piperidine-3-carboxylic acid (3R,4R)-4-[3-(R,S)-Fluoro-3-(6-methoxyquinolin-4-yl)propyl]-1-[3-(4-chloro-2-fluorophenyl)prop-2-ynyl]-piperidine-3-carboxylic acid (3R,4R)-4-[3-(R,S)-Fluoro-3-(6-methoxyquinolin-4-yl)propyl]-1-[3-(3-fluoro-4-methylphenyl)prop-2-ynyl]-piperidine-3-carboxylic acid (3R,4R)-4-[3-(R,S)-Fluoro-3-(6-methoxyquinolin-4-yl)propyl]-1-[3-(4-chloro-3-(trifluoromethyl)phenyl)prop-2-ynyl]piperidine-3-carboxylic acid (3R,4R)-4-[3-(R,S)-Fluoro-3-(6-methoxyquinolin-4-yl)propyl]-1-[3-(2-chloro-4-(trifluoromethyl)phenyl)prop-2-ynyl]piperidine-3-carboxylic acid (3R,4R)-4-[3-(R,S)-Fluoro-3-(6-methoxyquinolin-4-yl)propyl]-1-[3-(2-chloro-5-(trifluoromethyl)phenyl)prop-2-ynyl]piperidine-3-carboxylic acid (3R,4R)-4-[3-(R,S)-Fluoro-3-(6-methoxyquinolin-4-yl)propyl]-1-[3-(5-chloro-2-methoxyphenyl)prop-2-ynyl]piperidine-3-carboxylic acid (3R,4R)-4-[3-(R,S)-Fluoro-3-(6-methoxyquinolin-4-yl)propyl]-1-[3-(3,5-bis(trifluoromethyl)phenyl)prop-2-ynyl]piperidine-3-carboxylic acid (3R,4R)-4-[3-(R,S)-Fluoro-3-(6-methoxyquinolin-4-yl)propyl]-1-[3-(3,5-dimethylphenyl)prop-2-ynyl]piperidine-3-carboxylic acid (3R,4R)-4-[3-(R,S)-Fluoro-3-(6-methoxyquinolin-4-yl)propyl]-1-[3-(2,4-dichloro-6-methylphenyl)prop-2-ynyl]piperidine-3-carboxylic acid (3R,4R)-4-[3-(R,S)-Fluoro-3-(6-methoxyquinolin-4-yl)propyl]-1-[3-(5-chlorothien-2-yl)prop-2-ynyl]-piperidine-3-carboxylic acid (3R,4R)-4-[3-(R,S)-Fluoro-3-(6-methoxyquinolin-4-yl)propyl]-1-[3-(3-chlorothien-2-yl)prop-2-ynyl]piperidine-3-carboxylic acid (3R,4R)-4-[3-(R,S)-Fluoro-3-(6-methoxyquinolin-4-yl)propyl]-1-[3-(5-methylthien-2-yl)prop-2-ynyl]-piperidine-3-carboxylic acid (3R,4R)-4-[3-(R,S)-Fluoro-3-(6-methoxyquinolin-4-yl)propyl]-1-[3-(3-methylthien-2-yl)prop-2-ynyl]-piperidine-3-carboxylic acid (3R,4R)-4-[3-(R,S)-Fluoro-3-(6-methoxyquinolin-4-yl)propyl]-1-[3-(thien-3-yl)prop-2-ynyl]piperidine-3-carboxylic acid (3R,4R)-4-[3-(R,S)-Fluoro-3-(6-methoxyquinolin-4-yl)propyl]-1-[3-(1-methylpyrrol-2-yl)prop-2-ynyl]piperidine-3-carboxylic acid (3R,4R)-4-[3-(R,S)-Fluoro-3-(6-methoxyquinolin-4-yl)propyl]-1-(3-(1-methylpyrrol-3-yl)prop-2-ynyl]-piperidine-3-carboxylic acid (3R,4R)-4-(3-(R,S)-Fluoro-3-(6-methoxyquinolin-4-yl)propyl]-1-[3-(1,3-thiazol-2-yl)prop-2-ynyl]piperidine-3-carboxylic acid (3R,4R)-4-[3-(R,S)-Fluoro-3-(6-methoxyquinolin-4-yl)propyl]-1-[3-(1,3-thiazol-4yl)prop-2-ynyl]piperidine-3-carboxylic acid (3R,4R)-4-[3-(R,S)-Fluoro-3-(6-methoxyquinolin-4-yl)propyl]-1-[3-(1,3-thiazol-5-yl)prop-2-ynyl]piperidine-3-carboxylic acid (3R,4R)-4-[3-(R,S)-Fluoro-3-(6-methoxyquinolin-4-yl)propyl]-1-[3-(1-methylimidazol-2-yl)prop-2-ynyl]-piperidine-3-carboxylic acid (3R,4R)-4-[3-(R,S)-Fluoro-3-(6-methoxyquinolin-4-yl)propyl]-1-[3-(3-methylimidazol-4-yl)prop-2-ynyl]-piperidine-3-carboxylic acid (3R,4R)-4-[3-(R,S)-Fluoro-3-(6-methoxyquinolin-4-yl)propyl]-1-[3-(3-methylpyrazol-4-yl)prop-2-ynyl]piperidine-3-carboxylic acid (3R,4R)-4-[3-(R,S)-Fluoro-3-(6-methoxyquinolin-4-yl)propyl]-1-[3-(oxazol-2-yl)prop-2-ynyl]piperidine-3-carboxylic acid (3R,4R)-4-[3-(R,S)-Fluoro-3-(6-methoxyquinolin-4-yl)propyl]- 1-[3-(oxazol-4-yl)prop-2-ynyl]piperidine-3-carboxylic acid (3R,4R)-4-[3-(R,S)-Fluoro-3-(6-methoxyquinolin-4-yl)propyl]-1-[3-(oxazol-5-yl)prop-2-ynyl]piperidine-3-carboxylic acid (3R,4R)-4-[3-(R,S)-Fluoro-3-(6-methoxyquinolin-4-yl)propyl]-1-[3-(pyridin-2yl)prop-2-ynyl]piperidine-3-carboxylic acid (3R,4R)-4-[3-(R,S)-Fluoro-3-(6-methoxyquinolin-4-yl)propyl]-1-[3-(pyridin-3-yl)prop-2-ynyl]piperidine-3-carboxylic acid (3R,4R)-4-[3-(R,S)-Fluoro-3-(6-methoxyquinolin-4-yl)propyl]-1-[3-(pyridin-2-yl)prop-2-ynyl]piperidine-3-carboxylic acid (3R,4R)-4-[3-(R,S)-Fluoro-3-(6-methoxyquinolin-4-yl)propyl]-1-[3-(pyrimidin-2-yl)prop-2-ynyl]piperidine-3-carboxylic acid (3R,4R)-4-[3-(R,S)-Fluoro-3-(6-methoxyquinolin-4-yl)propyl]-1-[3-(pyrimidin-4-yl)prop-2-ynyl]piperidine-3-carboxylic acid (3R,4R)-4-[3-(R,S)-Fluoro-3-(6-methoxyquinolin-4-yl)propyl]-1-[3-(pyrimidin-5-yl)prop-2-ynyl]piperidine-3-carboxylic acid (3R,4R)-4-[3-(R,S)-Fluoro-3-(6-methoxyquinolin-4-yl)propyl]-1-[3-(pyrazin-2-yl)prop-2-ynyl]piperidine-3-carboxylic acid (3R,4R)-4-[3-(R,S)-Fluoro-3-(6-methoxyquinolin-4-yl)propyl]-1-(3-(pyridazin-3-yl)prop-2-ynyl]piperidine-3-carboxylic acid (3R,4R)-4-[3-(R,S)-Fluoro-3-(6-methoxyquinolin-4-yl)propyl]-1-[3-(pyridazin-4-yl)prop-2-ynyl]piperidine-3-carboxylic acid (3R,4R)-4-[3-(R,S)-Fluoro-3-(6-methoxyquinolin-4-yl)propyl]-1-[3-phenylpropen-2-yl]piperidine-3-carboxylic acid (3R,4R)-4-[3-(R,S)-Fluoro-3-(6-methoxyquinolin-4-yl)propyl]-1-[4-phenylbuten-3-yl]piperidine-3-carboxylic acid (3R,4R)-4-[3-(6-Methoxyquinolin-4-yl)propyl]-1-[4-phenylbutyl]piperidine-3-acetic acid (3R,4R)-4-[3-(6-Methoxyquinolin-4-yl)propyl]-1-[3-(2-fluorophenyl)propyl]piperidine-3-acetic acid (3R,4R)-4-[3-(6-Methoxyquinolin-4-yl)propyl]-1-[4-(2-fluorophenyl)butyl]piperidine-3-acetic acid (3R,4R)-4-[3-(6-Methoxyquinolin-4-yl)propyl]-1-[3-(3-fluorophenyl)propyl]piperidine-3-acetic acid (3R,4R)-4-[3-(6-Methoxyquinolin-4-yl)propyl]-1-[4-(3-fluorophenyl)butyl]piperidine-3-acetic acid (3R,4R)-4-[3-(6-Methoxyquinolin-4-yl)propyl]-1-[3-(4-fluorophenyl)propyl]piperidine-3-acetic acid (3R,4R)-4-[3-(6-Methoxyquinolin-4-yl)propyl]-1-[4-(4-fluorophenyl)butyl]piperidine-3-acetic acid (3R,4R)-4-[3-(6-Methoxyquinolin-4-yl)propyl]1-[3-(2,3-difluorophenyl)propyl]piperdine-3-acetic acid (3R,4R)-4-[3-(6-Methoxyquinolin-4-yl)propyl]-1-[4-(2,3-difluorophenyl)butyl]piperidine-3-acetic acid (3R,4R)-4-[3-(6-Methoxyquinolin-4-yl)propyl]-1-[3-(2,6-difluorophenyl)propyl]piperidine-3-acetic acid (3R,4R)-4-[3-(6-Methoxyquinolin-4-yl)propyl]-1-[4-(2,6-difluorophenyl)butyl]piperidine-3-acetic acid (3R,4R)-4-[3-(6-Methoxyquinolin-4-yl)propyl]-1-[3-(2-chlorophenyl)propyl]piperidine-3-acetic acid (3R,4R)-4-[3-(6-Methoxyquinolin-4-yl)propyl]-1-[4-(2-chlorophenyl)butyl]piperidine-3-acetic acid (3R,4R)-4-[3-(6-Methoxyquinolin-4-yl)propyl]-1-[3-(3-chlorophenyl)propyl]piperidine-3-acetic acid (3R,4R)-4-[3-(6-Methoxyquinolin-4-yl)propyl]-1-[4-(3-chlorophenyl)butyl]piperidine-3-acetic acid (3R,4R)-4-[3-(6-Methoxyquinolin-4-yl)propyl]-1-[3-(4-chlorophenyl)propyl]piperidine-3-acetic acid (3R,4R)-4-[3-(6-Methoxyquinolin-4-yl)propyl]-1-[4-(4-chlorophenyl)butyl]piperidine-3-acetic acid (3R,4R)-4-[3-(6-Methoxyquinolin-4-yl)propyl]-1-[3-(2,3-dichlorophenyl)propyl]piperidine-3-acetic acid (3R,4R)-4-[3-(6-Methoxyquinolin-4-yl)propyl]-1-[4-(2,3-dichlorophenyl)butyl]piperidine-3-acetic acid (3R,4R)-4-[3-(6-Methoxyquinolin-4-yl)propyl]-1-[3-(2,6-dichlorophenyl)propyl]piperidine-3-acetic acid (3R,4R)-4-[3-(6-Methoxyquinolin-4-yl)propyl]-1-[4-(2,6-dichlorophenyl)butyl]piperidine-3-acetic acid (3R,4R)-4-[3-(6-Methoxyquinolin-4-yl)propyl]-1-[3-(2-methylphenyl)propyl]piperidine-3-acetic acid (3R,4R)-4-[3-(6-Methoxyquinolin-4-yl)propyl]-1-[4-(2-methylphenyl)butyl]piperidine-3-acetic acid (3R,4R)-4-[3-(6-Methoxyquinolin-4-yl)propyl]-1-[5-(2-methylphenyl)pentyl]piperidine-3-acetic acid (3R,4R)-4-[3-(6-Methoxyquinolin-4-yl)propyl]-1-[3-(3-methylphenyl)propyl]piperidine-3-acetic acid (3R,4R)-4-[3-(6-Methoxyquinolin-4-yl)propyl]-1-[4-(3-methylphenyl)butyl]piperidine-3-acetic acid (3R,4R)-4-[3-(6-Methoxyquinolin-4-yl)propyl]-1-[3-(4-methylphenyl)propyl]piperidine-3-acetic acid (3R,4R)-4-[3-(6-Methoxyquinolin-4-yl)propyl]-1-[4-(4-methylphenyl)butyl]piperidine-3-acetic acid (3R,4R)-4-[3-(6-Methoxyquinolin-4-yl)propyl]-1-[3-(2-methoxyphenyl)propyl]piperidine-3-acetic acid (3R,4R)-4-[3-(6-Methoxyquinolin-4-yl)propyl]-1-[4-(2-methoxyphenyl)butyl]piperidine-3-acetic acid (3R,4R)-4-[3-(6-Methoxyquinolin-4-yl)propyl]-1-[3-(3-methoxyphenyl)propyl]piperidine-3-acetic acid (3R,4R)-4-[3-(6-Methoxyquinolin-4-yl)propyl]-1-[4-(3-methoxyphenyl)butyl]piperidine-3-acetic acid (3R,4R)-4-[3-(6-Methoxyquinolin-4-yl)propyl]-1-[3-(4-methoxyphenyl)propyl]piperidine-3-acetic acid (3R,4R)-4-[3-(6-Methoxyquinolin-4-yl)propyl]-1-[4-(4-methoxyphenyl)butyl]piperidine-3-acetic acid (3R,4R)-4-[3-(6-Methoxyquinolin-4-yl)propyl]-1-[3-(2-trifluoromethylphenyl)propyl]piperidine-3-acetic acid
(3R,4R)-4-[3-(6-Methoxyquinolin-4-yl)propyl]-1-[4-(2-trifluoromethylphenyl)butyl]piperidine-3-acetic acid
(3R,4R)-4-[3-(6-Methoxyquinolin-4-yl)propyl]-1-[3-(3-trifluoromethylphenyl)propyl]piperidine-3-acetic acid
(3R,4R)-4-[3-(6-Methoxyquinolin-4-yl)propyl]-1-[4-(3-trifluoromethylphenyl)butyl]piperidine-3-acetic acid
(3R,4R)-4-[3-(6-Methoxyquinolin-4-yl)propyl]-1-[3-(4-trifluoromethylphenyl)propyl]piperidine-3-acetic acid
(3R,4R)-4-[3-(6-Methoxyquinolin-4-yl)propyl]-1-[4-(4-trifluoromethylphenyl)butyl]piperidine-3-acetic acid
(3R,4R)-4-[3-(6-Methoxyquinolin-4-yl)propyl]-1-[2-phenylthioethyl]piperidine-3-acetic acid
(3R,4R)-4-[3-(6-Methoxyquinolin-4-yl)propyl]-1-[3-phenylthiopropyl]piperidine-3-acetic acid
(3R,4R)-4-[3-(6-Methoxyquinolin-4-yl)propyl]-1-[2-(2-fluorophenylthio)ethyl]piperidine-3-acetic acid
(3R,4R)-4-[3-(6-Methoxyquinolin-4-yl)propyl]-1-[3-(2-fluorophenylthio)propyl]piperidine-3-acetic acid
(3R,4R)-4-[3-(6-Methoxyquinolin-4-yl)propyl]-1-[3-(3-fluorophenylthio)propyl]piperidine-3-acetic acid
(3R,4R)-4-[3-(6-Methoxyquinolin-4-yl)propyl]-1-[2-(4-fluorophenylthio)ethyl]piperidine-3-acetic acid
(3R,4R)-4-[3-(6-Methoxyquinolin-4-yl)propyl]-1-[3-(4-fluorophenylthio)propyl]piperidine-3-acetic acid
(3R,4R)-4-[3-(6-Methoxyquinolin-4-yl)propyl]-1-[2-(2,3-difluorophenylthio)ethyl]piperidine-3-acetic acid
(3R,4R)-4-[3-(6-Methoxyquinolin-4-yl)propyl]-1-[3-(2,3-difluorophenylthio)propyl]piperidine-3-acetic acid
(3R,4R)-4-[3-(6-Methoxyquinolin-4-yl)propyl]-1-[2-(2,6-difluorophenylthio)ethyl]piperidine-3-acetic acid
(3R,4R)-4-[3-(6-Methoxyquinolin-4-yl)propyl]-1-[3-(2,6-difluorophenylthio)propyl]piperidine-3-acetic acid
(3R,4R)-4-[3-(6-Methoxyquinolin-4-yl)propyl]-1-[2-(2-chlorophenylthio)ethyl]piperidine-3-acetic acid
(3R,4R)-4-[3-(6-Methoxyquinolin-4-yl)propyl]-1-[3-(2-chlorophenylthio)propyl]piperidine-3-acetic acid
(3R,4R)-4-[3-(6-Methoxyquinolin-4-yl)propyl]-1-[2-(3-chlorophenylthio)ethyl]piperidine-3-acetic acid
(3R,4R)-4-[3-(6-Methoxyquinolin-4-yl)propyl]-1-[3-(3-chlorophenylthio)propyl]piperidine-3-acetic acid
(3R,4R)-4-[3-(6-Methoxyquinolin-4-yl)propyl]-1-[2-(4-chlorophenylthio)ethyl]piperidine-3-acetic acid
(3R,4R)-4-[3-(6-Methoxyquinolin-4-yl)propyl]-1-[3-(4-chlorophenylthio)propyl]piperidine-3-acetic acid
(3R,4R)-4-[3-(6-Methoxyquinolin-4-yl)propyl]-1-[2-(2,3-dichlorophenylthio)ethyl]piperidine-3-acetic acid
(3R,4R)-4-[3-(6-Methoxyquinolin-4-yl)propyl]-1-[3-(2,3-dichlorophenylthio)propyl]piperidine-3-acetic acid
(3R,4R)-4-[3-(6-Methoxyquinolin-4-yl)propyl]-1-[2-(2,6-dichlorophenylthio)ethyl]piperidine-3-acetic acid
(3R,4R)-4-[3-(6-Methoxyquinolin-4-yl)propyl]-1-[3-(2,6-dichlorophenylthio)propyl]piperidine-3-acetic acid
(3R,4R)-4-[3-(6-Methoxyquinolin-4-yl)propyl]-1-[2-(2-methylphenylthio)ethyl]piperidine-3-acetic acid
(3R,4R)-4-[3-(6-Methoxyquinolin-4-yl)propyl]-1-[3-(2-methylphenylthio)propyl]piperidine-3-acetic acid
(3R,4R)-4-[3-(6-Methoxyquinolin-4-yl)propyl]-1-[2-(3-methylphenylthio)ethyl]piperidine-3-acetic acid
(3R,4R)-4-[3-(6-Methoxyquinolin-4-yl)propyl]-1-[3-(3-methylphenylthio)propyl]piperidine-3-acetic acid
(3R,4R)-4-[3-(6-Methoxyquinolin-4-yl)propyl]-1-[2-(4-methylphenylthio)ethyl]piperidine-3-acetic acid
(3R,4R)-4-[3-(6-Methoxyquinolin-4-yl)propyl]-1-[3-(4-methylphenylthio)propyl]piperidine-3-acetic acid
(3R,4R)-4-[3-(6-Methoxyquinolin-4-yl)propyl]-1-[2-(2-trifluoromethylphenylthio)ethyl]piperidine-3-acetic acid
(3R,4R)-4-[3-(6-Methoxyquinolin-4-yl)propyl]-1-[3-(2-trifluoromethylphenylthio)propyl]piperidine-3-acetic acid
(3R,4R)-4-[3-(6-Methoxyquinolin-4-yl)propyl]-1-[2-(3-trifluoromethylphenylthio)ethyl]piperidine-3-acetic acid
(3R,4R)-4-[3-(6-Methoxyquinolin-4-yl)propyl]-1-[3-(3-trifluoromethylphenylthio)propyl]piperidine-3-acetic acid
(3R,4R)-4-[3-(6-Methoxyquinolin-4-yl)propyl]-1-[2-(4-trifluoromethylphenylthio)ethyl]piperidine-3-acetic acid
(3R,4R)-4-[3-(6-Methoxyquinolin-4-yl)propyl]-1-[3-(4-trifluoromethylphenylthio)propyl]piperidine-3-acetic acid
(3R,4R)-4-[3-(6-Methoxyquinolin-4-yl)propyl]-1-[2-(2-methoxyphenylthio)ethyl]piperidine-3-acetic acid
(3R,4R)-4-[3-(6-Methoxyquinolin-4-yl)propyl]-1-[3-(2-methoxyphenylthio)propyl]piperidine-3-acetic acid
(3R,4R)-4-[3-(6-Methoxyquinolin-4-yl)propyl]-1-[2-(3-methoxyphenylthio)ethyl]piperidine-3-acetic acid
(3R,4R)-4-[3-(6-Methoxyquinolin-4-yl)propyl]-1-[3-(3-methoxyphenylthio)propyl]piperidine-3-acetic acid
(3R,4R)-4-[3-(6-Methoxyquinolin-4-yl)propyl]-1-[2-(4-methoxyphenylthio)ethyl]piperidine-3-acetic acid
(3R,4R)-4-[3-(6-Methoxyquinolin-4-yl)propyl]-1-[3-(4-methoxyphenylthio)propyl]piperidine-3-acetic acid
(3R,4R)-4-[3-(6-Methoxyquinolin-4-yl)propyl]-1-[cyclopropylmethyl]piperidine-3-acetic acid
(3R,4R)-4-[3-(6-Methoxyquinolin-4-yl)propyl]-1-[2-(cyclopropyl)ethyl]piperidine-3acetic acid
(3R,4R)-4-[3-(6-Methoxyquinolin-4-yl)propyl]-1-[cyclobutylmethyl]piperidine-3-acetic acid
(3R,4R)-4-[3-(6-Methoxyquinolin-4-yl)propyl]-1-[2-(cyclobutyl)ethyl]piperidine-3acetic acid
(3R,4R)-4-[3-(6-Methoxyquinolin-4-yl)propyl]-1-[cyclopentylmethyl]piperidine-3-acetic acid
(3R,4R)-4-[3-(6-Methoxyquinolin-4-yl)propyl]-1-[2-(cyclopentyl)ethyl]piperidine-3acetic acid
(3R,4R)-4-[3-(6-Methoxyquinolin-4-yl)propyl]-1-[cyclohexylmethyl]piperidine-3-acetic acid
(3R,4R)-4-[3-(6-Methoxyquinolin-4-yl)propyl]-1-[2-(cyclohexyl)ethyl]piperidine-3acetic acid
(3R,4R)-4-[3-(6-Methoxyquinolin-4-yl)propyl]-1-[2-(cyclopropylthio)ethyl]piperidine-3-acetic acid
(3R,4R)-4-[3-(6-Methoxyquinolin-4-yl)propyl]-1-[3-(cyclopropylthiopropyl]piperidine-3-acetic acid
(3R,4R)-4-[3-(6-Methoxyquinolin-4-yl)propyl]-1-[2-(cyclobutylthio)ethyl]piperidine-3-acetic acid
(3R,4R)-4-[3-(6-Methoxyquinolin-4-yl)propyl]-1-[3-(cyclobutylthio)propyl]piperidine-3-acetic acid
(3R,4R)-4-[3-(6-Methoxyquinolin-4-yl)propyl]-1-[2-(cyclopentylthio)ethyl]piperidine-3-acetic acid
(3R,4R)-4-[3-(6-Methoxyquinolin-4-yl)propyl]-1-[3-(cyclopentylthio)propyl]piperidine-3-acetic acid
(3R,4R)-4-[3-(6-Methoxyquinolin-4-yl)propyl]-1-[3-(cyclohexylthio)propyl]piperidine-3-acetic acid
(3R,4R)-4-[3-(6-Methoxyquinolin-4-yl)propyl]-1-[2-methylthioethyl]piperidine-3-acetic acid
(3R,4R)-4-[3-(6-Methoxyquinolin-4-yl)propyl]-1-[3-methylthiopropyl]piperidine-3-acetic acid
(3R,4R)-4-[3-(6-Methoxyquinolin-4-yl)propyl]-1-[2-ethylthioethyl]piperidine-3-acetic acid
(3R,4R)-4-[3-(6-Methoxyquinolin-4-yl)propyl]-1-[3-ethylthiopropyl]piperidine-3-acetic acid
(3R,4R)-4-[3-(6-Methoxyquinolin-4-yl)propyl]-1-[2-(n-propylthio)ethyl]piperidine-3-acetic acid
(3R,4R)-4-[3-(6-Methoxyquinolin-4-yl)propyl]-1-[3-(n-propylthio)propyl]piperidine-3-acetic acid (3R,4R)-4-[3-(6-Methoxyquinolin-4-yl)propyl]-1-[2-(n-butylthio)ethyl]piperidine-3-acetic acid
(3R,4R)-4-[3-(6-Methoxyquinolin-4-yl)propyl]-1-[3-(n-butylthio)propyl]piperidine-3-acetic acid
(3R,4R)-4-[3-(6-Methoxyquinolin-4-yl)propyl]-1-[3-(thien-2-yl)propyl]piperidine-3-acetic acid
(3R,4R)-4-[3-(6-Methoxyquinolin-4-yl)propyl]-1-[4-(thien-2-yl)butyl]piperidine-3-acetic acid
(3R,4R)-4-[3-(6-Methoxyquinolin-4-yl)propyl]-1-[3-(thien-2-yl)thiopropyl]piperidine-3-acetic acid
(3R,4R)-4-[3-(6-Methoxyquinolin-4-yl)propyl]-1-[3-(5-chlorothien-2-yl)propyl]piperidine-3-acetic acid
(3R,4R)-4-[3-(6-Methoxyquinolin-4-yl)propyl]-1-[4-(5-chlorothien-2-yl)butyl]piperidine-3-acetic acid
(3R,4R)-4-[3-(6-Methoxyquinolin-4-yl)propyl]-1-[2-(5-chlorothien-2-yl)thioethyl]piperidine-3-acetic acid
(3R,4R)-4-[3-(6-Methoxyquinolin-4-yl)propyl]-1-[3-(5-chlorothien-2-yl)thiopropyl]piperidine-3-acetic acid
(3R,4R)-4-[3-(6-Methoxyquinolin-4-yl)propyl]-1-[3-(3-chlorothien-2-yl)propyl]piperidine-3-acetic acid
(3R,4R)-4-[3-(6-Methoxyquinolin-4-yl)propyl]-1-[4-(3-chlorothien-2-yl)butyl]piperidine-3-acetic acid
(3R,4R)-4-[3-(6-Methoxyquinolin-4-yl)propyl]-1-[2-(3-chlorothien-2-yl)thioethyl]piperidine-3-acetic acid
(3R,4R)-4-[3-(6-Methoxyquinolin-4-yl)propyl]-1-[3-(3-chlorothien-2-yl)thiopropyl]piperidine-3-acetic acid
(3R,4R)-4-[3-(6-Methoxyquinolin-4-yl)propyl]-1-[3-(5-methylthien-2-yl)propyl]piperidine-3-acetic acid
(3R,4R)-4-[3-(6-Methoxyquinolin-4-yl)propyl]-1-[4-(5-methylthien-2-yl)butyl]piperidine-3-acetic acid
(3R,4R)-4-[3-(6-Methoxyquinolin-4-yl)propyl]-1-[2-(5-methylthien-2-yl)thioethyl]piperidine-3-acetic acid
(3R,4R)-4-[3-(6-Methoxyquinolin-4-yl)propyl]-1-[3-(5-methylthien-2-yl)thiopropyl]piperidine-3-acetic acid
(3R,4R)-4-[3-(6-Methoxyquinolin-4-yl)propyl]-1-[3-(3-methylthien-2-yl)propyl]piperidine-3-acetic acid
(3R,4R)-4-[3-(6-Methoxyquinolin-4-yl)propyl]-1-[4-(3-methylthien-2-yl)butyl]piperidine-3-acetic acid
(3R,4R)-4-[3-(6-Methoxyquinolin-4-yl)propyl]-1-[2-(3-methylthien-2-yl)thioethyl]piperidine-3-acetic acid
(3R,4R)-4-[3-(6-Methoxyquinolin-4-yl)propyl]-1-[3-(3-methylthien-2-yl)thiopropyl]piperidine-3-acetic acid
(3R,4R)-4-[3-(6-Methoxyquinolin-4-yl)propyl]-1-[3-(thien-3-yl)propyl]piperidine-3-acetic acid
(3R,4R)-4-[3-(6-Methoxyquinolin-4-yl)propyl]-1-[4-(thien-3-yl)butyl]piperidine-3-acetic acid
(3R,4R)-4-[3-(6-Methoxyquinolin-4-yl)propyl]-1-[2-(thien-3-yl)thioethyl]piperidine-3-acetic acid
(3R,4R)-4-[3-(6-Methoxyquinolin-4-yl)propyl]-1-[3-(thien-3-yl)thiopropyl]piperidine-3-acetic acid
(3R,4R)-4-[3-(6-Methoxyquinolin-4-yl)propyl]-1-[3-(fur-2-yl)propyl]piperidine-3-acetic acid
(3R,4R)-4-[3-(6-Methoxyquinolin-4-yl)propyl]-1-[4-(fur-2-yl)butyl]piperidine-3-acetic acid
(3R,4R)-4-[3-(6-Methoxyquinolin-4-yl)propyl]-1-[2-(fur-2-yl)thioethyl]piperidine-3-acetic acid
(3R,4R)-4-[3-(6-Methoxyquinolin-4-yl)propyl]-1-[3-(fur-2-yl)thiopropyl]piperidine-3-acetic acid
(3R,4R)-4-[3-(6-Methoxyquinolin-4-yl)propyl]-1-[3-(fur-3-yl)propyl]piperidine-3-acetic acid
(3R,4R)-4-[3-(6-Methoxyquinolin-4-yl)propyl]-1-[4-(fur-3-yl)butyl]piperidine-3-acetic acid
(3R,4R)-4-[3-(6-Methoxyquinolin-4-yl)propyl]-1-[2-(fur-3-yl)thioethyl]piperidine-3-acetic acid
(3R,4R)-4-[3-(6-Methoxyquinolin-4-yl)propyl]-1-[3-(fur-3-yl)thiopropyl]piperidine-3-acetic acid
(3R,4R)-4-[3-(6-Methoxyquinolin-4-yl)propyl]-1-[3-(1-methylpyrrol-2-yl)propyl]piperidine-3-acetic acid
(3R,4R)-4-[3-(6-Methoxyquinolin-4-yl)propyl]-1-[4-(1-methylpyrrol-2-yl)butyl]piperidine-3-acetic acid
(3R,4R)-4-[3-(6-Methoxyquinolin-4-yl)propyl]-1-[2-(1-methylpyrrol-2-yl)thioethyl]piperidine-3-acetic acid
(3R,4R)-4-[3-(6-Methoxyquinolin-4-yl)propyl]-1-[3-(1-methylpyrrol-2-yl)thiopropyl]piperidine-3-acetic acid
(3R,4R)-4-[3-(6-Methoxyquinolin-4-yl)propyl]-1-[3-(1-methylpyrrol-2-yl)propyl]piperidine-3-acetic acid
(3R,4R)-4-[3-(6-Methoxyquinolin-4-yl)propyl]-1-[4-(1-methylpyrrol-3-yl)butyl]piperidine-3-acetic acid
(3R,4R)-4-[3-(6-Methoxyquinolin-4-yl)propyl]-1-[2-(1-methylpyrrol-3-yl)thioethyl]piperidine-3-acetic acid
(3R,4R)-4-[3-(6-Methoxyquinolin-4-yl)propyl]-1-[3-(1-methylpyrrol-3-yl)thiopropyl]piperidine-3-acetic acid
(3R,4R)-4-[3-(6-Methoxyquinolin-4-yl)propyl]-1-[3-(thiazol-2-yl)propyl]piperidine-3-acetic acid
(3R,4R)-4-[3-(6-Methoxyquinolin-4-yl)propyl]-1-[4-(thiazol-2-yl)butyl]piperidine-3-acetic acid
(3R,4R)-4-[3-(6-Methoxyquinolin-4-yl)propyl]-1-[2-(thiazol-2-yl)thioethyl]piperidine-3-acetic acid
(3R,4R)-4-[3-(6-Methoxyquinolin-4-yl)propyl]-1-[3-(thiazol-2-yl)thiopropyl]piperidine-3-acetic acid
(3R,4R)-4-[3-(6-Methoxyquinolin-4-yl)propyl]-1-[3-(1-methylimidazol-2-yl)propyl]piperidine-3-acetic acid
(3R,4R)-4-[3-(6-Methoxyquinolin-4-yl)propyl]-1-[4-(1-methylimidazol-2-yl)butyl]piperidine-3-acetic acid
(3R,4R)-4-[3-(6-Methoxyquinolin-4-yl)propyl]-1-[2-(1-methylimidazol-2-yl)thioethyl]piperidine-3-acetic acid
(3R,4R)-4-[3-(6-Methoxyquinolin-4-yl)propyl]-1-[3-(1-methylimidazol-2-yl)thiopropyl]piperidine-3-acetic acid
(3R,4R)-4-[3-(6-Methoxyquinolin-4-yl)propyl]-1-[3-(3-methylimidazol4-yl)propyl]piperidine-3-acetic acid
(3R,4R)-4-[3-(6-Methoxyquinolin-4-yl)propyl]-1-[4-(3-methylimidazol-4-yl)butyl]piperidine-3-acetic acid
(3R,4R)-4-[3-(6-Methoxyquinolin-4-yl)propyl]-1-[2-(3-methylimidazol4-yl)thioethyl]piperidine-3-acetic acid
(3R,4R)-4-[3-(6-Methoxyquinolin-4-yl)propyl]-1-[3-(3-methylimidazol-4-yl)thiopropyl]piperidine-3-acetic acid
(3R,4R)-4-[3-(6-Methoxyquinolin-4-yl)propyl]-1-[3-(3-methylpyrazol-4-yl)propyl]piperidine-3-acetic acid
(3R,4R)-4-[3-(6-Methoxyquinolin-4-yl)propyl]-1-[4-(3-methylpyrazol-4-yl)butyl]piperidine-3-acetic acid
(3R,4R)-4-[3-(6-Methoxyquinolin-4-yl)propyl]-1-[2-(3-methylpyrazol-4-yl)thioethyl]piperidine-3-acetic acid
(3R,4R)-4-[3-(6-Methoxyquinolin-4-yl)propyl]-1-[3-(3-methylpyrazol-4-yl)thiopropyl]piperidine-3-acetic acid
(3R,4R)-4-[3-(6-Methoxyquinolin-4-yl)propyl]-1-[3-(oxazol-2-yl)propyl]piperidine-3-acetic acid
(3R,4R)-4-[3-(6-Methoxyquinolin-4-yl)propyl]-1-[4-(oxazol-2-yl)butyl]piperidine-3-acetic acid
(3R,4R)-4-[3-(6-Methoxyquinolin-4-yl)propyl]-1-[2-(oxazol-2-yl)thioethyl]piperidine-3-acetic acid
(3R,4R)-4-[3-(6-Methoxyquinolin-4-yl)propyl]-1-[3-(oxazol-2-yl)thiopropyl]piperidine-3-acetic acid
(3R,4R)-4-[3-(6-Methoxyquinolin-4-yl)propyl]-1-[3-(pyridin-2-yl)propyl]piperidine-3-acetic acid
(3R,4R)-4-[3-(6-Methoxyquinolin-4-yl)propyl]-1-[4-(pyridin-2-yl)butyl]piperidine-3-acetic acid
(3R,4R)-4-[3-(6-Methoxyquinolin-4-yl)propyl]-1-[2-(pyridin-2-yl)thioethyl]piperidine-3-acetic acid
(3R,4R)-4-[3-(6-Methoxyquinolin-4-yl)propyl]-1-[3-(pyridin-2-yl)thiopropyl]piperidine-3-acetic acid
(3R,4R)-4-[3-(6-Methoxyquinolin-4-yl)propyl]-1-[3-(pyridin-3-yl)propyl]piperidine-3-acetic acid
(3R,4R)-4-[3-(6-Methoxyquinolin-4-yl)propyl]-1-[4-(pyridin-3-yl)butyl]piperidine-3-acetic acid (3R,4R)-4-[3-(6-Methoxyquinolin-4-yl)propyl]-1-[2-(pyridin-3-yl)thioethyl]piperidine-3-acetic acid
(3R,4R)-4-[3-(6-Methoxyquinolin-4-yl)propyl]-1-[3-(pyridin-3-yl)thiopropyl]piperidine-3-acetic acid
(3R,4R)-4-[3-(6-Methoxyquinolin-4-yl)propyl]-1-[3-(pyridin-4-yl)propyl]piperidine-3-acetic acid
(3R,4R)-4-[3-(6-Methoxyquinolin-4-yl)propyl]-1-[4-(pyridin-4-yl)butyl]piperidine-3-acetic acid
(3R,4R)-4-[3-(6-Methoxyquinolin-4-yl)propyl]-1-[5-(pyridin-4-yl)pentyl]piperidine-3-acetic acid
(3R,4R)-4-[3-(6-Methoxyquinolin-4-yl)propyl]-1-[2-(pyridin-4-yl)thioethyl]piperidine-3-acetic acid
(3R,4R)-4-[3-(6-Methoxyquinolin-4-yl)propyl]-1-[3-(pyridin-4-yl)thiopropyl]piperidine-3-acetic acid
(3R,4R)-4-[3-(6-Methoxyquinolin-4-yl)propyl]-1-[3-(pyrimidin-2-yl)propyl]piperidine-3-acetic acid
(3R,4R)-4-[3-(6-Methoxyquinolin-4-yl)propyl]-1-[4-(pyrimidin-2-yl)butyl]piperidine-3-acetic acid
(3R,4R)-4-[3-(6-Methoxyquinolin-4-yl)propyl]-1-[2-(pyrimidin-2-yl)thioethyl]piperidine-3-acetic acid
(3R,4R)-4-[3-(6-Methoxyquinolin-4-yl)propyl]-1-[3-(pyrimidin-2-yl)thiopropyl]piperidine-3-acetic acid
(3R,4R)-4-[3-(6-Methoxyquinolin-4-yl)propyl]-1-[3-(pyrimidin-4-yl)propyl]piperidine-3-acetic acid
(3R,4R)-4-[3-(6-Methoxyquinolin-4-yl)propyl]-1-[4-(pyrimidin-3-acetic acid
(3R,4R)-4-[3-(6-Methoxyquinolin-4-yl)propyl]-1-[2-(pyrimidin-4-yl)butyl]piperidine-3-acetic acid
(3R,4R)-4-[3-(6-Methoxyquinolin-4-yl)propyl]-1-[2-(pyrimidin-4-yl)thioethyl]piperidine-3-acetic acid
(3R,4R)-4-[3-(6-Methoxyquinolin-4-yl)propyl]-1-[3-(pyrimidin-4-yl)thiopropyl]piperidine-3-acetic acid
(3R,4R)-4-[3-(6-Methoxyquinolin-4-yl)propyl]-1-[3-(pyrimidin-5-yl)propyl]piperidine-3-acetic acid
(3R,4R)-4-[3-(6-Methoxyquinolin-4-yl)propyl]-1-[4-(pyrimidin-5-yl)butyl]piperidine-3-acetic acid
(3R,4R)-4-[3-(6-Methoxyquinolin-4-yl)propyl]-1-[2-(pyrimidin-5-yl)thioethyl]piperidine-3-acetic acid
(3R,4R)-4-[3-(6-Methoxyquinolin-4-yl)propyl]-1-[3-(pyrimidin-5-yl)thiopropyl]piperidine-3-acetic acid
(3R,4R)-4-[3-(6-Methoxyquinolin-4-yl)propyl]-1-[3-(pyrazin-2-yl)propyl]piperidine-3-acetic acid
(3R,4R)-4-[3-(6-Methoxyquinolin-4-yl)propyl]-1-[4-(pyrazin-2-yl)butyl]piperidine-3-acetic acid
(3R,4R)-4-[3-(6-Methoxyquinolin-4-yl)propyl]-1-[2-(pyrazin-2-yl)thioethyl]piperidine-3-acetic acid
(3R,4R)-4-[3-(6-Methoxyquinolin-4-yl)propyl]-1-[3-(pyrazin-2-yl)thiopropyl]piperidine-3-acetic acid
(3R,4R)-4-[3-(6-Methoxyquinolin-4-yl)propyl]-1-[3-(pyridazin-3-yl)propyl]piperidine-3-acetic acid
(3R,4R)-4-[3-(6-Methoxyquinolin-4-yl)propyl]-1-[4-(pyridazin-3-yl)butyl]piperidine-3-acetic acid
(3R,4R)-4-[3-(6-Methoxyquinolin-4-yl)propyl]-1-[2-(pyridazin-3-yl)thioethyl]piperidine-3-acetic acid
(3R,4R)-4-[3-(6-Methoxyquinolin-4-yl)propyl]-1-[3-(pyridazin-3-yl)thiopropyl]piperidine-3-acetic acid
(3R,4R)-4-[3-(6-Methoxyquinolin-4-yl)propyl]-1-[3-(pyridazin-4-yl)propyl]piperidine-3-acetic acid
(3R,4R)-4-[3-(6-Methoxyquinolin-4-yl)propyl]-1-[4-(pyridazin4-yl)butyl]piperidine-3-acetic acid
(3R,4R)-4-[3-(6-Methoxyquinolin-4-yl)propyl]-1-[2-(pyridazin-4-yl)thioethyl]piperidine-3-acetic acid
(3R,4R)-4-[3-(6-Methoxyquinolin-4-yl)propyl]-1-[3-(pyridazin-4-yl)thiopropyl]piperidine-3-acetic acid
(3R,4R)-4-[3-(6-Methoxyquinolin-4-yl)propyl]-1-[3-phenylprop-2-ynyl]piperidine-3-acetic acid
(3R,4R)-4-[3-(6-Methoxyquinolin-4-yl)propyl]-1-[3-(2-fluorophenyl)prop-2-ynyl]piperidine-3-acetic acid
(3R,4R)-4-[3-(6-Methoxyquinolin-4-yl)propyl]-1-[3-(3-fluorophenyl)prop-2-ynyl]piperidine-3-acetic acid
(3R,4R)-4-[3-(6-Methoxyquinolin-4-yl)propyl]-1-[3-(4-fluorophenyl)prop-2-ynyl]piperidine-3-acetic acid
(3R,4R)-4-[3-(6-Methoxyquinolin-4-yl)propyl]-1-[3-(2-chlorophenyl)prop-2-ynyl]piperidine-3-acetic acid
(3R,4R)-4-[3-(6-Methoxyquinolin-4-yl)propyl]-1-[3-(3-chlorophenyl)prop-2-ynyl]piperidine-3-acetic acid
(3R,4R)-4-[3-(6-Methoxyquinolin-4-yl)propyl]-1-[3-(4-chlorophenyl)prop-2-ynyl]piperidine-3-acetic acid
(3R,4R)-4-[3-(6-Methoxyquinolin-4-yl)propyl]-1-[3-(2-methylphenyl)prop-2-ynyl]piperidine-3-acetic acid
(3R,4R)-4-[3-(6-Methoxyquinolin-4-yl)propyl]-1-[3-(3-methylphenyl)prop-2-ynyl]piperidine-3-acetic acid
(3R,4R)-4-[3-(6-Methoxyquinolin-4-yl)propyl]-1-[3-(4-methylphenyl)prop-2-ynyl]piperidine-3-acetic acid
(3R,4R)-4-[3-(6-Methoxyquinolin-4-yl)propyl]-1-[3-(2-(trifluoromethyl)phenyl)prop-2-ynyl]piperidine-3-acetic acid
(3R,4R)-4-[3-(6-Methoxyquinolin-4-yl)propyl]-1-[3-(3-(trifluoromethyl)phenyl)prop-2-ynyl]piperidine-3-acetic acid
(3R,4R)-4-[3-(6-Methoxyquinolin-4-yl)propyl]-1-[3-(4-(trifluoromethyl)phenyl)prop-2-ynyl]piperidine-3-acetic acid
(3R,4R)-4-[3-(6-Methoxyquinolin-4-yl)propyl-1-[3-(2-methoxyphenyl)prop-2-ynyl]piperidine-3-acetic acid
(3R,4R)-4-[3-(6-Methoxyquinolin-4-yl)propyl]-1-[3-(3-methoxyphenyl)prop-2-ynyl]piperidine-3-acetic acid
(3R,4R)-4-[3-(6-Methoxyquinolin-4-yl)propyl]-1-[3-(4-methoxyphenyl)prop-2-ynyl]piperidine-3-acetic acid
(3R,4R)-4-[3-(6-Methoxyquinolin-4-yl)propyl]-1-[3-(3,4-difluorophenyl)prop-2-ynyl]piperidine-3-acetic acid
(3R,4R)-4-[3-(6-Methoxyquinolin-4-yl)propyl]-1-[3-(2,4-difluorophenyl)prop-2-ynyl]piperidine-3-acetic acid
(3R,4R)-4-[3-(6-Methoxyquinolin-4-yl)propyl]-1-[3-(3,4-dichlorophenyl)prop-2-ynyl]piperidine-3-acetic acid
(3R,4R)-4-[3-(6-Methoxyquinolin-4-yl)propyl]-1-[3-(2,3-dichlorophenyl)prop-2-ynyl]piperidine-3-acetic acid
(3R,4R)-4-[3-(6-Methoxyquinolin-4-yl)propyl]-1-[3-(2,4-dichlorophenyl)prop-2-ynyl]piperidine-3-acetic acid
(3R,4R)-4-[3-(6-Methoxyquinolin-4-yl)propyl]-1-[3-(2,4,6-trichlorophenyl)prop-2-ynyl]piperidine-3-acetic acid
(3R,4R)-4-[3-(6-Methoxyquinolin-4-yl)propyl]-1-[3-(3,5-dichlorophenyl)prop-2-ynyl]piperidine-3-acetic acid
(3R,4R)-4-[3-(6-Methoxyquinolin-4-yl)propyl]-1-[3-(4-chloro-3-fluorophenyl)prop-2ynyl]-piperidine-3-acetic acid
(3R,4R)-4-[3-(6-Methoxyquinolin-4-yl)propyl]-1-[3-(3-chloro-4-fluorophenyl)prop-2ynyl]-piperidine-3-acetic acid
(3R,4R)-4-[3-(6-Methoxyquinolin-4-yl)propyl]-1-[3-(2-chloro4-fluorophenyl)prop-2ynyl]-piperidine-3-acetic acid
(3R,4R)-4-[3-(6-Methoxyquinolin-4-yl)propyl]-1-[3-(3-chloro-5-fluorophenyl)prop-2ynyl]-piperidine-3-acetic acid
(3R,4R)-4-[3-(6-Methoxyquinolin-4-yl)propyl]-1-[3-(4-chloro-2-fluorophenyl)prop-2ynyl]-ynyl]piperidine-3-acetic acid
(3R,4R)-4-[3-(6-Methoxyquinolin-4-yl)propyl]-1-[3-(3-fluoro-4-methylphenyl)prop-2ynyl]-piperidine-3-acetic acid
(3R,4R)-4-[3-(6-Methoxyquinolin-4-yl)propyl]-1-[3-(4-chloro-3-(trifluoromethyl)phenyl)prop-2-ynyl]-piperidine-3-acetic acid
(3R,4R)-4-[3-(6-Methoxyquinolin-4-yl)propyl]-1-[3-(2-chloro-4-(trifluoromethyl)phenyl)prop-2-ynyl]-piperidine-3-acetic acid (3R,4R)-4-[3-(6-Methoxyquinolin-4-yl)propyl]-1-[3-(2-chloro-5-(trifluoromethyl)phenyl)prop-2-ynyl]-piperidine-3-acetic acid (3R,4R)-4-[3-(6-Methoxyquinolin-4-yl)propyl]-1-[3-(5-chloro-2-methoxyphenyl)prop-2-ynyl]piperidine-3-acetic acid (3R,4R)-4-[3-(6-Methoxyquinolin-4-yl)propyl]-1-[3-(3,5-bis(trifluoromethyl)phenyl)prop-2-ynyl]piperidine-3-acetic acid (3R,4R)-4-[3-(6-Methoxyquinolin-4-yl)propyl]-1-[3-(3,5-dimethylphenyl)prop-2-ynyl]piperidine-3-acetic acid (3R,4R)-4-[3-(6-Methoxyquinolin-4-yl)propyl]-1-[3-(2,4-dichloro-6-methylphenyl)prop-2-ynyl]piperidine-3-acetic acid (3R,4R)-4-[3-(6-Methoxyquinolin-4-yl)propyl]-1-[3-(5-chlorothien-2-yl)prop-2-ynyl]piperidine-3-acetic acid (3R,4R)-4-[3-(6-Methoxyquinolin-4-yl)propyl]-1-[3-(3-chlorothien-2-yl)prop-2-ynyl]piperidine-3-acetic acid (3R,4R)-4-[3-(6-Methoxyquinolin-4-yl)propyl]-1-[3-(5-methylthien-2-yl)prop-2-ynyl]piperidine-3-acetic acid (3R,4R)-4-[3-(6-Methoxyquinolin-4-yl)propyl]-1-[3-(3-methylthien-2-yl)prop-2-ynyl]piperidine-3-acetic acid (3R,4R)-4-[3-(6-Methoxyquinolin-4-yl)propyl]-1-[3-(thien-3-yl)prop-2-ynyl]piperidine-3-acetic acid (3R,4R)-4-[3-(6-Methoxyquinolin-4-yl)propyl]-1-[3-(1-methylpyrrol-2-yl)prop-2-ynyl]piperidine-3-acetic acid (3R,4R)-4-[3-(6-Methoxyquinolin-4-yl)propyl-1-[3-(1-methylpyrrol-3-yl)prop-2-ynyl]piperidine-3-acetic acid (3R,4R)-4-[3-(6-Methoxyquinolin-4-yl)propyl]-1-[3-(thiazol-2-yl)prop-2-ynyl]piperidine-3-acetic acid (3R,4R)-4-[3-(6-Methoxyquinolin-4-yl)propyl]-1-[3-(thiazol4-yl)prop-2-ynyl]piperidine-3-acetic acid (3R,4R)-4-[3-(6-Methoxyquinolin-4-yl)propyl]-1-[3-(thiazol-5-yl)prop-2-ynyl]piperidine-3-acetic acid (3R,4R)-4-[3-(6-Methoxyquinolin-4-yl)propyl]-1-[3-(1-methylimidazol-2-yl)prop-2-ynyl]piperidine-3-acetic acid (3R,4R)-4-[3-(6-Methoxyquinolin-4-yl)propyl]-1-[3-(3-methylimidazol4-yl)prop-2-ynyl]piperidine-3-acetic acid (3R,4R)-4-[3-(6-Methoxyquinolin-4-yl)propyl]-1-[3-(3-methylpyrazol-4-yl)prop-2-ynyl]piperidine-3-acetic acid (3R,4R)-4-[3-(6-Methoxyquinolin-4-yl)propyl]-1-[3-(oxazol-2-yl)prop-2-ynyl]piperidine-3-acetic acid (3R,4R)-4-[3-(6-Methoxyquinolin-4-yl)propyl]-1-3-(oxazol-4-yl)prop-2-ynyl]piperidine-3-acetic acid (3R,4R)-4-[3-(6-Methoxyquinolin-4-yl)propyl-1-[3-(oxazol-5-yl)prop-2-ynyl]piperidine-3-acetic acid (3R,4R)-4-[3-(6-Methoxyquinolin-2-yl)prop-2-ynyl]piperidine-3-acetic acid (3R,4R)-4-3-(6-Methoxyquinolin-4-yl)propyl]-1-3-(pyridin-3-yl)prop-2-ynyl]piperidine-3-acetic acid (3R,4R)-4-[3-(6-Methoxyquinolin-4-yl)propyl-1-[3-(pyridin-4-yl)prop-2-ynyl]piperidine-3-acetic acid (3R,4R)-4-[3-(6-Methoxyquinolin-4-yl)propyl]-1-[3-(pyrimidin-2-yl)prop-2-ynyl]piperidine-3-acetic acid (3R,4R)-4-[3-(6-Methoxyquinolin-4-yl)propyl]-1-[3-(pyrimidin-4-yl)prop-2-ynyl]piperidine-3-acetic acid (3R,4R)-4-[3-(6-Methoxyquinolin-4-yl)propyl]-1-[3-(pyrazin-2-yl)prop-2-ynyl]piperidine-3-acetic acid (3R,4R)-4-[3-(6-Methoxyquinolin-4-yl)propyl]-1-[3-(pyrazin-3-yl)prop-2-ynyl]piperidine-3-acetic acid (3R,4R)-4-[3-(6-Methoxyquinolin-4-yl)propyl]-1-[3-(pyridazin-4-yl)prop-2-ynyl]piperidine-3-acetic acid (3R,4R)-4-[3-(6-Methoxyquinolin-4-yl)propyl]-1-1-[3-phenylpropen-2-yl]piperidine-3-acetic acid (3R,4R)-4-[3-(6-Methoxyquinolin-4-yl)propyl]-1-[4-phenylbuten-3-yl]piperidine3-acetic acid (3R,4R)-4-[3-(R,S)-Hydroxy-3-(6-methoxyquinolin-4-yl)propyl]-1-[3-phenylpropyl]piperidine-3-acetic acid (3R,4R)-4-[3-(R,S)-Hydroxy-3-(6-methoxyquinolin-4-yl)propyl]-1-[4-phenylbutyl]piperidine-3-acetic acid (3R,4R)-4-[3-(R,S)-Hydroxy-3-(6-methoxyquinolin-4-yl)propyl]-1-[3-(2-fluorophenyl)propyl]piperidine-3-acetic acid (3R,4R)-4-[3-(R,S)-Hydroxy-3-(6-methoxyquinolin-4-yl)propyl]-1-[4-(2-fluorophenyl)butyl]piperidine-3-acetic acid (3R,4R)-4-[3-(R,S)-Hydroxy-3-(6-methoxyquinolin-4-yl)propyl]-1-[3-(3-fluorophenyl)propyl]piperidine-3-acetic acid (3R,4R)-4-[3-(R,S)-Hydroxy-3-(6-methoxyquinolin-4-yl)propyl]-1-[4-(3-fluorophenyl)butyl]piperidine-3-acetic acid (3R,4R)-4-[3-(R,S)-Hydroxy-3-(6-methoxyquinolin-4-yl)propyl]-1-[3-(4-fluorophenyl)propyl]piperidine-3-acetic acid (3R,4R)-4-[3-(R,S)-Hydroxy-3-(6-methoxyquinolin-4-yl)propyl]-1-[4-(4-fluorophenyl)butyl]piperidine-3-acetic acid (3R,4R)-4-[3-(R,S)-Hydroxy-3-(6-methoxyquinolin-4-yl)propyl]-1-[3-(2,3-difluorophenyl)propyl]piperidine-3-acetic acid (3R,4R)-4-[3-(R,S)-Hydroxy-3-(6-methoxyquinolin-4-yl)propyl]-1-[4-(2,3-difluorophenyl)butyl]piperidine-3-acetic acid (3R,4R)-4-[3-(R,S)-Hydroxy-3-(6-methoxyquinolin-4-yl)propyl]-1-[3-(2,6-difluorophenyl)propyl]piperidine-3-acetic acid (3R,4R)-4-[3-(R,S)-Hydroxy-3-(6-methoxyquinolin-4-yl)propyl]-1-[4-(2,6-difluorophenyl)butyl]piperidine-3-acetic acid (3R,4R)-4-[3-(R,S)-Hydroxy-3-(6-methoxyquinolin-4-yl)propyl]-1-[3-(2-chlorophenyl)propyl]piperidine-3-acetic acid (3R,4R)-4-[3-(R,S)-Hydroxy-3-(6-methoxyquinolin-4-yl)propyl]-1-[4-(2-chlorophenyl)butyl]piperidine-3-acetic acid (3R,4R)-4-[3-(R,S)-Hydroxy-3-(6-methoxyquinolin-4-yl)propyl]-1-[3-(3-chlorophenyl)propyl]piperidine-3-acetic acid (3R,4R)-4-[3-(R,S)-Hydroxy-3-(6-methoxyquinolin-4-yl)propyl]-1-[4-(3-chlorophenyl)butyl]piperidine-3-acetic acid (3R,4R)-4-[3-(R,S)-Hydroxy-3-(6-methoxyquinolin-4-yl)propyl]-1-[3-(4-chlorophenyl)propyl]piperidine-3-acetic acid (3R,4R)-4-[3-(R,S)-Hydroxy-3-(6-methoxyquinolin-4-yl)propyl]-1-[4-(4-chlorophenyl)butyl]piperidine-3-acetic acid (3R,4R)-4-[3-(R,S)-Hydroxy-3-(6-methoxyquinolin-4-yl)propyl]-1-[3-(2,3-dichlorophenyl)propyl]piperidine-3-acetic acid (3R,4R)-4-[3-(R,S)-Hydroxy-3-(6-methoxyquinolin-4-yl)propyl]-1-[4-(2,3-dichlorophenyl)butyl]piperidine-3-acetic acid (3R,4R)-4-[3-(R,S)-Hydroxy-3-(6-methoxyquinolin-4-yl)propyl]-1-[3-(2,6-dichlorophenyl)propyl]piperidine-3-acetic acid (3R,4R)-4-[3-(R,S)-Hydroxy-3-(6-methoxyquinolin-4-yl)propyl]-1-[4-(2,6-dichlorophenyl)butyl]piperidine-3-acetic acid (3R,4R)-4-[3-(R,S)-Hydroxy-3-(6-methoxyquinolin-4-yl)propyl]-1-[3-(2-methylphenyl)propyl]piperidine-3-acetic acid (3R,4R)-4-[3-(R,S)-Hydroxy-3-(6-methoxyquinolin-4-yl)propyl]-1-(4-(2-methylphenyl)butyl]piperidine-3-acetic acid (3R,4R)-4-[3-(R,S)-Hydroxy-3-(6-methoxyquinolin-4-yl)propyl]-1-[5-(2-methylphenyl)pentyl]piperidine-3-acetic acid (3R,4R)-4-[3-(R,S)-Hydroxy-3-(6-methoxyquinolin-4-yl)propyl]-1-[3-(3-methylphenyl)propyl]piperidine-3-acetic acid (3R,4R)-4-[3-(R,S)-Hydroxy-3-(6-methoxyquinolin-4-yl)propyl]-1-[4-(3-methylphenyl)butyl]piperidine-3-acetic acid (3R,4R)-4-[3-(R,S)-Hydroxy-3-(6-methoxyquinolin-4-yl)propyl]-1-[3-(4-methylphenyl)propyl]piperidine-3-acetic acid (3R,4R)-4-[3-(R,S)-Hydroxy-3-(6-methoxyquinolin-4-yl)propyl]-1-[4-(4-methylphenyl)butyl]piperidine-3-acetic acid (3R,4R)-4-[3-(R,S)-Hydroxy-3-(6-methoxyquinolin-4-yl)propyl]-1-[3-(2-methoxyphenyl)propyl]piperidine-3-acetic acid (3R,4R)-4-[3-(R,S)-Hydroxy-3-(6-methoxyquinolin-4-yl)propyl]-1-[4-(2-methoxyphenyl)butyl]piperidine-3-acetic acid (3R,4R)-4-[3-(R,S)-Hydroxy-3-(6-methoxyquinolin-4-yl)propyl]-1-[3-(3-methoxyphenyl)propyl]piperidine-3-acetic acid (3R,4R)-4-[3-(R,S)-Hydroxy-3-(6-methoxyquinolin-4-yl)propyl]-1-[4-(3-methoxyphenyl)butyl]piperidine-3-acetic acid (3R,4R)-4-[3-(R,S)-Hydroxy-3-(6-methoxyquinolin-4-yl)propyl]-1-[3-(4-methoxyphenyl)propyl]piperidine-3-acetic acid (3R,4R)-4-[3-(R,S)-Hydroxy-3-(6-methoxyquinolin-4-yl)propyl]-1-[4-(4-methoxyphenyl)butyl]piperidine-3-acetic acid (3R,4R)-4-[3-(R,S)-Hydroxy-3-(6-methoxyquinolin-4-yl)propyl]-1-[3-(2-trifluoromethylphenyl)propyl]piperidine-3-acetic acid (3R,4R)-4-[3-(R,S)-Hydroxy-3-(6-methoxyquinolin-4-yl)propyl]-1-[4-(2-trifluoromethylphenyl)butyl]piperidine-3-acetic acid (3R,4R)-4-[3-(R,S)-Hydroxy-3-(6-methoxyquinolin-4-yl)propyl]-1-[3-(3-trifluoromethylphenyl)propyl]piperidine-3-acetic acid (3R,4R)-4-[3-(R,S)-Hydroxy-3-(6-methoxyquinolin-4-yl)propyl]-1-[4-(3-trifluoromethylphenyl)butyl]piperidine-3-acetic acid (3R,4R)-4-[3-(R,S)-Hydroxy-3-(6-methoxyquinolin-4-yl)propyl]-1-[3-(4-trifluoromethylphenyl)propyl]piperidine-3-acetic acid (3R,4R)-4-[3-(R,S)-Hydroxy-3-(6-methoxyquinolin-4-yl)propyl]-1-[4-(4-trifluoromethylphenyl)butyl]piperidine-3-acetic acid (3R,4R)-4-[3-(R,S)-Hydroxy-3-(6-methoxyquinolin-4-yl)propyl]-1-[2-phenylthioethyl]piperidine-3-acetic acid (3R,4R)-4-[3-(R,S)-Hydroxy-3-(6-methoxyquinolin-4-yl)propyl]-1-[3-phenylthiopropyl]piperidine-3-acetic acid (3R,4R)-4-[3-(R,S)-Hydroxy-3-(6-methoxyquinolin-4-yl)propyl]-1-[2-(2-fluorophenylthio)ethyl]piperidine-3-acetic acid (3R,4R)-4-[3-(R,S)-Hydroxy-3-(6-methoxyquinolin-4-yl)propyl]-1-[3-(2-fluorophenylthio)propyl]piperidine-3-acetic acid (3R,4R)-4-[3-(R,S)-Hydroxy-3-(6-methoxyquinolin-4-yl)propyl]-1-[3-(3-fluorophenylthio)propyl]piperidine-3-acetic acid (3R,4R)-4-[3-(R,S)-Hydroxy-3-(6-methoxyquinolin-4-yl)propyl]-1-[2-(4-fluorophenylthio)ethyl]piperidine-3-acetic acid (3R,4R)-4-(3-(R,S)-Hydroxy-3-(6-methoxyquinolin-4-yl)propyl]-1-[3-(4-fluorophenylthio)propyl]piperidine-3-acetic acid (3R,4R)-4-[3-(R,S)-Hydroxy-3-(6-methoxyquinolin-4-yl)propyl]-1-[2-(2,3-difluorophenylthio)ethyl]piperidine-3-acetic acid (3R,4R)-4-[3-(R,S)-Hydroxy-3-(6-methoxyquinolin-4-yl)propyl-1-3-(2,3-difluorophenylthio)propyl]piperidine-3-acetic acid (3R,4R)-4-[3-(R,S)-Hydroxy-3-(6-methoxyquinolin-4-yl)propyl]-1-[2-(2,6-difluorophenylthio)ethyl]piperidine-3-acetic acid (3R,4R)-4-[3-(R,S)-Hydroxy-3-(61methoxyquinolin-4-yl)propyl]-1-[3-(2,6-difluorophenylthio)propyl]piperidine-3-acetic acid (3R,4R)-4-[3-(R,S)-Hydroxy-3-(6-methoxyquinolin-4-yl)propyl]-1-[2-(2-chlorophenylthio)ethyl]piperidine-3-acetic acid (3R,4R)-4-3-(R,S)-Hydroxy-3-(6-methoxyquinolin-4-yl)propyl]-1-[3-(2-chlorophenylthio)propyl]piperidine-3-acetic acid (3R,4R)-4-[3-(R,S)-Hydroxy-3-(6-methoxyquinolin-4-yl)propyl]-1-[2-(3-chlorophenylthio)ethyl]piperidine-3 acetic acid (3R,4R)-4-[3-(R,S)-Hydroxy-3-(6-methoxyquinolin-4-yl)propyl]-1-[3-(3-chlorophenylthio)propyl]piperidine-3-acetic acid (3R,4R)-4-[3-(R,S)-Hydroxy-3-(6-methoxyquinolin-4-yl)propyl]-1-[2-(4-chlorophenylthio)ethyl]piperidine-3-acetic acid (3R,4R)-4-[3-(R,S)-Hydroxy-3-(6-methoxyquinolin-4-yl)propyl]-1-[3-($^4$-chlorophenylthio)propyl]piperidine-3-acetic acid (3R,4R)-4-[3-(R,S)-Hydroxy-3-(6-methoxyquinolin-4-yl)propyl]-1-[2-(2,3-dichlorophenylthio)ethyl]piperidine-3-acetic acid (3R,4R)-4-[3-(R,S)-Hydroxy-3-(6-methoxyquinolin-4-yl)propyl]-1-[3-(2,3-dichlorophenylthio)propyl]piperidine-3-acetic acid (3R,4R)-4-[3-(R,S)-Hydroxy-3-(6-methoxyquinolin-4-yl)propyl]-1-[2-(2,6-dichlorophenylthio)ethyl]piperidine-3-acetic acid (3R,4R)-4-[3-(R,S)-Hydroxy-3-(6-methoxyquinolin-4-yl)propyl]-1-[3-(2,6-dichlorophenylthio)propyl]piperidine-3-acetic acid (3R,4R)-4-[3-(R,S)-Hydroxy-3-(6-methoxyquinolin-4-yl)propyl]-1-[2-(2-methylphenylthio)ethyl]piperidine-3-acetic acid (3R,4R)-4-[3-(R,S)-Hydroxy-3-(6-methoxyquinolin-4-yl)propyl]-1-[3-(2-methylphenylthio)propyl]piperidine-3-acetic acid (3R,4R)-4-[3-(R,S)-Hydroxy-3-(6-methoxyquinolin-4-yl)propyl]-1-[2-(3-methylphenylthio)ethyl]piperidine-3-acetic acid (3R,4R)-4-[3-(R,S)-Hydroxy-3-(6-methoxyquinolin-4-yl)propyl]-1-[3-(3-methylphenylthio)propyl]piperidine-3-acetic acid (3R,4R)-4-[3-(R,S)-Hydroxy-3-(6-methoxyquinolin-4-yl)propyl]-1-[2-(4-methylphenylthio)ethyl]piperidine-3-acetic acid (3R,4R)-4-[3-(R,S)-Hydroxy-3-(6-methoxyquinolin-4-yl)propyl]-1-[3-(4-methylphenylthio)propyl]piperidine-3-acetic acid (3R,4R)-4-[3-(R,S)-Hydroxy-3-(6-methoxyquinolin-4-yl)propyl]-1-[2-(2-trifluoromethylphenylthio)ethyl]piperidine-3-acetic acid (3R,4R)-4-[3-(R,S)-Hydroxy-3-(6-methoxyquinolin-4-yl)propyl]-1-[3-(2-trifluoromethylphenylthio)propyl]piperidine-3-acetic acid (3R,4R)-4-[3-(R,S)-Hydroxy-3-(6-methoxyquinolin-4-yl)propyl]-1-[2-(3-trifluoromethylphenylthio)ethyl]piperidine-3-acetic acid (3R,4R)-4-[3-(R,S)-Hydroxy-3-(6-methoxyquinolin-4-yl)propyl]-1-[3-(3-trifluoromethylphenylthio)propyl]piperidine-3-acetic acid (3R,4R)-4-[3-(R,S)-Hydroxy-3-(6-methoxyquinolin-4-yl)propyl]-1-[2-(4-trifluoromethylphenylthio)ethyl]piperidine-3-acetic acid (3R,4R)-4-[3-(R,S)-Hydroxy-3-(6-methoxyquinolin-4-yl)propyl]-1-[3-(4-trifluoromethylphenylthio)propyl]piperidine-3-acetic acid (3R,4R)-4-[3-(R,S)-Hydroxy-3-(6-methoxyquinolin-4-yl)propyl]-1-[2-(2-methoxyphenylthio)ethyl]piperidine-3-acetic acid (3R,4R)-4-[3-(R,S)-Hydroxy-3-(6-methoxyquinolin-4-yl)propyl]-1-[3-(2-methoxyphenylthio)propyl]piperidine-3-acetic acid (3R,4R)-4-[3-(R,S)-Hydroxy-3-(6-methoxyquinolin-4-yl)propyl]-1-[2-(3-methoxyphenylthio)ethyl]piperidine-3-acetic acid (3R,4R)-4-[3-(R,S)-Hydroxy-3-(6-methoxyquinolin-4-yl)propyl]-1-[3-(3-methoxyphenylthio)propyl]piperidine-3-acetic acid (3R,4R)-4-[3-(R,S)-Hydroxy-3-(6-methoxyquinolin-4-yl)propyl]-1-[2-(4methoxyphenylthio)ethyl]piperidine-3-acetic acid (3R,4R)-4-[3-(R,S)-Hydroxy-3-(6-methoxyquinolin-4-yl)propyl]1-[3-(4-methoxyphenylthio)propyl]piperidine-3-acetic acid (3R,4R)-4-[3-(R,S)-Hydroxy-3-(6-methoxyquinolin-4-yl)propyl)-1-[cyclopropylmethyl]piperidine-3-acetic acid (3R,4R)-4-[3-(R,S)-Hydroxy-3-(6-methoxyquinolin-4-yl)propyl]-1-[2-(cyclopropyl)ethyl]piperidine-3-acetic acid (3R,4R)-4-[3-(R,S)-Hydroxy-3-(6-methoxyquinolin-4-yl)propyl]-1-[cyclobutylmethyl]piperidine-3-acetic acid (3R,4R)-4-[3-(R,S)-Hydroxy-3-(6-methoxyquinolin-4-yl)propyl]-1-[2-(cyclobutyl)ethyl]piperidine-3-acetic acid (3R,4R)-4-[3-(R,S)-Hydroxy-3-(6-methoxyquinolin-4-yl)propyl]-1-[cyclopentylmethyl]piperidine-3-acetic acid (3R,4R)-4-[3-(R,S)-Hydroxy-3-(6-methoxyquinolin-4-yl)propyl]-1-[2-(cyclopentyl)ethyl]piperidine-3-acetic acid (3R,4R)-4-[3-(R,S)-Hydroxy-3-(6-methoxyquinolin-4-yl)propyl]-1-[cyclohexylmethyl]piperidine-3-acetic acid (3R,4R)-4-[3-(R,S)-Hydroxy-3-(6-methoxyquinolin-4-yl)propyl]-1-[2-(cyclohexyl)ethyl]piperidine-3-acetic acid (3R,4R)-4-[3-(R,S)-Hydroxy-3-(6-methoxyquinolin-4-yl)propyl]-1-[2-(cyclopropylthio)ethyl]piperidine-3-acetic acid (3R,4R)-4-[3-(R,S)-Hydroxy-3-(6-methoxyquinolin-4-yl)propyl]-1-[3-(cyclopropylthio)propyl]piperidine-3-acetic acid (3R,4R)-4-[3-(R,S)-Hydroxy-3-(6-methoxyquinolin-4-yl)propyl]-1-[2-(cyclobutylthio)ethyl]piperidine-3-acetic acid (3R,4R)-4-[3-(R,S)-Hydroxy-3-(6-methoxyquinolin-4-yl)propyl]-1-[3-(cyclobutylthio)propyl]piperidine-3-acetic acid (3R,4R)-4-[3-(R,S)-Hydroxy-3-(6-methoxyquinolin-4-yl)propyl]-1-[3-(cyclopentylthio)propyl]piperidine-3-acetic acid (3R,4R)-4-[3-(R,S)-Hydroxy-3-(6-methoxyquinolin-4-yl)propyl]-1-[3-(cyclohexylthio)propyl]piperidine-3-acetic acid (3R,4R)-4-[3-(R,S)-Hydroxy-3-(6-methoxyquinolin-4-yl)propyl]-1-[2-methylthioethyl]piperidine-3-acetic acid (3R,4R)-4-[3-(R,S)-Hydroxy-3-(6-methoxyquinolin-4-yl)propyl]-1-[3-methylthiopropyl]piperidine-3-acetic acid (3R,4R)-4-[3-(R,S)-Hydroxy-3-(6-methoxyquinolin-4-yl)propyl]-1-[2-ethylthioethyl]piperidine-3-acetic acid (3R,4R)-4-[3-(R,S)-Hydroxy-3-(6-methoxyquinolin-4-yl)propyl]-1-[3-ethylthiopropyl]piperidine-3-acetic acid (3R,4R)-4-[3-(R,S)-Hydroxy-3-(6-methoxyquinolin-4-yl)propyl]-1-[2-(n-propylthio)ethyl]piperidine-3-acetic acid (3R,4R)-4-[3-(R,S)-Hydroxy-3-(6-methoxyquinolin-4-yl)propyl]-1-[3-(n-propylthio)propyl]piperidine-3-acetic acid (3R,4R)-4-[3-(R,S)-Hydroxy-3-(6-methoxyquinolin-4-yl)propyl]-1-[2-(n-butylthio)ethyl]piperidine-3-acetic acid (3R,4R)-4-[3-(R,S)-Hydroxy-3-(6-methoxyquinolin-4-yl)propyl]-1-[3-(n-butylthio)propyl]piperidine-3-acetic acid (3R,4R)-4-[3-(R,S)-Hydroxy-3-(6-methoxyquinolin-4-yl)propyl]-1-[3-(thien-2-yl)propyl]piperidine-3-acetic acid (3R,4R)-4-[3-(R,S)-Hydroxy-3-(6-methoxyquinolin-4-yl)propyl]-1-[4-(thien-2-yl)butyl]piperidine-3-acetic acid (3R,4R)-4-[3-(R,S)-Hydroxy-3-(6-methoxyquinolin-4-yl)propyl-1-[3-(thien-2-yl)thiopropyl]piperidine-3-acetic acid (3R,4R)-4-[3-(R,S)-Hydroxy-3-(6-methoxyquinolin-4-yl)propyl]-1-[3-(5-chlorothien-2-yl)propyl]piperidine-3-acetic acid (3R,4R)-4-[3-(R,S)-Hydroxy-3-(6-methoxyquinolin-4-yl)propyl]-1-[4-(5-chlorothien-2-yl)butyl]piperidine-3-acetic acid (3R,4R)-4-[3-(R,S)-Hydroxy-3-(6-methoxyquinolin-4-yl)propyl]-1-[2-(5-chlorothien-2-yl)thioethyl]piperidine-3-acetic acid (3R,4R)-4-[3-(R,S)-Hydroxy-3-(6-methoxyquinolin-4-yl)propyl]-1-[3-(5-chlorothien-2-yl)thiopropyl]piperidine-3-acetic acid (3R,4R)-4-[3-(R,S)-Hydroxy-3-(6-methoxyquinolin-4-yl)propyl]-1-[3-(3-chlorothien-2-yl)propyl]piperidine-3-acetic acid (3R,4R)-4-[3-(R,S)-Hydroxy-3-(6-methoxyquinolin-4-yl)propyl]-1-[4-(3-chlorothien-2-yl)butyl]piperidine-3-acetic acid (3R,4R)-4-[3-(R,S)-Hydroxy-3-(6-methoxyquinolin-14-yl)propyl]-1-[2-(3-chlorothien-2-yl)thioethyl]piperidine-3-acetic acid (3R,4R)-4-[3-(R,S)-Hydroxy-3-(6-methoxyquinolin-4-y)propyl-1-[3-(3-chlorothien-2-yl)thiopropyl]piperidine-3-acetic acid (3R,4R)-4-[3-(R,S)-Hydroxy-3-(6-methoxyquinolin-4-yl)propyl]-1-[3-(5-methylthien-2-yl)propyl]piperidine-3-acetic acid (3R,4R)-4-[3-(R,S)-Hydroxy-3-(6-methoxyquinolin-4-yl)propyl]-1-[4-(5-methylthien-2-yl)butyl]piperidine-3-acetic acid (3R,4R)-4-[3-(R,S)-Hydroxy-3-(6-methoxyquinolin-4-yl)propyl]-1-[2-(5-methylthien-2-yl)thioethyl]piperidine-3-acetic acid (3R,4R)-4-[3-(R,S)-Hydroxy-3-(6-methoxyquinolin-4-yl)propyl]-1-[3-(5-methylthien-2-yl)thiopropyl]piperidine-3-acetic acid (3R,4R)-4-[3-(R,S)-Hydroxy-3-(6-methoxyquinolin-4-yl)propyl]-1-[3-(3-methylthien-2-yl)propyl]piperidine-3-acetic acid (3R,4R)-4-[3-(R,S)-Hydroxy-3-(6-methoxyquinolin-4-yl)propyl]-1-[4-(3-methylthien-2-yl)butyl]piperidine-3-acetic acid (3R,4R)-4-[3-(R,S)-Hydroxy-3-(6-methoxyquinolin-4-yl)propyl]-1-[2-(3-methylthien-2-yl)thioethyl]piperidine-3-acetic acid (3R,4R)-4-[3-(R,S)-Hydroxy-3-(6-methoxyquinolin-4-yl)propyl]-1-[3-(3-methylthien-2-yl)thiopropyl]piperidine-3-acetic acid (3R,4R)-4-[3-(R,S)-Hydroxy-3-(6-methoxyquinolin-4-yl)propyl]-1-[3-(thien-3-yl)propyl]piperidine-3-acetic acid (3R,4R)-4-[3-(R,S)-Hydroxy-3-(6-methoxyquinolin-4-yl)propyl]-1-[4-(thien-3-yl)butyl]piperidine-3-acetic acid (3R,4R)-4-[3-(R,S)-Hydroxy-3-(6-methoxyquinolin-4-yl)propyl]-1-[2-(thien-3-yl)thioethyl]piperidine-3-acetic acid (3R,4R)-4-[3-(R,S)-Hydroxy-3-(6-methoxyquinolin-4-yl)propyl]-1-[3-(thien-3-yl)thiopropyl]piperidine-3-acetic acid (3R,4R)-4-[3-(R,S)-Hydroxy-3-(6-methoxyquinolin-4-yl)propyl]-1-[3-(fur-2-yl)propyl]piperidine-3-acetic acid (3R,4R)-4-[3-(R,S)-Hydroxy-3-(6-methoxyquinolin-4-yl)propyl]-1-[4-(fur-2-yl)butyl]piperidine-3-acetic acid (3R,4R)-4-[3-(R,S)-Hydroxy-3-(6-methoxyquinolin-4-yl)propyl]-1-[2-(fur-2-yl)thioethyl]piperidine-3-acetic acid (3R,4R)-4-[3-(R,S)-Hydroxy-3-(6-methoxyquinolin-4-yl)propyl]-1-[3[-(fur-2-yl)thiopropyl]piperidine-3-acetic acid (3R,4R)-4-[3-(R,S)-Hydroxy-3-(6-methoxyquinolin-4-yl)propyl]-1-[3-(fur-3-yl)propyl]piperidine-3-acetic acid (3R,4R)-4-[3-(R,S)-Hydroxy-3-(6-methoxyquinolin-4-yl)propyl]-1-[4-(fur-3-yl)butyl]piperidine-3-acetic acid (3R,4R)-4-[3-(R,S)-Hydroxy-3-(6-methoxyquinolin-4-yl)propyl]-1-[2-(fur-3-yl)thioethyl]piperidine-3-acetic acid (3R,4R)-4-[3-(R,S)-Hydroxy-3-(6-methoxyquinolin-4-yl)propyl]-1-[3-(fur-3-yl)thiopropyl]piperidine-3-acetic acid (3R,4R)-4-[3-(R,S)-Hydroxy-3-(6-methoxyquinolin-4-yl)propyl]-1-[3-(1-methylpyrrol-2-yl)propyl]piperidine-3-acetic acid (3R,4R)-4-[3-(R,S)-Hydroxy-3-(6-methoxyquinolin-4-yl)propyl]-1-[4-(1-methylpyrrol-2-yl)butyl]piperidine-3-acetic acid (3R,4R)-4-[3-(R,S)-Hydroxy-3-(6-methoxyquinolin-4-yl)propyl]-1-[2-( 1-methylpyrrol-2-yl)thioethyl]piperidine-3-acetic acid (3R,4R)-4-[3-(R,S)-Hydroxy-3-(6-methoxyquinolin-4-yl)propyl]-1-[3-(1-methylpyrrol-2-yl)thiopropyl]piperidine-3-acetic acid (3R,4R)-4-[3-(R,S)-Hydroxy-3-(6-methoxyquinolin-4-yl)propyl]-1-[3-(1-methylpyrrol-2-yl)propyl]piperidine-3-acetic acid (3R,4R)-4-[3-(R,S)-Hydroxy-3-(6-methoxyquinolin-4-yl)propyl]-1-[4-(1-methylpyrrol-3-yl)butyl]piperidine-3-acetic acid (3R,4R)-4-[3-(R,S)-Hydroxy-3-(6-methoxyquinolin-4-yl)propyl]-1-[2-(1-methylpyrrol-3-yl)thioethyl]piperidine-3-acetic acid (3R,4R)-4-[3-(R,S)-Hydroxy-3-(6-methoxyquinolin-4-yl)propyl]-1-[3-( 1-methylpyrrol-3-yl)thiopropyl]piperidine-3-acetic acid (3R,4R)-4-[3-(R,S)-Hydroxy-3-(6-methoxyquinolin-4-yl)propyl]-1-[3-(thiazol-2-yl)propyl]piperidine-3-acetic acid (3R,4R)-4-[3-(R,S)-Hydroxy-3-(6-methoxyquinolin-4-yl)propyl]-1-[4-(thiazol-2-yl)butyl]piperidine-3-acetic acid (3R,4R)-4-[3-(R,S)-Hydroxy-3-(6-methoxyquinolin-4-yl)propyl]-1-[2-(thiazol-2-yl)thioethyl]piperidine-3-acetic acid (3R,4R)-4-[3-(R,S)-Hydroxy-3-(6-methoxyquinolin-4-yl)propyl]-1-[3-(thiazol-2-yl)thiopropyl]piperidine-3-acetic acid (3R,4R)-4-[3-(R,S)-Hydroxy-3-(6-methoxyquinolin-4-yl)propyl]-1-[3-( 1-methylimidazol-2-yl)propyl]piperidine-3-acetic acid (3R,4R)-4-[3-(R,S)-Hydroxy-3-(6-methoxyquinolin-4-yl)propyl]-1-[4-( 1-methylimidazol-2-yl)butyl]piperidine-3-acetic acid (3R,4R)-4-[3-(R,S)-Hydroxy-3-(6-methoxyquinolin-4-yl)propyl]-1-[2-(1-methylimidazol-2-yl)thioethyl]piperidine-3-acetic acid (3R,4R)-4-[3-(R,S)-Hydroxy-3-(6-methoxyquinolin-4-yl)propyl]-1-[3-(1-methylimidazol-2-yl)thiopropyl]piperidine-3-acetic acid (3R,4R)-4-[3-(R,S)-Hydroxy-3-(6-methoxyquinolin-4-yl)propyl]-1-[3-(3-methylimidazol-4-yl)propyl]piperidine-3-acetic acid (3R,4R)-4-[3-(R,S)-Hydroxy-3-(6-methoxyquinolin-4-yl)propyl]-1-[4-(3-methylimidazol-4-yl)butyl]piperidine-3-acetic acid (3R,4R)-4-[3-(R,S)-Hydroxy-3-(6-methoxyquinolin-4-yl)propyl]-1-[2-(3-methylimidazol-4-yl)thioethyl]piperidine-3-acetic acid (3R,4R)-4-[3-(R,S)-Hydroxy-3-(6-methoxyquinolin-4-yl)propyl]-1-[3-(3-methylimidazol-4-yl)thiopropyl]piperidine-3-acetic acid (3R,4R)-4-[3-(R,S)-Hydroxy-3-(6-methoxyquinolin-4-yl)propyl]-1-[3-(3-methylimidazol-4-yl)propyl]piperidine-3-acetic acid (3R,4R)-4-[3-(R,S)-Hydroxy-3-(6-methoxyquinolin-4-yl)propyl]-1-[4-(3-methylimidazol-4-yl)butyl]piperidine-3-acetic acid (3R,4R)-4-[3-(R,S)-Hydroxy-3-(6-methoxyquinolin-4-yl)propyl]-1-[2-(3-methylimidazol-4-yl)thioethyl]piperidine-3-acetic acid (3R,4R)-4-[3-(R,S)-Hydroxy-3-(6-methoxyquinolin-4-yl)propyl]-1-[3-(3-methylimidazol-4-yl)thiopropyl]piperidine-3-acetic acid (3R,4R)-4-[3-(R,S)-Hydroxy-3-(6-methoxyquinolin-4-yl)propyl]-1-[3-(oxazol-2-yl)propyl]piperidine-3-acetic acid (3R,4R)-4-[3-(R,S)-Hydroxy-3-(6-methoxyquinolin-4-yl)propyl]-1-[4-(oxazol-2-yl)butyl]piperidine-3-acetic acid (3R,4R)-4-[3-(R,S)-Hydroxy-3-(6-methoxyquinolin-4-yl)propyl]-1-[2-(oxazol-2-yl)thioethyl]piperidine-3-acetic acid (3R,4R)-4-[3-(R,S)-Hydroxy3-(6-methoxyquinolin-4-yl)propyl]-1-[3-(oxazol-2-yl)thiopropyl]piperidine-3-acetic acid (3R,4R)-4-[3-(R,S)-Hydroxy-3-(6-methoxyquinolin-4-yl)propyl]-1-[3-(pyridin-2yl)propyl]piperidine-3-acetic acid (3R,4R)-4-[3-(R,S)-Hydroxy-3-(6-methoxyquinolin-4-yl)propyl]-1-[4-(pyridin-2-yl)butyl]piperidine-3-acetic acid (3R,4R)-4-[3-(R,S)-Hydroxy-3-(6-methoxyquinolin-4-yl)propyl]-1-[2-(pyridin-2-yl)thioethyl]piperidine-3-acetic acid (3R,4R)-4-[3-(R,S)-Hydroxy-3-(6-methoxyquinolin-4-yl)propyl-1-[3-(pyridin-2-yl)thiopropyl]piperidine-3-acetic acid (3R,4R)-4-[3-(R,S)-Hydroxy-3-(6-methoxyquinolin-4-yl)propyl]-1-[3-(pyridin-3-yl)propyl]piperidine-3-acetic acid (3R,4R)-4-[3-(R,S)-Hydroxy-3-(6-methoxyquinolin-4-yl)propyl]-1-[4-(pyridin-3-yl)butyl]piperidine-3-acetic acid (3R,4R)-4-[3-(R,S)-Hydroxy-3-(6-methoxyquinolin-4-yl)propyl]-1-[2-(pyridin-3-yl)thioethyl]piperidine-3-acetic acid (3R,4R)-4-[3-(R,S)-Hydroxy-3-(6-methoxyquinolin-4-yl)propyl]-1-[3-(pyridin-3-yl)thiopropyl]piperidine-3-acetic acid (3R,4R)-4-[3-(R,S)-Hydroxy-3-(6-methoxyquinolin-4-yl)propyl]-1-[3-(pyridin-4-yl)propyl]piperidine-3-acetic acid (3R,4R)-4-[3-(R,S)-Hydroxy-3-(6-methoxyquinolin-4-yl)propyl]-1-[4-(pyridin-4-yl)butyl]piperidine-3-acetic acid (3R,4R)-4-[3-(R,S)-Hydroxy-3-(6-methoxyquinolin-4-yl)propyl]-1-[5-(pyridin-4-yl)pentyl]piperidine-3-acetic acid (3R,4R)-4-[3-(R,S)-Hydroxy-3-(6-methoxyquinolin-4-yl)propyl]-1-[2-(pyridin-4-yl)thioethyl]piperidine-3-acetic acid (3R,4R)-4-[3-(R,S)-Hydroxy-3-(6-methoxyquinolin-4-yl)propyl]-1-[3-(pyridin-4-yl)thiopropyl]piperidine-3-acetic acid (3R,4R)-4-[3-(R,S)-Hydroxy-3-(6-methoxyquinolin-4-yl)propyl]-1-[3-(pyrimidin-2-yl)propyl]piperidine-3-acetic acid (3R,4R)-4-[3-(R,S)-Hydroxy-3-(6-methoxyquinolin-4-yl)propyl]-1-[4-(pyrimidin-2-yl)butyl]piperidine-3-acetic acid (3R,4R)-4-[3-(R,S)-Hydroxy-3-(6-methoxyquinolin-4-yl)propyl]-1-[2-(pyrimidin-2-yl)thioethyl]piperidine-3-acetic acid (3R,4R)-4-[3-(R,S)-Hydroxy-3-(6-methoxyquinolin-4-yl)propyl]-1-[3-(pyrimidin-2-yl)thiopropyl]piperidine-3-acetic acid (3R,4R)-4-[3-(R,S)-Hydroxy-3-(6-methoxyquinolin-4-yl)propyl]-1-[3-(pyrimidin-4-yl)propyl]piperidine-3-acetic acid (3R,4R)-4-[3-(R,S)-Hydroxy-3-(6-methoxyquinolin-4-yl)propyl]-1-[4-(pyrimidin-4-yl)butyl]piperidine-3-acetic acid (3R,4R)-4-[3-(R,S)-Hydroxy-3-(6-methoxyquinolin-4-yl)propyl]-1-[2-(pyrimidin-4-yl)thioethyl]piperidine-3-acetic acid (3R,4R)-4-[3-(R,S)-Hydroxy-3-(6-methoxyquinolin-4-yl)propyl]-1-[3-(pyrimidin-4-yl)thiopropyl]piperidine-3-acetic acid (3R,4R)-4-[3-(R,S)-Hydroxy-3-(6-methoxyquinolin-4-yl)propyl]-1-[3-(pyrimidin-5-yl)propyl]piperidine-3-acetic acid (3R,4R)-4-[3-(R,S)-Hydroxy-3-(6-methoxyquinolin-4-yl)propyl]-1-[4-(pyrimidin-5-yl)butyl]piperidine-3-acetic acid (3R,4R)-4-[3-(R,S)-Hydroxy-3-(6-methoxyquinolin-4-yl)propyl]-1-[2-(pyrimidin-5-yl)thioethyl]piperidine-3-acetic acid (3R,4R)-4-[3-(R,S)-Hydroxy-3-(6-methoxyquinolin-4-yl)propyl]-1-[3-(pyrimidin-5-yl)thiopropyl]piperidine-3-acetic acid (3R,4R)-4-[3-(R,S)-Hydroxy-3-(6-methoxyquinolin-4-yl)propyl]-1-[3-(pyrazin-2-yl)propyl]piperidine-3-acetic acid (3R,4R)-4-[3-(R,S)-Hydroxy-3-(6-methoxyquinolin-4-yl)propyl]-1-[4-(pyrazin-2-yl)butyl]piperidine-3-acetic acid (3R,4R)-4-[3-(R,S)-Hydroxy-3-(6-methoxyquinolin-4-yl)propyl]-1-[2-(pyrazin-2-yl)thioethyl]piperidine-3-acetic acid (3R,4R)-4-[3-(R,S)-Hydroxy-3-(6-methoxyquinolin-4-yl)propyl]-1-[3-(pyrazin-2-yl)thiopropyl]piperidine-3-acetic acid (3R,4R)-4-[3-(R,S)-Hydroxy-3-(6-methoxyquinolin-4-yl)propyl]-1-[3-(pyridazin-3-yl)propyl]piperidine-3-acetic acid (3R,4R)-4-[3-(R,S)-Hydroxy-3-(6-methoxyquinolin-4-yl)propyl]-1-[4-(pyridazin-3-yl)butyl]piperidine-3-acetic acid (3R,4R)-4-[3-(R,S)-Hydroxy-3-(6-methoxyquinolin-4-yl)propyl]-1-[2-(pyridazin-3-yl)thioethyl]piperidine-3-acetic acid (3R,4R)-4-[3-(R,S)-Hydroxy-3-(6-methoxyquinolin-4-yl)propyl]-1-[3-(pyridazin-3-yl)thiopropyl]piperidine-3-acetic acid (3R,4R)-4-[3-(R,S)-Hydroxy-3-(6-methoxyquinolin-4-yl)propyl]-1-[3-(pyridazin-4-yl)propyl]piperidine-3-acetic acid (3R,4R)-4-[3-(R,S)-Hydroxy-3-(6-methoxyquinolin-4-yl)propyl]-1-[4-(pyridazin-4-yl)butyl]piperidine-3-acetic acid (3R,4R)-4-[3-(R,S)-Hydroxy-3-(6-methoxyquinolin-4-yl)propyl]-1-(2-(pyridazin-4-yl)thioethyl]piperidine-3-acetic acid (3R,4R)-4-[3-(R,S)-Hydroxy-3-(6-methoxyquinolin-4-yl)propyl]-1-[3-(pyridazin-4-yl)thiopropyl]piperidine-3-acetic acid (3R,4R)-4-[3-(R,S)-Hydroxy-3-(6-methoxyquinolin-4-yl)propyl]-1-[3-phenylprop-2-ynyl]piperidine-3-acetic acid (3R,4R)-4-[3-(R,S)-Hydroxy-3-(6-methoxyquinolin-4-yl)propyl]-1-[3-(2-fluorophenyl)prop-2-ynyl]piperidine-3-acetic acid (3R,4R)-4-[3-(R,S)-Hydroxy-3-(6-methoxyquinolin-4-yl)propyl]-1-[3-(3-fluorophenyl)prop-2-ynyl]piperidine-3-acetic acid (3R,4R)-4-[3-(R,S)-Hydroxy-3-(6-methoxyquinolin-4-yl)propyl]-1-[3-(4-fluorophenyl)prop-2-ynyl]piperidine-3-acetic acid (3R,4R)-4-[3-(R,S)-Hydroxy-3-(6-methoxyquinolin-4-yl)propyl]-1-[3-(2-chlorophenyl)prop-2-ynyl]piperidine-3-acetic acid (3R,4R)-4-[3-(R,S)-Hydroxy-3-(6-methoxyquinolin-4-yl)propyl]-1-[3-(3-chlorophenyl)prop-2-ynyl]piperidine-3-acetic acid (3R,4R)-4-[3-(R,S)-Hydroxy-3-(6-methoxyquinolin-4-yl)propyl]-1-[3-(4-chlorophenyl)prop-2-ynyl]piperidine-3-acetic acid (3R,4R)-4-[3-(R,S)-Hydroxy-3-(6-methoxyquinolin-4-yl)propyl]-1-[3-(2-methylphenyl)prop-2-ynyl]piperidine-3-acetic acid (3R,4R)-4-[3-(R,S)-Hydroxy-3-(6-methoxyquinolin-4-yl)propyl]-1-[3-(3-methylphenyl)prop-2-ynyl]piperidine-3-acetic acid (3R,4R)-4-[3-(R,S)-Hydroxy-3-(6-methoxyquinolin-4-yl)propyl]1-[3-(4-methylphenyl)prop-2-ynyl]piperidine-3-acetic acid (3R,4R)-4-[3-(R,S)-Hydroxy-3-(6-methoxyquinolin-4-yl)propyl]-1-[3-(2-(trifluoromethyl)phenyl)prop-2-ynyl]piperidine-3-acetic acid (3R,4R)-4-[3-(R,S)-Hydroxy-3-(6-methoxyquinolin-4-yl)propyl]-1-[3-(3-(trifluoromethyl)phenyl)prop-2-ynyl]-piperidine-3-acetic acid (3R,4R)-4-[3-(R,S)-Hydroxy-3-(6-methoxyquinolin-4-yl)propyl]-1-[3-(4-(trifluoromethyl)phenyl)prop-2-ynyl]-piperidine-3-acetic acid (3R,4R)-4-[3-(R,S)-Hydroxy-3-(6-methoxyquinolin-4-yl)propyl]-1-[3-(2-methoxyphenyl)prop-2-ynyl]piperidine-3-acetic acid (3R,4R)-4-[3-(R,S)-Hydroxy-3-(6-methoxyquinolin-4-yl)propyl]-1-[3-(3-methoxyphenyl)prop-2-ynyl]piperidine-3-acetic acid (3R,4R)-4-[3-(R,S)-Hydroxy-3-(6-methoxyquinolin-4-yl)propyl]-1-[3-(4-methoxyphenyl)prop-2-ynyl]piperidine-3-acetic acid (3R,4R)-4-[3-(R,S)-Hydroxy-3-(6-methoxyquinolin-4-yl)propyl]-1-[3-(3,4-difluorophenyl)prop-2-ynyl]-piperidine-3-acetic acid (3R,4R)-4-[3-(R,S)-Hydroxy-3-(6-methoxyquinolin-4-yl)propyl]-1-[3-(2,4-difluorophenyl)prop-2-ynyl]-piperidine-3-acetic acid (3R,4R)-4-[3-(R,S)-Hydroxy-3-(6-methoxyquinolin-4-yl) propyl]-1-[3-(3,4-dichlorophenyl)prop-2-ynyl]-piperidine-3-acetic acid
(3R,4R)-4-[3-(R,S)-Hydroxy-3-(6-methoxyquinolin-4-yl) propyl]-1-[3-(2,3-dichlorophenyl)prop-2-ynyl]-piperidine-3-acetic acid
(3R,4R)-4-[3-(R,S)-Hydroxy-3-(6-methoxyquinolin-4-yl) propyl]-1-[3-(2,4-dichlorophenyl)prop-2-ynyl]-piperidine-3-acetic acid
(3R,4R)-4-[3-(R,S)-Hydroxy-3-(6-methoxyquinolin-4-yl) propyl]-1-[3-(2,4,6-trichlorophenyl)prop-2-ynyl]-piperidine-3-acetic acid
(3R,4R)-4-[3-(R,S)-Hydroxy-3-(6-methoxyquinolin-4-yl) propyl]-1-[3-(3,5-dichlorophenyl)prop-2-ynyl]-piperidine-3-acetic acid
(3R,4R)-4-[3-(R,S)-Hydroxy-3-(6-methoxyquinolin-4-yl) propyl]-1-[3-(4-chloro-3-fluorophenyl)prop-2-ynyl]-piperidine-3-acetic acid
(3R,4R)-4-[3-(R,S)-Hydroxy-3-(6-methoxyquinolin-4-yl) propyl]-1-[3-(3-chloro-4-fluorophenyl)prop-2-ynyl]-piperidine-3-acetic acid
(3R,4R)-4-[3-(R,S)-Hydroxy-3-(6-methoxyquinolin-4-yl) propyl]-1-[3-(2-chloro-4-fluorophenyl)prop-2-ynyl]-piperidine-3-acetic acid
(3R,4R)-4-[3-(R,S)-Hydroxy-3-(6-methoxyquinolin-4-yl) propyl]-1-[3-(3-chloro-4-fluorophenyl)prop-2-ynyl]-piperidine-3-acetic acid
(3R,4R)-4-[3-(R,S)-Hydroxy-3-(6-methoxyquinolin-4-yl) propyl]-1-[3-(4-chloro-5-fluorophenyl)prop-2-ynyl]-piperidine-3-acetic acid
(3R,4R)-4-[3-(R,S)-Hydroxy-3-(6-methoxyquinolin-4-yl) propyl]-1-[3-(3-fluoro4-methylphenyl)prop-2-ynyl]-piperidine-3-acetic acid
(3R,4R)-4-[3-(R,S)-Hydroxy-3-(6-methoxyquinolin-4-yl) propyl]-1-[3-(4-chloro-3-(trifluoromethyl)phenyl)prop-2-ynyl]piperidine-3-acetic acid
(3R,4R)-4-[3-(R,S)-Hydroxy-3-(6-methoxyquinolin-4-yl) propyl]-1-[3-(2-chloro-4-(trifluoromethyl)phenyl)prop-2-ynyl]piperidine-3-acetic acid
(3R,4R)-4-[3-(R,S)-Hydroxy-3-(6-methoxyquinolin-4-yl) propyl]-1 -13-(2-chloro-5-(trifluoromethyl)phenyl)prop-2-ynyl]piperidine-3-acetic acid
(3R,4R)-4-[3-(R,S)-Hydroxy-3-(6-methoxyquinolin-4-yl) propyl]-1-[3-(5-chloro-2-methoxyphenyl)prop-2-ynyl] piperidine-3-acetic acid
(3R,4R)-3-[3-(R,S)-Hydroxy-3-(6-methoxyquinolin-4-yl) propyl]-1-[3-(3,5 -bis(trifluoromethyl)phenyl)prop-2-ynyl]piperidine-3-acetic acid
(3R,4R)-4-[3-(R,S)-Hydroxy-3-(6-methoxyquinolin-4-yl) propyl]-1-[3-(3,5-dimethylphenyl)prop-2-ynyl]-piperidine-3-acetic acid
(3R,4R)-4-[3-(R,S)-Hydroxy-3-(6-methoxyquinolin-4-yl) propyl]-1-[3-(2,4-dichloro-6-methylphenyl)prop-2-ynyl] piperidine-3-acetic acid
(3R,4R)-4-[3-(R,S)-Hydroxy-3-(6-methoxyquinolin-4-yl) propyl]-1-[3-(5-chlorothien-2-yl)prop-2-ynyl]-piperidine-3-acetic acid
(3R,4R)-4-[3-(R,S)-Hydroxy-3-(6-methoxyquinolin-4-yl) propyl]-1-[3-(3-chlorothien-2-yl)prop-2-ynyl]-piperidine-3-acetic acid
(3R,4R)-4-[3-(R,S)-Hydroxy-3-(6-methoxyquinolin-4-yl) propyl]-1-[3-(5-methylthien-2-yl)prop-2-ynyl]-piperidine-3-acetic acid
(3R,4R)-4-[3-(R,S)-Hydroxy-3-(6-methoxyquinolin-4-yl) propyl]-1-[3-(3-methylthien-2-yl)prop-2-ynyl]-piperidine-3-acetic acid
(3R,4R)-4-[3-(R,S)-Hydroxy-3-(6-methoxyquinolin-4-yl) propyl]-1-[3-(thien-3-yl)prop-2-ynyl]piperidine-3-acetic acid
(3R,4R)-4-[3-(R,S)-Hydroxy-3-(6-methoxyquinolin-4-yl) propyl]-1-[3-(1-methylpyrrol-3-yl)prop-2-ynyl]-piperidine-3-acetic acid
(3R,4R)-4-[3-(R,S)-Hydroxy-3-(6-methoxyquinolin-4-yl) propyl]-1-[3-(1-methylpyrrol-3-yl)prop-2-ynyl]-piperidine-3-acetic acid
(3R,4R)-4-[3-(R,S)-Hydroxy-3-(6-methoxyquinolin-4-yl) propyl]-1-[3-(thiazol-2-ynyl]piperidine-3-acetic acid
(3R,4R)-4-[3-(R,S)-Hydroxy-3-(6-methoxyquinolin-4-yl) propyl]-1-[3-(thiazol-4-ynyl]piperidine-3-acetic acid
(3R,4R)-4-[3-(R,S)-Hydroxy-3-(6-methoxyquinolin-4-yl) propyl]-1-[3-(thiazol-5-yl)prop-2-ynyl]piperidine-3-acetic acid
(3R,4R)-4-[3-(R,S)-Hydroxy-3-(6-methoxyquinolin-4-yl) propyl]-1-[3-(1-methylimidazol-2-yl)prop-2-ynyl]-piperidine-3-acetic acid
(3R,4R)-4-[3-(R,S)-Hydroxy-3-(6-methoxyquinolin-4-yl) propyl]-1-[3-(3-methylimidazol-4-yl)prop-2-ynyl]-piperidine-3-acetic acid
(3R,4R)-4-[3-(R,S)-Hydroxy-3-(6-methoxyquinolin-4-yl) propyl]-1-[3-(3-methylimidazol-4-yl)prop-2-ynyl]-piperidine-3-acetic acid
(3R,4R)-4-[3-(R,S)-Hydroxy-3-(6-methoxyquinolin-4-yl) propyl]-1-[3-(oxazol-2-yl)prop-2-ynyl]piperidine-3-acetic acid
(3R,4R)-4-[3-(R,S)-Hydroxy-3-(6-methoxyquinolin-4-yl) propyl]-1-[3-(oxazol4-yl)prop-2-ynyl]piperidine-3-acetic acid
(3R,4R)-4-[3-(R,S)-Hydroxy-3-(6-methoxyquinolin-4-yl) propyl]-1-(3-(oxazol-5-yl)prop-2-ynyl]piperidine-3-acetic acid
(3R,4R)-4-[3-(R,S)-Hydroxy-3-(6-methoxyquinolin-4-yl) propyl]-1-[3-(pyridin-2-ynyl]piperidine-3-acetic acid
(3R,4R)-4-[3-(R,S)-Hydroxy-3-(6-methoxyquinolin-4-yl) propyl]-1-[3-(pyridin-3-yl)prop-2-ynyl]piperidine-3-acetic acid
(3R,4R)-4-[3-(R,S)-Hydroxy-3-(6-methoxyquinolin-4-yl) propyl]-1-[3-(pyridin-4-yl)prop-2-ynyl]piperidine-3-acetic acid
(3R,4R)-4-[3-(R,S)-Hydroxy-3-(6-methoxyquinolin-4-yl) propyl]-1-[3-(pyrimidin-2-yl)prop-2-ynyl]piperidine-3-acetic acid
(3R,4R)-4-[3-(R,S)-Hydroxy-3-(6-methoxyquinolin-4-yl) propyl]-1-[3-(pyrimidin-4-yl)prop-2-ynyl]piperidine-3-acetic acid
(3R,4R)-4-[3-(R,S)-Hydroxy-3-(6-methoxyquinolin-4-yl) propyl]-1-[3-(pyrimidin-5-yl)prop-2-ynyl]piperidine-3-acetic acid
(3R,4R)-4-[3-(R,S)-Hydroxy-3-(6-methoxyquinolin-4-yl) propyl]-1-[3-(pyrazin-2-yl)prop-2-ynyl]piperidine-3-acetic acid
(3R,4R)-4-[3-(R,S)-Hydroxy-3-(6-methoxyquinolin-4-yl) propyl]-1-[3-(pyridazin-3-yl)prop-2-ynyl]piperidine-3-acetic acid
(3R,4R)-4-[3-(R,S)-Hydroxy-3-(6-methoxyquinolin-4-yl) propyl]-1-[3-(pyridazin-4-yl)prop-2-ynyl]piperidine-3-acetic acid
(3R,4R)-4-[3-(R,S)-Hydroxy-3-(6-methoxyquinolin-4-yl) propyl]-1-[3-phenylpropen-2-yl]piperidine-3-acetic acid
(3R,4R)-4-[3-(R,S)-Hydroxy-3-(6-methoxyquinolin-4-yl) propyl]-1-[4-phenylbuten-3-yl]piperidine-3-acetic acid
(3R,4R)-4-[3-(R,S)-Fluoro-3-(6-methoxyquinolin-4-yl) propyl]-1-[3-phenylpropyl]piperidine-3-acetic acid
(3R,4R)-4-[3-(R,S)-Fluoro-3-(6-methoxyquinolin-4-yl) propyl]-1-[4-phenylbutyl]piperidine-3-acetic acid
(3R,4R)-4-[3-(R,S)-Fluoro-3-(6-methoxyquinolin-4-yl) propyl]-1-[3-(2-fluorophenyl)propyl]piperidine-3-acetic acid (3R,4R)-4-[3-(R,S)-Fluoro-3-(6-methoxyquinolin-4-yl)propyl]-1-[4-(2-fluorophenyl)butyl]piperidine-3-acetic acid (3R,4R)-4-[3-(R,S)-Fluoro-3-(6-methoxyquinolin-4-yl)propyl]-1-[3-(3-fluorophenyl)propyl]piperidine-3-acetic acid (3R,4R)-4-[3-(R,S)-Fluoro-3-(6-methoxyquinolin-4-yl)propyl]-1-[4-(3-fluorophenyl)butyl]piperidine-3-acetic acid (3R,4R)-4-[3-(R,S)-Fluoro-3-(6-methoxyquinolin-4-yl)propyl]-1-[3-(4-fluorophenyl)propyl]piperidine-3-acetic acid (3R,4R)-4-[3-(R,S)-Fluoro-3-(6-methoxyquinolin-4-yl)propyl]-1-[4-(4-fluorophenyl)butyl]piperidine-3-acetic acid (3R,4R)-4-[3-(R,S)-Fluoro-3-(6-methoxyquinolin-4-yl)propyl]-1-[3-(2,3-difluorophenyl)propyl]piperidine-3-acetic acid (3R,4R)-4-[3-(R,S)-Fluoro-3-(6-methoxyquinolin-4-yl)propyl]-1-[4-(2,3-difluorophenyl)butyl]piperidine-3-acetic acid (3R,4R)-4-[3-(R,S)-Fluoro-3-(6-methoxyquinolin-4-yl)propyl]-1-[3-(2,6-difluorophenyl)propyl]piperidine-3-acetic acid (3R,4R)-4-[3-(R,S)-Fluoro-3-(6-methoxyquinolin-4-yl)propyl]-1-[4-(2,6-difluorophenyl)butyl]piperidine-3-acetic acid (3R,4R)-4-[3-(R,S)-Fluoro-3-(6-methoxyquinolin-4-yl)propyl]-1-[3-(2-chlorophenyl)propyl]piperidine-3-acetic acid (3R,4R)-4-[3-(R,S)-Fluoro-3-(6-methoxyquinolin-4-yl)propyl]-1-[4-(2-chlorophenyl)butyl]piperidine-3-acetic acid (3R,4R)-4-[3-(R,S)-Fluoro-3-(6-methoxyquinolin-4-yl)propyl]-1-[3-(3-chlorophenyl)propyl]piperidine-3-acetic acid (3R,4R)-4-[3-(R,S)-Fluoro-3-(6-methoxyquinolin-4-yl)propyl]-1-[4-(3-chlorophenyl)butyl]piperidine-3-acetic acid (3R,4R)-4-[3-(R,S)-Fluoro-3-(6-methoxyquinolin-4-yl)propyl]-1-[3-(4-chlorophenyl)propyl]piperidine-3-acetic acid (3R,4R)-4-(3-(R,S)-Fluoro-3-(6-methoxyquinolin-4-yl)propyl]-1-[4-(4-chlorophenyl)butyl]piperidine-3-acetic acid (3R,4R)-4-[3-(R,S)-Fluoro-3-(6-methoxyquinolin-4-yl)propyl]-1-[3-(2,3-dichlorophenyl)propyl]piperidine-3-acetic acid (3R,4R)-4-[3-(R,S)-Fluoro-3-(6-methoxyquinolin-4-yl)propyl]-1-[4-(2,3-dichlorophenyl)butyl]piperidine-3-acetic acid (3R,4R)-4-[3-(R,S)-Fluoro-3-(6-methoxyquinolin-4-yl)propyl]-1-[3-(2,6-dichlorophenyl)propyl]piperidine-3-acetic acid (3R,4R)-4-[3-(R,S)-Fluoro-3-(6-methoxyquinolin-4-yl)propyl]-1-[4-(2,6-dichlorophenyl)butyl]piperidine-3-acetic acid (3R,4R)-4-[3-(R,S)-Fluoro-3-(6-methoxyquinolin-4-yl)propyl]-1-[3-(2-methylphenyl)propyl]piperidine-3-acetic acid (3R,4R)-4-[3-(R,S)-Fluoro-3-(6-methoxyquinolin-4-yl)propyl]-1-[4-(2-methylphenyl)butyl]piperidine-3-acetic acid (3R,4R)-4-[3-(R,S)-Fluoro-3-(6-methoxyquinolin-4-yl)propyl]-1-[5-(2-methylphenyl)pentyl]piperidine-3-acetic acid (3R,4R)-4-[3-(R,S)-Fluoro-3-(6-methoxyquinolin-4-yl)propyl]-1-[3-(3-methylphenyl)propyl]piperidine-3-acetic acid (3R,4R)-4-[3-(R,S)-Fluoro-3-(6-methoxyquinolin-4-yl)propyl]-1-[4-(3-methylphenyl)butyl]piperidine-3-acetic acid (3R,4R)-4-(3-(R,S)-Fluoro-3-(6-methoxyquinolin-4-yl)propyl]-1-[3-(4-methylphenyl)propyl]piperidine-3-acetic acid (3R,4R)-4-[3-(R,S)-Fluoro-3-(6-methoxyquinolin-4-yl)propyl]-1-[4-(4-methylphenyl)butyl]piperidine-3-acetic acid (3R,4R)-4-[3-(R,S)-Fluoro-3-(6-methoxyquinolin-4-yl)propyl]-1-[3-(2-methoxyphenyl)propyl]piperidine-3-acetic acid (3R,4R)-4-[3-(R,S)-Fluoro-3-(6-methoxyquinolin-4-yl)propyl]-1-[4-(2-methoxyphenyl)butyl]piperidine-3-acetic acid (3R,4R)-4-[3-(R,S)-Fluoro-3-(6-methoxyquinolin-4-yl)propyl]-1-[3-(3-methoxyphenyl)propyl]piperidine-3-acetic acid (3R,4R)-4-[3-(R,S)-Fluoro-3-(6-methoxyquinolin-4-yl)propyl]-1-[4-(3-methoxyphenyl)butyl]piperidine-3-acetic acid (3R,4R)-4-[3-(R,S)-Fluoro-3-(6-methoxyquinolin-4-yl)propyl]-1-[3-(4-methoxyphenyl)propyl]piperidine-3-acetic acid (3R,4R)-4-[3-(R,S)-Fluoro-3-(6-methoxyquinolin-4-yl)propyl]-1-[4-(4-methoxyphenyl)butyl]piperidine-3-acetic acid (3R,4R)-4-[3-(R,S)-Fluoro-3-(6-methoxyquinolin-4-yl)propyl]-1-[3-(2-trifluoromethylphenyl)propyl]piperidine-3-acetic acid (3R,4R)-4-[3-(R,S)-Fluoro-3-(6-methoxyquinolin-4-yl)propyl]-1-[4-(2-trifluoromethylphenyl)butyl]piperidine-3-acetic acid (3R,4R)-4-[3-(R,S)-Fluoro-3-(6-methoxyquinolin-4-yl)propyl]-1-[3-(3-trifluoromethylphenyl)propyl]piperidine-3-acetic acid (3R,4R)-4-[3-(R,S)-Fluoro-3-(6-methoxyquinolin-4-yl)propyl]-1-[4-(3-trifluoromethylphenyl)butyl]piperidine-3-acetic acid (3R,4R)-4-[3-(R,S)-Fluoro-3-(6-methoxyquinolin-4-yl)propyl]-1-[3-(4-trifluoromethylphenyl)propyl]piperidine-3-acetic acid (3R,4R)-4-[3-(R,S)-Fluoro-3-(6-methoxyquinolin-4-yl)propyl]-1-[4-(4-trifluoromethylphenyl)butyl]piperidine-3-acetic acid (3R,4R)-4-[3-(R,S)-Fluoro-3-(6-methoxyquinolin-4-yl)propyl]-1-[2-phenylthioethyl]piperidine-3-acetic acid (3R,4R)-4-[3-(R,S)-Fluoro-3-(6-methoxyquinolin-4-yl)propyl]-1-[3-phenylthiopropyl]piperidine-3-acetic acid (3R,4R)-4-[3-(R,S)-Fluoro-3-(6-methoxyquinolin-4-yl)propyl]-1-[2-(2-fluorophenylthio)ethyl]piperidine-3-acetic acid (3R,4R)-4-[3-(R,S)-Fluoro-3-(6-methoxyquinolin-4-yl)propyl]-1-[3-(2-fluorophenylthio)propyl]piperidine-3-acetic acid (3R,4R)-4-[3-(R,S)-Fluoro-3-(6-methoxyquinolin-4-yl)propyl]-1-[2-(3-fluorophenylthio)ethyl]piperidine-3-acetic acid (3R,4R)-4-[3-(R,S)-Fluoro-3-(6-methoxyquinolin-4-yl)propyl]-1-[3-(3-fluorophenylthio)propyl]piperidine-3-acetic acid (3R,4R)-4-[3-(R,S)-Fluoro-3-(6-methoxyquinolin-4-yl)propyl]-1-[2-(4-fluorophenylthio)ethyl]piperidine-3-acetic acid (3R,4R)-4-[3-(R,S)-Fluoro-3-(6-methoxyquinolin-4-yl)propyl]-1-[3-(4-fluorophenylthio)propyl]piperidine-3-acetic acid (3R,4R)-4-[3-(R,S)-Fluoro-3-(6-methoxyquinolin-4-yl)propyl]-1-[2-(2,3-difluorophenylthio)ethyl]piperidine-3-acetic acid (3R,4R)-4-[3-(R,S)-Fluoro-3-(6-methoxyquinolin-4-yl)propyl]-1-[3-(2,3-difluorophenylthio)propyl]piperidine-3-acetic acid (3R,4R)-4-[3-(R,S)-Fluoro-3-(6-methoxyquinolin-4-yl)propyl]-1-[2-(2,6-difluorophenylthio)ethyl]piperidine-3-acetic acid (3R,4R)-4-[3-(R,S)-Fluoro-3-(6-methoxyquinolin-4-yl)propyl]-1-[3-(2,6-difluorophenylthio)propyl]piperidine-3-acetic acid (3R,4R)-4-[3-(R,S)-Fluoro-3-(6-methoxyquinolin-4-yl)propyl]-1-[2-(2-chlorophenylthio)ethyl]piperidine-3-acetic acid (3R,4R)-4-[3-(R,S)-Fluoro-3-(6-methoxyquinolin-4-yl)propyl]-1-[3-(2-chlorophenylthio)propyl]piperidine-3-acetic acid (3R,4R)-4-[3-(R,S)-Fluoro-3-(6-methoxyquinolin-4-yl)propyl]-1-[2-(3-chlorophenylthio)ethyl]piperidine-3-acetic acid (3R,4R)-4-[3-(R,S)-Fluoro-3-(6-methoxyquinolin-4-yl)propyl]-1-[3-(3-chlorophenylthio)propyl]piperidine-3-acetic acid (3R,4R)-4-[3-(R,S)-Fluoro-3-(6-methoxyquinolin-4-yl)propyl]-1-[2-(4-chlorophenylthio)ethyl]piperidine-3-acetic acid (3R,4R)-4-(3-(R,S)-Fluoro-3-(6-methoxyquinolin-4-yl)propyl]-1-[3-(4-chlorophenylthio)propyl]piperidine-3-acetic acid (3R,4R)-4-[3-(R,S)-Fluoro-3-(6-methoxyquinolin-4-yl)propyl]-1-[2-(2,3-dichlorophenylthio)ethyl]piperidine-3-acetic acid (3R,4R)-4-[3-(R,S)-Fluoro-3-(6-methoxyquinolin-4-yl)propyl]-1-[3-(2,3-dichlorophenylthio)propyl]piperidine-3-acetic acid (3R,4R)-4-[3-(R,S)-Fluoro-3-(6-methoxyquinolin-4-yl)propyl]-1-[2-(2,6-dichlorophenylthio)ethyl]piperidine-3-acetic acid (3R,4R)-4-[3-(R,S)-Fluoro-3-(6-methoxyquinolin-4-yl)propyl]-1-[3-(2,6-dichlorophenylthio)propyl]piperidine-3-acetic acid (3R,4R)-4-[3-(R,S)-Fluoro-3-(6-methoxyquinolin-4-yl)propyl]-1-[2-(2-methylphenylthio)ethyl]piperidine-3-acetic acid (3R,4R)-4-[3-(R,S)-Fluoro-3-(6-methoxyquinolin-4-yl)propyl]-1-[3-(2methylphenylthio)propyl]piperidine-3-acetic acid (3R,4R)-4-[3-(R,S)-Fluoro-3-(6-methoxyquinolin-4-yl)propyl]-1-[2-(3-methylphenylthio)ethyl]piperidine-3-acetic acid (3R,4R)-4-[3-(R,S)-Fluoro-3-(6-methoxyquinolin-4-yl)propyl]-1-[3-(3-methylphenylthio)propyl]piperidine-3-acetic acid (3R,4R)-4-[3-(R,S)-Fluoro-3-(6-methoxyquinolin-4-yl)propyl]-1-[2-(4-methylphenylthio)ethyl]piperidine-3-acetic acid (3R,4R)-4-[3-(R,S)-Fluoro-3-(6-methoxyquinolin-4-yl)propyl]-1-[3-(4-methylphenylthio)propyl]piperidine-3-acetic acid (3R,4R)-4-[3-(R,S)-Fluoro-3-(6-methoxyquinolin-4-yl)propyl]-1-[2-(2-trifluoromethylphenylthio)ethyl]piperidine-3-acetic acid (3R,4R)-4-[3-(R,S)-Fluoro-3-(6-methoxyquinolin-4-yl)propyl]-1-[3-(2-trifluoromethylphenylthio)propyl]piperidine-3-acetic acid (3R,4R)-4-[3-(R,S)-Fluoro-3-(6-methoxyquinolin-4-yl)propyl]-1-[2-(3trifluoromethylphenylthio)ethyl]piperidine-3-acetic acid (3R,4R)-4-[3-(R,S)-Fluoro-3-(6-methoxyquinolin-4-yl)propyl]-1-[3-(3-trifluoromethylphenylthio)propyl]piperidine-3-acetic acid (3R,4R)-4-[3-(R,S)-Fluoro-3-(6-methoxyquinolin-4-yl)propyl]-1-[2-(4-trifluoromethylphenylthio)ethyl]piperidine-3-acetic acid (3R,4R)-4-[3-(R,S)-Fluoro-3-(6-methoxyquinolin-4-yl)propyl]-1-[3-(4-trifluoromethylphenylthio)propyl]piperidine-3-acetic acid (3R,4R)-4-[3-(R,S)-Fluoro-3-(6-methoxyquinolin-4-yl)propyl]-1-[2-(2-methoxyphenylthio)ethyl]piperidine-3-acetic acid (3R,4R)-4-[3-(R,S)-Fluoro-3-(6-methoxyquinolin-4-yl)propyl]-1-[3-(2-methoxyphenylthio)propyl]piperidine-3-acetic acid (3R,4R)-4-[3-(R,S)-Fluoro-3-(6-methoxyquinolin-4-yl)propyl]-1-[2-(3-methoxyphenylthio)ethyl]piperidine-3-acetic acid (3R,4R)-4-[3-(R,S)-Fluoro-3-(6-methoxyquinolin-4-yl)propyl]-1-[3-(3-methoxyphenylthio)propyl]piperidine-3-acetic acid (3R,4R)-4-[3-(R,S)-Fluoro-3-(6-methoxyquinolin-4-yl)propyl]-1-[2-(4-methoxyphenylthio)ethyl]piperidine-3-acetic acid (3R,4R)-4-[3-(R,S)-Fluoro-3-(6-methoxyquinolin-4-yl)propyl]-1-[3-(4-methoxyphenylthio)propyl]piperidine-3-acetic acid (3R,4R)-4-[3-(R,S)-Fluoro-3-(6-methoxyquinolin-4-yl)propyl]-1-[cyclopropylmethyl]piperidine-3-acetic acid (3R,4R)-4-[3-(R,S)-Fluoro-3-(6-methoxyquinolin-4-yl)propyl]-1-[2-(cyclopropyl)ethyl]piperidine-3-acetic acid (3R,4R)-4-[3-(R,S)-Fluoro-3-(6-methoxyquinolin-4-yl)propyl]-1-[cyclobutylmethyl]piperidine-3-acetic acid (3R,4R)-4-[3-(R,S)-Fluoro-3-(6-methoxyquinolin-4-yl)propyl]-1-[2-(cyclobutyl)ethyl]piperidine-3-acetic acid (3R,4R)-4-[3-(R,S)-Fluoro-3-(6-methoxyquinolin-4-yl)propyl]-1-[cyclopentylmethyl]piperidine-3-acetic acid (3R,4R)-4-[3-(R,S)-Fluoro-3-(6-methoxyquinolin-4-yl)propyl]-1-[2-(cyclopentyl)ethyl]piperidine-3-acetic acid (3R,4R)-4-[3-(R,S)-Fluoro-3-(6-methoxyquinolin-4-yl)propyl]-1-[cyclohexylmethyl]piperidine-3-acetic acid (3R,4R)-4-[3-(R,S)-Fluoro-3-(6-methoxyquinolin-4-yl)propyl]-1-[2-(cyclohexyl)ethyl]piperidine-3-acetic acid (3R,4R)-4-[3-(R,S)-Fluoro-3-(6-methoxyquinolin-4-yl)propyl]-1-[2-(cyclopropylthio)ethyl]piperidine-3-acetic acid (3R,4R)-4-[3-(R,S)-Fluoro-3-(6-methoxyquinolin-4-yl)propyl]-1-[3-(cyclopropylthio)propyl]piperidine-3-acetic acid (3R,4R)-4-[3-(R,S)-Fluoro-3-(6-methoxyquinolin-4-yl)propyl]-1-[2-(cyclobutylthio)ethyl]piperidine-3-acetic acid (3R,4R)-4-[3-(R,S)-Fluoro-3-(6-methoxyquinolin-4-yl)propyl]-1-[3-(cyclobutylthio)propyl]piperidine-3-acetic acid (3R,4R)-4-[3-(R,S)-Fluoro-3-(6-methoxyquinolin-4-yl)propyl]-1-[2-(cyclopentylthio)ethyl]piperidine-3-acetic acid (3R,4R)-4-[3-(R,S)-Fluoro-3-(6-methoxyquinolin-4-yl)propyl]-1-[3-(cyclopentylthio)propyl]piperidine-3-acetic acid (3R,4R)-4-[3-(R,S)-Fluoro-3-(6-methoxyquinolin-4-yl)propyl]-1-[2-(cyclohexylthio)ethyl]piperidine-3-acetic acid (3R,4R)-4-[3-(R,S)-Fluoro-3-(6-methoxyquinolin-4-yl)propyl]-1-[3-(cyclohexylthio)propyl]piperidine-3-acetic acid (3R,4R)-4-[3-(R,S)-Fluoro-3-(6-methoxyquinolin-4-yl)propyl]-1-[2-methylthioethyl]piperidine-3-acetic acid
(3R,4R)-4-[3-(R,S)-Fluoro-3-(6-methoxyquinolin-4-yl)propyl]-1-[3-methylthiopropyl]piperidine-3-acetic acid
(3R,4R)-4-[3-(R,S)-Fluoro-3-(6-methoxyquinolin-4-yl)propyl]-1-[2-ethylthioethyl]piperidine-3-acetic acid
(3R,4R)-4-[3-(R,S)-Fluoro-3-(6-methoxyquinolin-4-yl)propyl]-1-[3-ethylthiopropyl]piperidine-3-acetic acid
(3R,4R)-4-[3-(R,S)-Fluoro-3-(6-methoxyquinolin-4-yl)propyl]-1-[2-(n-propylthio)ethyl]piperidine-3-acetic acid
(3R,4R)-4-[3-(R,S)-Fluoro-3-(6-methoxyquinolin-4-yl)propyl]-1-[3-(n-propylthio)propyl]piperidine-3-acetic acid
(3R,4R)-4-[3-(R,S)-Fluoro-3-(6-methoxyquinolin-4-yl)propyl]-1-[2-(n-butylthio)ethyl]piperidine-3-acetic acid
(3R,4R)-4-[3-(R,S)-Fluoro-3-(6-methoxyquinolin-4-yl)propyl]-1-[3-(n-butylthio)propyl]piperidine-3-acetic acid
(3R,4R)-4-[3-(R,S)-Fluoro-3-(6-methoxyquinolin-4-yl)propyl]-1-[3-(thien-2-yl)propyl]piperidine-3-acetic acid
(3R,4R)-4-[3-(R,S)-Fluoro-3-(6-methoxyquinolin-4-yl)propyl]-1-[4-(thien-2-yl)butyl]piperidine-3-acetic acid
(3R,4R)-4-[3-(R,S)-Fluoro-3-(6-methoxyquinolin-4-yl)propyl]-1-[2-(thien-2-yl)thioethyl]piperidine-3-acetic acid
(3R,4R)-4-[3-(R,S)-Fluoro-3-(6-methoxyquinolin-4-yl)propyl]-1-[3-(thien-2-yl)thiopropyl]piperidine-3-acetic acid
(3R,4R)-4-[3-(R,S)-Fluoro-3-(6-methoxyquinolin-4-yl)propyl]-1-[3-(5-chlorothien-2-yl)propyl]piperidine-3-acetic acid
(3R,4R)-4-[3-(R,S)-Fluoro-3-(6-methoxyquinolin-4-yl)propyl]-1-[4-(5-chlorothien-2-yl)butyl]piperidine-3-acetic acid
(3R,4R)-4-[3-(R,S)-Fluoro-3-(6-methoxyquinolin-4-yl)propyl]-1-[2-(5-chlorothien-2-yl)thioethyl]piperidine-3-acetic acid
(3R,4R)-4-[3-(R,S)-Fluoro-3-(6-methoxyquinolin-4-yl)propyl]-1-[3-(5-chlorothien-2-yl)thiopropyl]piperidine-3-acetic acid
(3R,4R)-4-[3-(R,S)-Fluoro-3-(6-methoxyquinolin-4-yl)propyl]-1-[3-(3-chlorothien-2-yl)propyl]piperidine-3-acetic acid
(3R,4R)-4-[3-(R,S)-Fluoro-3-(6-methoxyquinolin-4-yl)propyl]-1-[4-(3-chlorothien-2-yl)butyl]piperidine-3-acetic acid
(3R,4R)-4-[3-(R,S)-Fluoro-3-(6-methoxyquinolin-4-yl)propyl]-1-[2-(3-chlorothien-2-yl)thioethyl]piperidine-3-acetic acid
(3R,4R)-4-[3-(R,S)-Fluoro-3-(6-methoxyquinolin-4-yl)propyl]-1-[3-(3-chlorothien-2-yl)thiopropyl]piperidine-3-acetic acid
(3R,4R)-4-[3-(R,S)-Fluoro-3-(6-methoxyquinolin-4-yl)propyl]-1-[3-(5-methylthien-2-yl)propyl]piperidine-3-acetic acid
(3R,4R)-4-[3-(R,S)-Fluoro-3-(6-methoxyquinolin-4-yl)propyl]-1-[4-(5-methylthien-2-yl)butyl]piperidine-3-acetic acid
(3R,4R)-4-[3-(R,S)-Fluoro-3-(6-methoxyquinolin-4-yl)propyl]-1-[2-(5-methylthien-2-yl)thioethyl]piperidine-3-acetic acid
(3R,4R)-4-[3-(R,S)-Fluoro-3-(6-methoxyquinolin-4-yl)propyl]-1-[3-(5-methylthien-2-yl)thiopropyl]piperidine-3-acetic acid
(3R,4R)-4-[3-(R,S)-Fluoro-3-(6-methoxyquinolin-4-yl)propyl]-1-[3-(3-methylthien-2-yl)propyl]piperidine-3-acetic acid
(3R,4R)-4-[3-(R,S)-Fluoro-3-(6-methoxyquinolin-4-yl)propyl]-1-[4-(3-methylthien-2-yl)butyl]piperidine-3-acetic acid
(3R,4R)-4-[3-(R,S)-Fluoro-3-(6-methoxyquinolin-4-yl)propyl]-1-[2-(3-methylthien-2-yl)thioethyl]piperidine-3-acetic acid
(3R,4R)-4-[3-(R,S)-Fluoro-3-(6-methoxyquinolin-4-yl)propyl]-1-[3-(3-methylthien-2-yl)thiopropyl]piperidine-3-acetic acid
(3R,4R)-4-[3-(R,S)-Fluoro-3-(6-methoxyquinolin-4-yl)propyl]-1-[3-(thien-3-yl)propyl]piperidine-3-acetic acid
(3R,4R)-4-[3-(R,S)-Fluoro-3-(6-methoxyquinolin-4-yl)propyl]-1-[4-(thien-3-yl)butyl]piperidine-3-acetic acid
(3R,4R)-4-[3-(R,S)-Fluoro-3-(6-methoxyquinolin-4-yl)propyl]-1-[2-(thien-3-yl)thioethyl]piperidine-3-acetic acid
(3R,4R)-4-[3-(R,S)-Fluoro-3-(6-methoxyquinolin-4-yl)propyl]-1-[3-(thien-3-yl)thiopropyl]piperidine-3-acetic acid
(3R,4R)-4-[3-(R,S)-Fluoro-3-(6-methoxyquinolin-4-yl)propyl]-1-[3-(fur-2-yl)propyl]piperidine-3-acetic acid
(3R,4R)-4-[3-(R,S)-Fluoro-3-(6-methoxyquinolin-4-yl)propyl]-1-[4-(fur-2-yl)butyl]piperidine-3-acetic acid
(3R,4R)-4-[3-(R,S)-Fluoro-3-(6-methoxyquinolin-4-yl)propyl]-1-[2-(fur-2-yl)thioethyl]piperidine-3-acetic acid
(3R,4R)-4-[3-(R,S)-Fluoro-3-(6-methoxyquinolin-4-yl)propyl]-1-[3-(fur-2-yl)thiopropyl]piperidine-3-acetic acid
(3R,4R)-4-[3-(R,S)-Fluoro-3-(6-methoxyquinolin-4-yl)propyl]-1-[3-(fur-3-yl)propyl]piperidine-3-acetic acid
(3R,4R)-4-[3-(R,S)-Fluoro-3-(6-methoxyquinolin-4-yl)propyl]-1-[4-(fur-3-yl)butyl]piperidine-3-acetic acid
(3R,4R)-4-[3-(R,S)-Fluoro-3-(6-methoxyquinolin-4-yl)propyl]-1-[2-(fur-3-yl)thioethyl]piperidine-3-acetic acid
(3R,4R)-4-[3-(R,S)-Fluoro-3-(6-methoxyquinolin-4-yl)propyl]-1-[3-(fur-3-yl)thiopropyl]piperidine-3-acetic acid
(3R,4R)-4-[3-(R,S)-Fluoro-3-(6-methoxyquinolin-4-yl)propyl]-1-[3-(1-methylpyrrol2-yl)propyl]piperidine-3-acetic acid
(3R,4R)-4-[3-(R,S)-Fluoro-3-(6-methoxyquinolin-4-yl)propyl]-1-[4-(1-methylpyrrol-2-yl)butyl]piperidine-3-acetic acid
(3R,4R)-4-[3-(R,S)-Fluoro-3-(6-methoxyquinolin-4-yl)propyl]-1-[2-(1-methylpyrrol-2-yl)thioethyl]piperidine-3-acetic acid
(3R,4R)-4-[3-(R,S)-Fluoro-3-(6-methoxyquinolin-4-yl)propyl]-1-[3-(1-methylpyrrol-2-yl)thiopropyl]piperidine-3-acetic acid
(3R,4R)-4-[3-(R,S)-Fluoro-3-(6-methoxyquinolin-4-yl)propyl]-1-[3-(1-methylpyrrol-2-yl)propyl]piperidine-3-acetic acid
(3R,4R)-4-[3-(R,S)-Fluoro-3-(6-methoxyquinolin-4-yl)propyl]-1-[4-(1-methylpyrrol-3-yl)butyl]piperidine-3-acetic acid
(3R,4R)-4-[3-(R,S)-Fluoro-3-(6-methoxyquinolin-4-yl)propyl]-1-[2-(1-methylpyrrol-3-yl)thioethyl]piperidine-3-acetic acid
(3R,4R)-4-[3-(R,S)-Fluoro-3-(6-methoxyquinolin-4-yl)propyl]-1-[3-(1-methylpyrrol-3-yl)thiopropyl]piperidine-3-acetic acid
(3R,4R)-4-[3-(R,S)-Fluoro-3-(6-methoxyquinolin-4-yl)propyl]-1-[3-(thiazol-2-yl)propyl]piperidine-3-acetic acid
(3R,4R)-4-[3-(R,S)-Fluoro-3-(6-methoxyquinolin-4-yl)propyl]-1-[4-(thiazol-2-yl)butyl]piperidine-3-acetic acid
(3R,4R)-4-[3-(R,S)-Fluoro-3-(6-methoxyquinolin-4-yl)propyl]-1-[2-(thiazol-2-yl)thioethyl]piperidine-3-acetic acid
(3R,4R)-4-[3-(R,S)-Fluoro-3-(6-methoxyquinolin-4-yl)propyl]-1-[3-(thiazol-2-yl)thiopropyl]piperidine-3-acetic acid
(3R,4R)-4-[3-(R,S)-Fluoro-3-(6-methoxyquinolin-4-yl)propyl]-1-[3-(1-methylimidazol-2-yl)propyl]piperidine-3-acetic acid (3R,4R)-4-[3-(R,S)-Fluoro-3-(6-methoxyquinolin-4-yl)propyl]-1-[4-(1-methylimidazol-2-yl)butyl]piperidine-3-acetic acid (3R,4R)-4-[3-(R,S)-Fluoro-3-(6-methoxyquinolin-4-yl)propyl]-1-[2-(1-methylimidazol-2-yl)thioethyl]piperidine-3-acetic acid (3R,4R)-4-[3-(R,S)-Fluoro-3-(6-methoxyquinolin-4-yl)propyl]-1-[3-(1-methylimidazol-2-yl)thiopropyl]piperidine-3-acetic acid (3R,4R)-4-[3-(R,S)-Fluoro-3-(6-methoxyquinolin-4-yl)propyl]-1-[3-(3-methylimimidazol-4-yl)propyl]piperidine-3-acetic acid (3R,4R)-4-[3-(R,S)-Fluoro-3-(6-methoxyquinolin-4-yl)propyl]-1-[4-(3-methylimidazol-4-yl)butyl]piperidine-3-acetic acid (3R,4R)-4-[3-(R,S)-Fluoro-3-(6-methoxyquinolin-4-yl)propyl]-1-[2-(3-methylimidazol-4-yl)thioethyl]piperidine-3-acetic acid (3R,4R)-4-[3-(R,S)-Fluoro-3-(6-methoxyquinolin-4-yl)propyl]-1-[3-(3-methylimidazol-4-yl)thiopropyl]piperidine-3-acetic acid (3R,4R)-4-[3-(R,S)-Fluoro-3-(6-methoxyquinolin-4-yl)propyl]-1-[3-(3-methylpyrazol-4-yl)propyl]piperidine-3-acetic acid (3R,4R)-4-[3-(R,S)-Fluoro-3-(6-methoxyquinolin-4-yl)propyl]-1-[4-(3-methylpyrazol-4-yl)butyl]piperidine-3-acetic acid (3R,4R)-4-[3-(R,S)-Fluoro-3-(6-methoxyquinolin-4-yl)propyl]-1-[2-(3-methylpyrazol-4-yl)thioethyl]piperidine-3-acetic acid (3R,4R)-4-[3-(R,S)-Fluoro-3-(6-methoxyquinolin-4-yl)propyl]-1-[3-(3-methylpyrazol-4-yl)thiopropyl]piperidine-3-acetic acid (3R,4R)-4-[3-(R,S)-Fluoro-3-(6-methoxyquinolin-4-yl)propyl]-1-[3-(oxazol-2-yl)propyl]piperidine-3-acetic acid (3R,4R)-4-[3-(R,S)-Fluoro-3-(6-methoxyquinolin-4-yl)propyl]-1-[4-(oxazol-2-yl)butyl]piperidine-3-acetic acid (3R,4R)-4-[3-(R,S)-Fluoro-3-(6-methoxyquinolin-4-yl)propyl]-1-[2-(oxazol-2-yl)thioethyl]piperidine-3-acetic acid (3R,4R)-4-[3-(R,S)-Fluoro-3-(6-methoxyquinolin-4-yl)propyl]-1-[3-(oxazol-2-yl)thiopropyl]piperidine-3-acetic acid (3R,4R)-4-[3-(R,S)-Fluoro-3-(6-methoxyquinolin-4-yl)propyl]-1-[3-(pyridin-2-yl)propyl]piperidine-3-acetic acid (3R,4R)-4-[3-(R,S)-Fluoro-3-(6-methoxyquinolin-4-yl)propyl]-1-[4-(pyridin-2-yl)butyl]piperidine-3-acetic acid (3R,4R)-4-[3-(R,S)-Fluoro-3-(6-methoxyquinolin-4-yl)propyl]-1-[2-(pyridin-2-yl)thioethyl]piperidine-3-acetic acid (3R,4R)-4-[3-(R,S)-Fluoro-3-(6-methoxyquinolin-4-yl)propyl]-1-[3-(pyridin-2-yl)thiopropyl]piperidine-3-acetic acid (3R,4R)-4-[3-(R,S)-Fluoro-3-(6-methoxyquinolin-4-yl)propyl]-1-[3-(pyridin-3-yl)propyl]piperidine-3-acetic acid (3R,4R)-4-[3-(R,S)-Fluoro-3-(6-methoxyquinolin-4-yl)propyl]-1-[4-(pyridin-3-yl)butyl]piperidine-3-acetic acid (3R,4R)-4-[3-(R,S)-Fluoro-3-(6-methoxyquinolin-4-yl)propyl]-1-[2-(pyridin-3-yl)thioethyl]piperidine-3-acetic acid (3R,4R)-4-[3-(R,S)-Fluoro-3-(6-methoxyquinolin-4-yl)propyl]-1-[3-(pyridin-3yl)thiopropyl]piperidine-3-acetic acid (3R,4R)-4-[3-(R,S)-Fluoro-3-(6-methoxyquinolin-4-yl)propyl]-1-[3-(pyridin-4yl)propyl]piperidine-3-acetic acid (3R,4R)-4-[3-(R,S)-Fluoro-3-(6-methoxyquinolin-4-yl)propyl]-1-[4-(pyridin-4yl)butyl]piperidine-3-acetic acid (3R,4R)-4-[3-(R,S)-Fluoro-3-(6-methoxyquinolin-4-yl)propyl]-1-[5-(pyridin-4-yl)pentyl]piperidine-3-acetic acid (3R,4R)-4-[3-(R,S)-Fluoro-3-(6-methoxyquinolin-4-yl)propyl]-1-[2-(pyridin-4-yl)thioethyl]piperidine-3-acetic acid (3R,4R)-4-[3-(R,S)-Fluoro-3-(6-methoxyquinolin-4-yl)propyl]-1-[3-(pyridin-4-yl)thiopropyl]piperidine-3-acetic acid (3R,4R)-4-[3-(R,S)-Fluoro-3-(6-methoxyquinolin-4-yl)propyl]-1-[3-(pyrimidin-2-yl)propyl]piperidine-3-acetic acid (3R,4R)-4-[3-(R,S)-Fluoro-3-(6-methoxyquinolin-4-yl)propyl]-1-[4-(pyrimidin-2-yl)butyl]piperidine-3-acetic acid (3R,4R)-4-[3-(R,S)-Fluoro-3-(6-methoxyquinolin-4-yl)propyl]-1-[2-(pyrimidin-2-yl)thioethyl]piperidine-3-acetic acid (3R,4R)-4-[3-(R,S)-Fluoro-3-(6-methoxyquinolin-4-yl)propyl]-1-[3-(pyrimidin-2-yl)thiopropyl]piperidine-3-acetic acid (3R,4R)-4-[3-(R,S)-Fluoro-3-(6-methoxyquinolin-4-yl)propyl]-1-[3-(pyrimidin-4-yl)propyl]piperidine-3-acetic acid (3R,4R)-4-[3-(R,S)-Fluoro-3-(6-methoxyquinolin-4-yl)propyl]-1-[4-(pyrimidin-4-yl)butyl]piperidine-3-acetic acid (3R,4R)-4-[3-(R,S)-Fluoro-3-(6-methoxyquinolin-4-yl)propyl]-1-[2-(pyrimidin-4-yl)thioethyl]piperidine-3-acetic acid (3R,4R)-4-[3-(R,S)-Fluoro-3-(6-methoxyquinolin-4-yl)propyl]-1-[3-(pyrimidin -4-yl)thiopropyl]piperidine-3-acetic acid (3R,4R)-4-[3-(R,S)-Fluoro-3-(6-methoxyquinolin-4-yl)propyl]-1-[3-(pyrimidin-5-yl)propyl]piperidine-3-acetic acid (3R,4R)-4-[3-(R,S)-Fluoro-3-(6-methoxyquinolin-4-yl)propyl]-1-[4-(pyrimidin-5-yl)butyl]piperidine-3-acetic acid (3R,4R)-4-[3-(R,S)-Fluoro-3-(6-methoxyquinolin-4-yl)propyl]-1-[2-(pyrimidin-5-yl)thioethyl]piperidine-3-acetic acid (3R,4R)-4-[3-(R,S)-Fluoro-3-(6-methoxyquinolin-4-yl)propyl]-1-[3-(pyrimidin-5-yl)thiopropyl]piperidine-3-acetic acid (3R,4R)-4-[3-(R,S)-Fluoro-3-(6-methoxyquinolin-4-yl)propyl]-1-[3-(pyrazin-2-yl)propyl]piperidine-3-acetic acid (3R,4R)-4-[3-(R,S)-Fluoro-3-(6-methoxyquinolin-4-yl)propyl]-1-[4-(pyrazin-2-yl)butyl]piperidine-3-acetic acid (3R,4R)-4-[3-(R,S)-Fluoro-3-(6-methoxyquinolin-4-yl)propyl]-1-[2-(pyrazin-2-yl)thioethyl]piperidine-3-acetic acid (3R,4R)-4-[3-(R,S)-Fluoro-3-(6-methoxyquinolin-4-yl)propyl]-1-[3-(pyrazin-2-yl)thiopropyl]piperidine-3-acetic acid (3R,4R)-4-[3-(R,S)-Fluoro-3-(6-methoxyquinolin-4-yl)propyl]-1-[3-(pyridazin-3-yl)propyl]piperidine-3-acetic acid (3R,4R)-4-[3-(R,S)-Fluoro-3-(6-methoxyquinolin-4-yl)propyl]-1-[4-(pyridazin-3-yl)butyl]piperidine-3-acetic acid (3R,4R)-4-[3-(R,S)-Fluoro-3-(6-methoxyquinolin-4-yl)propyl]-1-[2-(pyridazin-3-yl)thioethyl]piperidine-3-acetic acid (3R,4R)-4-[3-(R,S)-Fluoro-3-(6-methoxyquinolin-4-yl)propyl]-1-[3-(pyridazin-3-yl)thiopropyl]piperidine-3-acetic acid (3R,4R)-4-[3-(R,S)-Fluoro-3-(6-methoxyquinolin-4-yl)propyl]-1-[3-(pyridazin4-yl)propyl]piperidine-3-acetic acid (3R,4R)-4-[3-(R,S)-Fluoro-3-(6-methoxyquinolin-4-yl)propyl]-1-[4-(pyridazin-4-yl)butyl]piperidine-3-acetic acid (3R,4R)-4-[3-(R,S)-Fluoro-3-(6-methoxyquinolin-4-yl)propyl]-1-[2-(pyridazin-4-yl)thioethyl]piperidine-3-acetic acid (3R,4R)-4-[3-(R,S)-Fluoro-3-(6-methoxyquinolin-4-yl)propyl]-1-[3-(pyridazin -4-yl)thiopropyl]piperidine-3-acetic acid (3R,4R)-4-[3-(R,S)-Fluoro-3-(6-methoxyquinolin-4-yl)propyl]-1-[3-phenylprop-2-ynyl]piperidine-3-acetic acid (3R,4R)-4-[3-(R,S)-Fluoro-3-(6-methoxyquinolin-4-yl)propyl]-1-[3-(2-fluorophenyl)prop-2-ynyl]piperidine-3-acetic acid (3R,4R)-4-[3-(R,S)-Fluoro-3-(6-methoxyquinolin-4-yl)propyl]-1-[3-(3-fluorophenyl)prop-2-ynyl]piperidine-3-acetic acid (3R,4R)-4-[3-(R,S)-Fluoro-3-(6-methoxyquinolin-4-yl)propyl]-1-[3-(4-fluorophenyl)prop-2-ynyl]piperidine-3-acetic acid (3R,4R)-4-[3-(R,S)-Fluoro-3-(6-methoxyquinolin-4-yl)propyl]-1-[3-(2-chlorophenyl)prop-2-ynyl]piperidine-3-acetic acid (3R,4R)-4-[3-(R,S)-Fluoro-3-(6-methoxyquinolin-4-yl)propyl]-1-[3-(3-chlorophenyl)prop-2-ynyl]piperidine-3-acetic acid (3R,4R)-4-[3-(R,S)-Fluoro-3-(6-methoxyquinolin-4-yl)propyl]-1-[3-(4-chlorophenyl)prop-2-ynyl]piperidine-3-acetic acid (3R,4R)-4-[3-(R,S)-Fluoro-3-(6-methoxyquinolin-4-yl)propyl]-1-[3-(2-methylphenyl)prop-2-ynyl]piperidine-3-acetic acid (3R,4R)-4-[3-(R,S)-Fluoro-3-(6-methoxyquinolin-4-yl)propyl]-1-[3-(3-methylphenyl)prop-2-ynyl]piperidine-3-acetic acid (3R,4R)-4-[3-(R,S)-Fluoro-3-(6-methoxyquinolin-4-yl)propyl]-1-[3-(4-methylphenyl)prop-2-ynyl]piperidine-3-acetic acid (3R,4R)-4-[3-(R,S)-Fluoro-3-(6-methoxyquinolin-4-yl)propyl]-1-[3-(2-(trifluoromethyl)phenyl)prop-2-ynyl]-piperidine-3-acetic acid (3R,4R)-4-[3-(R,S)-Fluoro-3-(6-methoxyquinolin-4-yl)propyl]-1-[3-(3-(trifluoromethyl)phenyl)prop-2-ynyl]piperidine-3-acetic acid (3R,4R)-4-[3-(R,S)-Fluoro-3-(6-methoxyquinolin-4-yl)propyl]-1-[3-(4-(trifluoromethyl)phenyl)prop-2-ynyl]piperidine-3-acetic acid (3R,4R)-4-[3-(R,S)-Fluoro-3-(6-methoxyquinolin-4-yl)propyl]-1-[3-(2-methoxyphenyl)prop-2-ynyl]piperidine-3-acetic acid (3R,4R)-4-[3-(R,S)-Fluoro-3-(6-methoxyquinolin-4-yl)propyl]-1-[3-(3-methoxyphenyl)prop-2-ynyl]piperidine-3-acetic acid (3R,4R)-4-[3-(R,S)-Fluoro-3-(6-methoxyquinolin-4-yl)propyl]-1-[3-(4-methoxyphenyl)prop-2-ynyl]piperidine3-acetic acid (3R,4R)-4-[3-(R,S)-Fluoro-3-(6-methoxyquinolin-4-yl)propyl]-1-[3-(3,4-difluorophenyl)prop-2-ynyl]piperidine-3-acetic acid (3R,4R)-4-[3-(R,S)-Fluoro-3-(6-methoxyquinolin-4-yl)propyl]-1-[3-(2,4-difluorophenyl)prop-2-ynyl]piperidine-3-acetic acid (3R,4R)-4-[3-(R,S)-Fluoro-3-(6-methoxyquinolin-4-yl)propyl]-1-[3-(3,4-dichlorophenyl)prop-2-ynyl]piperidine-3-acetic acid (3R,4R)-4-[3-(R,S)-Fluoro-3-(6-methoxyquinolin-4-yl)propyl]-1-[3-(2,3-dichlorophenyl)prop-2-ynyl]piperidine-3-acetic acid (3R,4R)-4-[3-(R,S)-Fluoro-3-(6-methoxyquinolin-4-yl)propyl]-1-[3-(2,4-dichlorophenyl)prop-2-ynyl]piperidine-3-acetic acid (3R,4R)-4-[3-(R,S)-Fluoro-3-(6-methoxyquinolin-4-yl)propyl]-1-[3-(2,4,6-trichlorophenyl)prop-2-ynyl]piperidine-3-acetic acid (3R,4R)-4-[3-(R,S)-Fluoro-3-(6-methoxyquinolin-4-yl)propyl]-1-[3-(3,5-dichlorophenyl)prop-2-ynyl]piperidine-3-acetic acid (3R,4R)-4-[3-(R,S)-Fluoro-3-(6-methoxyquinolin-4-yl)propyl]-1-[3-(4-chloro-3-fluorophenyl)prop-2-ynyl]piperidine-3-acetic acid (3R,4R)-4-[3-(R,S)-Fluoro-3-(6-methoxyquinolin-4-yl)propyl]-1-[3-(3-chloro-4-fluorophenyl)prop-2-ynyl]piperidine-3-acetic acid (3R,4R)-4-[3-(R,S)-Fluoro-3-(6-methoxyquinolin-4-yl)propyl]-1-[3-(2-chloro-4-fluorophenyl)prop-2-ynyl]piperidine-3-acetic acid (3R,4R)-4-[3-(R,S)-Fluoro-3-(6-methoxyquinolin-4-yl)propyl]-1-[3-(3-chloro-5-fluorophenyl)prop-2-ynyl]piperidine-3-acetic acid (3R,4R)-4-[3-(R,S)-Fluoro-3-(6-methoxyquinolin-4-yl)propyl]-1-[3-(4-chloro-2-fluorophenyl)prop-2-ynyl]piperidine-3-acetic acid (3R,4R)-4-[3-(R,S)-Fluoro-3-(6-methoxyquinolin-4-yl)propyl]-1-[3-(3-fluoro-4-methylphenyl)prop-2-ynyl]piperidine-3-acetic acid (3R,4R)-4-[3-(R,S)-Fluoro-3-(6-methoxyquinolin-4-yl)propyl]-1-[3-(4-chloro-3-(trifluoromethyl)phenyl)prop-2-ynyl]piperidine-3-acetic acid (3R,4R)-4-[3-(R,S)-Fluoro-3-(6-methoxyquinolin-4-yl)propyl]-1-[3-(2-chloro-4-(trifluoromethyl)phenyl)prop-2-ynyl]piperidine-3-acetic acid (3R,4R)-4-[3-(R,S)-Fluoro-3-(6-methoxyquinolin-4-yl)propyl]-1-[3-(2-chloro-5-(trifluoromethyl)phenyl)prop-2-ynyl]piperidine-3-acetic acid (3R,4R)-4-[3-(R,S)-Fluoro-3-(6-methoxyquinolin-4-yl)propyl]-1-[3-(5-chloro-2-methoxyphenyl)prop-2-ynyl]piperidine-3-acetic acid (3R,4R)-4-[3-(R,S)-Fluoro-3-(6-methoxyquinolin-4-yl)propyl]-1-[3-(3,5-bis(trifluoromethyl)phenyl)prop-2-ynyl]piperidine-3-acetic acid (3R,4R)-4-[3-(R,S)-Fluoro-3-(6-methoxyquinolin-4-yl)propyl]-1-[3-(3,5-dimethylphenyl)prop-2-ynyl]piperidine-3-acetic acid (3R,4R)-4-[3-(R,S)-Fluoro-3-(6-methoxyquinolin-4-yl)propyl]-1-[3-(2,4-dichloro-6-methylphenyl)prop-2-ynyl]piperidine-3-acetic acid (3R,4R)-4-[3-(R,S)-Fluoro-3-(6-methoxyquinolin-4-yl)propyl]-1-[3-(thien-2-yl)prop-2-ynyl]piperidine-3-acetic acid (3R,4R)-4-[3-(R,S)-Fluoro-3-(6-methoxyquinolin-4-yl)propyl]-1-[3-(5-chlorothien-2-yl)prop-2-ynyl]-piperidine-3-acetic acid (3R,4R)-4-[3-(R,S)-Fluoro-3-(6-methoxyquinolin-4-yl)propyl]-1-[3-(3-chlorothien-2-yl)prop-2-ynyl]-piperidine-3-acetic acid (3R,4R)-4-[3-(R,S)-Fluoro-3-(6-methoxyquinolin-4-yl)propyl]-1-[3-(5-methylthien-2-yl)prop-2-ynyl]-piperidine-3-acetic acid (3R,4R)-4-[3-(R,S)-Fluoro-3-(6-methoxyquinolin-4-yl)propyl]-1-[3-(3-methylthien-2-yl)prop-2-ynyl]-piperidine-3-acetic acid (3R,4R)-4-[3-(R,S)-Fluoro-3-(6-methoxyquinolin-4-yl)propyl]-1-[3-(thien-3-yl)prop-2-ynyl]piperidine-3-acetic acid
(3R,4R)-4-[3-(R,S)-Fluoro-3-(6-methoxyquinolin-4-yl)propyl]-1-[3-(1-methylpyrrol-2-yl)prop-2-ynyl]-piperidine-3-acetic acid
(3R,4R)-4-[3-(R,S)-Fluoro-3-(6-methoxyquinolin-4-yl)propyl]-1-[3-(1-methylpyrrol-3-yl)prop-2-ynyl]-piperidine-3-acetic acid
(3R,4R)-4-[3-(R,S)-Fluoro-3-(6-methoxyquinolin-4-yl)propyl]-1-[3-(thiazol-2-yl)prop-2-ynyl]piperidine-3-acetic acid
(3R,4R)-4-[3-(R,S)-Fluoro-3-(6-methoxyquinolin-4-yl)propyl]-1-[3-(thiazol-4-yl)prop-2-ynyl]piperidine-3-acetic acid
(3R,4R)-4-[3-(R,S)-Fluoro-3-(6-methoxyquinolin-4-yl)propyl]-1-[3-(thiazol-5-yl)prop-2-ynyl]piperidine-3-acetic acid
(3R,4R)-4-[3-(R,S)-Fluoro-3-(6-methoxyquinolin-4-yl)propyl]-1-[3-(1-methylimidazol-2-yl)prop-2-ynyl]-piperidine-3-acetic acid
(3R,4R)-4-[3-(R,S)-Fluoro-3-(6-methoxyquinolin-4-yl)propyl]-1-[3-(3-methylimidazol-4-yl)prop-2-ynyl]-piperidine-3-acetic acid
(3R,4R)-4-[3-(R,S)-Fluoro-3-(6-methoxyquinolin-4-yl)propyl]-1-[3-(3-methylpyrazol-4-yl)prop-2-ynyl]-piperidine-3-acetic acid
(3R,4R)-4-[3-(R,S)-Fluoro-3-(6-methoxyquinolin-4-yl)propyl]-1-[3-(oxazol-2-yl)prop-2-ynyl]piperidine-3-acetic acid
(3R,4R)-4-[3-(R,S)-Fluoro-3-(6-methoxyquinolin-4-yl)propyl]-1-[3-(oxazol-4-yl)prop-2-ynyl]piperidine-3-acetic acid
(3R,4R)-4-[3-(R,S)-Fluoro-3-(6-methoxyquinolin-4-yl)propyl]-1-[3-(oxazol-5-yl)prop-2-ynyl]piperidine-3-acetic acid
(3R,4R)-4-[3-(R,S)-Fluoro-3-(6-methoxyquinolin-4-yl)propyl]-1-[3-(pyridin-2-yl)prop-2-ynyl]piperidine-3-acetic acid
(3R,4R)-4-[3-(R,S)-Fluoro-3-(6-methoxyquinolin-4-yl)propyl]-1-[3-(pyridin-3-yl)prop-2-ynyl]piperidine-3-acetic acid
(3R,4R)-4-[3-(R,S)-Fluoro-3-(6-methoxyquinolin-4-yl)propyl]-1-[3-(pyridin-4-yl)prop-2-ynyl]piperidine-3-acetic acid
(3R,4R)-4-[3-(R,S)-Fluoro-3-(6-methoxyquinolin-4-yl)propyl]-1-[3-(pyrimidin-2-yl)prop-2-ynyl]piperidine-3-acetic acid
(3R,4R)-4-[3-(R,S)-Fluoro-3-(6-methoxyquinolin-4-yl)propyl]-1-[3-(pyrimidin-4-yl)prop-2-ynyl]piperidine-3-acetic acid
(3R,4R)-4-[3-(R,S)-Fluoro-3-(6-methoxyquinolin-4-yl)propyl]-1-[3-(pyrimidin-5-yl)prop-2-ynyl]piperidine-3-acetic acid
(3R,4R)-4-[3-(R,S)-Fluoro-3-(6-methoxyquinolin-4-yl)propyl]-1-[3-(pyrazin-2-yl)prop-2-ynyl]piperidine-3-acetic acid
(3R,4R)-4-[3-(R,S)-Fluoro-3-(6-methoxyquinolin-4-yl)propyl]-1-[3-(pyridazin-3-yl)prop-2-ynyl]piperidine-3-acetic acid
(3R,4R)-4-[3-(R,S)-Fluoro-3-(6-methoxyquinolin-4-yl)propyl]-1-[3-(pyridazin-4-yl)prop-2-ynyl]piperidine-3-acetic acid
(3R,4R)-4-[3-(R,S)-Fluoro-3-(6-methoxyquinolin-4-yl)propyl]-1-[3-phenylpropen-2-yl]piperidine-3-acetic acid
(3R,4R)-4-[3-(R,S)-Fluoro-3-(6-methoxyquinolin-4-yl)propyl]-1-[4-phenylbuten-3-yl]piperidine-3-acetic acid
(3R,4R)-3-{4-[3-(6-Methoxyquinolin-4-yl)propyl]-1-[3-phenylpropyl]piperidin-3-yl}propan-1-oic acid
(3R,4R)-3-{4-[3-(6-Methoxyquinolin-4-yl)propyl]-1-[4-phenylbutyl]piperidin-3-yl}propan-1-oic acid
(3R,4R)-3-{4-[3-(6-Methoxyquinolin-4-yl)propyl]-1-[3-(2-fluorophenyl)propyl]piperidin-3-yl}propan-1-oic acid
(3R,4R)-3-{4-[3-(6-Methoxyquinolin-4-yl)propyl]-1-[4-(2-fluorophenyl)butyl]piperidin-3-yl}propan-1-oic acid
(3R,4R)-3-{4-[3-(6-Methoxyquinolin-4-yl)propyl]-1-[3-(3-fluorophenyl)propyl]piperidin-3-yl}propan-1-oic acid
(3R,4R)-3-{4-[3-(6-Methoxyquinolin-4-yl)propyl]-1-[4-(3-fluorophenyl)butyl]piperidin-3-yl}propan-1-oic acid
(3R,4R)-3-{4-[3-(6-Methoxyquinolin-4-yl)propyl]-1-[3-(4-fluorophenyl)propyl]piperidin-3-yl}propan-1-oic acid
(3R,4R)-3-{4-[3-(6-Methoxyquinolin-4-yl)propyl]-1-[4-(4-fluorophenyl)butyl]piperidin-3-yl}propan-1-oic acid
(3R,4R)-3-{4-[3-(6-Methoxyquinolin-4-yl)propyl]-1-[3-(2,3-difluorophenyl)propyl]piperidin-3-yl}propan-1-oic acid
(3R,4R)-3-{4-[3-(6-Methoxyquinolin-4-yl)propyl]-1-[4-(2,3-difluorophenyl)butyl]piperidin-3-yl}propan-1-oic acid
(3R,4R)-3-{4-[3-(6-Methoxyquinolin-4-yl)propyl]-1-[3-(2,6-difluorophenyl)propyl]piperidin-3-yl}propan-1-oic acid
(3R,4R)-3-{4-[3-(6-Methoxyquinolin-4-yl)propyl]-1-[4-(2,6-difluorophenyl)butyl]piperidin-3-yl}propan-1-oic acid
(3R,4R)-3-{4-[3-(6-Methoxyquinolin-4-yl)propyl]-1-[3-(2-chlorophenyl)propyl]piperidin-3-yl}propan-1-oic acid
(3R,4R)-3-{4-[3-(6-Methoxyquinolin-4-yl)propyl]-1-[4-(2-chlorophenyl)butyl]piperidin-3-yl}propan-1-oic acid
(3R,4R)-3-{4-[3-(6-Methoxyquinolin-4-yl)propyl]-1-[3-(3-chlorophenyl)propyl]piperidin-3-yl}propan-1-oic acid
(3R,4R)-3-{4-[3-(6-Methoxyquinolin-4-yl)propyl]-1-[4-(3-chlorophenyl)butyl]piperidin-3-yl}propan-1-oic acid
(3R,4R)-3-{4-[3-(6-Methoxyquinolin-4-yl)propyl]-1-[3-(4-chlorophenyl)propyl]piperidin-3-yl}propan-1-oic acid
(3R,4R)-3-{4-[3-(6-Methoxyquinolin-4-yl)propyl]-1-[4-(4-chlorophenyl)butyl]piperidin-3-yl}propan-1-oic acid
(3R,4R)-3-{4-[3-(6-Methoxyquinolin-4-yl)propyl]-1-[3-(2,3-dichlorophenyl)propyl]piperidin-3-yl}propan-1-oic acid
(3R,4R)-3-{4-[3-(6-Methoxyquinolin-4-yl)propyl]-1-[4-(2,3-dichlorophenyl]piperidin-3-yl}propan-1-oic acid
(3R,4R)-3-{4-[3-(6-Methoxyquinolin-4-yl)propyl]-1-[3-(2,6-dichlorophenyl)propyl]piperidin-3-yl}propan-1-oic acid
(3R,4R)-3-{4-[3-(6-Methoxyquinolin-4-yl)propyl]-1-[4-(2,6-dichlorophenyl)butyl]piperidin-3-yl}propan-1-oic acid
(3R,4R)-3-{4-[3-(6-Methoxyquinolin-4-yl)propyl]-1-[3-(2-methylphenyl)propyl]piperidin-3-yl}propan-1-oic acid
(3R,4R)-3-{4-[3-(6-Methoxyquinolin-4-yl)propyl]-1-[4-(2-methylphenyl)butyl]piperidin-3-yl}propan-1-oic acid
(3R,4R)-3-{4-[3-(6-Methoxyquinolin-4-yl)propyl]-1-[5-(2-methylphenyl)pentyl]piperidin-3-yl}propan-1-oic acid
(3R,4R)-3-{4-[3-(6-Methoxyquinolin-4-yl)propyl]-1-[3-(3-methylphenyl)propyl]piperidin-3-yl}propan-1-oic acid
(3R,4R)-3-{4-[3-(6-Methoxyquinolin-4-yl)propyl]-1-[4-(3-methylphenyl)butyl]piperidin-3-yl}propan-1-oic acid
(3R,4R)-3-{4-[3-(6-Methoxyquinolin-4-yl)propyl]-1-[3-(4-methylphenyl)propyl]piperidin-3-yl}propan-1-oic acid
(3R,4R)-3-{4-[3-(6-Methoxyquinolin-4-yl)propyl]-1-[4-(4-methylphenyl)butyl]piperidin-3-yl}propan-1-oic acid
(3R,4R)-3-{4-[3-(6-Methoxyquinolin-4-yl)propyl]-1-[3-(2-methoxyphenyl)propyl]piperidin-3-yl}propan-1-oic acid
(3R,4R)-3-{4-[3-(6-Methoxyquinolin-4-yl)propyl]-1-[4-(2-methoxyphenyl)butyl]piperidin-3-yl}propan-1-oic acid
(3R,4R)-3-{4-[3-(6-Methoxyquinolin-4-yl)propyl]-1-[3-(3-methoxyphenyl)propyl]piperidin-3-yl}propan-1-oic acid (3R,4R)-3-{4-[3-(6-Methoxyquinolin-4-yl)propyl]-1-[4-(3-methoxyphenyl)butyl]piperidin-3-yl}propan-1-oic acid
(3R,4R)-3-{4-[3-(6-Methoxyquinolin-4-yl)propyl]-1-[3-(4-methoxyphenyl)propyl]piperidin-3-yl}propan-1-oic acid
(3R,4R)-3-{4-[3-(6-Methoxyquinolin-4-yl)propyl]-1-[4-(4-methoxyphenyl)butyl]piperidin-3-yl}propan-1-oic acid
(3R,4R)-3-{4-[3-(6-Methoxyquinolin-4-yl)propyl]-1-[3-(2-trifluoromethylphenyl)propyl]piperidin-3-yl}propan-1-oic acid
(3R,4R)-3-{4-[3-(6-Methoxyquinolin-4-yl)propyl]-1-[4-(2-trifluoromethylphenyl)butyl]piperidin-3-yl}propan-1-oic acid
(3R,4R)-3-{4-[3-(6-Methoxyquinolin-4-yl)propyl]-1-[3-(3-trifluoromethylphenyl)propyl]piperidin-3-yl}propan-1-oic acid
(3R,4R)-3-{4-[3-(6-Methoxyquinolin-4-yl)propyl]-1-[4-(3-trifluoromethylphenyl)butyl]piperidin-3-yl}propan-1-oic acid
(3R,4R)-3-{4-[3-(6-Methoxyquinolin-4-yl)propyl]-1-[3-(4-trifluoromethylphenyl)propyl]piperidin-3-yl}propan-1-oic acid
(3R,4R)-3-{4-[3-(6-Methoxyquinolin-4-yl)propyl]-1-[4-(4-trifluoromethylphenyl)butyl]piperidin-3-yl}propan-1-oic acid
(3R,4R)-3-{4-[3-(6-Methoxyquinolin-4-yl)propyl]-1-[2-phenylthioethyl]piperididin-3-yl}propan-1-oic acid
(3R,4R)-3-{4-[3-(6-Methoxyquinolin-4-yl)propyl]-1-[3-phenylthiopropyl]piperididin-3-yl}propan-1-oic acid
(3R,4R)-3-{4-[3-(6-Methoxyquinolin-4-yl)propyl]-1-[2-(2-fluorophenylthio)ethyl]piperidin-3-yl}propan-1-oic acid
(3R,4R)-3-{4-[3-(6-Methoxyquinolin-4-yl)propyl]-1-[3-(2-fluorophenylthio)propyl]piperidin-3-yl}propan-1-oic acid
(3R,4R)-3-{4-[3-(6-Methoxyquinolin-4-yl)propyl]-1-[2-(3-fluorophenylthio)ethyl]piperidin-3-yl}propan-1-oic acid
(3R,4R)-3-{4-[3-(6-Methoxyquinolin-4-yl)propyl]-1-[3-(3-fluorophenylthio)propyl]piperidin-3-yl}propan-1-oic acid
(3R,4R)-3-{4-[3-(6-Methoxyquinolin-4-yl)propyl]-1-[2-(4-fluorophenylthio)ethyl]piperidin-3-yl}propan-1-oic acid
(3R,4R)-3-{4-[3-(6-Methoxyquinolin-4-yl)propyl]-1-[3-(4-fluorophenylthio)propyl]piperidin-3-yl}propan-1-oic acid
(3R,4R)-3-{4-[3-(6-Methoxyquinolin-4-yl)propyl]-1-[2-(2,3-difluorophenylthio)ethyl]piperidin-3-yl}propan-1-oic acid
(3R,4R)-3-{4-[3-(6-Methoxyquinolin-4-yl)propyl]-1-[3-(2,3-difluorophenylthio)propyl]piperidin-3-yl}propan-1-oic acid
(3R,4R)-3-{4-[3-(6-Methoxyquinolin-4-yl)propyl]-1-[2-(2,6-difluorophenylthio)ethyl]piperidin-3-yl}propan-1-oic acid
(3R,4R)-3-{4-[3-(6-Methoxyquinolin-4-yl)propyl]-1-[3-(2,6-difluorophenylthio)propyl]piperidin-3-yl}propan-1-oic acid
(3R,4R)-3-{4-[3-(6-Methoxyquinolin-4-yl)propyl]-1-[2-(2-chlorophenylthio)ethyl]piperidin-3-yl}propan-1-oic acid
(3R,4R)-3-{4-[3-(6-Methoxyquinolin-4-yl)propyl]-1-[3-(2-chlorophenylthio)propyl]piperidin-3-yl}propan-1-oic acid
(3R,4R)-3-{4-[3-(6-Methoxyquinolin-4-yl)propyl]-1-[2-(3-chlorophenylthio)ethyl]piperidin-3-yl}propan-1-oic acid
(3R,4R)-3-{4-[3-(6-Methoxyquinolin-4-yl)propyl]-1-[3-(3-chlorophenylthio)propyl]piperidin-3-yl}propan-1-oic acid
(3R,4R)-3-{4-[3-(6-Methoxyquinolin-4-yl)propyl]-1-[2-(4-chlorophenylthio)ethyl]piperidin-3-yl}propan-1-oic acid
(3R,4R)-3-{4-[3-(6-Methoxyquinolin-4-yl)propyl]-1-[3-(4-chlorophenylthio)propyl]piperidin-3-yl}propan-1-oic acid
(3R,4R)-3-{4-[3-(6-Methoxyquinolin-4-yl)propyl]-1-[2-(2,3-dichlorophenylthio)ethyl]piperidin-3-yl}propan-1-oic acid
(3R,4R)-3-{4-[3-(6-Methoxyquinolin-4-yl)propyl]-1-[3-(2,3-dichlorophenylthio)propyl]piperidin-3-yl}propan-1-oic acid
(3R,4R)-3-{4-[3-(6-Methoxyquinolin-4-yl)propyl]-1-[2-(2,6-dichlorophenylthio)ethyl]piperidin-3-yl}propan-1-oic acid
(3R,4R)-3-{4-[3-(6-Methoxyquinolin-4-yl)propyl]-1-[3-(2,6-dichlorophenylthio)propyl]piperidin-3-yl}propan-1-oic acid
(3R,4R)-3-{4-[3-(6-Methoxyquinolin-4-yl)propyl]-1-[2-(2-methylphenylthio)ethyl]piperidin-3-yl}propan-1-oic acid
(3R,4R)-3-{4-[3-(6-Methoxyquinolin-4-yl)propyl]-1-[3-(2-methylphenylthio)propyl]piperidin-3-yl}propan-1-oic acid
(3R,4R)-3-{4-[3-(6-Methoxyquinolin-4-yl)propyl]-1-[2-(3-methylphenylthio)ethyl]piperidin-3-yl}propan-1-oic acid
(3R,4R)-3-{4-[3-(6-Methoxyquinolin-4-yl)propyl]-1-[3-(3-methylphenylthio)propyl]piperidin-3-yl}propan-1-oic acid
(3R,4R)-3-{4-[3-(6-Methoxyquinolin-4-yl)propyl]-1-[2-(4-methylphenylthio)ethyl]piperidin-3-yl}propan-1-oic acid
(3R,4R)-3-{4-[3-(6-Methoxyquinolin-4-yl)propyl]-1-[3-(4-methylphenylthio)propyl]piperidin-3-yl}propan-1-oic acid
(3R,4R)-3-{4-[3-(6-Methoxyquinolin-4-yl)propyl]-1-[2-(2-trifluoromethylphenylthio)ethyl]piperidin-3-yl}propan-1-oic acid
(3R,4R)-3-{4-[3-(6-Methoxyquinolin-4-yl)propyl]-1-[3-(2-trifluoromethylphenylthio)propyl]piperidin-3-yl}propan-1-oic acid
(3R,4R)-3-{-[8-(6-Methoxyquinolin-4-yl)propyl]-1-[2-(3-trifluoromethylphenylthio)ethyl]piperidin-3-yl}propan-1-oic acid
(3R,4R)-3-{4-[3-(6-Methoxyquinolin-4-yl)propyl]-1-[3-(3-trifluoromethylphenylthio)propyl]piperidin-3-yl}propan-1-oic acid
(3R,4R)-3-{4-[3-(6-Methoxyquinolin-4-yl)propyl]-1-[2-(4-trifluoromethylphenylthio)ethyl]piperidin-3-yl}propan-1-oic acid
(3R,4R)-3-{4-[3-(6-Methoxyquinolin-4-yl)propyl]-1-[3-(4-trifluoromethylphenylthio)propyl]piperidin-3-yl}propan-1-oic acid
(3R,4R)-3-{4-[3-(6-Methoxyquinolin-4-yl)propyl]-1-[2-(2-methoxyphenylthio)ethyl]piperidin-3-yl}propan-1-oic acid
(3R,4R)-3-{4-[3-(6-Methoxyquinolin-4-yl)propyl]-1-[3-(2-methoxyphenylthio)propyl]piperidin-3-yl}propan-1-oic acid
(3R,4R)-3-{4-[3-(6-Methoxyquinolin-4-yl)propyl]-1-[2-(3-methoxyphenylthio)ethyl]piperidin-3-yl}propan-1-oic acid
(3R,4R)-3-{4-[3-(6-Methoxyquinolin-4-yl)propyl]-1-[3-(3-methoxyphenylthio)propyl]piperidin-3-yl}propan-1-oic acid
(3R,4R)-3-{4-[3-(6-Methoxyquinolin-4-yl)propyl]-1-[2-(4-methoxyphenylthio)ethyl]piperidin-3-yl}propan-1-oic acid
(3R,4R)-3-{4-[3-(6-Methoxyquinolin-4-yl)propyl]-1-[3-(4-methoxyphenylthio)propyl]piperidin-3-yl}propan-1-oic acid
(3R,4R)-3-{4-[3-(6-Methoxyquinolin-4-yl)propyl]-1-[cyclopropylmethyl]piperidin-3-yl}propan-1-oic acid (3R,4R)-3-{4-[3-(6-Methoxyquinolin-4-yl)propyl]-1-[2-(cyclopropyl)ethyl]piperidin-3-yl}propan-1-oic acid
(3R,4R)-3-{4-[3-(6-Methoxyquinolin-4-yl)propyl]-1-[cyclobutylmethyl]piperidin-3-yl}propan-1-oic acid
(3R,4R)-3-{4-[3-(6-Methoxyquinolin-4-yl)propyl]-1-[2-(cyclobutyl)ethyl]piperidin-3-yl}propan-1-oic acid
(3R,4R)-3-{4-[3-(6-Methoxyquinolin-4-yl)propyl]-1-[cyclopentylmethyl]piperidin-3-yl}propan-1-oic acid
(3R,4R)-3-{4-[3-(6-Methoxyquinolin-4-yl)propyl]-1-[2-(cyclopentyl)ethyl]piperidin-3-yl}propan-1-oic acid
(3R,4R)-3-{4-[3-(6-Methoxyquinolin-4-yl)propyl]-1-[cyclohexylmethyl]piperidin-3-yl}propan-1-oic acid
(3R,4R)-3-{4-[3-(6-Methoxyquinolin-4-yl)propyl]-1-[2-(cyclohexyl)ethyl]piperidin-3-yl}propan-1-oic acid
(3R,4R)-3-{4-[3-(6-Methoxyquinolin-4-yl)propyl]-1-[2-(cyclopropylthio)ethyl]piperidin-3-yl}propan-1-oic acid
(3R,4R)-3-{4-[3-(6-Methoxyquinolin-4-yl)propyl]-1-[3-(cyclopropylthio)propyl]piperidin-3-yl}propan-1-oic acid
(3R,4R)-3-{4-[3-(6-Methoxyquinolin-4-yl)propyl]-1-[2-(cyclobutylthio)ethyl]piperidin-3-yl}propan-1-oic acid
(3R,4R)-3-{4-[3-(6-Methoxyquinolin-4-yl)propyl]-1-[3-(cyclobutylthio)propyl]piperidin-3-yl}propan-1-oic acid
(3R,4R)-3-{4-[3-(6-Methoxyquinolin-4-yl)propyl]-1-[2-(cyclopentylthio)ethyl]piperidin-3-yl}propan-1-oic acid
(3R,4R)-3-{4-[3-(6-Methoxyquinolin-4-yl)propyl]-1-[3-(cyclopentylthio)propyl]piperidin-3-yl}propan-1-oic acid
(3R,4R)-3-{4-[3-(6-Methoxyquinolin-4-yl)propyl]-1-[2-(cyclohexylthio)ethyl]piperidin-3-yl}propan-1-oic acid
(3R,4R)-3-{4-[3-(6-Methoxyquinolin-4-yl)propyl]-1-[3-(cyclohexylthio)propyl]piperidin-3-yl}propan-1-oic acid
(3R,4R)-3-{4-[3-(6-Methoxyquinolin-4-yl)propyl]-1-[2-methylthioethyl]piperidin-3-yl}propan-1-oic acid
(3R,4R)-3-{4-[3-(6-Methoxyquinolin-4-yl)propyl]-1-[3-methylthiopropyl]piperidin-3-yl}propan-1-oic acid
(3R,4R)-3-{4-[3-(6-Methoxyquinolin-4-yl)propyl]-1-[2-ethylthioethyl]piperidin-3-yl}propan-1-oic acid
(3R,4R)-3-{4-[3-(6-Methoxyquinolin-4-yl)propyl]-1-[3-ethylthiopropyl]piperidin-3-yl}propan-1-oic acid
(3R,4R)-3-{4-[3-(6-Methoxyquinolin-4-yl)propyl]-1-[2-(n-propylthio)ethyl]piperidin-3-yl}propan-1-oic acid
(3R,4R)-3-{4-[3-(6-Methoxyquinolin-4-yl)propyl]-1-[3-(n-propylthio)propyl]piperidin-3-yl}propan-1-oic acid
(3R,4R)-3-{4-[3-(6-Methoxyquinolin-4-yl)propyl]-1-[2-(n-butylthio)ethyl]piperidin-3-yl}propan-1-oic acid
(3R,4R)-3-{4-[3-(6-Methoxyquinolin-4-yl)propyl]-1-[3-(n-butylthio)propyl]piperidin-3-yl}propan-1-oic acid
(3R,4R)-3-{4-[3-(6-Methoxyquinolin-4-yl)propyl]-1-[3-(thien-2-yl)propyl]piperidin-3-yl}propan-1-oic acid
(3R,4R)-3-{4-[3-(6-Methoxyquinolin-4-yl)propyl]-1-[4-(thien-2-yl)butyl]piperidin-3-yl}propan-1-oic acid
(3R,4R)-3-{4-[3-(6-Methoxyquinolin-4-yl)propyl]-1-[2-(thien-2-yl)thioethyl]piperidin-3-yl}propan-1-oic acid
(3R,4R)-3-{4-[3-(6-Methoxyquinolin-4-yl)propyl]-1-[3-(thien-2-yl)thiopropyl]piperidin-3-yl}propan-1-oic acid
(3R,4R)-3-{4-[3-(6-Methoxyquinolin-4-yl)propyl]-1-[3-(5-chlorothien-2-yl)propyl]piperidin-3-yl}propan-1-oic acid
(3R,4R)-3-{4-[3-(6-Methoxyquinolin-4-yl)propyl]-1-[4-(5-chlorothien-2-yl)butyl]piperidin-3-yl}propan-1-oic acid
(3R,4R)-3-{4-[3-(6-Methoxyquinolin-4-yl)propyl]-1-[2-(5-chlorothien-2-yl)thioethyl]piperidin-3-yl}propan-1-oic acid
(3R,4R)-3-{4-[3-(6-Methoxyquinolin-4-yl)propyl]-1-[3-(5-chlorothien-2-yl)thiopropyl]piperidin-3-yl}propan-1-oic acid
(3R,4R)-3-{4-[3-(6-Methoxyquinolin-4-yl)propyl]-1-[3-(3-chlorothien-2-yl)propyl]piperidin-3-yl}propan-1-oic acid
(3R,4R)-3-{4-[3-(6-Methoxyquinolin-4-yl)propyl]-1-[4-(3-chlorothien-2-yl)butyl]piperidin-3-yl}propan-1-oic acid
(3R,4R)-3-{4-[3-(6-Methoxyquinolin-4-yl)propyl]-1-[2-(3-chlorothien-2-yl)thioethyl]piperidin-3-yl}propan-1-oic acid
(3R,4R)-3-{4-[3-(6-Methoxyquinolin-4-yl)propyl]-1-[3-(3-chlorothien-2-yl)thiopropyl]piperidin-3-yl}propan-1-oic acid
(3R,4R)-3-{4-[3-(6-Methoxyquinolin-4-yl)propyl]-1-[3-(5-methylthien-2-yl)propyl]piperidin-3-yl}propan-1-oic acid
(3R,4R)-3-{4-[3-(6-Methoxyquinolin-4-yl)propyl]-1-[4-(5-methylthien-2-yl)butyl]piperidin-3-yl}propan-1-oic acid
(3R,4R)-3-{4-[3-(6-Methoxyquinolin-4-yl)propyl]-1-[2-(5-methylthien-2-yl)thioethyl]piperidin-3-yl}propan-1-oic acid
(3R,4R)-3-{4-[3-(6-Methoxyquinolin-4-yl)propyl]-1-[3-(5-methylthien-2-yl)thiopropyl]piperidin-3-yl}propan-1-oic acid
(3R,4R)-3-{4-[3-(6-Methoxyquinolin-4-yl)propyl]-1-[3-(3-methylthien-2-yl)propyl]piperidin-3-yl}propan-1-oic acid
(3R,4R)-3-{4-[3-(6-Methoxyquinolin-4-yl)propyl]-1-[4-(3-methylthien-2-yl)butyl]piperidin-3-yl}propan-1-oic acid
(3R,4R)-3-{4-[3-(6-Methoxyquinolin-4-yl)propyl]-1-[2-(3-methylthien-2-yl)thioethyl]piperidin-3-yl}propan-1-oic acid
(3R,4R)-3-{4-[3-(6-Methoxyquinolin-4-yl)propyl]-1-[3-(3-methylthien-2-yl)thiopropyl]piperidin-3-yl}propan-1-oic acid
(3R,4R)-3-{4-[3-(6-Methoxyquinolin-4-yl)propyl]-1-[3-(thien-3-yl)propyl]piperidin-3-yl}propan-1-oic acid
(3R,4R)-3-{4-[3-(6-Methoxyquinolin-4-yl)propyl]-1-[4-(thien-3-yl)butyl]piperidin-3-yl}propan-1-oic acid
(3R,4R)-3-{4-[3-(6-Methoxyquinolin-4-yl)propyl]-1-[2-(thien-3-yl)thioethyl]piperidin-3-yl}propan-1-oic acid
(3R,4R)-3-{4-[3-(6-Methoxyquinolin-4-yl)propyl]-1-[3-(thien-3-yl)thiopropyl]piperidin-3-yl}propan-1-oic acid
(3R,4R)-3-{4-[3-(6-Methoxyquinolin-4-yl)propyl]-1-[3-(fur-2-yl)propyl]piperidin-3-yl}propan-1-oic acid
(3R,4R)-3-{4-[3-(6-Methoxyquinolin-4-yl)propyl]-1-[4-(fur-2-yl)butyl]piperidin-3-yl}propan-1-oic acid
(3R,4R)-3-{4-[3-(6-Methoxyquinolin-4-yl)propyl]-1-[2-(fur-2-yl)thioethyl]piperidin-3-yl}propan-1-oic acid
(3R,4R)-3-{4-[3-(6-Methoxyquinolin-4-yl)propyl]-1-[3-(fur-2-yl)thiopropyl]piperidin-3-yl}propan-1-oic acid
(3R,4R)-3-{4-[3-(6-Methoxyquinolin-4-yl)propyl]-1-[3-(fur-3-yl)propyl]piperidin-3-yl}propan-1-oic acid
(3R,4R)-3-{4-[3-(6-Methoxyquinolin-4-yl)propyl]-1-[4-(fur-3-yl)butyl]piperidin-3-yl}propan-1-oic acid
(3R,4R)-3-{4-[3-(6-Methoxyquinolin-4-yl)propyl]-1-[2-(fur-3-yl)thioethyl]piperidin-3-yl}propan-1-oic acid
(3R,4R)-3-{4-[3-(6-Methoxyquinolin-4-yl)propyl]-1-[3-(fur-3-yl)thiopropyl]piperidin-3-yl}propan-1-oic acid
(3R,4R)-3-{4-[3-(6-Methoxyquinolin-4-yl)propyl]-1-[3-(1-methylpyrrol-2-yl)propyl]piperidin-3-yl}propan-1-oic acid
(3R,4R)-3-{4-[3-(6-Methoxyquinolin-4-yl)propyl]-1-[4-(1-methylpyrrol-2-yl)butyl]piperidin-3-yl}propan-1-oic acid
(3R,4R)-3-{4-[3-(6-Methoxyquinolin-4-yl)propyl]-1-[2-(1-methylpyrrol-2-yl)thioethyl]piperidin-3-yl}propan-1-oic acid
(3R,4R)-3-{4-[3-(6-Methoxyquinolin-4-yl)propyl]-1-[3-(1-methylpyrrol-2-yl)thiopropyl]piperidin-3-yl}propan-1-oic acid
(3R,4R)-3-{4-[3-(6-Methoxyquinolin-4-yl)propyl]-1-[3-(1-methylpyrrol-2-yl)propyl]piperidin-3-yl}propan-1-oic acid (3R,4R)-3-{4-[3-(6-Methoxyquinolin-4-yl)propyl]-1-[4-(1-methylpyrrol-3-yl)butyl]piperidin-3-yl}propan-1-oic acid (3R,4R)-3-{4-[3-(6-Methoxyquinolin-4-yl)propyl]-1-[2-(1-methylpyrrol-3-yl)thioethyl]piperidin-3-yl}propan-1-oic acid (3R,4R)-3-{4-[3-(6-Methoxyquinolin-4-yl)propyl]-1-[3-(1-methylpyrrol-3-yl)thiopropyl]piperidin-3-yl}propan-1-oic acid (3R,4R)-3-{4-[3-(6-Methoxyquinolin-4-yl)propyl]-1-[3-(thiazol-2-yl)propyl]piperidin-3-yl}propan-1-oic acid (3R,4R)-3-{4-[3-(6-Methoxyquinolin-4-yl)propyl]-1-[4-(thiazol-2-yl)butyl]piperidin-3-yl}propan-1-oic acid (3R,4R)-3-{4-[3-(6-Methoxyquinolin-4-yl)propyl]-1-[2-(thiazol-2-yl)thioethyl]piperidin-3-yl}propan-1-oic acid (3R,4R)-3-{4-[3-(6-Methoxyquinolin-4-yl)propyl]-1-[3-(thiazol-2-yl)thiopropyl]piperidin-3-yl}propan-1-oic acid (3R,4R)-3-{4-[3-(6-Methoxyquinolin-4-yl)propyl]-1-[3-(1-methylimidazol-2-yl)propyl]piperidin-3-yl}propan-1-oic acid (3R,4R)-3-{4-[3-(6-Methoxyquinolin-4-yl)propyl]-1-[4-(1-methylimidazol-2-yl)butyl]piperidin-3-yl}propan-1-oic acid (3R,4R)-3-{4-[3-(6-Methoxyquinolin-4-yl)propyl]-1-[2-(1-methylimidazol-2-yl)thioethyl]piperidin-3-yl}propan-1-oic acid (3R,4R)-3-{4-[3-(6-Methoxyquinolin-4-yl)propyl]-1-[3-(1-methylimidazol-2-yl)thiopropyl]piperidin-3-yl}propan-1-oic acid (3R,4R)-3-{4-[3-(6-Methoxyquinolin-4-yl)propyl]-1-[3-(3-methylimidazol-4-yl)propyl]piperidin-3-yl}propan-1-oic acid (3R,4R)-3-{4-[3-(6-Methoxyquinolin-4-yl)propyl]-1-[4-(3-methylimidazol-4-yl)butyl]piperidin-3-yl}propan-1-oic acid (3R,4R)-3-{4-[3-(6-Methoxyquinolin-4-yl)propyl]-1-[2-(3-methylimidazol-4-yl)thioethyl]piperidin-3-yl}propan-1-oic acid (3R,4R)-3-{4-[3-(6-Methoxyquinolin-4-yl)propyl]-1-[3-(3-methylimidazol-4-yl)thiopropyl]piperidin-3-yl}propan-1-oic acid (3R,4R)-3-{4-[3-(6-Methoxyquinolin-4-yl)propyl]-1-[3-(3-methylpyrazol-4-yl)propyl]piperidin-3-yl}propan-1-oic acid (3R,4R)-3-{4-[3-(6-Methoxyquinolin-4-yl)propyl]-1-[4-(3-methylpyrazol-4-yl)butyl]piperidin-3-yl}propan-1-oic acid (3R,4R)-3-{4-[3-(6-Methoxyquinolin-4-yl)propyl]-1-[2-(3-methylpyrazol-4-yl)thioethyl]piperidin-3-yl}propan-1-oic acid (3R,4R)-3-{4-[3-(6-Methoxyquinolin-4-yl)propyl]-1-[3-(3-methylpyrazol-4-yl)thiopropyl]piperidin-3-yl}propan-1-oic acid (3R,4R)-3-{4-[3-(6-Methoxyquinolin-4-yl)propyl]-1-[3-(oxazol-2-yl)propyl]piperidin-3-yl}propan-1-oic acid (3R,4R)-3-{4-[3-(6-Methoxyquinolin-4-yl)propyl]-1-[4-(oxazol-2-yl)butyl]piperidin-3-yl}propan-1-oic acid (3R,4R)-3-{4-[3-(6-Methoxyquinolin-4-yl)propyl]-1-[2-(oxazol-2-yl)thioethyl]piperidin-3-yl}propan-1-oic acid (3R,4R)-3-{4-[3-(6-Methoxyquinolin-4-yl)propyl]-1-[3-(oxazol-2-yl)thiopropyl]piperidin-3-yl}propan-1-oic acid (3R,4R)-3-{4-[3-(6-Methoxyquinolin-4-yl)propyl]-1-[3-(pyridin-2-yl)propyl]piperidin-3-yl}propan-1-oic acid (3R,4R)-3-{4-[3-(6-Methoxyquinolin-4-yl)propyl]-1-[4-(pyridin-2-yl)butyl]piperidin-3-yl}propan-1-oic acid (3R,4R)-3-{4-[3-(6-Methoxyquinolin-4-yl)propyl]-1-[2-(pyridin-2-yl)thioethyl]piperidin-3-yl}propan-1-oic acid (3R,4R)-3-{4-[3-(6-Methoxyquinolin-4-yl)propyl]-1-[3-(pyridin-2-yl)thiopropyl]piperidin-3-yl}propan-1-oic acid (3R,4R)-3-{4-[3-(6-Methoxyquinolin-4-yl)propyl]-1-[3-(pyridin-3-yl)propyl]piperidin-3-yl}propan-1-oic acid (3R,4R)-3-{4-[3-(6-Methoxyquinolin-4-yl)propyl]-1-[4-(pyridin-3-yl)butyl]piperidin-3-yl}propan-1-oic acid (3R,4R)-3-{4-[3-(6-Methoxyquinolin-4-yl)propyl]-1-[2-(pyridin-3-yl)thioethyl]piperidin-3-yl}propan-1-oic acid (3R,4R)-3-{4-[3-(6-Methoxyquinolin-4-yl)propyl]-1-[3-(pyridin-3-yl)thiopropyl]piperidin-3-yl}propan-1-oic acid (3R,4R)-3-{4-[3-(6-Methoxyquinolin-4-yl)propyl]-1-[3-(pyridin-4-yl)propyl]piperidin-3-yl}propan-1-oic acid (3R,4R)-3-{4-[3-(6-Methoxyquinolin-4-yl)propyl]-1-[4-(pyridin-4-yl)butyl]piperidin-3-yl}propan-1-oic acid (3R,4R)-3-{4-[3-(6-Methoxyquinolin-4-yl)propyl]-1-[5-(pyridin-4-yl)pentyl]piperidin-3-yl}propan-1-oic acid (3R,4R)-3-{4-[3-(6-Methoxyquinolin-4-yl)propyl]-1-[2-(pyridin-4-yl)thioethyl]piperidin-3-yl}propan-1-oic acid (3R,4R)-3-{4-[3-(6-Methoxyquinolin-4-yl)propyl]-1-[3-(pyridin-4-yl)thiopropyl]piperidin-3-yl}propan-1-oic acid (3R,4R)-3-{4-[3-(6-Methoxyquinolin-4-yl)propyl]-1-[3-(pyrimidin-2-yl)propyl]piperidin-3-yl}propan-1-oic acid (3R,4R)-3-{4-[3-(6-Methoxyquinolin-4-yl)propyl]-1-[4-(pyrimidin-2-yl)butyl]piperidin-3-yl}propan-1-oic acid (3R,4R)-3-{4-[3-(6-Methoxyquinolin-4-yl)propyl]-1-[2-(pyrimidin-2-yl)thioethyl]piperidin-3-yl}propan-1-oic acid (3R,4R)-3-{4-[3-(6-Methoxyquinolin-4-yl)propyl]-1-[3-(pyrimidin-2-yl)thiopropyl]piperidin-3-yl}propan-1-oic acid (3R,4R)-3-{4-[3-(6-Methoxyquinolin-4-yl)propyl]-1-[3-(pyrimidin-4-yl)propyl]piperidin-3-yl}propan-1-oic acid (3R,4R)-3-{4-[3-(6-Methoxyquinolin-4-yl)propyl]-1-[4-(pyrimidin-4-yl)butyl]piperidin-3-yl}propan-1-oic acid (3R,4R)-3-{4-[3-(6-Methoxyquinolin-4-yl)propyl]-1-[2-(pyrimidin-4-yl)thioethyl]piperidin-3-yl}propan-1-oic acid (3R,4R)-3-{4-[3-(6-Methoxyquinolin-4-yl)propyl]-1-[3-(pyrimidin-4-yl)thiopropyl]piperidin-3-yl}propan-1-oic acid (3R,4R)-3-{4-[3-(6-Methoxyquinolin-4-yl)propyl]-1-[3-(pyrimidin-5-yl)propyl]piperidin-3-yl}propan-1-oic acid (3R,4R)-3-{4-[3-(6-Methoxyquinolin-4-yl)propyl]-1-[4-(pyrimidin-5-yl)butyl]piperidin-3-yl}propan-1-oic acid (3R,4R)-3-{4-[3-(6-Methoxyquinolin-4-yl)propyl]-1-[2-(pyrimidin-5-yl)thioethyl]piperidin-3-yl}propan-1-oic acid (3R,4R)-3-{4-[3-(6-Methoxyquinolin-4-yl)propyl]-1-[3-(pyrimidin-5-yl)thiopropyl]piperidin-3-yl}propan-1-oic acid (3R,4R)-3-{4-[3-(6-Methoxyquinolin-4-yl)propyl]-1-[3-(pyrazin-2-yl)propyl]piperidin-3-yl}propan-1-oic acid (3R,4R)-3-{4-[3-(6-Methoxyquinolin-4-yl)propyl]-1-[4-(pyrazin-2-yl)butyl]piperidin-3-yl}propan-1-oic acid (3R,4R)-3-{4-[3-(6-Methoxyquinolin-4-yl)propyl]-1-[2-(pyrazin-2-yl)thioethyl]piperidin-3-yl}propan-1-oic acid (3R,4R)-3-{4-[3-(6-Methoxyquinolin-4-yl)propyl]-1-[3-(pyrazin-2-yl)thiopropyl]piperidin-3-yl}propan-1-oic acid (3R,4R)-3-{4-[3-(6-Methoxyquinolin-4-yl)propyl]-1-[3-(pyridazin-3-yl)propyl]piperidin-3-yl}propan-1-oic acid (3R,4R)-3-{4-[3-(6-Methoxyquinolin-4-yl)propyl]-1-[4-(pyridazin-3-yl)butyl]piperidin-3-yl}propan-1-oic acid (3R,4R)-3-{4-[3-(6-Methoxyquinolin-4-yl)propyl]-1-[2-(pyridazin-3-yl)thioethyl]piperidin-3-yl}propan-1-oic acid (3R,4R)-3-{4-[3-(6-Methoxyquinolin-4-yl)propyl]-1-[3-(pyridazin-3-yl)thiopropyl]piperidin-3-yl}propan-1-oic acid (3R,4R)-3-{4-[3-(6-Methoxyquinolin-4-yl)propyl]-1-[3-(pyridazin-4-yl)propyl]piperidin-3-yl}propan-1-oic acid (3R,4R)-3-{4-[3-(6-Methoxyquinolin-4-yl)propyl]-1-[4-(pyridazin-4-yl)butyl]piperidin-3-yl}propan-1-oic acid (3R,4R)-3-{4-[3-(6-Methoxyquinolin-4-yl)propyl]-1-[2-(pyridazin-4-yl)thioethyl]piperidin-3-yl}propan-1-oic acid (3R,4R)-3-{4-[3-(6-Methoxyquinolin-4-yl)propyl]-1-[3-(pyridazin-4-yl)thiopropyl]piperidin-3-yl}propan-1-oic acid (3R,4R)-3-{4-[3-(6-Methoxyquinolin-4-yl)propyl]-1-[3-phenylprop-2-ynyl]piperidin-3-yl}propan-1-oic acid (3R,4R)-3-{4-[3-(6-Methoxyquinolin-4-yl)propyl]-1-[3-(2-fluorophenyl)prop-2-ynyl]piperidin-3-yl}propan-1-oic acid (3R,4R)-3-{4-[3-(6-Methoxyquinolin-4-yl)propyl]-1-[3-(3-fluorophenyl)prop-2-ynyl]piperidin-3-yl}propan-1-oic acid (3R,4R)-3-{4-[3-(6-Methoxyquinolin-4-yl)propyl]-1-[3-(4-fluorophenyl)prop-2-ynyl]piperidin-3-yl}propan-1-oic acid (3R,4R)-3-{4-[3-(6-Methoxyquinolin-4-yl)propyl]-1-[3-(2-chlorophenyl)prop-2-ynyl]piperidin-3-yl}propan-1-oic acid (3R,4R)-3-{4-[3-(6-Methoxyquinolin-4-yl)propyl]-1-[3-(3-chlorophenyl)prop-2-ynyl]piperidin-3-yl}propan-1-oic acid (3R,4R)-3-{4-[3-(6-Methoxyquinolin-4-yl)propyl]-1-[3-(4-chlorophenyl)prop-2-ynyl]piperidin-3-yl}propan-1-oic acid (3R,4R)-3-{4-[3-(6-Methoxyquinolin-4-yl)propyl]-1-[3-(2-methylphenyl)prop-2-ynyl]piperidin-3-yl}propan-1-oic acid (3R,4R)-3-{4-[3-(6-Methoxyquinolin-4-yl)propyl]-1-[3-(3-methylphenyl)prop-2-ynyl]piperidin-3-yl}propan-1-oic acid (3R,4R)-3-{4-[3-(6-Methoxyquinolin-4-yl)propyl]-1-[3-(4-methylphenyl)prop-2-ynyl]piperidin-3-yl}propan-1-oic acid (3R,4R)-3-{4-[3-(6-Methoxyquinolin-4-yl)propyl]-1-[3-(2-(trifluoromethyl)phenylprop-2-ynyl]piperidin-3-yl}propan-1-oic acid (3R,4R)-3-{4-[3-(6-Methoxyquinolin-4-yl)propyl]-1-[3-(3-(trifluoromethyl)phenyl)prop-2-ynyl]piperidin-3-yl}propan-1-oic acid (3R,4R)-3-{4-[3-(6-Methoxyquinolin-4-yl)propyl]-1-[3-(4-(trifluoromethyl)phenyl)prop-2-ynyl]piperidin-3-yl}propan-1-oic acid (3R,4R)-3-{4-[3-(6-Methoxyquinolin-4-yl)propyl]-1-[3-(2-methoxyphenyl)prop-2-ynyl]piperidin-3-yl}propan-1-oic acid (3R,4R)-3-{4-[3-(6-Methoxyquinolin-4-yl)propyl]-1-[3-(3-methoxyphenyl)prop-2-ynyl]piperidin-3-yl}propan-1-oic acid (3R,4R)-3-{4-[3-(6-Methoxyquinolin-4-yl)propyl]-1-[3-(4-methoxyphenyl)prop-2-ynyl]piperidin-3-yl}propan-1-oic acid (3R,4R)-3-{4-[3-(6-Methoxyquinolin-4-yl)propyl]-1-[3-(3,4-difluorophenyl)prop-2-ynyl]piperidin-3-yl}propan-1-oic acid (3R,4R)-3-{4-[3-(6-Methoxyquinolin-4-yl)propyl]-1-[3-(2,4-difluorophenyl)prop-2-ynyl]piperidin-3-yl}propan-1-oic acid (3R,4R)-3-{4-[3-(6-Methoxyquinolin-4-yl)propyl]-1-[3-(3,4-dichlorophenyl)prop-2-ynyl]piperidin-3-yl}propan-1-oic acid (3R,4R)-3-{4-[3-(6-Methoxyquinolin-4-yl)propyl]-1-[3-(2,3-dichlorophenyl)prop-2-ynyl]piperidin-3-yl}propan-1-oic acid (3R,4R)-3-{4-[3-(6-Methoxyquinolin-4-yl)propyl]-1-[3-(2,4-dichlorophenyl)prop-2-ynyl]piperidin-3-yl}propan-1-oic acid (3R,4R)-3-{4-[3-(6-Methoxyquinolin-4-yl)propyl]-1-[3-(2,4,6-trichlorophenyl)prop-2-ynyl]piperidin-3-yl}propan-1-oic acid (3R,4R)-3-{4-[3-(6-Methoxyquinolin-4-yl)propyl]-1-[3-(3,5-dichlorophenyl)prop-2-ynyl]piperidin-3-yl}propan-1-oic acid (3R,4R)-3-{4-[3-(6-Methoxyquinolin-4-yl)propyl]-1-[3-(4-chloro-3-fluorophenyl)prop-2-ynyl]piperidin-3-yl}propan-1-oic acid (3R,4R)-3-{4-[3-(6-Methoxyquinolin-4-yl)propyl]-1-[3-(3-chloro4-fluorophenyl)prop-2-ynyl]piperidin-3-yl}propan-1-oic acid (3R,4R)-3-{4-[3-(6-Methoxyquinolin-4-yl)propyl]-1-[3-(2-chloro4-fluorophenyl)prop-2-ynyl]piperidin-3-yl}propan-1-oic acid (3R,4R)-3-{4-[3-(6-Methoxyquinolin-4-yl)propyl]-1-[3-(3-chloro-5-fluorophenyl)prop-2-ynyl]piperidin-3-yl}propan-1-oic acid (3R,4R)-3-{4-[3-(6-Methoxyquinolin-4-yl)propyl]-1-[3-(4-chloro-2-fluorophenyl)prop-2-ynyl]piperidin-3-yl}propan-1-oic acid (3R,4R)-3-{4-[3-(6-Methoxyquinolin-4-yl)propyl]-1-[3-(3-fluoro4-methylphenyl)prop-2-ynyl]piperidin-3-yl}propan-1-oic acid (3R,4R)-3-{4-[3-(6-Methoxyquinolin-4-yl)propyl]-1-[3-(4-chloro-3-(trifluoromethyl)phenyl)prop-2-ynyl]-piperidin-3-yl}propan-1-oic acid (3R,4R)-3-{4-[3-(6-Methoxyquinolin-4-yl)propyl]-1-[3-(2-chloro-4-(trifluoromethyl)phenyl)prop-2-ynyl]piperidin-3-yl}propan-1-oic acid (3R,4R)-3-{4-[3-(6-Methoxyquinolin-4-yl)propyl]-1-[3-(2-chloro-5-(trifluoromethyl)phenyl)prop-2-ynyl]piperidin-3-yl}propan-1-oic acid (3R,4R)-3-{4-[3-(6-Methoxyquinolin-4-yl)propyl]-1-[3-(5-chloro-2-methylphenyl)prop-2-ynyl]piperidin-3-yl}propan 1-oic acid (3R,4R)-3-{4-[3-(6-Methoxyquinolin-4-yl)propyl]-1-[3-(3,5-bis(trifluoromethyl)phenyl)prop-2-ynyl]piperidin-3-yl}propan-1-oic acid (3R,4R)-3-{4-[3-(6-Methoxyquinolin-4-yl)propyl]-1-[3-(3,5-dimethylphenyl)prop-2-ynyl]piperidin-3-yl}propan-1-oic acid (3R,4R)-3-{4-[3-(6-Methoxyquinolin-4-yl)propyl]-1-[3-(2,4-dichloro-6-methylphenyl)prop-2-ynyl]-piperidin-3-yl}propan-1-oic acid (3R,4R)-3-{4-[3-(6-Methoxyquinolin-4-yl)propyl]-1-[3-(thien-2-yl)prop-2-ynyl]piperidin-3-yl}propan-1-oic acid (3R,4R)-3-{4-[3-(6-Methoxyquinolin-4-yl)propyl]-1-[3-(5-chlorothien-2-yl)prop-2-ynyl]piperidin-3-yl}propan-1-oic acid (3R,4R)-3-{4-[3-(6-Methoxyquinolin-4-yl)propyl]-1-[3-(3-chlorothien-2-yl)prop-2-ynyl]piperidin-3-yl}propan-1-oic acid (3R,4R)-3-{4-[3-(6-Methoxyquinolin-4-yl)propyl]-1-[3-(5-methylthien-2-yl)prop-2-ynyl]piperidin-3-yl}propan-1-oic acid (3R,4R)-3-{4-[3-(6-Methoxyquinolin-4-yl)propyl]-1-[3-(3-methylthien-2yl)prop-2-ynyl]piperidin-3-yl}propan-1-oic acid (3R,4R)-3-{4-[3-(6-Methoxyquinolin-4-yl)propyl]-1-[3-(thien-3-yl)prop-2ynyl]piperidin-3-yl}propan-1l-oic acid (3R,4R)-3-{4-[3-(6-Methoxyquinolin-4-yl)propyl]-1-[3-(1-methylpyrrol-2-yl)prop-2-ynyl]piperidin-3-yl}propan-1-oic acid (3R,4R)-3-{4-[3-(6-Methoxyquinolin-4-yl)propyl]-1-[3-(1-methylpyrrol-3-yl)prop-2-ynyl]piperidin-3-yl}propan-1-oic acid (3R,4R)-3-{4-[3-(6-Methoxyquinolin-4-yl)propyl]-1-[3-(thiazol-2-yl)prop-2-ynyl]piperidin-3-yl}propan-1-oic acid (3R,4R)-3-{4-[3-(6-Methoxyquinolin-4-yl)propyl]-1-[3-(thiazol-4-yl)prop-2-ynyl]piperidin-3-yl}propan-1-oic acid (3R,4R)-3-{4-[3-(6-Methoxyquinolin-4-yl)propyl]-1-[3-(thiazol-5-yl)prop-2-ynyl]piperidin-3-yl}propan-1-oic acid (3R,4R)-3-{4-[3-(6-Methoxyquinolin-4-yl)propyl]-1-[3-(1-methylimidazol-2-yl)prop-2-ynyl]piperidin-3-yl}propan-1-oic acid (3R,4R)-3-{4-[3-(6-Methoxyquinolin-4-yl)propyl]-1-[3-(3-methylimidazol-4-yl)prop-2-ynyl]piperidin-3-yl}propan-1-oic acid (3R,4R)-3-{4-[3-(6-Methoxyquinolin-4-yl)propyl]-1-[3-(3-methylpyrazol-4-yl)prop-2-ynyl]piperidin-3-yl}propan-1-oic acid (3R,4R)-3-{4-[3-(6-Methoxyquinolin-4-yl)propyl]-1-[3-(oxazol-2-yl)prop-2-ynyl]piperidin-3-yl}propan-1-oic acid (3R,4R)-3-{4-[3-(6-Methoxyquinolin-4-yl)propyl]-1-[3-(oxazol-4-yl)prop-2-ynyl]piperidin-3-yl}propan-1-oic acid (3R,4R)-3-{4-[3-(6-Methoxyquinolin-4-yl)propyl]-1-[3-(oxazol-5-yl)prop-2-ynyl]piperidin-3-yl}propan-1-oic acid (3R,4R)-3-{4-[3-(6-Methoxyquinolin-4-yl)propyl]-1-[3-(pyridin-2-yl)prop-2-ynyl]piperidin-3-yl}propan-1-oic acid (3R,4R)-3-{4-[3-(6-Methoxyquinolin-4-yl)propyl]-1-[3-(pyridin-3-yl)prop-2-ynyl]piperidin-3-yl}propan-1-oic acid (3R,4R)-3-{4-[3-(6-Methoxyquinolin-4-yl)propyl]-1-[3-(pyridin-4-yl)prop-2-ynyl]piperidin-3-yl}propan-1-oic acid (3R,4R)-3-{4-[3-(6-Methoxyquinolin-4-yl)propyl]-1-[3-(pyrimidin-2-yl)prop-2-ynyl]piperidin-3-yl}propan-1-oic acid (3R,4R)-3-{4-[3-(6-Methoxyquinolin-4-yl)propyl]-1-[3-(pyrimidin-4-yl)prop-2-ynyl]piperidin-3-yl}propan-1-oic acid (3R,4R)-3-{4-[3-(6-Methoxyquinolin-4-yl)propyl]-1-[3-(pyrimidin-5-yl)prop-2-ynyl]piperidin-3-yl}propan-1-oic acid (3R,4R)-3-{4-[3-(6-Methoxyquinolin-4-yl)propyl]-1-[3-(pyrazin-2-yl)prop-2-ynyl]piperidin-3-yl}propan-1-oic acid (3R,4R)-3-{4-[3-(6-Methoxyquinolin-4-yl)propyl]-1-[3-(pyridazin-3-yl)prop-2-ynyl]piperidin-3-yl}propan-1-oic acid (3R,4R)-3-{4-[3-(6-Methoxyquinolin-4-yl)propyl]-1-[3-(pyridazin-4-yl)prop-2-ynyl]piperidin-3-yl}propan-1-oic acid (3R,4R)-3-{4-[3-(R,S)-Hydroxy-3-(6-methoxyquinolin-4-yl)propyl]-1-3-phenylpropyl]piperidin-3-yl}propan-1-oic acid (3R,4R)-3-{4-[3-(R,S)-Hydroxy-3-(6-methoxyquinolin-4-yl)propyl]-1-[4-phenylbutyl]piperidin-3-yl}propan-1-oic acid (3R,4R)-3-{4-[3-(R,S)-Hydroxy-3-(6-methoxyquinolin-4-yl)propyl]-1-[3-(2-fluorophenyl)propyl]piperidin-3-yl}propan-1-oic acid (3R,4R)-3-{4-[3-(R,S)-Hydroxy-3-(6-methoxyquinolin-4-yl)propyl]-1-[4-(2-fluorophenyl)butyl]piperidin-3-yl}propan-1-oic acid (3R,4R)-3-{4-[3-(R,S)-Hydroxy-3-(6-methoxyquinolin-4-yl)propyl]-1-[3-(3-fluorophenyl)propyl]piperidin-3-yl}propan-1-oic acid (3R,4R)-3-{4-[3-(R,S)-Hydroxy-3-(6-methoxyquinolin-4-yl)propyl]-1-[4-(3-fluorophenyl)butyl]piperidin-3-yl}propan-1-oic acid (3R,4R)-3-{4-[3-(R,S)-Hydroxy-3-(6-methoxyquinolin-4-yl)propyl]-1-[3-(4-fluorophenyl)propyl]piperidin-3-yl}propan-1-oic acid (3R,4R)-3-{4-[3-(R,S)-Hydroxy-3-(6-methoxyquinolin-4-yl)propyl]-1-[4-(4-fluorophenyl)butyl]piperidin-3-yl}propan-1-oic acid (3R,4R)-3-{4-[3-(R,S)-Hydroxy-3-(6-methoxyquinolin-4-yl)propyl]-1-[3-(2,3-difluorophenyl)propyl]piperidin-3-yl}propan-1-oic acid (3R,4R)-3-{4-[3-(R,S)-Hydroxy-3-(6-methoxyquinolin-4-yl)propyl]-1-[4-(2,3-difluorophenyl)butyl]piperidin-3-yl}propan-1-oic acid (3R,4R)-3-{4-[3-(R,S)-Hydroxy-3-(6-methoxyquinolin-4-yl)propyl]-1-[3-(2,6-difluorophenyl)propyl]piperidin-3-yl}propan-1-oic acid (3R,4R)-3-{4-[3-(R,S)-Hydroxy-3-(6-methoxyquinolin-4-yl)propyl]-1-[4-(2,6-difluorophenyl)butyl]piperidin-3-yl}propan-1-oic acid (3R,4R)-3-{4-[3-(R,S)-Hydroxy-3-(6-methoxyquinolin-4-yl)propyl]-1-[3-(2-chlorophenyl)propyl]piperidin-3-yl}propan-1-oic acid (3R,4R)-3-{4-[3-(R,S)-Hydroxy-3-(6-methoxyquinolin-4-yl)propyl]-1-[4-(2-chlorophenyl)butyl]piperidin-3-yl}propan-1-oic acid (3R,4R)-3-{4-[3-(R,S)-Hydroxy-3-(6-methoxyquinolin-4-yl)propyl]-1-[3-(3-chlorophenyl)propyl]piperidin-3-yl}propan-1-oic acid (3R,4R)-3-{4-[3-(R,S)-Hydroxy-3-(6-methoxyquinolin-4-yl)propyl]-1-[4-(3-chlorophenyl)butyl]piperidin-3-yl}propan-1-oic acid (3R,4R)-3-{4-[3-(R,S)-Hydroxy-3-(6-methoxyquinolin-4-yl)propyl]-1-[3-(4-chlorophenyl)propyl]piperidin-3-yl}propan-1-oic acid (3R,4R)-3-{4-[3-(R,S)-Hydroxy-3-(6-methoxyquinolin-4-yl)propyl]-1-[4-(4-chlorophenyl)butyl]piperidin-3-yl}propan-1-oic acid (3R,4R)-3-{4-[3-(R,S)-Hydroxy-3-(6-methoxyquinolin-4-yl)propyl]-1-[3-(2,3-dichlorophenyl)propyl]piperidin-3-yl}propan-1-oic acid (3R,4R)-3-{4-[3-(R,S)-Hydroxy-3-(6-methoxyquinolin-4-yl)propyl]-1-[4-(2,3-dichlorophenyl)butyl]piperidin-3-yl}propan-1-oic acid (3R,4R)-3-{4-[3-(R,S)-Hydroxy-3-(6-methoxyquinolin-4-yl)propyl]-1-[3-(2,6-dichlorophenyl)propyl]piperidin-3-yl}propan-1-oic acid (3R,4R)-3-{4-[3-(R,S)-Hydroxy-3-(6-methoxyquinolin-4-yl)propyl]-1-[4-(2,6-dichlorophenyl)butyl]piperidin-3-yl}propan-1-oic acid (3R,4R)-3-{4-[3-(R,S)-Hydroxy-3-(6-methoxyquinolin-4-yl)propyl]-1-[3-(2-methylphenyl)propyl]piperidin-3-yl}propan-1-oic acid (3R,4R)-3-{4-[3-(R,S)-Hydroxy-3-(6-methoxyquinolin-4-yl)propyl]-1-[4-(2-methylphenyl)butyl]piperidin-3-yl}propan-1-oic acid (3R,4R)-3-{4-[3-(R,S)-Hydroxy-3-(6-methoxyquinolin-4-yl)propyl]-1-[5-(2-methylphenyl)pentyl]piperidin-3-yl}propan-1-oic acid (3R,4R)-3-{4-[3-(R,S)-Hydroxy-3-(6-methoxyquinolin-4-yl)propyl]-1-[3-(3-methylphenyl)propyl]piperidin-3-yl}propan-1-oic acid (3R,4R)-3-{4-[3-(R,S)-Hydroxy-3-(6-methoxyquinolin-4-yl)propyl]-1-[4-(3-methylphenyl)butyl]piperidin-3-yl}propan-1-oic acid (3R,4R)-3-{4-[3-(R,S)-Hydroxy-3-(6-methoxyquinolin-4-yl)propyl]-1-[3-(4-methylphenyl)propyl]piperidin-3-yl}propan-1-oic acid
(3R,4R)-3-{4-[3-(R,S)-Hydroxy-3-(6-methoxyquinolin-4-yl)propyl]-1-[4-(4-methylphenyl)butyl]piperidin-3-yl}propan-1-oic acid
(3R,4R)-3-{4-[3-(R,S)-Hydroxy-3-(6-methoxyquinolin-4-yl)propyl]-1-[3-(2-methoxyphenyl)propyl]piperidin-3-yl}propan-1-oic acid
(3R,4R)-3-{4-[3-(R,S)-Hydroxy-3-(6-methoxyquinolin-4-yl)propyl]-1-[4-(2-methoxyphenyl)butyl]piperidin-3-yl}propan-1-oic acid
(3R,4R)-3-{4-[3-(R,S)-Hydroxy-3-(6-methoxyquinolin-4-yl)propyl]-1-[3-(3-methoxyphenyl)propyl]piperidin-3-yl}propan-1-oic acid
(3R,4R)-3-{4-[3-(R,S)-Hydroxy-3-(6-methoxyquinolin-4-yl)propyl]-1-[4-(3-methoxyphenyl)butyl]piperidin-3-yl}propan-1-oic acid
(3R,4R)-3-{4-[3-(R,S)-Hydroxy-3-(6-methoxyquinolin-4-yl)propyl]-1-[3-(4-methoxyphenyl)propyl]piperidin-3-yl}propan-1-oic acid
(3R,4R)-3-{4-[3-(R,S)-Hydroxy-3-(6-methoxyquinolin-4-yl)propyl]-1-[4-(4-methoxyphenyl)butyl]piperidin-3-yl}propan-1-oic acid
(3R,4R)-3-{4-[3-(R,S)-Hydroxy-3-(6-methoxyquinolin-4-yl)propyl]-1-[3-(2-trifluoromethylphenyl)propyl]piperidin-3-yl}propan-1-oic acid
(3R,4R)-3-{4-[3-(R,S)-Hydroxy-3-(6-methoxyquinolin-4-yl)propyl]-1-[4-(2-trifluoromethylphenyl)butyl]piperidin-3-yl}propan-1-oic acid
(3R,4R)-3-{4-[3-(R,S)-Hydroxy-3-(6-methoxyquinolin-4-yl)propyl]-1-[3-(3-trifluoromethylphenyl)propyl]piperidin-3-yl}propan-1-oic acid
(3R,4R)-3-{4-[3-(R,S)-Hydroxy-3-(6-methoxyquinolin-4-yl)propyl]-1-[4-(3-trifluoromethylphenyl)butyl]piperidin-3-yl}propan-1-oic acid
(3R,4R)-3-{4-[3-(R,S)-Hydroxy-3-(6-methoxyquinolin-4-yl)propyl]-1-[3-(4-trifluoromethylphenyl)propyl]piperidin-3-yl}propan-1-oic acid
(3R,4R)-3-{4-[3-(R,S)-Hydroxy-3-(6-methoxyquinolin-4-yl)propyl]-1-[4-(4-trifluoromethylphenyl)butyl]piperidin-3-yl}propan-1-oic acid
(3R,4R)-3-{4-[3-(R,S)-Hydroxy-3-(6-methoxyquinolin-4-yl)propyl]-1-[2-phenylthioethyl]piperidin-3-yl}propan-1-oic acid
(3R,4R)-3-{4-[3-(R,S)-Hydroxy-3-(6-methoxyquinolin-4-yl)propyl]-1-[3-phenylthiopropyl]piperidin-3-yl}propan-1-oic acid
(3R,4R)-3-{4-[3-(R,S)-Hydroxy-3-(6-methoxyquinolin-4-yl)propyl]-1-[2-(2-fluorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(2-fluorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(3-fluorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(3-fluorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(4-fluorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(4-fluorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(2,3-difluorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(2,3-difluorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(2,6-difluorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(2,6-difluorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(2-chlorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(2-chlorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(3-chlorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(3-chlorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(4-chlorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(4-chlorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(2,3-dichlorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(2,3-dichlorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(2,6-dichlorophenylthio)ethyl]piperidin-3-yl}propan-1-oic acid
(3R,4R)-3-{4-[3-(R,S)-Hydroxy-3-(6-methoxyquinolin-4-yl)propyl]-1-[3-(2,6-dichlorophenylthio)propyl]piperidin-3-yl}propan-1-oic acid
(3R,4R)-3-{4-[3-(R,S)-Hydroxy-3-(6-methoxyquinolin-4-yl)propyl]-1-[2-(2-methylphenylthio)ethyl]piperidin-3-yl}propan-1-oic acid
(3R,4R)-3-{4-[3-(R,S)-Hydroxy-3-(6-methoxyquinolin-4-yl)propyl]-1-[3-(2-methylphenylthio)propyl]piperidin-3-yl}propan-1-oic acid
(3R,4R)-3-{4-[3-(R,S)-Hydroxy-3-(6-methoxyquinolin-4-yl)propyl]-1-[2-(3-methylphenylthio)ethyl]piperidin-3-yl}propan-1-oic acid
(3R,4R)-3-{4-[3-(R,S)-Hydroxy-3-(6-methoxyquinolin-4-yl)propyl]-1-[3-(3-methylphenylthio)propyl]piperidin-3-yl}propan-1-oic acid
(3R,4R)-3-{4-[3-(R,S)-Hydroxy-3-(6-methoxyquinolin-4-yl)propyl]-1-[2-(4-methylphenylthio)ethyl]piperidin-3-yl}propan-1-oic acid
(3R,4R)-3-{4-[3-(R,S)-Hydroxy-3-(6-methoxyquinolin-4-yl)propyl]-1-[3-(4-methylphenylthio)propyl]piperidin-3-yl}propan-1-oic acid
(3R,4R)-3-{4-[3-(R,S)-Hydroxy-3-(6-methoxyquinolin-4-yl)propyl]-1-[2-(2-trifluoromethylphenylthio)ethyl]piperidin-3-yl}propan-1-oic acid
(3R,4R)-3-{4-[3-(R,S)-Hydroxy-3-(6-methoxyquinolin-4-yl)propyl]-1-[3-(2-trifluoromethylphenylthio)propyl]piperidin-3-yl}propan-1-oic acid
(3R,4R)-3-{4-[3-(R,S)-Hydroxy-3-(6-methoxyquinolin-4-yl)propyl]-1-[2-(3-trifluoromethylphenylthio)ethyl]piperidin-3-yl}propan-1-oic acid
(3R,4R)-3-{4-[3-(R,S)-Hydroxy-3-(6-methoxyquinolin-4-yl)propyl]-1-[3-(3-trifluoromethylphenylthio)propyl]piperidin-3-yl}propan-1-oic acid (3R,4R)-3-{4-[3-(R,S)-Hydroxy-3-(6-methoxyquinolin-4-yl)propyl]-1-[2-(4-trifluoromethylphenylthio)ethyl]piperidin-3-yl}propan-1-oic acid (3R,4R)-3-{4-[3-(R,S)-Hydroxy-3-(6-methoxyquinolin-4-yl)propyl]-1-[3-(4-trifluoromethylphenylthio)propyl]piperidin-3-yl}propan-1-oic acid (3R,4R)-3-{4-[3-(R,S)-Hydroxy-3-(6-methoxyquinolin-4-yl)propyl]-1-[2-(2-methoxyphenylthio)ethyl]piperidin-3-yl}propan-1-oic acid (3R,4R)-3-{4-[3-(R,S)-Hydroxy-3-(6-methoxyquinolin-4-yl)propyl]-1-[3-(2-methoxyphenylthio)propyl]piperidin-3-yl}propan-1-oic acid (3R,4R)-3-{4-[3-(R,S)-Hydroxy-3-(6-methoxyquinolin-4-yl)propyl]-1-[2-(3-methoxyphenylthio)ethyl]piperidin-3-yl}propan-1-oic acid (3R,4R)-3-{4-[3-(R,S)-Hydroxy-3-(6-methoxyquinolin-4-yl)propyl]-1-[3-(3-methoxyphenylthio)propyl]piperidin-3-yl}propan-1-oic acid (3R,4R)-3-{4-[3-(R,S)-Hydroxy-3-(6-methoxyquinolin-4-yl)propyl]-1-[2-(4-methoxyphenylthio)ethyl]piperidin-3-yl}propan-1-oic acid (3R,4R)-3-{4-[3-(R,S)-Hydroxy-3-(6-methoxyquinolin-4-yl)propyl]-1-[3-(4-methoxyphenylthio)propyl]piperidin-3-yl}propan-1-oic acid (3R,4R)-3-{4-[3-(R,S)-Hydroxy-3-(6-methoxyquinolin-4-yl)propyl]-1-[cyclopropylmethyl]piperidin-3-yl}propan-1-oic acid (3R,4R)-3-{4-[3-(R,S)-Hydroxy-3-(6-methoxyquinolin-4-yl)propyl]-1-[2-(cyclopropyl)ethyl]piperidin-3-yl}propan-1-oic acid (3R,4R)-3-{4-[3-(R,S)-Hydroxy-3-(6-methoxyquinolin-4-yl)propyl]-1-[cyclobutylmethyl]piperidin-3-yl}propan-1-oic acid (3R,4R)-3-{4-[3-(R,S)-Hydroxy-3-(6-methoxyquinolin-4-yl)propyl]-1-[2-(cyclobutyl)ethyl]piperidin-3-yl}propan-1-oic acid (3R,4R)-3-{4-[3-(R,S)-Hydroxy-3-(6-methoxyquinolin-4-yl)propyl]-1-[cyclopentylmethyl]piperidin-3-yl}propan-1-oic acid (3R,4R)-3-{4-[3-(R,S)-Hydroxy-3-(6-methoxyquinolin-4-yl)propyl]-1-[2-(cyclopentyl)ethyl]piperidin-3-yl}propan-1-oic acid (3R,4R)-3-{4-[3-(R,S)-Hydroxy-3-(6-methoxyquinolin-4-yl)propyl]-1-[cyclohexylmethyl]piperidin-3-yl}propan-1-oic acid (3R,4R)-3-{4-[3-(R,S)-Hydroxy-3-(6-methoxyquinolin-4-yl)propyl]-1-[2-(cyclohexyl)ethyl]piperidin-3-yl}propan-1-oic acid (3R,4R)-3-{4-[3-(R,S)-Hydroxy-3-(6-methoxyquinolin-4-yl)propyl]-1-[2-(cyclopropylthio)ethyl]piperidin-3-yl}propan-1-oic acid (3R,4R)-3-{4-[3-(R,S)-Hydroxy-3-(6-methoxyquinolin-4-yl)propyl]-1-[3-(cyclopropylthio)propyl]piperidin-3-yl}propan-1-oic acid (3R,4R)-3-{4-[3-(R,S)-Hydroxy-3-(6-methoxyquinolin-4-yl)propyl]-1-[2-(cyclobutylthio)ethyl]piperidin-3-yl}propan-1-oic acid (3R,4R)-3-{4-[3-(R,S)-Hydroxy-3-(6-methoxyquinolin-4-yl)propyl]-1-[3-(cyclobutylthio)propyl]piperidin-3-yl}propan-1-oic acid (3R,4R)-3-{4-[3-(R,S)-Hydroxy-3-(6-methoxyquinolin-4-yl)propyl]-1-[2-(cyclopentylthio)ethyl]piperidin-3-yl}propan-1-oic acid (3R,4R)-3-{4-[3-(R,S)-Hydroxy-3-(6-methoxyquinolin-4-yl)propyl]-1-[3-(cyclopentylthio)propyl]piperidin-3-yl}propan-1-oic acid (3R,4R)-3-{4-[3-(R,S)-Hydroxy-3-(6-methoxyquinolin-4-yl)propyl]-1-[2-(cyclohexylthio)ethyl]piperidin-3-yl}propan-1-oic acid (3R,4R)-3-{4-[3-(R,S)-Hydroxy-3-(6-methoxyquinolin-4-yl)propyl]-1-[3-(cyclohexylthio)propyl]piperidin-3-yl}propan-1-oic acid (3R,4R)-3-{4-[3-(R,S)-Hydroxy-3-(6-methoxyquinolin-4-yl)propyl]-1-[2-methylthioethyl]piperidin-3-yl}propan-1-oic acid (3R,4R)-3-{4-[3-(R,S)-Hydroxy-3-(6-methoxyquinolin-4-yl)propyl]-1-[3-methylthiopropyl]piperidin-3-yl}propan-1-oic acid (3R,4R)-3-{4-[3-(R,S)-Hydroxy-3-(6-methoxyquinolin-4-yl)propyl]-1-[2-ethylthioethyl]piperidin-3-yl}propan-1-oic acid (3R,4R)-3-{4-[3-(R,S)-Hydroxy-3-(6-methoxyquinolin-4-yl)propyl]-1-[3-ethylthiopropyl]piperidin-3-yl}propan-1-oic acid (3R,4R)-3-{4-[3-(R,S)-Hydroxy-3-(6-methoxyquinolin-4-yl)propyl]-1-[2-(n-propylthio)ethyl]piperidin-3-yl}propan-1-oic acid (3R,4R)-3-{4-[3-(R,S)-Hydroxy-3-(6-methoxyquinolin-4-yl)propyl]-1-[3-(n-propylthio)propyl]piperidin-3-yl}propan-1-oic acid (3R,4R)-3-{4-[3-(R,S)-Hydroxy-3-(6-methoxyquinolin-4-yl)propyl]-1-[2-(n-butylthio)ethyl]piperidin-3-yl}propan-1-oic acid (3R,4R)-3-{4-[3-(R,S)-Hydroxy-3-(6-methoxyquinolin-4-yl)propyl]-1-[3-(n-butylthio)propyl]piperidin-3-yl}propan-1-oic acid (3R,4R)-3-{4-[3-(R,S)-Hydroxy-3-(6-methoxyquinolin-4-yl)propyl]-1-[3-(thien-2-yl)propyl]piperidin-3-yl}propan-1-oic acid (3R,4R)-3-{4-[3-(R,S)-Hydroxy-3-(6-methoxyquinolin-4-yl)propyl]-1-[4-(thien-2-yl)butyl]piperidin-3-yl}propan-1-oic acid (3R,4R)-3-{4-[3-(R,S)-Hydroxy-3-(6-methoxyquinolin-4-yl)propyl]-1-[2-(thien-2-yl)thioethyl]piperidin-3-yl}propan-1-oic acid (3R,4R)-3-{4-[3-(R,S)-Hydroxy-3-(6-methoxyquinolin-4-yl)propyl]-1-[3-(thien-2-yl)thiopropyl]piperidin-3-yl}propan-1-oic acid (3R,4R)-3-{4-[3-(R,S)-Hydroxy-3-(6-methoxyquinolin-4-yl)propyl]-1-[3-(5-chlorothien-2-yl)propyl]piperidin-3-yl}propan-1-oic acid (3R,4R)-3-{4-[3-(R,S)-Hydroxy-3-(6-methoxyquinolin-4-yl)propyl]-1-[4-(5-chlorothien-2-yl)butyl]piperidin-3-yl}propan-1-oic acid (3R,4R)-3-{4-[3-(R,S)-Hydroxy-3-(6-methoxyquinolin-4-yl)propyl]-1-[2-(5-chlorothien-2-yl)thioethyl]piperidin-3-yl}propan-1-oic acid (3R,4R)-3-{4-[3-(R,S)-Hydroxy-3-(6-methoxyquinolin-4-yl)propyl]-1-[3-(5-chlorothien-2-yl)thiopropyl]piperidin-3-yl}propan-1-oic acid (3R,4R)-3-{4-[3-(R,S)-Hydroxy-3-(6-methoxyquinolin-4-yl)propyl]-1-[3-(3-chlorothien-2-yl)propyl]piperidin-3-yl}propan-1-oic acid (3R,4R)-3-{4-[3-(R,S)-Hydroxy-3-(6-methoxyquinolin-4-yl)propyl]-1-[4-(3-chlorothien-2-yl)butyl]piperidin-3-yl}propan-1-oic acid (3R,4R)-3-{4-[3-(R,S)-Hydroxy-3-(6-methoxyquinolin-4-yl)propyl]-1-[2-(3-chlorothien-2-yl)thioethyl]piperidin-3-yl}propan-1-oic acid (3R,4R)-3-{4-[3-(R,S)-Hydroxy-3-(6-methoxyquinolin-4-yl)propyl]-1-[3-(3-chlorothien-2-yl)thiopropyl]piperidin-3-yl}propan-1-oic acid (3R,4R)-3-{4-[3-(R,S)-Hydroxy-3-(6-methoxyquinolin-4-yl)propyl]-1-[3-(5-methylthien-2-yl)propyl]piperidin-3-yl}propan-1-oic acid (3R,4R)-3-{4-[3-(R,S)-Hydroxy-3-(6-methoxyquinolin-4-yl)propyl]-1-[4-(5-methylthien-2-yl)butyl]piperidin-3-yl}propan-1-oic acid (3R,4R)-3-{4-[3-(R,S)-Hydroxy-3-(6-methoxyquinolin-4-yl)propyl]-1-[2-(5-methylthien-2-yl)thioethyl]piperidin-3-yl}propan-1-oic acid
(3R,4R)-3-{4-[3-(R,S)-Hydroxy-3-(6-methoxyquinolin-4-yl)propyl]-1-[3-(5-methylthien-2-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(3-methylthien-2-yl)propyl]piperidin-3-yl}propan-1-oic acid
(3R,4R)-3-{4-[3-(R,S)-Hydroxy-3-(6-methoxyquinolin-4-yl)propyl]-1-[4-(3-methylthien-2-yl)butyl]piperidin-3-yl}propan-1-oic acid
(3R,4R)-3-{4-[3-(R,S)-Hydroxy-3-(6-methoxyquinolin-4-yl)propyl]-1-[2-(3-methylthien-2-yl)thioethyl]piperidin-3-yl}propan-1-oic acid
(3R,4R)-3-{4-[3-(R,S)-Hydroxy-3-(6-methoxyquinolin-4-yl)propyl]-1-[3-(3-methylthien-2-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(thien-3-yl)propyl]piperidin-3-yl}propan-1-oic acid
(3R,4R)-3-{4-[3-(R,S)-Hydroxy-3-(6-methoxyquinolin-4-yl)propyl]-1-[4-(thien-3-yl)butyl]piperidin-3-yl}propan-1-oic acid
(3R,4R)-3-{4-[3-(R,S)-Hydroxy-3-(6-methoxyquinolin-4-yl)propyl]-1-[2-(thien-3-yl)thioethyl]piperidin-3-yl}propan-1-oic acid
(3R,4R)-3-{4-[3-(R,S)-Hydroxy-3-(6-methoxyquinolin-4-yl)propyl]-1-[3-(thien-3-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(fur-2-yl)propyl]piperidin-3-yl}propan-1-oic acid
(3R,4R)-3-{4-[3-(R,S)-Hydroxy-3-(6-methoxyquinolin-4-yl)propyl]-1-[4-(fur-2-yl)butyl]piperidin-3-yl}propan-1-oic acid
(3R,4R)-3-{4-[3-(R,S)-Hydroxy-3-(6-methoxyquinolin-4-yl)propyl]-1-[2-(fur-2-yl)thioethyl]piperidin-3-yl}propan-1-oic acid
(3R,4R)-3-{4-[3-(R,S)-Hydroxy-3-(6-methoxyquinolin-4-yl)propyl]-1-[3-(fur-2-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(fur-3-yl)propyl]piperidin-3-yl}propan-1-oic acid
(3R,4R)-3-{4-[3-(R,S)-Hydroxy-3-(6-methoxyquinolin-4-yl)propyl]-1-[4-(fur-3-yl)butyl]piperidin-3-yl}propan-1-oic acid
(3R,4R)-3-{4-[3-(R,S)-Hydroxy-3-(6-methoxyquinolin-4-yl)propyl]-1-[2-(fur-3-yl)thioethyl]piperidin-3-yl}propan-1-oic acid
(3R,4R)-3-{4-[3-(R,S)-Hydroxy-3-(6-methoxyquinolin-4-yl)propyl]-1-[3-(fur-3-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(1 methylpyrrol-2-yl)propyl]piperidin-3-yl}propan-1-oic acid
(3R,4R)-3-{4-[3-(R,S)-Hydroxy-3-(6-methoxyquinolin-4-yl)propyl]-1-[4-(1 methylpyrrol-2-yl)butyl]piperidin-3-yl}propan-1-oic acid
(3R,4R)-3-{4-[3-(R,S)-Hydroxy-3-(6-methoxyquinolin-4-yl)propyl]-1-[2-(1-methylpyrrol-2-yl)thioethyl]piperidin-3-yl}propan-1-oic acid
(3R,4R)-3-{4-[3-(R,S)-Hydroxy-3-(6-methoxyquinolin-4-yl)propyl]-1-[3-(1 methylpyrrol-2-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(1 methylpyrrol-2-yl)propyl]piperidin-3-yl}propan-1-oic acid
(3R,4R)-3-{4-[3-(R,S)-Hydroxy-3-(6-methoxyquinolin-4-yl)propyl]-1-[4-(1 methylpyrrol-3-yl)butyl]piperidin-3-yl}propan-1-oic acid
(3R,4R)-3-{4-[3-(R,S)-Hydroxy-3-(6-methoxyquinolin-4-yl)propyl]-1-[2-(1 methylpyrrol-3-yl)thioethyl]piperidin-3-yl}propan-1-oic acid
(3R,4R)-3-{4-[3-(R,S)-Hydroxy-3-(6-methoxyquinolin-4-yl)propyl]-1-[3-(1 methylpyrrol-3-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(thiazol-2-yl)propyl]piperidin-3-yl}propan-1-oic acid
(3R,4R)-3-{4-[3-(R,S)-Hydroxy-3-(6-methoxyquinolin-4-yl)propyl]-1-[4-(thiazol-2-yl)butyl]piperidin-3-yl}propan-1-oic acid
(3R,4R)-3-{4-[3-(R,S)-Hydroxy-3-(6-methoxyquinolin-4-yl)propyl]-1-[2-(thiazol-2-yl)thioethyl]piperidin-3-yl}propan-1-oic acid
(3R,4R)-3-{4-[3-(R,S)-Hydroxy-3-(6-methoxyquinolin-4-yl)propyl]-1-[3-(thiazol-2-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(1-methylimidazol-2-yl)propyl]piperidin-3-yl}propan-1-oic acid
(3R,4R)-3-{4-[3-(R,S)-Hydroxy-3-(6-methoxyquinolin-4-yl)propyl]-1-[4-(1-methylimidazol-2-yl)butyl]piperidin-3-yl}propan-1-oic acid
(3R,4R)-3-{4-[3-(R,S)-Hydroxy-3-(6-methoxyquinolin-4-yl)propyl]-1-[2-(1-methylimidazol-2-yl)thioethyl]piperidin-3-yl}propan-1-oic acid
(3R,4R)-3-{4-[3-(R,S)-Hydroxy-3-(6-methoxyquinolin-4-yl)propyl]-1-[3-(1-methylimidazol-2-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(3-methylimidazol-4-yl)propyl]piperidin-3-yl}propan-1-oic acid
(3R,4R)-3-{4-[3-(R,S)-Hydroxy-3-(6-methoxyquinolin-4-yl)propyl]-1-[4-(3-methylimidazol-4-yl)butyl]piperidin-3-yl}propan-1-oic acid
(3R,4R)-3-{4-[3-(R,S)-Hydroxy-3-(6-methoxyquinolin-4-yl)propyl]-1-[2-(3-methylimidazol-4-yl)thioethyl]piperidin-3-yl}propan-1-oic acid
(3R,4R)-3-{4-[3-(R,S)-Hydroxy-3-(6-methoxyquinolin-4-yl)propyl]-1-[3-(3-methylimidazol-4-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(3-methylpyrazol-4-yl)propyl]piperidin-3-yl}propan-1-oic acid
(3R,4R)-3-{4-[3-(R,S)-Hydroxy-3-(6-methoxyquinolin-4-yl)propyl]-1-[4-(3-methylpyrazol-4-yl)butyl]piperidin-3-yl}propan-1-oic acid
(3R,4R)-3-{4-[3-(R,S)-Hydroxy-3-(6-methoxyquinolin-4-yl)propyl]-1-[2-(3-methylpyrazol-4-yl)thioethyl]piperidin-3-yl}propan-1-oic acid
(3R,4R)-3-{4-[3-(R,S)-Hydroxy-3-(6-methoxyquinolin-4-yl)propyl]-1-[3-(3-methylpyrazol-4-yl)thiopropyl]piperidin-3-yl}propan-1-oic acid
(3R,4R)-3-{4-[3-(R,S)-Hydroxy-3-(6-methoxyquinolin-4-yl)propyl]-1-[3-(oxazol-2-yl)propyl]piperidin-3-yl}propan-1-oic acid
(3R,4R)-3-{4-[3-(R,S)-Hydroxy-3-(6-methoxyquinolin-4-yl)propyl]-1-[4-(oxazol-2-yl)butyl]piperidin-3-yl}propan-1-oic acid
(3R,4R)-3-{4-[3-(R,S)-Hydroxy-3-(6-methoxyquinolin-4-yl)propyl]-1-[2-(oxazol-2-yl)thioethyl]piperidin-3-yl}propan-1-oic acid
(3R,4R)-3-{4-[3-(R,S)-Hydroxy-3-(6-methoxyquinolin-4-yl)propyl]-1-[3-(oxazol-2-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyridin-2-yl)propyl]piperidin-3-yl}propan-1-oic acid (3R,4R)-3-{4-[3-(R,S)-Hydroxy-3-(6-methoxyquinolin-4-yl)propyl]-1-[4-(pyridin-2-yl)butyl]piperidin-3-yl}propan-1-oic acid (3R,4R)-3-{4-[3-(R,S)-Hydroxy-3-(6-methoxyquinolin-4-yl)propyl]-1-[2-(pyridin-2-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyridin-2-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyridin-3-yl)propyl]piperidin-3-yl}propan-1-oic acid (3R,4R)-3-{4-[3-(R,S)-Hydroxy-3-(6-methoxyquinolin-4-yl)propyl]-1-[4-(pyridin-3-yl)butyl]piperidin-3-yl}propan-1-oic acid (3R,4R)-3-{4-[3-(R,S)-Hydroxy-3-(6-methoxyquinolin-4-yl)propyl]-1-[2-(pyridin-3-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyridin-3-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyridin-4-yl)propyl]piperidin-3-yl}propan-1-oic acid (3R,4R)-3-{4-[3-(R,S)-Hydroxy-3-(6-methoxyquinolin-4-yl)propyl]-1-[4-(pyridin-4-yl)butyl]piperidin-3-yl}propan-1-oic acid (3R,4R)-3-{4-[3-(R,S)-Hydroxy-3-(6-methoxyquinolin-4-yl)propyl]-1-[5(pyridin-4-yl)pentyl]piperidin-3-yl}propan-1-oic acid (3R,4R)-3-{4-[3-(R,S)-Hydroxy-3-(6-methoxyquinolin-4-yl)propyl]-1-[2-(pyridin-4-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyridin-4-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyridin-2-yl)propyl]piperidin-3-yl}propan-1-oic acid (3R,4R)-3-{4-[3-(R,S)-Hydroxy-3-(6-methoxyquinolin-4-yl)propyl]-1-[4-(pyridin-2-yl)butyl]piperidin-3-yl}propan-1-oic acid (3R,4R)-3-{4-[3-(R,S)-Hydroxy-3-(6-methoxyquinolin-4-yl)propyl]-1-[2-(pyrimidin-2-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyrimidin-2-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyrimidin-4-yl)propyl]piperidin-3-yl}propan-1-oic acid (3R,4R)-3-{4-[3-(R,S)-Hydroxy-3-(6-methoxyquinolin-4-yl)propyl]-1-[4-(pyrimidin-4-yl)butyl]piperidin-3-yl}propan-1-oic acid (3R,4R)-3-{4-[3-(R,S)-Hydroxy-3-(6-methoxyquinolin-4-yl)propyl]-1-[2-(pyrimidin-4-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyrimidin-4-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyrimidin-5-yl)propyl]piperidin-3-yl}propan-1-oic acid (3R,4R)-3-{4-[3-(R,S)-Hydroxy-3-(6-methoxyquinolin-4-yl)propyl]-1-[4-(pyrimidin-5-yl)butyl]piperidin-3-yl}propan-1-oic acid (3R,4R)-3-{4-[3-(R,S)-Hydroxy-3-(6-methoxyquinolin-4-yl)propyl]-1-[2-(pyrimidin-5-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyrimidin-5-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyrazin-2-yl)propyl]piperidin-3-yl}propan-1-oic acid (3R,4R)-3-{4-[3-(R,S)-Hydroxy-3-(6-methoxyquinolin-4-yl)propyl]-1-[4-(pyrazin-2-yl)butyl]piperidin-3-yl}propan-1-oic acid (3R,4R)-3-{4-[3-(R,S)-Hydroxy-3-(6-methoxyquinolin-4-yl)propyl]-1-[2-(pyrazin-2-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyrazin-2-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyridazin-3-yl)propyl]piperidin-3-yl}propan-1-oic acid (3R,4R)-3-{4-[3-(R,S)-Hydroxy-3-(6-methoxyquinolin-4-yl)propyl]-1-[4-(pyrazin-3-yl)butyl]piperidin-3-yl}propan-1-oic acid (3R,4R)-3-{4-[3-(R,S)-Hydroxy-3-(6-methoxyquinolin-4-yl)propyl]-1-[2-(pyridazin-3-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyridazin-3-yl)thiopropyl]piperidin-3-yl}propan-1-oic acid (3R,4R)-3-{4-[3-(R,S)-Hydroxy-3-(6-methoxyquinolin-4-yl)propyl]-1-[3-(pyridazin-3-yl)propyl]piperidin-3-yl}propan-1-oic acid (3R,4R)-3-{4-[3-(R,S)-Hydroxy-3-(6-methoxyquinolin-4-yl)propyl]-1-[4-(pyridazin-4-yl)butyl]piperidin-3-yl}propan-1-oic acid (3R,4R)-3-{4-[3-(R,S)-Hydroxy-3-(6-methoxyquinolin-4-yl)propyl]-1-[2-(pyridazin-4-yl)thioethyl]piperidin-3-yl}propan-1-oic acid (3R,4R)-3-{4-[3-(R,S)-Hydroxy-3-(6-methoxyquinolin-4-yl)propyl]-1-[3-(pyridazin-4-yl)thiopropyl]piperidin-3-yl}propan-1-oic acid (3R,4R)-3-{4-[3-(R,S)-Hydroxy-3-(6-methoxyquinolin-4-yl)propyl]-1-[3-(phenylprop-2-ynyl]piperidin-3-yl}propan-1-oic acid (3R,4R)-3-{4-[3-(R,S)-Hydroxy-3-(6-methoxyquinolin-4-yl)propyl]-1-[3-(2-fluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-fluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(4-fluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2-chlorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-chlorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(4-chlorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2-methylphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-methylphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(4-methylphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2-(trifluoromethyl)phenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-(trifluoromethyl)phenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(4-(trifluoromethyl)phenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2-methoxyphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-methoxyphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(4-methoxyphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3,4-difluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2,4-difluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3,4-dichlorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2,3-dichlorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2,4-dichlorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2,4,6-trichlorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3,5-dichlorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(4-chloro-3-fluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-chloro-4-fluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2-chloro-4-fluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-chloro-5-fluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(4-chloro-2-fluorophenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-fluoro-4-methylphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(4-chloro-3-(trifluoromethyl)phenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2-chloro-4-(trifluoromethyl)phenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2-chloro-5-(trifluoromethyl)phenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(5-chloro-2-methoxyphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3,5-bis(trifluoromethyl)phenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3,5-dimethylphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(2,4-dichloro-6-methylphenyl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(thien-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(5-chlorothien-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-chlorothien-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(5-methylthien-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-methylthien-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(thien-3-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(1-methylpyrrol-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(1-methylpyrrol-3-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(thiazol-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(thiazol-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(thiazol-5-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(1-methylimidazol-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-methylimidazol-4-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(3-methylpyrazol-4-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(oxazol-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(oxazol-4-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(oxazol-5-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyridin-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyridin-3-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyridin-4-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyrimidin-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyrimidin-4-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyrimidin-5-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyrazin-2-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyridazin-3-yl)prop-2-ynyl]piperidin-3-yl}propan-1-oic acid (3R,4R)-3-{4-[3-(R,S)-Hydroxy-3-(6-methoxyquinolin-4-yl)propyl]-1-[3-(pyridazin-4-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-phenylpropyl]piperidin-3-yl}propan-1-oic acid (3R,4R)-3-{4-[3-(R,S)-Fluoro-3-(6-methoxyquinolin-4-yl)propyl]-1-[4-phenylbutyl]piperidin-3-yl}propan-1-oic acid (3R,4R)-3-{4-[3-(R,S)-Fluoro-3-(6-methoxyquinolin-4-yl)propyl]-1-[3-(2-fluorophenyl)propyl]piperidin-3-yl}propan-1-oic acid (3R,4R)-3-{4-[3-(R,S)-Fluoro-3-(6-methoxyquinolin-4-yl)propyl]-1-[4-(2-fluorophenyl)butyl]piperidin-3-yl}propan-1-oic acid (3R,4R)-3-{4-[3-(R,S)-Fluoro-3-(6-methoxyquinolin-4-yl)propyl]-1-[3-(3-fluorophenyl)propyl]piperidin-3-yl}propan-1-oic acid (3R,4R)-3-{4-[3-(R,S)-Fluoro-3-(6-methoxyquinolin-4-yl)propyl]-1-[4-(3-fluorophenyl)butyl]piperidin-3-yl}propan-1-oic acid (3R,4R)-3-{4-[3-(R,S)-Fluoro-3-(6-methoxyquinolin-4-yl)propyl]-1-[3-(4-fluorophenyl)propyl]piperidin-3-yl}propan-1-oic acid (3R,4R)-3-{4-[3-(R,S)-Fluoro-3-(6-methoxyquinolin-4-yl)propyl]-1-[4-(4-fluorophenyl)butyl]piperidin-3-yl}propan-1-oic acid (3R,4R)-3-{4-[3-(R,S)-Fluoro-3-(6-methoxyquinolin-4-yl)propyl]-1-[3-(2,3-difluorophenyl)propyl]piperidin-3-yl}propan-1-oic acid (3R,4R)-3-{4-[3-(R,S)-Fluoro-3-(6-methoxyquinolin-4-yl)propyl]-1-[4-(2,3-difluorophenyl)butyl]piperidin-3-yl}propan-1-oic acid (3R,4R)-3-{4-[3-(R,S)-Fluoro-3-(6-methoxyquinolin-4-yl)propyl]-1-[3-(2,6-difluorophenyl)propyl]piperidin-3-yl}propan-1-oic acid (3R,4R)-3-{4-[3-(R,S)-Fluoro-3-(6-methoxyquinolin-4-yl)propyl]-1-[4-(2,6-difluorophenyl)butyl]piperidin-3-yl}propan-1-oic acid (3R,4R)-3-{4-[3-(R,S)-Fluoro-3-(6-methoxyquinolin-4-yl)propyl]-1-[3-(2-chlorophenyl)propyl]piperidin-3-yl}propan-1-oic acid (3R,4R)-3-{4-[3-(R,S)-Fluoro-3-(6-methoxyquinolin-4-yl)propyl]-1-[4-(2-chlorophenyl)butyl]piperidin-3-yl}propan-1-oic acid (3R,4R)-3-{4-[3-(R,S)-Fluoro-3-(6-methoxyquinolin-4-yl)propyl]-1-[3-(3-chlorophenyl)propyl]piperidin-3-yl}propan-1-oic acid (3R,4R)-3-{4-[3-(R,S)-Fluoro-3-(6-methoxyquinolin-4-yl)propyl]-1-[4-(3-chlorophenyl)butyl]piperidin-3-yl}propan-1-oic acid (3R,4R)-3-{4-[3-(R,S)-Fluoro-3-(6-methoxyquinolin-4-yl)propyl]-1-[3-(4-chlorophenyl)propyl]piperidin-3-yl}propan-1-oic acid (3R,4R)-3-{4-[3-(R,S)-Fluoro-3-(6-methoxyquinolin-4-yl)propyl]-1-[4-(4-chlorophenyl)butyl]piperidin-3-yl}propan-1-oic acid (3R,4R)-3-{4-[3-(R,S)-Fluoro-3-(6-methoxyquinolin-4-yl)propyl]-1-[3-(2,3-dichlorophenyl)propyl]piperidin-3-yl}propan-1-oic acid (3R,4R)-3-{4-[3-(R,S)-Fluoro-3-(6-methoxyquinolin-4-yl)propyl]-1-[4-(2,3-dichlorophenyl)butyl]piperidin-3-yl}propan-1-oic acid (3R,4R)-3-{4-[3-(R,S)-Fluoro-3-(6-methoxyquinolin-4-yl)propyl]-1-[3-(2,6-dichlorophenyl)propyl]piperidin-3-yl}propan-1-oic acid (3R,4R)-3-{4-[3-(R,S)-Fluoro-3-(6-methoxyquinolin-4-yl)propyl]-1-[4-(2,6-dichlorophenyl)butyl]piperidin-3-yl}propan-1-oic acid (3R,4R)-3-{4-[3-(R,S)-Fluoro-3-(6-methoxyquinolin-4-yl)propyl]-1-[3-(2-methylphenyl)propyl]piperidin-3-yl}propan-1-oic acid (3R,4R)-3-{4-[3-(R,S)-Fluoro-3-(6-methoxyquinolin-4-yl)propyl]-1-[4-(2-methylphenyl)butyl]piperidin-3-yl}propan-1-oic acid (3R,4R)-3-{4-[3-(R,S)-Fluoro-3-(6-methoxyquinolin-4-yl)propyl]-1-[5-(2-methylphenyl)pentyl]piperidin-3-yl}propan-1-oic acid (3R,4R)-3-{4-[3-(R,S)-Fluoro-3-(6-methoxyquinolin-4-yl)propyl]-1-[3-(3-methylphenyl)propyl]piperidin-3-yl}propan-1-oic acid (3R,4R)-3-{4-[3-(R,S)-Fluoro-3-(6-methoxyquinolin-4-yl)propyl]-1-[4-(3-methylphenyl)butyl]piperidin-3-yl}propan-1-oic acid (3R,4R)-3-{4-[3-(R,S)-Fluoro-3-(6-methoxyquinolin-4-yl)propyl]-1-[3-(4-methylphenyl)propyl]piperidin-3-yl}propan-1-oic acid (3R,4R)-3-{4-[3-(R,S)-Fluoro-3-(6-methoxyquinolin-4-yl)propyl]-1-[4-(4-methylphenyl)butyl]piperidin-3-yl}propan-1-oic acid (3R,4R)-3-{4-[3-(R,S)-Fluoro-3-(6-methoxyquinolin-4-yl)propyl]-1-[3-(2-methoxyphenyl)propyl]piperidin-3-yl}propan-1-oic acid (3R,4R)-3-{4-[3-(R,S)-Fluoro-3-(6-methoxyquinolin-4-yl)propyl]-1-[4-(2-methoxyphenyl)butyl]piperidin-3-yl}propan-1-oic acid (3R,4R)-3-{4-[3-(R,S)-Fluoro-3-(6-methoxyquinolin-4-yl)propyl]-1-[3-(3-methoxyphenyl)propyl]piperidin-3-yl}propan-1-oic acid (3R,4R)-3-{4-[3-(R,S)-Fluoro-3-(6-methoxyquinolin-4-yl)propyl]-1-[4-(3-methoxyphenyl)butyl]piperidin-3-yl}propan-1-oic acid (3R,4R)-3-{4-[3-(R,S)-Fluoro-3-(6-methoxyquinolin-4-yl)propyl]-1-[3-(4-methoxyphenyl)propyl]piperidin-3-yl}propan-1-oic acid (3R,4R)-3-{4-[3-(R,S)-Fluoro-3-(6-methoxyquinolin-4-yl)propyl]-1-[4-(4-methoxyphenyl)butyl]piperidin-3-yl}propan-1-oic acid (3R,4R)-3-{4-[3-(R,S)-Fluoro-3-(6-methoxyquinolin-4-yl)propyl]-1-[3-(2-trifluoromethylphenyl)propyl]piperidin-3-yl}propan-1-oic acid (3R,4R)-3-{4-[3-(R,S)-Fluoro-3-(6-methoxyquinolin-4-yl)propyl]-1-[4-(2-trifluoromethylphenyl)butyl]piperidin-3-yl}propan-1-oic acid (3R,4R)-3-{4-[3-(R,S)-Fluoro-3-(6-methoxyquinolin-4-yl)propyl]-1-[3-(3-trifluoromethylphenyl)propyl]piperidin-3-yl}propan-1-oic acid (3R,4R)-3-{4-[3-(R,S)-Fluoro-3-(6-methoxyquinolin-4-yl)propyl]-1-[4-(3-trifluoromethylphenyl)butyl]piperidin-3-yl}propan-1-oic acid (3R,4R)-3-{4-[3-(R,S)-Fluoro-3-(6-methoxyquinolin-4-yl)propyl]-1-[3-(4-trifluoromethylphenyl)propyl]piperidin-3-yl}propan-1-oic acid (3R,4R)-3-{4-[3-(R,S)-Fluoro-3-(6-methoxyquinolin-4-yl)propyl]-1-[4-(4-trifluoromethylphenyl)butyl]piperidin-3-yl}propan-1-oic acid (3R,4R)-3-{4-[3-(R,S)-Fluoro-3-(6-methoxyquinolin-4-yl)propyl]-1-[2-phenylthioethyl]piperidin-3-yl}propan-1-oic acid (3R,4R)-3-{4-[3-(R,S)-Fluoro-3-(6-methoxyquinolin-4-yl)propyl]-1-[3-phenylthiopropyl]piperidin-3-yl}propan-1-oic acid (3R,4R)-3-{4-[3-(R,S)-Fluoro-3-(6-methoxyquinolin-4-yl)propyl]-1-[2-(2-fluorophenylthio)ethyl]piperidin-3-yl}propan-1-oic acid (3R,4R)-3-{4-[3-(R,S)-Fluoro-3-(6-methoxyquinolin-4-yl)propyl]-1-[3-(2-fluorophenylthio)propyl]piperidin-3-yl}propan-1-oic acid (3R,4R)-3-{4-[3-(R,S)-Fluoro-3-(6-methoxyquinolin-4-yl)propyl]-1-[2-(3-fluorophenylthio)ethyl]piperidin-3-yl}propan-1-oic acid (3R,4R)-3-{4-[3-(R,S)-Fluoro-3-(6-methoxyquinolin-4-yl)propyl]-1-[3-(3-fluorophenylthio)propyl]piperidin-3-yl}propan-1-oic acid (3R,4R)-3-{4-[3-(R,S)-Fluoro-3-(6-methoxyquinolin-4-yl)propyl]-1-[2-(4-fluorophenylthio)ethyl]piperidin-3-yl}propan-1-oic acid (3R,4R)-3-{4-[3-(R,S)-Fluoro-3-(6-methoxyquinolin-4-yl)propyl]-1-[3-(4-fluorophenylthio)propyl]piperidin-3-yl}propan-1-oic acid (3R,4R)-3-{4-[3-(R,S)-Fluoro-3-(6-methoxyquinolin-4-yl)propyl]-1-[2-(2,3-difluorophenylthio)ethyl]piperidin-3-yl}propan-1-oic acid (3R,4R)-3-{4-[3-(R,S)-Fluoro-3-(6-methoxyquinolin-4-yl)propyl]-1-[3-(2,3-difluorophenylthio)propyl]piperidin-3-yl}propan-1-oic acid (3R,4R)-3-{4-[3-(R,S)-Fluoro-3-(6-methoxyquinolin-4-yl)propyl]-1-[2-(2,6-difluorophenylthio)ethyl]piperidin-3-yl}propan-1-oic acid (3R,4R)-3-{4-[3-(R,S)-Fluoro-3-(6-methoxyquinolin-4-yl)propyl]-1-[3-(2,6-difluorophenylthio)propyl]piperidin-3-yl}propan-1-oic acid (3R,4R)-3-{4-[3-(R,S)-Fluoro-3-(6-methoxyquinolin-4-yl)propyl]-1-[2-(2-chlorophenylthio)ethyl]piperidin-3-yl}propan-1-oic acid (3R,4R)-3-{4-[3-(R,S)-Fluoro-3-(6-methoxyquinolin-4-yl)propyl]-1-[3-(2-chlorophenylthio)propyl]piperidin-3-yl}propan-1-oic acid (3R,4R)-3-{4-[3-(R,S)-Fluoro-3-(6-methoxyquinolin-4-yl)propyl]-1-[2-(3-chlorophenylthio)ethyl]piperidin-3-yl}propan-1-oic acid (3R,4R)-3-{4-[3-(R,S)-Fluoro-3-(6-methoxyquinolin-4-yl)propyl]-1-[3-(3-chlorophenylthio)propyl]piperidin-3-yl}propan-1-oic acid (3R,4R)-3-{4-[3-(R,S)-Fluoro-3-(6-methoxyquinolin-4-yl)propyl]-1-[2-(4-chlorophenylthio)ethyl]piperidin-3-yl}propan-1-oic acid (3R,4R)-3-{4-[3-(R,S)-Fluoro-3-(6-methoxyquinolin-4-yl)propyl]-1-[3-(4-chlorophenylthio)propyl]piperidin-3-yl}propan-1-oic acid (3R,4R)-3-{4-[3-(R,S)-Fluoro-3-(6-methoxyquinolin-4-yl)propyl]-1-[2-(2,3-dichlorophenylthio)ethyl]piperidin-3-yl}propan-1-oic acid (3R,4R)-3-{4-[3-(R,S)-Fluoro-3-(6-methoxyquinolin-4-yl)propyl]-1-[3-(2,3-dichlorophenylthio)propyl]piperidin-3-yl}propan-1-oic acid (3R,4R)-3-{4-[3-(R,S)-Fluoro-3-(6-methoxyquinolin-4-yl)propyl]-1-[2-(2,6-dichlorophenylthio)ethyl]piperidin-3-yl}propan-1-oic acid (3R,4R)-3-{4-[3-(R,S)-Fluoro-3-(6-methoxyquinolin-4-yl)propyl]-1-[3-(2,6-dichlorophenylthio)propyl]piperidin-3-yl}propan-1-oic acid (3R,4R)-3-{4-[3-(R,S)-Fluoro-3-(6-methoxyquinolin-4-yl)propyl]-1-[2-(2-methylphenylthio)ethyl]piperidin-3-yl}propan-1-oic acid (3R,4R)-3-{4-[3-(R,S)-Fluoro-3-(6-methoxyquinolin-4-yl)propyl]-1-[3-(2-methylphenylthio)propyl]piperidin-3-yl}propan-1-oic acid (3R,4R)-3-{4-[3-(R,S)-Fluoro-3-(6-methoxyquinolin-4-yl)propyl]-1-[2-(3-methylphenylthio)ethyl]piperidin-3-yl}propan-1-oic acid (3R,4R)-3-{4-[3-(R,S)-Fluoro-3-(6-methoxyquinolin-4-yl)propyl]-1-[3-(3-methylphenylthio)propyl]piperidin-3-yl}propan-1-oic acid (3R,4R)-3-{4-[3-(R,S)-Fluoro-3-(6-methoxyquinolin-4-yl)propyl]-1-[2-(4-methylphenylthio)ethyl]piperidin-3-yl}propan-1-oic acid (3R,4R)-3-{4-[3-(R,S)-Fluoro-3-(6-methoxyquinolin-4-yl)propyl]-1-[3-(4-methylphenylthio)propyl]piperidin-3-yl}propan-1-oic acid (3R,4R)-3-{4-[3-(R,S)-Fluoro-3-(6-methoxyquinolin-4-yl)propyl]-1-[2-(2-trifluoromethylphenylthio)ethyl]piperidin-3-yl}propan-1-oic acid (3R,4R)-3-{4-[3-(R,S)-Fluoro-3-(6-methoxyquinolin-4-yl)propyl]-1-[3-(2-trifluoromethylphenylthio)propyl]piperidin-3-yl}propan-1-oic acid (3R,4R)-3-{4-[3-(R,S)-Fluoro-3-(6-methoxyquinolin-4-yl)propyl]-1-[2-(3-trifluoromethylphenylthio)ethyl]piperidin-3-yl}propan-1-oic acid (3R,4R)-3-{4-[3-(R,S)-Fluoro-3-(6-methoxyquinolin-4-yl)propyl]-1-[3-(3-trifluoromethylphenylthio)propyl]piperidin-3-yl}propan-1-oic acid (3R,4R)-3-{4-[3-(R,S)-Fluoro-3-(6-methoxyquinolin-4-yl)propyl]-1-[2-(4-trifluoromethylphenylthio)ethyl]piperidin-3-yl}propan-1-oic acid (3R,4R)-3-{4-[3-(R,S)-Fluoro-3-(6-methoxyquinolin-4-yl)propyl]-1-[3-(4-trifluoromethylphenylthio)propyl]piperidin-3-yl}propan-1-oic acid (3R,4R)-3-{4-[3-(R,S)-Fluoro-3-(6-methoxyquinolin-4-yl)propyl]-1-[2-(2-methoxyphenylthio)ethyl]piperidin-3-yl}propan-1-oic acid (3R,4R)-3-{4-[3-(R,S)-Fluoro-3-(6-methoxyquinolin-4-yl)propyl]-1-[3-(2-methoxyphenylthio)propyl]piperidin-3-yl}propan-1-oic acid (3R,4R)-3-{4-[3-(R,S)-Fluoro-3-(6-methoxyquinolin-4-yl)propyl]-1-[2-(3-methoxyphenylthio)ethyl]piperidin-3-yl}propan-1-oic acid (3R,4R)-3-{4-[3-(R,S)-Fluoro-3-(6-methoxyquinolin-4-yl)propyl]-1-[3-(3-methoxyphenylthio)propyl]piperidin-3-yl}propan-1-oic acid (3R,4R)-3-{4-[3-(R,S)-Fluoro-3-(6-methoxyquinolin-4-yl)propyl]-1-[2-(4-methoxyphenylthio)ethyl]piperidin-3-yl}propan-1-oic acid (3R,4R)-3-{4-[3-(R,S)-Fluoro-3-(6-methoxyquinolin-4-yl)propyl]-1-[3-(4-methoxyphenylthio)propyl]piperidin-3-yl}propan-1-oic acid (3R,4R)-3-{4-[3-(R,S)-Fluoro-3-(6-methoxyquinolin-4-yl)propyl]-1-[cyclopropylmethyl]piperidin-3-yl}propan-1-oic acid (3R,4R)-3-{4-[3-(R,S)-Fluoro-3-(6-methoxyquinolin-4-yl)propyl]-1-[2-(cyclopropyl)ethyl]piperidin-3-yl}propan-1-oic acid (3R,4R)-3-{4-[3-(R,S)-Fluoro-3-(6-methoxyquinolin-4-yl)propyl]-1-[cyclobutylmethyl]piperidin-3-yl}propan-1-oic acid (3R,4R)-3-{4-[3-(R,S)-Fluoro-3-(6-methoxyquinolin-4-yl)propyl]-1-[2-(cyclobutyl)ethyl]piperidin-3-yl}propan-1-oic acid (3R,4R)-3-{4-[3-(R,S)-Fluoro-3-(6-methoxyquinolin-4-yl)propyl]-1-[cyclopentylmethyl]piperidin-3-yl}propan-1-oic acid (3R,4R)-3-{4-[3-(R,S)-Fluoro-3-(6-methoxyquinolin-4-yl)propyl]-1-[2-(cyclopentyl)ethyl]piperidin-3-yl}propan-1-oic acid (3R,4R)-3-{4-[3-(R,S)-Fluoro-3-(6-methoxyquinolin-4-yl)propyl]-1-[cyclohexylmethyl]piperidin-3-yl}propan-1-oic acid (3R,4R)-3-{4-[3-(R,S)-Fluoro-3-(6-methoxyquinolin-4-yl)propyl]-1-[2-(cyclohexyl)ethyl]piperidin-3-yl}propan-1-oic acid (3R,4R)-3-{4-[3-(R,S)-Fluoro-3-(6-methoxyquinolin-4-yl)propyl]-1-[2-(cyclopropylthio)ethyl]piperidin-3-yl}propan-1-oic acid (3R,4R)-3-{4-[3-(R,S)-Fluoro-3-(6-methoxyquinolin-4-yl)propyl]-1-[3-(cyclopropylthio)propyl]piperidin-3-yl}propan-1-oic acid (3R,4R)-3-{4-[3-(R,S)-Fluoro-3-(6-methoxyquinolin-4-yl)propyl]-1-[2-(cyclobutylthio)ethyl]piperidin-3-yl}propan-1-oic acid (3R,4R)-3-{4-[3-(R,S)-Fluoro-3-(6-methoxyquinolin-4-yl)propyl]-1-[3-(cyclobutylthio)propyl]piperidin-3-yl}propan-1-oic acid (3R,4R)-3-{4-[3-(R,S)-Fluoro-3-(6-methoxyquinolin-4-yl)propyl]-1-[2-(cyclopentylthio)ethyl]piperidin-3-yl}propan-1-oic acid (3R,4R)-3-{4-[3-(R,S)-Fluoro-3-(6-methoxyquinolin-4-yl)propyl]-1-[3-(cyclopentylthio)propyl]piperidin-3-yl}propan-1-oic acid (3R,4R)-3-{4-[3-(R,S)-Fluoro-3-(6-methoxyquinolin-4-yl)propyl]-1-[2-(cyclohexylthio)ethyl]piperidin-3-yl}propan-1-oic acid (3R,4R)-3-{4-[3-(R,S)-Fluoro-3-(6-methoxyquinolin-4-yl)propyl]-1-[3-(cyclohexylthio)propyl]piperidin-3-yl}propan-1-oic acid (3R,4R)-3-{4-[3-(R,S)-Fluoro-3-(6-methoxyquinolin-4-yl)propyl]-1-[2-methylthioethyl]piperidin-3-yl}propan-1-oic acid (3R,4R)-3-{4-[3-(R,S)-Fluoro-3-(6-methoxyquinolin-4-yl)propyl]-1-[3-methylthiopropyl]piperidin-3-yl}propan-1-oic acid (3R,4R)-3-{4-[3-(R,S)-Fluoro-3-(6-methoxyquinolin-4-yl)propyl]-1-[2-ethylthioethyl]piperidin-3-yl}propan-1-oic acid (3R,4R)-3-{4-[3-(R,S)-Fluoro-3-(6-methoxyquinolin-4-yl)propyl]-1-[3-ethylthiopropyl]piperidin-3-yl}propan-1-oic acid (3R,4R)-3-{4-[3-(R,S)-Fluoro-3-(6-methoxyquinolin-4-yl)propyl]-1-[2-(n-propylthio)ethyl]piperidin-3-yl}propan-1-oic acid (3R,4R)-3-{4-[3-(R,S)-Fluoro-3-(6-methoxyquinolin-4-yl)propyl]-1-[3-(n-propylthio)propyl]piperidin-3-yl}propan-1-oic acid (3R,4R)-3-{4-[3-(R,S)-Fluoro-3-(6-methoxyquinolin-4-yl)propyl]-1-[2-(n-butylthio)ethyl]piperidin-3-yl}propan-1-oic acid (3R,4R)-3-{4-[3-(R,S)-Fluoro-3-(6-methoxyquinolin-4-yl)propyl]-1-[3-(n-butylthio)propyl]piperidin-3-yl}propan-1-oic acid (3R,4R)-3-{4-[3-(R,S)-Fluoro-3-(6-methoxyquinolin-4-yl)propyl]-1-[3-(thien-2-yl)propyl]piperidin-3-yl}propan-1-oic acid (3R,4R)-3-{4-[3-(R,S)-Fluoro-3-(6-methoxyquinolin-4-yl)propyl]-1-[4-(thien-2-yl)butyl]piperidin-3-yl}propan-1-oic acid (3R,4R)-3-{4-[3-(R,S)-Fluoro-3-(6-methoxyquinolin-4-yl)propyl]-1-[2-(thien-2-yl)thioethyl]piperidin-3-yl}propan-1-oic acid (3R,4R)-3-{4-[3-(R,S)-Fluoro-3-(6-methoxyquinolin-4-yl)propyl]-1-[3-(thien-2-yl)thiopropyl]piperidin-3-yl}propan-1-oic acid (3R,4R)-3-{4-[3-(R,S)-Fluoro-3-(6-methoxyquinolin-4-yl)propyl]-1-[3-(5-chlorothien-2-yl)propyl]piperidin-3-yl}propan-1-oic acid (3R,4R)-3-{4-[3-(R,S)-Fluoro-3-(6-methoxyquinolin-4-yl)propyl]-1-[4-(5-chlorothien-2-yl)butyl]piperidin-3-yl}propan-1-oic acid (3R,4R)-3-{4-[3-(R,S)-Fluoro-3-(6-methoxyquinolin-4-yl)propyl]-1-[2-(5-chlorothien-2-yl)thioethyl]piperidin-3-yl}propan-1-oic acid (3R,4R)-3-{4-[3-(R,S)-Fluoro-3-(6-methoxyquinolin-4-yl)propyl]-1-[3-(5-chlorothien-2-yl)thiopropyl]piperidin-3-yl}propan-1-oic acid (3R,4R)-3-{4-[3-(R,S)-Fluoro-3-(6-methoxyquinolin-4-yl)propyl]-1-[3-(3-chlorothien-2-yl)propyl]piperidin-3-yl}propan-1-oic acid (3R,4R)-3-{4-[3-(R,S)-Fluoro-3-(6-methoxyquinolin-4-yl)propyl]-1-[4-(3-chlorothien-2-yl)butyl]piperidin-3-yl}propan-1-oic acid (3R,4R)-3-{4-[3-(R,S)-Fluoro-3-(6-methoxyquinolin-4-yl)propyl]-1-[2-(3-chlorothien-2-yl)thioethyl]piperidin-3-yl}propan-1-oic acid (3R,4R)-3-{4-[3-(R,S)-Fluoro-3-(6-methoxyquinolin-4-yl)propyl]-1-[3-(3-chlorothien-2-yl)thiopropyl]piperidin-3-yl}propan-1-oic acid (3R,4R)-3-{4-[3-(R,S)-Fluoro-3-(6-methoxyquinolin-4-yl)propyl]-1-[3-(5-chlorothien-2-yl)propyl]piperidin-3-yl}propan-1-oic acid (3R,4R)-3-{4-[3-(R,S)-Fluoro-3-(6-methoxyquinolin-4-yl)propyl]-1-[4-(5-chlorothien-2-yl)butyl]piperidin-3-yl}propan-1-oic acid (3R,4R)-3-{4-[3-(R,S)-Fluoro-3-(6-methoxyquinolin-4-yl)propyl]-1-[2-(5-chlorothien-2-yl)thioethyl]piperidin-3-yl}propan-1-oic acid (3R,4R)-3-{4-[3-(R,S)-Fluoro-3-(6-methoxyquinolin-4-yl)propyl]-1-[3-(5-methylthien-2-yl)thiopropyl]piperidin-3-yl}propan-1-oic acid (3R,4R)-3-{4-[3-(R,S)-Fluoro-3-(6-methoxyquinolin-4-yl)propyl]-1-[3-(3-methylthien-2-yl)propyl]piperidin-3-yl}propan-1-oic acid (3R,4R)-3-{4-[3-(R,S)-Fluoro-3-(6-methoxyquinolin-4-yl)propyl]-1-[4-(3-methylthien-2-yl)butyl]piperidin-3-yl}propan-1-oic acid (3R,4R)-3-{4-[3-(R,S)-Fluoro-3-(6-methoxyquinolin-4-yl)propyl]-1-[2-(3-methylthien-2-yl)thioethyl]piperidin-3-yl}propan-1-oic acid (3R,4R)-3-{4-[3-(R,S)-Fluoro-3-(6-methoxyquinolin-4-yl)propyl]-1-[3-(3-methylthien-2-yl)thiopropyl]piperidin-3-yl}propan-1-oic acid (3R,4R)-3-{4-[3-(R,S)-Fluoro-3-(6-methoxyquinolin-4-yl)propyl]-1-[3-(thien-3-yl)propyl]piperidin-3-yl}propan-1-oic acid (3R,4R)-3-{4-[3-(R,S)-Fluoro-3-(6-methoxyquinolin-4-yl)propyl]-1-[4-(thien-3-yl)butyl]piperidin-3-yl}propan-1-oic acid (3R,4R)-3-{4-[3-(R,S)-Fluoro-3-(6-methoxyquinolin-4-yl)propyl]-1-[2-(thien-3-yl)thioethyl]piperidin-3-yl}propan-1-oic acid (3R,4R)-3-{4-[3-(R,S)-Fluoro-3-(6-methoxyquinolin-4-yl)propyl]-1-[3-(thien-3-yl)thiopropyl]piperidin-3-yl}propan-1-oic acid (3R,4R)-3-{4-[3-(R,S)-Fluoro-3-(6-methoxyquinolin-4-yl)propyl]-1-[3-(fur-2-yl)propyl]piperidin-3-yl}propan-1-oic acid (3R,4R)-3-{4-[3-(R,S)-Fluoro-3-(6-methoxyquinolin-4-yl)propyl]-1-[4-(fur-2-yl)butyl]piperidin-3-yl}propan-1-oic acid (3R,4R)-3-{4-[3-(R,S)-Fluoro-3-(6-methoxyquinolin-4-yl)
propyl]-1-[2-(fur-2-yl)thioethyl]piperidin-3-yl}propan-1-
oic acid
(3R,4R)-3-{4-[3-(R,S)-Fluoro-3-(6-methoxyquinolin-4-yl)
propyl]-1-[3-(fur-2-yl)thiopropyl]piperidin-3-yl}propan-
1-oic acid
(3R,4R)-3-{4-[3-(R,S)-Fluoro-3-(6-methoxyquinolin-4-yl)
propyl]-1-[3-(fur-3-yl)propyl]piperidin-3-yl}propan-1-
oic acid
(3R,4R)-3-{4-[3-(R,S)-Fluoro-3-(6-methoxyquinolin-4-yl)
propyl]-1-[4-(fur-3-yl)butyl]piperidin-3-yl}propan-1-oic
acid
(3R,4R)-3-{4-[3-(R,S)-Fluoro-3-(6-methoxyquinolin-4-yl)
propyl]-1-[2-(fur-3-yl)thioethyl]piperidin-3-yl}propan-1-
oic acid
(3R,4R)-3-{4-[3-(R,S)-Fluoro-3-(6-methoxyquinolin-4-yl)
propyl]-1-[3-(fur-3-yl)thiopropyl]piperidin-3-yl}propan-
1-oic acid
(3R,4R)-3-{4-[3-(R,S)-Fluoro-3-(6-methoxyquinolin-4-yl)
propyl]-1-[3-(1-methylpyrrol-2-yl)propyl]piperidin-3-
yl}propan-1-oic acid
(3R,4R)-3-{4-[3-(R,S)-Fluoro-3-(6-methoxyquinolin-4-yl)
propyl]-1-[4-(1-methylpyrrol-2-yl)butyl]piperidin-3-
yl}propan-1-oic acid
(3R,4R)-3-{4-[3-(R,S)-Fluoro-3-(6-methoxyquinolin-4-yl)
propyl]-1-[2-(1-methylpyrrol-2-yl)thioethyl]piperidin-3-
yl}propan-1-oic acid
(3R,4R)-3-{4-[3-(R,S)-Fluoro-3-(6-methoxyquinolin-4-yl)
propyl]-1-[3-(1-methylpyrrol-2-yl)thiopropyl]piperidin-
3-yl}propan-1-oic acid
(3R,4R)-3-{4-[3-(R,S)-Fluoro-3-(6-methoxyquinolin-4-yl)
propyl]-1-[3(1-methylpyrrol-2-yl)propyl]piperidin-3-
yl}propan-1-oic acid
(3R,4R)-3-{4-[3-(R,S)-Fluoro-3-(6-methoxyquinolin-4-yl)
propyl]-1-[4-(1-methylpyrrol-3-yl)butyl]piperidin-3-
yl}propan-1-oic acid
(3R,4R)-3-{4-[3-(R,S)-Fluoro-3-(6-methoxyquinolin-4-yl)
propyl]-1-[2-(1-methylpyrrol-3-yl)thioethyl]piperidin-3-
yl}propan-1-oic acid
(3R,4R)-3-{4-[3-(R,S)-Fluoro-3-(6-methoxyquinolin-4-yl)
propyl]-1-[3-(1-methylpyrrol-3-yl)thiopropyl]piperidin-
3-yl}propan-1-oic acid
(3R,4R)-3-{4-[3-(R,S)-Fluoro-3-(6-methoxyquinolin-4-yl)
propyl]-1-[3-(thiazol-2-yl)propyl]piperidin-3-yl}propan-
1-oic acid
(3R,4R)-3-{4-[3-(R,S)-Fluoro-3-(6-methoxyquinolin-4-yl)
propyl]-1-[4-(thiazol-2-yl)butyl]piperidin-3-yl}propan-1-
oic acid
(3R,4R)-3-{4-[3-(R,S)-Fluoro-3-(6-methoxyquinolin-4-yl)
propyl]-1-[2-(thiazol-2-yl)thioethyl]piperidin-3-
yl}propan-1-oic acid
(3R,4R)-3-{4-[3-(R,S)-Fluoro-3-(6-methoxyquinolin-4-yl)
propyl]-1-[3-(thiazol-2-yl)thiopropyl]piperidin-3-
yl}propan-1-oic acid
(3R,4R)-3-{4-[3-(R,S)-Fluoro-3-(6-methoxyquinolin-4-yl)
propyl]-1-[3-(1-methylimidazol-2-yl)propyl]piperidin-3-
yl}propan-1-oic acid
(3R,4R)-3-{4-[3-(R,S)-Fluoro-3-(6-methoxyquinolin-4-yl)
propyl]-1-[4-(1-methylimidazol-2-yl)butyl]piperidin-3-
yl}propan-1-oic acid
(3R,4R)-3-{4-[3-(R,S)-Fluoro-3-(6-methoxyquinolin-4-yl)
propyl]-1-[2-(1-methylimidazol-2-yl)thioethyl]piperidin-
3-yl}propan-1-oic acid
(3R,4R)-3-{4-[3-(R,S)-Fluoro-3-(6-methoxyquinolin-4-yl)
propyl]-1-[3-(1-methylimidazol-2-yl)thiopropyl]
piperidin-3-yl}propan-1-oic acid
(3R,4R)-3-{4-[3-(R,S)-Fluoro-3-(6-methoxyquinolin-4-yl)
propyl]-1-(3-(3-methylimidazol-4-yl)propyl]piperidin-3-
yl}propan-1-oic acid
(3R,4R)-3-{4-[3-(R,S)-Fluoro-3-(6-methoxyquinolin-4-yl)
propyl]-1-[4-(3-methylimidazol-4-yl)butyl]piperidin-3-
yl}propan-1-oic acid
(3R,4R)-3-{4-[3-(R,S)-Fluoro-3-(6-methoxyquinolin-4-yl)
propyl]-1-[2-(3-methylimidazol-4-yl)thioethyl]piperidin-
3-yl}propan-1-oic acid
(3R,4R)-3-{4-[3-(R,S)-Fluoro-3-(6-methoxyquinolin-4-yl)
propyl]-1-[3-(3-methylimidazol-4-yl)thiopropyl]
piperidin-3-yl}propan-1-oic acid
(3R,4R)-3-{4-[3-(R,S)-Fluoro-3-(6-methoxyquinolin-4-yl)
propyl]-1-[3-(3methylpyrazol-4-yl)propyl]piperidin-3-
yl}propan-1-oic acid
(3R,4R)-3-{4-[3-(R,S)-Fluoro-3-(6-methoxyquinolin-4-yl)
propyl]-1-[4-(3methylpyrazol-4-yl)butyl]piperidin-3-
yl}propan-1-oic acid
(3R,4R)-3-{4-[3-(R,S)-Fluoro-3-(6-methoxyquinolin-4-yl)
propyl]-1-[2-(3methylpyrazol-4-yl)thioethyl]piperidin-3-
yl}propan-1-oic acid
(3R,4R)-3-{4-[3-(R,S)-Fluoro-3-(6-methoxyquinolin-4-yl)
propyl]-1-[3-(3methylpyrazol-4-yl)thiopropyl]piperidin-
3-yl}propan-1-oic acid
(3R,4R)-3-{4-[3-(R,S)-Fluoro-3-(6-methoxyquinolin-4-yl)
propyl]-1-[3-(oxazol-2-yl)propyl]piperidin-3-yl}propan-
1-oic acid
(3R,4R)-3-{4-[3-(R,S)-Fluoro-3-(6-methoxyquinolin-4-yl)
propyl]-1-[4-(oxazol-2-yl)butyl]piperidin-3-yl}propan-1-
oic acid
(3R,4R)-3-{4-[3-(R,S)-Fluoro-3-(6-methoxyquinolin-4-yl)
propyl]-1-[2-(oxazol-2-yl)thioethyl]piperidin-3-
yl}propan-1-oic acid
(3R,4R)-3-{4-[3-(R,S)-Fluoro-3-(6-methoxyquinolin-4-yl)
propyl]-1-[3-(oxazol-2-yl)thiopropyl]piperidin-3-
yl}propan-1-oic acid
(3R,4R)-3-{4-[3-(R,S)-Fluoro-3-(6-methoxyquinolin-4-yl)
propyl]-1-[3-(pyridin-2-yl)propyl]piperidin-3-yl}propan-
1-oic acid
(3R,4R)-3-{4-[3-(R,S)-Fluoro-3-(6-methoxyquinolin-4-yl)
propyl]-1-[4-(pyridin-2-yl)butyl]piperidin-3-yl}propan-
1-oic acid
(3R,4R)-3-{4-[3-(R,S)-Fluoro-3-(6-methoxyquinolin-4-yl)
propyl]-1-[2-(pyridin-2-yl)thioethyl]piperidin-3-
yl}propan-1-oic acid
(3R,4R)-3-{4-[3-(R,S)-Fluoro-3-(6-methoxyquinolin-4-yl)
propyl]-1-[3-(pyridin-2-yl)thiopropyl]piperidin-3-
yl}propan-1-oic acid
(3R,4R)-3-{4-[3-(R,S)-Fluoro-3-(6-methoxyquinolin-4-yl)
propyl]-1-[3-(pyridin-3-yl)propyl]piperidin-3-yl}propan-
1-oic acid
(3R,4R)-3-{4-[3-(R,S)-Fluoro-3-(6-methoxyquinolin-4-yl)
propyl]-1-[4-(pyridin-3-yl)butyl]piperidin-3-yl}propan-
1-oic acid
(3R,4R)-3-{4-[3-(R,S)-Fluoro-3-(6-methoxyquinolin-4-yl)
propyl]-1-(2-(pyridin-3-yl)thioethyl]piperidin-3-
yl}propan-1-oic acid
(3R,4R)-3-{4-[3-(R,S)-Fluoro-3-(6-methoxyquinolin-4-yl)
propyl]-1-[3-(pyridin-3-yl)thiopropyl]piperidin-3-
yl}propan-1-oic acid
(3R,4R)-3-{4-[3-(R,S)-Fluoro-3-(6-methoxyquinolin-4-yl)
propyl]-1-[3-(pyridin-4-yl)propyl]piperidin-3-yl}propan-
1-oic acid
(3R,4R)-3-{4-[3-(R,S)-Fluoro-3-(6-methoxyquinolin-4-yl)
propyl]-1-[4-(pyridin-4-yl)butyl]piperidin-3-yl}propan-
1-oic acid
(3R,4R)-3-{4-[3-(R,S)-Fluoro-3-(6-methoxyquinolin-4-yl)
propyl]-1-[5-(pyridin-4-yl)pentyl]piperidin-3-yl}propan-
1-oic acid
(3R,4R)-3-{4-[3-(R,S)-Fluoro-3-(6-methoxyquinolin-4-yl)
propyl]-1-[2-(pyridin-4-yl)thioethyl]piperidin-3-
yl}propan-1-oic acid (3R,4R)-3-{4-[3-(R,S)-Fluoro-3-(6-methoxyquinolin-4-yl)propyl]-1-[3-(pyridin-4-yl)thiopropyl]piperidin-3-yl}propan-1-oic acid (3R,4R)-3-{4-[3-(R,S)-Fluoro-3-(6-methoxyquinolin-4-yl)propyl]-1-[3-(pyrimidin-2-yl)propyl]piperidin-3-yl}propan-1-oic acid (3R,4R)-3-{4-[3-(R,S)-Fluoro-3-(6-methoxyquinolin-4-yl)propyl]-1-[4-(pyrimidin-2-yl)butyl]piperidin-3-yl}propan-1-oic acid (3R,4R)-3-{4-[3-(R,S)-Fluoro-3-(6-methoxyquinolin-4-yl)propyl]-1-[2-(pyrimidin-2-yl)thioethyl]piperidin-3-yl}propan-1-oic acid (3R,4R)-3-{4-[3-(R,S)-Fluoro-3-(6-methoxyquinolin-4-yl)propyl]-1-[3-(pyrimidin-2-yl)thiopropyl]piperidin-3-yl}propan-1-oic acid (3R,4R)-3-{4-[3-(R,S)-Fluoro-3-(6-methoxyquinolin-4-yl)propyl]-1-[3-(pyrimidin-4-yl)propyl]piperidin-3-yl}propan-1-oic acid (3R,4R)-3-{4-[3-(R,S)-Fluoro-3-(6-methoxyquinolin-4-yl)propyl]-1-[4-(pyrimidin-4-yl)butyl]piperidin-3-yl}propan-1-oic acid (3R,4R)-3-{4-[3-(R,S)-Fluoro-3-(6-methoxyquinolin-4-yl)propyl]-1-[2-(pyrimidin-4-yl)thioethyl]piperidin-3-yl}propan-1-oic acid (3R,4R)-3-{4-[3-(R,S)-Fluoro-3-(6-methoxyquinolin-4-yl)propyl]-1-[3-(pyrimidin-4-yl)thiopropyl]piperidin-3-yl}propan-1-oic acid (3R,4R)-3-{4-[3-(R,S)-Fluoro-3-(6-methoxyquinolin-4-yl)propyl]-1-[3-(pyrimidin-5-yl)propyl]piperidin-3-yl}propan-1-oic acid (3R,4R)-3-{4-[3-(R,S)-Fluoro-3-(6-methoxyquinolin-4-yl)propyl] 1-[4-(pyrimidin-5-yl)butyl]piperidin-3-yl}propan-1-oic acid (3R,4R)-3-{4-[3-(R,S)-Fluoro-3-(6-methoxyquinolin-4-yl)propyl]-1-[2-(pyrimidin-5-yl)thioethyl]piperidin-3-yl}propan-1-oic acid (3R,4R)-3-{4-[3-(R,S)-Fluoro-3-(6-methoxyquinolin-4-yl)propyl]-1-[3-(pyrimidin-5-yl)thiopropyl]piperidin-3-yl}propan-1-oic acid (3R,4R)-3-{4-[3-(R,S)-Fluoro-3-(6-methoxyquinolin-4-yl)propyl]-1-[3-(pyrazin-2-yl)propyl]piperidin-3-yl}propan-1-oic acid (3R,4R)-3-{4-[3-(R,S)-Fluoro-3-(6-methoxyquinolin-4-yl)propyl]-1-[4-(pyrazin-2-yl)butyl]piperidin-3-yl}propan-1-oic acid (3R,4R)-3-{4-[3-(R,S)-Fluoro-3-(6-methoxyquinolin-4-yl)propyl]-1-[2-(pyrazin-2-yl)thioethyl]piperidin-3-yl}propan-1-oic acid (3R,4R)-3-{4-[3-(R,S)-Fluoro-3-(6-methoxyquinolin-4-yl)propyl]-1-[3-(pyrazin-2-yl)thiopropyl]piperidin-3-yl}propan-1-oic acid (3R,4R)-3-{4-[3-(R,S)-Fluoro-3-(6-methoxyquinolin-4-yl)propyl]-1-[3-(pyridazin-3-yl)propyl]piperidin-3-yl}propan-1-oic acid (3R,4R)-3-{4-[3-(R,S)-Fluoro-3-(6-methoxyquinolin-4-yl)propyl]-1-[4-(pyridazin-3-yl)butyl]piperidin-3-yl}propan-1-oic acid (3R,4R)-3-{4-[3-(R,S)-Fluoro-3-(6-methoxyquinolin-4-yl)propyl]-1-[2-(pyridazin-3-yl)thioethyl]piperidin-3-yl}propan-1-oic acid (3R,4R)-3-{4-[3-(R,S)-Fluoro-3-(6-methoxyquinolin-4-yl)propyl]-1-[3-(pyridazin-3-yl)thiopropyl]piperidin-3-yl}propan-1-oic acid (3R,4R)-3-{4-[3-(R,S)-Fluoro-3-(6-methoxyquinolin-4-yl)propyl]-1-[3-(pyridazin-4-yl)propyl]piperidin-3-yl}propan-1-oic acid (3R,4R)-3-{4-[3-(R,S)-Fluoro-3-(6-methoxyquinolin-4-yl)propyl]-1-[4-(pyridazin-4-yl)butyl]piperidin-3-yl}propan-1-oic acid (3R,4R)-3-{4-[3-(R,S)-Fluoro-3-(6-methoxyquinolin-4-yl)propyl]-1-[2-(pyridazin-4-yl)thioethyl]piperidin-3-yl}propan-1-oic acid (3R,4R)-3-{4-[3-(R,S)-Fluoro-3-(6-methoxyquinolin-4-yl)propyl]-1-[3-(pyridazin-4-yl)thiopropyl]piperidin-3-yl}propan-1-oic acid (3R,4R)-3-{4-[3-(R,S)-Fluoro-3-(6-methoxyquinolin-4-yl)propyl]-1-[3-phenylprop-2-ynyl]piperidin-3-yl}propan-1-oic acid (3R,4R)-3-{4-[3-(R,S)-Fluoro-3-(6-methoxyquinolin-4-yl)propyl]-1-[3-(2-fluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-fluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(4-fluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2-chlorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-chlorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(4-chlorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2-methylphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-methylphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(4-methylphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2-(trifluoromethyl)phenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-(trifluoromethyl)phenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(4-(trifluoromethyl)phenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2-methoxyphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-methoxyphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(4-methoxyphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3,4-difluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2,4-difluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3,4-dichlorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2,3-dichlorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2,4-dichlorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2,4,6-trichlorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3,5-dichlorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(4-chloro-3-fluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-chloro-4-fluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2-chloro-4-fluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-chloro-5-fluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(4-chloro-4-fluorophenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-fluoro-4-methylphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(4-chloro-3-(trifluoromethyl)phenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2-chloro-4-(trifluoromethyl)phenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2-chloro-5-(trifluoromethyl)phenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(5-chloro-2-methoxyphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3,5-bis(trifluoromethyl)phenyl)prop-2-ynyl]piperidin-3-yl}propan-1-oic acid (3R,4R)-3-{4-[3-(R,S)-Fluoro-3-(6-methoxyquinolin-4-yl)propyl]1-[3-(3,5-dimethylphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(2,4-dichloro-6-methylphenyl)prop-2-ynyl]piperidin-3-yl}propan-1-oic acid (3R,4R)-3-{4-[3-(R,S)-Fluoro-3-(6-methoxyquinolin-4-yl)propyl]-1-[3-(thien-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(5-chlorothien-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3chlorothien-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(5-methylthien-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-methylthien-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(thien-3-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(1-methylpyrrol-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(1-methylpyrrol-3-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(thiazol-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(thiazol-4-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(thiazol-5-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(1-methylimidazol-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-methylimidazol-4-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(3-methylpyrazol-4-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(oxazol-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(oxazol-4-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(oxazol-5-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyridin-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyridin-3-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyridin-4-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyrimidin-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyrimidin-4-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyrimidin-5-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyrazin-2-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyridazin-3-yl)prop-2-ynyl]piperidin-3-yl}propan-1-oic acid (3R,4R)-3-{4-[3-(R,S)-Fluoro-3-(6-methoxyquinolin-4-yl)propyl]-1-[3-(pyridazin-4-yl)prop-2-ynyl]piperidin-3-yl}propan-1-oic acid (3R,4R)-3-{4-[3-(6-Methoxyquinolin-4-yl)propyl]-1-[3-phenylpropen-2-yl]piperidin-3-yl}propan-1-oic acid (3R,4R)-3-{4-[3-(6-Methoxyquinolin-4-yl)propyl]-1-[4-phenylbuten-3-yl]piperidin-3-yl}propan-1-oic acid (3R,4R)-3-{4-[3-(R,S)-Hydroxy-3-(6-methoxyquinolin-4-yl)propyl]-1-[3-phenylpropen-2-yl]piperidin-3-yl}propan-1-oic acid (3R,4R)-3-{4-[3-(R,S)-Hydroxy-3-(6-methoxyquinolin-4-yl)propyl]-1-[4-phenylbuten-3-yl]piperidin-3-yl}propan-1-oic acid (3R,4R)-3-{4-[3-(R,S)-fluoro-3-(6-methoxyquinolin-4-yl)propyl]-1-[3-phenylpropen-2-yl]piperidin-3-yl}propan-1-oic acid (3R,4R)-3-{4-[3-(R,S)-fluoro-3-(6-methoxyquinolin-4-yl)propyl]-1-[4-phenylbuten-3-yl]piperidin-3-yl}propan-1-oic acid (3R,4R)-3-Hydroxymethyl-4-[3-(6-methoxyquinolin-4-yl)propyl]-1-[2-phenylthioethyl]piperidine (3R,4R)-3-Hydroxymethyl-4-[3-(6-methoxyquinolin-4-yl)propyl]-1-[3-phenylthiopropyl]piperidine (3R,4R)-3-Hydroxymethyl-4-[3-(6-methoxyquinolin-4-yl)propyl]-1-[2-(2-fluorophenylthio)ethyl]piperidine (3R,4R)-3-Hydroxymethyl-4-[3-(6-methoxyquinolin-4-yl)propyl]-1-[3-(2-fluorophenylthio)propyl]piperidine (3R,4R)-3-Hydroxymethyl-4-[3-(6-methoxyquinolin-4-yl)propyl]-1-[2-(3-fluorophenylthio)ethyl]piperidine (3R,4R)-3-Hydroxymethyl-4-[3-(6-methoxyquinolin-4-yl)propyl]-1-[3-(3-fluorophenylthio)propyl]piperidine (3R,4R)-3-Hydroxymethyl-4-[3-(6-methoxyquinolin-4-yl)propyl]-1-[2-(4-fluorophenylthio)ethyl]piperidine (3R,4R)-3-Hydroxymethyl-4-[3-(6-methoxyquinolin-4-yl)propyl]-1-[3-(4-fluorophenylthio)propyl]piperidine (3R,4R)-3-Hydroxymethyl-4-[3-(6-methoxyquinolin-4-yl)propyl]-1-[2-(2-chlorophenylthio)ethyl]piperidine (3R,4R)-3-Hydroxymethyl-4-[3-(6-methoxyquinolin-4-yl)propyl]-1-[3-(2-chlorophenylthio)propyl]piperidine (3R,4R)-3-Hydroxymethyl-4-[3-(6-methoxyquinolin-4-yl)propyl]-1-[2-(3-chlorophenylthio)ethyl]piperidine (3R,4R)-3-Hydroxymethyl-4-[3-(6-methoxyquinolin-4-yl)propyl]-1-[3-(3-chlorophenylthio)propyl]piperidine (3R,4R)-3-Hydroxymethyl-4-[3-(6-methoxyquinolin-4-yl)propyl]-1-[2-(4-chlorophenylthio)ethyl]piperidine (3R,4R)-3-Hydroxymethyl-4-[3-(6-methoxyquinolin-4-yl)propyl]-1-[3-(4-chlorophenylthio)propyl]piperidine (3R,4R)-3-Hydroxymethyl-4-[3-(6-methoxyquinolin-4-yl)propyl]-1-[2-(2-methylphenylthio)ethyl]piperidine (3R,4R)-3-Hydroxymethyl-4-[3-(6-methoxyquinolin-4-yl)propyl]-1-[3-(2-methylphenylthio)propyl]piperidine (3R,4R)-3-Hydroxymethyl-4-[3-(6-methoxyquinolin-4-yl)propyl]-1-[2-(3-methylphenylthio)ethyl]piperidine (3R,4R)-3-Hydroxymethyl-4-[3-(6-methoxyquinolin-4-yl)propyl]-1-[3-(3-methylphenylthio)propyl]piperidine (3R,4R)-3-Hydroxymethyl-4-[3-(6-methoxyquinolin-4-yl)propyl]-1-[2-(4-methylphenylthio)ethyl]piperidine (3R,4R)-3-Hydroxymethyl-4-[3-(6-methoxyquinolin-4-yl)propyl]-1-[3-(4-methylphenylthio)propyl]piperidine (3R,4R)-3-Hydroxymethyl-4-[3-(6-methoxyquinolin-4-yl)propyl]-1-[2-(2-trifluoromethylphenylthio)ethyl]piperidine (3R,4R)-3-Hydroxymethyl-4-[3-(6-methoxyquinolin-4-yl)propyl]-1-[3-(2-trifluoromethylphenylthio)propyl]piperidine (3R,4R)-3-Hydroxymethyl-4-[3-(6-methoxyquinolin-4-yl)propyl]-1-[2-(3-trifluoromethylphenylthio)ethyl]piperidine (3R,4R)-3-Hydroxymethyl-4-[3-(6-methoxyquinolin-4-yl)propyl]-1-[3-(3-trifluoromethylphenylthio)propyl]piperidine (3R,4R)-3-Hydroxymethyl-4-[3-(6-methoxyquinolin-4-yl)propyl]-1-[2-(4-trifluoromethylphenylthio)ethyl]piperidine (3R,4R)-3-Hydroxymethyl-4-[3-(6-methoxyquinolin-4-yl)propyl]-1-[3-(4-trifluoromethylphenylthio)propyl]piperidine (3R,4R)-3-Hydroxymethyl-4-[3-(6-methoxyquinolin-4-yl)propyl]-1-[2-(2-methoxyphenylthio)ethyl]piperidine (3R,4R)-3-Hydroxymethyl-4-[3-(6-methoxyquinolin-4-yl)propyl]-1-[3-(2-methoxyphenylthio)propyl]piperidine (3R,4R)-3-Hydroxymethyl-4-[3-(6-methoxyquinolin-4-yl)propyl]-1-[2-(3-methoxyphenylthio)ethyl]piperidine (3R,4R)-3-Hydroxymethyl-4-[3-(6-methoxyquinolin-4-yl)propyl]-1-[3-(3-methoxyphenylthio)propyl]piperidine (3R,4R)-3-Hydroxymethyl-4-[3-(6-methoxyquinolin-4-yl)propyl]-1-[2-(4-methoxyphenylthio)ethyl]piperidine (3R,4R)-3-Hydroxymethyl-4-[3-(6-methoxyquinolin-4-yl)propyl]-1-[3-(4-methoxyphenylthio)propyl]piperidine (3R,4R)-3-Hydroxymethyl-4-[3-(6-methoxyquinolin-4-yl)propyl]-1-[2-(thien-3-yl)thioethyl]piperidine (3R,4R)-3-Hydroxymethyl-4-[3-(6-methoxyquinolin-4-yl)propyl]-1-[3-(thien-3-yl)thiopropyl]piperidine (3R,4R)-3-Hydroxymethyl-4-[3-(6-methoxyquinolin-4-yl)propyl]-1-[2-(fur-2-yl)thioethyl]piperidine (3R,4R)-3-Hydroxymethyl-4-[3-(6-methoxyquinolin-4-yl)propyl]-1-[3-(fur-2-yl)thiopropyl]piperidine (3R,4R)-3-Hydroxymethyl-4-[3-(6-methoxyquinolin-4-yl)propyl]-1-[2-(fur-3-yl)thioethyl]piperidine (3R,4R)-3-Hydroxymethyl-4-[3-(6-methoxyquinolin-4-yl)propyl]-1-[3-(fur-3-yl)thiopropyl]piperidine (3R,4R)-3-Hydroxymethyl-4-[3-(6-methoxyquinolin-4-yl)propyl]-1-[2-(thiazol-2-yl)thioethyl]piperidine (3R,4R)-3-Hydroxymethyl-4-[3-(6-methoxyquinolin-4-yl)propyl]-1-[3-(thiazol-2-yl)thiopropyl]piperidine (3R,4R)-3-Hydroxymethyl-4-[3-(6-methoxyquinolin-4-yl)propyl]-1-[2-(oxazol-2-yl)thioethyl]piperidine (3R,4R)-3-Hydroxymethyl-4-[3-(6-methoxyquinolin-4-yl)propyl]-1-[3-(oxazol-2-yl)thiopropyl]piperidine (3R,4R)-3-Hydroxymethyl-4-[3-(6-methoxyquinolin-4-yl)propyl]-1-[2-(pyridin-2-yl)thioethyl]piperidine (3R,4R)-3-Hydroxymethyl-4-[3-(6-methoxyquinolin-4-yl)propyl]-1-[3-(pyridin-2-yl)thiopropyl]piperidine (3R,4R)-3-Hydroxymethyl-4-[3-(6-methoxyquinolin-4-yl)propyl]-1-[2-(pyridin-3-yl)thioethyl]piperidine (3R,4R)-3-Hydroxymethyl-4-[3-(6-methoxyquinolin-4-yl)propyl]-1-[3-(pyridin-3-yl)thiopropyl]piperidine (3R,4R)-3-Hydroxymethyl-4-[3-(6-methoxyquinolin-4-yl)propyl]-1-[2-(pyridin-4-yl)thioethyl]piperidine (3R,4R)-3-Hydroxymethyl-4-[3-(6-methoxyquinolin-4-yl)propyl]-1-[3-(pyridin-4-yl)thiopropyl]piperidine (3R,4R)-3-Hydroxymethyl-4-[3-(6-methoxyquinolin-4-yl)propyl]-1-[2-(pyrimidin-2-yl)thioethyl]piperidine (3R,4R)-3-Hydroxymethyl-4-[3-(6-methoxyquinolin-4-yl)propyl]-1-[3-(pyrimidin-2-yl)thiopropyl]piperidine (3R,4R)-3-Hydroxymethyl-4-[3-(6-methoxyquinolin-4-yl)propyl]-1-[2-(pyrazin-2-yl)thioethyl]piperidine (3R,4R)-3-Hydroxymethyl-4-[3-(6-methoxyquinolin-4-yl)propyl]-1-[3-(pyrazin-2-yl)thiopropyl]piperidine (3R,4R)-3-Hydroxymethyl-4-[3-(6-methoxyquinolin-4-yl)propyl]-1-[2-(pyridazin-3-yl)thioethyl]piperidine (3R,4R)-3-Hydroxymethyl-4-[3-(6-methoxyquinolin-4-yl)propyl]-1-[3-(pyridazin-3-yl)thiopropyl]piperidine (3R,4R)-3-Hydroxymethyl-4-[3-(6-methoxyquinolin-4-yl)propyl]-1-[2-(pyridazin-4-yl)thioethyl]piperidine (3R,4R)-3-Hydroxymethyl-4-[3-(6-methoxyquinolin-4-yl)propyl]-1-[3-(pyridazin-4-yl)thiopropyl]piperidine (3R,4R)-3-Hydroxymethyl-4-[3-(6-methoxyquinolin-4-yl)propyl]-1-[3-phenylprop-2-ynyl]piperidine (3R,4R)-3-Hydroxymethyl-4-[3-(6-methoxyquinolin-4-yl)propyl]-1-[3-(2-fluorophenyl)prop-2-ynyl]piperidine (3R,4R)-3-Hydroxymethyl-4-[3-(6-methoxyquinolin-4-yl)propyl]-1-[3-(3-fluorophenyl)prop-2-ynyl]piperidine (3R,4R)-3-Hydroxymethyl-4-[3-(6-methoxyquinolin-4-yl)propyl]-1-[3-(4-fluorophenyl)prop-2-ynyl]piperidine (3R,4R)-3-Hydroxymethyl-4-[3-(6-methoxyquinolin-4-yl)propyl]-1-[3-(2-chlorophenyl)prop-2-ynyl]piperidine (3R,4R)-3-Hydroxymethyl-4-[3-(6-methoxyquinolin-4-yl)propyl]-1-[3-(3-chlorophenyl)prop-2-ynyl]piperidine (3R,4R)-3-Hydroxymethyl-4-[3-(6-methoxyquinolin-4-yl)propyl]-1-[3-(4-chlorophenyl)prop-2-ynyl]piperidine (3R,4R)-3-Hydroxymethyl-4-[3-(6-methoxyquinolin-4-yl)propyl]-1-[3-(2-methylphenyl)prop-2-ynyl]piperidine
(3R,4R)-3-Hydroxymethyl-4-[3-(6-methoxyquinolin-4-yl)propyl]-1-[3-(3-methylphenyl)prop-2-ynyl]piperidine
(3R,4R)-3-Hydroxymethyl-4-[3-(6-methoxyquinolin-4-yl)propyl]-1-[3-(4-methylphenyl)prop-2-ynyl]piperidine
(3R,4R)-3-Hydroxymethyl-4-[3-(6-methoxyquinolin-4-yl)propyl]-1-[3-(2-(trifluoromethyl)phenyl)prop-2-ynyl]piperidine
(3R,4R)-3-Hydroxymethyl-4-[3-(6-methoxyquinolin-4-yl)propyl]-1-[3-(3-(trifluoromethyl)phenyl)prop-2-ynyl]-piperidine
(3R,4R)-3-Hydroxymethyl-4-[3-(6-methoxyquinolin-4-yl)propyl]-1-[3-(4-(trifluoromethyl)phenyl)prop-2-ynyl]-piperidine
(3R,4R)-3-Hydroxymethyl-4-[3-(6-methoxyquinolin-4-yl)propyl]-1-[3-(2-methoxyphenyl)prop-2-ynyl]piperidine
(3R,4R)-3-Hydroxymethyl-4-[3-(6-methoxyquinolin-4-yl)propyl]-1-[3-(3-methoxyphenyl)prop-2-ynyl]piperidine
(3R,4R)-3-Hydroxymethyl-4-[3-(6-methoxyquinolin-4-yl)propyl]-1-[3-(4-methoxyphenyl)prop-2-ynyl]-piperidine
(3R,4R)-3-Hydroxymethyl-4-[3-(6-methoxyquinolin-4-yl)propyl]-1-[3-(thien-2-yl)prop-2-ynyl]piperidine
(3R,4R)-3-Hydroxymethyl-4-[3-(6-methoxyquinolin-4-yl)propyl]-1-[3-(thien-3-yl)prop-2-ynyl]piperidine
(3R,4R)-3-Hydroxymethyl-4-[3-(6-methoxyquinolin-4-yl)propyl]-1-[3-(thiazol-2-yl)prop-2-ynyl]piperidine
(3R,4R)-3-Hydroxymethyl-4-[3-(6-methoxyquinolin-4-yl)propyl]-1-[3-(thiazol4-yl)prop-2-ynyl]piperidine
(3R,4R)-3-Hydroxymethyl-4-[3-(6-methoxyquinolin-4-yl)propyl]-1-[3-(thiazol-5-yl)prop-2-ynyl]piperidine
(3R,4R)-3-Hydroxymethyl-4-[3-(6-methoxyquinolin-4-yl)propyl]-1-[3-(oxazol-2-yl)prop-2-ynyl]piperidine
(3R,4R)-3-Hydroxymethyl-4-[3-(6-methoxyquinolin-4-yl)propyl]-1-[3-(oxazol4-yl)prop-2-ynyl]piperidine
(3R,4R)-3-Hydroxymethyl-4-[3-(6-methoxyquinolin-4-yl)propyl]-1-[3-(oxazol-5-yl)prop-2-ynyl]piperidine
(3R,4R)-3-Hydroxymethyl-4-[3-(6-methoxyquinolin-4-yl)propyl]-1-[3-(pyridin-2-yl)prop-2-ynyl]piperidine (3R,4R)-3-Hydroxymethyl-4-[3-(6-methoxyquinolin-4-yl)propyl]-1-[3-(pyridin-3-yl)prop-2-ynyl]piperidine
(3R,4R)-3-Hydroxymethyl-4-[3-(6-methoxyquinolin-4-yl)propyl]-1-[3-(pyridin-4-yl)prop-2-ynyl]piperidine
(3R,4R)-3-Hydroxymethyl-4-[3-(6-methoxyquinolin-4-yl)propyl]-1-[3-(pyrimidin-2-yl)prop-2-2-ynyl]piperidine
(3R,4R)-3-Hydroxymethyl-4-[3-(6-methoxyquinolin-4-yl)propyl]-1-[3-(pyrazin-2-yl)prop-2-ynyl]piperidine
(3R,4R)-3-Hydroxymethyl-4-[3-(6-methoxyquinolin-4-yl)propyl]-1-[3-(pyridazin-3-yl)prop-2-2-ynyl]piperidine
(3R,4R)-3-Hydroxymethyl-4-[3-(6-methoxyquinolin-4-yl)propyl]-1-[3-(pyridazin-4-yl)prop-2-ynyl]piperidine
(3R,4R)-3-Hydroxymethyl-4-[3-(R,S)-hydroxy-3-(6-methoxyquinolin-4-yl)propyl]-1-[2-phenylthio-ethyl]piperidine
(3R,4R)-3-Hydroxymethyl4-[3-(R,S)-hydroxy-3-(6-methoxyquinolin-4-yl)propyl]-1-[3-phenylthiopropyl]piperidine
(3R,4R)-3-Hydroxymethyl4-[3-(R,S)-hydroxy-3-(6-methoxyquinolin-4-yl)propyl]-1-[2-(2-fluorophenylthio)ethyl]piperidine
(3R,4R)-3-Hydroxymethyl-4-[3-(R,S)-hydroxy-3-(6-methoxyquinolin-4-yl)propyl]-1-[3-(2-fluorophenylthio)propyl]piperidine
(3R,4R)-3-Hydroxymethyl-4-[3-(R,S)-hydroxy-3-(6-methoxyquinolin-4-yl)propyl]-1-[2-(3-fluorophenylthio)ethyl]piperidine
(3R,4R)-3-Hydroxymethyl-4-[3-(R,S)-hydroxy-3-(6-methoxyquinolin-4-yl)propyl]-1-[3-(3-fluorophenylthio)propyl]piperidine
(3R,4R)-3-Hydroxymethyl-4-[3-(R,S)-hydroxy-3-(6-methoxyquinolin-4-yl)propyl]-1-[2-(4-fluorophenylthio)ethyl]piperidine
(3R,4R)-3-Hydroxymethyl-4-[3-(R,S)-hydroxy-3-(6-methoxyquinolin-4-yl)propyl]-1-[3-(4-fluorophenylthio)propyl]piperidine
(3R,4R)-3-Hydroxymethyl-4-[3-(R,S)-hydroxy-3-(6-methoxyquinolin-4-yl)propyl]-1-[2-(2-chlorophenylthio)ethyl]piperidine
(3R,4R)-3-Hydroxymethyl-4-[3-(R,S)-hydroxy-3-(6-methoxyquinolin-4-yl)propyl]-1-[3-(2-chlorophenylthio)propyl]piperidine
(3R,4R)-3-Hydroxymethyl-4-[3-(R,S)-hydroxy-3-(6-methoxyquinolin-4-yl)propyl]-1-[2-(3-chlorophenylthio)ethyl]piperidine
(3R,4R)-3-Hydroxymethyl-4-[3-(R,S)-hydroxy-3-(6-methoxyquinolin-4-yl)propyl]-1-[3-(3-chlorophenylthio)propyl]piperidine
(3R,4R)-3-Hydroxymethyl-4-[3-(R,S)-hydroxy-3-(6-methoxyquinolin-4-yl)propyl]-1-[2-(4-chlorophenylthio)ethyl]piperidine
(3R,4R)-3-Hydroxymethyl-4-[3-(R,S)-Hydroxy-3-(6-methoxyquinolin-4-yl)propyl]-1-[3-(4-chlorophenylthio)propyl]piperidine
(3R,4R)-3-Hydroxymethyl4-[3-(R,S)-hydroxy-3-(6-methoxyquinolin-4-yl)propyl]-1-[2-(2-methylphenylthio)ethyl]piperidine
(3R,4R)-3-Hydroxymethyl-4-[3-(R,S)-hydroxy-3-(6-methoxyquinolin-4-yl)propyl]-1-[3-(2-methylphenylthio)propyl]piperidine
(3R,4R)-3-Hydroxymethyl-4-[3-(R,S)-hydroxy-3-(6-methoxyquinolin-4-yl)propyl]-1-[2-(3-methylphenylthio)ethyl]piperidine
(3R,4R)-3-Hydroxymethyl-4-[3-(R,S)-hydroxy-3-(6-methoxyquinolin-4-yl)propyl]-1-[3-(3-methylphenylthio)propyl]piperidine
(3R,4R)-3-Hydroxymethyl-4-[3-(R,S)-hydroxy-3-(6-methoxyquinolin-4-yl)propyl]-1-[2-(4-methylphenylthio)ethyl]piperidine
(3R,4R)-3-Hydroxymethyl-4-[3-(R,S)-hydroxy-3-(6-methoxyquinolin-4-yl)propyl]-1-[3-(4-methylphenylthio)propyl]piperidine
(3R,4R)-3-Hydroxymethyl-4-[3-(R,S)-hydroxy-3-(6-methoxyquinolin-4-yl)propyl]-1-[2-(2-trifluoromethylphenylthio)ethyl]piperidine
(3R,4R)-3-Hydroxymethyl-4-[3-(R,S)-hydroxy-3-(6-methoxyquinolin-4-yl)propyl]-1-[3-(2-trifluoromethylphenylthio)propyl]piperidine
(3R,4R)-3-Hydroxymethyl-4-[3-(R,S)-hydroxy-3-(6-methoxyquinolin-4-yl)propyl]-1-[2-(3-trifluoromethylphenylthio)ethyl]piperidine
(3R,4R)-3-Hydroxymethyl-4-[3-(R,S)-hydroxy-3-(6-methoxyquinolin-4-yl)propyl]-1-[3-(3-trifluoromethylphenylthio)propyl]piperidine
(3R,4R)-3-Hydroxymethyl-4-[3-(R,S)-hydroxy-3-(6-methoxyquinolin-4-yl)propyl]-1-[2-(4-trifluoromethylphenylthio)ethyl]piperidine
(3R,4R)-3-Hydroxymethyl-4-[3-(R,S)-hydroxy-3-(6-methoxyquinolin-4-yl)propyl]-1-[3-(4-trifluoromethylphenylthio)propyl]piperidine
(3R,4R)-3-Hydroxymethyl-4-[3-(R,S)-hydroxy-3-(6-methoxyquinolin-4-yl)propyl)-1-[2-(2-methoxyphenylthio)ethyl]piperidine
(3R,4R)-3-Hydroxymethyl-4-[3-(R,S)-hydroxy-3-(6-methoxyquinolin-4-yl)propyl]-1-[3-(2-methoxyphenylthio)propyl]piperidine
(3R,4R)-3-Hydroxymethyl-4-[3-(R,S)-hydroxy-3-(6-methoxyquinolin-4-yl)propyl]-1-[2-(3-methoxyphenylthio)ethyl]piperidine (3R,4R)-3-Hydroxymethyl-4-[3-(R,S)-hydroxy-3-(6-methoxyquinolin-4-yl)propyl]-1-[3-(3-methoxyphenythoethio)propyl]piperidine (3R,4R)-3-Hydroxymethyl-4-[3-(R,S)-hydroxy-3-(6-methoxyquinolin-4-yl)propyl]-1-[-2-(4-methoxyphenylthio)ethyl]piperidine (3R,4R)-3-Hydroxymethyl-4-[3-(R,S)-hydroxy-3-(6-methoxyquinolin-4-yl)propyl]-1-[3-(4-methoxyphenylthio)propyl]piperidine (3R,4R)-3-Hydroxymethyl-4-[3-(R,S)-hydroxy-3-(6-methoxyquinolin-4-yl)propyl]-1-[2-(thien-3-yl)thioethyl]piperidine (3R,4R)-3-Hydroxymethyl-4-[3-(R,S)-hydroxy-3-(6-methoxyquinolin-4-yl)propyl]-1-(thien-3-yl)thiopropyl]piperidine (3R,4R)-3-Hydroxymethyl-4-[3-(R,S)-hydroxy-3-(6-methoxyquinolin -4-yl)propyl]-1-[2-(fur-2-yl)thioethyl]piperidine (3R,4R)-3-Hydroxymethyl-4-[3-(R,S)-hydroxy-3-(6-methoxyquinolin-4-yl)propyl]-1-[3-(fur-2-yl)thiopropyl]piperidine (3R,4R)-3-Hydroxymethyl-4-[3-(R,S)-hydroxy-3-(6-methoxyquinolin-4-yl)propyl]-1-[2-(fur-3-yl)thioethyl]piperidine (3R,4R)-3-Hydroxymethyl-4-[3-(R,S)-hydroxy-3-(6-methoxyquinolin-4-yl)propyl]-1-[3-(fur-3-yl)thiopropyl]piperidine (3R,4R)-3-Hydroxymethyl-4-[3-(R,S)-hydroxy-3-(6-methoxyquinolin-4-yl)propyl]-1-[2-(thiazol-2-yl)thioethyl]piperidine (3R,4R)-3-Hydroxymethyl-4-[3-(R,S)-hydroxy-3-(6-methoxyquinolin-4-yl)propyl]-1-[3-(thiazol-2-yl)thiopropyl]piperidine (3R,4R)-3-Hydroxymethyl-4-[3-(R,S)-hydroxy-3-(6-methoxyquinolin-4-yl)propyl]-1-[2-(oxazol-2-yl)thioethyl]piperidine (3R,4R)-3-Hydroxymethyl-4-[3-(R,S)-hydroxy-3-(6-methoxyquinolin-4-yl)propyl]-1-[3-(oxazol-2-yl)thiopropyl]piperidine (3R,4R)-3-Hydroxymethyl-4-[3-(R,S)-hydroxy-3-(6-methoxyquinolin-4-yl)propyl]-1-[2-(pyridin-2-yl)thioethyl]piperidine (3R,4R)-3-Hydroxymethyl4-[3-(R,S)-hydroxy-3-(6-methoxyquinolin-4-yl)propyl]-1-[3- (pyridin-2-yl)thiopropyl]piperidine (3R,4R)-3-Hydroxymethyl-4-[3-(R,S)-hydroxy-3-(6-methoxyquinolin-4-yl)propyl]-1-[2-(pyridin-3-yl)thioethyl]piperidine (3R,4R)-3-Hydroxymethyl4-[3-(R,S)-hydroxy-3-(6-methoxyquinolin-4-yl)propyl]-1-[3-(pyridin-3-yl)thiopropyl]piperidine (3R,4R)-3-Hydroxymethyl-4-[3-(R,S)-hydroxy-3-(6-methoxyquinolin-4-yl)propyl]-1-[2-(pyridin-4-yl)thioethyl]piperidine (3R,4R)-3-Hydroxymethyl4-[3-(R,S)-hydroxy-3-(6-methoxyquinolin-4-yl)propyl]-1-[3-(pyridin-4-yl)thiopropyl]piperidine (3R,4R)-3-Hydroxymethyl-4-[3-(R,S)-hydroxy-3-(6-methoxyquinolin-4-yl)propyl]-1-[2-(pyrimidin-2-yl)thioethyl]piperidine (3R,4R)-3-Hydroxymethyl-4-[3-(R,S)-hydroxy-3-(6-methoxyquinolin-4-yl)propyl]-1-[3-(pyrimidin-2-yl)thiopropyl]piperidine (3R,4R)-3-Hydroxymethyl-4-[3-(R,S)-hydroxy-3-(6-methoxyquinolin-4-yl)propyl]-1-[2-(pyrazin-2-yl)thioethyl]piperidine (3R,4R)-3-Hydroxymethyl-4-[3-(R,S)-hydroxy-3-(6-methoxyquinolin-4-yl)propyl]-1-[3-(pyrazin-2-yl)thiopropyl]piperidine (3R,4R)-3-Hydroxymethyl-4-[3-(R,S)-hydroxy-3-(6-methoxyquinolin-4-yl)propyl]-1-[2-(pyridazin-3-yl)thioethyl]piperidine (3R,4R)-3-Hydroxymethyl-4-[3-(R,S)-hydroxy-3-(6-methoxyquinolin-4-yl)propyl]-1-[3-(pyridazin-3-yl)thiopropyl]piperidine (3R,4R)-3-Hydroxymethyl-4-[3-(R,S)-hydroxy-3-(6-methoxyquinolin-4-yl)propyl]-1-[2-(pyridazin4-yl)thioethyl]piperidine (3R,4R)-3-Hydroxymethyl-4-[3-(R,S)-hydroxy-3-(6-methoxyquinolin-4-yl)propyl]-1-[3-(pyridazin-4-yl)thiopropyl]piperidine (3R,4R)-3-Hydroxymethyl-4-[3-(R,S)-hydroxy-3-(6-methoxyquinolin-4-yl)propyl]-1-[3-phenylprop-2-ynyl]piperidine (3R,4R)-3-Hydroxymethyl-4-[3-(R,S)-hydroxy-3-(6-methoxyquinolin-4-yl)propyl]-1-[3(2-fluorophenyl)prop-2-ynyl]piperidine (3R,4R)-3-Hydroxymethyl-4-[3-(R,S)-hydroxy-3-(6-methoxyquinolin-4-yl)propyl]-1-[3-(3-fluorophenyl)prop-2-ynyl]piperidine (3R,4R)-3-Hydroxymethyl-4-[3-(R,S)-hydroxy-3-(6-methoxyquinolin-4-yl)propyl]-1-[3-(4-fluorophenyl)prop-2-ynyl]piperidine (3R,4R)-3-Hydroxymethyl-4-[3-(R,S)-hydroxy-3-(6-methoxyquinolin-4-yl)propyl]-1-[3-(2-chlorophenyl)prop-2-ynyl]piperidine (3R,4R)-3-Hydroxymethyl-4-[3-(R,S)-hydroxy-3-(6-methoxyquinolin-4-yl)propyl]-1-[3-(3-chlorophenyl)prop-2-ynyl]piperidine (3R,4R)-3-Hydroxymethyl-4-[3-(R,S)-hydroxy-3-(6-methoxyquinolin-4-yl)propyl]-1-[3-(4-chlorophenyl)prop-2-ynyl]piperidine (3R,4R)-3-Hydroxymethyl-4-[3-(R,S)-hydroxy-3-(6-methoxyquinolin-4-yl)propyl]-1-[3-(2-methyl-phenyl)prop-2-ynyl]piperidine (3R,4R)-3-Hydroxymethyl-4-[3-(R,S)-hydroxy-3-(6-methoxyquinolin-4-yl)propyl]-1-[3-(3-methyl-phenyl)prop-2-ynyl]piperidine (3R,4R)-3-Hydroxymethyl-4-[3-(R,S)-hydroxy-3-(6-methoxyquinolin-4-yl)propyl]-1-[3-(4-methyl-phenyl)prop-2-ynyl]piperidine (3R,4R)-3-Hydroxymethyl-4-[3-(R,S)-hydroxy-3-(6-methoxyquinolin-4-yl)propyl]-1-[3-(2-(trifluoromethyl)phenyl)prop-2-ynyl]piperidine (3R,4R)-3-Hydroxymethyl-4-[3-(R,S)-hydroxy-3-(6-methoxyquinolin-4-yl)propyl]-1-[3-(3-(trifluoromethyl)phenyl)prop-2-ynyl]piperidine (3R,4R)-3-Hydroxymethyl-4-[3-(R,S)-hydroxy-3-(6-methoxyquinolin-4-yl)propyl]-1-[3-(4-(trifluoromethyl)phenyl)prop-2-ynyl]piperidine (3R,4R)-3-Hydroxymethyl-4-[3-(R,S)-hydroxy-3-(6-methoxyquinolin-4-yl)propyl]-1-[3-(2-methoxy-phenyl)prop-2-ynyl]piperidine (3R,4R)-3-Hydroxymethyl-4-[3-(R,S)-hydroxy-3-(6-methoxyquinolin-4-yl)propyl]-1-[3-(3-methoxy-phenyl)prop-2-ynyl]piperidine (3R,4R)-3-Hydroxymethyl-4-[3-(R,S)-hydroxy-3-(6-methoxyquinolin-4-yl)propyl]-1-[3-(4-methoxy-phenyl)prop-2-ynyl]piperidine (3R,4R)-3-Hydroxymethyl-4-[3-(R,S)-hydroxy-3-(6-methoxyquinolin-4-yl)propyl]-1-[3-(thien-2-yl)prop-2-ynyl]piperidine (3R,4R)-3-Hydroxymethyl-4-[3-(R,S)-hydroxy-3-(6-methoxyquinolin-4-yl)propyl]-1-[3-(thien-3-yl)prop-2-ynyl]piperidine (3R,4R)-3-Hydroxymethyl-4-[3-(R,S)-hydroxy-3-(6-methoxyquinolin-4-yl)propyl]-1-[3-(thiazol-2-yl)prop-2-ynyl]piperidine (3R,4R)-3-Hydroxymethyl-4-[3-(R,S)-hydroxy-3-(6-methoxyquinolin-4-yl)propyl]-1-[3-(thiazol-4-yl)prop-2-ynyl]piperidine
(3R,4R)-3-Hydroxymethyl-4-[3-(R,S)-hydroxy-3-(6-methoxyquinolin-4-yl)propyl]-1-[3-(thiazol-5-yl)prop-2-ynyl]piperidine
(3R,4R)-3-Hydroxymethyl-4-[3-(R,S)-hydroxy-3-(6-methoxyquinolin-4-yl)propyl]-1-[3-(oxazol-2-yl)prop-2-ynyl]piperidine
(3R,4R)-3-Hydroxymethyl-4-[3-(R,S)-hydroxy-3-(6-methoxyquinolin-4-yl)propyl]-1-[3-(oxazol-4-yl)prop-2-ynyl]piperidine,
(3R,4R)-3-Hydroxymethyl-4-[3-(R,S)-hydroxy-3-(6-methoxyquinolin-4-yl)propyl]-1-[3-(oxazol-5-yl)prop-2-ynyl]piperidine
(3R,4R)-3-Hydroxymethyl-4-[3-(R,S)-hydroxy-3-(6-methoxyquinolin-4-yl)propyl]-1-[3-(pyridin-2-yl)prop-2-ynyl]piperidine
(3R,4R)-3-Hydroxymethyl-4-[3-(R,S)-hydroxy-3-(6-methoxyquinolin-4-yl)propyl]-1-[3-(pyridin-3-yl)prop-2-ynyl]piperidine
(3R,4R)-3-Hydroxymethyl-4-[3-(R,S)-hydroxy-3-(6-methoxyquinolin-4-yl)propyl]-1-[3-(pyridin-4-yl)prop-2-ynyl]piperidine
(3R,4R)-3-Hydroxymethyl-4-[3-(R,S)-hydroxy-3-(6-methoxyquinolin-4-yl)propyl]-1-[3-(pyrimidin-2-yl)prop-2-ynyl]piperidine
(3R,4R)-3-Hydroxymethyl-4-[3-(R,S)-hydroxy-3-(6-methoxyquinolin-4-yl)propyl]-1-[3-(pyrazin-2-yl)prop-2-ynyl]piperidine
(3R,4R)-3-Hydroxymethyl-4-[3-(R,S)-hydroxy-3-(6-methoxyquinolin-4-yl)propyl]-1-[3-(pyridazin-3-yl)prop-2-ynyl]piperidine
(3R,4R)-3-Hydroxymethyl-4-[3-(R,S)-hydroxy-3-(6-methoxyquinolin-4-yl)propyl]-1-[3-(pyridazin4-yl)prop-2-ynyl]piperidine
(3R,4R)-3-Hydroxymethyl-4-[3-(R,S)-fluoro-3-(6-methoxyquinolin-4-yl)propyl]-1-[2-phenylthioethyl]piperidine
(3R,4R)-3-Hydroxymethyl-4-[3-(R,S)-fluoro-3-(6-methoxyquinolin-4-yl)propyl]-1-[3-phenylthiopropyl]piperidine (3R,4R)-3-Hydroxymethyl-4-[3-(R,S)-fluoro-3-(6-methoxyquinolin-4-yl)propyl]-1-[2-(2-fluorophenylthio)ethyl]piperidine
(3R,4R)-3-Hydroxymethyl-4-[3-(R,S)-fluoro-3-(6-methoxyquinolin-4-yl)propyl]-1-[3-(2-fluorophenylthio)propyl]piperidine
(3R,4R)-3-Hydroxymethyl-4-[3-(R,S)-fluoro-3-(6-methoxyquinolin-4-yl )propyl]-1-[2-(3-fluorophenylthio)ethyl]piperidine
(3R,4R)-3-Hydroxymethyl-4-[3-(R,S)-fluoro-3-(6-methoxyquinolin-4-yl)propyl]-1-[3-(3-fluorophenylthio)propyl]piperidine
(3R,4R)-3-Hydroxymethyl-4-[3-(R,S)-fluoro-3-(6-methoxyquinolin4-yl)propyl]-1-[2-(4-fluorophenylthio)ethyl]piperidine
(3R,4R)-3-Hydroxymethyl-4-[3-(R,S)-fluoro-3-(6-methoxyquinolin4-yl)propyl]-1-[3-(4-fluorophenylthio)propyl]piperidine
(3R,4R)-3-Hydroxymethyl-4-[3-(R,S)-fluoro-3-(6-methoxyquinolin4-yl)propyl]-1-[2-(2-chlorophenylthio)ethyl]piperidine
(3R,4R)-3-Hydroxymethyl-4-[3-(R,S)-fluoro-3-(6-methoxyquinolin4-yl)propyl]-1-[3(2-chlorophenylthio)propyl]piperidine
(3R,4R)-3-Hydroxymethyl-4-[3-(R,S)-fluoro-3-(6-methoxyquinolin-4-yl)propyl]-1-[2(3-chlorophenylthio)ethyl]piperidine
(3R,4R)-3-Hydroxymethyl-4-[3-(R,S)-fluoro-3-(6-methoxyquinolin4-yl)propyl]-1-[3-(3-chlorophenylthio)propyl]piperidine
(3R,4R)-3-Hydroxymethyl-4-[3-(R,S)-fluoro-3-(6-methoxyquinolin-4-yl)propyl]-1-[2(4-chlorophenylthio)ethyl]piperidine
(3R,4R)-3-Hydroxymethyl-4-[3-(R,S)-fluoro-3-(6-methoxyquinolin-4-yl)propyl]-1-[3-(4-chlorophenylthio)propyl]piperidine
(3R,4R)-3-Hydroxymethyl-4-[3-(R,S)-fluoro-3-(6-methoxyquinolin-4-yl)propyl]-1-[2(2-methylphenylthio)ethyl]piperidine
(3R,4R)-3-Hydroxymethyl-4-[3-(R,S)-fluoro-3-(6-methoxyquinolin4-yl)propyl]-1-[3(2-methylphenylthio)propyl]piperidine
(3R,4R)-3-Hydroxymethyl-4-[3-(R,S)-fluoro-3-(6-methoxyquinolin-4-yl)propyl]-1-[2(3-methylphenylthio)ethyl]piperidine
(3R,4R)-3-Hydroxymethyl-4-[3-(R,S)-fluoro-3-(6-methoxyquinolin-4-yl)propyl]-1-[3-(3-methylphenylthio)propyl]piperidine
(3R,4R)-3-Hydroxymethyl-4-[3-(R,S)-fluoro-3-(6-methoxyquinolin4-yl)propyl]-1-[2(4-methylphenylthio)ethyl]piperidine
(3R,4R)-3-Hydroxymethyl-4-[3-(R,S)-fluoro-3-(6-methoxyquinolin4-yl)propyl]-1-[3-(4-methylphenylthio)propyl]piperidine
(3R,4R)-3-Hydroxymethyl-4-[3-(R,S)-fluoro-3-(6-methoxyquinolin-4-yl)propyl]-1-[2(2-trifluoromethylphenylthio)ethyl]piperidine
(3R,4R)-3-Hydroxymethyl-4-[3-(R,S)-fluoro-3-(6-methoxyquinolin4-yl)propyl]-1-[3(2-trifluoromethylphenylthio)propyl]piperidine
(3R,4R)-3-Hydroxymethyl-4-[3-(R,S)-fluoro-3-(6-methoxyquinolin4-yl)propyl]-1-[2(3-trifluoromethylphenylthio)ethyl]piperidine
(3R,4R)-3-Hydroxymethyl-4-[3-(R,S)-fluoro-3-(6-methoxyquinolin4-yl)propyl]-1-[3-(3-trifluoromethylphenylthio)propyl]piperidine
(3R , 4R)-3-Hydroxymethyl-4-[3-(R,S)-fluoro-3-(6-methoxyquinolin-4-yl)propyl]-1-[2(4-trifluoromethylphenylthio)ethyl]piperidine
(3R,4R)-3-Hydroxymethyl-4-[3-(R,S)-fluoro-3-(6-methoxyquinolin-4-yl)propyl]-1-[3-(4-trifluoromethylphenylthio)propyl]piperidine
(3R,4R)-3-Hydroxymethyl-4-[3-(R,S)-fluoro-3-(6-methoxyquinolin-4-yl)propyl]-1-[2(2-methoxyphenylthio)ethyl]piperidine
(3R,4R)-3-Hydroxymethyl-4-[3-(R,S)-fluoro-3-(6-methoxyquinolin-4-yl)propyl]-1-[3(2-methoxyphenylthio)propyl]piperidine
(3R,4R)-3-Hydroxymethyl-4-[3-(R,S)-fluoro-3-(6-methoxyquinolin4-yl)propyl]-1-[2(3-methoxyphenylthio)ethyl]piperidine
(3R,4R)-3-Hydroxymethyl-4-[3-(R,S)-fluoro-3-(6-methoxyquinolin-4-yl)propyl]-1-[3-(3-methoxyphenylthio)propyl]piperidine
(3R,4R)-3-Hydroxymethyl-4-[3-(R,S)-fluoro-3-(6-methoxyquinolin4-yl)propyl]-1-[2(4-methoxyphenylthio)ethyl]piperidine
(3R,4R)-3-Hydroxymethyl-4-[3-(R,S)-fluoro-3-(6-methoxyquinolin-4-yl)propyl]-1-[3-(4-methoxyphenylthio)propyl]piperidine
(3R,4R)-3-Hydroxymethyl-4-[3-(R,S)-fluoro-3-(6-methoxyquinolin4-yl)propyl]-1-[2-(thien-3-yl)thioethyl]piperidine
(3R,4R)-3-Hydroxymethyl-4-[3-(R,S)-fluoro-3-(6-methoxyquinolin-4-yl)propyl]-1-[3-(thien-3-yl)thiopropyl]piperidine (3R,4R)-3-Hydroxymethyl-4-[3-(R,S)-fluoro-3-(6-methoxyquinolin4-yl)propyl]-1-[2-(fur2-yl)thioethyl]piperidine (3R,4R)-3-Hydroxymethyl-4-[3-(R,S)-fluoro-3-(6-methoxyquinolin-4-yl)propyl]-1-[3-(fur-2-yl)thiopropyl]piperidine (3R,4R)-3-Hydroxymethyl-4-[3-(R,S)-fluoro-3-(6-methoxyquinolin4-yl)propyl]-1-[2-(fur-3-yl)thioethyl]piperidine (3R,4R)-3-Hydroxymethyl-4-[3-(R,S)-fluoro-3-(6-methoxyquinolin-4-yl)propyl]-1-[3-(fur-3-yl)thiopropyl]piperidine (3R,4R)-3-Hydroxymethyl-4-[3-(R,S)-fluoro-3-(6-methoxyquinolin-4-yl)propyl]-1-[2-(thiazol-2-yl)thioethyl]piperidine (3R,4R)-3-Hydroxymethyl-4-[3-(R,S)-fluoro-3-(6-methoxyquinolin4-yl)propyl]-1-[3-(thiazol-2-yl)thiopropyl]piperidine (3R,4R)-3-Hydroxymethyl-4-[3-(R,S)-fluoro-3-(6-methoxyquinolin-4-yl)propyl]-1-[2-(oxazol-2-yl)thioethyl]piperidine (3R,4R)-3-Hydroxymethyl-4-[3-(R,S)-fluoro-3-(6-methoxyquinolin4-yl)propyl]-1-[3-(oxazol-2-yl)thiopropyl]piperidine (3R,4R)-3-Hydroxymethyl-4-[3-(R,S)-fluoro-3-(6-methoxyquinolin4-yl)propyl]-1-[2-(pyridin-2-yl)thioethyl]piperidine (3R , 4R)-3-Hydroxymethyl-4-[3-(R,S)-fluoro-3-(6-methoxyquinolin-4-yl)propyl]-1-[3-(pyridin-2-yl)thiopropyl]piperidine (3R,4R)-3-Hydroxymethyl-4-[3-(R,S)-fluoro-3-(6-methoxyquinolin4-yl)propyl]-1-[2-(pyridin-3-yl)thioethyl]piperidine (3R,4R)-3-Hydroxymethyl-4-[3-(R,S)-fluoro-3-(6-methoxyquinolin-4-yl)propyl]-1-[3-(pyridin-3-yl)thiopropyl]piperidine (3R,4R)-3-Hydroxymethyl-4-[3-(R,S)-fluoro-3-(6-methoxyquinolin4-yl)propyl]-1-[2-(pyridin4-yl)thioethyl]piperidine (3R,4R)-3-Hydroxymethyl-4-[3-(R,S)-fluoro-3-(6-methoxyquinolin4-yl)propyl]-1-[3-(pyridin4-yl)thiopropyl]piperidine (3R,4R)-3-Hydroxymethyl-4-[3-(R,S)-fluoro-3-(6-methoxyquinolin-4-yl)propyl]-1-[2-(pyrimidin-2-yl)thioethyl]piperidine (3R,4R)-3-Hydroxymethyl-4-[3-(R,S)-fluoro-3-(6-methoxyquinolin-4-yl)propyl]-1-[3-(pyrimidin-2-yl)thiopropyl]piperidine (3R,4R)-3-Hydroxymethyl-4-[3-(R,S)-fluoro-3-(6-methoxyquinolin-4-yl)propyl]-1-[2-(pyrazin-2-yl)thioethyl]piperidine (3R,4R)-3-Hydroxymethyl-4-[3-(R,S)-fluoro-3-(6-methoxyquinolin-4-yl)propyl]-1-[3-(pyrazin-2-yl)thiopropyl]piperidine (3R,4R)-3-Hydroxymethyl4-[3-(R,S)-fluoro-3-(6-methoxyquinolin4-yl)propyl]-1-[2-(pyridazin-3-yl)thioethyl]piperidine (3R,4R)-3-Hydroxymethyl-4-[3-(R,S)-fluoro-3-(6-methoxyquinolin-4-yl)propyl]-1-[3-(pyridazin-3-yl)thiopropyl]piperidine (3R,4R)-3-Hydroxymethyl-4-[3-(R,S)-fluoro-3-(6-methoxyquinolin-4-yl)propyl]-1-[2-(pyridazin-4-yl)thioethyl]piperidine (3R,4R)-3-Hydroxymethyl-4-[3-(R,S)-fluoro-3-(6-methoxyquinolin4-yl)propyl]-1-[3-(pyridazin4-yl)thiopropyl]piperidine (3R,4R)-3-Hydroxymethyl-4-[3-(R,S)-fluoro-3-(6-methoxyquinolin-4-yl)propyl]-1-[2-phenylprop-2-ynyl]piperidine (3R,4R)-3-Hydroxymethyl-4-[3-(R,S)-fluoro-3-(6-methoxyquinolin-4-yl)propyl]-1-[3-fluorophenyl)prop-2-ynyl]piperidine (3R,4R)-3-Hydroxymethyl-4-[3-(R,S)-fluoro-3-(6-methoxyquinolin4-yl)propyl]-1-[3-(3-fluorophenyl)prop-2-ynyl]piperidine (3R,4R)-3-Hydroxymethyl-4-[3-(R,S)-fluoro-3-(6-methoxyquinolin-4-yl)propyl]-1-[3-(4-fluorophenyl)prop-2-ynyl]piperidine (3R,4R)-3-Hydroxymethyl-4-[3-(R,S)-fluoro-3-(6-methoxyquinolin-4-yl)propyl]-1-[3-(2-chlorophenyl)prop-2-ynyl]piperidine (3R,4R)-3-Hydroxymethyl-4-[3-(R,S)-fluoro-3-(6-methoxyquinolin-4-yl)propyl]-1-[3-(3-chlorophenyl)prop-2-ynyl]piperidine (3R,4R)-3-Hydroxymethyl-4-[3-(R,S)-fluoro-3-(6-methoxyquinolin4-yl)propyl]-1-[3-(4-chlorophenyl)prop-2-ynyl]piperidine (3R,4R)-3-Hydroxymethyl-4-[3-(R,S)-fluoro-3-(6-methoxyquinolin-4-yl)propyl]-1-[3-(2-methylphenyl)prop-2-ynyl]piperidine (3R,4R)-3-Hydroxymethyl-4-[3-(R,S)-fluoro-3-(6-methoxyquinolin-4-yl)propyl]-1-[3-(3-methylphenyl)prop-2-ynyl]piperidine (3R,4R)-3-Hydroxymethyl-4-[3-(R,S)-fluoro-3-(6-methoxyquinolin-4-yl)propyl]-1-[3-(4-methylphenyl)prop-2-ynyl]piperidine (3R,4R)-3-Hydroxymethyl-4-[3-(R,S)-fluoro-3-(6-methoxyquinolin-4-yl)propyl]-1-[3-(2-(trifluoromethyl)phenyl)prop-2-ynyl]piperidine (3R,4R)-3-Hydroxymethyl-4-[3-(R,S)-fluoro-3-(6-methoxyquinolin--yl) propyl]-1-[3-(3-(trifluoromethyl)phenyl)prop-2-ynyl]piperidine (3R,4R)-3-Hydroxymethyl-4-[3-(R,S)-fluoro-3-(6-methoxyquinolin4-yl)propyl]-1-[3-(4-(trifluoromethyl)phenyl)prop-2-ynyl]piperidine (3R,4R)-3-Hydroxymethyl-4-[3-(R,S)-fluoro-3-(6-methoxyquinolin-4-yl)propyl]-1-[3-(2- methoxyphenyl)prop-2-ynyl]piperidine (3R,4R)-3-Hydroxymethyl-4-[3-(R,S)-fluoro-3-(6-methoxyquinolin4-yl)propyl]-1-[3-(3-methoxyphenyl)prop-2-ynyl]piperidine (3R,4R)-3-Hydroxymethyl-4-[3-(R,S)-fluoro-3-(6-methoxyquinolin-4-yl)propyl]-1-[3-(4-methoxy-phenyl)prop-2-ynyl]piperidine (3R,4R)-3-Hydroxymethyl-4-[3-(R,S)-fluoro-3-(6-methoxyquinolin-4-yl)propyl]-1-[3-(2-(thien-2-yl)prop-2-ynyl]piperidine (3R,4R)-3-Hydroxymethyl-4-[3-(R,S)-fluoro-3-(6-methoxyquinolin-4-yl)propyl]-1-[3-(2-(thien-3-yl)prop-2-ynyl]piperidine (3R,4R)-3-Hydroxymethyl-4-[3-(R,S)-fluoro-3-(6-methoxyquinolin-4-yl)propyl]-1-[3-(2-(thiazol-2-yl)prop-2-ynyl]piperidine (3R,4R)-3-Hydroxymethyl-4-[3-(R,S)-fluoro-3-(6-methoxyquinolin-4-yl)propyl]-1-[3-(2-(thiazol-4-yl)prop-2-ynyl]piperidine (3R,4R)-3-Hydroxymethyl-4-[3-(R,S)-fluoro-3-(6-methoxyquinolin-4-yl)propyl]-1-[3-(2-(thiazol-5-yl)prop-2-ynyl]piperidine (3R,4R)-3-Hydroxymethyl-4-[3-(R,S)-fluoro-3-(6-methoxyquinolin-4-yl)propyl]-1-[3-(2-(oxazol-2-yl)prop-2-ynyl]piperidine (3R,4R)-3-Hydroxymethyl-4-[3-(R,S)-fluoro-3-(6-methoxyquinolin4-yl)propyl]-1-[3-(2-(oxazol-4-yl)prop-2-ynyl]piperidine (3R,4R)-3-Hydroxymethyl-4-[3-(R,S)-fluoro-3-(6-methoxyquinolin-4-yl)propyl]-1-[3-(2-(oxazol-5-yl)prop-2-ynyl]piperidine (3R,4R)-3-Hydroxymethyl-4-[3-(R,S)-fluoro-3-(6-methoxyquinolin4-yl)propyl]-1-[3-(2-(pyridin-2-yl)prop-2-ynyl]piperidine (3R,4R)-3-Hydroxymethyl-4-[3-(R,S)-fluoro-3-(6-methoxyquinolin-4-yl)propyl]-1-[3-(2-(pyridin-3-yl)prop-2-ynyl]piperidine (3R,4R)-3-Hydroxymethyl-4-[3-(R,S)-fluoro-3-(6-methoxyquinolin4-yl)propyl]-1-[3-(2-(pyridin4-yl)prop-2-ynyl]piperidine (3R,4R)-3-Hydroxymethyl-4-[3-(R,S)-fluoro-3-(6-methoxyquinolin4-yl)propyl]-1-[3-(2-(pyrimidin-2-yl)prop-2-ynyl]piperidine (3R,4R)-3-Hydroxymethyl-4-[3-(R,S)-fluoro-3-(6-methoxyquinolin-4-yl)propyl]-1-[3-(2-(pyrazin-2-yl)prop-2-ynyl]piperidine (3R,4R)-3-Hydroxymethyl-4-[3-(R,S)-fluoro-3-(6-methoxyquinolin-4-yl)propyl]-1-[3-(2-(pyridazin-3-yl)prop-2-ynyl]piperidine (3R,4R)-3-Hydroxymethyl-4-[3-(R,S)-fluoro-3-(6-methoxyquinolin-4-yl)propyl]-1-[3-(2-(pyridazin4-yl)prop-2-ynyl]piperidine (3R,4R)-4-[3-(6-Methoxyquinolin-4-yl)propyl]-1-[4-fluoro-4-phenylbutyl]piperidine-3-carboxylic acid (3R,4R)-4-[3-(6-Methoxyquinolin-4-yl)propyl]-1-[2-(3,5-difluorophenylthio)ethyl]piperidine-3-carboxylic acid (3R,4R)-4-[3-(6-Methoxyquinolin4-yl)propyl]-1-[3-(3,5-difluorophenylthio)propyl]piperidine-3-carboxylic acid (3R,4R)-4-[3-(6-Methoxyquinolin-4-yl)propyl]-1-[2-(2,5--difluorophenylthio)ethyl]piperidine-3-carboxylic acid (3R,4R)-4-[3-(6-Methoxyquinolin4-yl)propyl]-1-[3-(2,5-difluorophenylthio)propyl]piperidine-3-carboxylic acid (3R,4R)-4-[3-(6-Methoxyquinolin-4-yl)propyl]-1-[2-(2,3,4,6-tetrafluorophenylthio)ethyl]piperidine-3-carboxylic acid (3R,4R)-4-[3-(6-Methoxyquinolin4-yl)propyl]-1-[3-(2,3,4,6-tetrafluorophenylthio)propyl]piperidine-3-carboxylic acid (3R,4R)-4-[3-(6-Methoxyquinolin4-yl)propyl]-1-[2-(3-fluoro-5-chlorophenylthio)ethyl]piperidine-3-carboxylic acid (3R,4R)-4-[3-(6-Methoxyquinolin-4-yl)propyl]-1-[3-(3-fluoro-5-chlorophenylthio)propyl]piperidine-3-carboxylic acid (3R,4R)-4-[3-(6-Methoxyquinolin-4-yl)propyl]-1-[2-(3-trifluoromethoxyphenylthio)ethyl]piperidine-3-carboxylic acid (3R,4R)-4-[3-(6-Methoxyquinolin-4-yl)propyl]-1-[3-(3-trifluoromethoxyphenylthio)propyl]piperidine-3-carboxylic acid (3R,4R)-4-[3-(6-Methoxyquinolin-4-yl)propyl]-1-[2-(3-cyanophenylthio)ethyl]piperidine-3-carboxylic acid (3R,4R)-4-[3-(6-Methoxyquinolin-4-yl)propyl]-1-[3-(3-cyanophenylthio)propyl]piperidine-3-carboxylic acid (3R,4R)-4-[3-(6-Methoxyquinolin-4-yl)propyl]-1-[2-(pyridin-2-yl)thioethyl]piperidine-3-carboxylic acid (3R,4R)-4-[3-(6-Methoxyquinolin-4-yl)propyl-1-[3-(pyridin-2-yl)thiopropyl]piperidine-3-carboxylic acid (3R,4R)-4-[3-(6-Methoxyquinolin-4-yl)propyl]-1-[2-(3-fluoropyridin-2yl)thioethyl]piperidine-3-carboxylic acid (3R,4R)-4-[3-(6-Methoxyquinolin4-yl)propyl]-1-[3-(3-fluoropyridin-2-yl)thiopropyl]piperidine-3-carboxylic acid (3R,4R)-4-[3-(6-Methoxyquinolin-4-yl)propyl]-1-[2-(cycloheptylthio)ethyl]piperidine-3-carboxylic acid (3R,4R)-4-[3-(6-Methoxyquinolin-4-yl)propyl]-1-[3-(cycloheptylthio)propyl]piperidine-3- carboxylic acid (3R,4R)-4-[3-(6-Methoxyquinolin4-yl)propyl]-1-[2-(tert-butylthio)ethyl]piperidine-3-carboxylic acid (3R,4R)-4-[3-(6-Methoxyquinolin4-yl)propyl]-1-[3-(tert-butylthio)propyl]piperidine-3-carboxylic acid (3R,4R)-4-[3-(6-Methoxyquinolin-4-yl)propyl]-1-[3(2,3-difluorophenyl)prop-2-ynyl]piperidine-3-carboxylic acid (3R,4R)-4-[3-(6-Methoxyquinolin-4-yl)propyl]-1-[3-(2,5-difluorophenyl)prop-2-ynyl]piperidine-3-carboxylic acid (3R,4R)-4-[3-(6-Methoxyquinolin-4-yl)propyl]-1-[3-(3,5-difluorophenyl)prop-2-ynyl]piperidine-3-carboxylic acid (3R,4R)-4-3-(6-Methoxyquinolin-4-yl)propyl]-1-[3-(2,6-difluorophenyl)prop-2-ynyl]piperidine-3-carboxylic acid (3R,4R)-4-[3-(6-Methoxyquinolin-4-yl)propyl]-1-[3-(2,3,5-trifluorophenyl)prop -2-ynyl]piperidine-3-carboxylic acid (3R,4R)-4-[3-(6-Methoxyquinolin-4-yl)propyl]-1-[3-(2,3,6-trifluorophenyl)prop -2-ynyl]piperidine-3-carboxylic acid (3R,4R-4-[3-(6-Methoxyquinolin-4-yl)propyl]-1-[3-(2-cyano-3-fluorophenyl)prop-2-ynyl]piperidine-3-carboxylic acid (3R,4R)-4-[3-(6-Methoxyquinolin4-yl)propyl]-1-[3-cyano-6-fluorophenyl)prop -2-ynyl]piperidine-3-carboxylic acid (3R,4R)-4-[3-(6-Methoxyquinolin-4-yl)propyl]-1-[3-(2-acetamido-5-fluorophenyl)prop-2-ynyl]piperidine-3-carboxylic acid (3R,4R)-4-[3-(6-Methoxyquinolin-4-yl)propyl]-1-[3-trifluoromethoxyphenyl)prop-2-ynyl]piperidine-3-carboxylic acid (3R,4R)-4-[3-(R,S)-Hydroxy-3-(6-methoxyquinolin-4-yl)propyl]-1-[3-fluoro-3-phenylpropyl]piperidine-3-carboxylic acid (3R,4R)-4-[3-(R,S)-Hydroxy-3-(6-methoxyquinolin-4-yl)propyl]-1-[4-fluoro-4-phenylbutyl]piperidine-3-carboxylic acid (3R,4R)-4-[3-(R,S)-Hydroxy-3-(6-methoxyquinolin-4-yl)propyl]-1-[3-(3,5-difluorophenylthio)propyl]piperidine-3-carboxylic acid (3R,4R)-4-[3-(R,S)-Hydroxy-3-(6-methoxyquinolin-4-yl)propyl]-1-[2-(2,5-difluorophenylthio)ethyl]piperidine-3-carboxylic acid (3R,4R)-4-[3-(R,S)-Hydroxy-3-(6-methoxyquinolin-4-yl)propyl]-1-[3-(2,5-difluorophenylthio)propyl]piperidine-3-carboxylic acid (3R,4R)-4-[3-(R,S)-Hydroxy-3-(6-methoxyquinolin-4-yl)propyl]-1-[2-(2,3,4,6-tetrafluorophenylthio)ethyl]piperidine-3-carboxylic acid (3R,4R)-4-[3-(R,S)-Hydroxy-3-(6-methoxyquinolin-4-yl)propyl]-1-[3-(2,3,4,6-tetrafluorophenylthio)propyl]piperidine-3-carboxylic acid (3R,4R)-4-[3-(R,S)-Hydroxy-3-(6-methoxyquinolin-4-yl)propyl]-1-[2-(3-fluoro-5-chlorophenylthio)ethyl]piperidine-3-carboxylic acid (3R,4R)-4-[3-(R,S)-Hydroxy-3-(6-methoxyquinolin-4-yl)propyl]-1-[3-(3-fluoro-5-chlorophenylthio)propyl]piperidine-3-carboxylic acid (3R,4R)-4-[3-(R,S)-Hydroxy-3-(6-methoxyquinolin-4-yl)propyl]-1-[2-(3-trifluoromethoxyphenylthio)ethyl]piperidine-3-carboxylic acid (3R,4R)-4-[3-(R,S)-Hydroxy-3-(6-methoxyquinolin-4-yl)propyl]-1-[3-(3-trifluoromethoxyphenylthio)propyl]piperidine-3-carboxylic acid (3R,4R)-4-[3-(R,S)-Hydroxy-3-(6-methoxyquinolin-4-yl)propyl]-1-[2-(3-cyanophenylthio)ethyl]piperidine-3-carboxylic acid (3R,4R)-4-[3-(R,S)-Hydroxy-3-(6-methoxyquinolin-4-yl)propyl]-1-[3-(3-cyanophenylthio)propyl]piperidine-3-carboxylic acid (3R,4R)-4-[3-(R,S)-Hydroxy-3-(6-methoxyquinolin-4-yl)propyl]-1-[3-(pyridin-2-yl)thiopropyl]piperidine-3-carboxylic acid (3R,4R)-4-[3-(R,S)-Hydroxy-3-(6-methoxyquinolin-4-yl)propyl]-1-[2-(3fluoropyridin-2-yl)thioethyl]piperidine-3-carboxylic acid (3R,4R)-4-[3-(R,S)-Hydroxy-3-(6-methoxyquinolin-4-yl)propyl]-1-[3-(3-fluoropyridin-2-yl)thiopropyl]piperidine-3-carboxylic acid (3R,4R)-4-[3-(R,S)-Hydroxy-3-(6-methoxyquinolin-4-yl)propyl]-1-[3-(cycloheptylthio)propyl]piperidine-3-carboxylic acid (3R,4R)-4-[3-(R,S)-Hydroxy-3-(6-methoxyquinolin-4-yl)propyl]-1-[3-(tert-butylthio)propyl]piperidine-3-carboxylic acid (3R,4R)-4-[3-(R,S)-Hydroxy-3-(6-methoxyquinolin-4-yl)propyl]-1-[3-(2,3,5-trifluorophenyl)prop-2-ynyl]piperidine-3-carboxylic acid (3R,4R)-4-[3-(R,S)-Hydroxy-3-(6-methoxyquinolin-4-yl)propyl]-1-[3-(2,3,6-trifluorophenyl)prop-2-ynyl]piperidine-3-carboxylic acid (3R,4R)-4-[3-(R,S)-Hydroxy-3-(6-methoxyquinolin-4-yl)propyl]-1-[3-(2-cyano-3-fluorophenyl)prop-2-ynyl]piperidine-3-carboxylic acid (3R,4R)-4-[3-(R,S)-Hydroxy-3-(6-methoxyquinolin-4-yl)propyl]-1-[3-cyano-6-fluorophenyl)prop-2-ynyl]piperidine-3-carboxylic acid (3R,4R)-4-[3-(R,S)-Hydroxy-3-(6-methoxyquinolin-4-yl)propyl]-1-[3-(2-acetamido-5-fluorophenyl)prop-2-ynyl]piperidine-3-carboxylic acid (3R,4R)-4-[3-(R,S)-Hydroxy-3-(6-methoxyquinolin4-yl)propyl]-1-[3-trifluoromethoxyphenyl)prop-2-ynyl]piperidine-3-carboxylic acid (3R,4R)-4-[3-(R,S)-Fluoro-3-(6-methoxyquinolin-4-yl)propyl]-1-[3-fluoro-3-phenylpropyl]-piperidine-3-carboxylic acid (3R,4R)-4-[3-(R,S)-Fluoro-3-(6-methoxyquinolin-4-yl)propyl]-1-[4-fluoro-4-phenylbutyl]piperidine-3-carboxylic acid (3R,4R)-4-[3-(R,S)-Fluoro-3-(6-methoxyquinolin-4-yl)propyl]-1-[2-(3,5-difluorophenylthio)ethyl]piperidine-3-carboxylic acid (3R,4R)-4-[3-(R,S)-Fluoro-3-(6-methoxyquinolin-4-yl)propyl]-1-[3-(3,5-difluorophenylthio)propyl]piperidine-3-carboxylic acid (3R,4R)-4-[3-(R,S)-Fluoro-3-(6-methoxyquinolin-4-yl)propyl]-1-[2-(2,5-difluorophenylthio)ethyl]piperidine-3-carboxylic acid (3R,4R)-4-[3-(R,S)-Fluoro-3-(6-methoxyquinolin-4-yl)propyl]-1-[3-(2,5-difluorophenylthio)propyl]piperidine-3-carboxylic acid (3R,4R)-4-[3-(R,S)-Fluoro-3-(6-methoxyquinolin-4-yl)propyl]-1-[2-(2,3,4,6-tetrafluorophenylthio)ethyl]piperidine-3-carboxylic acid (3R,4R)-4-[3-(R,S)-Fluoro-3-(6-methoxyquinolin-4-yl)propyl]-1-[3-(2,3,4,6-tetrafluorophenylthio)propyl]piperidine-3-carboxylic acid (3R,4R)-4-[3-(R,S)-Fluoro-3-(6-methoxyquinolin-4-yl)propyl]-1-[2-(3-fluoro-5-chlorophenylthio)ethyl]piperidine-3-carboxylic acid (3R,4R)-4-[3-(R,S)-Fluoro-3-(6-methoxyquinolin-4-yl)propyl]-1-[3-(3-fluoro-5-chlorophenylthio)propyl]piperidine-3-carboxylic acid (3R,4R)-4-[3-(R,S)-Fluoro-3-(6-methoxyquinolin-4-yl)propyl]-1-[2-(3-trifluoromethoxyphenylthio)ethyl]piperidine-3-carboxylic acid (3R,4R)-4-[3-(R,S)-Fluoro-3-(6-methoxyquinolin-4-yl)propyl]-1-[3-(3-trifluoromethoxyphenylthio)propyl]piperidine-3-carboxylic acid (3R,4R)-4-[3-(R,S)-Fluoro-3-(6-methoxyquinolin-4-yl)propyl]-1-[2-(3-cyanophenylthio)ethyl]piperidine-3-carboxylic acid (3R,4R)-4-[3-(R,S)-Fluoro-3-(6-methoxyquinolin-4-yl)propyl]-1-[3-(3-cyanophenylthio)propyl]piperidine-3-carboxylic acid (3R,4R)-4-[3-(R,S)-Fluoro-3-(6-methoxyquinolin-4-yl)propyl]-1-[2-(pyridin-2-yl)thioethyl]-piperidine-3-carboxylic acid (3R,4R)-4-[3-(R,S)-Fluoro-3-(6-methoxyquinolin-4-yl)propyl]-1-[3-(pyridin-2-yl)thiopropyl]-piperidine-3-carboxylic acid (3R,4R)-4-[3-(R,S)-Fluoro-3-(6-methoxyquinolin-4-yl)propyl]-1-[2-(3-fluoropyridin-2-yl)thioethyl]piperidine-3-carboxylic acid (3R,4R)-4-[3-(R,S)-Fluoro-3-(6-methoxyquinolin-4-yl)propyl]-1-[3-(3-fluoropyridin-2-yl)thiopropyl]piperidine-3-carboxylic acid (3R,4R)-4-[3-(R,S)-Fluoro-3-(6-methoxyquinolin4-yl)propyl]-1-(2-(cycloheptylthio)ethyl]-piperidine-3-carboxylic acid (3R,4R)-4-[3-(R,S)-Fluoro-3-(6-methoxyquinolin-4-yl)propyl]-1-[3-(cycloheptylthio)propyl]piperidine-3-carboxylic acid (3R,4R)-4-[3-(R,S)-Fluoro-3-(6-methoxyquinolin-4-yl)propyl]-1-[2-(tert-butylthio)ethyl]-piperidine-3-carboxylic acid (3R,4R)-4-[3-(R,S)-Fluoro-3-(6-methoxyquinolin-4-yl)propyl]-1-[3-(tert-butylthio)propyl]-piperidine-3-carboxylic acid (3R,4R)-4-[3-(R,S)-Fluoro-3-(6-methoxyquinolin-4-yl)propyl]-1-[3-(2,3-difluorophenyl)prop-2-ynyl]piperidine-3-carboxylic acid (3R,4R)-4-[3-(R,S)-Fluoro-3-(6-methoxyquinolin-4-yl)propyl]-1-[3-(2,5-difluorophenyl)prop-2-ynyl]piperidine-3-carboxylic acid (3R,4R)-4-[3-(R,S)-Fluoro-3-(6-methoxyquinolin-4-yl)propyl]-1-[3-(3,5-difluorophenyl)prop-2-ynyl]piperidine-3-carboxylic acid (3R,4R)-4-[3-(R,S)-Fluoro-3-(6-methoxyquinolin-4-yl)propyl]-1-[3-(2,6-difluorophenyl)prop-2-ynyl]piperidine-3-carboxylic acid (3R,4R)-4-[3-(R,S)-Fluoro-3-(6-methoxyquinolin-4-yl)propyl]-1-[3-(2,3,5-trifluorophenyl)prop-2-ynyl]piperidine-3-carboxylic acid (3R,4R)-4-[3-(R,S)-Fluoro-3-(6-methoxyquinolin-4-yl)propyl]-1-[3-(2,3,6-trifluorophenyl)prop-2-ynyl]piperidine-3-carboxylic acid (3R,4R)-4-[3-(R,S)-Fluoro-3-(6-methoxyquinolin-4-yl)propyl]-1-[3-(2-cyano-3-fluorophenyl)prop-2-ynyl]piperidine-3-carboxylic acid (3R,4R)-4-[3-(R,S)-Fluoro-3-(6-methoxyquinolin-4-yl)propyl]-1-[3-cyano-6-fluorophenyl)prop-2-ynyl]piperidine-3-carboxylic acid (3R,4R)-4-[3-(R,S)-Fluoro-3-(6-methoxyquinolin-4-yl)propyl]-1-[3-(2-acetamido-5-fluorophenyl)prop-2-ynyl]piperidine-3-carboxylic acid (3R,4R)-4-[3-(R,S)-Fluoro-3-(6-methoxyquinolin-4-yl)propyl]-1-[3-trifluoromethoxyphenyl)prop-2-ynyl]piperidine-3-carboxylic acid (3R,4R)-4-[3-(6-Methoxyquinolin-4-yl)propyl]-1-[3-fluoro-3-phenylpropyl]piperidine-3-acetic acid (3R,4R)-4-[3-(6-Methoxyquinolin-4-yl)propyl]-1-[4-fluoro4-phenylbutyl]piperidine-3-acetic acid (3R,4R)-4-[3-(6-Methoxyquinolin-4-yl)propyl]-1-[2-(3,5-difluorophenylthio)ethyl]piperidine-3-acetic acid (3R,4R)-4-[3-(6-Methoxyquinolin-4-yl)propyl]-1-[2-(3,5-difluorophenylthio)propyl]piperidine-3-acetic acid (3R,4R)-4-[3-(6-Methoxyquinolin-4-yl)propyl]-1-[2-(2,5-difluorophenylthio)ethyl]piperidine-3-acetic acid (3R,4R)-4-[3-(6-Methoxyquinolin-4-yl)propyl]-1-[3-(2,5-difluorophenylthio)propyl]piperidine-3-acetic acid
(3R,4R)-4-[3-(6-Methoxyquinolin-4-yl)propyl]-1-[2-(2,3,4,6-tetrafluorophenylthio)ethyl]piperidine-3-acetic acid
(3R,4R)-4-[3-(6-Methoxyquinolin-4-yl)propyl]-1-[3-(2,3,4,6-tetrafluorophenylthio)propyl]piperidine-3-acetic acid
(3R,4R)-4-[3-(6-Methoxyquinolin-4-yl)propyl]-1-[2-(3-fluoro-5-chlorophenylthio)ethyl]piperidine-3-acetic acid
(3R,4R)-4-[3-(6-Methoxyquinolin-4-yl)propyl]-1-[3-(3-fluoro-5-chlorophenylthio)propyl]piperidine-3-acetic acid
(3R,4R)-4-[3-(6-Methoxyquinolin-4-yl)propyl]-1-[2-(3-trifluoromethoxyphenylthio)ethyl]piperidine-3-acetic acid
(3R,4R)-4-[3-(6-Methoxyquinolin-4-yl)propyl]-1-[3-(3-trifluoromethoxyphenylthio)propyl]piperidine-3-acetic acid
(3R,4R)-4-[3-(6-Methoxyquinolin-4-yl)propyl]-1-[2-(3-cyanophenylthio)ethyl]piperidine-3-acetic acid
(3R,4R)-4-[3-(6-Methoxyquinolin-4-yl)propyl]-1-[3-(3-cyanophenylthio)propyl]piperidine-3-3-acetic acid
(3R,4R)-4-[3-(6-Methoxyquinolin-4-yl)propyl]-1-[2-(pyridin-2-yl)thioethyl]piperidine-3-acetic acid
(3R,4R)-4-[3-(6-Methoxyquinolin-4-yl)propyl]-1-[3-(pyridin-2-yl)thiopropyl]piperidine-3-acetic acid
(3R,4R)-4-[3-(6-Methoxyquinolin-4-yl)propyl]-1-[2-(3-fluoropyridin-2-yl)thioethyl]piperidine-3-acetic acid
(3R,4R)-4-[3-(6-Methoxyquinolin-4-yl)propyl]-1-[3-(3-fluoropyridin-2-yl)thiopropyl]piperidine-3-acetic acid
(3R,4R)-4-[3-(6-Methoxyquinolin-4-yl)propyl]-1-[2-(cycloheptylthio)ethyl]piperidine-3-acetic acid
(3R,4R)-4-[3-(6-Methoxyquinolin-4-yl)propyl]-1-[3-(cycloheptylthio)propyl]piperidine-3-acetic acid
(3R,4R)-4-[3-(6-Methoxyquinolin-4-yl)propyl]-1-[2-(tert-butylthio)ethyl]piperidine-3-acetic acid
(3R,4R)-4-[3-(6-Methoxyquinolin-4-yl)propyl]-1-[3-(tert-butylthio)propyl]piperidine-3-acetic acid
(3R,4R)-4-[3-(6-Methoxyquinolin-4-yl)propyl]-1-[3-(2,3-difluorophenyl)prop-2-ynyl]piperidine-3-acetic acid
(3R,4R)-4-[3-(6-Methoxyquinolin-4-yl)propyl]-1-[3-(2,5-difluorophenyl)prop-2-ynyl]piperidine-3-acetic acid
(3R,4R)-4-[3-(6-Methoxyquinolin-4-yl)propyl]-1-[3-(2,6-difluorophenyl)prop-2-ynyl]piperidine-3-acetic acid
(3R,4R)-4-[3-(6-Methoxyquinolin-4-yl)propyl]-1-[3-(2,3,5-trifluorophenyl)prop-2-ynyl]piperidine-3-acetic acid
(3R,4R)-4-[3-(6-Methoxyquinolin-4-yl)propyl]-1-[3-(2,3,6-trifluorophenyl)prop-2-ynyl]piperidine-3-acetic acid
(3R,4R)-4-[3-(6-Methoxyquinolin-4-yl)propyl]-1-[3-(2-cyano-3-fluorophenyl)prop-2-ynyl]piperidine-3-acetic acid
(3R,4R)-4-[3-(6-Methoxyquinolin-4-yl)propyl]-1-[3-cyano-6-fluorophenyl)prop-2-ynyl]piperidine-3-acetic acid
(3R,4R)-4-[3-(6-Methoxyquinolin-4-yl)propyl]-1-[3-(2-acetamido-5-fluorophenyl)prop-2-ynyl]piperidine-3-acetic acid
(3R,4R)-4-[3-(6-Methoxyquinolin-4-yl)propyl]-1-[3-trifluoromethoxyphenyl)prop-2-ynyl]piperidine-3-acetic acid
(3R,4R)-4-[3-(R,S)-Hydroxy-3-(6-methoxyquinolin-4-yl)propyl]-1-[3-fluoro-3-phenylpropyl]piperidine-3-acetic acid
(3R,4R)-4-[3-(R,S)-Hydroxy-3-(6-methoxyquinolin-4-yl)propyl]-1-[4-fluoro-4-phenylbutyl]piperidine-3-acetic acid
(3R,4R)-4-[3-(R,S)-Hydroxy-3-(6-methoxyquinolin-4-yl)propyl]-1-[2-(3,5-difluorophenylthio)ethyl]piperidine-3-acetic acid
(3R,4R)-4-[3-(R,S)-Hydroxy-3-(6-methoxyquinolin-4-yl)propyl]-1-[3-(3,5-difluorophenylthio)propyl]piperidine-3-acetic acid
(3R,4R)-4-[3-(R,S)-Hydroxy-3-(6-methoxyquinolin-4-yl)propyl]-1-[2-(2,5-difluorophenylthio)ethyl]piperidine-3-acetic acid
(3R,4R)-4-[3-(R,S)-Hydroxy-3-(6-methoxyquinolin-4-yl)propyl]-1-[3-(2,5-difluorophenylthio)propyl]piperidine-3-acetic acid
(3R,4R)-4-[3-(R,S)-Hydroxy-3-(6-methoxyquinolin-4-yl)propyl]-1-[2-(2,3,4,6-tetrafluorophenylthio)ethyl]piperidine-3-acetic acid
(3R,4R)-4-[3-(R,S)-Hydroxy-3-(6-methoxyquinolin -4-yl)propyl]-1-[3-(2,3,4,6-tetrafluorophenylthio)propyl]piperidine-3-acetic acid
(3R,4R)-4-[3-(R,S)-Hydroxy-3-(6-methoxyquinolin-4-yl)propyl]-1-[2-(3-fluoro-5-chlorophenylthio)ethyl]piperidine-3-acetic acid
(3R,4R)-4-[3-(R,S)-Hydroxy-3-(6-methoxyquinolin-4-yl)propyl]-1-[3-(3-fluoro-5-chlorophenylthio)propyl]piperidine-3-acetic acid
(3R,4R)-4-[3-(R,S)-Hydroxy-3-(6-methoxyquinolin-4-yl)propyl]-1-[2-(3-trifluoromethoxyphenylthio)ethyl]piperidine-3-acetic acid
(3R,4R)-4-[3-(R,S)-Hydroxy-3-(6-methoxyquinolin-4-yl)propyl]-1-[3-(3-trifluoromethoxyphenylthio)propyl]piperidine-3-acetic acid
(3R,4R)-4-[3-(R,S)-Hydroxy-3-(6-methoxyquinolin-4-yl)propyl]-1-[2-(3-cyanophenylthio)-ethyl]piperidine-3-acetic acid
(3R,4R)-4-[3-(R,S)-Hydroxy-3-(6-methoxyquinolin-4-yl)propyl]-1-[3-(3-cyanophenylthio)-propyl]piperidine-3-acetic acid
(3R,4R)-4-[3-(R,S)-Hydroxy-3-(6-methoxyquinolin-4-yl)propyl]-1-[2-(pyridin-2-yl)thioethyl]piperidine-3-acetic acid
(3R,4R)-4-[3-(R,S)-Hydroxy-S-(6-methoxyquinolin-4-yl)propyl]-1-[3-(pyridin-2-yl)thiopropyl]piperidine-3-acetic acid
(3R,4R)-4-[3-(R,S)-Hydroxy-3-(6-methoxyquinolin-4-yl)propyl]-1-[2-(3-fluoropyridin-2-yl)thioethyl]piperidine-3-acetic acid
(3R,4R)-4-[3-(R,S)-Hydroxy-3-(6-methoxyquinolin-4-yl)propyl]-1-[3-(3-fluoropyridin-2-yl)thiopropyl]piperidine-3-acetic acid
(3R,4R)-4-[3-(R,S)-Hydroxy-3-(6-methoxyquinolin-4-yl propyl]-1-[2-(cycloheptylthio)ethyl]piperidine-3-acetic acid
(3R,4R)-4-[3-(R,S)-Hydroxy-3-(6-methoxyquinolin-4yl)propyl]-1-[3-(cycloheptylthio)propyl]piperidine-3-acetic acid
(3R,4R)-4-[3-(R,S)-Hydroxy-(6-methoxyquinolin-4-yl)propyl]-1-[2-(tert-butylthio)ethyl]-piperidine-3-acetic acid
(3R,4R)-4-[3-(R,S )-Hydroxy-3-(6-methoxyquinolin-4-yl)propyl]-1-[3-(tert-butylthio)propyl]piperidine-3-acetic acid
(3R,4R)-4-[3-(R,S)-Hydroxy-3-(6-methoxyquinolin-4-yl)propyl]-1-[3-(2,3-difluorophenyl)prop-2-ynyl]piperidine-3-acetic acid
(3R,4R)-4-[3-(R,S)-Hydroxy-3-(6-methoxyquinolin-4-yl propyl]-1-[3-(2,5-difluorophenyl)prop-2-ynyl]piperidine-3-acetic acid
(3R,4R)-4-[3-(R,S)-Hydroxy-3-(6-methoxyquinolin-4-yl)propyl]-1-[3-(3,5-difluorophenyl)prop-2-ynyl]piperidine-3-acetic acid
(3R,4R)-4-[3-(R,S)-Hydroxy-3-(6-methoxyquinolin-4-yl)propyl]-1-[3-(2,6-difluorophenyl)prop-2-ynyl]piperidine-3-acetic acid (3R,4R)-4-[3-(R,S)-Hydroxy-3-(6-methoxyquinolin4-yl)propyl]-1-[3-(2,3,5-trifluorophenyl)prop-2-ynyl]piperidine-3-acetic acid
(3R,4R)-4-[3-(R,S)-Hydroxy-3-(6-methoxyquinolin-4-yl)propyl]-1-[3-(2,3,6-trifluorophenyl)prop-2-ynyl]piperidine-3-acetic acid
(3R,4R)-4-[3-(R,S)-Hydroxy-3-(6-methoxyquinolin-4-yl)propyl]-1-[3-(2-cyano-3-fluorophenyl)prop-2-ynyl]piperidine-3-acetic acid
(3R,4R)-4-[3-(R,S)-Hydroxy-3-(6-methoxyquinolin-4-yl)propyl]-1-[3-cyano-6-fluorophenyl)prop-2-ynyl]piperidine-3-acetic acid
(3R,4R)-4-[3-(R,S)-Hydroxy-3-(6-methoxyquinolin-4-yl)propyl]-1-[3-(2-acetamido-5-fluorophenyl)prop-2-ynyl]piperidine-3-acetic acid
(3R,4R)-4-[3-(R,S)-Hydroxy-3-(6-methoxyquinolin-4-yl)propyl]-1-[3-trifluoromethoxyphenyl)prop-2-ynyl]piperidine-3-acetic acid
(3R,4R)-4-[3-(R,S)-Fluoro-3-(6-methoxyquinolin-4-yl)propyl]-1-[3-fluoro-3-phenylpropyl]-piperidine-3-acetic acid
(3R,4R)-4-[3-(R,S)-Fluoro-3-(6-methoxyquinolin-4-yl)propyl]-1-[4-fluoro4-phenylbutyl]-piperidine-3-acetic acid
(3R,4R)-4-[3-(R,S)-Fluoro-3-(6-methoxyquinolin4-yl)propyl]-1-[2-(3,5-difluorophenylthio)ethyl]piperidine-3-acetic acid
(3R,4R)-4-[3-(R,S)-Fluoro-3-(6-methoxyquinolin-4-yl)propyl]-1-[3-(3,5-difluorophenylthio)propyl]piperidine-3-acetic acid
(3R,4R)-4-[3-(R,S)-Fluoro-3-(6-methoxyquinolin-4-yl)propyl]-1-[2-(2,5-difluorophenylthio)ethyl]piperidine-3-acetic acid
(3R,4R)-4-[3-(R,S)-Fluoro-3-(6-methoxyquinolin-4-yl)propyl]-1-[3-(2,5-difluorophenylthio)propyl]piperidine-3-acetic acid
(3R,4R)-4-[3-(R,S)-Fluoro-3-(6-methoxyquinolin-4-yl)propyl]-1-[2-(2,3,4,6-tetrafluorophenylthio)ethyl]piperidine-3-acetic acid
(3R,4R)-4-[3-(R,S)-Fluoro-3-(6-methoxyquinolin-4-yl)propyl]-1-[3-(2,3,4,6-tetrafluorophenylthio)propyl]piperidine-3-acetic acid
(3R,4R)-4-[3-(R,S)-Fluoro-3-(6-methoxyquinolin4-yl)propyl]-1-[2-(3-fluoro-5-chlorophenylthio)ethyl]piperidine-3-acetic acid
(3R,4R)-4-[3-(R,S)-Fluoro-3-(6-methoxyquinolin4-yl)propyl]-1-[3-(3-fluoro-5-chlorophenylthio)propyl]piperidine-3-acetic acid
(3R,4R)-4-[3-(R,S)-Fluoro-3-(6-methoxyquinolin-4-yl)propyl]-1-[2-(3-trifluoromethoxyphenylthio)ethyl]piperidine-3-acetic acid
(3R,4R)-4-[3-(R,S)-Fluoro-3-(6-methoxyquinolin-4-yl)propyl]-1-[3-(3-trifluoromethoxyphenylthio)propyl]piperidine-3-acetic acid
(3R,4R)-4-[3-(R,S)-Fluoro-3-(6-methoxyquinolin4-yl)propyl]-1-[2-(3-cyanophenylthio)-ethyl]piperidine-3-acetic acid
(3R,4R)-4-[3-(R,S)-Fluoro-3-(6-methoxyquinolin-4-yl)propyl]-1-[3-(3-cyanophenylthio)-propyl]piperidine-3-acetic acid
(3R,4R)-4-[3-(R,S)-Fluoro-3-(6-methoxyquinolin4-yl)propyl]-1-[2-(pyridin-2-yl)thioethyl]-piperidine-3-acetic acid
(3R,4R)-4-[3-(R,S)-Fluoro-3-(6-methoxyquinolin-4-yl)propyl]-1-[3-(pyridin-2-yl)thiopropyl]piperidine-3-acetic acid
(3R,4R)-4-[3-(R,S)-Fluoro-3-(6-methoxyquinolin-4-yl)propyl]-1-[2-(3-fluoropyridin-2-yl)thioethyl]piperidine-3-acetic acid
(3R,4R)-4-[3-(R,S)-Fluoro-3-(6-methoxyquinolin-4-yl)propyl]-1-[3-(3-fluoropyridin-2-yl)thiopropyl]piperidine-3-acetic acid
(3R,4R)-4-[3-(R,S)-Fluoro-3-(6-methoxyquinolin-4-yl)propyl]-1-[2-(cycloheptylthio)ethyl]-piperidine-3-acetic acid
(3R,4R)-4-[3-(R,S)-Fluoro-3-(6-methoxyquinolin-4-yl)propyl]-1-[3-(cycloheptylthio)propyl]piperidine-3-acetic acid
(3R,4R)-4-[3-(R,S)-Fluoro-3-(6-methoxyquinolin-4-yl)propyl]-1-[2-(tert-butylthio)ethyl]-piperidine-3-acetic acid
(3R,4R)-4-[3-(R,S)-Fluoro-3-(6-methoxyquinolin-4-yl)propyl]-1-[3-(tert-butylthio)propyl]-piperidine-3-acetic acid
(3R,4R)-4-[3-(R,S)-Fluoro-3-(6-methoxyquinolin-4-yl)propyl]-1-[3-(2,3-difluorophenyl)prop-2-ynyl]piperidine-3-acetic acid
(3R,4R)-4-[3-(R,S)-Fluoro-3-(6-methoxyquinolin-4-yl)propyl]-1-[3-(2,5-difluorophenyl)prop-2-ynyl]piperidine-3-acetic acid
(3R,4R)-4-[3-(R,S)-Fluoro-3-(6-methoxyquinolin-4-yl)propyl]-1-[3-(3,5-difluorophenyl)prop-2-ynyl]piperidine-3-acetic acid
(3R,4R)-4-[3-(R,S)-Fluoro-3-(6-methoxyquinolin-4-yl)propyl]-1-[3-(2,6-difluorophenyl)prop-2-ynyl]piperidine-3-acetic acid
(3R,4R)-4-[3-(R,S)-Fluoro-3-(6-methoxyquinolin-4-yl)propyl]-1-[3-(2,3,5-trifluorophenyl)prop-2-ynyl]piperidine-3-acetic acid
(3R,4R)-4-[3-(R,S)-Fluoro-3-(6-methoxyquinolin-4-yl)propyl]-1-[3-(2,3,6-trifluorophenyl)prop-2-ynyl]piperidine-3-acetic acid
(3R,4R)-4-[3-(R,S)-Fluoro-3-(6-methoxyquinolin-4-yl)propyl]-1-[3-(2-cyano-3-fluorophenyl)prop-2-ynyl]piperidine-3-acetic acid
(3R,4R)-4-[3-(R,S)-Fluoro-3-(6-methoxyquinolin-4-yl)propyl]-1-[3-cyano-6-fluorophenyl)prop-2-ynyl]piperidine-3-acetic acid
(3R,4R)-4-[3-(R,S)-Fluoro-3-(6-methoxyquinolin-4-yl)propyl]-1-[3-(2-acetamido-5-fluorophenyl)prop-2-ynyl]piperidine-3-acetic acid
(3R,4R)-4-[3-(R,S)-Fluoro-3-(6-methoxyquinolin-4-yl)propyl]-1-[3-trifluoromethoxyphenyl)prop-2-ynyl]piperidine-3-acetic acid
(3R,4R)-3-Hydroxymethyl-4-[3-(6-methoxyquinolin-4-yl)propyl]-1-[2-(3,5-difluorophenylthio)ethyl]piperidine
(3R,4R)-3-Hydroxymethyl-4-[3-(6-methoxyquinolin4-yl)propyl]-1-[3-(3,5-difluorophenylthio)propyl]piperidine
(3R,4R)-3-Hydroxymethyl-4-[3-(6-methoxyquinolin-4-yl)propyl]-1-[2-(2,5-difluorophenylthio)ethyl]piperidine
(3R,4R)-3-Hydroxymethyl-4-[3-(6-methoxyquinolin-4-yl)propyl]-1-[3-(2,5-difluorophenylthio)propyl]piperidine
(3R,4R)-3-Hydroxymethyl-4-[3-(6-methoxyquinolin-4-yl)propyl]-1-[2-(2,3,4,6-tetrafluorophenylthio)ethyl]piperidine
(3R,4R)-3-Hydroxymethyl-4-[3-(6-methoxyquinolin-4-yl)propyl]-1-[3-(2,3,4,6-tetrafluorophenylthio)propyl]piperidine
(3R,4R)-3-Hydroxymethyl-4-[3-(6-methoxyquinolin-4-yl)propyl]-1-[2-(3-fluoro-5-chlorophenylthio)ethyl]piperidine
(3R,4R)-3-Hydroxymethyl-4-[3-(6-methoxyquinolin-4-yl)propyl]-1-[3-(3-fluoro-5-chlorophenylthio)propyl]piperidine
(3R,4R)-3-Hydroxymethyl-4-[3-(6-methoxyquinolin-4-yl)propyl]-1-[2-(3-trifluoromethoxyphenylthio)ethyl]piperidine (3R,4R)-3-Hydroxymethyl-4-[3-(6-methoxyquinolin-4-yl)propyl]-1-[3-(3-trifluoromethoxyphenylthio)propyl]piperidine
(3R,4R)-3-Hydroxymethyl-4-[3-(6-methoxyquinolin-4-yl)propyl]-1-[2-(3-cyanophenylthio)ethyl]piperidine
(3R,4R)-3-Hydroxymethyl-4-[3-(6-methoxyquinolin-4-yl)propyl]-1-[3-(3-cyanophenylthio)propyl]piperidine
(3R,4R)-3-Hydroxymethyl-4-[3-(6-methoxyquinolin-4-yl)propyl]-1-[2-(pyridin-2-yl)thioethyl]piperidine
(3R,4R)-3-Hydroxymethyl-4-[3-(6-methoxyquinolin-4-yl)propyl-1-[3-(pyridin-2-yl)thiopropyl]piperidine
(3R,4R)-3-Hydroxymethyl-4-[3-(6-methoxyquinolin-4-yl)propyl]-1-[2-(3-fluoropyridin-2-yl)thioethyl]piperidine
(3R,4R)-3-Hydroxymethyl-4-[3-(6-methoxyquinolin-4-yl)propyl]-1-[2-(3-fluoropyridin-2-yl)thiopropyl]piperidine
(3R,4R)-3-Hydroxymethyl-4-[3-(6-methoxyquinolin-4-yl)propyl]-1-[2-(cycloheptylthio)ethyl]piperidine
(3R,4R)-3-Hydroxymethyl-4-[3-(6-methoxyquinolin-4-yl)propyl]-1-[3-(cycloheptylthio)propyl]piperidine
(3R,4R)-3-Hydroxymethyl-4-[3-(6-methoxyquinolin-4-yl)propyl]-1-[2-(tert-butylthio)ethyl]-piperidine
(3R,4R)-3-Hydroxymethyl-4-[3-(6-methoxyquinolin-4-yl)propyl]-1-[3-(tert-butylthio)propyl]piperidine
(3R,4R)-3-Hydroxymethyl-4-[3-(6-methoxyquinolin-4-yl)propyl]-1-[3-(2,3-difluorophenyl)prop-2-ynyl]piperidine
(3R,4R)-3-Hydroxymethyl-4-[3-(6-methoxyquinolin-4-yl)propyl]-1-[3-(2,5-difluorophenyl)prop-2-ynyl]piperidine
(3R,4R)-3-Hydroxymethyl-4-[3-(6-methoxyquinolin-4-yl)propyl]-1-[3-(3,5-difluorophenyl)prop-2-ynyl]piperidine
(3R,4R)-3-Hydroxymethyl-4-[3-(6-methoxyquinolin-4-yl)propyl]-1-[3-(2,6-difluorophenyl)prop-2-ynyl]piperidine
(3R,4R)-3-Hydroxymethyl-4-[3-(6-methoxyquinolin-4-yl)propyl]-1-[3-(2,3,5-trifluorophenyl)prop-2-ynyl]piperidine
(3R,4R)-3-Hydroxymethyl-4-[3-(6-methoxyquinolin-4-yl)propyl]-1-3-(2,3,6-trifluorophenyl)prop-2-ynyl]piperidine
(3R,4R)-3-Hydroxymethyl-4-[3-(6-methoxyquinolin-4-yl)propyl]-1-[3-(2-cyano-3-fluorophenyl)prop-2-ynyl]piperidine
(3R,4R)-3-Hydroxymethyl-4-[3-(6-methoxyquinolin-4-yl)propyl]-1-[3-cyano-6-fluorophenyl)prop-2-ynyl]piperidine
(3R,4R)-3-Hydroxymethyl-4-[3-(6-methoxyquinolin-4-yl)propyl]-1-[3-(2-acetamido-5-fluorophenyl)prop-2-ynyl]piperidine
(3R,4R)-3-Hydroxymethyl-4-[3-(6-methoxyquinolin-4-yl)propyl]-1-[3-trifluoromethoxyphenyl)prop-2-ynyl]piperidine
(3R,4R)-3-Hydroxymethyl-4-[3-(R,S)-hydroxy-3-(6-methoxyquinolin-4-yl)propyl]-1-[2-(3,5-difluorophenylthio)ethyl]piperidine
(3R,4R)-3-Hydroxymethyl-4-[3-(R,S)-hydroxy-3-(6-methoxyquinolin-4-yl)propyl]-1-[3-(3,5-difluorophenylthio)propyl]piperidine
(3R,4R)-3-Hydroxymethyl-4-[3-(R,S)-hydroxy-3-(6-methoxyquinolin-4-yl)propyl]-1-[2-(2,5-difluorophenylthio)ethyl]piperidine
(3R,4R)-3-Hydroxymethyl-4-[3-(R,S)-hydroxy-3-(6-methoxyquinolin-4-yl)propyl]-1-[3-(2,5-difluorophenylthio)propyl]piperidine
(3R,4R)-3-Hydroxymethyl-4-[3-(R,S)-hydroxy-3-(6-methoxyquinolin-4-yl)propyl]-1-[2-(2,3,4,6-tetrafluorophenylthio)ethyl]piperidine
(3R,4R)-3-Hydroxymethyl-4-[3-(R,S)-hydroxy-3-(6-methoxyquinolin-4-yl)propyl]-1-[3-(2,3,4,6-tetrafluorophenylthio)propyl]piperidine
(3R,4R)-3-Hydroxymethyl-4-[3-(R,S)-hydroxy-3-(6-methoxyquinolin-4-yl)propyl]-1-[2-(3-fluoro-5-chlorophenylthio)ethyl]piperidine
(3R,4R)-3-Hydroxymethyl-4-[3-(R,S)-hydroxy-3-(6-methoxyquinolin-4-yl)propyl]-1-[3-(3-fluoro-5-chlorophenylthio)propyl]piperidine
(3R,4R)-3-Hydroxymethyl-4-[3-(R,S)-hydroxy-3-(6-methoxyquinolin-4-yl)propyl]-1-[2-(3-trifluoromethoxyphenylthio)ethyl]piperidine
(3R,4R)-3-Hydroxymethyl-4-[3-(R,S)-hydroxy-3-(6-methoxyquinolin-4-yl)propyl]-1-[3-(3-trifluoromethoxyphenylthio)propyl]piperidine
(3R,4R)-3-Hydroxymethyl-4-[3-(R,S)-hydroxy-3-(6-methoxyquinolin-4-yl)propyl]-1-[2-(3-trifluoromethylthiophenylthio)ethyl]piperidine
(3R,4R)-3-Hydroxymethyl-4-[3-(R,S)-hydroxy-3-(6-methoxyquinolin-4-yl)propyl]-1-[3-(3-trifluoromethylthiophenylthio)propyl]piperidine
(3R,4R)-3-Hydroxymethyl-4-[3-(R,S)-hydroxy-3-(6-methoxyquinolin4-yl)propyl]-1-[2-(3-cyanophenylthio)ethyl]piperidine
(3R,4R)-3-Hydroxymethyl-4-[3-(R,S)-hydroxy-3-(6-methoxyquinolin-4-yl)propyl]-1-[3-(3-cyanophenylthio)propyl]piperidine
(3R,4R)-3-Hydroxymethyl-4-[3-(R,S)-hydroxy-3-(6-methoxyquinolin-4-yl)propyl]-1-[2-(pyridin-2-yl)thioethyl]piperidine
(3R,4R)-3-Hydroxymethyl-4-[3-(R,S)-hydroxy-3-(6-methoxyquinolin-4-yl)propyl]-1-[3-(pyridin-2-yl)thiopropyl]piperidine
(3R,4R)-3-Hydroxymethyl-4-[3-(R,S)-hydroxy-3-(6-methoxyquinolin-4-yl)propyl]-1-[2-(3-fluoropyridin-2-yl)thioethyl]piperidine
(3R,4R)-3-Hydroxymethyl-4-[3-(R,S)-hydroxy-3-(6-methoxyquinolin-4-yl)propyl]-1-[3-(3-fluoropyridin-2-yl)thiopropyl]piperidine
(3R,4R)-3-Hydroxymethyl-4-[3-(R,S)-hydroxy-3-(6-methoxyquinolin-4-yl)propyl]-1-[2-(cycloheptylthio)ethyl]piperidine
(3R,4R)-3-Hydroxymethyl-4-[3-(R,S)-hydroxy-3-(6-methoxyquinolin-4-yl)propyl]-1-[3-(cycloheptylthio)propyl]piperidine
(3R,4R)-3-Hydroxymethyl-4-[3-(R,S)-hydroxy-3-(6-methoxyquinolin-4-yl)propyl]-1-[2-(tert-butylthio)ethyl]piperidine
(3R,4R)-3-Hydroxymethyl-4-[3-(R,S)-hydroxy-3-(6-methoxyquinolin-4-yl)propyl]-1-[3-(tert-butylthio)propyl]piperidine
(3R,4R)-3-Hydroxymethyl-4-[3-(R S)-hydroxy-3-(6-methoxyquinolin-4-yl)propyl]-1-[3-(2,3-difluorophenyl)prop-2-ynyl]piperidine
(3R,4R)-3-Hydroxymethyl-4-[3-(R,S)-hydroxy-3-(6-methoxyquinolin-4-yl)propyl]-1-[3-(2,5-difluorophenyl)prop-2-ynyl]piperidine
(3R,4R)-3-Hydroxymethyl-4-[3-(R,S)-hydroxy-3-(6-methoxyquinolin-4-yl)propyl]-1-[3-(3,5-difluorophenyl)prop-2-ynyl]piperidine
(3R,4R)-3-Hydroxymethyl-4-[3-(R,S)-hydroxy-3-(6-methoxyquinolin-4-yl)propyl]-1-[3-(2,6-difluorophenyl)prop-2-ynyl]piperidine
(3R,4R)-3-Hydroxymethyl-4-[3-(R,S)-hydroxy-3-(6-methoxyquinolin-4-yl)propyl]-1-[3-(2,3,5-trifluorophenyl)prop-2-ynyl]piperidine
(3R,4R)-3-Hydroxymethyl-4-[3-(R,S )-hydroxy-3-(6-methoxyquinolin-4-yl)propyl]-1-[3-(2,3,6-trifluorophenyl)prop-2-ynyl]piperidine
(3R,4 R)-3-Hydroxymethyl-4-[3-(R,S )-hydroxy-3-(6-methoxyquinolin-4-yl)propyl]-1-[3-(2-cyano-3-fluorophenyl)prop-2-ynyl]piperidine (3R,4R)-3-Hydroxymethyl-4-[3-(R,S)-hydroxy-3-(6-methoxyquinolin-4-yl)propyl]-1-[3-cyano-6-fluorophenyl)prop-2-ynyl]piperidine (3R,4R)-3-Hydroxymethyl-4-[3-(R,S)-hydroxy-3-(6-methoxyquinolin-4-yl)propyl]-1-[3-(2acetamido-5-fluorophenyl)prop-2-ynyl]piperidine (3R,4R)-3-Hydroxymethyl-4-[3-(R,S)-hydroxy-3-(6-methoxyquinolin-4-yl)propyl]-1-[3-trifluoromethoxyphenyl)prop-2-ynyl]piperidine (3R,4R)-3-Hydroxymethyl-4-[3-(R,S)-fluoro-3-(6-methoxyquinolin-4-yl)propyl]-1-[2-(3,5-difluorophenylthio)ethyl]piperidine (3R,4R)-3-Hydroxymethyl-4-[3-(R,S)-fluoro-3-(6-methoxyquinolin-4-yl)propyl]-1-[3-(3,5-difluorophenylthio)propyl]piperidine (3R,4R)-3-Hydroxymethyl-4-[3-(R,S)-fluoro-3-(6-methoxyquinolin-4-yl)propyl]-1-[2-(2,5-difluorophenylthio)ethyl]piperidine (3R,4R)-3-Hydroxymethyl-4-[3-(R,S)-fluoro-3-(6-methoxyquinolin-4-yl)propyl]-1-[3-(2,5-difluorophenylthio)propyl]piperidine (3R,4R)-3-Hydroxymethyl-4-[3-(R,S)-fluoro-3-(6-methoxyquinolin-4-yl)propyl]-1-[2-(2,3,4,6-tetrafluorophenylthio)ethyl]piperidine (3R,4R)-3-Hydroxymethyl-4-[3-(R,S)-fluoro-3-(6-methoxyquinolin-4-yl)propyl]-1-[3-(2,3,4,6-tetrafluorophenylthio)propyl]piperidine (3R,4R)-3-Hydroxymethyl-4-(3-(R,S)-fluoro-3-(6-methoxyquinolin-4-yl)propyl]-1-[2-(3-fluoro-5-chlorophenylthio)ethyl]piperidine (3R,4R)-3-Hydroxymethyl-4-[3-(R,S)-fluoro-3-(6-methoxyquinolin-4-yl)propyl]-1-[3-(3-fluoro-5-chlorophenylthio)propyl]piperidine (3R,4R)-3-Hydroxymethyl-4-[3-(R,S)-fluoro-3-(6-methoxyquinolin-4-yl)propyl]-1-[2-(3-trifluoromethoxyphenylthio)ethyl]piperidine (3R,4R)-3-Hydroxymethyl-4-[3-(R,S)-fluoro-3-(6-methoxyquinolin-4-yl)propyl]-1-[3-(3-trifluoromethoxyphenylthio)propyl]piperidine (3R,4R)-3-Hydroxymethyl-4-[3-(R,S)-fluoro-3-(6-methoxyquinolin-4-yl)propyl]-1-[2-(3-cyanophenylthio)ethyl]piperidine (3R,4R)-3-Hydroxymethyl-4-[3-(R,S)-fluoro-3-(6-methoxyquinolin-4-yl)propyl]-1-[3-(3-cyanophenylthio)propyl]piperidine (3R,4R)-3-Hydroxymethyl-4-[3-(R,S )-fluoro-3-(6-methoxyquinolin-4-yl)propyl]-1-[2-(pyridin-2-yl)thioethyl]piperidine (3R,4R)-3-Hydroxymethyl-4-[3-(R,S)-fluoro-3-(6-methoxyquinolin-4-yl)propyl]-1-[3-(pyridin-2-yl)thiopropyl]piperidine (3R,4R)-3-Hydroxymethyl-4-[3-(R,S)-fluoro-3-(6-methoxyquinolin-4-yl)propyl]-1-[2-(3-fluoropyridin-2-yl)thioethyl]piperidine (3R,4R)-3-Hydroxymethyl-4-[3-(R,S)-fluoro-3-(6-methoxyquinolin-4-yl)propyl]-1-[3-(3-fluoropyridin-2-yl)thiopropyl]piperidine (3R,4R)-3-Hydroxymethyl-4-[3-(R,S)-fluoro-3-(6-methoxyquinolin-4-yl)propyl]-1-[2-(cycloheptylthio)ethyl]piperidine (3R,4R)-3-Hydroxymethyl-4-[3-(R,S)-fluoro-3-(6-methoxyquinolin-4-yl)propyl]-1-[3-(cycloheptylthio)propyl]piperidine (3R,4R)-3-Hydroxymethyl-4-[3-(R,S)-fluoro-3-(6-methoxyquinolin-4-yl)propyl]-1-[2-(tert-butylthio)ethyl]piperidine (3R,4R)-3-Hydroxymethyl-4-[3-(R,S)-fluoro-3-(6-methoxyquinolin-4-yl)propyl]-1-[3-(tert-butylthio)propyl]piperidine (3R,4R)-3-Hydroxymethyl-4-[3-(R,S)-fluoro-3-(6-methoxyquinolin-4-yl)propyl]-1-[3-(2,3-difluorophenyl)prop-2-ynyl]piperidine (3R,4R)-3-Hydroxymethyl-4-[3-(R,S)-fluoro-3-(6-methoxyquinolin-4-yl)propyl]-1-[3-(2,5-difluorophenyl)prop-2-ynyl]piperidine (3R,4R)-3-Hydroxymethyl-4-[3-(R,S)-fluoro-3-(6-methoxyquinolin-4-yl)propyl]-1-[3-(3,5-difluorophenyl)prop-2-ynyl]piperidine (3R,4R)-3-Hydroxymethyl-4-[3-(R,S)-fluoro-3-(6-methoxyquinolin-4-yl)propyl]-1-[3-(2,6-difluorophenyl)prop-2-ynyl]piperidine (3R,4R)-3-Hydroxymethyl-4-[3-(R,S)-fluoro-3-(6-methoxyquinolin-4-yl)propyl]-1-[3-(2,3,5-trifluorophenyl)prop-2-ynyl]piperidine (3R,4R)-3-Hydroxymethyl-4-[3-(R,S)-fluoro-3-(6-methoxyquinolin-4-yl)propyl]-1-[3-(2,3,6-trifluorophenyl)prop-2-ynyl]piperidine (3R,4R)-3-Hydroxymethyl-4-[3-(R,S)-fluoro-3-(6-methoxyquinolin-4-yl)propyl]-1-[3-(2-cyano-3-fluorophenyl)prop-2-ynyl]piperidine (3R,4R)-3-Hydroxymethyl-4-[3-(R,S)-fluoro-3-(6-methoxyquinolin-4-yl)propyl]-1-[3-cyano-6-fluorophenyl)prop-2-ynyl]piperidine (3R,4R)-3-Hydroxymethyl-4-[3-(R,S)-fluoro-3-(6-methoxyquinolin-4-yl)propyl]-1-[3-(2-acetamido-5-fluorophenyl)prop-2-ynyl]piperidine (3R,4R)-3-Hydroxymethyl-4-[3-(R,S)-fluoro-3-(6-methoxyquinolin-4-yl)propyl]-1-[3-trifluoromethoxyphenyl)prop-2-ynyl]piperidine (3R,4R)-4-[3-(6-Methoxyquinolin-4-yl)propyl]-1-[2-(6-fluoropyridin-yl)thioethyl]piperidine-3-carboxylic acid (3R,4R)-4-[3-(6-Methoxyquinolin-4-yl)propyl]-1-[3-(6-fluoropyridin-2-yl)thiopropyl]piperidine-3-carboxylic acid (3R,4R)-4-[3-(R,S)-Hydroxy-3-(6-methoxyquinolin-4-yl)propyl]-1-[2-(6-fluoropyridin-2-yl)thioethyl]piperidine-3-carboxylic acid (3R,4R)-4-[3-(R,S)-Hydroxy-3-(6-methoxyquinolin-4-yl)propyl]-1-[3-(6-fluoropyridin-2-yl)thiopropyl]piperidine-3-carboxylic acid (3R,4R)-4-[3-(R,S)-Hydroxy-3-(6-methoxyquinolin-4-yl)propyl]-1-[2-(6-fluoropyridin-2-yl)thioethyl]piperidine-3-carboxylic acid (3R,4R)-4-[3-(R,S)-Fluoro-3-(6-methoxyquinolin-4-yl)propyl]-1-(3-(6-fluoropyridin-2-yl)thiopropyl]piperidine-3-carboxylic acid (3R,4R)-4-[3-(6-Methoxyquinolin-4-yl)propyl]-1-[2-(6-fluoropyridin-2-yl)thioethyl]piperidine-3-acetic acid (3R,4R)-4-[3-(6-Methoxyquinolin-4-yl)propyl]-1-[3-(6-fluoropyridin-2-yl)thiopropyl]piperidine-3-acetic acid (3R,4R)-4-[3-(R,S)-3-(6-Methoxyquinolin-4-yl)propyl]-1-[2-(6-fluoropyridin-2-yl)thioethyl]piperidine-3-acetic acid (3R,4R)-4-[3-(R,S)-Hydroxy-3-(6-methoxyquinolin-4-yl)propyl]-1-[3-(6-fluoropyridin-2-yl)thiopropyl]piperidine-3-acetic acid (3R,4R)-4-[3-(R,S)-Fluoro-3-(6-methoxyquinolin-4-yl)propyl]-1-[2-(6-fluoropyridin-2-yl)thioethyl]piperidine-3-acetic acid (3R,4R)-4-[3-(R,S)-Fluoro-3-(6-methoxyquinolin-4-yl)propyl]-1-[3-(6-fluoropyridin-2-yl)thiopropyl]piperidine-3-acetic acid (3R,4R)-4-[3-Hydroxy-3-(6-methoxyquinolin-4-yl)propyl]-1-[3-(2,3,5-trifluorophenyl)-prop-2-ynyl]piperidine-3-carboxylic acid.

The following examples, given without implied limitation, illustrate the present invention.

EXAMPLE 1

(3R,4R)-4-[3-(6-Methoxyquinolin-4-yl)propyl]-1-(3-phenylpropyl)piperidine-3-carboxylic acid A mixture of 0.2 g of 3-phenylpropyl (3R,4R)-4-[3-(6-methoxyquinolin-4-yl)propyl]-1-(3-phenylpropyl)piperidine-3-carboxylate, 3 cm³ dioxane, and 1 cm³ of normal aqueous sodium hydroxide was brought to 60° C., with stirring, for 16 hours. After cooling the reaction mixture and diluting with 25 cm³ of water, extraction was carried out 3 times with 20 cm³ of ether. The combined ethereal phases were washed 3 times with 10 cm³ of water.

After drying the ethereal solution over magnesium sulfate in the presence of animal charcoal and then filtering through paper, mixing was carried out under reduced pressure (5 kPa) at a temperature in the region of 25° C. 0.060 g of (3R,4R)-4-[3-(6-methoxyquinolin-4-yl)propyl]-1-(3-phenylpropyl)piperidine-3-carboxylic acid was obtained in the form of a colorless lacquer.

$^1$H N.M.R. spectrum (400 MHz, d6-(CD$_3$)$_2$SO, δ in ppm): from 1.35 to 1.95 (mt, 9H), 2.30 (broad t, J=11 Hz, 1H), 2.38 (broad d, J=11 Hz, 1H), from 2.45 to 2.65 (mt, 3H), 2.60 (t, J=7.5 Hz, 2H), 2.90 (unresolved peak, 1H), from 2.95 to 3.15 (unresolved peak, 3H), 3.95 (s, 3H), from 7.15 to 7.25 (mt, 3H), from 7.25 to 7.35 (mt, 3H), from 7.35 to 7.45 (mt, 2H), 7.93 (d, J=9 Hz,.1H), 8.63 (d, J=4.5 Hz, 1H).

3-Phenylpropyl (3R,4R)-4-[3-(6-methoxyquinolin-4-yl)propyl]-1-(3-phenylpropyl)piperidine-3-carboxylate 1.75 g of potassium carbonate and then 1.15 cm³ of 1-bromophenylpropane were added with stirring, at a temperature in the region of 25° C., to a solution of 0.91 g of (3R,4R)-4-[3-(6-methoxyquinolin-4-yl)propyl]piperidine-3-carboxylic acid hydrochloride in 20 cm³ of anhydrous dimethylformamide. The suspension was brought to a temperature in the region of 60° C. for 17 hours. After cooling, the mixture was poured onto 200 cm³ of water and extracted with 3 times 30 cm³ of ether. The combined ethereal extracts were washed with 2 times 20 cm³ of water. The ethereal solution was extracted with 20 cm³ of normal aqueous hydrochloric acid and twice with 20 cm³ of water. The combined aqueous extracts were rendered alkaline by addition of solid sodium hydrogencarbonate. After extracting with 3 times 20 cm³ of ether and washing the ethereal extracts with 3 times 20 cm³ of water, drying was carried out over magnesium sulfate in the presence of 0.1 g of animal charcoal. After filtering through paper and then concentrating under reduced pressure (5 kPa) at a temperature in the region of 30° C, 0.84 g of 3-phenylpropyl (3R,4R)-4-[3-(6-methoxyquinolin-4-yl)propyl]-1-(3-phenylpropyl)piperidine-3-carboxylate was obtained in the form of an oil with a light brown color.

(3R,4R)-4-[3-(6-Methoxyquinolin-4-yl)propyl]piperidine-3-carboxylic acid hydrochloride was prepared in the following way:

8.8 g of (3R,4R)-1-benzoyl-4-[3-(6-methoxyquinolin-4-yl)propyl]piperidine-3-carboxylic acid were heated, with stirring, in 200 cm³ of 5N aqueous hydrochloric acid at a temperature in the region of 100° C. for 48 hours. The reaction mixture was concentrated under reduced pressure (5 kPa) at a temperature in the region of 50° C. The residue was taken up in 100 cm³ of acetone. The mixture was concentrated under reduced pressure (5 kPa) at a temperature in the region of 60° C. This operation was repeated an additional two times. The residue was finally triturated in 100 cm³ of acetone until it crystallized. After filtering off the crystals and drying in a desiccator under reduced pressure (10 kPa), 7.2 g of (3R,4R)-4-[3-(6-methoxyquinolin4-yl)propyl] piperidine-3-carboxylic acid hydrochloride were obtained in the form of a beige solid melting at approximately 270° C. (melting with softening).

(3R,4R)-1-Benzoyl-4-[3-(6-methoxyquinolin-4-yl) propyl]piperidine-3-carboxylic acid was prepared in the following way:

25 g of (3R,4R)-1-benzoyl-4-[3-(6-methoxyquinolin-4-yl)propyl]-3-vinylpiperidine were dissolved in a mixture of 250 cm³ of carbon tetrachloride and 250 cm³ of acetonitrile. 51.3 g of sodium metaperiodate, in solution in 325 cm³ of water, was added at a temperature in the region of 20° C. with, good stirring, followed by 0.27 g of ruthenium trichloride hydrate. The slightly exothermic. reaction was maintained in the region of 30° C. for 15 minutes after the addition of the reactants. The mixture was stirred for 2 hours at room temperature. The suspension obtained was filtered and the insoluble material was washed with 5 times 80 cm³ of dichloromethane. After stirring the filtrate, the organic phase was separated by settling and the aqueous phase was saturated with sodium chloride and then extracted with two additional 300 cm³ portions of dichloromethane. The combined organic extracts were washed with water (3 times 200 cm³), dried over magnesium sulfate, filtered through paper, and then concentrated under reduced pressure (5 kPa) at a temperature in the region of 40° C. 23.2 g of an oil were obtained, which oil was purified by chromatography, at atmospheric pressure, on silica gel (particle size 20-45 μm; diameter 6.5 cm; height 30 cm), elution was carried out with a dichloromethane/methanol (97/3 by volume) mixture, and 400-cm³ fractions were collected. Fractions 4 to 8 were combined and then concentrated under reduced pressure (5 kPa). 11.8 g of a brown oil were obtained. The latter was dissolved in 60 cm³ of acetonitrile brought to reflux for a few minutes in the presence of 0.5 g of animal charcoal. After filtering, the solution obtained was cooled. The product which crystallized was filtered off and washed with 2 times 10 cm³ of acetonitrile. The solid was dried in a desiccator under vacuum in the presence of potassium hydroxide (10 kPa). 8.8 g of (3R,4R)-1-benzoyl-4-[3-(6-methoxyquinolin-4-yl)propyl]piperidine-3-carboxylic acid were obtained in the form of a beige solid melting at 160° C.

(3R,4R)-1-Benzoyl-4-[3-(6-methoxyquinolin-4-yl) propyl]-3-vinylpiperidine was prepared in the following way:

18.4 cm³ of triethylamine were added to a stirred solution of 20.8 g of (3R,4R)-4-[3-(6-methoxyquinolin-4-yl)propyl]-3-vinylpiperidine in 270 cm³ of chloroform, followed, over 1 hour, by a solution of 7.2 cm³ of benzoyl chloride in 50 cm³ of chloroform. After stirring the mixture at a temperature in the region of 20° C. for 1 hour 30 minutes, 100 cm³ of distilled water were added to the reaction mixture. The chloroform phase was separated by settling, washed with 2 times 100 cm³ of water, and then dried over magnesium sulfate. After filtering through paper, the chloroform solution was concentrated under reduced pressure (5 kPa) at a temperature in the region of 40° C. 25 g of (3R,4R)-1-benzoyl-4-[3-(6-methoxyquinolin-4-yl)propyl]-3-vinylpiperidine were obtained in the form of a brown oil.

(3R,4R)-4-[3-(6-Methoxyquinolin-4-yl)propyl]-3-vinylpiperidine can be obtained by application of the method disclosed in Patent Application FR 2,354,771, the disclosure of which is specifically incorporated by reference herein.

EXAMPLE 2

(3R,4R)-4-[3-(6-Methoxyquinolin-4-yl)propyl]-1-[3-(thien-2-yl)prop-2-ynyl)]piperidine-3-carboxylic acid dihydrochloride 0.057 cm$^3$ of 2-iodothiophene and 1.42 cm$^3$ of triethylamine were added with stirring to a solution of 0.185 g of (3R,4R)-4-[3-(6-methoxyquinolin-4-yl)propyl]-1-(prop-2-ynyl)piperidine-3-carboxylic acid in 4 cm$^3$ of anhydrous dimethylformamide, followed by 0.038 g of tetrakis(triphenylphosphine)palladium and 0.019 g of cuprous iodide. The solution was stirred for 20 hours at a temperature in the region of 20° C. 75 cm$^3$ of ethyl acetate and 75 cm$^3$ of water were added to the reaction mixture. After stirring the mixture, the aqueous phase was separated by settling and then neutralized to pH 6 by addition of a 0.1N aqueous hydrochloric acid solution. The aqueous phase was extracted with 50 cm$^3$ of ethyl acetate; the extract was washed with 2 times 75 cm$^3$ of a saturated aqueous sodium chloride solution. The organic solution was dried over magnesium sulfate, filtered, and then evaporated under reduced pressure (5 kPa) at a temperature in the region of 40° C. 0.090 g of an oil with a yellow color was obtained, which oil was purified by chromatography on a column of silica gel (particle size 20-45 µm; diameter 1 cm; height 30 cm), elution was carried out, under a pressure of 50 kPa of nitrogen, with a dichloromethane/methanol (92/8 by volume) mixture, and 50-cm$^3$ fractions were collected. Fractions 12 to 15 were combined and concentrated under reduced pressure (5 kPa) at a temperature in the region of 40° C. The oil obtained was taken up in 1 cm$^3$ of a 4N solution of hydrochloric acid in dioxane. After concentrating under the same conditions as above and taking up the residue in 10 cm$^3$ of diethyl ether, 0.030 g of (3R,4R)-4-[3-(6-methoxyquinolin-4-yl)propyl]-1-[3-(thien-2-yl)prop-2-ynyl)]piperidine-3-carboxylic acid dihydrochloride was collected, after filtration, in the form of a white solid.

$^1$H N.M.R. spectrum (400 MHz, d6-(CD$_3$)$_2$SO, δ in ppm): from 1.15 to 2.10 and from 3.00 to 3.65 (mts, 14H), 3.98 (s, 3H), from 4.25 to 4.55 (unresolved peak, 2H), 7.16 (dd, J=5 and 3 Hz, 1H), from 7.40 to 7.60 (mt, 4H), 7.75 (broad d, J=5 Hz, 1H), 7.96 (mt, 1H), 8.79 (mt, 1H), from 10.50 to 10.70 (broad unresolved peak, 1H), from 12.85 to 13.15 (broad unresolved peak, 1H).

(3R,4R)-4-[3-(6-Methoxyquinolin-4-yl)propyl]-1-(prop-2-ynyl)piperidine-3-carboxylic acid was prepared in the following way:

0.3 g of (prop-2-ynyl) (3R,4R)-4-[3-(6-methoxyquinolin-4-yl)propyl]-1-(prop-2-ynyl)piperidine-3-carboxylate in 3 cm$^3$ of dioxane and 1.48 cm$^3$ of N sodium hydroxide were heated, with stirring, at a temperature in the region of 70° C. for 17 hours. The reaction mixture was concentrated under reduced pressure (5 kPa) at a temperature in the region of 50° C. 1.48 cm$^3$ of normal aqueous hydrochloric acid were added to the solid residue obtained, followed by 10 cm$^3$ of water. The solution obtained was extracted with 5 times 20 cm$^3$ of dichloromethane. The organic extracts were combined and then concentrated under reduced pressure (5 kPa). 0.189 g of (3R,4R)-4-[3-(6-methoxyquinolin-4-yl)propyl]-1-(prop-2-ynyl)piperidine-3-carboxylic acid was obtained in the form of a foam with a white color.

Prop-2-ynyl (3R,4R)-4-[3-(6-methoxyquinolin-4-yl)propyl]-1-(prop-2-ynyl)piperidine-3-carboxylate was prepared in the following way:

0.95 g of potassium carbonate was added to a solution of 0.835 g of (3R,4R)-4-[3-(6-methoxyquinolin-4-yl)propyl] piperidine-3-carboxylic acid hydrochloride in 15 cm$^3$ of anhydrous dimethylformamide, followed by 0.36 cm$^3$ of propargyl bromide. The mixture was stirred under a nitrogen atmosphere at a temperature in the region of 70° C. for 18 hours. 100 cm$^3$ of ethyl acetate and 100 cm$^3$ of distilled water were added to the reaction mixture. The organic phase was separated by settling and then washed with 5 times 40 cm$^3$ of water and 2 times 50 cm$^3$ of a saturated sodium chloride solution. The organic solution was dried over magnesium sulfate, filtered, and then evaporated under reduced pressure (5 kPa) at a temperature in the region of 40° C. to maximum concentration. The oil obtained was purified by chromatography on a column of silica gel (particle size 20-45 µm; diameter 2 cm; height 40 cm), elution was carried out, under a nitrogen pressure of 50 kPa, with ethyl acetate, and 50-cm$^3$ fractions were collected. Fractions 17 to 21 were combined and concentrated under reduced pressure (5 kPa) at a temperature of 40° C. 0.300 g of prop-2ynyl (3R,4R)-4-[3-(6-methoxyquinolin-4-yl) propyl]-1-(prop-2-ynyl)-3-piperidinecarboxylate was obtained in the form of an oil with a yellow color.

(3R,4R)-4-[3-(6-methoxyquinolin-4-yl)propyl] piperidine-3-carboxylic acid hydrochloride was obtained as described in Example 1.

EXAMPLE 3

(3R,4R)-4-[3-(6-methoxyquinolin-4-yl)propyl]-1-[2-(3-fluorophenylthio)ethyl]piperidine-3-carboxylic acid dihydrochloride A mixture of 0.54 g of methyl (3R,4R)-4-[3-(6-methoxyquinolin-4-yl)propyl]-1-[2-(3-fluorophenylthio) ethyl]piperidine-3-carboxylate in 4 cm$^3$ of methanol and 0.8 cm$^3$ of 5N aqueous sodium hydroxide was heated with stirring at 60° C. for 20 hours. After evaporating the solvents under reduced pressure (5 kPa) at a temperature in the region of 40° C. the residue obtained was taken up in 10 cm$^3$ of water and then acidified with 0.4 cm$^3$ of concentrated hydrochloric acid. The solution was evaporated under the same conditions and then the residue obtained was triturated in a dichloromethane/methanol (90/10 by volume) mixture. The insoluble material was filtered off and washed with 5 cm$^3$ of dichloromethane. The filtrate was dried over sodium sulfate and then concentrated under reduced pressure (5 kPa) at a temperature in the region of 40° C. The residue was triturated in 10 cm$^3$ of diisopropyl ether and then 1 cm$^3$ of a 5N solution of hydrochloric acid in diisopropyl ether was added with stirring. The crystals were separated by filtration and then washed with 2 times 5 cm$^3$ of diisopropyl ether. After drying in the air, 0.45 g of (3R,4R)-4-[3-(6-methoxyquinolin-4-yl)propyl]-1-[2-(3-fluorophenylthio) ethyl]piperidine-3-carboxylic acid dihydrochloride was obtained in the form of an amorphous solid with a pale yellow color which melts in the region of 140° C. with softening.

Infrared spectrum (KBr): 3058 and 3012 cm$^{-1}$ (aromatic CH ν), 2935 and 2862 cm$^{-1}$ (CH$_2$ ν), 3000 and 2750 cm$^{-1}$ (acidic OH ν), 2800 and 1900 cm$^{-1}$ (N$^+$H ν (tertiary amine salt + quinoline salt)), 1719 cm$^{-1}$ (acidic C=O ν), 1618, 1600, 1578, 1541, and 1496 cm$^{-1}$ (aromatic nuclei C=C ν), 1274 cm$^{-1}$ (acidic C—O ν), 1251 and 1216 cm$^{-1}$ (either C—O ν$_{as}$), 1021 cm$^{-1}$ (ether C—O ν$_s$+alcohol C—O ν), 847 cm$^{-1}$ (4,6-disubstituted quinoline CH γ), 781 and 729 cm$^{-1}$ (1,3-disubstituted phenyl CH γ).

Mass spectrum (EI-m/z):=482 (M$^+$), 438 (M-CO$_2$)$^+$, 341 (M-C$_7$H$_6$SF)$^+$ base peak, 297, 341, (M-CO$_2$)$^+$, 186 (C$_{12}$H$_{12}$NO$^+$), 128 (C$_6$H$_5$SF$^+$), 36 (HCl$^+$).

Methyl (3R,4R)-4-[3-(6-methoxyquinolin-4-yl)propyl]-1-[2-(3-fluorophenylthio)ethyl]piperidine-3-carboxylate was prepared in the following way:

By carrying out the preparation by analogy with

Example 4 hereinbelow but from methyl (3R , 4R)-4-[3-(6-methoxyquinolin-4-yl)propyl]piperidine-3-carboxylate hydrochloride and 2-bromo-1-(3-fluorophenyl)thioethane, 0.55 g of methyl (3R,4R)-4-[3-(6-methoxyquinolin-4-yl)propyl]-1-[2-(3-fluorophenylthio)ethyl]piperidine-3-carboxylate was obtained in the form of a viscous oil with a yellow color.

Infrared spectrum ($CCl_4$): 2949 $cm^{-1}$, (aliphatic CH ν), 1737 $cm^{-1}$ (C=O ν), 1227 $cm^{-1}$ (ether C—O ν), 845 $cm^{-1}$ (quinoline CH γ).

Methyl (3R,4R)-4-[3-(6-methoxyquinolin-4-yl)propyl]piperidine-3-carboxylate hydrochloride was prepared under the conditions of Example 6.

EXAMPLE 4

(3R,4R)-4-[3-(6-methoxyquinolin-4-yl)propyl]-1-]2-(phenylthio)ethyl[piperidine-3-carboxylic acid A suspension of 0.7 g of methyl (3R,4R)-4-[3-(6-methoxyquinolin-4-yl)propyl]-1-[2-(phenylthio)ethyl]piperidine-3-carboxylate in 5 $cm^3$ of methanol, to which methanol had been added 2.9 $Cm^3$ of N aqueous sodium hydroxide, was stirred for 2 hours at a temperature in the region of 80° C. The solution obtained was neutralized with 0.18 $cm^3$ of acetic acid and then evaporated under reduced pressure (5 kPa) at a temperature in the region of 40° C. The residue obtained was purified by chromatography at atmospheric pressure on a column of silica gel (particle size 40–63 μm; diameter 3 cm; height 20 cm), elution was carried out with a dichloromethane/ethanol (90/10 by volume) mixture, and 20-$cm^3$ fractions were collected. Fractions 21 to 52 were region of 40° C. 0.53 g of (3R,4R)-4-[3-(6-methoxyquinolin-4-yl)propyl]-1-[2-(phenylthio)ethyl]piperidine-3-carboxylic acid was obtained in the form of an oil with a beige color.

$^1$H N.M.R. spectrum (400 MHz, d6-$(CD_3)_2SO$, δ in ppm): from 1.35 to 1.95 (mt, 7H), 2.28 (broad t, J=10.5 Hz, 1H), 2.43 (broad d, J=10.5 Hz, 1H), 2.59 (mt, 1H), 2.64 (t, J =7 Hz, 2H), 2.77 (unresolved peak, 1H), 2.93 (unresolved peak, 1H), 3.03 (mt, 2H), 3.13 (mt, 2H), 3.95 (s, 3H), 7.21 (tt, J=7.5 and 2 Hz, 1H), from 7.25 to 7.45 (mt, 7H ) 7.39 (d, J=9 Hz, 1H), 8.63 (d, J=4.5 Hz, 1H).

Methyl (3R,4R)-4-[3-(6-methoxyquinolin-4-yl)propyl]-1-(2-phenylthio)ethyl]piperidine-3-carboxylate was prepared in the following way:

1 g of methyl (3R,4R)-4-[3-(6-methoxyquinolin-4-yl)propyl]piperidine-3-carboxylate hydrochloride and 1 g of potassium carbonate were stirred at a temperature in the region of 20° C. in 100 $cm^3$ of acetonitrile for 20 minutes. After addition of 0.61 g of 2-bromo-1-phenylthioethane, dissolved beforehand in 5 $cm^3$ of acetonitrile, the mixture was heated at a temperature in the region of 60° C. for 5 hours. After addition of 20 $cm^3$ of dimethylformamide and an additional 0.61 g of 2-bromo-1-phenylthioethane, heating was maintained for a further 8 hours 30 minutes. After cooling, the reaction mixture was filtered; the solution obtained was concentrated under reduced pressure (5 kPa) at a temperature in the region of 70° C. The residue was taken up in 50 $cm^3$ of ethanol and then concentrated again under the same conditions as above. The residue was diluted with 30 $cm^3$ of water and then extracted with 3 times 20 $cm^3$ of dichloromethane. The combined extracts were dried over magnesium sulfate and concentrated under reduced pressure (5 kPa) at a temperature in the region of 40° C. 1 g of an oil was obtained, which oil was purified by chromatography at atmospheric pressure on a column of silica gel (particle size 40–63 μm; diameter 3.5 cm; height 20 cm), elution was carried out with a dichloromethane/ethanol (90/10 by volume) mixture, and 25-$cm^3$ fractions were collected. Fractions 15 to 26 were combined and then concentrated under reduced pressure (5 kPa ) at a temperature in the region of 40° C. 0.79 g of methyl (3R,4R)-4-[3-(6-methoxyquinolin-4-yl)propyl]-1-(2-phenylthioethyl)piperidine-3-carboxylate was obtained in the form of an oil with a yellow color.

Methyl (3R,4R)-4-[3-(6-methoxyquinolin-4-yl)propyl]piperidine-3-carboxylate hydrochloride was prepared under the conditions of Example 6.

EXAMPLE 5

(3R,4R)-4-13-(R,S)-Hydroxy-3-(6-methoxyquinolin-4-yl)propyl]-1-(3-phenylpropyl)piperidine-3-carboxylic acid dihydrochloride A mixture composed of 0.5 g of methyl (3R,4R)-4-[3-(R, S)-hydroxy-3-(6-methoxyquinolin-4-yl)propyl]-1-(3-phenylpropyl)piperidine-3-carboxylate, 0.8 $cm^3$ of 5N sodium hydroxide, and 5 $cm^3$ of methanol was stirred at 70° C. for 3 hours. After evaporating the solution obtained under reduced pressure (5 kPa) at a temperature in the region of 40° C., a solid residue (0.67 g) was obtained, which residue was taken up in 10 $cm^3$ of dichloromethane. The mixture was cooled to a temperature in the region of 0° C. and then 1 $cm^3$ of a 6.3N solution of hydrochloric acid in diisopropyl ether was added. 10 $cm^3$ of ethyl ether were added dropwise with stirring. After standing for 15 minutes, the suspension was filtered off and then washed with 2 times 5 $cm^3$ of a dichloromethane/ethyl ether (5/5 by volume) mixture and then 2 times 5-$cm^3$ of ether. 0.34 g of a solid was obtained, which solid was purified by chromatography at atmospheric pressure on a column of silica gel (particle size 20–45 μm; diameter 1.5 cm; 8.5 g), elution was carried out with a dichloromethane/methanol (80/20 by volume) mixture, and 3-$cm^3$ fractions were collected. Fractions 7 to 35 were combined and concentrated under reduced pressure (5 kPa) at a temperature in the region of 40° C. The residue obtained was triturated by twice in 10 $cm^3$ of ethyl ether and then concentrated under reduced pressure under the same conditions as above. 0.14 g of (3R,4R)-4-[3-(R,S)-hydroxy-3-(6-methoxyquinolin-4-yl)propyl]-1-(3-phenylpropyl)piperidine-3-carboxylic acid dihydrochloride was obtained in the form of a solid with a cream color which melts in the region of 168° C. with softening.

$^1$H N.M.R. spectrum (300 MHz, d6-$(CD_3)_2SO$, with addition of a few drops of d4-$CD_3COOD$, δ in ppm): from 1.35 to 2.30 and from 2.90 to 3.65 (mts, 12H), 3.99 (s, 3H), from 4.20 to 4.50 (mt, 2H), from 5.40 to 5.60 (mt, 1H), from 7.25 to 7.70 (mt, 5H), from 770 to 7.80 (mt, 1H), 7.99 (mt, 1H), 8.20 (d, J 9 Hz, 1H), 9.01 (broad d, J 5 Hz, 1H).

Methyl (3R,4R)-4-[3-(R,S)-hydroxy-3-(6-methoxyquinolin-4-yl)propyl]-1-(3-phenylpropyl)piperidine-3-carboxylate 0.15 g of sodium borohydride was added portionwise at a temperature in the region of 20° C. and under an inert atmosphere to a stirred solution of 1.59 g of methyl (3R, 4R)-4-[3-oxo-3-(6-methoxyquinolin-4-yl)propyl]-1-(3- phenylpropyl)piperidine-3-carboxylate in 25 cm³ of methanol. The mixture was subsequently stirred for 75 minutes at a temperature in the region of 20° C. 15 cm³ of distilled water were then added while maintaining the same temperature. The mixture, with a milky appearance, was concentrated under reduced pressure (5 kPa) at a temperature in the region of 30° C. The residue obtained was taken up in 40 cm³ of distilled water to which have been added 80 cm³ of dichloromethane, stirred, and then separated by settling. The organic phase was withdrawn and then washed with one times 40 cm of water and dried over magnesium sulfate. After filtering through paper and then evaporating the solvent under reduced pressure (5 kPa) at a temperature in the region. of 40° C., 1.39 g of methyl (3R,4R)-4-[3-(R,S)-hydroxy-3-(6-methoxyquinolin-4-yl)propyl]-1-(3-phenylpropyl)piperidine-3-carboxylate were obtained in the form of a sticky solid with a foamy appearance and an orange color.

Methyl (3R,4R)-4-[3-oxo-3-(6-methoxyquinolin-4-yl) propyl]-1-(3-phenylpropyl)piperidine-3-carboxylate was prepared in the following way:

A suspension of 4.51 g of methyl (3R,4R)-4-[3-oxo-3-(6-methoxyquinolin-4-yl)propyl]piperidine-3-carboxylate and 2.3 g of potassium carbonate in 75 cm³ of acetone was heated with stirring at a temperature in the region of 58° C. A solution of 2.5 cm³ of 1-bromo-3-phenylpropane in 7.5 cm³ of acetone was added dropwise at this temperature. Heating was extended for 19 hours. After cooling, the reaction mass was filtered; the cake was washed with 2 times 30 cm³ of acetone. The filtrate and the wash liquors were combined and concentrated under reduced pressure (5 kPa) at a temperature in the region of 30° C. 7.12 g of a product were obtained in the form of an oil which was purified by chromatography at atmospheric pressure on a column of silica gel (particle size 20–45 μm; diameter 7 cm; mass 7.12 g), elution was carried out with a chloroform/methanol/aqueous ammonia (12/2.25/0.38 by volume) mixture, and 65-cm³ fractions were collected. Fractions 9 to 14 were combined and then concentrated under reduced pressure (5 kPa) at a temperature in the region of 30° C. 6.7 g of an oil were obtained, which oil was subjected to a second purification by chromatography at atmospheric pressure on a column of silica gel (particle size 20–45 μm; diameter 4.8 cm, mass 336 g), elution was carried out with a mixture of ethyl acetate and methanol (9/1 by volume), and 20-cm³ fractions were collected. Fractions 71 to 122 were combined and then concentrated under reduced pressure (5 kPa) at a temperature in the region of 30° C. 1.66 g of methyl (3R,4R)-4-[3-oxo-3-(6-methoxyquinolin-4-yl)propyl1-1-(3-phenylpropyl)piperidine-3-carboxylate were obtained in the form of an oil with a brown color.

Methyl (3R,4R)-4-[3-oxo-3-(6-methoxyquinolin-4-yl) propyl]piperidine-3-carboxylate was prepared in the following way:

A solution of 19.4 g of (3R,4R)-4-[3-oxo-3-(6-methoxyquinolin4-yl)propyl]-1-1(t-butyloxycarbonyl) piperidine-3-carboxylic acid (80% content) in 355 cm³ of methanol was cooled to a temperature in the region of −30° C. 7.7 cm³ of thionyl chloride were added with stirring while maintaining the temperature between −25 and −30° C. After the addition, the mixture was maintained at approximately −30° C. for 30 minutes and then the temperature was allowed to return to approximately 20° C. After stirring at room temperature for 19 hours, the reaction mixture was concentrated under reduced pressure (5 kPa) at a temperature in the region of 30° C. The residue obtained was taken up in 300 cm³ of water to which have been added 200 cm³ of dichloromethane and was then stirred. The organic phase was separated by settling; the aqueous phase was again extracted with 200 cm³ of dichloromethane. The aqueous solution was brought to pH 8 by gradual addition of solid sodium hydrogencarbonate. After extracting the alkaline solution obtained with 3 times 200 cm³ of dichloromethane, the combined organic extracts were washed with 2 times 200 cm³ of water and then dried over magnesium sulfate. After filtering through paper, the organic solution was concentrated under reduced pressure (5 kPa) at a temperature in the region of 40° C. 4.51 g of methyl (3R,4R)-4-[3-oxo-3-(6-methoxyquinolin-4-yl)propyl]piperidine-3-carboxylate were obtained in the form of a lacquer with a brown color.

(3R,4R)-4-[3-Oxo-3-(6-methoxyquinolin-4-yl)propyl]-1-(tert-butoxycarbonyl)piperidine-3-carboxylic acid was prepared in the following way:

A solution of 36 g of (3R,4R)-4-[3-oxo-3-(6-methoxyquinolin-4-yl)propyl]-3-vinylpiperidine in 54 cm³ of acetone was cooled to a temperature in the region of 0° C. 150 cm³ of 3M sulfuric acid were added over 15 minutes, with stirring, while maintaining the temperature between 0 and 5° C. The temperature was lowered to approximately 0° C. and a solution of 32 g of sodium permanganate in 200 cm³ of distilled water was added dropwise to the mixture. The reaction mixture was stirred for an additional 45 minutes at a temperature of between 10 and 15° C. and then the temperature was allowed to rise to within the region of 20° C. After stirring for 3 hours at this temperature, the reaction mass was cooled to a temperature in the region of 0° C. and then 160 cm³ of 38% potassium hydroxide solution were added slowly at a temperature of less than 10° C. After stirring for 30 minutes at a temperature in the region of 10° C., the mixture was filtered. The cake was taken up in 300 cm³ of water to which have been added 15 cm⁻¹ of 38% potassium hydroxide solution and was stirred for 20 minutes. After filtering and then washing the cake with 2 times 200 cm³ of distilled water, the filtrates were combined and then 24 g of di-tert-butyl dicarbonate were added. The solution was stirred at a temperature in the region of 20° C. for 15 hours. After adding one liter of ethyl acetate and stirring, the mixture was separated by settling and the separated aqueous phase was then brought to pH 5 by addition of 38 cm³ of 37% concentrated aqueous hydrochloric acid. The mixture was extracted again with 5 times 1 liter of ethyl acetate. The extracts were combined and then washed with 2 times 1 liter of water saturated with sodium chloride. The organic solution was dried over magnesium sulfate, filtered through paper, and concentrated under reduced pressure (5 kPa) at a temperature in the region of 40° C. 21.2 g of (3R,4R)-4-[3-oxo-3(6-methoxyquinolin-4-yl)propyl1-1-(t-butyloxycarbonyl)piperidine-3-carboxylic acid were obtained in the form of a brown solid melting at 114° C. with softening.

(3R,4R)-4-[3-Oxo-3-(6-methoxyquinolin-4-yl)propyl]-3-vinylpiperidine was obtained by application of the method disclosed in Patent Application FR 2,354,771, the disclosure of which is specifically incorporated by reference herein.

EXAMPLE 6

(3R,4R)-4-[3-(6-Methoxyquinolin-4-yl)propyl]-1-(3-phenylprop-2-ynyl)piperidine-3-carboxylic acid A solution of 0.25 g of methyl (3R,4R)-4-[3-(6-methoxyquinolin-4-yl)propyl]-1-(3-phenylprop-2-ynyl) piperidine-3-carboxylate in 6 cm³ of methanol has 0.41 cm³ of 5N aqueous sodium hydroxide added to it and was then heated at a temperature in the region of 57° C. for 18 hours 30 minutes under an inert atmosphere. The mixture was cooled and then concentrated under reduced pressure (2 kPa) at a temperature in the region of 40° C. The residue was taken up in 10 cm³ of water, acidified with 2 cm³ of N aqueous hydrochloric acid, and concentrated under reduced pressure (2 kPa) at a temperature in the region of 45° C. The residue obtained was triturated in 10 cm³ of a dichloromethane/methanol (90/10 by volume) mixture and then filtered. The residue obtained was triturated in 10 cm³ of a dichloromethane/methanol (90/10 by volume) mixture and then filtered off. The insoluble material was washed with 2 times 10 cm³ of dichloromethane. The combined organic filtrates were concentrated under reduced pressure (2 kPa) at a temperature in the region of 30° C. A 0.22 g residue was obtained, which residue was stirred in a mixture of 20 cm³ of water and 15 cm³ of dichloromethane. The aqueous phase was separated by settling and then extracted with 3 times 10 cm³ of dichloromethane. This aqueous phase was concentrated to dryness under reduced pressure (5 kPa) at a temperature in the region of 40° C. The residue was triturated in 10 cm³ of a dichloromethane/methanol (90/10 by volume) mixture. The insoluble material was filtered off and then the cake was washed with 5 cm³ of the same mixture. The filtrate was dried over magnesium sulfate, then concentrated under reduced pressure under the same conditions as above and finally dried under partial pressure (13 Pa) at a temperature in the region of 40° C. for 2 hours. 0.11 g of (3R,4R)-4-[3-(6-methoxyquinolin-4-yl)propyl]1-(3-phenylprop-2-ynyl)piperidine-3-carboxylic acid was obtained in the form of a foamy solid with a pale yellow color melting at approximately 166° C. with softening. Infrared spectrum (KBr): 2931, 2859 cm⁻¹ ($CH_2$ ν), 3000 and 2750 cm⁻¹ (acidic OH ν), 2800 and 1900 cm⁻¹ ($N^+H$ ν (tertiary amine salt+quinoline salt)), 1719 cm⁻¹ (acidic C=O ν), 1618, 1601, 1542, and 1492 cm⁻¹ (aromatic nuclei C=C ν), 1275 cm⁻¹ (acidic C—O ν), 1225 cm⁻¹ (ether C—O $ν_{as}$), 1022 cm⁻ (ether C—O $ν_s$), 846 cm⁻¹ (4,6-disubstituted quinoline CH γ), 761 and 693 cm⁻¹ (monosubstituted phenyl CH γ).

Mass spectrum (EI-m/z): 442 (M⁺), 398 (M-$CO_2$)⁺, 327 (M-$C_9H_7$)⁺, 283, 327 (M-$CO_2$)⁺, 186 ($C_{12}H_{12}ON^+$), 115 ($C_9H_7^+$), 44 ($CO_2^+$), 327 (M-$C_9$ $H_7$)⁺, 283, 327 (M-$CO_2$)⁺, Methyl (3R,4R)4-[3-(6-methoxyquinolin-4-yl) propyl]-1-(3-phenylprop-2-ynyl)piperidine-3-carboxylate 0.138 g of tetrakis(triphenylphosphine)palladium, 0.041 g of triphenylphosphine, and 0.070 g of cuprous iodide were added under an inert atmosphere, at a temperature in the region of 20° C., to a stirred solution of 0.7 g of methyl (3R,4R)-4-[3-(6-methoxy-quinolin-4-yl)propyl]-1-(prop-2-ynyl)piperidine-3-carboxylate in 12 cm³ of acetonitrile. 0.56 g of iodobenzene was subsequently added, followed by 0.51 cm³ of triethylamine. The mixture was stirred for 22 hours at a temperature in the region of 20° C. and was then filtered. The cake was washed with 3 times 10 cm³ of acetonitrile. The combined filtrates have 100 cm³ of dichloromethane and 100 cm³ of water added to them and were then stirred. The organic phase was separated by settling and washed with 3 times 50 cm³ of a saturated sodium chloride solution. After drying over magnesium sulfate and then filtering, the organic solution was evaporated under reduced pressure (2 kPa) at a temperature in the region of 40° C. 1.1 g of an oil were obtained, which oil was purified by chromatography under argon pressure (50 kPa) on a column of silica gel (particle size 40–60 μm; diameter 3 cm, 65 g), elution was carried out with ethyl acetate, and 2.5-cm³ fractions were collected. Fractions 52 to 210 were combined and concentrated under reduced pressure (2 kPa) at a temperature in the region of 35° C. 0.64 g of methyl (3R,4R)-4-[3-(6-methoxyquinolin-4-yl)propyl]-1-(3-phenylprop-2-ynyl) piperidine-3-carboxylate was obtained in the form of an oil with a light brown color.

Methyl (3R,4R)-4-[3-(6-methoxyquinolin-4-yl)propyl]-1-(prop-2-ynyl)piperidine-3-carboxylate was prepared in the following way:

14.7 cm³ of triethylamine were added, at a temperature in the region of 20° C., to a stirred suspension of 10 g of methyl (3R,4R)-4-(3-(6-methoxyquinolin-4-yl)propyl]piperidine-3-carboxylate hydrochloride in 100 cm³ of anhydrous dimethylformamide and under an inert atmosphere, followed, after 45 minutes, by 3 cm³ of propargyl bromide diluted in 10 cm³ of anhydrous dimethylformamide. After stirring for 15 minutes at a temperature in the region of 20° C., the mixture was heated for 4 hours at a temperature in the region of 45° C. After cooling, the reaction mixture was poured into a mixture of 250 cm³ of ethyl acetate and 250 cm³ of distilled water. The mixture was stirred for a few minutes and then the organic phase was. separated by settling. The aqueous phase was extracted with 2 times 250 cm³ of ethyl acetate. The organic phases were combined, washed with 3 times 200 cm³ of distilled water, and dried over magnesium sulfate. After filtering and then evaporating the solvent under reduced pressure (2 kPa) at a temperature in the region of 40° C., 7.8 g of an oil were obtained, which oil was purified by chromatography under argon pressure (50 kPa) on a column of silica gel (particle size 40–63 μm; diameter 7 cm; 475 g), elution was carried out with ethyl acetate, and 8-cm³ fractions was collected. Fractions 468 to 612 were combined and then concentrated under reduced pressure (2 kPa) at a temperature in the region of 45° C. 4.7 g of methyl (3R,4R)-4-[3-(6-methoxyquinolin-4-yl)propyl]-1-(prop-2-ynyl)piperidine-3-carboxylate were obtained in the form of an oil with an orange color.

Methyl (3R,4R)-4-[3-(6-methoxyquinolin-4-yl)propyl] piperidine-3-carboxylate hydrochloride was prepared in the following way:

2 cm³ of thionyl chloride were added dropwise to a stirred suspension, cooled to a temperature in the region of –30° C. with a cooling bath of acetone and solid carbon dioxide, of 4.29 g of (3R,4R)-4-[3-(6-methoxyquinolin-4-yl)propyl]-1-(tert-butyloxy-carbonyl)piperidine-3-carboxylic acid in 50 cm³ of methanol. The solution obtained was brought to a temperature in the region of 20° C. and the reaction mixture was stirred for 16 hours at this temperature. After evaporating the solution under reduced pressure (5 kPa) at a temperature in the region of 40 ° C., the residue obtained was triturated in approximately 30 cm3 of diisopropyl ether. The crystals obtained were filtered off, washed with 2 times 10 cm³ of diisopropyl ether, and then dried in the air. 4.20 g of methyl (3R,4R)-4-[3-(6-methoxyquinolin-4-yl)propyl] piperidine-3-carboxylate hydrochloride were obtained in the form of a solid with a light yellow color which melts with softening at a temperature in the region of 140° C.

(3R,4R)-4-[3-(6-methoxyquinolin-4-yl)propyl]-1-(tert-butyloxycarbonyl)piperidine-3-carboxylic acid was prepared in the following way:

3 g of (3R,4R)-4-[3-(6-methoxyquinolin-4-yl)propyl]-3-vinylpiperidine were dissolved in 3 cm³ of acetone. 14.5 cm³ of 3M sulfuric acid, cooled beforehand to a temperature in the region of 5° C., were added with stirring to this solution, which was cooled to the same temperature with a bath of ice and acetone. A solution of 4.64 g of sodium permanganate monohydrate in 25 cm³ of water was added over 30 minutes to the solution obtained while maintaining a temperature of between 0 and 7° C. The reaction mixture was stirred for 4 hours at a temperature of between 10 and 17° C. The reaction mass was filtered; the insoluble material was washed with 2 times 10 cm³ of water. On the one hand, a solution with an orange color and, on the other hand, an inorganic mass with a black color were obtained. The orange solution was brought to pH 10 by addition of 4.6 g of sodium carbonate. The mixture was filtered: a solution (1) and an insoluble inorganic material (2) were obtained. The inorganic mass with a black color was stirred for 30 minutes in 20 cm³ of water, after which the pH was brought to 12 by addition of 2 cm³ of potassium hydroxide solution. After filtering the mixture, a solution (3) and an insoluble inorganic material (4) were. obtained. The insoluble materials (2) and (4) were stirred for 15 minutes in 15 cm³ of water to which had been added 3 cm³ of potassium hydroxide solution. The suspension was filtered. A solution (5) was obtained. The aqueous solutions (1), (3), and (5) were combined, 2.31 g of di-tert-butyl dicarbonate were added, and stirring was carried out for 15 hours at a temperature in the region of 20° C. The mixture was extracted with 6 times 10 cm³ of ethyl acetate. The organic phases were combined and washed with 20 cm³ of water and then with 20 cm³ of a saturated aqueous sodium chloride solution. After drying with sodium sulfate, filtering, and then concentrating under reduced pressure (5 kPa) at a temperature in the region of 35° C., 2.86 g of (3R,4R)-4-[3-(6-methoxyquinolin-4-yl)propyl]-1-(tert-butyloxycarbonyl)piperidine-3-carboxylic acid were obtained in the form of a solid with a beige color which becomes pasty at 154° C.

(3R,4R)-4-[3-(6-Methoxyquinolin-4-yl)propyl]-3-vinylpiperidine was obtained by application of the method disclosed in Patent Application FR 2,354,771, the disclosure of which is specifically incorporated by reference herein.

EXAMPLE 7

(3R,4R)-4-[3-(G-Methoxyquinolin-4-yl)propyl]-1-[3-(2-fluorophenyl)prop-2-ynyl]piperidine-3-carboxylic acid 0.44 cm³ of 5N aqueous sodium hydroxide was added to a solution of 0.28 g of methyl (3R,4R)-4-[3-(6-methoxyquinolin-4-yl)propyl]-1-[3-(2-fluorophenyl)prop-2-ynyl]piperidine-3-carboxylate in 10 cm³ of methanol and then the mixture was heated at a temperature in the region of 57° C. for 20 hours. After cooling, the solution was evaporated under reduced pressure (2 kPa) at a temperature in the region of 40° C. A 0.41 g residue was obtained, which residue was taken up in 20 cm³ of water to which had been added 3.5 cm³ of 1N hydrochloric acid. After extracting the aqueous phase with 5 times 15 cm³ of dichloromethane, the aqueous phase was concentrated to dryness under reduced pressure (5 kPa) at a temperature in the region of 40° C. The residue obtained was triturated in 10 cm³ of a dichloromethane/methanol (90/10 by volume) mixture. The insoluble material was filtered off and then the cake was washed with 10 cm³ of the same mixture. The filtrate was dried over magnesium sulfate, then concentrated under reduced pressure (5 kPa) at a temperature in the region of 40° C. and finally dried under vacuum (13 Pa) at a temperature in the region of 40° C. for 2 hours. 0.15 g of (3R,4R)-4-[3-(6-methoxyquinolin-4-yl)propyl]-1-[3-(2-fluorophenyl)prop-2-ynyl]piperidine-3-carboxylic acid was obtained in the form of a foamy solid with a pale yellow color which melts at approximately 154° C. with softening.

Infrared spectrum (KBr): 3057 cm$^{-1}$ (aromatic CH ν), 2933, 2864 cm$^{-1}$ (CH$_2$ ν), 3000, 2750 cm$^{-1}$ (acidic OH ν), 2800 and 1900 cm$^{-1}$ (N$^+$H ν (tertiary amine salt+quinoline salt)), 1722 cm$^{-1}$ (acidic C=O ν), 1618, 1601, 1542, and 1493 cm$^{-1}$ (aromatic nuclei C=C ν), 1275 cm$^{-1}$(acidic C—O ν), 1217 cm$^{-1}$ (ether C—O ν$_{as}$), 1022 cm$^{-1}$ (ether C=O ν$_s$), 847 cm$^{-1}$ (4,6-disubstituted quinoline CH γ), 765 cm$^{-1}$ (ortho-disubstituted phenyl CH γ).

Mass spectrum: (DCl) m/z=461 MH$^+$

Methyl (3R,4R)-4-[3-(6-methoxyquinolin-4-yl)propyl]-1-[3-(2-fluorophenyl)prop-2-ynyl]piperidine-3-carboxylate 0.041 g of tetrakis(triphenylphosphine)palladium and 0.070 g of cuprous iodide were added, at a temperature in the region of 20° C. and under an inert atmosphere, to a stirred solution of 0.7 g of methyl (3R,4R)-4-[3-(6-methoxyquinolin-4-yl)propyl]-1-(prop-2-ynyl)piperidine-3-carboxylate in 14 cm³ of acetonitrile. 0.32 cm³ of 1-fluoro-2-iodobenzene and 0.51 cm³ of triethylamine were subsequently added. The mixture was stirred at a temperature in the region of 20° C. for 20 hours. The reaction mixture was filtered and the cake was washed with 3 times 10 cm³ of acetonitrile. The combined filtrates were taken up with stirring in a mixture of 100 cm³ of dichloromethane and 100 cm³ of water. The organic phase was separated by settling, washed with 3 times 50 cm³ of a saturated sodium chloride solution, dried over magnesium sulfate, and then, after filtration, concentrated under reduced pressure (2 kPa) at a temperature in the region of 35° C. The residue obtained was purified by chromatography under argon pressure (50 kPa) on a column of silica gel (particle size 40–63 μm; diameter 4 cm; height 14 cm), elution was carried out with ethyl acetate, and 2-cm³ fractions were collected. Fractions 33 to 160 were combined and then evaporated under reduced pressure (2 kPa) at a temperature in the region of 40° C. 0.56 g of methyl (3R,4R)-4-(3-(6-methoxyquinolin-4-yl)propyl]-1-[3-(2-fluorophenyl)prop-2-ynyl]piperidine-3-carboxylate was obtained in the form of an oil with a light brown color.

Methyl (3R,4R)-4-[3-(6-methoxyquinolin-4-yl)propyl]-1-(prop-2-ynyl)piperidine-3-carboxylate was prepared under the conditions of Example 6.

EXAMPLE 8

(3R,4R)-4-[3-(6-methoxyquinolin-4-yl)propyl]-1-[3-(3-fluorophenyl)prop-2-ynyl]piperidine-3-carboxylic acid dihydrochloride 10.5 cm³ of a 6N aqueous hydrochloric acid solution were added to a solution of 0.66 g of methyl (3R,4R)-4-[3-(6-methoxyquinolin-4-yl)propyl]-1-l[3-(3-fluorophenyl)prop-2-ynyl]piperidine-3-carboxylate and then the mixture was heated at a temperature in the region of 100° C. for 3 hours, after which were added an additional 3.5 cm³ of 6N aqueous hydrochloric acid solution. After 4 hours, the reaction mixture was cooled to a temperature in the region of 40° C. and then concentrated under reduced pressure (2 kPa) at a temperature in the region of 60° C. The residue obtained was taken up in 10 cm³ of water and 8 cm³ of dichloromethane and then separated by settling. The aqueous phase was extracted with 2 times 6 cm³ of dichloromethane. The aqueous solution was concentrated to dryness under reduced pressure (1 kPa) at a temperature in the region of 50° C. The residue obtained was dissolved in 5 cm³ of a dichloromethane/methanol (90/10 by volume) mixture and dried over sodium sulfate and then, after filtration, the solvent was evaporated under reduced pressure (1 kPa) at a temperature in the region of 40° C. The residue was taken up in a mixture of 2-propanol and isopropyl ether, dissolved under hot conditions, and then filtered through paper. The filtrate was cooled to a temperature in the region of 25° C. and then evaporated under reduced pressure (1 kPa) at a temperature in the region of 45° C. The residue was taken up in 10 cm$^3$ of a dichloromethane/methanol (90/10 by volume) mixture and reconcentrated under the same conditions. 0.44 g of (3R,4R)-4-[3-(6-methoxyquinolin-4-yl)propyl]-1-[3-(3-fluorophenyl)prop-2-ynyl]piperidine-3-carboxylic acid dihydrochloride was obtained in the form of a foam with a yellow color which melts at approximately 222° C. with softening.

$^1$H N.M.R. spectrum (400 MHz, d6-$(CD_3)_2$SO, δ in ppm): from 1.20 to 2.15 (unresolved peak, 6H), 2.35 (unresolved peak, 1H), from 3.00 to 3.90 (mt, 7H), 4.02 (s, 3H), 4.40 (broad s, 2H), from 7.25 to 7.55 (mt, 4H), 7.60 (broad S, 1H), 7.75 (dd, J=9 and 2 H 1H), 7.82 (d, J=5 Hz, 1H), 8.27 (d, J=9 Hz, 1H), 8.97 (d, J=5 Hz, 1H), from 11.45 (broad unresolved peak, 1H).

Methyl (3R,4R) 4-[3-(6-methoxyquinolin-4-yl) propyl]-1-[3-(3-fluorophenyl)prop-2-ynyl] piperidine-3-carboxylate 0.07 g of triphenylphosphine, 0.237 g of tetrakis (triphenylphosphine)palladium, and 0.12 g of cuprous iodide were added, under an inert atmosphere and at a temperature in the region of 20° C., to a stirred solution of 1.2 g of methyl (3R,4R)-4-[3 -(6-methoxyquinolin-4-yl)propyl]-1-[prop-2-ynyl]piperidine-3-carboxylate in 25 cm$^3$ of acetonitrile. 0.56 cm$^3$ of 1-fluoro-3-iodobenzene and 0.88 cm$^3$ of triethylamine were subsequently added. After stirring for 20 hours at a temperature in the region of 20° C., the reaction mixture was filtered through Celite and the cake was washed with acetonitrile. The filtrate was evaporated under reduced pressure (2 kPa) at a temperature in the region of 35° C. The residue obtained was taken up in a mixture of 80 cm$^3$ of dichloromethane and 80 cm$^3$ of water. After separating by settling, the organic phase was washed with 3 times 50 cm$^3$ of a saturated sodium chloride solution. The organic solution was dried over magnesium sulfate, filtered, and then concentrated under reduced pressure (2 kPa) at a temperature in the region of 40° C. 1.91 g of an oil were obtained, which oil was purified by chromatography under argon pressure (50 kPa) on a column of silica gel (particle size 40–63 μm; diameter 3 cm; 77 g), elution was carried out with ethyl acetate, and 5-cm$^3$ fractions were collected. The fractions comprising the expected product were combined and then evaporated under reduced pressure (2 kPa) at a temperature in the region of 40° C. 1.08 g of methyl (3R,4R)-4-[3-(6-methoxyquinolin-4-yl)propyl]-1-[3-(3-fluorophenyl)prop-2-ynyl]piperidine-3-carboxylate were obtained in the form of an oil with a yellow color.

Methyl (3R,4R)-4-[3-(6-methoxyquinolin-4-yl)propyl]-1-[prop-2-ynyl]piperidine-3-carboxylate was prepared under the conditions of Example 6.

EXAMPLE 9

(3R,4R)-4-[3-(6-Methoxyquinolin-4-yl)propyl]-1-[3-(thien-2-yl)propyl]piperidine-3carboxylic acid A solution of 0.37 g of methyl (3R,4R)-4-[3-(6-methoxyquinolin-4-yl)propyl]-1-[3-(thien-2-yl)propyl] piperidine-3-carboxylate in 6 cm$^3$ of dioxane, to which dioxane had been added 1.6 cm$^3$ of N aqueous hydroxide, was stirred at a temperature in the region of 60° C. for 20 hours. After evaporating the solvents under reduced pressure (5 kPa) at a temperature in the region of 45° C., the residue obtained was taken up in 20 cm$^3$ of water and then the aqueous phase was washed with 20 cm$^3$ of ethyl ether. After separating the ether by settling, the aqueous phase was neutralized with 1.6 cm$^3$ of N hydrochloric acid and then extracted with 2 times 30 cm$^3$ of ethyl acetate. The combined extracts were dried over magnesium sulfate. The organic solution, after filtration, was evaporated under reduced pressure (5 kPa) at a temperature in the region of 40° C. 0.21 g of (3R,4R)-4-[3-(6-methoxyquinolin-4-yl) propyl]-1 -[3-(thien-2- yl)propyl]piperidine-3-carboxylic acid was obtained in the form of a foam with a beige color which melts at approximately 60° C. with softening.

$^1$H N.M.R. spectrum (400 MHz, d6-$(CD_3)_2$SO, δ in ppm): from 1.35 to 1.90 (mt, 9H), 2.29 (broad t, J=11 Hz, 1H), 2.39 (broad d, 1=11 Hz, 1H), from 2.45 to 2.55 (mt, 2H), 2.58 (mt, 1H), 2.83 (t, J=8 Hz, 2H), from 2.85 to 3.15 (mt, 4H), 3.95 (s, 3H), 6.88 (broad d, J=3 Hz, 1H), 6.95 (dd, J=5 Hz), from 7.30 to 7.45 (mt, 4H), 7.93 (d, J=9 Hz, 1H), 8.63 (d, J=5 Hz, 1H).

Methyl (3R,4R)-4-[3-(6-methoxyquinolin-4-yl) propyl]-1-[3-(thien-2-yl)propyl]piperidine-3-carboxylate By carrying out the reaction by analogy with Example 4 but from methyl (3R,4R)-4-[3-(6-methoxyquinolin-4-yl) propyl]piperidine-3-carboxylate and 3-bromo-1-(thieny-2-yl)propane, 0.37 g of methyl (3R,4R)-4-[3-(6-methoxyquinolin-4-yl)propyl]-1-[3-(thien-2-yl)propyl] piperidine-3-carboxylate was obtained in the form of a gum with a light brown color.

Mass spectrum (El-m/z): 466 (M$^+$), 369 (M-$C_5H_5S$)$^+$, 355 (M-$C_6H_7S$)$^+$base peak, 294 (M-$C_{11}H_{10}NO$)$^+$, 186 ($C_{12}H_{12}NO^+$), 97 ($C_5H_5S^+$).

EXAMPLE 10

(3R,4R)-4-[3-(6-Methoxyquinolin-4-yl)propyl]-1-[2-(1,3-thiazol-2-ylthio)ethyl]piperidine-3-carboxylic acid trihydrochloride.

A mixture of 0.3 g of methyl (3R,4R)-4-[3-(6-methoxyquinolin-4-yl)propyl)-1-[2-(1,3-thiazol-2-ylthio) ethyl]piperidine-3-carboxylate and 0.44 cm$^3$ of 5N aqueous sodium hydroxide in 2.5 cm$^3$ of methanol was heated at a temperature in the region of 60° C. with stirring for 20 hours. After cooling, the reaction mixture was evaporated under reduced pressure (5 kPa) at a temperature in the region of 40° C.; the residue was taken up in 5 cm$^3$ of water, and then acidified by addition of 1 cm$^3$ of 35% hydrochloric acid. The mixture was evaporated under the same conditions as above and then the residue obtained was triturated in 10 cm$^3$ of a dichloromethane/methanol (90/10 by volume) mixture. After filtering off the insoluble material, the filtrate was evaporated under reduced pressure (5 kPa) at a temperature in the region of 40° C. 0.34 g of (3R,4R)-4-[3-(6-methoxyquinolin-4-yl)propyl]-1-[2-(1, 3-thiazol-2-ylthio) ethyl]piperidine-3-carboxylic acid trihydrochloride was obtained in the form of a foam with a pale yellow color.

Infrared spectrum (KBr): 3097 cm$^{-1}$ (thiazole CH ν), 3058 and 3012 cm$^{-1}$ (aromatic CH ν), 2929 and 28615 cm$^{-1}$ ($CH_2$ ν), 3000 and 2750 cm$^{-1}$ (acidic OH ν), 2800 and 1900 cm$^{-1}$ (N$^+$Hν (tertiary amine salt+quinoline salt)), 1715 cm$^{-1}$ (acidic C═O ν), 1617, 1600, 1543, and 1496 cm$^{-1}$ (aromatic nuclei C═C ν), 1274 cm$^{-1}$ (acidic C—O ν), 1250 and 1219 cm$^{-1}$ (ether C—O $v_{as}$), 1020 cm$^{-1}$ $^1$ (ether C—O $v_s$+alcohol C O v), 846 cm$^{-1}$ (4,6-disubstituted quinoline CH γ), 740 cm$^{-1}$ (thiazole CH γ).

Mass spectrum (El-m/z): 471 (M$^+$), 355 (M-C$_3$H$_2$NS$_2$)$^+$, 341 (M-C$_4$H$_4$S$_2$)+base peak, 297, 341 (M-CO$_2$)$^+$, 186 (C$_{12}$H$_{12}$NO$^+$), 117 (C$_3$H$_3$NS$_2$$^+$), 44 (CO$_2$$^{+)}$.

Methyl (3R,4R)-4-[3-(6-methoxyquinolin-4-yl)propyl]-1-[2-(1,3-thiazol-2-ylthio)ethyl]piperidine-3-carboxylate By carrying out the reaction by analogy with Example 4 but from methyl (3R,4R)-4-[3-(6-methoxyquinolin-4-yl)propyl]piperidine-3-carboxylate and 2-bromo-1-[(1,3-thiazol-2-yl)thio]ethane, 0.31 g of methyl (3R,4R)-4-[3-(6-methoxyquinolin-4-yl)propyl]-1-[2-(1,3-thiazol-2-ylthio)ethyl]piperidine-3-carboxylate was obtained in the form of a lacquer with an orange color.

$^1$H N.M.R. spectrum (300 MHz, d6-(CD$_3$)$_2$SO, δ in ppm): from 1.30 to 1.85 (mt, 7H), from 2.20 to 2.35 (mt, 1H), 2.35 (dd, J=11 and 3 Hz, 1H), from 2.50 to 2.85 (mt, 5H J=7 Hz, 2H), from 3.25 to 3.40 (mt, 2H), 3.53 (s, 3H), 3.94 (s, 3H), 7.31 (d, J-32 5 Hz, 1H), 7.35 (d, J=2.5 Hz, 1H), 7.40 (dd, J=9 and 2.5 Hz, 1H), 7.63 (d, J=3.5 Hz, 1H), 7.72 (d, J=3.5 Hz, 1H), 7.93 (d, J=9 Hz, 1H), 8.63 (d, J=5 Hz, 1H).

EXAMPLE 11

(3R,4R)-4-[3-(6-Methoxyquinolin-4-yl)propyl]-1-[2-(2-fluorophenylthio)ethyl]piperidine-3-carboxylic acid hydrochloride A mixture of 0.12 g of methyl (3R,4R)-4-[3-(6-methoxyquinolin-4-yl)propyl]-1-[2-(2-fluorophenylthio)ethyl]piperidine-3-carboxylate and 0.6 cm$^3$ of N aqueous sodium hydroxide in 1.8 cm$^3$ of methanol was stirred for 20 hours at a temperature in the region of 60° C. The reaction mixture was evaporated under reduced pressure (5 kPa) at a temperature in the region of 40° C. The residue obtained was taken up in 5 cm$^3$ of water and acidified with 1 cm$^3$ of 2N aqueous hydrochloric acid. The mixture was again evaporated under the same conditions as above and then the new residue was triturated in 5 cm$^3$ of a dichloromethane/methanol (90/10 by volume) mixture. After filtering and evaporating the filtrate under reduced pressure (5 kPa) at a temperature in the region of 40° C., the residue obtained was triturated in 3 cm$^3$ of diisopropyl ether. The insoluble material was filtered off, washed with 2 times 1 cm$^3$ of diisopropyl ether, and dried in the air. 0.14 g of (3R,4R)-4-(3-(6-methoxyquinolin-4-yl)propyl]-1-[2-(2-fluorophenylthio)ethyl]piperidine-3-carboxylic acid hydrochloride was obtained in the form of a solid with a beige color which melts with softening at approximately 148° C.

Infrared spectrum (KBr): 3058 and 3013 cm$^{-1}$ (aromatic CH v), 2934 and 2862 cm$^{-1}$ (CH$_2$ v), 3000 and 2750 cm$^{-1}$ (acidic OH v), 2800 and 1900 cm$^{-1}$ (N$^+$H v (tertiary amine salt + quinoline salt)), 1719 cm$^{-1}$ (acidic C=O v), 1618, 1600, 1541, and 1497 cm$^{-1}$ (aromatic nuclei C=C v), 1276 cm$^{-1}$ (acidic C—O v), 1251 and 1219 cm$^{-1}$ (ether C—O $v_{as}$), 1022 cm$^{-1}$ (ether C—O $v_s$ +alcohol C—O v), 847 cm$^-$ (4,6-disubstituted quinoline CH γ), 760 cm$^{-1}$ (1,2-disubstituted phenyl CH γ).

Mass spectrum (El-m/z): 438 (M-CO$_2$)$^+$, 355 (M-C$_6$H$_4$SF)$^+$, 341 (M-C$_7$H$_6$SF)$^+$ base peak, 297, 341 (M-CO$_2$)$^+$, 186 (C$_{12}$H$_{12}$NO$^{30}$), 128 (C$_6$H$_5$SF$^+$), 36 (HCl$^+$).

Mass spectrum (DCl): m/z=483 (M+H)$^+$.

Methyl (3R,4R)-4-[3-(6-methoxyquinolin-4-yl)propyl]-1-[2-(2-fluorophenylthio)ethyl]piperidine-3-carboxylate By carrying out the reaction by analogy with Example 4 but from methyl (3R,4R)-4-[3-(6-methoxyquinolin-4-yl)propyl]piperidine-3-carboxylate and 2-bromo-1-(2-fluorophenylthio)ethane, 0.17 g of methyl (3R,4R)-4-[3-(6-methoxyquinolin-4-yl)propyl]-1-[2-(2-fluorophenylthio)ethyl]piperidine-3-carboxylate was obtained in the form of a lacquer with an orange color. Infrared spectrum (CH$_2$Cl$_2$): 2942 cm$^{-1}$ (aliphatic CH v), 1727 cm$^{-1}$ C=O v), 1227 cm$^-$ (ether C—O v), 848 cm$^-$ (quinoline CH γ).

EXAMPLE 12

(3R,4R)-4-[3-(6-Methoxyquinolin-4-yl)propyl]-1-[2-(thien-2-ylthio)ethyl[piperidine-3-carboxylic acid dihydrochloride 0.5 cm$^3$ of 5N aqueous sodium hydroxide was added to a stirred solution of 0.34 g of methyl (3R,4R)-4-[3-(6-methoxyquinolin-4-yl)propyl]-1-[2-(thien-2-ylthio)ethyl]piperidine-3-carboxylate in 3 cm$^3$ of methanol and then the mixture was heated at a temperature in the region of 60° C. for 20 hours. After evaporating the solvents under reduced pressure (5 kPa) at a temperature in the region of 40° C., the residue obtained was taken up in 5 cm$^3$ of water and then acidified by addition of 1 cm$^3$ of 35% hydrochloric acid. The mixture was again evaporated under reduced pressure under the same conditions as above; the residue obtained was taken up in 5 cm$^3$ of a dichloromethane/methanol (90/10 by volume) mixture. The insoluble material was filtered off and then the solvent was evaporated under reduced pressure (5 kPa) at a temperature in the region of 40° C. 0.35 g of (3R,4R)-4-[3-(6-methoxyquinolin-4-yl)propyl]-1-[2-(thien-2-ylthio)ethyl]piperidine-3-carboxylic acid dihydrochloride was obtained in the form of a solid with a beige color which melts with softening in the region of 150° C.

Infrared spectrum (KBr). 3102 cm$^{-1}$ thiophene CH v), 3058 and 3012 cm$^{-1}$ aromatic CH v), 2932 and 2865 cm$^{-1}$ CH$_2$ v), 3000 and 2750 cm$^{-1}$ (acidic OH v), 2800 and 1900 cm$^{-(N+}$Hv (tertiary amine salt+quinoline salt)), 1717 cm$^{-1}$ acidic C=O v), 1618, 1600, 1541, and 1496 cm$^{-1}$ (aromatic nuclei C=C v), 1276 cm$^{-1}$ (acidic C—O v), 1250 and 1218 cm$^{-1}$ ether C—O $v_{as}$), 1020 cm$^{-1}$ ether C—O $v_s$ +alcohol C—O v), 846 cm$^{-1}$ 4,6-disubstituted quinoline CH γ), 725 cm$^{-1}$ thiophene CH γ).

Mass spectrum (El-m/z): 355 (M-C$_4$H$_3$S$_2$)$^+$, 341 (M-C$_5$H$_5$S$_2$)$^+$base peak, 297, 341 (M-CO$_2$)$^+$, 186 (C$_{12}$H$_{12}$NO$^+$), 115 (C$_4$H$_3$S$_2$$^+$).

Mass spectrum (DCl) m/z=471 (M+H)$^+$.

Methyl (3R,4R)-4-[3-(6-methoxyquinolin-4-yl)propyl]-1-[2-(thien-2-ylthio)ethyl]piperidine-3-carboxylate By carrying out the reaction by analogy with Example 4 but from methyl (3R,4R)-4-[3-(6-methoxyquinolin-4-yl)propyl]piperidine-3-carboxylate and 2-bromo-1-(thien-2-ylthio)ethane, 0.34 g of methyl (3R,4R)-4-[3-(6-methoxyquinolin-4-yl)propyl]-1-[2-(thien-2-ylthio)ethyl]piperidine-3-carboxylate was obtained in the form of a lacquer with a green color.

$^1$H N.M.R. spectrum (300 MHz, d6-(CD$_3$)$_2$SO, δ in ppm): from 1.30 to 1.90 (mt, 7H), from 2.15 to 2.30 (mt, 1H), from 2.35 to 2.60 (mt, 4H), from 2.65 to 2.80 (mt, 2H), 3.02 (t, J=7 Hz, 2H), 3.03 (broad t, J=7.5 Hz, 2H), 3.54 (s, 3H), 3.95 (s, 3H), 7.06 (dd, J=5.5 and 3.5 Hz, 1H), 7.19 (dd, J=3.5 and 1.5 Hz, 1H), 7.32 (d, J=4.5 Hz, 1H), 7.36 (d, J=3 Hz, 1H), 7.42 (dd, J=9 and 3 Hz, 1H), 7.62 (dd, J=5.5 and 1.5 Hz, 1H), 7.95 (d, J=9 Hz, 1H), 8.64 (d, J=4.5 Hz, 1H).

EXAMPLE 13

(3R,4R)-4-[3-(R,S)-Fluoro-3-(6-methoxyquinolin-4-yl)propyl]-1-(3-phenylpropyl)piperidine-3-carboxylic acid dihydrochloride A stirred solution of 0.51 g of methyl (3R, S)-fluoro-3-(6-methoxyquinolin-4-yl)propyl]-1-(3- phenylpropyl)piperidine-3-carboxylate in 15 cm³ of methanol, to which had been added 0.86 cm³ of 5N aqueous sodium hydroxide, was stirred and then heated at a temperature in the region of 60° C. for 22 hours. The reaction mixture was evaporated under reduced pressure (5 kPa) at a temperature in the region of 30° C. The residue obtained was taken up in 15 cm³ of 2-propanol to which have been added 6 cm³ of dichloromethane. 2 cm³ of a 6N solution of hydrochloric acid in 2-propanol were poured into the solution obtained. The solvents were evaporated under reduced pressure (5 kPa) at a temperature in the region of 40° C. A solid was obtained, which solid was taken up in 15 cm³ of 2-propanol. After stirring for 15 minutes, the insoluble material was filtered off; the cake was washed with 2 times 10 cm³ of 2-propanol. The combined filtrates were concentrated under reduced pressure (5 kPa) at a temperature in the region of 30° C. 0.55 g of a solid product was obtained, which product was triturated in 10 cm³ of diethyl ether. The solvent was evaporated under reduced pressure (5 kPa) at a temperature in the region of 40° C. 0.54 g of (3R,4R)-4-[3-(R,S)-fluoro-3-(6-methoxyquinolin4-yl)propyl]-1-(3-phenylpropyl)piperidine-3-carboxylic acid dihydrochloride was obtained in the form of a solid with a light brown color which melts at 116° C. with softening.

1H N.M.R. spectrum (600 MHz, d6-$(CD_3)_2SO$, at a temperature of 373K, δ in ppm): from 1.40 to 2.30 (mt, 9H), 2.70 (mt, 2H), from 2.80 to 3.70 (mts, 7H), 3.99 (s, 3H), 6.32 (broad d, $J_{HF}$=48 Hz, 1H), from 7.15 to 7.45 (mt, 6H), from 7.50 to 7.60 (mt, 2H), 8.09 (d, J=9 Hz, 1H), 8.82 (d, J=5 Hz, 1H), from 10.90 to 11.40 (broad unresolved peak, 1H).

Methyl (3R,4R)-4-[3-(R,S)-fluoro-3-(6-methoxyquinolin-4-yl)propyl]-1-(3-phenylpropyl)piperidine-3-carboxylate 0.31 cm³ of diethylaminosulfur trifluoride was added with stirring, at a temperature in the region of 20° C., to a solution of 0.9 g of methyl (3R,4R)-4-[3 -(R,S)-hydroxy-3-(6-methoxyquinolin-4-yl)propyl]-1-(3-phenylpropyl)piperidine-3-carboxylate in 5 cm³ of dichloromethane. After 2 hours, the reaction mixture was poured onto 15 cm³ of a saturated aqueous sodium hydrogencarbonate solution. After extracting with 10 cm³ and then 2 times 5 cm³ of dichloromethane, the organic extracts were washed with 2 times 15 cm³ of water, dried over magnesium sulfate, filtered, and then evaporated under reduced pressure (5 kPa) at a temperature in the region of 30° C. 0.88 g of an oil was obtained, which oil was purified by chromatography at atmospheric pressure on a column of silica gel (particle size 20–45 μm; diameter 2.5 cm; 44 g), elution was carried out with an ethyl acetate/methanol (9/1 by volume) mixture, and 20-cm³ fractions were collected. Fractions 5 to 10 were combined and evaporated under reduced pressure (5 kPa) at a temperature in the region of 35° C. 0.57 g of methyl (3R,4R)-4-[3-(R,S)-fluoro-3-(6-methoxyquinolin-4-yl)propyl]-1-(3-phenylpropyl)piperidine-3-carboxylate was obtained in the form of an oil with a yellow color.

Methyl (3R , 4R)-4-[3-(R,S)-hydroxy-3-(6-methoxyquinolin-4-yl)propyl]-1-(3-phenylpropyl)piperidine-3-carboxylate was prepared under the conditions of Example 5.

EXAMPLE 14

(3R,4R)-4-[3-(6-methoxyquinolin-4-yl)propyl]-1-12-(pyridin-2-ylthio)ethyl]piperidine-3-carboxylic acid trihydrochloride A solution of 0.5 g of methyl (3R,4R)-4-[3-(6-methoxyquinolin-4-yl)propyl]-1-[2-(pyridin-2-ylthio)ethyl] piperidine-3-carboxylate in 7.8 cm³ of 6N hydrochloric acid was heated with stirring at a temperature in the region of 100° C. for 2 hours. After concentrating the reaction mixture to dryness under reduced pressure (5 kPa) at a temperature in the region of 80° C. the residue obtained was triturated in 10 cm³ of diisopropyl ether. The insoluble material was filtered off and then dried under reduced pressure (13 kPa) at a temperature in the region of 60° C. 0.55 g of (3R,4R)-4-[3-(6-methoxyquinolin-4-yl)propyl]-1-[2-(pyridin-2-ylthio)ethyl]piperidine-3-carboxylic acid trihydrochloride was obtained in the form of a solid with a cream color which melts with softening in the region of 165° C.

1H N.M.R. spectrum (400 MHz, d6-$(CD_3)_2SO$, δ in ppm): from 1.20 to 2.40 and from 3.00 to 3.60 (mts, 16H), 3.62 (broad t, J=7.5 Hz, 2H), 4.05 (s, 3H), 7.21 (dd, J =5 Hz, 1H), 7.43 (d, J=8 Hz, 1H), 7.67 (broad s, 1H), 7.73 (double t, J=8 and 1.5 Hz, 1H), 7.84 (dd,J=9 and 2.5 Hz, 1H), 7.95(d, J=5 Hz, 1 Hz), 8.45 (d, J=9 Hz 8.49 (broad d, J 5 Hz, 1H), 9.05 (d, J=5 Hz, 1H), 1 1.25 (unresolved peak, 1H).

Methyl (3R,4R)-4-[3-(6-methoxyquinolin-4-yl)propyl]-1-[2-(pyridin-2-ylthio)ethyl]piperidine-3-carboxylate By carrying out the reaction by analogy with Example 4 but from methyl (3R,4R)-4-[3-(6-methoxyquinolin-4-yl)propyl]piperidine-3-carboxylate and 2-bromo-1-(pyridin-2-ylthio)ethane, 0.52 g of methyl (3R,4R)-4-[3-(6-methoxyquinolin-4-yl)propyl]-1-[2-(pyridin-2-ylthio)ethyl] piperidine-3-carboxylate was obtained in the form of an oil with a yellow color.

Infrared spectrum ($CH_2Cl_2$): 2949 $cm^{-1}$ aliphatic CH ν), 1737 $cm^{-1}$ C=O ν), 1227 $cm^{-1}$ (ether C—O ν), 845 $cm^-$ (quinoline CH γ).

EXAMPLE 15

(3R,4R)-4-[3-(6-Methoxyquinolin-4-yl)propyl]-1-[2-(cyclohexylthio)ethyl]piperidine-3-carboxylic acid dihydrochloride A solution of 0.55 g of methyl (3R,4R)-4-[3-(6-methoxyquinolin-4-yl)propyl]-1-[2-cyclohexylthio)ethyl] piperidine-3-carboxylate in 8.5 cm³ of 6N hydrochloric acid was heated with stirring at a temperature in the region of 100° C. for 2 hours. The reaction mixture was cooled and then concentrated to dryness under reduced pressure (5 kPa) at a temperature in the region of 80° C. The residue obtained was triturated in 15 cm³ of diisopropyl ether. The insoluble material was filtered off and then the cake was washed with 10 cm³ of diisopropyl ether. The solid obtained was dried under reduced pressure (13 Pa) at a temperature in the region of 60° C. for 2 hours. 0.51 g of (3R,4R)-4-[3-(6-methoxyquinolin-4-yl)propyl]-1-[2-(cyclohexylthio)ethyl] piperidine-3-carboxylic acid dihydrochloride was obtained in the form of a solid with a beige color which melts with softening at approximately 150° C.

1H N.M.R. spectrum (400 MHz, d6-$(CD_3)_2SO_1$, with addition of a few drops of d4-$CD_3COOD$, at a temperature of 373K, δ in ppm): from 1.20 to 2.35 and from 2.75 to 3.50 (mts, 29H), 4.03 (s, 3H), 7.57 (mt, 1H), from 7.60 to 7.75 (mt, 2H), 8.24 (d, Hz, 1H), 8.85 (d, J=5 Hz, 1H).

Methyl (3R,4R)-4-[3-(6-methoxyquinolin-4-yl)propyl]-1-[2-(cyclohexylthio)ethyl]piperidine-3-carboxylate By carrying out the reaction by analogy with Example 4 but from methyl (3R,4R)-4-[3-(6-methoxyquinolin-4-yl)

propyl]piperidine-3-carboxylate and 2-bromo-1-(cyclohexylthio)ethane, 0.57 g of methyl (3R,4R)-4-[3-(6-methoxyquinolin-4-yl)propyl]-1-[2-(cyclohexylthio)ethyl]piperidine-3-carboxylate was obtained in the form of an oil with an orange color.

Infrared spectrum (CH$_2$Cl$_2$): 2934 cm$^{-1}$ (aliphatic CH v),. 1732 cm$^{-1}$ C=O v), 1227 cm$^{-1}$ ether C—O v), 848 cm$^-$ (quinoline CH γ).

EXAMPLE 16

(3R,4R)-4-[3-(6-methoxyquinolin-4-yl)propyl]-1-[4-oxo-4-(2-thienyl)butyl]piperidine-3-carboxylic acid ditrifluoroacetate 1.76 cm$^3$ of 4-chloro-2'-butyrothienone were added at a temperature in the region of 20° C., with stirring and under an inert atmosphere, to a solution of 1.55 g of (3R,4R)-4-[3-(6-methoxy-4-quinolin-4-yl)propyl]piperidine-3-carboxylic acid ditrifluoroacetate in 40 cm$^3$ of anhydrous acetone, followed by 3.86 g of potassium carbonate. The mixture was heated at a temperature in the region of 57° C. for 20 hours. After cooling the reaction mixture and then filtering off the insoluble material, the cake was washed with 10 cm$^3$ of acetone and then the filtrate was evaporated under reduced pressure (5 kPa) at a temperature in the region of 40° C. The residue obtained was purified by chromatography at atmospheric pressure on a column of silica gel (particle size 20–45 μm; diameter 4 cm; height 35 cm), elution was carried out with a dichloromethane/methanol (90/10 by volume) mixture, and 100-cm$^3$ fractions were collected. Fractions 43 to 122 were combined and then evaporated under reduced pressure (5 kPa) at a temperature in the region of 40° C. 1.09 g of an oil were obtained, which oil was subjected to a fresh purification by chromatography at atmospheric pressure on a column of silica gel (particle size 20–45 μm; diameter 4 cm; height 35 cm), elution was carried out with a dichloromethane/methanol (90/10 by volume) mixture, and 100-cm$^3$ fractions were collected. Fractions 125 to 216 were combined and then evaporated under reduced pressure (5 kPa) at a temperature in the region of 40° C. 0.48 g of an oil was obtained, which oil was purified in the form of the ditrifluoroacetate, prepared from 0.1 cm$^3$ of trifluoroacetic acid in a mixture of 10 cm$^3$ of dichloromethane and 5 cm$^3$ of methanol. After evaporating the reaction mixture (under a partial pressure of 5 kPa and at a temperature in the region of 40° C.), then taking up the residue obtained in 10 cm$^3$ of diethyl ether and filtering off the solid, 0.35 g of (3R,4R)-4-[3-(6-methoxyquinolin-4-yl)propyl]-1-[4-oxo-4-(2-thienyl)butyl]piperidine-3-carboxylic acid ditrifluoroacetate was obtained, with a purity of 90%, in the form of a solid with a beige color.

1H N.M.R. spectrum (400 MHz, d6-(CD$_3$)$_2$SO, with addition of a few drops of d4-CD3COOD, at a temperature of 383K, δ in ppm): from 1.50 to 2.25 and from 2.95 to 3.55 (mts, 20H), 3.96 (s, 3H), 7.23 (mt, 1H), 7.36 (d, J=5 Hz, 1H), from 7.40 to 7.50 (mt, 2H), 7.88 (d, J=4 Hz, 1H), 7.92 (d, J=5 Hz, 1H), 7.99 (d, J=9 Hz, 1H) =5 Hz, 1H).

(3R,4R)-4-[3-(6-Methoxyquinolin-4-yl)propyl]piperidine-3-carboxylic acid ditrifluoroacetate 1.75 cm$^3$ of pure trifluoroacetic acid were added, at a temperature in the region of 20° C., to a stirred suspension of 1.5 g of (3R,4R)-1-(tert-butyloxycarbonyl)-4-(3-(6methoxyquinolin-4-yl)propyl]piperidine-3-carboxylic acid in 15 cm$^3$ of dichloromethane. The solution obtained was stirred for 20 hours at the same temperature and then evaporated under reduced pressure (5 kPa) at a temperature in the region of 40° C. 2.46 g of (2R,4R)-4-[3-(6-methoxyquinolin-4-yl)propyl]piperidine-3-carboxylic acid ditrifluoroacetate were obtained in the form of an oil with a brown color.

(3R,4R)-1-(t-Butyloxycarbonyl)-4-[3-(6-methoxyquinolin-4-yl)propyl]piperidine-3-carboxylic acid was prepared as in Example 6.

EXAMPLE 17

(3R,4R)-4-[3-(6-Methoxyquinolin-4-yl)propyl]-1-[3-(2-fluorophenyl)propyl]piperidine-3-carboxylic acid dihydrochloride 0.71 cm$^3$ of 5N aqueous sodium hydroxide was added to a solution of 0.46 g of methyl (3R,4R)-4-[3-(6-methoxyquinolin-4-yl)propyl]-1-[3-(2-fluorophenyl)propyl]piperidine-3-carboxylate in 16.5 cm$^3$ of methanol and the mixture was then heated at a temperature in the region of 60° C. for 20 hours. After cooling to a temperature in the region of 25° C. the solution was evaporated under reduced pressure (1 kPa) at a temperature in the region of 40° C. 0.76 g of a residue was obtained, which residue was taken up in 35 cm$^3$ of water and then treated with 5.8 cm$^3$ of 1N hydrochloric acid. After extracting the aqueous phase with 5 times 10 cm$^3$ of dichloromethane, the aqueous phase was evaporated to dryness under reduced pressure (1 kPa) at a temperature in the region of 40° C. The residue obtained was triturated in 10 cm$^3$ of a dichloromethane/methanol (90/10 by volume) mixture. The insoluble material was filtered off and then the cake was washed with 2 times 5 cm$^3$ of the same mixture. The filtrate was evaporated under reduced pressure (1 kPa) at a temperature in the region of 40° C. The residue was taken up in 20 cm$^3$ of water and the aqueous phase was extracted with 4 times 5 cm$^3$ of dichloromethane. The aqueous phase was evaporated to dryness under reduced pressure (1 kPa) at a temperature in the region of 50° C. The residue obtained was triturated in 5 cm$^3$ of a dichloromethane/methanol (90/10 by volume) mixture. The insoluble material was filtered off and then the cake was washed with 2 times 2 cm$^3$ of the same mixture. The filtrate was dried over sodium sulfate, then evaporated to dryness under reduced pressure (1 kPa) at a temperature in the region of 40° C. and finally dried under partial pressure (13 Pa) at a temperature in the region of 25° C. for 2.5 days. 0.35 g of (3R,4R)-4-[3-(6-methoxyquinolin-4-yl)propyl]-1-[3-(2-fluorophenyl)propyl]piperidine-3-carboxylic acid was obtained in the form of a foamy solid with a pale yellow color which melts at approximately 194° C.

Infrared spectrum (KBr): 3051 and 3016 cm$^{-1}$ aromatic CH v), 2935 and 2869 cm$^{-1}$ CH$_2$ v), 3000 and 2750 cm$^{-1}$ (acidic OH v), 2800 and 1900 cm$^{-1}$ (N$^+$Hv (tertiary amine salt+quinoline salt)), 1721 cm$^{-1}$ acidic C=O v), 1618, 1601, 1542, and 1493 cm$^{-1}$ aromatic nuclei C=C v), 1276 cm$^{-1}$ (acidic C=O v), 1226 cm$^{-1}$ (ether C—O v$_{as}$), 1021 cm$^{-1}$ (ether C—O v$_s$)-847 cm$^{-1}$ (4,6-disubstituted quinoline CH γ), 764 cm$^{-1}$ ortho-disubstituted phenyl CH γ).

Mass spectrum (El-m/z): 464 (M$^+$), 420 (M-CO$_2$)$^+$, 355 (M-C$_7$H$_6$F)$^+$341 (M-C$_8$H$_8$F)+ base peak, 297 (m/z=341-CO$_2$)$^+$, 355 (M-C$_7$H$_6$F$^+$)$^+$, 341 (M-C$_8$)+

Methyl (3R,4R)-4-[3-(6-methoxyquinolin-4-yl)propyl]-1-[3-(2-fluorophenyl)propyl]piperidine-3-carboxylate By carrying out the reaction by analogy with Example 4 but from methyl (3R,4R)-4-[3-(6-methoxyquinolin-4-yl)

propyl]piperidine-3-carboxylate and 3-bromo-1-(2-fluorophenyl)propane, 0.47 g of methyl (3R,4R)-4-[3-(6-methoxyquinolin-4-yl)propyl]-1-[3-(2-fluorophenyl)propyl]piperidine-3-carboxylate was obtained in the form of an oil with a pale yellow color.

$^1$H N.M.R. spectrum (300 MHz, d6-$(CD_3)_2$SO, δ in ppm): from 1.30 to 1.85 (mt, 9H), from 2.05 to 2.35 (mt, 4H), from 2.40 to 2.85 (mt, 5H), 3.03 (t, J=7 Hz, 2H), 3.53 (s, 3H), 3.94 (s, 3H), from 7.05 to 7.35 (mt, 4H), 7.32 (d, J=5 Hz, 1H), 7.35 (d, J=2.5 Hz, 1H), 7.40 (dd, J=9 and 2.5 Hz, 1H), 7.93 (d, J=9 Hz, 1H), 8.63 (d, J=5 Hz, 1H).

EXAMPLE 18

(3R,4R)-4-[3-(6-methoxyquinolin-4-yl)propyl]-1-[3-(3-fluorophenyl)propyl]piperidine-3-carboxylic acid 0.9 cm$^3$ of 5N aqueous sodium hydroxide was added to a solution of 0.58 g of methyl (3R,4R)-4-[3-(6-methoxyquinolin-4-yl)propyl]-1-[3-(3-fluorophenyl)propyl]piperidine-3-carboxylate in 21 cm$^3$ of methanol and then the mixture was heated at a temperature in the region of 60° C. for 20 hours, on conclusion of which 0.2 cm$^3$ of 5N aqueous sodium hydroxide was added. Heating was subsequently continued for 3 hours. After cooling to a temperature in the region of 25° C., the solution was evaporated under reduced pressure (1 kPa) at a temperature in the region of 40° C. The residue was taken up in 30 cm$^3$ of water and then treated with 7.8 cm$^3$ of 1N hydrochloric acid. After extracting the aqueous phase with 5 times 10 cm$^3$ of dichloromethane, the aqueous phase was evaporated to dryness under reduced pressure (1 kPa) at a temperature in the region of 60° C. The residue obtained was triturated in 10 cm$^3$ of a dichloromethane/methanol (90/10 by volume) mixture. The insoluble material was filtered off and then the cake was washed with 2 times 5 cm$^3$ of the same mixture. The filtrate was dried over sodium sulfate and then evaporated to dryness under reduced pressure (1 kPa) at a temperature in the region of 40° C. 0.46 g of (3R,4R)-4-[3-(6-methoxyquinolin-4-yl)propyl]-1-[3-(3-fluorophenyl)propyl]piperidine-3-carboxylic acid was obtained in the form of a foamy solid with a pale yellow color which melts at approximately 206° C.

$^1$H N.M.R. spectrum (400 MHz, d6-$(CD_3)_2$SO, at a temperature of 403K, δ in ppm): from 1.35 to 2.30 and from 2.75 to 3.60 (mts, 18H), 2.75 (t, J=7.5 Hz, 2H), 3.99 (s, 3H), 7.00 (mt, 1H), from 7.05 to 7.15 (mt, 2H), from 7.30 to 7.40 (mt, 1H), 7.35 (d, J=5 Hz, 1H), 7.45 (mt, 2H), 8.01 (d, J=9 Hz, 1H), 8.67 (d, J=5 Hz, 1H).

Methyl (3R,4R)-4-[3-(6-methoxyquinolin-4-yl)propyl]-1-[3-(3-fluorophenyl)propyl]piperidine-3-carboxylate By carrying out the reaction by analogy with Example 4 but from methyl (3R,4R)-4-[3-(6-methoxyquinolin-4-yl)propyl]piperidine-3-carboxylate and 3-bromo-1-(3-fluorophenyl)propane, 0.58 g of methyl (3R,4R)-4-[3-(6-methoxyquinolin-4-yl)propyl]-1-[3-(3-fluorophenyl)propyl]piperidine-3-carboxylate was obtained in the form of an oil with a dark yellow color.

Infrared spectrum ($CH_2Cl_2$): 2949 cm$^{-1}$ (aliphatic CH ν), 1733 cm$^{-1}$ (C=O ν), 1228 cm$^{-1}$ (ether C—O ν), 848 cm$^{-1}$ (quinoline CH γ),

EXAMPLE 19

(3R,4R)-4-[3-(6-Methoxyquinolin-4-yl)propyl]-1-[3-(thien-3-yl)prop-2ynyl]piperidine-3-carbocyclic acid 3.9 cm$^3$ of 1N aqueous sodium hydroxide were added to a solution of 0.6 g of methyl (3R,4R)-4-[3-(6-methoxyquinolin-4-yl)propyl]-1-[3-(thien-3-yl)prop-2ynyl]piperidine-3-carboxylate in 10 cm$^3$ of dioxane and then the mixture was heated at a temperature in the region of 65° C. for 16 hours. The mixture was cooled and then the organic phase was extracted with 3 times 50 cm$^3$ of ethyl acetate. The aqueous phase was acidified with 3.9 cm$^3$ of 1N hydrochloric acid. The solution was taken up in 10 cm$^3$ of a saturated aqueous sodium bicarbonate solution and then the organic phase was extracted with 2 times 20 cm$^3$ of ethyl acetate and 2 times 20 cm$^3$ of dichloromethane, dried over sodium sulfate, filtered, and concentrated to dryness under reduced pressure (2 kPa) at a temperature in the region of 45° C. 0.32 g of (3R,4R)- 4-[3-(6-methoxyquinolin-4-yl)propyl]-1-[3-(thien-3-yl)prop-2-ynyl]piperidine-3-carboxylic acid was obtained in the form of a foam with a white color.

$^1$H N.M.R. spectrum (300 MHz, d6-$(CD_3)_2$SO, δ in ppm): from 1.20 to 1.90 (mt, 7H), 2.43 (mt, 1H), from 2.50 to 3.00 (mt, 4H), 3.04 (broad t, J=7.5 Hz, 2H), 3.55 (s, 2H), 3.93 (s, 3H), 7.15 (dd, J=5 and 1.5 Hz, 1H), 7.32 (d, J=5 Hz, 1H), from 7.35 to 7.50 (mt, 2H), 7.62 (dd, J=5 and 3 Hz, 1H), 7.75 (dd, J=3 and 1.5 Hz, 1H), 7.92 (d, J=9 Hz, 1H), 8.62 (d, J=5 Hz, 1H), from 12.00 and 13.00 (very broad unresolved peak, 1H).

Methyl (3R,4R)-4-[3-(6-methoxyquinolin-4-yl)propyl]-1-[3-(thien-3-yl)prop-2-ynyl]piperidine-3-carboxylate The reaction was carried out as in Example. 9, for the preparation of methyl (3R,4R)-4-[3-(6-methoxyquinolin-4-yl)propyl]-1-[3-(thien-2-yl)prop-2-ynyl]piperidine-3-carboxylate, from 1 g of methyl (3R,4R)-4-[3-(6-methoxyquinolin-4-yl)propyl]-1-[prop-2-ynyl]piperidine-3-carboxylate, 0.9 g of 3-iodothiophene, 0.2 g of tetrakis (triphenylphosphine)palladium, 0.1 g of cuprous iodide, 0.060 g of triphenylphosphine, and 0.75 cm$^3$ of triethylamine. The residue obtained was purified by chromatography at atmospheric pressure on a column of silica gel (particle size 40-63 μm; diameter 3.5 cm; height of the column 35 cm), elution was carried out with ethyl acetate, and 40-cm$^3$ fractions were collected. Fractions 18 to 49 were combined and then evaporated under reduced pressure (5 kPa) at a temperature in the region of 40° C. 0.6 g of methyl (3R,4R)-4-[3-(6-methoxyquinolin-4-yl)propyl]-1-[3-yl)prop-2-ynyl]piperidine-3-carboxylate was obtained in the form of a brown oil.

3-iodothiophene was prepared according to N. A. Petasis et al., Synlett., 1999, 141, the disclosure of which is specifically incorporated by reference herein.

EXAMPLE 20

(3R,4R)-4-[3-(6-methoxyquinolin4-yl)prop-2-enyl]-1-(3-phenylpropyl)piperidine -3-carboxylic acid hydrochloride A mixture of 0.23 g of methyl (3R,4R)-1-(3-phenylpropyl)-4-[3-(6-methoxyquinolin-4-yl)prop-2-enyl]piperidine-3-carboxylate, 7 cm$^3$ of methanol, and 0.4 cm$^3$ of 5N aqueous sodium hydroxide was heated with stirring at 60° C. for 20 hours. After evaporating the solvents under reduced pressure (5 kPa) at a temperature in the region of 40° C., the residue obtained was taken up in 6 cm$^3$ of water, washed with 3 cm$^3$ of dichloromethane, and then acidified with 2 cm$^3$ of 1N hydrochloric acid. The solution was evaporated under the same conditions and then the residue obtained was triturated in a mixture of 9 cm$^3$ of dichloromethane and 3 cm³ of isopropanol. The insoluble material was filtered off and washed with 20 cm³ of dichloromethane. The filtrate was dried over sodium sulfate and then concentrated under reduced pressure (5 kPa) at a temperature in the region of 40° C. After drying in the air, 0.16 g of (3R,4R)-1-(3-phenylpropyl)-4-[3-(6-methoxyquinolin-4-yl)prop-2-enyl]piperidine-3-carboxylic acid hydrochloride was obtained in the form of an amorphous solid with a brown color.

Infrared spectrum (KBr): 2936 and 2857 cm⁻¹ $CH_2$ ν), 2838 cm⁻¹ (O—$CH_3$CH ν), 3000 and 2750 cm⁻¹ (acidic OH ν), 2800 and 1900 cm⁻¹ $N^+H$ ν (tertiary amine salt+quinoline salt)), 1716 cm⁻¹ acidic C=O ν), 1621, 1603, 1589, 1509, and 1473 cm⁻¹ aromatic nuclei C=C ν), 1229 cm⁻¹ ether C—O $ν_{as}$), 1031 cm⁻¹ ether C—O $ν_s$), 969 cm⁻¹ (trans CH=CH γ), 849 cm⁻¹ 4,6-disubstituted quinoline CH γ).

Mass spectrum (DCl): m/z=445 ($MH^+$).

Methyl (3R,4R)-1-(3-phenylpropyl)-4-[3-(6-methoxyquinolin-4-yl)prop-2-enyl]piperidine-3-carboxylate A solution of 0.25 g of methyl (3R,4R)-1-(3-phenylpropyl)-4-[3-(R,S)-chloro-3-(6-methoxyquinolin-4-yl)propyl]piperidine-3-carboxylate and 1.52 g of 1,8-diazabicyclo[5.4.0]undec-7-ene in 5 cm³ of toluene was brought to 110° C. for 4 hours. The reaction mixture was concentrated under reduced pressure (5 kPa) at a temperature in the region of 50° C. The residue was purified by chromatography on a column of silica gel (particle size 20–45 μm; diameter 3 cm; silica mass 78.5 g), elution was carried out, under a pressure of 50 kPa of nitrogen, with an ethyl acetate/methanol (97/3 by volume) mixture, and 25-cm³ fractions were collected. Fractions 71 to 120 were combined and concentrated under reduced pressure (5 kPa) at a temperature in the region of 40° C. 0.08 g of methyl (3R,4R)-1-(3-phenylpropyl)-4-[3-6-methoxyquinolin-4-yl)prop-2-enyl]piperidine-3-carboxylate was obtained in the form of a pale yellow lacquer.

Methyl (3R,4R)-1-(3-phenylpropyl)-4-[3-(R,S)-chloro-3-(6-methoxyquinolin-4-yl)propyl]piperidine-3-carboxylate was obtained in the following way:

0.46 cm³ of thionyl chloride was added dropwise to a solution of 1 g of methyl (3R,4R)-1-(3-phenylpropyl)-4-[3-(R,S)-hydroxy-3-(6-methoxyquinolin-4-yl)-propyl]piperidine-3-carboxylate in 15 cm³ of chloroform while maintaining the temperature at 0° C. The reaction mixture was allowed to return to a temperature in the region of 20° C. with stirring over 2 hours. The reaction mixture was subsequently concentrated under reduced pressure (5 kPa) at a temperature in the region of 50° C. The residue was dissolved in 30 cm³ of distilled water and the aqueous phase was washed with 15 cm³ of dichloromethane, then basified to pH 9 with solid potassium carbonate and, finally, extracted with 3 times 20 cm³ of dichloromethane. The organic phases were combined, washed with 2 times 20 cm³ of distilled water, and dried over magnesium sulfate. After filtering and then concentrating under reduced pressure (5 kPa) at a temperature in the region of 45° C., 1.16 g of methyl (3R,4R)-1-(3-phenylpropyl)-4-[3-(R,S)-chloro-3-(6-methoxyquinolin-4-yl)propyl]piperidine-3-carboxylate were obtained in the form of a brown oil.

Methyl (3R,4R)-1-(3-phenylpropyl)-4-[3-(R,S)-hydroxy-3-(6-methoxyquinolin-4-yl)propyl]piperidine-3-carboxylate was prepared as described in Example 5.

EXAMPLE 21

(3R,4R)-1-[2-(3-Fluorophenylthio)ethyl]-4-[3-(R,S)-hydroxy-3-(6-methoxyquinolin-4-yl)propyl]piperidine-3-carboxylic acid dihydrochloride 0.8 g of methyl (3R,4R)-1-[2-(3-fluorophenylthio)ethyl]-4-[3-(R,S)-hydroxy-3-(6methoxyquinolin-4-yl)propyl] piperidine-3-carboxylate in 10 cm³ of methanol and 1.25 cm³ of 5N sodium hydroxide were heated, with stirring, at a temperature in the region of 60° C. for 4 hours. The reaction mixture was evaporated under reduced pressure (5 kPa) at a temperature in the region of 50° C. 15 cm³ of water were added to the residue obtained and then 2 cm³ of 5N aqueous hydrochloric acid were added. The reaction mixture was again evaporated to dryness. The residue obtained was triturated with a dichloromethane/methanol (90/10 by volume) mixture. The sodium chloride was filtered off and then the filtrate was concentrated under reduced pressure (5 kPa) at a temperature in the region of 30° C. The foam obtained was triturated with ethyl ether. The solid formed was filtered off. 0.75 g of beige solid was obtained. This solid was dissolved in a mixture of 50 cm³ of chloroform and 50 cm³ of acetonitrile. The insoluble material was filtered off and then the filtrate was acidified with 20 cm³ of a 1N solution of hydrochloric acid in ether. The reaction mixture was evaporated under reduced pressure (5 kPa) at a temperature in the region of 30° C. The residue obtained was triturated with ethyl ether. The solid formed was filtered off and then dried under vacuum. 0.7 g of (3R,4R)-1-[2-(3-fluorophenylthio)ethyl]-4-[3-(R,S)-hydroxy-3-(6-methoxyquinolin-4-yl)propyl]piperidine-3-carboxylic acid dihydrochloride was obtained in the form of a solid with a beige color.

¹H N.M.R. spectrum (400 MHz, d6-$(CD_3)_2SO$, δ in ppm): from 1.25 to 1.90 (mt, 8H), 2.22 (mt, 2H), from 2.65 to 2.90 (mt, 2H), from 3.35 to 3.60 (mt, 4H), 3.91 and 3.93 (2s, 3H), 4.29 (unresolved peak, 1H), 5.28 (mt, 1H), 5.50 and 5.52 (2d, J=4.5 Hz, 1H), 7.07 (mt, 1H), 7.28 (dd, J=4 and 1 Hz, 1H), from 7.35 to 7.45 (mt, 2H), from 7.50 to 7.60 (mt, 2H), 7.95 (d, J=9 Hz, 1H), 8.71 (d, J=5 Hz, 1H).

Methyl (3R,4R)-1-[2-(3-fluorophenylthio)ethyl]-4-[3-(R,S)-hydroxy-3-(6-methoxyquinolin-4-yl)propyl]piperidine-3-carboxylate 0.16 g of sodium borohydride was added with stirring, at a temperature of less than 25° C., to a solution of 1.8 g of methyl (3R,4R)-1-[2-(3-fluorophenylthio)ethyl]4-(6-methoxyquinolin-4-yl) -3-oxopropyl]piperidine-3-carboxylate in 20 cm³ of methanol. The reaction mixture was stirred at room temperature for 2 hours. After evaporating the methanol under reduced pressure (5 kPa), the mixture was stirred with 50 cm⁻¹ of dichloromethane and 50 cm³ of a saturated ammonium chloride solution. The organic phase was separated by settling and then dried over magnesium sulfate. After filtering through paper and concentrating under reduced pressure (5 kPa) at a temperature in the region of 40° C., 1.6 g of a product were obtained, which product was purified by chromatography at atmospheric pressure on a column of silica gel (particle size 20–45 μm; diameter 3 cm; 60 g), elution was carried out with a dichloromethane/methanol (96/4 by volume) mixture, and 10-cm³ fractions were collected. The fractions from 30 to 45 were collected. These fractions were combined and then concentrated under reduced pressure (5 kPa) at approximately 40° C. 1.05 g of methyl (3R,4R)-1-[2-(3-fluorophenylthio)ethyl]-4-[3-hydroxy-3-(6-methoxyquinolin-4-yl)]piperidine-3carboxylate were obtained in the form of a mobile brown oil.

Methyl (3R,4R)-1-[2-(3-fluorophenylthio)ethyl]-4-[3-(6-methoxyquinolin-4-yl)-3-oxopropyl]piperidine-3-carboxylate was prepared in the following way:

A mixture of 6.44 g of methyl (3R,4R)-4-[3-(6-methoxyquinolin-4-yl)-3-oxopropyl]piperidine-3- carboxylate in 100 cm³ of acetonitrile, 3.43 g of 2-(3-fluorophenylthio)ethyl-1-chloride, 8.85 g of potassium carbonate, and 1.24 g of potassium iodide was heated at a temperature in the region of 65° C. for 48 hours. After cooling, the insoluble material was filtered off. The filtrate was concentrated under reduced pressure (5 kPa) at a temperature in the region of 40° C. The oily residue was purified by chromatography at atmospheric pressure on a column of silica gel (particle size 20–45 µm; diameter 6 cm; 250 g), elution was carried out with a dichloromethane/ethyl acetate/methanol (50/50/3 by volume) mixture, and 50-cm³ fractions were collected. The fractions from 19 to 25 were collected. These fractions were combined and then concentrated under reduced pressure (5 kPa) at approximately 40° C. 2.1 g of methyl (3R,4R)-1-[2-(3-fluorophenylthio)ethyl]-4-[3-(6-methoxyquinolin-4-yl)-3-oxopropyl]piperidine-3-carboxylate were obtained in the form of a mobile brown oil. Methyl (3R,4R)-4-[3-(6-methoxyquinolin-4-yl)-3-oxopropyl]-piperidine-3-carboxylate was prepared as described in Example 5.

2-(3-Fluorophenylthio)ethyl-1-chloride was obtained in the following way:

A solution of 3.75 g of sodium hydroxide pellet in 50 cm3 of distilled water was added dropwise to a solution of 10 g of 3-fluorothiophenol and 0.1 cm³ of Aliquat 336 in 125 cm³ of 1,2-dichloroethane. The temperature rose to 33° C. The reaction mixture was stirred at room temperature for 5 hours. The reaction mixture was separated by settling. The organic phase was washed with 50 cm³ of 0.1N HCl and with 50 cm³ of distilled water and then dried over magnesium sulfate. After filtering through paper and concentrating under reduced pressure (5 kPa) at a temperature in the region of 40° C., 15 g of a residue were obtained, which residue was purified by chromatography at atmospheric pressure on a column of silica gel (particle size 20–45 µm; diameter 6 cm, 400 g), elution was carried out with cyclohexane, and 100-cm³ fractions were collected. The fractions from 15 to 40 were collected. These fractions were combined and then concentrated under reduced pressure (5 kPa) at approximately 40° C. 13.6 g of 2-(3-fluorophenylthio)ethyl-1-chloride were obtained in the form of a mobile colorless oil.

EXAMPLE 22

(3R,4R)-1-[2-(3-Fluorophenylthio)ethyl]-4-[3-(R,S)-fluoro-3-(6-methoxyquinolin-4-yl)propyl]piperidine-3-carboxylic acid dihydrochloride 0.9 g of methyl (3R,4R)-1-[2-(3-fluorophenylthio)ethyl]-4-[3-(R,S)-fluoro-3-(6-methoxyquinolin-4-yl)propyl] piperidine-3-carboxylate in 12 cm³ of methanol and 1.4 cm³ of 5N sodium hydroxide were heated, with stirring, at a temperature in the region of 60° C. for 4 hours. The reaction mixture was evaporated under reduced pressure (5 kPa) at a temperature in the region of 50° C. 15 cm³ of water were added to the residue obtained and then 2.1 Cm³ of 5N aqueous hydrochloric acid were added. The reaction mixture was again evaporated to dryness. The residue obtained was taken up in a dichloromethane/methanol (90/10 by volume) mixture. The sodium chloride was filtered off and then the filtrate was concentrated under reduced pressure (5 kPa) at a temperature in the region of 30° C. The foam obtained was triturated with ethyl ether. The solid formed was filtered off. 0.9 g of beige solid was obtained. This solid was dissolved in a mixture of 50 cm³ of chloroform and 50 cm³ of acetonitrile. The insoluble material was filtered off and then the filtrate was acidified with 20 cm³ of a 1N solution of hydrochloric acid in ether. The reaction mixture was evaporated under reduced pressure (5 kPa) at a temperature in the region of 30° C. The residue obtained was triturated with ethyl ether. The solid formed was filtered off and then dried under vacuum. 0.9 g of (3R,4R)-1-[2-(3-fluorophenylthio) ethyl]-4-[3-(R,S)-fluoro-3-(6-methoxyquinolin-4-yl)propyl] piperidine-3-carboxylic acid dihydrochloride was obtained in the form of a solid with a beige color.

¹H N.M.R. spectrum (600 MHz, d6-(CD₃)₂SO, with addition of a few drops of d4-CD₃COOD, at a temperature of 383K, δ in ppm): from 1.40 to 2.25 and from 2.65 to 3.65 (mts, 16H), 3.96 (s, 3H), 6.31 (mt, JHF=47 Hz, 1H), 7.03 (mt, 1H), 7.25 ( mt, 2H), from 7.30 to 7.45 (mt, 2H), 7.53 (mt, 1H), 7.57 (mt, 1H), 8.09 (d, J=9 Hz, 1H), 8.82 (d, J=5 Hz, 1H).

Methyl (3R,4R)-1-[2-(3-fluorophenylthio)ethyl]-4-[3-(R,S)-fluoro-3-(6-methoxyquinolin-4-yl)propyl] piperidine-3-carboxylate 1.7 g of methyl (3R,4R)-1-[2-(3-fluorophenylthio)ethyl]-4-[3-(R,S)-hydroxy-3-(6-methoxyquinolin-4-yl)propyl] piperidine-3-carboxylate were dissolved in 17 cm³ of dichloromethane under an argon atmosphere. 0.53 cm³ of diethylaminosulfur trifluoride was added dropwise with stirring at 20° C. After stirring for 2 hours at room temperature, the reaction mixture was cooled to 15° C. and then 20 cm³ of a saturated sodium hydrogencarbonate solution were added dropwise. The organic phase was separated by settling and then the aqueous phase was extracted with 2 times 50 cm³ of dichloromethane. The combined organic extracts were washed with 2 times 50 cm³ of distilled water and then dried over magnesium sulfate. After filtering through paper, the solution was evaporated under reduced pressure (5 kPa) at a temperature in the region of 30° C. 1.6 g of a brown oil were obtained, which oil was purified twice by chromatography at atmospheric pressure on a column of silica gel. (particle size 20-45 µm; diameter 3 cm; 60 g), elution was carried out with a dichloromethane/methanol (98/2 by volume) mixture, and 10-cm³ fractions were collected. For the first purification, the fractions from 15 to 25 were collected. For the second purification, the fractions from 18 to 30 were collected. These fractions were combined and then concentrated under reduced pressure (5 kPa). 0.92 g of methyl (3R,4R)-1-[2-(3-fluorophenylthio)ethyl]-4-[3-(R,S)-fluoro-3-(6-methoxyquinolin-4-yl)propyl]piperidine-3-carboxylate was obtained in the form of a brown oil.

Methyl (3R,4R)-1-[2-(3-fluorophenylthio)ethyl]-4-[3-(R, S)-hydroxy-3-(6-methoxyquinolin-4-yl)propyl]piperidine-3-carboxylate was obtained as described in Example 21.

EXAMPLE 23

(3R,4R)-4-[3-(R,S)-Hydroxy-3-(6-methoxyquinolin-4-yl)propyl]-1-[2-(1,3-thiazol-2-ylthio)ethyl] piperidine-3-carboxylic acid dihydrochloride A mixture of 0.21 g of methyl (3R,4R)-4-[3-(R,S)-hydroxy-3-(6-methoxyquinolin-4-yl)propyl]-1-[2-(1,3-thiazol-2-ylthio)ethyl]piperidine-3-carboxylate and 0.33 cm³ of 5N aqueous sodium hydroxide in 3 cm³ of methanol was heated at a temperature in the region of 60° C., with stirring, for 18 hours. After cooling, the reaction mixture was evaporated under reduced pressure (5 kPa) at a temperature in the region of 40° C.; the residue was taken up in 6 cm³ of water and then washed with 6 cm³ of ethyl acetate. The aqueous phase was evaporated to dryness under reduced pressure (5 kPa) at a temperature in the region of 80° C. The residue obtained was triturated in 5 cm³ of dichloromethane and then acidified by addition of 1 cm³ of a 3.3N solution of hydrochloric acid in diisopropyl ether. The insoluble material was filtered off and washed with 2 times 3 cm³ of a dichloromethane/methanol (90/10 by volume) mixture. The filtrate was evaporated under reduced pressure (5 kPa) at a temperature in the region of 40° C. 0.19 g of (3R,4R)-4-[3-(R,S)-hydroxy-3-(6-methoxyquinolin-4-yl) propyl]-1-[2-(1,3-thiazol-2-ylthio)ethyl]piperidine-3-carboxylic acid dihydrochloride was obtained in the form of an amorphous solid with a beige color which melts at approximately 75° C. with softening.

$^1$H N.M.R. spectrum (400 MHz, d6-$(CD_3)_2SO$, with addition of a few drops of d4-$CD_3COOD$, at a temperature of 373K, δ in ppm): from 1.35 to 2.15 and from 2.50 to 3.70 (mt, 16H), 3.94 (s, 3H), 5.28 (mt, 1H), from 7.40 to 7.75 (mt, 5H), 7.99 (d, J 1H), 8.72 (d, J 5 Hz, 1H).

Methyl (3R,4R)-4-[3-(R,S)-hydroxy-3-(6-methoxyquinolin-4-yl)propyl]-1-[2-(1,3-thiazol-2-ylthio)ethyl]piperidine-3-carboxylate By carrying out the reaction by analogy with Example 5 but from methyl (3R,4R)-4-[3-oxo-3-(6-methoxyquinolin-4-yl)propyl]-1-[2-(1,3-thiazol-2-ylthio)ethyl]piper carboxylate and sodium borohydride, 0.17 g of methyl (3R,4R)-4-[3(R,S)-hydroxy-3-(6-methoxyquinolin-4-yl)propyl]-1-[2-(1,3-thiazol-2-ylthio)ethyl]piperidine-3-carboxylate was obtained in the form of a viscous oil with a yellow color.

Infrared spectrum ($CCl_4$): 3550–3150 cm$^{-1}$ (alcohol OH ν), 2949 cm$^{-1}$ (aliphatic CH ν), 1736 cm$^{-1}$ (C═O ν), 1228 cm$^{-1}$ (ether C—O ν), 1031 cm$^{-1}$ (alcohol C—O ν), 854 cm$^{-1}$ (quinoline CH γ).

Methyl (3R,4R)-4-[3-oxo-3-(6-methoxyquinolin-4-yl)propyl]-1-[2-(1,3-thiazol-2ylthio)ethyl]piperidine-3-carboxylate was prepared, by analogy with Example 4, from methyl (3R,4R)-4-[3-oxo-3-(6-methoxyquinolin-4-yl)propyl]piperidine-3-carboxylate and 2-(2-chloroethylthio)thiazole. 2-(2-Chloroethylthio)thiazole was prepared in the following way:

1.2 cm³ of 1-bromo-2-chloroethane were run, at a temperature in the region of 20° C., into a stirred solution of 1.47 g of 2-mercaptothiazole and 1.95 g of potassium carbonate in 12.5 cm³ of dimethylformamide. The mixture was subsequently stirred for 2 hours at a temperature in the region of 20° C. The insoluble material was filtered off and washed with 2 times 5 cm³ of dimethylformamide. The filtrate was run onto a mixture of 50 g of crushed ice and 50 cm³ of distilled water, 50 cm³ of ethyl ether were then added and the mixture was stirred and then separated by settling. The aqueous phase was separated by settling and then extracted with 2 times 25 cm³ of ethyl ether. The combined ethereal phases were washed with 2 times 25 cm³ of water and then dried over magnesium sulfate. After filtering through paper, the organic solution was evaporated under reduced pressure (5 kPa) at a temperature in the region of 40° C. 2.11 g of 2-(2-chloroethylthio)thiazole were obtained in the form of a mobile oil with a yellow color.

EXAMPLE 24

(3R,4R)-4-[3-(R,S)-Hydroxy-3-(6-methoxyquinolin-4-yl)propyl]-1-[2-(2-thienylthio)ethyl]piperidine-3-carboxylic acid dihydrochloride A mixture of 0.45 g of methyl (3R,4R)-4-[3-(R,S)-hydroxy-3-(6-methoxyquinolin-4-yl)propyl]-1-[2-(2-thienylthio)ethyl]piperidine-3-carboxylate, 3.5 cm³ of methanol, and 0.54 cm³ of 5N aqueous sodium hydroxide was heated with stirring at a temperature in the region of 60° C. for 20 hours. After evaporating the solvents under reduced pressure (5 kPa) at a temperature in the region of 40° C., the residue obtained was taken up in 3 cm³ of a 6N aqueous hydrochloric acid solution. The solution was evaporated under the same conditions and then the residue obtained was triturated in a dichloromethane/methanol (90/10 by volume) mixture. The insoluble material was filtered off and washed with 2 times 1 cm³ of this mixture. The filtrate was dried over sodium sulfate and then concentrated under reduced pressure (5 kPa) at a temperature in the region of 4° C. After drying in the air, 0.16 g of (3R,4R)-4-[3-(R,S)-hydroxy-3-(6-methoxyquinolin-4-yl)propyl]-1-[2-(2-thienylthio)ethyl]piperidine-3-carboxylic acid dihydrochloride was obtained in the form of a beige solid which melts, with softening, at approximately 148° C.

$^1$H N.M.R. spectrum (300 MHz, d6-$(CD_3)_2SO$, with addition of a few drops of d4-$CD_3COOD$, δ in ppm): from 1.35 to 2.30 and from 2.80 to 3.75 (mts, 16H), 3.98 and 4.00 (2s, 3H), from 5.40 to 5.63 (mt, 1H), from 7.05 to 7.15 (mt, 1H), from 7.25 to 7.40 (mt, 1H), from 7.50 to 7.80 (mt, 3H), 8.00 (mt, 1H), 8.24 (broad d, J=9 Hz, 1H), 9.05 (d,J=5 Hz, 1H).

Methyl (3R,4R)-4-[3-(R,S)-hydroxy-3-(6-methoxyquinolin-4-yl)propyl]-1-[2-(2-thienylthio)ethyl]piperidine-3carboxylate By carrying out the reaction by analogy with Example 5 but from methyl (3R,4R)-4-[3-oxo-3-(6-methoxyquinolin-4-yl)propyl]-1-[2-(2-thienylthio)ethyl]piperidine-3-carboxylate and sodium borohydride, 0.95 g of methyl (3R,4R)-4-[3-(R,S)-hydroxy-3-(6-methoxyquinolin-4-yl)propyl]-1-(2-(2-thienylthio)ethyl]piperidine-3-carboxylate was obtained in the form of an orange oil.

Infrared spectrum ($CH_2Cl_2$): 3600–3150 cm$^{-1}$ (alcohol OH ν), 2951 cm$^{-1}$ (aliphatic CH ν), 1732 cm$^{-1}$ (C═O ν), 1228 cm$^{-1}$ (ether C—O ν), 1031 cm$^{-1}$ (alcohol C—O ν), 847 cm$^{-1}$ (quinoline CH γ).

Methyl (3R,4R)-4-[3-oxo-3-(6-methoxyquinolin-4-yl)propyl]-1-[2-(2-thienylthio)ethyl]piperidine-3-carboxylate was prepared, by analogy with Example 4, from methyl (3R,4R)-4-[3-oxo-3-(6-methoxyquinolin-4-yl)propyl]piperidine-3-carboxylate and 2-(2-chloroethylthio)thiophene.

2-(2-Chloroethylthio)thiophene was prepared in the following way:

4.72 cm³ of thiophene-2-thiol were run, with stirring at a temperature in the region of 20° C., into a stirred solution of 8.25 cm³ of 20% aqueous sodium hydroxide solution and 14.6 cm³ of 1-bromo-2-chloroethane. The mixture was subsequently stirred for 6 hours at a temperature in the region of 20° C. 40 cm³ of ethyl ether were subsequently added and the organic phase was washed with water and then dried over magnesium sulfate. After filtering through paper, the organic solution was evaporated under reduced pressure (5 kPa) at a temperature in the region of 40° C. The residue obtained was purified by chromatography, under a pressure reduced to 50 kPa of nitrogen, on a column of silica gel (particle size 20–45 μm; diameter 4.5 cm; weight of silica 250 g), elution was carried out with a cyclohexane/ethyl acetate (95/5 by volume) mixture. 7.27 g of 2-(2-chloroethylthio)thiophene were obtained in the form of a mobile oil with a yellow color.

EXAMPLE 25

(3R,4R)-4-[3-(R,S)-Hydroxy-(6-methoxyquinolin4-yl)propyl]-1-[3-(3-fluorophenyl)prop-2-ynyl] piperidine-3-carboxylic acid dihydrochloride 2.1 cm³ of 5N aqueous sodium hydroxide were added to a solution of 1.3 g of methyl (3R,4R)-4-[3-(R,S)-hydroxy- (6-methoxyquinolin4-yl)propyl]-1-[3-(3-fluorophenyl) prop-2-ynyl]piperidine-3-carboxylate in 15 cm³ of dioxane and then the solution was heated at a temperature in the region of 60° C. for 16 hours. After cooling, the solution obtained was concentrated under reduced pressure (2 kPa) at a temperature in the region of 45° C. The residue obtained was purified by chromatography under argon pressure (50 kPa) on a column of Amicon silica gel (particle size 20–45 μm; diameter 4 cm; height 24 cm), elution was carried out with a mixture of chloroform, methanol, and ammonia (24/12/1 by volume), and 30-cm³ fractions were collected. Fractions 41 to 58 were combined and then evaporated under reduced pressure (2 kPa) at a temperature in the region of 40° C. 1.0 g of a foam was obtained, which foam was dissolved in 8 cm³ of acetone. This solution was added to 5 cm³ of a 1N solution of hydrochloric acid in ether. After stirring for 5 minutes, the solid obtained was filtered and then dried to constant weight under reduced pressure (2 kPa) at a temperature in the region of 40° C. 820 mg of (3R,4R)-4-[3-(R,S)-hydroxy-3-(6-methoxyquinolin-4-yl)propyl]-1-[3-(3-fluorophenyl)prop-2-ynyl]piperidine-3-carboxylic acid dihydrochloride were obtained in the form of a hygroscopic white solid.

¹H N.M.R. spectrum (300 MHz, d6-(CD₃)₂SO, with addition of a few drops of d4-CD₃COOD, δ in ppm): from 1.35 to 2.30 and from 2.90 to 3.65 (mts, 12H), 3.99 (s, 3H), from 4.20 to 4.50 (mt, 2H), from 5.40 to 5.60 (mt, 1H), from 7.25 to 7.70 (mt, 5H), from 7.70 to 7.80 (mt, 1H), 7.99 (mt, 1H), 8.20 (d, J=9 Hz, 1H), 9.01 (broad d, J=5 Hz, 1H).

Methyl (3R,4R)-4-[3-(R,S)-hydroxy-(6-methoxyquinolin4-yl)propyl]-1-[3-(3-fluorophenyl) prop-2-ynyl]piperidine-3-carboxylate 0.193 g of sodium borohydride was added in two portions, at a temperature in the region of 20° C. and under an inert atmosphere, to a stirred solution of 2 g of methyl (3R,4R)-4-[3-oxo-3-(6-methoxyquinolin-4-yl)propyl]-1-[3-(3-fluorophenyl)prop-2-ynyl]piperidine-3-carboxylate in 30 cm³ of methanol. The mixture was subsequently stirred for 3 hours at a temperature in the region of 20° C. 10 cm³ of distilled water were then added while maintaining the same temperature. The mixture was concentrated under reduced pressure (5 kPa) at a temperature in the region of 40° C. The residue obtained was taken up in 25 cm³ of distilled water. The mixture was extracted with a total of 150 cm³ of dichloromethane. The organic phases were combined, then washed three times with 30 cm³ of water and then dried over magnesium sulfate. After filtering through paper and then evaporating the solvent under reduced pressure (5 kPa) at a temperature in the region of 40° C., 1.8 g of a foam were obtained, which foam was purified by chromatography at atmospheric pressure on a column of Amicon silica gel (particle size 20–45 μm; diameter 3 cm; height 30 cm), elution was carried out with ethyl acetate, and 50-cm³ fractions were collected. Fractions 17 to 28 were combined and then evaporated under reduced pressure (2 kPa) at a temperature in the region of 40° C. 1.4 g of methyl (3R,4R)-4-[3-(R,S)-hydroxy-(6-methoxyquinolin-4-yl)propyl]-1-[3-(3-fluorophenyl)prop-2-ynyl]piperidine-3-carboxylate were thus obtained in the form of a light yellow foam.

Methyl (3R,4R)-4-[3-oxo-3-(6-methoxyquinolin-4-yl) propyl]-1-[3-(3-fluorophenyl)prop-2-ynyl]piperidine-3-carboxylate was obtained in the following way:

0.404 g of tetrakis(triphenylphosphine)palladium, 0.118 g of triphenylphosphine, and 0.191 g of cuprous iodide were added under an inert atmosphere, at a temperature in the region of 20° C., to a stirred solution of 1.97 g of methyl (3R,4R)-4-[3-oxo-3-(6-methoxyquinolin-4-yl)propyl]-1-(prop-2-ynyl)piperidine-3-carboxylate in 40 cm³ of acetonitrile. 0.90 cm³ of 3-fluoroiodobenzene was subsequently added, followed by 1.40 cm³ of triethylamine. The mixture was stirred for 15 hours at a temperature in the region of 20° C. and then filtered through celite. The cake was washed with 3 times 10 cm³ of acetonitrile. The combined filtrates were concentrated under reduced pressure (2 kPa) at a temperature in the region of 40° C. 4.3 g of an oil were obtained, which oil was purified by chromatography at atmospheric pressure on a column of silica gel (particle size 20–45 μm; diameter 3 cm; height 60 cm), elution was carried out with ethyl acetate, and 50-cm³ fractions were collected. Fractions 21 to 42 were combined and evaporated under reduced pressure (2 kPa) at a temperature in the region of 35° C. 2 g of methyl (3R,4R)-4-[3-oxo-3-(6-methoxyquinolin-4-yl)propyl]-1-[3-(3-fluorophenyl)-prop-2-ynyl]piperidine-3-carboxylate were obtained in the form of an oil with a yellow color.

Methyl (3R , 4R)-4-[3-oxo-3-(6-methoxyquinolin-4-yl) propyl]-1-(prop-2-ynyl)piperidine-3-carboxylate was obtained in the following way:

19.6 cm³ of triethylamine were added, at a temperature in the region of 20° C., to a stirred suspension of 15 g of methyl (3R,4R)-4-[3-oxo-3-(6-methoxyquinolin-4-yl)propyl] piperidine-3-carboxylate dihydrochloride in 150 cm³ of anhydrous dimethylformamide and under an inert atmosphere, followed, after 45 minutes, by 3.95 cm³ of propargyl bromide diluted in 5 cm³ of anhydrous dimethylformamide. After stirring for 15 minutes at a temperature in the region of 20° C., the mixture was heated for 4 hours at a temperature in the region of 45° C. After cooling, the reaction mixture was poured into a mixture of 150 cm³ of ethyl acetate and 150 cm³ of distilled water. The mixture was stirred for a few minutes and then the organic phase was separated by settling. The aqueous layer was extracted with 2 times 150 cm³ of ethyl acetate. The organic phases were combined, washed with 3 times 200 cm³ of distilled water, and dried over sodium sulfate. After filtering and then evaporating the solvent under reduced pressure (2 kPa) at a temperature in the region of 40° C., 13.8 g of an oil were obtained, which oil was purified by chromatography under argon pressure (50 kPa) on a column of silica gel (particle size 40–63 μm; diameter 5 cm; height 34 cm), elution was carried out with a mixture of ethyl acetate and cyclohexane (9/1 by volume) up to the fraction 40 and then with ethyl acetate for the following fractions, and 50-cm³ fractions were collected. Fractions 23 to 70 were combined and then evaporated under reduced pressure (2 kPa) at a temperature in the region of 45° C. 8.2 g of methyl (3R,4R)-4-[3-oxo-3-(6-methoxyquinolin-4-yl)propyl]-1-(prop-2-ynyl) piperidine-3-carboxylate were obtained in the form of an oil with an orange color.

Methyl (3R , 4 R)-4-[3-oxo-3-(6-methoxyquinolin-4-yl) propyl]piperidine-3-carboxylate dihydrochloride was obtained as described in Example 5.

EXAMPLE 26

(3R,4R)-4-[3-(R,S)-Hydroxy-3-(6-methoxyquinolin4-yl)propyl]-1-[3-(thien-2-yl)prop-2-ynyl]piperidine-3-carboxylic acid dihydrochloride 2 cm³ of 5N aqueous sodium hydroxide were added to a solution of 1.3 g of methyl (3R , 4R)-4-[3-(R,S)-hydroxy-3-(6-methoxyquinolin-4-yl)propyl]-1-[3-(thien-3-yl)propyl- 2-ynyl]piperidine-3-carboxylate in 13 cm³ of dioxane and the solution was then heated at a temperature in the region of 60° C. for 3 hours. After cooling, the solution obtained was concentrated under reduced pressure (2 kPa) at a temperature in the region of 45° C. The residue obtained was taken up in 75 cm³ of distilled water. The aqueous phase was washed with a total of 75 cm³ of dichloromethane. The aqueous phase was concentrated to a volume in the region of 10 cm³, cooled to a temperature in the region of 5° C., and then acidified to a pH in the region of 1 by addition of 5N hydrochloric acid. After stirring for 12 hours at a temperature in the region of 20° C., the aqueous phase was concentrated under reduced pressure (2 kPa) at a temperature in the region of 45° C. The residue obtained was taken up in 50 cm³ of acetone. The solution obtained was concentrated under reduced pressure (2 kPa) at a temperature in the region of 45° C. The residue obtained was purified by chromatography under argon pressure (50 kPa) on a column of silica gel (particle size 20–45 μm; diameter 3 cm; height 30 cm), elution was carried out with a mixture of chloroform, methanol, and ammonia (24/12/1 by volume), and 15-cm³ fractions were collected. Fractions 19 to 53 were combined and then evaporated under reduced pressure (2 kPa) at a temperature in the region of 40° C. 0.8 g of a foam was obtained, which foam was dissolved in 7 cm³ of dichloromethane. This solution was added to 9 cm³ of a 1N solution of hydrochloric acid in ether. After stirring for 5 minutes at a temperature in the region of 20° C., the solid obtained was filtered off, washed with a total of 50 cm³ of diethyl ether, and then dried to constant weight under reduced pressure (2 kPa) at a temperature in the region of 40° C. 0.92 g of (3R,4R)-4-[3-(R,S)-hydroxy-3-(6-methoxyquinolin-4-yl)propyl]-1-[3-(thien-2-yl)prop-2-ynyl]piperidine-3-carboxylic acid dihydrochloride was obtained in the form of crystals with an off-white color.

¹H N.M.R. spectrum (400 MHz, d4-CD₃OD, δ in ppm): from 1.50 to 2.30 (mt, 7H), 3.06 and 3.11 (2 mts, 1H), from 3.15 to 3.95 (mt, 4H), 4.03 and 4.04 (2s, 3H), from 4.15 to 4.45 (mt, 2H), 5.55 and 5.66 (2 mts, 1H), 7.04 (mt, 1H), 7.37 (mt, 1H), 7.51 (d, J=5 Hz, 1H), 7.62 and 7.69 (2 broad s, 1H), 7.77 (dd, J=9 and 2 Hz, 1H), from 8.10 to 8.20 mt, 2H), 8.92 and 8.94 (mt, 1H).

Methyl (3R,4R)-4-[3-(R,S)-hydroxy-(6-methoxyquinolin-4-yl)propyl]-1-[3-(thien-2-yl)prop-2-ynyl]piperidine-3-carboxylate 0.15 g of sodium borohydride was added in one portion, at a temperature in the region of 20° C. and under an inert atmosphere, to a stirred solution of 1.6 g of methyl (3R,4R)-4-[3-oxo-3-(6-methoxyquinolin-4-yl)propyl]-1-[3-(thien-2-yl)prop-2-ynyl]-piperidine-3-carboxylate in 15 cm³ of methanol. The mixture was subsequently stirred for 2.5 hours at a temperature in the region of 25° C. 15 cm³ of distilled water were then added dropwise over approximately 10 minutes while maintaining at a temperature in the region of 15° C. The mixture was concentrated under reduced pressure (5 kPa) at a temperature in the region of 40° C. The residue obtained was taken up in 20 cm³ of distilled water. The mixture was extracted with a total of 100 cm³ of dichloromethane. The organic phases were combined, dried over sodium sulfate, and then evaporated under reduced pressure (5 kPa) at a temperature in the region of 40° C. The solid obtained was purified by chromatography under argon pressure (50 kPa) on a column of silica gel (particle size 20–45 μm; diameter 3 cm; height 35 cm), elution was carried out with a mixture of ethyl acetate and cyclohexane (8/2 by volume), and 15-cm³ fractions were collected. Fractions 38 to 59 were combined and then evaporated under reduced pressure (2 kPa) at a temperature in the region of 40° C. 1.3 g of methyl (3R,4R)-4-[3-(R,S)-hydroxy-3-(6-methoxyquinolin4-yl)propyl]-1-[3-(thien-2-yl)prop-2-ynyl]piperidine-3-carboxylate were thus obtained in the form of a foam.

Methyl (3R,4R)-4-[3-oxo-3-(6-methoxyquinolin-4-yl)propyl]-1-[3-(thien-2-yl)prop-2-ynyl]piperidine-3-carboxylate was obtained in the following way:

0.404 g of tetrakis(triphenylphosphine)palladium, 0.118 g of triphenylphosphine, and 0.191 g of cuprous iodide were added under an inert atmosphere, at a temperature in the region of 20° C., to a stirred solution of 1.97 g of methyl (3R,4R)-4-[3-oxo-3-(6-methoxyquinolin-4-yl)propyl]-1-(prop-2-ynyl)piperidine-3-carboxylate in 40 cm³ of acetonitrile. 0.84 cm³ of 2-iodothiophene was subsequently added, followed by 1.40 cm³ of triethylamine. The mixture was stirred for 48 hours at a temperature in the region of 20° C. and then filtered through celite. The cake was washed with acetonitrile. The combined filtrates were concentrated under reduced pressure (2 kPa) at a temperature in the region of 40° C. 4.2 g of an oil were obtained, which oil was purified by chromatography under argon pressure (50 kPa) on a column of silica gel (particle size 20–45 μm; diameter 3 cm; height 30 cm), elution was carried out with a mixture of ethyl acetate and cyclohexane (8/2 by volume), and 15-cm³ fractions were collected. Fractions 16 to 32 were combined and evaporated under reduced pressure (2 kPa) at a temperature in the region of 35° C. 1.6 g of methyl (3R,4R)-4-[3-oxo-3-(6-methoxyquinolin4-yl)propyl]-1-[3-(thien-2-yl)prop-2-ynyl]piperidine-3-carboxylate were obtained in the form of an oil with an orange color.

Methyl (3R,4R)-4-[3-oxo-3-(6-methoxyquinolin-4-yl)propyl]-1-(prop-2-ynyl)piperidine-3-carboxylate was obtained as shown in Example 25.

EXAMPLE 27

(3R,4R)-4-[3-(R,S)-Fluoro-3-(6-methoxyquinolin-4-yl)propyl]-1-[3-(thien-2-yl)prop-2-ynyl]piperidine-3-carboxylic acid monohydrochloride 2.5 cm³ of 5N aqueous sodium hydroxide were added to a solution of 1.6 g of methyl (3R,4R)-4-[3-(R,S)-fluoro-3-(6-methoxyquinolin-4-yl)propyl]-1-[3-(thien-2yl)prop-2-ynyl]piperidine-3-carboxylate in 16 cm³ of dioxane and then the solution was heated at a temperature in the region of 60° C. for 50 hours. After cooling, the solution obtained was concentrated under reduced pressure (2 kPa) at a temperature in the region of 45° C. The residue obtained was taken up in 50 cm³ of acetone and then concentrated under reduced pressure (2 kPa) at a temperature in the region of 45° C. The residue obtained was purified by chromatography under argon pressure (50 kPa) on a column of silica gel (particle size 20–45 μm; diameter 3.5 cm; height 34 cm), elution was carried out with a mixture of chloroform, methanol, and ammonia (24/12/1 by volume), and 15 -cm³ fractions were collected. Fractions 16 to 28 were combined and then evaporated under reduced pressure (2 kPa) at a temperature in the region of 40° C. The solid was taken up in acetone and then concentrated under reduced pressure (2 kPa) at a temperature in the region of 45° C. 0.72 g of a foam was obtained, which foam was dissolved in 8 cm³ of dichloromethane. This solution was added to 8 cm³ of a 1N solution of hydrochloric acid in ether. After stirring for 15 minutes at a temperature in the region of 20° C., the solid obtained was filtered off and then dried to constant weight under reduced pressure (2 kPa) at a temperature in the region of 40° C. 0.74 g of (3R,4R)-4-[3-(R,S)-fluoro-3-(6-methoxyquinolin-4-yl)propyl]-1-[3-(thien-2-yl)prop-2-ynyl]piperidine-3-carboxylic acid monohydrochloride was obtained in the form of crystals with an off-white color which melt at 166° C.

$^1$H N.M.R. spectrum (400 MHz, d6-$(CD_3)_2SO$, at a temperature of 383K, δ in ppm): 1.68 (mt, 2H), 1.87 (mt, 1H), 1.89 (mt, 1H), from 2.05 to 2.25 (mt, 3H), from 3.05 to 3.45 (mt, 5H), 3.98 (s, 3H), 4.25 (limit AB, 2H), 6.31 (mt, $J_{HF}$=16 Hz, 1H), 7.12 (dd, J=5 and 3.5 Hz, 1H), from 7.35 to 7.45 (mt, 2H), from 7.45 to 7.55 (mt, 2H), 7.64 (d, J=5 Hz, 1H), 8.05 (d, J=9 Hz, 1H), 8.80 (d, J=5 Hz, 1H).

Methyl (3R,4R)-4-[3-(R,S)-fluoro-(6-methoxyquinolin-4-yl)propyl]-1-[3-(thien-2-yl)prop-2-ynyl]piperidine-3-carboxylate A solution of 1.14 cm$^3$ of sulfur diethylaminotrisulfide in 10 cm$^3$ of dichloromethane was added dropwise over approximately 15 minutes to a solution of 3.4 g of methyl (3R,4R)-4-[3-(R,S)-hydroxy-3-(6-methoxyquinolin-4-yl)propyl]-1-[3-(thien-2-yl)prop-2-ynyl]piperidine-3-carboxylate under an inert atmosphere in 50 cm$^3$ of dichloromethane. After stirring for 9 hours at a temperature in the region of 20° C., the reaction mixture was cooled to a temperature in the region of 10° C. and 60 cm$^3$ of a saturated sodium hydrogencarbonate solution were added over approximately 15 minutes. The organic phase was separated by settling and then washed with a total of 300 cm$^3$ of distilled water. The organic phase was dried over sodium sulfate, filtered, and then concentrated under reduced pressure (2 kPa) at a temperature in the region of 40° C. The residue obtained was purified by chromatography under argon pressure (50 kPa) on a column of silica gel (particle size 20–45 μm; diameter 4 cm; height 31 cm), elution was carried out with a mixture of ethyl acetate and cyclohexane (1/1 by volume), and 15-cm$^3$ fractions were collected. Fractions 34 to 65 were combined and then evaporated under reduced pressure (2 kPa) at a temperature in the region of 40° C. The solid was taken up in acetone and then concentrated under reduced pressure (2 kPa) at a temperature in the region of 45° C. 1.8 g of 0.74 g of methyl (3R,4R)-4-[3-(R,S)-fluoro-3-(6-methoxyquinolin-4-yl)propyl]-1-[3-(thien-2-yl)prop-2-ynyl]piperidine-3-carboxylate were obtained in the form of a yellow oil.

Methyl (3R,4R)-4-[3-(R,S)-hydroxy-3-(6-methoxyquinolin-4-yl)propyl]-1-[3-(thien-2-yl)prop-2-ynyl]piperidine-3-carboxylate was prepared as described in Example 26.

EXAMPLE 28

(3R,4R)-4-[3-(R,S)-Fluoro-3-(6-methoxyquinolin-4-yl)propyl]-1-[3-(3-fluorophenyl)prop-2-ynyl] piperidine-3-carboxylic acid dihydrochloride A solution of 1.48 g of methyl (3R,4R)-4-[3-(R,S)-fluoro-3-(6-methoxyquinolin-4-yl)propyl]-1-[3-(3-fluorophenyl)prop-2-ynyl]piperidine-3-carboxylate in 15 cm$^3$ of dioxane and of 2.4 cm$^3$ of 5N aqueous sodium hydroxide was heated at a temperature in the region of 60° C. for 17 hours. After cooling, the solution obtained was concentrated under reduced pressure (2 kPa) at a temperature in the region of 45° C. The residue obtained was taken up in 50 cm$^3$ of acetone and then concentrated under reduced pressure (2 kPa) at a temperature in the region of 45° C. The residue obtained was purified by chromatography at atmospheric pressure on a column of silica gel (particle size 20–45 μm; diameter 2.8 cm; volume: 150 cm$^3$), elution was carried out with a mixture of dichloromethane, methanol, and ammonia (120/20/3 by volume), and 20-cm$^3$ fractions were collected. The fractions comprising the expected product were combined and then evaporated under reduced pressure (2 kPa) at a temperature in the region of 40° C. The solid was taken up in 25 cm$^3$ of acetone and then 5 cm$^3$ of a 1N solution of hydrochloric acid in ether and 20 cm$^3$ of diethyl ether were added. After stirring for 2 hours at a temperature in the region of 20° C., the solid obtained was filtered off and then dried to constant weight under reduced pressure (2 kPa) at a temperature in the region of 40° C. 0.6 g of (3R,4R)-4-[3-(R,S)-fluoro-3-(6-methoxyquinolin-4-yl)propyl]-1-[3-(3-fluorophenyl)prop-2-ynyl]piperidine-3-carboxylic acid dihydrochloride was obtained in the form of a solid.

$^1$H N.M.R. spectrum (400 MHz, d6-$(CD_3)_2SO$, at a temperature of 373K, δ in ppm): from 1.55 to 1.95 (mt, 3H), from 2.00 to 2.30 (mts, 4H), from 3.15 to 3.50 (mt, 5H), 3.99 (s, 3H), 4.31 (limit AB, 2H), 6.38 (mt, $J_{HF}$=47 Hz, 1H), from 7.25 to 7.55 (mt, 5H), 7.55 (dd, J=9 and 2.5 Hz, 1H), 7.60 (d, J=5 Hz, 1H), 8.12 (d, J=9 Hz, 1H), 8.84 (d, J=5 Hz, 1H).

Methyl (3R,4R)-4-[3-(R,S)-fluoro-3-(6-methoxyquinolin-4-yl)propyl]-1-[3-(3-fluorophenyl)prop-2-ynyl]piperidine-3-carboxylate A solution of 1.4 cm$^3$ of sulfur diethylaminotrisulfide in 5 cm$^3$ of dichloromethane was added dropwise over approximately 15 minutes to a solution, cooled to a temperature in the region of 15° C., of 4.2 g of methyl (3R,4R)-4-[3-(R,S)-hydroxy-3-(6-methoxyquinolin-4-yl)propyl]-1-[3-(3-fluorophenyl)prop-2-ynyl]piperidine-3-carboxylate under an inert atmosphere in 75 cm$^3$ of dichloromethane. After stirring for 9 hours at a temperature in the region of 25° C., 100 cm$^3$ of a saturated sodium hydrogencarbonate solution were added while taking care that the temperature did not exceed 25° C. The organic phase was separated by settling and then washed with a total of 100 cm$^3$ of distilled water. The organic phase was dried over magnesium sulfate, filtered, and then concentrated under reduced pressure (2 kPa) at a temperature in the region of 40° C. The residue obtained was purified by chromatography at atmospheric pressure on a column of silica gel (particle size 20–45 μm; diameter 4 cm; height 42 cm), elution was carried out with ethyl acetate, and 70-cm$^3$ fractions were collected. Fractions 19 to 35 were combined and then evaporated under reduced pressure (2 kPa) at a temperature in the region of 40° C. The solid was taken up in acetone and then concentrated under reduced pressure (2 kPa) at a temperature in the region of 45° C. 3.1 g of methyl (3R,4R)-4-[3-(R,S)-fluoro-3-(6-methoxyquinolin-4-yl)propyl]-1-[3-(3-fluorophenyl)prop-2-ynyl]piperidine-3-carboxylate were obtained in the form of a yellow oil.

Methyl (3R,4R)-4-[3-(R,S)-hydroxy-3-(6-methoxyquinolin-4-yl)propyl]-1-[3-(3-fluorophenyl)prop-2-ynyl]piperidine-3-carboxylate was prepared as described in Example 25.

EXAMPLE 29

(3R,4R)-3-Hydroxymethyl-4-[3-(R,S)-hydroxy-3-(6-methoxyquinolin-4-yl)propyl]-1-[3-(thien-2-yl)prop-2-ynyl]piperidine 4.2 cm$^3$ of a 20% solution of diisobutylaluminum hydride in toluene were added to a mixture, cooled to −20° C., with stirring, of 0.5 g of methyl (3R,4R)-4-[3-(R,S)-hydroxy-3-

(6-methoxyquinolin-4-yl)propyl]-1-[3-(thien-2-yl)prop-2-ynyl]piperidine-3-carboxylate in 10 cm³ of toluene. Stirring was maintained for 3 hours at this temperature and then 15 cm³ of a saturated ammonium chloride solution were added, stirring was maintained for 15 minutes and the temperature was allowed to rise to a temperature in the region of 20° C. The aqueous phase was separated by settling, dried over anhydrous magnesium sulfate, filtered, and concentrated to dryness under reduced pressure (2 kPa). The residue obtained was purified by chromatography on a column of silica gel (particle size 20–45 μm; diameter 2 cm; height 20 cm), elution was carried out, under a pressure of 50 kPa of nitrogen, with dichloromethane and then a mixture of dichloromethane and methanol (95/5 by volume), and 30-cm³ fractions were collected. Fractions 14 to 16 were combined and then evaporated under reduced pressure (5 kPa) at a temperature in the region of 40° C. The residue obtained was taken up in 5 cm³ of dichloromethane and filtered. The filtrate was concentrated to dryness under reduced pressure (2 kPa). 0.17 g of (3R,4R)-3-hydroxymethyl-4-[3-(R,S)-hydroxy-3-(6-methoxyquinolin-4-yl)propyl]-1-[3-(thien-2-yl)prop-2-ynyl]piperidine was obtained in the form of a gum.

¹H N.M.R. spectrum (400 MHz, d6-(CD₃)₂SO, δ in ppm): from 1.25 to 1.90 (mt, 8H), 2.22 (mt, 2H), from 2.65 to 2.90 (mt, 2H), from 3.35 to 3.60 (mt, 4H), 3.91 and 3.93 (2s, 3H), 4.29 (unresolved peak, 1H), 5.28 (mt, 1H), 5.50 and 5.52 (2d, J=4.5 Hz, 1H), 7.07 (mt, 1H), 7.28 (dd, J=4 and 1 Hz, 1H), from 7.35 and 7.45 (mt, 2H), from 7.50 to 7.60 (mt, 2H), 7.95 (d, J=9 Hz, 1H), 8.71 (d, J=5 Hz, 1H).

Methyl (3R,4R)-4-[3-(R,S)-hydroxy-3-(6-methoxyquinolin-4-yl)propyl]-1-[3-(thien-2-yl)prop-2-ynyl]piperidine-3-carboxylate was obtained as described in Example 26.

EXAMPLE 30

(3R,4R)-4-[3-(R,S)-Hydroxy-3-(6-methoxyquinolin-4-yl)propyl]-3-hydroxymethyl-1-[2-(1,3-thiazol-2-ylthio)ethyl]piperidine By carrying out the reaction by analogy with Example 5 but from methyl (3R,4R)-4-[3-oxo-3-(6-methoxyquinolin-4-yl)propyl]-1-[2-(1,3-thiazol-2-ylthio)ethyl]piperidine-3-carboxylate and sodium borohydride, 0.33 g of (3R,4R)-4-[3-(R,S)-hydroxy-3-(6-methoxyquinolin-4-yl)propyl]-3-hydroxymethyl-1-[2-(1,3-thiazol-2-ylthio)ethyl]-3-piperidine was obtained in the form of an oil.

¹H N.M.R. spectrum (300 MHz, d6-(CD₃)₂SO, δ in ppm): from 1.10 to 2.20, from 2.55 to 2.90 and from 3.30 to 3.60 (mts, 16H), 2.60 (t, J=6.5 Hz, 2H), 3.93 and 3.94 (2s, 3H). 4.26 (unresolved peak, 1H), 5.27 (mt, 1H), from 5.50 to 5.60 (mt, 1H), from 7.35 to 7.45 (mt, 2H), 7.56 (mt, 1H), 7.63 (d, J=3 Hz, 1H), 7.71 (d, J=3 Hz, 1H), 7.95 (d, J=9 Hz, 1H), 8.72 (d, J=5 Hz, 1H).

Methyl (3R,4R)-4-[3-oxo-3-(6-methoxyquinolin-4-yl)propyl]-1-[2-(1,3-thiazol-2-ylthio)ethyl]piperidine-3-carboxylate was prepared, by analogy with Example 4, from methyl (3R,4R)-4-[3-oxo-3-(6-methoxyquinolin-4-yl)propyl]piperidine-3-carboxylate and 2-bromo-1-(1,3-thiazol-2-ylthio)ethane.

Methyl (3R,4R)-4-[3-oxo-3-(6-methoxyquinolin-4-yl)propyl]piperidine-3-carboxylate was prepared as described in Example 5.

EXAMPLE 31

(3R,4R)-4-[3-(6-Methoxyquinolin-4-yl)propyl]-1-[3-phenylpropyl]piperidine-3-acetic acid A mixture of 0.25 g of methyl (3R,4R)-4-[3-(6-methoxyquinolin-4-yl)propyl]-1-[3-phenylpropyl]piperidine-3-acetate and 0.42 cm³ of 5N aqueous sodium hydroxide in 5 cm³ of dioxane was stirred for 9 days at a temperature in the region of 20° C. The reaction mixture was concentrated under reduced pressure (5 kPa) at a temperature in the region of 20° C. 0.48 g of an oil was obtained, which oil was purified by chromatography at atmospheric pressure on a column of silica gel (particle size 20–45 μm; diameter 1.9 cm; 28 9), elution was carried out with a chloroform/methanol/28% aqueous ammonia (12/3/0.5 by volume) mixture, and 10-cm³ fractions were collected. Fractions 5 to 8 were combined and then evaporated under reduced pressure (5 kPa) at a temperature in the region of 40° C. 0.18 g of a product was obtained, which product was purified in the hydrochloride form: the product was dissolved in a mixture of 5 cm³ of diethyl ether and 1 cm³ of acetone; 0.4 cm³ of a 1N solution of hydrochloric acid in ether was added to the solution. The precipitate was filtered off and dried under reduced pressure (13 Pa) at a temperature in the region of 40° C. for 1 hour. 0.14 g of (3R,4R)-4-[3-(6-methoxyquinolin-4-yl)propyl]-1-[3-phenylpropyl]piperidine-3-acetic acid was obtained in the form of a very hygroscopic solid with a cream color.

¹H N.M.R. spectrum (400 MHz, d6-(CD₃)₂SO, with addition of a few drops of d4-CD₃COOD, δ in ppm): from 1.30 to 2.50 and from 2.75 to 3.85 (mts, 20H), 2.63 (t, J=7.5 Hz, 2H), 3.93 (s, 3H), from 7.20 to 7.30 (mt, 3H), 7.30 (t, J=8 Hz, 2H), 7.38 (mt, 2H), 7.44 (dd, J=9 and 2.5 Hz, 1H), 7.96 (d, J 9 Hz, 1H), 8.66 (d, J=5 Hz, 1H).

Methyl (3R,4R)-4-[3-(6-methoxyquinolin-4-yl)propyl]-1-[3-phenylpropyl]piperidine-3-acetate Anhydrous gaseous hydrochloric acid was sparged into a solution, stirred at a temperature in the region of 20° C., of 0.3 g of (3R,4R)-4-[3-(6-methoxyquinolin-4-yl)propyl]-1-[3-phenylpropyl]piperidine-3-acetonitrile in 10 cm³ of methanol. The mixture was subsequently diluted with 20 cm³ of water and then poured onto 15 cm³ of a saturated sodium hydrogencarbonate solution. After extracting with 2 times 20 cm³ of dichloromethane, the combined extracts were washed with 25 cm³ of water, then dried over magnesium sulfate, filtered and, finally, evaporated under reduced pressure (5 kPa) at a temperature in the region of 40° C. 0.27 g of methyl (3R,4R)-4-[3-(6-methoxyquinolin-4-yl)propyl]-1-[3-phenylpropyl]piperidine-3-acetate was obtained in the form of an oil with a yellow color.

(3R,4R)-4-[3-(6-Methoxyquinolin-4-yl)propyl]-1-[3-phenylpropyl]piperidine-3-acetonitrile was obtained in the following way:

0.565 g of sodium cyanide was added to a stirred solution of 1.3 g of (3R,4R)-3-chloromethyl-4-[3-(6-methoxyquinolin-4-yl)propyl]-1-(3-phenylpropyl)piperidine in 50 cm³ of dimethyl sulfoxide and then the mixture was heated at a temperature in the region of 60° C. for 20 hours. After cooling, the reaction mixture was poured onto 500 cm³ of water and then extracted with 2 times 200 cm³ of diethyl ether. The combined extracts were dried over magnesium sulfate, filtered, and then evaporated under reduced pressure (5 kPa) at a temperature in the region of 40° C. The residue obtained was purified by chromatography at atmospheric pressure on a column of silica gel (particle size 20–45 μm, diameter 2 cm; 32 g), elution was carried out with ethyl acetate, and 15-cm³ fractions were collected. Fractions 12 to 19 were combined and then evaporated (5 kPa) at a temperature in the region of 40° C. 0.34 g of (3R,4R)-4-[3-(6-methoxyquinolin-4-yl)propyl]-1-[3-phenylpropyl]piperidine-3-acetonitrile was obtained in the form of an oil with a yellow color.

(3R,4R)-3-Chloromethyl-4-[3-(6-methoxyquinolin-4-yl) propyl]-1-(3-phenylpropyl)piperidine was obtained in the following way:

3.6 cm³ of thionyl chloride were added dropwise, at a temperature in the region of 20° C., to a stirred solution of 2.9 g of (3R,4R)-3-hydroxymethyl4-[3-(6-methoxyquinolin-4-yl)propyl]-1-(3-phenylpropyl) piperidine oxalate in 20 cm³ of chloroform. The mixture was heated for 2 hours at a temperature in the region of 60° C. and then, after cooling, was poured onto 50 cm³ of water to which 250 g of ice had been added. After separating by settling from the chloroform phase, the mixture was extracted with 100 cm³ of dichloromethane. 5 g of sodium hydrogencarbonate were added to the aqueous phase, which was then extracted with 2 times 200 cm³ of dichloromethane. The organic extracts were dried over magnesium sulfate, filtered, and then evaporated under reduced pressure (5 kPa) at a temperature in the region of 40°. 1.3 g of (3R,4R)-3-chloromethyl-4-[3-(6-methoxyquinolin-4-yl) propyl]-1-(3-phenylpropyl)piperidine were obtained in the form of an oil with a brown color.

(3R,4R)-3-Hydroxymethyl-4-[3-(6-methoxyquinolin-4-yl)propyl]-1-(3-phenylpropyl)piperidine oxalate was obtained in the following way:

A mixture of 0.25 g of (3R,4R)-3-hydroxymethyl-4-[3-(6-methoxyquinolin-4-yl)propyl]piperidine, 0.14 cm³ of 1-bromo-3-phenylpropane and 0.197 g of potassium carbonate in 10 cm³ of anhydrous dimethylformamide was stirred for 4 hours at a temperature in the region of 60° C. under a nitrogen atmosphere. 200 cm³ of ethyl acetate were added to the reaction mixture, followed by 200 cm³ of water. After separating the organic phase by settling and then washing with 4 times 100 cm³ of water and one times 100 cm³ of a saturated sodium chloride solution, drying was carried out over magnesium sulfate. After filtering and then concentrating under reduced pressure (5 kPa) at a temperature in the region of 45° C., 0.31 g of a colorless oil was obtained, which oil was purified by chromatography on a column of silica gel (particle size 40–63 µm; diameter 2 cm; height 20 cm), elution was carried out, under a pressure of 50 kPa of nitrogen, with a dichloromethane/methanol (90/10 by volume) mixture, and 10-cm³ fractions were collected. Fractions 8 to 12 were combined and concentrated under reduced pressure (5 kPa) at a temperature in the region of 40° C. 0.243 g of 6-methoxy-4-[3-(3-hydroxymethyl-1-phenylpropyl-4-piperidyl)propyl]quinoline was obtained in the form of a colorless oil. The product was purified in the form of the oxalate, which was prepared in ethyl acetate. 0.243 g of (3R,4R)-3-hydroxymethyl-4-[3-(6-methoxyquinolin-4-yl)propyl]-1-(3-phenylpropyl) piperidine oxalate was obtained in the form of a white solid which melts with softening at 55° C.

(3R,4R)-3-Hydroxymethyl-4-[3-(6-methoxyquinolin-4-yl)propyl]piperidine was obtained as described in Patent Application WO99/37635,the disclosure of which is specifically incorporated by reference herein.

EXAMPLE 32

(3R,4R)-4-[3-(R,S)-Hydroxy-3-(6-methoxyquinolin-4-yl)propyl]-1-[3-(thien-3-yl)prop-2-ynyl]piperidine-3-carboxylic acid A solution of 0.73 g of methyl. (3R,4R)-4-[3-(R,S)-hydroxy-3-(6-methoxyquinolin-4-yl)propyl]-1-[3-(thien-3-yl)prop-2-ynyl]piperidine-3-carboxylate, 7.6 cm³ of dioxane, and 1.22 cm³ of 5N aqueous sodium hydroxide solution was heated at a temperature in the region of 60° C. with stirring for 3 hours 30 minutes. After cooling to a temperature in the region of 20° C., the reaction mixture was concentrated under reduced pressure (5 kPa) at a temperature in the region of 40° C. The residue obtained was purified by chromatography under argon pressure (55 kPa) on a column of silica gel (particle size 40–63 µm; diameter 5 cm; silica volume 120 cm³), elution was carried out first with 1120 cm³ of a dichloromethane/methanol/acetonitrile (92/8/7 by volume) mixture. Elution was subsequently carried out with 224 cm³ of the same mixture (but with a composition of 92/12/7 by volume), then 224 cm³ of the same mixture (with a composition of 92/16/7 by volume), then 400 cm³ of a dichloromethanel methanol (50/50 by volume) mixture, and finally 400 cm³ of pure methanol. A fraction of 112 cm³ was collected, followed by 7-cm³ fractions. Fractions 173 to 468 were combined and then evaporated under reduced pressure (2 kPa) at a temperature in the region of 35° C. A foam was obtained, which foam was dried under reduced pressure (30 Pa) at a temperature in the region of 30° C. for 4 to 5 hours. 0.33 g of (3R,4R)-4-[3-(R,S)-hydroxy-3-(6-methoxyquinolin-4-yl)propyl]-1-[3-(thien-3-yl)prop-2-ynyl]piperidine-3-carboxylic acid was obtained in the form of a beige-colored solid with a foamy appearance melting at 113–115° C.

$^1$H N.M.R. spectrum (300 MHz, d6-(CD$_3$)$_2$SO, δ in ppm). A mixture of two diastereoisomers was observed: from 1.40 to 1.95 and from 2.30 to 2.95 (mts, 12H), 3.53 and 3.55 (2s, 2H in all), 3.90 and 3.92 (2s, 3H in all), 5.24 (mt, 1H), from 5.35 to 5.65 (broad unresolved peak, 1H), 7.14 (d, J 5 Hz, 1H), from 7.30 to 7.45 (mt, 2H), 7.53 and 7.55 (2d, J=5 Hz, 1H in all), 7.60 (dd, J=5 and 3 Hz, 1H), 7.74 (mt, 1H), 7.94 (d, J=9.5 Hz, 1H), 8.70 (d, J=5 Hz, 1H).

Methyl (3R,4R)-4-[3-(R,S)-hydroxy-3-(6-methoxyquinolin-4-yl)propyl]-1-[3-(thien-3-yl)prop-2-ynyl]piperidine-3-carboxylate The preparation was carried out as in the preparation of methyl (3R,4R)-4-[3-(6-methoxyquinolin-4-yl)propyl]-1-[3-(thien-3-yl)prop-2-ynyl]piperidine-3-carboxylate, from 1.2 g of methyl (3R,4R)-4-[3-(R,S)-hydroxy-3-(6-methoxyquinolin-4-yl)propyl]-1-(prop-2-ynyl)piperidine-3-carboxylate in 20 cm³ of acetonitrile, 0.067 g of triphenylphosphine, 0.227 g of tetrakis(triphenylphosphine) palladium, 0.115 g of cuprous iodide, and 10 cm³ of acetonitrile, followed by 0.84 cm³ of triethylamine, 0.95 g of 3-iodothiophene, and 5 cm³ of acetonitrile. The reaction mixture was filtered and then the cake was washed with 30 cm³ of acetonitrile. The filtrate was evaporated under reduced pressure (2 kPa) at a temperature in the region of 40° C. The residue obtained was taken up in 100 cm³ of dichloromethane. The resulting organic solution was washed with 3 times 50 cm³ of a saturated sodium chloride solution, dried over sodium sulfate, filtered, and then concentrated under reduced pressure under the same conditions as above. The residue obtained was purified by chromatography under an argon pressure of 55 kPa on a column of silica gel (particle size 40–63 µm; diameter 4 cm; silica volume 220 cm³), elution was carried out with ethyl acetate. A fraction of 180 cm³ was collected, followed by 10-cm³ fractions. Fractions 73 to 300 were combined and then concentrated under reduced pressure (2 kPa) at a temperature in the region of 45° C. 0.96 g of a product was obtained, which product was rereacted with 0.76 g of 3-iodothiophene, 0.092 g of cuprous iodide, 0.054 g of triphenylphosphine, 0.67 cm³ of triethylamine, and 0.181 g of tetrakis(triphenylphosphine) palladium in 27 cm³ of acetonitrile at a temperature in the region of 20° C. for 16 hours. The reaction mixture was filtered; the cake was washed with 30 cm³ of acetonitrile. The filtrate was concentrated under reduced pressure (2 kPa) at a temperature in the region of 40° C. The residue obtained was dissolved in 50 cm³ of dichloromethane; the solution was washed with 3 times 25 cm³ of a saturated sodium chloride solution, separated by settling, and then dried over sodium sulfate, filtered, and concentrated under reduced pressure (2 kPa) at a temperature in the region of 35° C. 1.15 g of a residue were obtained, which residue was purified by chromatography under an argon pressure of 55 kPa on a column of silica gel (particle size 40–63 μm; diameter 4 cm; silica volume 120 cm³), elution was carried out with ethyl acetate. A fraction of 110 cm³ was first collected, followed by 8-cm³ fractions. Fractions 68 to 260 were combined and concentrated under reduced pressure (2 kPa) at a temperature in the region of 45° C. 0.73 g of methyl (3R,4R)-4-[3-(R,S)-hydroxy-3 -(6-methoxyquinolin-4-yl)propyl]-1-[3-(thien-3-yl)prop-2-ynyl]piperidine-3-carboxylate was obtained in the form of a foam with a yellow color.

Infrared spectrum (CCl₄): 3600–3200 cm$^{-1}$ (OH ν), 2950 cm$^{-1}$ (aliphatic CH ν), 1739 cm$^{-1}$ (C=O ν), 1241 cm$^{-1}$ (ether C—O ν), 626 cm$^{-1}$ (thiophene CH γ).

Methyl (3R,4R)-4-[3-(R,S)-hydroxy-3-(6-methoxyquinolin-4-yl)propyl]-1-(prop-2-ynyl)piperidine-3-carboxylate A suspension of 2.45 g of methyl (3R,4R)-4-[3-(R,S)-hydroxy-3-(6-methoxyquinolin-4-yl)propyl]piperidine-3-carboxylate, 2.1 g of potassium carbonate, 0.95 g of potassium iodide, and 0.6 cm³ of propargyl bromide in 50 cm³ of acetonitrile was stirred for 40 hours at a temperature in the region of 20° C. in an inert atmosphere. After filtering the reaction mass, the filtrate was evaporated under reduced pressure (5 kPa) at a temperature in the region of 40° C. The residue obtained was purified by chromatography on a column of silica gel (particle size 20–45 μm; diameter 2.5 cm; mass 50 g), elution was carried out with ethyl acetate, and 60-cm³ fractions were collected. Fractions 6 to 12 were combined and then concentrated under reduced pressure (5 kPa) at a temperature in the region of 40° C. 1.35 g of methyl (3R,4R)-4-[3-(R,S)-hydroxy-3-(6-methoxyquinolin-4-yl)propyl]-1-(prop-2-ynyl)piperidine-3-carboxylate were obtained in the form of a gum.

Infrared spectrum (CCl₄): 3600–3200 cm$^{-1}$ (OH ν), 3311 cm$^{-1}$ (acetylenic CH ν), 2950 cm$^{-1}$ (aliphatic CH ν), 1740 cm$^{-1}$ (C=O ν), 1242 cm$^{-1}$ (ether C—O ν).

3-Iodothiophene was prepared according to N. A. Petasis et al., Synlett., 141 (1988), the disclosure of which is specifically incorporated by reference herein.

EXAMPLE 33

(3R,4R)-4-[3-Hydroxy-3-(6-methoxyquinolin-4-yl)propyl]-1-[2-(2-thienylthio)ethyl]piperidine-3-carboxylic acid, diastereoisomer A, and (3R,4R)-4-[3-hydroxy-3-(6-methoxyquinolin-4-yl)propyl]-1-[2-(2-thienylthio)ethyl]piperidine-3-carboxylic acid, diastereoisomer B.

1.36 g of (3R,4R)-4-[3-(R,S)-hydroxy-3-(6-methoxyquinolin-4-yl)propyl]-1-[2-(2-thienylthio)ethyl]piperidine-3-carboxylic acid, dissolved in 100 cm³ of dichloromethane, were chromatographed on a 35-cm column with a diameter of 6 cm packed with 700 g of silica (particle size 5–15 μm) from Daiso. The elution was carried out using a dichloromethane/methanol (92/8 by volume) mixture comprising 0.05% of triethylamine. The flow rate was 90 cm³ per minute and detection was carried out using ultraviolet radiation at 280 nm. This operation resulted in two diastereoisomers were obtained. The fractions corresponding to the first were concentrated to dryness under reduced pressure (5 kPa) at a temperature in the region of 40° C. and then the residue obtained was dried in an oven under reduced pressure (13 Pa) at a temperature in the region of 40° C. 0.28 g of (3R,4R)-4-[3-hydroxy-3-(6-methoxyquinolin-4-yl)propyl]-1-[2-(2-thienylthio)ethyl] piperidine-3-carboxylic acid, diastereoisomer A ($[\alpha]_D^{20}$=−73.8°+/−1.4, in dichloromethane at 0.5%), was obtained in the form of a foam with a yellow color. The fractions corresponding to the second diastereoisomer were treated as above., 0.46 g of (3R,4R)-4-[3-hydroxy-3-(6-methoxyquinolin4-yl)propyl]-1-[2-(2-thienylthio)ethyl]-piperidine-3-carboxylic acid, diastereoisomer B ($[\alpha]_D^{20}$=+71.2°+/−1.2, in dichloromethane at 0.5%), was obtained in the form of a yellow foam.

Diastereoisomer A: $^1$H N.M.R. spectrum (300 MHz, (CD₃)₂SO, δ in ppm): from 1.35 to 1.75 and 1.94 (mts, 7H), 2.22 (mt, 1H), 2.36 (broad d, J=10.5 Hz, 1H), from 2.50 to 2.65 (mt, 1H), 2.61 (t, J=7 Hz, 2H), 2.76 (mt, 1H), from 2.85 to 3.05 (mt, 1H), 2.98 mt, 2H), 3.95 (s, 3H), 5.22 (mt, 1H), 5.51 (broad d, J=4.5 Hz, 1H), 7.07 (dd, J=5 and 4 Hz, 1H), 7.22 (broad d, J=4 Hz, 1H), 7.36 (mt, 1H), from 7.35 to 7.45 (mt, 2H), 7.64 (broad d, J=5 Hz, 1H), 7.95 (d, J=9.5 Hz, 1H), 8.72 (d, J=5 Hz, 1H).

Diastereoisomer B: $^1$H N.M.R. spectrum (300 MHz, (CD₃)₂SO, δ in ppm) from 1.20 to 1.95 (mts, 7H), 2.22 (mt, 1H), 2.39 (broad d, J=10.5 Hz, 1H), from 2.50 to 2.95 (mt, 3H), 2.60 (t, J=7 Hz, 2H), 2.97 (mt, 2H), 3.92 (s, 3H), 5.25 (mt, 1H), 5.51 (unresolved peak, 1H), 7.06 (dd, J=5 and 3.5 Hz, 1H), 7.20 (dd, J=3.5 and 1.5 Hz, 1H), 7.40 mt, 2H), 7.53 (d, J=5 Hz, 1H), 7.63 (dd, J=5 and 1.5 Hz, 1H), 7.93 (d, J=10 Hz, 1H), 8.70 (d, J=5 Hz, 1H).

EXAMPLE 34

(3R,4R)-4-[3-(R,S)-Hydroxy-3-(6-methoxyquinolin-4-yl)propyl]-1-[2-(tert-butylthio)ethyl]piperidine-3-carboxylic acid dihydrochloride 1 cm³ of 5N aqueous sodium hydroxide solution was added, with stirring and under an inert atmosphere, to a solution of 0.26 g of methyl (3R,4R)-4-[3-(R,S)-hydroxy-3-(6-methoxyquinolin-4-yl)propyl]-1-[2-(tert-butylthio) ethyl]piperidine-3-carboxylate in 5 cm³ of methanol. After heating the solution to a temperature in the region of 60° C. and then cooling to room temperature, the reaction mass was evaporated under reduced pressure (2.8 kPa) at a temperature in the region of 60° C. The residue obtained was taken up in 5 cm³ of distilled water and then 5 cm³ of concentrated hydrochloric acid (d=1.18) were added. The mixture was evaporated under reduced pressure (2.8 kPa) at a temperature in the region of 60° C. The residue obtained was taken up in 4 cm³ of a dichloromethane/methanol (90/10 by volume) mixture. The white precipitate obtained was filtered off and washed with 2 times 2 cm³ of this same mixture. The filtrate was concentrated under reduced pressure (2.8 kPa) at a temperature in the region of 40° C. The product obtained was dried under reduced pressure (16 Pa) at a temperature in the region of 60° C. 0.29 g of (3R,4R)-4-[3-(R,S)-hydroxy-3-(6-methoxyquinolin-4-yl)propyl]-1-[2-(tert-butylthio) ethyl]piperidine-3-carboxylic acid dihydrochloride was obtained in the form of a solid with a beige color melting with softening in the region of 169° C.

$^1$H N.M.R. spectrum (400 MHz, d6-(CD₃)₂SO at a temperature of 383 K, δ in ppm). A mixture of two diastereoisomers was observed: 1.34 and 1.36 (2s, 9H in all), from 1.40 to 2.35 and from 2.90 to 3.70 (mts, 12H), 3.00 (broad t, J=8 Hz, 2H), 3.26 (t, J=8 Hz, 2H), 4.01 (s, 3H), 5.40 (mt, 1H), from 7.55 to 7.70 (mt, 2H), 7.82 (mt, 1H), 8.22 (d, J=9 Hz, 1H), 8.88 (d, J 5 Hz, 1H), from 10.90 to 11.45 (broad unresolved peak, 1H).

Methyl (3R,4R)-4-[3-(R,S)-hydroxy-3-(6-methoxyquinolin-4-yl)propyl]-1-[2-(tert-butylthio)ethyl]piperidine-3-carboxylate 0.717 g of methyl (3R,4R)-4-[3-(R,S)-hydroxy-3-(6-methoxyquinolin-4-yl)propyl]piperidine-3-carboxylate in 15 cm$^3$ of acetonitrile and 15 cm$^3$ of methanol was heated for 16 hours at a temperature in the region of the reflux temperature, with stirring and under an inert atmosphere, with 0.43 g of 2-chloroethyl tert-butyl sulfide in the presence of 0.33 g of potassium carbonate and 0.4 g of potassium iodide. After cooling the reaction mixture to a temperature in the region of 20° C., the insoluble material was filtered off. The filtrate was evaporated under reduced pressure (5 kPa) at a temperature in the region of 40° C. The residue obtained was purified by chromatography under a nitrogen pressure of 100 kPa on a column of silica gel (particle size 40–63 μm; diameter 3.5 cm; height 35 cm), elution being was out with a dichloromethane/methanol (97/3 by volume) mixture, and 35-cm$^3$ fractions were collected. Fractions 54 to 70 were combined and then evaporated under reduced pressure (5 kPa) at a temperature in the region of 40° C. 0.265 g of methyl (3R,4R)-4-[3-(R,S)-hydroxy-3-(6-methoxyquinolin-4-yl)propyl]-1-[2-(tert-butylthio)ethyl]piperidine-3-carboxylate was obtained in the form of a lacquer with a brown color.

Infrared spectrum (CCl$_4$): 3550–3100 cm$^{-1}$ (alcohol OH ν), 2959 cm$^{-1}$ (aliphatic CH ν), 1736 cm$^{-1}$ (C=O ν), 1242, 1228 cm$^{-1}$ (ether C—O ν), 1034 cm$^{-1}$ (alcohol C—O ν), 853 cm$^{-1}$ (quinoline CH γ).

2-Chloroethyl tert-butyl sulfide was prepared by application of the method disclosed in Patent EP 136878, the disclosure of which is specifically incorporated by reference herein.

EXAMPLE 35

(3R,4R)-4-[3-(R,S)-Hydroxy-3-(6-methoxyquinolin-4-yl)propyl]-1-[2-(cyclopentylthio)ethyl]piperidine-3-carboxylic acid dihydrochloride 2 cm$^3$ of 5N aqueous sodium hydroxide solution were added, with stirring and under an inert atmosphere, to a solution of 0.48 g of methyl (3R,4R)-4-[3-(R,S)-hydroxy-3-(6-methoxyquinolin-4-yl)propyl]-1-[2-(cyclopentylthio)ethyl]piperidine-3-carboxylate in 10 cm$^3$ of methanol. After heating the mixture for 16 hours at a temperature in the region of 60° C., the reaction mass was evaporated under reduced pressure (2.9 kPa) at a temperature in the region of 60° C. and the residue obtained was taken up in 4.3 cm$^3$ of distilled water to which had been added 4.3 cm$^3$ of 28% hydrochloric acid. The remaining insoluble material was filtered off and then the filtrate was evaporated under the same conditions as above. The residue obtained was stirred in a dichloromethane/methanol (90/10 by volume) mixture. The resulting precipitate was filtered off and washed with 3 times 2.5 cm$^3$ of the same mixture. The filtrate was evaporated under reduced pressure (5 kPa) at a temperature in the region of 40° C. 0.48 g of (3R,4R)-4-[3-(R,S)-hydroxy-3-(6-methoxyquinolin-4-yl)propyl]-1-[2-(cyclopentylthio)ethyl]piperidine-3-carboxylic acid dihydrochloride was obtained in the form of a foam with a green color melting with softening at a temperature in the region of 156° C.

$^1$H N.M.R. spectrum (400 MHz, d6-(CD$_3$)$_2$SO at a temperature of 373 K, δ in ppm). A mixture of two diastereoisomers was observed: from 1.45 to 2.30 and from 2.90 to 3.60 (mts, 20H), 2.98 (broad t, J=7.5 Hz, 2H), 3.22 (mt, 1H), 3.30 (t, J=7.5 Hz, 2H), 4.00 (s, 3H), 5.37 (mt, 1H), from 7.50 to 7.65 (mt, 2H), 7.77 (mt, 1H), 8.17 (d, J=9 Hz, 1H), 8.85 (d, J=5 Hz, 1H).

Methyl (3R,4R)-4-[3-(R,S)-hydroxy-3-(6-methoxyquinolin-4-yl)propyl]-1-[2-(cyclopentylthio)ethyl]piperidine-3-carboxylate 0.717 g of methyl (3R,4R)-4-[3-(R,S)-hydroxy-3-(6-methoxyquinolin-4-yl)propyl]piperidine-3-carboxylate in 15 cm$^3$ of acetonitrile and 15 cm$^3$ of methanol was heated for 3½ h at a temperature in the region of the reflux temperature, with stirring and under an inert atmosphere, with 0.439 g of 90% 2-chloroethyl cyclopentyl sulfide in the presence of 0.332 g of potassium carbonate and 0.4 g of potassium iodide. After cooling the reaction mixture to a temperature in the region of 20° C., the insoluble material was filtered off and then washed with acetonitrile. The filtrate was evaporated under reduced pressure (5 kPa) at a temperature in the region of 40° C. The residue obtained was purified by chromatography under a nitrogen pressure of 100 kPa on a column of silica gel (particle size 40–63 μm; diameter 3.5 cm; height 45 cm), elution was carried out with a dichloromethane/methanol (95/5 by volume) mixture, and 35-cm$^3$ fractions were collected. Fractions 25 to 45 were combined and then evaporated under reduced pressure (5 kPa) at a temperature in the region of 40° C. 0.48 g of methyl (3R,4R)-4-[3-(R,S)-hydroxy-3-(6-methoxyquinolin-4-yl) propyl]-1-[2-(cyclopentylthio)-ethyl]piperidine-3-carboxylate was obtained in the form of a lacquer with a dark-green color.

Infrared spectrum (CCl$_4$): 3550–3100 cm$^{-1}$ (alcohol OH ν), 2951 cm$^{-1}$ (aliphatic CH ν), 1736 cm$^{-1}$ (C=O ν), 1242, 1228 cm$^{-1}$ (ether C—O ν), 1034 cm$^{-1}$ (alcohol C—O ν), 853 cm$^{-1}$ (quinoline CH γ).

2-Chloroethyl cyclopentyl sulfide was prepared by application of the method disclosed in Patent Application FR 2,395,260, the disclosure of which is specifically incorporated by reference herein.

EXAMPLE 36

(3R,4R)-1-[2-(3-Fluorophenylthio)ethyl]-4-[3-(6-methoxyquinolin-4-yl)propyl]piperidine-3-acetic acid dihydrochloride A mixture of 0.48 g of methyl (3R,4R)-1-[2-(3-fluorophenylthio)ethyl]-4-[3-(6-methoxyquinolin-4-yl)propyl]piperidine-3-acetate in 10 cm$^3$ of dioxane to which had been added 0.78 cm$^3$ of 5N aqueous sodium hydroxide solution was stirred for 20 hours at a temperature in the region of 60° C. After cooling to a temperature in the region of 20° C., the reaction mass was evaporated under reduced pressure (5 kPa) at a temperature in the region of 40° C. and then diluted with 10 cm$^3$ of water. The pH was brought to 4 by addition of a sufficient amount of an aqueous citric acid solution. The mixture was evaporated under reduced pressure (5 kPa) at a temperature in the region of 40° C. and then the residue obtained was taken up in 70 cm$^3$ of water and 20 cm$^3$ of ethanol. The mixture was brought back to pH 9 and then evaporated under reduced pressure (5 kPa) at a temperature in the region of 50° C. After taking the residue obtained up in 50 cm$^3$ of a chloroform/methanol/28% aqueous ammonia (12/3/0.5 by volume) mixture, the inorganic salts were filtered off. The filtrate was evaporated under reduced pressure (5 kPa) at a temperature in the region of 40° C. 1.2 g of a product were obtained, which product was purified by chromatography at atmospheric pressure on a column of silica gel (particle size 20–45 μm; diameter 2 cm; height 25 cm), elution was carried out with a chloroform/methanol/28% aqueous ammonia (12/3/0.5 by volume) mixture, and first a fraction of 100 cm³ and then approximately 15-cm³ fractions were collected. Fractions 8 to 18 were combined and then concentrated under reduced pressure (5 kPa) at a temperature in the region of 40° C. 0.31 g of a product was obtained in the form of a foam with a pale-yellow color, which product was stirred with 13 cm³ of 0.1N aqueous hydrochloric acid for 2 hours at a temperature in the region of 20° C. After adding 5 cm³ of dioxane and stirring for an additional 2 hours at a temperature in the region of 20° C., the dioxane was evaporated under reduced pressure (5 kPa) at a temperature in the region of 40° C. The solution obtained was frozen and then lyophilized. 0.35 g of (3R,4R)-1-[2-(3-fluorophenylthio)ethyl]-4-[3-(6-methoxyquinolin-4-yl)propyl]piperidine-3-acetic acid dihydrochloride was obtained in the form of lyophilizate with a white color.

$^1$H N.M.R. spectrum (400 MHz, d6-(CD$_3$)$_2$SO at a temperature of 383 K, δ in ppm): from 1.45 to 1.95 (mt, 8H), 2.33 (dd, J=16 and 5.5 Hz, 1H), from 2.45 to 2.60 (mt, 1H), from 2.90 to 3.55 (mt, 10H), 4.00 (s, 3H), 7.06 (broad t, J=8 Hz, 1H), 7.28 (d, J=8 Hz, 2H), 7.41 (mt, 1H), 7.46 (d, J=5 Hz, 1H), 7.48 (d, J=2.5 Hz, 1H), 7.51 (dd, J=9.5 and 2.5 Hz, 1H), 8.07 (d, J=9.5 Hz, 1H), 8.72 (d, J=5 Hz, 1H).

Methyl (3R,4R)-1-[2-(3-fluorophenylthio)ethyl]-4-[3-(6-methoxyquinolin-4-yl)propyl]piperidine-3-acetate A mixture of 0.76 g of methyl (3R,4R)-4-[3-(6-methoxyquinolin-4-yl)propyl]piperidine-3-acetate and 0.42 g of 2-(3-fluorophenylthio)ethyl chloride in 15 cm³ of acetonitrile to which have been added 1.4 g of potassium carbonate and 0.15 g of potassium iodide was heated with stirring and under an inert atmosphere at a temperature in the region of 70° C. for 20 hours. After adding 0.15 g of potassium iodide and heating for an additional 5 hours, the reaction mixture was cooled to a temperature in the region of 20° C., diluted with 15 cm³ of water and then extracted with 2 times 20 cm³ of ethyl acetate. The combined extracts were washed with 30 cm³ of N aqueous hydrochloric acid. The acid solution was separated and then rendered alkaline (pH 8–9) with the sufficient amount of a saturated aqueous sodium hydrogencarbonate solution. The mixture was extracted with 2 times 30 cm³ of ethyl acetate. The combined extracts were dried over magnesium sulfate, filtered, and then evaporated under reduced pressure (5 kPa) at a temperature in the region of 40° C. 0.71 g of an oil was obtained, which oil was purified by chromatography at atmospheric pressure on a column of silica gel (particle size 20–45 μm; diameter 2.5 cm; silica volume 120 cm³), elution was carried out with the dichloromethane/methanol (99/1 by volume) mixture. A fraction of 500 cm³ was first collected and then approximately 15-cm³ fractions were collected. Fractions 10 to 20 were combined and then evaporated under reduced pressure (5 kPa) at a temperature in the region of 40° C. 0.48 g of methyl (3R,4R)-1-[2-(3-fluorophenylthio)ethyl]-4-[3-(6-methoxyquinolin-4-yl)propyl]piperidine-3-acetate was obtained in the form of an oil with a yellow color.

Infrared spectrum (CH$_2$Cl$_2$): 2934, 2861 cm$^{-1}$ (aliphatic CH ν), 2807, 2767 cm$^{-1}$ (N(CH$_2$)$_3$ CH$_2$ ν), 1730 cm$^{-1}$ (ester C—O ν), 1242, 1227 cm$^{-1}$ (ether C—O ν), 848 cm$^{-1}$ (quinoline CH γ).

Methyl (3R,4R)-4-[3-(6-methoxyquinolin-4-yl)propyl]piperidine-3-acetate

A mixture of 2.8 g of (3R,4R)-4-(3-(6-methoxyquinolin-4-yl)propyl]-1-(tert-butyloxycarbonyl)piperidine-3-acetic acid in 100 cm³ of anhydrous methanol to which had been added 1 cm³ of 95% sulfuric acid was heated with stirring at a temperature in the region of the boiling point for 2 hours. After cooling to a temperature in the region of 20° C., the reaction mass was evaporated under reduced pressure (5 kPa) at a temperature in the region of 40° C. and then 20 cm³ of a saturated aqueous sodium hydrogencarbonate solution were added to the residue obtained. The mixture was extracted with 4 times 20 cm³ of dichloromethane. The combined extracts were dried over magnesium sulfate, filtered, and then evaporated under reduced pressure (5 kPa) at a temperature in the region of 40° C. 2.25 g of methyl (3R,4R)-4-[3-(6-methoxyquinolin-4-yl)propyl]piperidine-3-acetate were obtained in the form of an oil with a brown color.

Infrared spectrum (CH$_2$Cl$_2$): 2954, 2865 cm$^{-1}$ (aliphatic CH ν), 2788 cm$^{-1}$ (N(CH$_2$)$_2$ CH$_2$ ν), 1736 cm$^{-1}$ (ester C=O ν), 1242, 1227 cm$^{-1}$ (ether C—O ν), 848 cm$^{-1}$ (quinoline CH γ).

(3R,4R)-4-[3-(6-Methoxyquinolin-4-yl)propyl]-1-(tert-butyloxycarbonyl)piperidine-3-acetic acid 1.48 g of potassium permanganate, dissolved beforehand in 45 cm³ of distilled water, followed by 220 cm³ of acetone, were added, with stirring and under an inert atmosphere at a temperature in the region of 20° C., to a solution of 2 g of (3R,4R)-4-[3-(6-methoxyquinolin-4-yl)propyl]-1-(tert-butyloxycarbonyl)piperidine-3-acetaldehyde in 100 cm³ of acetone. The mixture obtained was stirred for 2 hours at a temperature in the region of 20° C. and then, after cooling to a temperature of between 0 and 5° C., a solution of 5 g of sodium sulfite in 150 cm³ of water was added. The brown manganese dioxide precipitate was filtered through celite and then the acetone was evaporated under reduced pressure (5 kPa) at a temperature in the region of 40° C. An amount of citric acid sufficient to produce a pH of 4–5 was added to the reaction mixture. The mixture was extracted with 2 times 100 cm³ of ethyl acetate. The combined extracts were dried over magnesium sulfate, filtered and then evaporated under reduced pressure (5 kPa) at a temperature in the region of 40° C. 2.8 g of (3R,4R)-4-[3-(6-methoxyquinolin-4-yl)propyl]-1-(tert-butyloxycarbonyl)piperidine-3-acetic acid were obtained in the form of a foam with a white color.

Infrared spectrum (KBr): 2977, 2932, 2868 cm$^{-1}$ (aliphatic CH ν), 3000–2200 cm$^{-1}$ (acid OH ν), 1734 cm$^{-1}$ (acid C=O ν), 1689 cm$^{-1}$ (carbamate C=O ν), 1391, 1365 cm$^{-1}$ (CH$_3$ δ$_{as}$), 1246 cm$^{-1}$ (ether C—O ν), 1170 cm$^{-1}$ (carbamate C—O ν), 848 cm$^{-1}$ (quinoline CH γ).

(3R,4R)-4-[3-(6-Methoxyquinolin-4-yl)propyl]-1-(tert-butyloxycarbonyl)piperidine-3-acetaldehyde A solution of 5.6 cm³ of dimethyl sulfoxide, dissolved in 80 cm³ of dichloromethane, then 13.5 g of (3R,4R)-3-(2-hydroxyethyl)-4-[3-(6-methoxyquinolin-4-yl)propyl]-1-(tert-butyloxycarbonyl)piperidine, dissolved in 80 cm³ of dichloromethane, and finally 26.5 cm³ of triethylamine, dissolved in 80 cm³ of dichloromethane, were successively added, with stirring and under a nitrogen atmosphere, to a solution, cooled to a temperature in the region of −60° C., of 3.5 cm³ of oxalyl chloride in 80 cm³ of dichloromethane. The solution obtained was held in the region of −60° C. for 1 hour and then at a temperature in the region of 20° C. for 3½ h. After diluting with 150 cm³ of dichloromethane, the reaction mixture was washed with 2 times 300 cm³ of water. The organic solution, separated by settling, was dried over magnesium sulfate, filtered, and then evaporated under reduced pressure (5 kPa) at a temperature in the region of 40° C. 12.7 g of a brown oil were obtained, which oil was taken up in 400 cm³ of diethyl ether. The resulting solution was washed with 2 times 300 cm³ of water, then once with 300 cm³ of a 5% aqueous citric acid solution, and finally with 2 times 300 cm³ of water. The organic solution was dried over magnesium sulfate and then concentrated under reduced pressure (5 kPa) at a temperature in the region of 40° C. 7.73 g of (3R,4R)-4-[3-(6-methoxyquinolin-4-yl)propyl]-1-(tert-butyloxycarbonyl)piperidine-3-acetaldehyde were obtained in the form of a sticky gum with a yellow color.

Infrared spectrum (CCl₄): 2978, 2932, 2864 cm⁻¹ (aliphatic CH ν), 2717 cm⁻¹ (aldehyde CH ν), 1729 cm⁻¹ (aldehyde C=O ν), 1694 cm⁻¹ (carbamate C=O ν), 1391, 1366 cm⁻¹ (CH₃ δ$_{as}$) 1242 cm⁻¹ (ether C—O ν), 1158 cm⁻¹ (carbamate C—O ν), 844 cm⁻¹ (quinoline CH γ).

(3R,4R)-3-(2-Hydroxyethyl)-4-[3-(6-methoxyquinolin-4-yl)propyl]-1-(tert-butyloxycarbonyl)piperidine A solution of 2 g of (3R,4R)-4-[3-(6-methoxyquinolin-4-yl)propyl]-1-(tert-butyloxycarbonyl)-3-vinylpiperidine and of 0.72 cm³ of triethylamineborane in 10 cm³ of toluene was stirred under an inert atmosphere at a temperature in the region of 110° C. for 10 hours. The reaction mass was concentrated to dryness under reduced pressure (5 kPa) at a temperature in the region of 60° C. 2.1 g of a foam with an orange color were obtained, which product was dissolved in 9 cm³ of acetone and to which were added 1.9 cm³ of 5% aqueous hydrochloric acid. After stirring the mixture for 20 minutes at a temperature in the region of 20° C., the reaction mass was concentrated under reduced pressure (5 kPa) at a temperature in the region of 40° C. The residue obtained was taken up in 7.5 cm³ of tetrahydrofuran, 6.2 cm³ of 30% aqueous sodium hydroxide solution, and 7.5 cm³ of hydrogen peroxide as a 30% aqueous solution. The mixture was heated for 3 hours at a temperature in the region of the reflux temperature. After cooling, the reaction mixture was stirred with 30 cm³ of chloroform at a temperature in the region of 20° C. The aqueous phase was separated by settling; the organic phase was washed with 3 times 30 cm³ of water and then 1 times 20 cm³ of a saturated sodium chloride solution. After drying over magnesium sulfate, the organic solution was concentrated under reduced pressure (5 kPa) at a temperature in the region of 40° C. 1.7 g of an oil with a brown-yellow color were obtained, which product was purified by chromatography at atmospheric pressure on a column of silica gel (particle size 40–63 μm; diameter 3.5 cm; mass 60 g), elution was carried out with a dichloromethane/methanol (95/5 by volume) mixture, and 20-cm³ fractions were collected. Fractions 4 and 5 were combined and evaporated under reduced pressure (5 kPa) at a temperature in the region of 40° C. 0.95 g of (3R 4R)-3-(2-hydroxyethyl)-4-[3-(6-methoxyquinolin-4-yl)propyl]-1-(tert-butyloxycarbonyl)piperidine was obtained in the form of a foam with an orange-yellow color.

Infrared spectrum (KBr): 3550–3100 cm⁻¹ (alcohol OH ν), 2972, 2931, 2865 cm⁻¹ (aliphatic CH ν), 1690 cm⁻¹ (carbamate C=O ν), 1391, 1365 cm⁻¹ (CH₃ δ$_{as}$) 1244, 1228 cm⁻¹ (ether C—O ν), 1158 cm⁻¹ (carbamate C—O ν), 1031 cm⁻¹ (alcohol C—O ν), 845 cm⁻¹ (quinoline CH γ).

(3R,4R)-4-[3-(6-Methoxyquinolin-4-yl)propyl]-1-(tert-butyloxycarbonyl)-3-vinylpiperidine 4 cm³ of triethylamine, followed by 3.15 g of di-tert-butyl dicarbonate, were added, with stirring at a temperature in the region of 20° C., to a suspension of 5 g of (3R,4R)-4-[3-(6-methoxyquinolin-4-yl)propyl]-3-vinylpiperidine hydrochloride in 50 cm³ of dichloromethane. After 45 minutes, the solution obtained was washed with 2 times 30 cm³ of water, dried over magnesium sulfate, and then concentrated under reduced pressure (5 kPa) at a temperature in the region of 40° C. 6 g of (3R,4R)-4-[3-(6-methoxyquinolin-4-yl)propyl]-1-(tert-butyloxycarbonyl)-3-vinylpiperidine were obtained in the form of an oil with a brown color.

Infrared spectrum (CH₂Cl₂): 2972, 2933, 2860 cm⁻¹ (aliphatic CH ν), 1680 cm⁻¹ (carbamate C=O ν), 1391, 1365 cm⁻¹ (CH₃ δ$_{as}$), 1244, 1228 cm⁻¹ (ether C—O ν), 1165 cm⁻¹ (carbamate C—O ν), 845 cm⁻¹ (quinoline CH γ).

(3R,4R)-4-[3-(6-Methoxyquinolin-4-yl)propyl]-3-vinylpiperidine hydrochloride was obtained by application of the method disclosed in Patent Application FR 2,354,771, the disclosure of which is specifically incorporated by reference herein.

EXAMPLE 37

(3R,4R)-4-[3-(6-Methoxyquinolin-4-yl)propyl]-1-[2-(cyclohexylthio)ethyl]piperidine-3-acetic acid dihydrochloride A mixture of 0.3 g of methyl (3R,4R)-4-[3-(6-methoxyquinolin-4-yl)propyl]-1-[2-(cyclohexylthio)ethyl]piperidine-3-acetate in 8 cm³ of dioxane in the presence of 0.5 cm³ of 5N aqueous sodium hydroxide solution was heated with stirring at a temperature in the region of 60° C. for 20 hours. After cooling to a temperature in the region of 20° C., the reaction mixture was evaporated under reduced pressure (5 kPa) at a temperature in the region of 40° C. A foam with a yellow color was obtained, which product was purified by chromatography at atmospheric pressure on a column of silica gel (particle size 20–45 μm; diameter 1.6 cm; silica volume 40 cm³), elution was carried out with a chloroform/methanol/28% aqueous ammonia (12/3/0.5 by volume) mixture, and first a fraction of 125 cm³ and then approximately 10-cm³ fractions were collected. Fractions 3 to 7 were combined and then evaporated under reduced pressure (5 kPa) at a temperature in the region of 40° C. 0.27 g of a lacquer was obtained, which product was taken up in 5 cm³ of dioxane, 11 cm³ of 0.1N aqueous hydrochloric acid and 14 cm³ of distilled water. The dioxane was evaporated under reduced pressure (5 kPa) at a temperature in the region of 40° C. and then the residual solution was lyophilized. 0.29 g of (3R,4R)-4-[3-(6-methoxyquinolin-4-yl)propyl]-1-[2-(cyclohexylthio)-ethyl]piperidine-3-acetic acid dihydrochloride was obtained in the form of a lyophilizate with a white color.

¹H N.M.R. spectrum (400 MHz, d6-(CD₃)₂SO at a temperature of 383 K, δ in ppm): from 1.25 to 2.05 (mt, 18H), 2.33 (dd, J=16 and 5.5 Hz, 1H), from 2.50 to 2.60 (mt, 1H), 2.83 (mt, 1H), from 2.95 to 3.30 (mt, 10H), 4.00 (s, 3H), 7.45 (d, J=5 Hz, 1H), 7.48 (d, J=2 Hz, 1H), 7.51 (dd, J=9.5 and 2 Hz, 1H), 8.08 (d, J=9.5 Hz, 1H), 8.72 (d, J=5 Hz, 1H).

Methyl (3R,4R)-4-[3-(6-Methoxyquinolin-4-yl)propyl]-1-[2-(cyclohexylthio)ethyl]piperidine-3-acetate A mixture of 1.2 g of methyl (3R,4R)-4-[3-(6-methoxyquinolin-4-yl)propyl]piperidine-3-acetate and 0.65 g of 2-chloroethyl cyclohexyl sulfide in 25 cm³ of acetonitrile to which had been added 2.3 g of potassium carbonate and 0.55 g of potassium iodide was heated with stirring and under an inert atmosphere at a temperature in the region of 80° C. for 4 hours. After cooling to a temperature in the region of 20° C., the reaction mixture had 30 cm³ of water added to it and was then extracted with 2 times 200 cm³ of ethyl acetate. The combined organic extracts were washed with 2 times 40 cm³ of N aqueous hydrochloric acid. After separating by settling, the combined acid extracts were basified with a saturated aqueous sodium hydrogencarbonate solution and then extracted with 2 times 100 cm³ of ethyl acetate. The organic extracts were combined, dried over magnesium sulfate, filtered, and evaporated under reduced pressure (5 kPa) at a temperature in the region of 40° C. 0.80 g of a brown oil was obtained, which product was purified by chromatography at atmospheric pressure on a column of silica gel (particle size 20–45 μm; diameter 2.5 cm; silica volume 120 cm³), elution was carried out first with a dichloromethane/methanol (99/1 by volume) mixture, and first a fraction of 250 cm³ were collected and then elution was carried out with a dichloromethane/methanol (90/1 by volume) mixture, and a fraction of 200 cm³ were collected. Elution was again carried out with a dichloromethane/methanol (99/1 by volume) mixture and approximately 10-cm³ fractions were collected. Fractions 10 to 33 were combined and then concentrated under reduced pressure (5 kPa) at a temperature in the region of 40° C. 0.30 g of methyl (3R,4R)-4-[3-(6-methoxyquinolin-4-yl)propyl]-1-[2-(cyclohexylthio)ethyl]piperidine-3-acetate was obtained in the form of a colorless oil.

Infrared spectrum (CCl₄): 2932, 2855 cm⁻¹ (aliphatic CH ν), 2800, 2763 cm⁻¹ (N(CH₂)₃ CH₂ ν), 1737 cm⁻¹ (ester C=O ν), 1241, 1227 cm⁻¹ (ether C—O ν), 844 cm⁻¹ (quinoline CH γ).

Methyl (3R,4R)-4-[3-(6-methoxyquinolin-4-yl)propyl]piperidine-3 acetate was prepared as described in Example 36.

EXAMPLE 38

(3R,4R)-4-[3-(R,S)-Fluoro-3-(6-methoxyquinolin-4-yl)propyl]-1-[2-(2-thienylthio)ethyl]piperidine-3-carboxylic acid dihydrochloride A solution of 0.2 g of methyl (3R,4R)-4-[3-(R,S)-fluoro-3-(6-methoxyquinolin-4-yl)propyl]-1-[2-(2-thienylthio)ethyl]piperidine-3-carboxylate in 3 cm³ of 6N aqueous hydrochloric acid was heated with stirring at a temperature in the region of 100° C. for 7 hours and then evaporated under reduced pressure (5 kPa) at a temperature in the region of 50° C. The residue obtained was stirred in 10 cm³ of diisopropyl ether. The crystals which resulted therefrom were filtered off, washed with 2 times 5 cm³ of diisopropyl ether, and dried under reduced pressure (13 Pa) at a temperature in the region of 60° C. 0.22 g of (3R,4R)-4-[3-(R,S)-fluoro-3-(6-methoxyquinolin-4-yl)propyl]-1-[2-(2-thienylthio)ethyl]piperidine-3-carboxylic acid dihydrochloride were obtained in the form of a solid with a beige color melting with softening at a temperature in the region of 140° C.

¹H N.M.R. spectrum (400 MHz, d6-(CD₃)₂SO with addition of a few drops of d4-CD₃COOD, at a temperature of 373 K, δ in ppm). A mixture of two diastereoisomers was observed: from 1.55 to 2.30 and from 3.10 to 3.50 (mts, 15H), 3.10 (broad s, 1H), 3.98 (s, 3H), 6.31 (mt, J$_{HF}$=48 Hz, 1H), 7.10 (mt, 1H), 7.29 (broad d, J=4 Hz, 1H), from 7.35 to 7.45 (mt, 1H), from 7.45 to 7.60 (mt, 2H), 7.64 (broad d, J=5.5 Hz, 1H), 8.06 (d, J=9 Hz, 1H), 8.82 (d, J=5 Hz, 1H).

Methyl (3R,4R)-4-[3-(R,S)-fluoro-3-(6-methoxyquinolin-4-yl)propyl]-1-[2-(2-thienylthio)ethyl]piperidine-3-carboxylate 0.16 cm³ of diethylaminosulfur trifluoride, dissolved in 2 cm³ of dichloromethane, was added, under an inert atmosphere, to a stirred solution, cooled to a temperature in the region of 10° C., of 0.5 g of methyl (3R,4R)-4-[3-(R,S)-hydroxy-3-(6-methoxyquinolin-4-yl)propyl]-1-[2-(2-thienylthio)ethyl]piperidine-3-carboxylate in 8 cm³ of dichloromethane. After stirring for 10 minutes at this temperature, the mixture was allowed to return to a temperature in the region of 20° C. and stirring was continued for 18 hours. After adding 8 cm³ of a saturated aqueous sodium hydrogencarbonate solution and stirring for 15 minutes, the organic phase was separated by settling. The aqueous phase was extracted once with 5 cm³ of dichloromethane and the organic extracts were combined, dried over magnesium sulfate, filtered, and evaporated under reduced pressure (5 kPa) at a temperature in the region of 40° C. 0.5 g of a red oil was obtained, which product was purified by chromatography under a nitrogen pressure of 100 kPa on a column of silica gel (particle size 40–63 μm; diameter 3.5 cm; silica height 35 cm), elution was carried out with dichloromethane/methanol (97.5/2.5 by volume) mixture, and 30-cm³ fractions were collected. Fractions 25 to 29 were combined and were evaporated under reduced pressure (5 kPa) at a temperature in the region of 40° C. 0.2 g of methyl (3R,4R)-4-[3-(R,S)-fluoro-3-(6-methoxyquinolin-4-yl)propyl]-1-[2-(2-thienylthio)ethyl]piperidine-3-carboxylate was obtained in the form of an oil with an orange color.

Infrared spectrum (CCl₄): 2950 cm⁻(aliphatic CH ν), 2804, 2767 cm⁻¹ (N(CH₂)₃ CH₂ ν), 1737 cm⁻¹ (ester C=O ν), 1243, 1229 cm⁻¹ (ether C—O ν), 852 cm⁻¹ (quinoline CH γ).

EXAMPLE 39

(3R,4R)-4-[3-(6-Methoxyquinolin-4-yl)propyl]-1-[3-(thien-2-yl)prop-2-ynyl]piperidine-3-acetic acid dihydrochloride 0.8 cm³ of a 5N aqueous sodium hydroxide solution was added, under an inert atmosphere, to a stirred solution of 0.43 g of methyl (3R,4R)-4-[3-(6-methoxyquinolin-4-yl)propyl]-1-[3-(thien-2-yl)prop-2-ynyl]piperidine-3-acetate in 10 cm³ of dioxane. The mixture was heated for 20 hours at a temperature in the region of 60° C. and then, after cooling to a temperature in the region of 20° C., the reaction mixture was evaporated under reduced pressure (5 kPa) at a temperature in the region of 45° C. 0.8 g of a product was obtained, which product was purified by chromatography at atmospheric pressure on a column of silica gel (particle size 20–44 μm; diameter 3 cm; silica height 30 cm), elution was carried out with a chloroform/methanol/28% aqueous ammonia (12/3/0.5 by volume) mixture and 25-cm³ fractions were collected. Fractions 14 to 29 were combined and then evaporated under reduced pressure (5 kPa) at a temperature in the region of 40° C. 0.350 g of a white solid was obtained, the hydrochloride of which was prepared in the following way: the solid obtained was dissolved in 5 cm³ of dichloromethane and then the solution obtained was added, with stirring and under an inert atmosphere, to 10 cm³ of a 1N solution of hydrochloric acid in ether. The mixture was diluted with 100 cm³ of anhydrous ether. A white suspension was obtained, which suspension was stirred for 3 hours at a temperature in the region of 20° C. The crystals were filtered off, washed with 5 times 10 cm³ of diethyl ether, and dried under partial pressure (10 Pa) at a temperature in the region of 20° C. 0.430 g of (3R,4R)-4-[3-(6-methoxyquinolin-4-yl)propyl]-1-[3-(thien-2-yl)prop-2-ynyl]piperidine-3-acetic acid dihydrochloride was obtained in the form of a white solid melting while softening and decomposing in the region of 180° C.

¹H N.M.R. spectrum (400 MHz, d6-(CD₃)₂SO, δ in ppm): from 1.35 to 3.80 (mts, 16H), 4.00 (s, 3H), 4.38 and 4.43 (unresolved peaks, 2H in all), 7.16 (mt, 1H), 7.46 (d, J=3.5 Hz, 1H), 7.53 (mt, 1H), 7.64 (mt, 2H), 7.74 (d, J=5 Hz, 1H), 8.12 (d, J=9.5 Hz, 1H), 8.86 (unresolved peak, 1H), 9.95 and 10.45 (2 broad unresolved peaks, 1H in all), from 12.20 to 12.55 (broad unresolved peak, 1H).

Methyl (3R,4R)-4-[3-(6-methoxyquinolin-4-yl)propyl]-1-[3-(thien-2-yl)prop-2-ynyl]piperidine-3-acetate 0.027 g of triphenylphosphine, 0.091 g of tetrakis(triphenylphosphine)palladium, and then 0.044 g of cuprous iodide were added, at a temperature in the region of 20° C., under an inert atmosphere, to a stirred solution of 0.44 g of methyl (3R,4R)-4-[3-(6 -methoxyquinolin-4-yl)propyl]-1-[prop-2-ynyl]piperidine-3-acetate in 15 cm³ of anhydrous acetonitrile. After stirring the solution obtained for 15 minutes, 0.2 cm³ of 2-iodothiophene and 0.32 cm³ of triethylamine were added. After stirring for 12 hours at a temperature in the region of 20° C., the reaction mixture was filtered through celite and then the cake was washed with 5 times 10 cm³ of acetonitrile. The combined organic extracts were evaporated under reduced pressure (5 kPa) at a temperature in the region of 40° C. 1.1 g of an oil were obtained, which product was purified by chromatography at atmospheric pressure on a column of silica gel (particle size 20-45 μm; diameter 4 cm; silica height 28 cm), elution was carried out with ethyl acetate, and 30-cm³ fractions were collected. Fractions 14 to 27 were combined and then evaporated under reduced pressure (5 kPa) at a temperature in the region of 40° C. 0.430 g of methyl (3R,4R)-4-[3-(6-methoxyquinolin4-yl)propyl]-1-[3-(thien-2-yl)prop-2-ynyl]piperidine-3-acetate was obtained in the form of a viscous oil with a yellow color.

Infrared spectrum (CH₂Cl₂): 2936, 2862 cm⁻¹ (aliphatic CH ν), 2806, 2763 cm⁻¹ (N(CH₂)₃ CH₂ ν), 1731 cm⁻¹ (ester C=O ν), 1242, 1227 cm⁻¹ (ether C—O ν), 848 cm⁻¹ (quinoline CH γ).

Methyl (3R,4R)-4-[3-(6-methoxyquinolin-4-yl)propyl]-1-[prop-2-ynyl]piperidine-3-acetate 1.28 cm³ of triethylamine, followed by 0.26 cm³ of 97% propargyl bromide were added at a temperature in the region of 20° C., under an inert atmosphere, to a stirred solution of 0.8 g of methyl (3R,4R)-4-(3-(6-methoxyquinolin-4-yl)propyl]piperidine-3-acetate in 15 cm³ of anhydrous dimethylformamide. The mixture was brought to a temperature in the region of 45° C. for 6 hours and then cooled to approximately 20° C. After diluting with 150 cm³ of water, the mixture was extracted with 5 times 50 cm³ of ethyl acetate. The combined extracts were washed with 3 times 50 cm³ of water, dried over magnesium sulfate, filtered, and concentrated under reduced pressure (5 kPa) at a temperature in the region of 40° C. 1 g of an oily residue was obtained, which product was purified by chromatography at atmospheric pressure on a column of silica gel (particle size 20–45 μm; diameter 3 cm; silica height 27 cm), elution was carried out with pure ethyl acetate. 50-cm³ fractions were collected. Fractions 7 to 10 were combined and then evaporated under reduced pressure (5 kPa) at a temperature in the region of 40° C. 0.45 g of methyl (3R,4R)-4-[3-(6-methoxyquinolin-4-yl)propyl]-1-[prop-2-ynyl]piperidine-3-acetate was obtained in the form of a colorless viscous oil.

Infrared spectrum (CH₂Cl₂): 3302 cm⁻¹ (acetylenic CH ν), 2936, 2863 cm⁻¹ (aliphatic CH ν), 2808, 2764 cm⁻¹ (N(CH₂)₃ CH₂ ν), 1731 cm⁻¹ (ester C=O ν), 1242, 1227 cm⁻¹ (ether C—O ν), 848 cm⁻¹ (quinoline CH γ).

Methyl (3R,4R)-4-(3-(6-methoxyquinolin-4-yl)propyl] piperidine-3-acetate was prepared according to the procedure described in Example 36.

EXAMPLE 40

(3R,4R)-4-[3-Hydroxy-3-(6-methoxyquinolin-4-yl)propyl]-1-[2-(cycloheptylthio)ethyl]piperidine-3-carboxylic acid dihydrochloride, diastereoisomer A, and (3R,4R)-4-[3-hydroxy-3-(6-methoxyquinolin-4-yl)propyl]-1-[2-(cycloheptylthio)ethyl]piperidine-3-carboxylic acid dihydrochloride, diastereoisomer B.

A mixture of 1.8 g of methyl (3R,4R)-4-[3-(R,S)-hydroxy-3-(6-methoxyquinolin-4-yl)propyl]-1-[2-(cycloheptylthio)ethyl]piperidine-3-carboxylate in 36 cm³ of dioxane with 2.8 cm³ of 5N aqueous sodium hydroxide solution was heated for 24 hours at a temperature in the region of 60° C. After cooling the reaction mixture to a temperature in the region of 20° C. and then concentrating under reduced pressure (5 kPa) at a temperature in the region of 40° C., the residue obtained was purified by chromatography at atmospheric pressure on a column of silica gel (particle size 20-45 μm; diameter 4 cm; mass 180 g), elution was carried out with a dichloromethane/methanol/28% aqueous ammonia (40/5/0.5 by volume) mixture, and 50-cm³ fractions were collected. 3 batches were obtained, which batches were evaporated under reduced pressure (5 kPa) at a temperature in the region of 40° C.: batch A (0.48 g) corresponding to the diastereoisomer A, batch B (0.6 g) corresponding to the diastereoisomer B, and batch C (0.5 g) corresponding to a mixture of the two diastereoisomers. Batch A was purified in the following way: after dissolving in 15 cm³ of dichloromethane and adding to 10 cm³ of an N solution of hydrochloric acid in diethyl ether, the gummy mixture obtained was evaporated under reduced pressure (5 kPa) at a temperature in the region of 40° C. After taking the residue up in 40 cm³ of acetonitrile and 2 cm³ of 0.5N hydrochloric acid, the solution obtained was evaporated under the same conditions as above. A white solid was obtained, which product was dried for 16 hours under reduced pressure (vacuum over phosphorus pentoxide, 5 kPa). After stirring in 100 cm³ of diethyl ether and then filtering, 0.514 g of (3R,4R)-4-[3-hydroxy-3-(6-methoxyquinolin-4-yl)propyl]-1-[2-(cycloheptylthio)ethyl] piperidine-3-carboxylic acid dihydrochloride, diastereoisomer A ($[\alpha]^{20}_D$=−58.3°+/−1.00, in methanol at 0.5%), was obtained in the form of a solid with a white color. Batches B and C were treated in the same way. In particular with batch B, 0.650 g of (3R,4R)-4-[3-hydroxy-3-(6-methoxyquinolin-4-yl)propyl]-1-[2-(cycloheptylthio)ethyl] piperidine-3-carboxylic acid dihydrochloride, diastereoisomer B ($[\alpha]^{20}_D$=+120.40°+/−1.7, in methanol at 0.5%), was obtained in the form of a solid with a white color.

Diastereoisomer A: ¹H N.M.R. spectrum (400 MHz, d6-(CD₃)₂SO, δ in ppm): from 1.40 to 2.35 and from 2.70 to 3.85 (mts, 29H), 4.01 (s, 3H), 5.50 (mt, 1H), from 5.60 to 6.40 (broad unresolved peak, 1H), 7.55 (mt, 1H), 7.75 (broad d, J=9 Hz, 1H), 7.99 (d, J=5 Hz, 1H), 8.30 (d, J=9 Hz, 1H), 9.04 (d, J=5 Hz, 1H), 10.80 (unresolved peak, 1H).

Diastereoisomer B: $^1$H N.M.R. spectrum (400 MHz, d6-$(CD_3)_2SO$, δ in ppm): from 1.35 to 2.25 and from 2.70 to 3.80 (mts, 29H), 4.00 (s, 3H), 5.49 and 5.55 (2 mts, 1H in all), from 5.75 to 6.20 (broad unresolved peak, 1H), 7.56 and 7.62 (2 broad s, 1H in all), 7.71 (broad d, J=9 Hz, 1H), 7.92 (mt, 1H), 8.24 (d, J=9 Hz, 1H), 9.00 (d, J=4 Hz, 1H), 10.56 (unresolved peak, 1H).

Methyl (3R,4R)-4-[3-(R,S)-hydroxy-3-(6-methoxyquinolin-4-yl)propyl]-1-[2-(cycloheptylthio)ethyl]piperidine-3-carboxylate 0.221 g of sodium borohydride was added portionwise at a temperature in the region of 20° C., with stirring an under a inert atmosphere, to a mixture of 2.5 g of methyl (3R,4R)-4-[3-oxo-3-(6-methoxyquinolin-4-yl)propyl]-1-[2-(cycloheptylthio)ethyl]-piperidine-3-carboxylate in 20 cm$^3$ of methanol. After addition, the mixture was stirred for 2 hours at a temperature in the region of 20° C. The reaction mixture was evaporated under reduced pressure (5 kPa) and then the residue obtained was taken up in 50 cm$^3$ of dichloromethane and 30 cm$^3$ of a saturated aqueous ammonium chloride solution. The organic phase, separated by settling, was dried over magnesium sulfate, filtered, and then concentrated under reduced pressure (5 kPa) at a temperature in the region of 40° C. 2.5 g of a product were obtained, which product was purified by chromatography at atmospheric pressure under a column of silica gel (particle size 20–45 μm; diameter 4 cm; mass 150 g), elution was carried out with a dichloromethane/methanol (95/5 by volume) mixture and 50-cm$^3$ fractions were collected. The fractions comprising the desired product were combined and then evaporated under reduced pressure (5 kPa) at a temperature in the region of 40° C. 1.95 g of methyl (3R,4R)-4-[3-(R,S)-hydroxy-3-(6-methoxyquinolin-4-yl)propyl]-1-[2-(cycloheptylthio)ethyl]piperidine-3-carboxylate were obtained in the form of a viscous oil.

Infrared spectrum (CCl$_4$): 3500–3100 cm$^{-1}$ (alcohol OH ν), 2930 cm$^-$(aliphatic CH ν), 2805, 2772 cm$^{-1}$ (N(CH$_2$)$_3$ CH$_2$ ν), 1736 cm$^{-1}$ (ester C=O ν), 1242, 1228 cm$^{-1}$ (ether C—O ν), 1034 cm$^{-1}$ (alcohol C—O ν), 854 cm$^{-1}$ (quinoline CH γ).

Methyl (3R,4R)-4-[3-oxo-3-(6-methoxyquinolin-4-yl)propyl]-1-[2-(cycloheptylthio)ethyl]piperidine-3-carboxylate A mixture composed of 3.06 g of methyl (3R,4R)-4-[3-oxo-3-(6-methoxyquinolin-4-yl)propyl]piperidine-3-carboxylate, 1.79 g of 2-chloroethyl cycloheptyl sulfide, 5.39 g of potassium carbonate, and 1.29 g of potassium iodide in 75 cm$^3$ of acetonitrile was heated with stirring and under an inert atmosphere at a temperature in the region of 72° C. for 24 hours. After cooling to approximately 20° C., the reaction mixture was filtered through celite and the filtrate was concentrated under reduced pressure (5 kPa) at a temperature in the region of 40° C. The residue obtained was purified by chromatography at atmospheric pressure on a column of silica gel (particle size 20–45 μ; diameter 4 cm; mass 150 g), elution was carried out with an ethyl acetate/methanol (95/5 by volume) mixture, and 50-cm$^3$ fractions were collected. The fractions comprising the desired product were combined and then concentrated under reduced pressure (5 kPa) at a temperature in the region of 40° C. 2.6 g of methyl (3R,4R)-4-[3-oxo-3-(6-methoxyquinolin-4-yl)propyl]-1-[2-(cycloheptylthio)ethyl]piperidine-3-carboxylate were obtained in the form of a viscous oil.

Infrared spectrum (CCl$_4$): 2930 cm$^{-1}$ (aliphatic CH ν), 2805, 2767 cm$^{-1}$ (N(CH$_2$)$_3$ CH$_2$ ν), 1740 cm$^{-1}$ (ester C=O ν), 1693 cm$^{-1}$ (ketone C=O ν), 1241, 1228 cm$^{-1}$ (ether C—O ν), 850 cm$^{-1}$ (quinoline CH γ).

2-Chloroethyl cycloheptyl sulfide 5.11 cm$^3$ of thionyl chloride were added dropwise, with stirring and under an inert atmosphere, at a temperature in the region of 20° C. to a solution of 1.74 g of 2-hydroxyethyl cycloheptyl sulfide in 30 cm$^3$ of chloroform. After the addition, the reaction mixture was first stirred for 15 minutes at the same temperature and then for 1 hour at a temperature in the region of 600° C. The mixture was evaporated to dryness under reduced pressure (5 kPa) at a temperature in the region of 40° C., then the residue obtained was taken up with 2 times 50 cm$^3$ of water and then 1 times 50 cm$^3$ of a saturated sodium hydrogencarbonate solution. The ethereal solution, separated by settling, was dried over magnesium sulfate, filtered, and then concentrated under reduced pressure (5 kPa) at a temperature in the region of 400° C. 1.89 g of 2-chloroethyl cycloheptyl sulfide were obtained in the form of an oil.

Infrared spectrum (CCl$_4$): 2930, 2855 cm$^{-1}$ (CH$_2$ ν), 1459, 1445 cm$^{-1}$ (CH$_2$ δ), 1210 cm$^{-1}$ (C—Cl ω)), 702 cm$^{-1}$ (C—Cl ν).

2-Hydroxyethyl cycloheptyl sulfide 2.32 g of 2-mercaptoethanol, dissolved beforehand in 10 cm$^3$ of dimethylformamide, were slowly added, under an inert atmosphere and at a temperature in the region of 20° C., to a stirred suspension of 0.91 g of 60% sodium hydride in 10 cm$^3$ of anhydrous dimethylformamide. After stirring for 20 minutes, 3.5 g of bromocycloheptane, dissolved in 10 cm$^3$ of dimethylformamide, were added. The reaction was brought to completion by stirring at a temperature in the region of 20° C. for 1 hour 30 minutes. The reaction mixture was poured onto 150 cm$^3$ of water to which have been added 100 cm$^3$ of diethyl ether. The ethereal phase was separated by settling and the aqueous phase was extracted once with 50 cm$^3$ of diethyl ether. The organic phases were combined and then washed with 2 times 100 cm$^3$ of water, dried over magnesium sulfate, filtered, and concentrated under reduced pressure (5 kPa) at a temperature in the region of 40° C. 3.2 g of 2-hydroxyethyl cycloheptyl sulfide were obtained in the form of an oil with a yellow color.

Infrared spectrum (CH$_2$Cl$_2$): 3608, 3457 cm$^-$(OH (free and bonded) ν), 2927, 2855 cm$^{-1}$ (aliphatic CH ν), 1057 cm$^{-1}$ (CO ν).

EXAMPLE 41

(3R,4R)-4-[3-(6-Methoxyquinolin4-yl)propyl]-1-[2-(2-thienylthio)ethyl]piperidine-3-acetic acid dihydrochloride A stirred mixture of 0.598 g of methyl (3R,4R)-4-[3-(6-methoxyquinolin-4-yl)propyl]-1-[2-(2-thienylthio)ethyl]piperidine-3-acetate in 13 cm$^3$ of dioxane with 1 cm$^3$ of 5N aqueous sodium hydroxide solution, in an inert atmosphere, was heated at 60° C. for 20 hours. After evaporating the reaction mixture under reduced pressure (5 kPa) at a temperature in the region of 50° C., 1 g of a yellow foam was obtained, which product was purified by chromatography at atmospheric pressure on a column of silica gel (particle size 20–45 μ; diameter 3 cm; silica height 21 cm), elution was carried out with a chloroform/methanol/28% aqueous ammonia (12/3/0.5 by volume) mixture, and 50-cm³ fractions were collected. Fractions 4 to 7 were combined and then evaporated under reduced pressure (5 kPa) at a temperature in the region of 40° C. 0.495 g of a product was obtained, which product was dissolved in 5 cm³ of dichloromethane. After adding 10 cm³ of a 1 N solution of hydrochloric acid in ether, a pasty precipitate was obtained, which precipitate was diluted with 100 cm³ of diethyl ether. The mixture was stirred at a temperature in the region of 20° C. The white suspension obtained was filtered off and washed with 3 times 30 cm³ of diethyl ether. The resulting white solid was dried under reduced pressure (10 kPa) at a temperature in the region of 40° C. until a constant weight was obtained. 0.55 g of (3R,4R)-4-[3-(6-methoxyquinolin4-yl)propyl]-1-[2-(2-thienylthio)ethyl]piperidine-3-acetic acid dihydrochloride was obtained in the form of a white solid melting while softening in the region of 200° C.

¹H N.M.R. spectrum (400 MHz, d6-(CD₃)₂SO at a temperature of 383 K, δ in ppm): from 1.40 to 1.95 (mt, 8H), 2.30 (dd, J=16 and 5.5 Hz, 1H), from 2.45 to 2.60 (mt, 1H), from 3.00 to 3.35 (mt, 10H), 4.00 (s, 3H), 7.08 (dd, J=5 and 3.5 Hz, 1H), 7.28 (broad, J=3.5 Hz, 1H), from 7.45 to 7.55 (mt, 2H), 7.56 (dd, J=9.5 and 3 Hz, 1H), 7.62 (broad d, J=7 Hz, 1H), 8.15 (d, J=9.5 Hz, 1H), 8.75 (d, J=5 Hz, 1H).

EXAMPLE 41A

Methyl (3R,4R)-4-[3-(6-methoxyquinolin-4-yl)propyl]-1-[2(2-thienylthio)ethyl]piperidine-3-acetate 4.06 g of potassium carbonate, followed by 1 g of potassium iodide, were added, under an inert atmosphere, to a stirred solution of 2.1 g of methyl (3R,4R)-4-[3-(6-methoxyquinolin-4-yl)propyl]piperidine-3-acetate and of 1.15 g of 2-(2-chloroethylthio)thiophene in 50 cm³ of acetonitrile. The mixture was heated at 70° C. for 20 hours. After cooling to a temperature in the region of 20° C., the reaction mixture was diluted with 100 cm³ of ethyl acetate and 100 cm³ of water. After stirring the mixture and separating the organic phase by settling, the aqueous phase was extracted with 2 times 50 cm³ of ethyl acetate. The organic phases were combined and extracted with 3 times 50 cm³ of N aqueous hydrochloric acid. The acid solutions were combined and brought to pH 8 with a sufficient amount of sodium hydrogencarbonate. The resulting oil released was extracted with 3 times 100 cm³ of ethyl acetate. The combined extracts were dried over magnesium sulfate, filtered, and evaporated under reduced pressure (5 kPa) at a temperature in the region of 4° C. 1.5 g of an oil with an orange color were obtained, which product was purified by chromatography at atmospheric pressure on a column of silica gel (particle size 20–45 μ; diameter 3 cm; silica height 55 cm), elution was carried out with pure ethyl acetate, and 50-cm³ fractions were collected. Fractions 12 to 30 were combined and then evaporated under the same conditions as above. 0.60 g of methyl (3R,4R)-4-[3-(6-methoxyquinolin4-yl)propyl]-1-[2-(2-thienylthio)ethyl]piperidine-3-acetate was obtained in the form of a colorless viscous oil.

Infrared spectrum (CH₂Cl₂): 2933, 2861 cm⁻¹ (aliphatic CH ν), 2803, 2766 cm⁻¹ (N(CH₂)₃ CH₂ ν), 1730 cm⁻¹ (ester C=O ν), 1242, 1277 cm⁻¹ (ether C—O ν), 847 cm⁻¹ (quinoline CH γ).

Methyl (3R,4R)-4-[3-(6-methoxyquinolin-4-yl)propyl]piperidine-3-acetate was prepared according to the procedure described in Example 36.

EXAMPLE 42

(3R,4R)-4-[3-(6-Methoxyquinolin-4-yl)propyl]-1-(3-phenylprop-2-ylene)piperidine-3-carboxylic acid hydrochloride By carrying out the preparation by analogy with the method described in Example 32, (3R,4R)-4-[3-(6-methoxyquinolin-4-yl)propyl]-1-(3-phenylprop-2-ylene)piperidine-3-carboxylic acid hydrochloride was prepared in. the form of a solid with an off-white color.

¹H N.M.R. spectrum (300 MHz, d6-(CD₃)₂SO, δ in ppm): from 1.20 to 2.40 and from 2.90 to 3.90 (mts, 14H), 3.95 (mt, 2H), 4.03 (s, 3H), 6.46 (dt, J=7.5 Hz, 1H), 6.84 (d, J=16 Hz, 1H), from 7.30 to 7.50 (mt, 3H), 7.53 (broad d, J=7.5 Hz, 2H), 7.63 (mt, 1H), 7.75 (dd, J=9.5 and 2 Hz, 1H), 7.84 (d, J=5.5 Hz, 1H) 8.31 (d, J=9.5 Hz, 1H), 8.99 (d, J=5.5 Hz, 1H), 10.93 (unresolved peak, 1H).

EXAMPLE 43

(3R,4R)-4-[3-Hydroxy-3-(6-methoxyquinolin-4-yl)propyl]-1-[2-(cyclohexylthio)ethyl]piperidine-3-carboxylic acid, diastereoisomer A, and (3R,4R)-4-[3-hydroxy-3-(6-methoxyquinolin4-yl)propyl]-1-[2-(cyclohexylthio)ethyl]piperidine-3-carboxylic acid, diastereoisomer B 5 g of (3R,4R)-4-[3-(R,S)-hydroxy-3-(6-methoxyquinolin-4-yl)propyl]-1-[2-(cyclohexylthio)ethyl] piperidine-3-carboxylic acid, dissolved in 100 cm³ of a dichloromethane/ethanol/tetrahydrofuran (65/15/20 by volume) mixture, were chromatographed on a column with a length of 35 cm and diameter of 8 cm, packed with 1.200 kg of Kromasil® silica (particle size 10 μm). Elution was carried out using the same mixture as above. The flow rate was 150 cm³ per minute for the first 30 minutes and then 200 cm³ per minute subsequently. Detection was carried out using ultraviolet radiation at 280 nm. This operation resulted in two diastereoisomers were obtained. The fractions corresponding to the first were concentrated to dryness under reduced pressure (5 kPa) at a temperature in the region of 40° C. A solid residue was obtained, which residue was taken up in diethyl ether, filtered off, and dried in the air at a temperature in the region of 20° C. 1.5 g of (3R,4R)-4-[3-hydroxy-3-(6-methoxyquinolin-4-yl)propyl]-1-[2-(cyclohexylthio)ethyl]piperidine-3-carboxylic acid, diastereoisomer A ([α]$_D^{20}$=−47.1°+/−0.9, in dichloromethane at 0.5%), were obtained in the form of a solid with a beige color. The fractions corresponding to the second diastereoisomer were treated as above. 1.7 g of (3R,4R)-4-[3-hydroxy-3-(6 -methoxyquinolin4-yl)propyl]-1-[2-(cyclohexylthio) ethyl]piperidine-3-carboxylic acid, diastereoisomer B ([α]$_D^{20}$=+98.7°+/−1.6, in dichloromethane at 0.5%), were obtained in the form of a solid with a beige color.

Diastereoisomer A: ¹H N.M.R. spectrum (300 MHz, d6-(CD₃)₂SO, δ in ppm): from 1.10 to 2.05 (mts, 17H), 2.33 (very broad t, J=10 Hz, 1H), 2.45 (broad d, J=10 Hz, 1H), 2.59 (unresolved peak, 1H), from 2.60 to 2.80 (mt, 5H), 2.90 (broad d, J=10 Hz, 1H), 3.06 (broad d, J=10 Hz, 1H), 3.96 (s, 3H), 5.22 (very broad d, J=7 Hz, 1H), from 5.40 to 5.70 (broad unresolved peak, 1H), from 7.30 to 7.45 (mt, 2H), 7.57 (d, J=4.5 Hz, 1H), 7.94 (d, J=9 Hz, 1H), 8.72 (d, J=4.5 Hz, 1H), from 12.50 to 13.40 (very broad unresolved peak, 1H).

Diastereoisomer B: ¹H N.M.R. spectrum (300 MHz, d6-(CD₃)₂SO, δ in ppm): from 1.10 to 2.00 (mts, 17H), 2.33 (mt, 1H), from 2.40 to 2.55 (mt, 1H), 2.57 (broad s, 1H), from 2.60 to 2.80 (mt, 5H), 2.82 (mt, 1H), 2.99 (mt, 1H), 3.92 (s, 3H), 5.25 (mt, 1H), from 5.40 to 5.70 (broad unresolved peak, 1H), from 7.35 to 7.45 (mt, 2H), 7.53 (d, J=4.5 Hz, 1H), 7.94 (d, J=10 Hz, 1H), 8.71 (d, J=4.5 Hz, 1H), from 12.40 to 13.50 (very broad unresolved peak, 1H).

(3R,4R)-4-[3-(R,S)-Hydroxy-3-(6-methoxyquinolin-4-yl)propyl]-1-[2-(cyclohexylthio)ethyl]piperidine-3-carboxylic acid was prepared from its hydrochloride according to the following process.

(3R,4R)-4-[3-(R,S)-Hydroxy-3-(6-methoxyquinolin4-yl)propyl]-1-[2-(cyclohexylthio)ethyl]piperidine-3-carboxylic acid dihydrochloride 0.4 gof methyl (3R,4R)-4-[3-(R,S)-hydroxy-3-(6-methoxyquinolin-4-yl)propyl]-1-[2-(cyclohexylthio)ethyl]piperidine-3-carboxylate was heated in 3 cm$^3$ of methanol to which had been added 0.48 cm$^3$ of 5N aqueous sodium hydroxide solution under an inert atmosphere for 16 hours. After concentrating the reaction mass under reduced pressure (5 kPa) at a temperature in the region of 40° C., the residue obtained was taken up in 5 cm$^3$ of 6N hydrochloric acid and then 2.5 cm$^3$ of methanol. The brown solution obtained was evaporated under the same conditions as above. The residue which resulted therefrom was taken up in 5 cm$^3$ of diisopropylether, filtered off, and washed with 2 times 3 cm$^3$ of the same solvent. The solid obtained was dried under reduced pressure (13 Pa) at a temperature in the region of 60° C. 0.37 g of (3R,4R)-4-[3-(R,S)-hydroxy-3-(6-methoxyquinolin-4-yl)propyl]-1-[2-(cyclohexylthio)ethyl]piperidine-3-carboxylic acid dihydrochloride was obtained in the form of a solid with a brown color melting while softening in the region of 170° C.

$^1$H N.M.R. spectrum (400 MHz, d6-(CD$_3$)$_2$SO, at a temperature of 383 K, δ in ppm). A mixture of two diastereoisomers was observed: from 1.20 to 2.25 and from 2.80 to 3.40 (mts, 25H), 3.28 (t, J=8 Hz, 2H), 4.00 (s, 3H), 5.36 (mt, 1H), from 7.50 to 7.65 (mt, 2H), 7.70 (mt, 1H), 8.13 (broad d, J=9 Hz, 1H), 8.81 (d, J=5 Hz, 1H).

Methyl (3R,4R)-4-[3-(R,S)-hydroxy-3-(6-methoxyquinolin-4-yl)propyl]-1-[2-(cyclohexylthio)ethyl]piperidine-3-carboxylate A stirred mixture of 0.54 g of methyl (3R,4R)-4-[3-(R,S)-hydroxy-3-(6-methoxyquinolin-4-yl)propyl]piperidine-3-carboxylate, 0.295 g of 2-chloroethyl cyclohexyl sulfide, 0.23 g of potassium carbonate, and 0.27 g of potassium iodide in 9 cm$^3$ of acetonitrile and 1 cm$^3$ of methanol was brought to a temperature in the region of the boiling point under an inert atmosphere for 20 hours. The reaction mixture was concentrated under reduced pressure (5 kPa) at a temperature in the region of 40° C. The residue obtained was purified by chromatography under an argon pressure of 80 kPa on a column of silica gel (particle size 40–63 μm; diameter 3.5 cm; height 35 cm), elution was carried out with a dichloromethane/methanol (95/5 by volume) mixture, and 35-cm$^3$ fractions were collected. Fractions 23 to 40 were combined and then concentrated under reduced pressure (5 kPa) at a temperature in the region of 40° C. 0.4 g of methyl (3R,4R)-4-[3-(R,S)-hydroxy-3-(6-methoxyquinolin-4-yl)propyl]-1-[2-(cyclohexylthio)ethyl]piperidine-3-carboxylate was obtained in the form of a lacquer with a brown color.

Infrared spectrum (CCl$_4$): 3600–3200 cm$^{-1}$ (OH ν), 2932, 2854 cm$^{-1}$ (aliphatic CH ν), 1736 cm$^{-1}$ (C=O ν), 1242 cm$^{-1}$ (ether C—O ν).

EXAMPLE 44

(3R,4R)-4-[3-Hydroxy-3-(6-methoxyquinolin-4-yl)propyl]-1-[3-(thien-2-yl)prop-2-ynyl]piperidine-3-carboxylic acid, diastereoisomer A, and (3R,4R)-4-[3-hydroxy-3-(6-methoxyquinolin-4-yl)propyl]-1-[3-(thien-2-yl)prop-2-ynyl]piperidine-3-carboxylic acid, diastereoisomer B 3 g of (3R,4R)-4-[3-(R,S)-hydroxy-3-(6-methoxyquinolin-4-yl)propyl]-1-[3-(thien-2-yl)prop-2-ynyl]piperidine-3-carboxylic acid, dissolved in 100 cm$^3$ of a dichloromethane/methanol/acetonitrile (85/8/7 by volume) mixture, were chromatographed on a column with a length of 35 cm and a diameter of 8 cm packed with 1.200 kg of Kromasil® silica (particle size 10 μm). Elution was carried out using the same mixture as above. Detection was carried out using ultraviolet radiation at 280 nm. This operation resulted in two diastereoisomers were obtained. The fractions corresponding to the first were concentrated to dryness under reduced pressure (5 kPa) at a temperature in the region of 40° C. A solid residue was obtained, which residue was dried under reduced pressure (23 Pa) at a temperature in the region of 20° C. 0.612 g of (3R,4R)-4-[3-hydroxy-3-(6-methoxyquinolin-4-yl)propyl]-1-[3-(thien-2-yl)prop- 2-ynyl]piperidine-3-carboxylic acid, diastereoisomer A ($[α]_D^{20}$=−67.5°+/−1.3, in dichloromethane at 0.5%), was obtained in the form of a foam with a white color. The fractions corresponding to the second diastereoisomer were treated as above. 0.596 g of (3R,4R)-4-[3-hydroxy-3-(6-methoxyquinolin-4-yl)propyl]-1-[3-(thien-2-yl)prop-2-ynyl]piperidine-3-carboxylic acid, diastereoisomer B ($[α]_D^{20}$=+106.0°+/−1.6, in dichloromethane at 0.5%), was obtained in the form of a foam with a white color.

Diastereoisomer A: $^1$H N.M.R. spectrum (300 MHz, d6-(CD$_3$)$_2$SO, δ in ppm): from 1.40 to 1.95 (mt, 7H), 2.40 (mt, 1H), from 2.50 to 2.60 (mt, 1H), from 2.60 to 2.80 (mt, 2H), 2.90 (unresolved peak, 1H), 3.63 (s, 2H), 3.94 (s, 3H), 5.24 (mt, 1H), 5.52 (mt, 1H), 7.08 (dd, J=5 and 4 Hz, 1H), 7.31 (dd, J=4 and 1 Hz, 1H), 7.35 (d, J=3 Hz, 1H), 7.40 (dd, J=9 and 3 Hz, 1H), 7.56 (d, J=4.5 Hz, 1H), 7.59 (dd, J=5 and 1 Hz, 1H), 7.95 (d, J=9 Hz, 1H), 8.71 (d, J=4.5 Hz, 1H).

Diastereoisomer B: $^1$H N.M.R. spectrum (300 MHz, d6-(CD$_3$)$_2$SO, δ in ppm): from 1.20 to 1.95 (mt, 7H), 2.38 (mt, 1H), from 2.50 to 2.75 (mt, 3H), 2.71 (unresolved peak, 1H), 3.58 (s, 2H), 3.90 (s, 3H), 5.25 (mt, 1H), 5.52 (mt, 1H), 7.07 (dd, J=5 and 3.5 Hz, 1H), 7.29 (broad d, J=3.5 Hz, 1H), from 7.30 to 7.45 (mt, 2H), 7.53 (d, J=4.5 Hz, 1H), 7.58 (broad d, J=5 Hz, 1H), 7.94 (d, J=10 Hz, 1H), 8.70 (d, J=4.5 Hz, 1H).

EXAMPLE 45

(3R,4R)-4-[3-(R,S)-Hydroxy-3-(6-methoxyquinolin-4-yl)propyl]-1-[2-(5-chlorothien-2-yl)ethyl]piperidine-3-carboxylic acid A solution of 0.460 g of methyl (3R,4R)-4-[3-(R,S)-hydroxy-3-(6-methoxyquinolin-4-yl)propyl]-1-[2-(5-chlorothien-2-yl)ethyl]piperidine-3-carboxylate in 5 cm$^3$ of dioxane which had been added 0.51 cm$^3$ of a 5N aqueous sodium hydroxide solution was stirred at a temperature in the region of 60° C. for 48 hours. After a further addition of 1 cm$^3$ of 5N sodium hydroxide solution, the mixture was again heated at a temperature in the region of 70° C. for 72 hours. The reaction mixture was evaporated under reduced pressure (5 kPa) at a temperature in the region of 45° C. and then the residue obtained was purified by chromatography under a nitrogen pressure of 40 kPa on a column of silica gel (particle size 40–63 μm; diameter 3 cm; silica height 27 cm), elution was carried out with a dichloromethane/methanol/ 28% aqueous ammonia (14/4/0.6 by volume) mixture, and 15-cm$^3$ fractions were collected. Fractions 7 to 16 were evaporated under reduced pressure (5 kPa) at a temperature in the region of 40° C. 0.30 g of (3R,4R)-4-[3-(R,S)-hydroxy-3-(6-methoxyquinolin-4-yl)propyl]-1-[2-(5-chlorothien-2-yl)ethyl]piperidine-3-carboxylic acid was obtained in the form of a foam with a white color.

$^1$H N.M.R. spectrum (300 MHz, d6-$(CD_3)_2SO$, δ in ppm). A mixture of two diastereoisomers was observed: from 1.40 to 3.10 (mts, 16H), 3.92 and 3.95 (2 s, 3H in all), 5.23 (mt, 1H), 5.50 (mt, 1H), from 7.05 to 7.15 (mt, 2H), from 7.30 to 7.45 (mt, 2H), 7.52 and 7.54 (2 d, J=5 Hz, 1H in all), 7.94 (mt, 1H), 8.70 (d, J=5 Hz, 1H).

Methyl (3R,4R)-4-[3-(R,S)-hydroxy-3-(6-methoxyquinolin-4-yl)propyl]-1-[2-(5-chlorothien-2-yl)ethyl]piperidine-3-carboxylate A solution of 1 g of methyl (3R,4R)-4-[3-(R,S)-hydroxy-3-(6-methoxyquinolin-4-yl)propyl]piperidine-3-carboxylate in 40 cm$^3$ of acetonitrile and 10 cm$^3$ of methanol was stirred at a temperature. in the region of 20° C. and then 1.16 g of potassium carbonate and 0.5 g of potassium iodide were added. 1 g of 2-chloro-5-(2-chloroethylthio)thiophene and 10 cm$^3$ of acetonitrile were added to the suspension obtained. The mixture was stirred for 72 hours at a temperature in the region of 80° C. The reaction mass was poured onto 75 cm$^3$ of ethyl acetate and then washed with 3 times 70 cm$^3$ of water. The organic phase was dried over sodium sulfate, filtered, and evaporated under reduced pressure (5 kPa) at a temperature in the region of 45° C. The residue obtained was purified by chromatography under a nitrogen pressure of 40 kPa on a column of silica gel (particle size 20–40 μm; diameter 3.5 cm; silica height 31 cm), elution was carried out with ethyl acetate, and 30-cm$^3$ fractions were collected. Fractions 24 to 52 were combined and concentrated under reduced pressure (5 kPa) at a temperature in the region of 40° C. 0.48 g of methyl (3R,4R)-4-[3-(R,S)-hydroxy-3-(6-methoxyquinolin-4-yl)propyl]-1-[2-(5-chlorothien-2-yl)ethyl]piperidine-3-carboxylate was obtained in the form of an oil with a brown color.

Mass spectrum: (Cl) m/z, 535 MH$^+$.

2-Chloro-5-(2-chloroethylthio)thiophene 28 cm$^3$ of a 5N aqueous sodium hydroxide solution were added, with stirring, to a solution, cooled to a temperature in the region of 5° C., of 17.9 g of 2-chloro-5-thiophenethiol in 30 cm$^3$ of 1-chloro-2-bromoethane, and then the temperature was allowed to return to the region of 20° C., while stirring was continued for 16 hours. The reaction mixture was diluted with 300 cm$^3$ of ethyl acetate and washed with 3 times 150 cm$^3$ of water. The organic solution was dried over sodium sulfate, filtered, and evaporated under reduced pressure (5 kPa) at a temperature in the region of 45° C. 20.6 g of 2-chloro-5-(2-chloroethylthio)thiophene were obtained in the form of an oil with a brown color.

Mass spectrum: DCl m/z=535 MH$^+$.

2-Chloro-5-thiophenethiol was prepared according to E. Jones and M. Moodie, Tetrahedron, 1965, vol. 21, 1333–1336, the disclosure of which is specifically incorporated by reference herein.

EXAMPLE 46

(3R,4R)-4-[3-(6-Methoxyquinolin-4-yl)propyl]-1-[3-fluoro-3-phenylpropyl]piperidine-3-carboxylic acid A mixture of 0.4 g of methyl (3R,4R)-4-[3-(6-methoxyquinolin-4-yl)propyl]-1-[3-5 (R,S)-fluoro-3-phenylpropyl]piperidine-3-carboxylate and 0.18 g of lithium hydroxide monohydrate in 2 cm$^3$ of water and 10 cm$^3$ of acetone was stirred for 3 days at a temperature in the region of 20° C. and then evaporated under reduced pressure (5 kPa) at a temperature in the region of 40° C. The residue obtained was purified by chromatography under an argon pressure of 50 kPa on a column of silica gel (particle size 20–45 μm; diameter 3 cm; 50 g), elution was carried out with a dichloromethane/methanol (95/5 by volume) mixture, and a fraction of 910 cm$^3$ was first collected. Elution was then carried out with a dichloromethane/methanol (90/10 by volume) mixture, 13-cm$^3$ fractions were collected. Fractions 47 to 69 were combined and then evaporated under reduced pressure (5 kPa) at a temperature in the region of 40° C. The evaporation residue was taken up in dichloromethane, filtered, and concentrated under the same conditions as above. The product obtained was stirred for 10 minutes in 10 cm$^3$ of diisopropyl ether. The crystals were filtered off and washed with 1 times 5 cm$^3$ of diisopropyl ether and 3 times 5 cm$^3$ of pentane. 0.102 g of (3R,4R)-4-[3-(6-methoxyquinolin-4-yl)propyl]-1-[3-fluoro-3-phenylpropyl]piperidine-3-carboxylic acid was obtained in the form of a solid with a gray color melting at 60° C. which corresponds to one of the diastereoisomers. $[\alpha]_D^{20}$=+37.5°+/−0.9, in methanol at 0.5%.

$^1$H N.M.R. spectrum (300 Mkz, d6-$(CD_3)_2SO$, δ in ppm): from 1.45 to 3.10 (mts, 16H), 3.02 (broad t, J=7 Hz, 2H), 4.04 (s, 3H), 5.59 (mt, $J_{HF}$=48 Hz, 1H), 7.32 (d, J=4.5 Hz, 1H), from 7.35 to 7.50 (mt, 7H), 7.42 (d, J=9 HZ, 1H), 8.62 (d, J=4.5 Hz, 1H).

Methyl (3R,4R)-4-[3-(6-methoxyquinolin-4-yl)propyl]-1-[3-(R,S)-fluoro-3-phenylpropyl]piperidine-3-carboxylate 0.425 cm$^3$ of diethylaminosulfur trifluoride was added, under an inert atmosphere at a temperature in the region of 20° C., to a stirred solution of 1.18 g of methyl (3R,4R)-4-[3-(6-methoxyquinolin-4-yl)propyl]-1-[3-(R,S)-hydroxy-3-phenylpropyl]piperidine-3-carboxylate in 17.7 cm$^3$ of dichloromethane. After stirring for 3 hours, the mixture was poured onto 32 cm$^3$ of a saturated aqueous sodium hydrogencarbonate solution. 15 cm$^3$ of dichloromethane were added and then the mixture was stirred for a further 10 minutes. After separating by settling, the organic phase was separated off, while the aqueous was extracted with 3 times 10 cm$^3$ of dichloromethane. The organic extracts were combined, washed with 3 times 20 cm$^3$ of water, dried over sodium sulfate, filtered, and concentrated under reduced pressure (5 kPa) at a temperature in the region of 40° C. 1.11 g of residue were obtained, which product was purified by chromatography under an argon pressure of 50 kPa on a silica column (particle size 20–45 μm; diameter 2.8 cm; 45 g of silica), elution was carried out with an ethyl acetate/methanol (98/2 by volume) mixture, and 15-cm$^3$ fractions were collected. Fractions 10 to 20 were combined and then evaporated under reduced pressure (5 kPa) at a temperature in the region of 40° C. 0.6 g of methyl (3R,4R)-4-[3-(6-methoxyquinolin-4-yl)propyl]-1-[3-(R,S)-fluoro-3-phenylpropyl]piperidine-3-carboxylate was obtained in the form of thick oil with a light yellow color.

Infrared spectrum ($CH_2Cl_2$): 2951, 1732, 1621, 1509, 1473, 1227, 1167, 1031, and 848 cm$^{-1}$.

Methyl (3R,4R)-4-[3-(6-methoxyquinolin-4-yl)propyl]-1-[3-(R,S)-hydroxy-3-phenylpropyl]piperidine-3-carboxylate was prepared by analogy with the method described in Example 1.

EXAMPLE 47

(3R,4R)-4-[3-(R,S)-Hydroxy-3-(6-methoxyquinolin-4-yl)propyl]-1-[2-(pyridin-2-ylthio)ethyl]piperidine-3-carboxylic acid trihydrochloride 1.33 cm$^3$ of a 5N aqueous sodium hydroxide solution were added, with stirring and under a nitrogen atmosphere, to a solution, maintained at a temperature in the region of 20° C., of 0.33 g of methyl (3R,4R)-4-[3-(R,S)-hydroxy-3-(6-methoxyquinolin-4-yl)propyl]-1-[2-(pyridin-2-ylthio) ethyl]piperidine-3-carboxylate in 6.66 cm³ of methanol. The solution obtained was heated in the region of 60° C. for 16 hours. The reaction mass was evaporated to dryness under reduced pressure (5 kPa) at a temperature in the region of 60° C. The residue obtained was taken up in 3.4 cm³ of distilled water and then 3.43 cm³ of 36% concentrated aqueous hydrochloric acid were added. A solution with a yellow color was obtained, which solution was evaporated under the same conditions as above. The evaporation residue was taken up in 10 cm³ of a dichloromethane/methanol (80/20 by volume) mixture. The insoluble material which resulted therefrom was filtered off and washed with 2 times 2.5 cm³ of a dichloromethane/methanol (90/10 by volume) mixture. The filtrate was evaporated under reduced pressure (5 kPa) at a temperature in the region of 40° C. 0.40 g of (3R,4R)-4-[3-(R,S)-hydroxy-3-(6-methoxyquinolin-4-yl) propyl]-1-[2-(pyridin-2-2 -ylthio)-ethyl]piperidine-3-carboxylic acid trihydrochloride was obtained in the form of a solid with a beige color melting at 155° C.

¹H N.M.R. spectrum (400 MHz, d6-($CD_3$)$_2$SO, at a temperature of 383 K, δ in ppm). A mixture of two diastereoisomers was observed: from 1.50 to 2.30 and from 3.15 to 3.65 (mts, 16H), 4.00 (s, 3H), 5.38 (mt, 1H), 7.18 (broad dd, J=8 and 5 Hz, 1H), 7.38 (d, J=8 Hz, 1H), from 7.55 to 7.65 (mt, 2H), 7.69 (t, J=8 and 2 Hz, 1 h), 7.80 (mt, 1H), 8.20 (broad d, J=10 Hz, 1H), 8.48 (dmt, J=5 Hz, 1H), 8.35 (broad d, J=5 Hz, 1H).

Methyl (3R,4R)-4-[3-(R,S)-hydroxy-3-(6-methoxyquinolin-4-yl)propyl]-1-[2-(pyridin-2-ylthio)ethyl]piperidine-3-carboxylate A stirred solution of 0.77 g of methyl (3R,4R)-4-[3-oxo-3-(6-methoxyquinolin-4-yl)propyl]-1-[2-(pyridin-2-ylthio)ethyl]piperidine-3-carboxylate in 15 cm³ of methanol was cooled to a temperature in the region of 0° C. under an inert atmosphere. 0.063 g of sodium borohydride was added and then, after 15 minutes, the temperature was brought back to the region of 20° C. for 16 hours. After adding 5 cm³ of a saturated aqueous ammonium chloride solution, the mixture was stirred for 10 minutes and then evaporated under reduced pressure (5 kPa) at a temperature in the region of 40° C. The residue obtained was taken up in 10 cm³ of a dichloromethane/methanol (95/5 by volume) mixture and then filtered. The insoluble material was washed with 2 times 5 cm³ of the same mixture. The filtrate was evaporated under the same conditions as above. A foam was obtained, which product was purified by chromatography under a nitrogen pressure of 100 kPa on a column of silica gel (particle size 40–63 μm; diameter 3.5 cm; silica height 35 cm), elution was carried out first with a dichloromethane/methanol (96/4 by volume) mixture, and 35-cm³ fractions were collected. After the first 50 fractions, elution was carried out with a dichloromethane/methanol (90/10 by volume) mixture. Fractions 61 to 90 were combined and then evaporated under reduced pressure (5 kPa) at a temperature in the region of 40° C. 0.33 g of methyl (3R,4R)-4-[3-(R,S)-hydroxy-3-(6-methoxyquinolin-4-yl)propyl]-1-[2-(pyridin-2-ylthio)ethyl]piperidine-3-carboxylate was obtained in the form of a lacquer with a beige color.

Infrared spectrum ($CH_2Cl_2$): 2596, 2951, 1622, 1579, 1508, 1455, 1415, 1242, 1228, 1125, 1031, 856, and 831 cm⁻¹.

Methyl (3R,4R)-4-[3-oxo-3-(6-methoxyquinolin-4-yl)propyl]-1-[2-(pyridin-2-ylthio)ethyl]piperidine-3-carboxylate A mixture of 1.35 g of methyl (3R,4R)-4-[3-oxo-3-(6-methoxyquinolin-4-yl)propyl]-1-(2-chloroethyl)piperidine-3-carboxylate dihydrochloride in 20 cm³ of acetonitrile was stirred at a temperature in the region of 20° C. under an inert atmosphere. 1.37 g of potassium carbonate and 0.456 g of potassium iodide were added, followed by 0.367 g of 2-mercaptopyridine and 1 cm³ of methanol. A red suspension was obtained, which suspension was heated at a temperature in the region of 80° C. for 1 hour 30 minutes. After cooling the reaction mass to a temperature in the region of 20° C., the insoluble material was filtered off and washed with acetonitrile. The filtrate was evaporated under reduced pressure (5 kPa) at a temperature in the region of 40° C. The evaporation residue was purified by chromatography under a nitrogen pressure of 100 kPa on a column of silica gel (particle size 40–63 μm; diameter 3.5 cm; silica height 35 cm), elution was carried out with an ethyl acetate/methanol (95/5 by volume) mixture, and 35-cm³ fractions were collected. Fractions 19 to 40 were combined and then evaporated under reduced pressure (5 kPa) at a temperature in the region of 40° C. 0.77 g of methyl (3R,4R)-4-[3-oxo-3-(6-methoxyquinolin-4-yl)propyl]-1-[2-(pyridin-2 -ylthio)ethyl] piperidine-3-carboxylate was obtained in the form of a viscous oil with a red color.

Infrared spectrum ($CH_2Cl_2$): 2952, 2809, 1733, 1692, 1620, 1580, 1455, 1415, 1243, 1125, 1029, and 853 cm⁻¹.

Methyl (3R,4R)-4-[3-oxo-3-(6-methoxyquinolin-4-yl) propyl]-1-[2-(pyridin-2-ylthio)ethyl]piperidine-3-carboxylate dihydrochloride was prepared by analogy with the method described in Example 5.

EXAMPLE 48

(3R,4R)-4-[3-Hydroxy-3-(6-methoxyquinolin-4-yl) propyl]-1-[2-(2-thienylthio)ethyl]piperidine-3-acetic acid dihydrochloride, diastereoisomer A, and (3R, 4R)-4-[3-hydroxy-3-(6-methoxyquinolin-4-yl) propyl]-1-[2-(2-thienylthio)-ethyl]piperidine-3-acetic acid, diastereoisomer B 1.2 g of (3R,4R)-4-[3-(R,S)-hydroxy-3-(6-methoxyquinolin4-yl)propyl]-1-[2-(2-thienylthio)ethyl] piperidine-3-acetic acid was chromatographed on a column with a length of 35 cm and a diameter of 6 cm packed with 700 g of Kromasil®-CN silica (particle size 10 μm). Elution was carried out using a dichloromethane/ethanol/ triethylamine (98/2/0.1 by volume) mixture. The flow rate was 70 cm³ per minute. Detection was carried out using ultraviolet radiation at 265 nm. After several preparative injections, the fractions corresponding to the diastereoisomer A were collected. These fractions were concentrated under reduced pressure (5 kPa) at a temperature in the region of 40° C. 0.34 gof a product was obtained, which product was salified in the following way: 0.3 g of this product was taken up in 30 cm³ of ether, filtered, and then dissolved in 25 cm³ of acetone. The solution obtained was poured onto 5 cm³ of a 5N solution of hydrochloric acid in ether. After concentrating the mixture under reduced pressure under the same conditions as above, the residue obtained was taken up in 20 cm³ of water and the solution was lyophilized. 0.190 g of (3R,4R)-4-[3-hydroxy-3-(6-methoxyquinolin-4-yl) propyl]-1-[2-(2-thienylthio)-ethyl]piperidine-3-acetic acid dihydrochloride, diastereoisomer A, was obtained in the form of a lyophilizate with an orange color. During the preparative separation of the two diastereoisomers, the mixture fractions were concentrated as above for retreatment. The separating conditions were as follows: column with a length of 35 cm and diameter of 6 cm packed with 700 g of Kromasil® silica (particle size 10 μm). Elution was carried out using a dichloromethane/acetonitrile/methanol/ triethylamine (60/40/4/0.1 by volume) mixture. The flow rate was 80 cm³/minute. After 3 preparative injections, the fractions corresponding to the diastereoisomer B were collected. These fractions were concentrated under the same conditions as above. 0.34 g of (3R,4R)-4-[3-hydroxy-3-(6-methoxyquinolin-4-yl)propyl]-1-[2-(2-thienylthio)ethyl]piperidine-3-acetic acid, diastereoisomer B, was obtained in the form of a foam with a yellow color ($[\alpha]_D^{20}$=+55.4°+/−1.1, in dichloromethane at 0.5%).

Diastereoisomer A: ¹H N.M.R. spectrum (400 MHz, d6-(CD₃)₂SO with addition of a few drops of d4-CD₃COOD at a temperature of 373 K, δ in ppm): from 1.40 to 1.90 and from 2.20 to 2.55 (mts, 10H), from 2.95 to 3.35 (mt, 8H), 3.99 (s, 3H), 5.40 (mt, 1H), 7.07 (dd, J=5.5 and 3.5 Hz, 1H), 7.27 (broad d, J=3.5 Hz, 1H), from 7.55 to 7.65 (mt, 3H), 7.85 (d, J=4.5 Hz, 1H), 8.17 (d, J=9 Hz, 1H), 8.88 (d, J=4.5 Hz, 1H).

Diastereoisomer B: ¹H N.M.R. spectrum (250 MHz, d6-(CD₃)₂SO, δ in ppm): from 1.20 to 2.80 (mts, 16H), 2.88 (broad t, J=7 Hz, 2H), 3.92 (s, 3H), 5.27 (mt, 1H), 7.04 (dd, J=5.5 and 3.5 Hz, 1H), 7.17 (dd, J=3.5 and 1.5 Hz, 1H), from 7.30 to 7.45 (mt, 2H), 7.54 (d, J=4.5 Hz, 1H), 7.60 (dd, J=5.5 and 1.5 Hz, 1H), 7.94 (d, J=9.5 Hz, 1H), 8.71 (d, J=4.5 Hz, 1H).

(3R,4R)-4-[3-(R,S)-Hydroxy-3-(6-methoxyquinolin-4-yl)propyl]-1-[2-(2-thienylthio)ethyl]piperidine-3-acetic acid A mixture of 0.22 g of methyl (3R,4R)-4-[3-(R,S)-hydroxy-3-(6-methoxyquinolin-4-yl)propyl]-1-[2-(2-thienylthio)ethyl]piperidine-3-acetate dihydrochloride in 5 cm³ of dioxane, to which had been added 0.683 cm³ of 5N aqueous sodium hydroxide solution, was stirred for 20 hours at a temperature in the region of 60° C. After evaporating under reduced pressure (5 kPa) at a temperature in the region of 40 ° C., the residue obtained was purified by chromatography at atmospheric pressure on a column of silica gel (particle size 20–45 μ; diameter 1 cm; silica volume 20 cm³), elution was carried out with a chloroform/methanol/aqueous ammonia (12/3/1 by volume) mixture. Fractions 1 to 3 were combined and concentrated under the above conditions. A product was obtained, which product was dried in an oven to constant weight under reduced pressure (10 Pa) at a temperature in the region of 40° C. 0.179 g of (3R,4R)-4-[3-(R,S)-hydroxy-3-(6-methoxyquinolin4-yl)propyl]-1-[2-(2-thienylthio)-ethyl]piperidine-3-acetic acid was obtained in the form of a white foam which was a mixture of two diastereoisomers.

¹H N.M.R. spectrum (300 MHz, d6-(CD₃)₂SO, δ in ppm). A mixture of two diastereoisomers was observed: from 1.15 to 2.80 (mts, 16H), 2.88 (broad t, J=7 Hz, 2H), 3.91 and 3.92 (2s, 3H in all), 5.26 (unresolved peak, 1H), 7.04 (dd, J=5.5 and 3.5 Hz, 1H), 7.16 (dd, J=3.5 and 1 Hz, 1H), from 7.30 to 7.45 (mt, 2H), 7.54 (mt, 1H), 7.60 (broad d, J=5.5 Hz, 1H), 7.94 (d, J=9 Hz, 1H), 8.70 (d, J=4.5 Hz, 1H).

Methyl (3R,4R)-4-[3-(R,S)-hydroxy-3-(6-methoxyquinolin-4-yl)propyl]-1-[2-(2-thienylthio)ethyl]piperidine-3-acetate dihydrochloride 1 drop of 5N aqueous sodium hydroxide solution and then, portionwise, 0.17 g of sodium borohydride were added, with stirring, to a solution, maintained at a temperature in the region of 20 ° C., of 0.84 g of methyl (3R,4R)-4-[3-oxo-3-(6-methoxyquinolin-4-yl)propyl]-1-[2-(2-thienylthio)ethyl]piperidine-3-acetate in 12 cm³ of methanol. The mixture was stirred for 3 hours at a temperature in the region of 20° C. After adding 10 cm³ of water, the methanol was evaporated under reduced pressure (5 kPa) at a temperature in the region of 40° C. The residue obtained was extracted with 2 times 20 cm³ of dichloromethane and then the combined extracts were washed with 2 times 30 cm³ of water, dried over magnesium sulfate, filtered, and concentrated under reduced pressure (5 kPa) at a temperature in the region of 40° C. An oil was obtained, which oil was purified by chromatography at atmospheric pressure on a column of silica gel (particle size 20–45 μm; diameter 2.5 cm; silica volume 150 cm³), elution was carried out with a dichloromethane/methanol (99/1 by volume) mixture. Fractions 56 to 115 were combined and then concentrated as above. An oil was obtained, the hydrochloride of which was prepared in the following way: the oil was dissolved in 20 cm³ of diethyl ether and then poured onto 2 cm³ of a 1 N solution of hydrochloric acid in ether. The precipitate formed was filtered off and dried in an oven under reduced pressure (10 Pa) at a temperature in the region of 40° C. 0.3 g of methyl (3R,4R)-4-[3-(R,S)-hydroxy-3-(6-methoxyquinolin-4-yl)propyl]-1-[2-(2-thienylthio)ethyl]piperidine-3-acetate dihydrochloride was obtained in the form of a white solid.

¹H N.M.R. spectrum (400 MHz, d6-(CD₃)₂SO at a temperature of 383 K, δ in ppm). A mixture of two diastereoisomers was observed: from 1.40 to 2.00 and from 2.25 to 2.70 (mts, 10H in all), from 2.90 to 3.40 (unresolved peak, 4H), 3.27 (mt, 4H), 3.61 and 3.63 (2s, 3H in all), 4.00 (s, 3H), 5.38 (mt, 1H), 7.10 (dd, J=5 and 3.5 Hz, 1H), 7.29 (broad d, J=3.5 Hz, 1H), from 7.55 to 7.60 (mt, 2H), 7.65 (d, J=5 Hz, 1H), 7.76 (mt, 1H), 8.16 (d, J=9.5 Hz, 1H), 8.85 (d, J=4.5 Hz, 1H).

Methyl (3R,4R)-4-[3-oxo-3-(6-methoxyquinolin-4-yl)propyl]-1-[2-(2-thienylthio)ethyl]piperidine-3-acetate 1.5 g of 2-(2-chloroethylthio)thiophene, followed by 5.2 g of potassium carbonate and 2.5 g of potassium iodide, were added with stirring, at a temperature in the region of 20° C., to a solution of 2.8 g of methyl (3R,4R)-4-[3-oxo-3-(6-methoxyquinolin-4-yl)propyl]piperidine-3-acetate in 60 cm³ of acetonitrile. The mixture was heated for 20 hours at a temperature in the region of the reflux temperature and then cooled to approximately 20° C. 130 cm³ of water and 50 cm³ of ethyl acetate were added to the reaction mixture. After separating the mixture by settling, the organic phase was washed with 150 cm³ of water, dried over magnesium sulfate, filtered, and then concentrated under reduced pressure (5 kPa) at a temperature in the region of 40° C. An oil was obtained, which oil was purified by chromatography at atmospheric pressure on a column of silica gel (particle size 20-45 μm; diameter 2.5 cm; silica volume 100 cm³), elution was carried out with a dichloromethane/methanol (95/5 by volume) mixture. A fraction of 30 cm³ was first collected, followed by approximately 10-cm³ fractions. Fractions 1 to 4 were combined and then evaporated as above. 2.3 g of a brown oil were obtained, which product was subjected a second time to purification by chromatography at atmospheric pressure on a column of silica gel (particle size 20–45 μm; diameter 2.5 cm; silica volume 300 cm³), elution was carried out with a dichloromethane/methanol (99/1 by volume) mixture, and approximately 10-cm³ fractions were collected. Fractions 21 to 30 were combined and then concentrated under the above conditions. 0.84 g of methyl (3R,4R)-4-[3-oxo-3-(6-methoxyquinolin-4-yl)propyl]-1-[2-(2-thienylthio)ethyl]piperidine-3-acetate was obtained in the form of a pale yellow oil.

Infrared spectrum (CH$_2$Cl$_2$): 2937, 2806, 2765, 1731, 1693, 1620, 1505, 1243, and 849 cm$^{-1}$.

Methyl (3R,4R)-4-[3-oxo-3-(6-methoxyquinolin-4-yl)propyl]piperidine-3-acetate A solution of 10.8 g of (3R,4R)-4-[3-oxo-3-(6-methoxyquinolin-4-yl)propyl]-1-(tert-butyloxycarbonyl) piperidine-3-acetic acid in 460 cm$^3$ of anhydrous methanol to which 4.3 cm$^3$ of concentrated sulfuric acid (d =1.83) had been added was heated at a temperature in the region of 65° C. with stirring for 2 hours. After cooling to approximately 20° C., the reaction mixture was evaporated under reduced pressure (5 kPa) at a temperature in the region of 40° C. and then the residue obtained was taken up in 200 cm$^3$ of water and rendered alkaline by addition of sodium hydrogencarbonate until a pH in the region of 8–9 was obtained. The mixture was extracted with 4 times 200 cm$^3$ of ethyl acetate. The aqueous phase was basified to a pH in the region of 11 by addition of the necessary amount of sodium carbonate. The mixture was extracted with 2 times 200 cm$^3$ of ethyl acetate. The organic extracts were combined, dried over magnesium sulfate, filtered, and evaporated under reduced pressure (5 kPa) at a temperature in the region of 40° C. 6.84 g of methyl (3R,4R)-4-[3-oxo-3-(6-methoxyquinolin-4-yl) propyl]piperidine-3-acetate were obtained in the form of an oil with a brown color.

Infrared spectrum (CCl$_4$): 2935, 2812, 1738, 1692, 1620, 1504, 1242, 1032, and 851 cm$^{-1}$.

(3R,4R)-4-[3-Oxo-3-(6-methoxyquinolin-4-yl)propyl]-1-(tert-butyloxycarbonyl)piperidine-3-acetic acid A solution of 0.85 g of potassium permanganate in 25 cm$^3$ of water and 120 cm$^3$ of acetone was added over approximately 1 hour, with stirring and at a temperature in the region of 25° C., to a solution of 1.2 g of (3R,4R)-4-[3-oxo-3-(6-methoxyquinolin-4-yl)propyl]-1-(tert-butyloxycarbonyl)piperidine-3-acetaldehyde in 60 cm$^3$ of acetone. The mixture was stirred for 3 hours at this same temperature and then cooled to approximately 10° C. A solution of 5 g of sodium sulfite in 200 cm$^3$ of water was added to the reaction mixture and then the mixture obtained was filtered through celite. The acetone of the filtrate was evaporated under reduced pressure (5 kPa) at a temperature in the region of 40° C. and then the evaporation residue was taken up in 200 cm$^3$ of water and washed with 200 cm$^3$ of diethyl ether. The aqueous phase was separated by settling, acidified with citric acid in the solid state to a pH in the region of 3–4 and extracted with 200 cm$^3$ of diethyl ether. The ethereal solution, separated by settling, was dried over magnesium sulfate, filtered, and evaporated under the above conditions. 0.74 g of (3R,4R)-4-[3-oxo-3-(6-methoxyquinolin-4-yl)propyl]-1-(tert-butyloxycarbonyl) piperidine-3-acetic acid was obtained in the form of a yellow solid.

Infrared spectrum (KBr): 2932, 2588, 1730, 1690, 1620, 1431, 1246, 1165, and 857 cm$^{-1}$.

(3R,4R)-4-[3-Oxo-3-(6-methoxyquinolin-4-yl)propyl]-(tert-butyloxycarbonyl)piperidine-3-acetaldehyde A mixture of 13.7 g of dimethyl sulfoxide in 65 cm$^3$ of dichloromethane was slowly added, with stirring and under an inert atmosphere, to a solution, cooled to a temperature in the region of –60° C., of 8.3 cm$^3$ of oxalyl chloride in 65 cm$^3$ of dichloromethane. After stirring the mixture for 15 minutes, 10 g of (3R,4R)-3-(2-hydroxyethyl)-4-[3-(R,S)-hydroxy-3-(6-methoxyquinolin-4-yl)propyl]-1-(tert-butyloxycarbonyl)piperidine, dissolved in 65 cm$^3$ of dichloromethane, were slowly added. After stirring the mixture for 30 minutes, 61.7 cm$^3$ of triethylamine, dissolved in 65 cm$^3$ of dichloromethane, were finally added dropwise. The mixture was stirred for a further 3 hours at approximately –60° C. and then poured onto 400 cm$^3$ of ice-cold water. After separating the mixture by settling, the organic phase was washed with 400 cm$^3$ of a 10% (by mass) aqueous citric acid solution and then dried over magnesium sulfate, filtered, and evaporated under reduced pressure (5 kPa) at a temperature in the region of 40° C. 9.95 g of (3R,4R)-4-[3-oxo-3-(6-methoxyquinolin-4-yl)propyl]-1-(tert-butyloxycarbonyl)piperidine-3-acetaldehyde were obtained in the form of an. oil with a brown color.

Infrared spectrum (CCl$_4$): 2932, 2720, 1729, 1694, 1430, 1244, 1164, and 850 cm$^{-1}$.

(3R,4R)-3-(2-Hydroxyethyl)-4-[3-(R,S)-hydroxy-3-(6-methoxyquinolin-4-yl)propyl]-1-(tert-butyloxycarbonyl)piperidine 33.4 cm$^3$ of triethylamineborane complex were added with stirring, at a temperature in the region of 20° C., to a solution of 52.6 g of (3R,4R)-4-[3-oxo-3-(6-methoxyquinolin-4-yl)propyl]-1-(tert-butyloxycarbonyl)-3-vinylpiperidine in 500 cm$^3$ of toluene and then the mixture was heated for 18 hours at a temperature in the region of 110° C. After having concentrated the reaction mixture under reduced pressure (5 kPa) at a temperature in the region of 45° C., the residue obtained was taken up in 500 cm$^3$ of tetrahydrofuran. The solution which resulted therefrom had approximately 63 cm$^3$ of water added over 20 minutes and then 47.5 g of sodium perborate were added portionwise over approximately 1 hour. The mixture was stirred for 4 hours at a temperature in the region of 20° C. and then 300 cm$^3$ of a saturated ammonium chloride solution were added. The organic solution was separated by settling, dried over magnesium sulfate, and concentrated under the same conditions as above. The residue obtained was purified by chromatography on a column of silica gel (particle size 20–45 μm; diameter 9 cm; silica volume 2500 cm$^3$), elution was carried out first with a dichloromethane/methanol (97.5/2.5 by volume) mixture, and 1-liter fractions were collected. Fractions 1 to 17 were separated and then elution was carried out with a dichloromethane/methanol (95/5 by volume) mixture, 1-liter fractions were collected. Fractions 30 to 35 were combined and, finally, elution was carried out with a dichloromethane/methanol (90/10 by volume) mixture, 1-liter fractions were collected. Fractions 36 to 41 were combined, while the combination of fractions 30 to 41 was evaporated under reduced pressure (5 kPa) at a temperature in the region of 40° C. 20 g of (3R,4R)-3-(2-hydroxyethyl)-4-[3-(R,S)-hydroxy-3-(6-methoxyquinolin-4-yl)propyl]-1-(tert-butyloxycarbonyl)piperidine were obtained in the form of an oil.

Infrared spectrum (CH$_2$Cl$_2$): 3612, 2480, 2937, 1680, 1432, 1243, 1163, and 859 cm$^{-1}$.

(3R,4R)-4-[3-Oxo-3-(6-methoxyquinolin-4-yl)propyl]-1-(tert-butyloxycarbonyl)-3-vinylpiperidine 162 cm$^3$ of triethylamine were added over approximately 20 minutes, at a temperature in the region of 20° C., followed, over 2 hours, by 85 g of di-tert-butyl dicarbonate, dissolved in 300 cm$^3$ of dichloromethane, to a stirred solution of 126 g of (3R,4R)-4-[3-oxo-3-(6- methoxyquinolin-4-yl)propyl]-3-vinylpiperidine in 1700 cm³ of dichloromethane. The mixture was stirred for 16 hours at a temperature in the region of 20° C. and then 400 cm³ of water were added thereto. The organic phase was separated by settling, dried over magnesium sulfate, filtered, and evaporated under reduced pressure (5 kPa) at a temperature in the region of 40° C. An oily residue was obtained, which product was taken up in 1000 cm³ of ethyl acetate and was washed with 2 times 200 cm³ of water, once with 250 cm³ of a saturated aqueous citric acid solution and 2 times with 200 cm³ of water. The organic solution was dried over magnesium sulfate, filtered, and concentrated under the above conditions. 148 g of (3R , 4R)-4-[3-oxo-3-(6-methoxyquinolin-4-yl)propyl]-1-(tert-butyloxycarbonyl)-3-vinylpiperidine were obtained in the form of an oil with a brown color.

Infrared spectrum (CH$_2$Cl$_2$): 2979, 1683, 1431, 1246, 1164, and 853 cm$^{-1}$.

(3R,4R)-4-[3-Oxo-3-(6-methoxyquinolin-4-yl)propyl]-3-vinylpiperidine was obtained by application of the method disclosed in Patent Application FR 2,354,771, the disclosure of which is specifically incorporated by reference herein.

EXAMPLE 49

(3R,4R)-1-[2-(3-Fluorophenylthio)ethyl]-4-[3-hydroxy-3-(6-methoxyquinolin-4-yl)propyl] piperidine-3-acetic acid, diastereoisomer A, and (3R,4R)-1-[2-(3-fluorophenylthio)ethyl]-4-[3-hydroxy-3-(6-methoxyquinolin-4-yl)propyl] piperidine-3-acetic acid, diastereoisomer B 0.7 g of (3R,4R)-1-[2-(3-fluorophenylthio)ethyl]-4-[3-(R,S)-hydroxy-3-(6-methoxyquinolin-4-yl)propyl]piperidine-3-acetic acid was chromatographed on a column with a length of 35 cm and a diameter of 6 cm packed with 700 g of Kromasil® silica (particle size 10 μm). Elution was carried but using a dichloromethane/acetonitrile/methanol/triethylamine (56/4014/0.5 by volume) mixture. The flow rate was 70 cm³/min. Detection was carried out using ultraviolet radiation at 265 nm. Several preparative injections had led to the separation of the 2 diastereoisomers. The fractions corresponding to the first, diastereoisomer A, were concentrated under reduced pressure (5 kPa) at a temperature in the region of 40° C. The crystalline mass obtained was dried in an oven under reduced pressure (10 Pa) at a temperature in the region of 20° C. 0.185 g of (3R,4R)-1-[2-(3-fluorophenylthio)ethyl]-4-[3-hydroxy-3-(6-methoxyquinolin-4-yl)propyl]piperidine-3-acetic acid, diastereoisomer A, was obtained in the form of a solid with an off-white color ([α]$_D^{20}$=−55.9°+/−1.2, in methanol at 0.5%). The mixture fractions were concentrated under the same conditions as above for retreatment. Fresh injections were carried out in order to obtain the second diastereoisomer. Three preparative injections make it possible to obtain the fractions corresponding to diastereoisomer B. These fractions were concentrated under reduced pressure (5 kPa) at a temperature in the region of 40° C. The crystalline mass obtained was dried in an oven under reduced pressure (10 Pa) at a temperature in the region of 20° C. 0.200 g of (3R,4R)-1-[2-(3-fluorophenylthio)ethyl]4-[3-hydroxy-3-(6-methoxyquinolin-4-yl)propyl]piperidine-3-acetic acid, diastereoisomer B, was obtained in the form of a solid with an off-white color ([α]$_D^{20}$=+41.0°+/−1.0, in methanol at 0.5%).

Diastereoisomer A: $^1$H N.M.R. spectrum (400 MHz, d6-(CD$_3$)$_2$SO, δ in ppm): from 1.15 to 1.85 and from 1.95 to 2.20 (2 series of mts, 11 H in all), from 2.40 to 2.60 (mt, 3H), 2.65 to 2.80 (mt, 2H), 3.08 (t, J=7 Hz, 2H), 3.92 (s, 3H), 5.27 (mt, 1H), 5.52 (unresolved peak, 1H), 6.98 (double t, J=8.5 and 2.5 Hz, 1H), from 7.10 to 7.20 (mt, 2H), from 7.25 to 7.45 (mt, 3H), 7.55 (d, J=4.5 Hz, 1H), 7.94 (d, J=9 Hz, 1H), 8.71 (d, J=4.5 Hz, 1H).

Diastereoisomer B: $^1$H N.M.R. spectrum (400 MHz, d6-(CD$_3$)$_2$SO, δ in ppm): from 1.30 to 1.90 and from 1.95 to 2.15 (2 series of mts, 10H in all), from 2.40 to 2.60 (mt, 3H), 2.75 (mt, 1H), from 2.95 to 3.15 (unresolved peak, 2H), 3.10 (t, J=7 Hz, 2H), 3.93 (s, 3H), 5.28 (mt, 1H), 5.53 (d, J=5 Hz, 1H), (double t, J=8.5 and 2.5 Hz, 1H), from 7.10 to 7.20 (mt, 2H), 7.35 (mt, 1H), from 7.35 to 7.45 (mt, 2H), 7.55 (d, J=4.5 Hz, 1H), 7.95 (d, J=9.5 Hz, 1H), 8.72 (d, J=4.5 Hz, 1H), from 11.00 to 12.5 (very broad unresolved peak, 1H).

(3R,4R)-1-[2-(3-Fluorophenylthio)ethyl]4-[3-(R,S)-hydroxy-3-(6-methoxyquinolin-4-yl)propyl] piperidine-3-acetic acid A solution of 1.3 g of methyl (3R,4R)-1-[2-(3-fluorophenylthio)ethyl]-4-[3-(R,S)-hydroxy-3-(6-methoxyquinolin-4-yl)propyl]piperidine-3-acetate in 20 cm³ of dioxane, to which 2 cm³ of 5N aqueous sodium hydroxide solution had been added, was heated with stirring for 20 hours at a temperature in the region of 60° C. The reaction mixture was evaporated under reduced pressure (5 kPa) at a temperature in the region of 40° C. and then the residue obtained was taken up in 30 cm³ of water and 5 cm³ of methanol, acidified with citric acid. The solvents were evaporated under the same conditions as above and then the residue obtained was taken up in 70 cm³ of a dichloromethane/methanol (80/20 by volume) mixture. The citric acid crystals were filtered off; the filtrate was evaporated as above and the evaporation residue was taken up in 30 cm³ of diethyl ether, filtered off, and dried in the air. 1.1 g of (3R,4R)-1-[2-(3-fluorophenylthio)ethyl]-4-[3-(R,S)-hydroxy-3-(6-methoxyquinolin-4-yl)propyl]piperidine-3-acetic acid were obtained in the form of a solid with a cream color.

$^1$H N.M.R. spectrum (300 MHz, d6-(CD$_3$)$_2$SO, δ in ppm). A mixture of two diastereoisomers was observed: from 1.15 to 1.90, from 2.00 to 2.25 and from 2.35 to 2.90 (mts, 16H in all), 3.13 (broad t, J=7 Hz, 2H), 3.92 (s, 3H), 5.27 (mt, 1H), 5.54 (mt, 1H), 7.00 (double t, J=8.5 Hz, 1H), from 7.10 to 7.25 (mt, 2H), from 7.30 to 7.50 (mt, 3H), 7.55 (mt, 1H), 7.94 (d, J=9 Hz, 1H), 8.71 (d, J=4.5 Hz, 1H), from 11.50 to 13.50 (very broad unresolved peak, 1H).

EXAMPLE 49A

Methyl (3R,4R)-1-[2-(3-fluorophenylthio)ethyl]-4-[3-(R,S)-hydroxy-3-(6-methoxyquinolin-4-yl) propyl]piperidine-3-acetate 0.28 g of sodium borohydride was added portionwise with stirring to a solution, maintained at a temperature in the range of 20° C. of 3.2 g of methyl (3R,4R)-1-[2-(3-fluorophenylthio)ethyl]-4-[3-oxo-3-(6-methoxyquinolin-4-yl)propyl]piperidine-3-acetate in 50 cm³ of methanol to which had been added 2 drops of 5N aqueous sodium hydroxide solution. The mixture was stirred for 4 hours at a temperature in the region of 20° C. After adding 30 cm³ of water, the mixture was extracted with 2 times 30 cm³ of dichloromethane. The combined organic phases were washed with 60 cm³ of water, dried over magnesium sulfate, filtered, and evaporated under reduced pressure (5 kPa) at a temperature in the region of 40° C. The residual oil was purified by chromatography at atmospheric pressure on a column of silica gel (particle size 20–45 μm; diameter 4 cm; silica volume 520 cm$^3$), elution was carried out with a dichloromethane/methanol (99/1) mixture, and approximately 60-cm$^3$ fractions were collected. Fractions 40 to 72 were combined and then evaporated as under the above conditions. 1.7 g of an oil were obtained, the hydrochloride of which was prepared in the following way: a solution of 0.30 g of oil in 5 cm$^3$ of diethyl ether was poured onto 5 cm$^3$ of a 5N solution of hydrochloric acid in ether. The gel obtained was diluted with 10 cm$^3$ of ether, stirred for 15 minutes at a temperature in the region of 20° C., and then evaporated under reduced pressure (5 kPa) at a temperature in the region of 30° C. The residue obtained was dissolved in 30 cm$^3$ of water and then lyophilized. 0.26 g of methyl (3R,4R)-1-[2-(3-fluorophenylthio)ethyl]-4-[3-(R,S)-hydroxy-3-(6-methoxyquinolin-4-yl)propyl]piperidine-3-acetate was obtained in the form of a lyophilizate with a cream color.

$^1$H N.M.R. spectrum (400 MHz, d6-(CD$_3$)$_2$SO with addition of a few drops of d4-CD$_3$COOD at a temperature of 373 K, δ in ppm). A mixture of two diastereoisomers was observed: from 1.45 to 2.00 and from 2.25 to 2.60 (mts, 10H in all), from 3.05 to 3.45 (mts, 8H), 3.60 and 3.63 (2s, 3H in all), 3.97 and 3.98 (2s, 3H in all), 5.39 (mt, 1H), 7.03 (mt, 1H), 7.23 (mt, 2H), 7.37 (mt, 1H), from 7.50 to 7.65 (mt, 2H), 7.80 (mt, 1H), 8.12 (d, J=9.5 Hz, 1H), 8.84 (d, J=5 Hz, 1H).

Methyl (3R,4R)-1-[2-(3-fluorophenylthio)ethyl]-4-[3-oxo-3-(6-methoxyquinolin-4-yl)propyl] piperidine-3-acetate 2.26 g of methyl(3R,4R)-4-[3-oxo-3-(6-methoxyquinolin-4-yl)propyl]piperidine-3-acetate, dissolved beforehand in 50 cm$^3$ of acetonitrile, were added dropwise, with stirring and at a temperature in the region of 20° C., followed by 6.91 g of potassium carbonate and 2 g of potassium iodide, to a solution of 4 g of 1-[(2-chloroethyl) thio]-3-fluorobenzene in 50 cm$^3$ of acetonitrile. The mixture was heated for 18 hours at a temperature in the region of 70° C. After a further addition of 0.3 g of potassium iodide and additional heating at a temperature in the region of 70° C. for 4 hours, the reaction mass was cooled to approximately 20° C., 200 cm$^3$ of water were added and extraction was carried out with 2 times 150 cm$^3$ of ethyl acetate. The combined extracts were washed with 300 cm$^3$ of water, dried over magnesium sulfate, filtered, and evaporated under reduced pressure (5 kPa) at a temperature in the region of 40° C. The residue obtained was purified by chromatography at atmospheric pressure on a column of silica gel (particle size 20–45 μ; diameter 5.2 cm; silica volume 950 cm$^3$), elution was carried out with a dichloromethane/methanol (99/1 by volume) mixture, and approximately 6-cm$^3$ fractions were collected. Fractions 24 to 36 were combined and concentrated under the above conditions. 3.3 g of methyl (3R,4R)-1-[2-(3-fluorophenylthio)ethyl]-4-[3-oxo-3-(6-methoxyquinolin-4-yl)propyl]piperidine-3-acetate were obtained in the form of an oil with a yellow color.

Infrared spectrum (CH$_2$Cl$_2$): 2936, 2806, 1731, 1692, 1620, 1505, 1474, 1243, 881, and 853 cm$^{-1}$.

Methyl(3R,4R)-4-[3-oxo-3-(6-methoxyquinolin-4-yl) propyl]piperidine-3-acetate was obtained in Example 48.

EXAMPLE 50

(3R,4R)-4-[3-(R,S)-Hydroxy-3-(6-methoxyquinolin-4-yl)propyl]-1-[3-(3,5-difluorophenyl)prop-2-ynyl] piperidine-3-carboxylic acid A mixture of 0.89 g of methyl (3R,4R)-4-[3-(R,S)-hydroxy-3-(6-methoxyquinolin-4-yl)propyl]-1-[3-(3,5-difluorophenyl)prop-2-ynyl]piperidine-3-carboxylate in 9 cm$^3$ of dioxane to which had been added 1.41 cm$^3$ of 5N aqueous sodium hydroxide solution was stirred for 18 hours at a temperature in the region of 60° C. After cooling to approximately 20° C., the reaction mixture was evaporated under reduced pressure (5 kPa) at a temperature in the region of 40° C. The residue obtained was purified by chromatography under a nitrogen pressure of 50 kPa on a column of silica gel (particle size 20–45 μm; diameter 3.3 cm; mass 56 g), elution first was carried out with a dichloromethane/methanol (95/5 by volume) mixture. A fraction of 100 cm$^3$ was first collected and then 16-cm$^3$ fractions. Fractions 1 to 36 were separated. Elution was subsequently carried out with a dichloromethane/methanol (75/25 by volume) mixture. A first fraction of 200 cm$^3$ a second of 150 cm$^3$, and then a third of 100 cm$^3$ were obtained. The latter two were combined and concentrated as above. The residue obtained was taken up in dichloromethane and filtered. The filtrate was evaporated as above and then the new residue obtained was triturated in 25 cm$^3$ of a diisopropyl ether/pentane (50/50 by volume) mixture. The product which crystallized was filtered off and washed with 2 times 10 cm$^3$ of the same mixture and then 3 times 10 cm$^3$ of pentane. 0.53 g of (3R,4R)-4-[3-(R,S)-hydroxy-3-(6-methoxyquinolin4-yl) propyl]-1-[3-(3,5-difluorophenyl)prop-2-ynyl]piperidine-3-carboxylic acid was obtained in the form of solid with a cream color melting at 106° C.

$^1$H N.M.R. spectrum (300 MHz, d6-(CD$_3$)$_2$SO, δ in ppm). A mixture of two diastereoisomers was observed: from 1.40 to 1.95 (mt, 7H), from 2.30 to 3.00 (mt, 5H), 3.57 and 3.59 (2s, 2H in all), 3.90 and 3.93 (2s, 3H in all), 5.25 (mt, 1H), 5.55 (unresolved peak, 1H), 7.22 (mt, 2H), from 7.25 to 7.45 (mt, 3H), 7.56 (mt, 1H), 7.94 (d, J=9 Hz, 1H), 8.70 (d, J=4.5 Hz, 1H), from 12.10 to 12.80 (broad unresolved peak, 1H).

Methyl (3R,4R)-4-[3-(R,S)-hydroxy-3-(6-methoxyquinolin-4-yl)propyl]-1-[3-(3,5-difluorophenyl)prop-2-ynyl]piperidine-3-carboxylate 0.138 g of tetrakis(triphenylphosphine)palladium, 0.046 g of cuprous iodide, and 0.42 cm$^3$ of 1-bromo-3,5-difluorobenzene were added to a mixture, stirred at a temperature in the region of 20° C. under an inert atmosphere, of 0.95 g of methyl (3R,4R)-4-[3-(R,S)-hydroxy-3-(6-methoxyquinolin-4-yl)propyl]-1-(prop-2-ynyl)piperidine-3-carboxylate in 9.5 cm$^3$ of triethylamine. The mixture was heated at a temperature in the region of 80° C. for 3 hours. After cooling to approximately 20° C., the reaction mixture was taken up in 30 cm$^3$ of ethyl acetate and 30 cm$^3$ of water and stirred for 5 minutes. The organic phase was separated by settling, while the aqueous layer was extracted with 2 times 30 cm$^3$ of ethyl acetate. The organic extracts were combined, washed with 3 times 30 cm$^3$ of water, dried over sodium sulfate, filtered, and concentrated under reduced pressure (5 kPa) at a temperature in the region of 40° C. The residue obtained was purified by chromatography under a nitrogen pressure of 50 kPa on a column of silica gel (particle size 20–45 μm; diameter 2.3 cm; 40 g), elution was carried out with pure ethyl acetate. 2 fractions of 100 cm$^3$ were first collected and then 20-cm$^3$ fractions were obtained. Fractions 8 to 40 were combined and evaporated under the above conditions. 0.967 g of methyl (3R,4R)-4-[3-(R,S)-hydroxy-3-(6-methoxyquinolin-4-yl)propyl]-1-[3-(3,5-difluorophenyl)prop-2-ynyl]piperidine-3-carboxylate was obtained in the form of a foam with an orange color.

Infrared spectrum (KBr): 3424, 2948, 1734, 1618, 1586, 1432, 1242, 1122, 1028, 990, and 373 cm$^{-1}$.

Methyl (3R,4R)-4-[3-(R,S)-hydroxy-3-(6-methoxyquinolin-4-yl)propyl]-1-(prop-2-ynyl)piperidine-3-carboxylate was prepared as described in Example 32.

EXAMPLE 51

(3R,4R)-4-[3-(R,S)-Hydroxy-3-(6-methoxyquinolin-4-yl)propyl]-1-[3-(2,5-difluorophenyl)prop-2-ynyl]piperidine-3-carboxylic acid A mixture of 0.874 g of methyl (3R,4R)-4-[3-(R,S)-hydroxy-3-(6-methoxyquinolin-4-yl)propyl]-1-[3-(2,5-difluorophenyl)prop-2-ynyl]piperidine-3-carboxylate in 8.8 cm³ of dioxane to which had been added 1.37 cm³ of 5N aqueous sodium hydroxide solution was stirred for 17 hours at a temperature in the region of 60° C. After cooling to approximately 20° C., the reaction mixture was evaporated under reduced pressure (5 kPa) at a temperature in the region of 40° C. An oil was obtained, which product was purified by chromatography under a nitrogen pressure of 50 kPa on a column of silica gel (particle size 20–45 μ; diameter 3 cm; 25 g), elution was carried out with a dichloromethane/methanol (85/15 by volume) mixture, first a fraction of 100 cm³ was collected and then 50-cm³ fractions were collected. Fractions 3 and 4 were combined and concentrated as above. The evaporation residue was taken up in dichloromethane and filtered. The filtrate was concentrated as under the above conditions and then the product obtained was taken up with stirring in 40 cm³ of a pentane/diisopropyl ether (50/50 by volume) mixture for 16 hours at a temperature in the region of 20° C. The crystals obtained were filtered off and washed with 2 times 10 cm³ of the same mixture as above and then 3 times 20 cm³ of pentane. 0.392 g of (3R,4R)-4-[3-(R,S)-hydroxy-3-(6-methoxyquinolin-4-yl)propyl]-1-[3-(2,5-difluorophenyl)prop-2-ynyl]piperidine-3-carboxylic acid was obtained in the form of a pale yellow solid melting at 109° C. which was a mixture of two diastereoisomers.

$^1$H N.M.R. spectrum (300 MHz, d6-(CD$_3$)$_2$SO, δ in ppm). A mixture of two diastereoisomers was observed: from 1.40 to 2.00 (mts, 7H), from 2.30 to 3.00 (mt, 5H), 3.64 and 3.65 (2s, 2H in all), 3.90 and 3.92 (2s, 3H in all), 5.26 (unresolved peak, 1H), 5.56 (unresolved peak, 1H), from 7.25 to 7.50 (mt, 5H), 7.56 (mt, 1H), 7.94 (d, J=9 Hz, 1H), 8.71 (d, J=4.5 Hz, 1H), from 12.40 to 12.70 (unresolved peak, 1H).

Methyl (3R,4R)-4-[3-(R,S)-hydroxy-3-(6-methoxyquinolin4-yl)propyl]-1-[3-(2,5-difluorophenyl)prop-2-ynyl]piperidine-3-carboxylate A mixture of 1.1 g of methyl (3R,4R)-4-[3-(R,S)-hydroxy-3-(6-methoxyquinolin-4-yl)propyl]-1-(prop-2-ynyl)piperidine-3-carboxylate, 11 cm³ of triethylamine, 0.16 cm³ of tetrakis(triphenylphosphine)palladium, 0.053 g of cuprous iodide, and 0.47 cm³ of 1-bromo-2,5-difluorobenzene was stirred for 3 hours 15 minutes under an inert atmosphere at a temperature in the region of 80° C. After cooling to approximately 20° C., the reaction mixture had 30 cm³ of ethyl acetate and 30 cm³ of water added with stirring. The organic phase was separated, while the aqueous phase was extracted with 2 times 30 cm³ of ethyl acetate. The organic extracts were combined, washed with 3 times 25 cm³ of water, dried over sodium sulfate, and concentrated under reduced pressure (5 kPa) at a temperature in the region of 40° C. A product was obtained, which product was purified by chromatography under a nitrogen pressure of 50 kPa on a column of silica gel (particle size 20–45 μm; diameter 3.3 cm; 50 g), elution was carried out with ethyl acetate, and a fraction of 300 cm³ first was collected, followed by 32-cm³ fractions. Fractions 7 to 22 were combined and then concentrated under the above conditions. 0.91 g of methyl (3R,4R)-4-[3-(R,S)-hydroxy-3-(6-methoxyquinolin-4-yl)propyl]-1-[3-(2,5-difluorophenyl)prop-2-ynyl]piperidine-3-carboxylate was obtained in the form of a foam with an off-white color.

Infrared spectrum (CCl$_4$): 3614, 2950, 1738, 1622, 1497, 1249, 1163, 1033, and 873 cm$^{-1}$.

Methyl (3R,4R)-4-[3-(R,S)-hydroxy-3-(6-methoxyquinolin-4-yl)propyl]-1-(prop-2-ynyl)piperidine-3-carboxylate was prepared in the Example 43.

EXAMPLE 52

(3R,4R)-1-[2-(Cyclohexylthio)ethyl]-4-[3-hydroxy-3-(6-methoxyquinolin4-yl)propyl]piperidine-3-acetic acid, diastereoisomer A, and (3R,4R)-1-[2-(cyclohexylthio)ethyl]-4-[3-hydroxy-3-(6-methoxyquinolin-4-yl)propyl]piperidine-3-acetic acid, diastereoisomer B 1.3 g of (3R,4R)-1-[2-(cyclohexylthio)ethyl]-4-[3-(R,S)-hydroxy-3-(6-methoxyquinolin-4-yl)propyl]piperidine-3-acetic acid were chromatographed on a column with a length of 35 cm and a diameter of 6 cm packed with 700 gof Kromasil® silica (particle size 10 μm). Elution was carried out using a dichloromethane/-acetonitrile/methanol/triethylamine (56/40/4/0.5 by volume) mixture. The flow rate was 70 cm³/min. Detection was carried out using ultraviolet radiation at 265 nm. Two preparative injections led to the separation of the two diastereoisomers. The fractions corresponding to the first, diastereoisomer A, were concentrated under reduced pressure (5 kPa) at a temperature in the region of 40° C. The evaporation residue obtained was dried in an oven under reduced pressure (10 Pa) at a temperature in the region of 20° C. 0.310 g of (3R,4R)-1-[2-(cyclohexylthio)ethyl]-4-[3-hydroxy-3-(6-methoxyquinolin-4-yl)propyl]piperidine-3-acetic acid, diastereoisomer A, was obtained in the form of a foam with a beige color ([α]$_D^{20}$=−43.6°+/−1.0, in dichloromethane at 0.5%). The fractions corresponding to the second, diastereoisomer B, were concentrated under reduced pressure (5 kPa) at a temperature in the region of 40° C. The evaporation residue obtained was dried in an oven under reduced pressure (10 Pa) at a temperature in the region of 20° C. 0.260 g of (3R,4R)-1-[2-(cyclohexylthio)ethyl]-4-[3-hydroxy-3-(6-methoxyquinolin-4-yl)propyl]piperidine-3-acetic acid, diastereoisomer B, was obtained in the form of a foam with a beige color ([α]$_D^{20}$=+55.4°+/−1.1, in dichloromethane at 0.5%).

Diastereoisomer A: $^1$H N.M.R. spectrum (300 MHz, d6-(CD$_3$)$_2$SO, δ in ppm): from 1.10 to 2.20 and from 2.30 to 2.80 (2 series of mts, 29H in all), 3.93 (s, 3H), 5.28 (broad dd, J=7.5 and 3 Hz, 1H), from 5.30 to 5.70 (broad unresolved peak, 1H), from 7.35 to 7.45 (mt, 2H), 7.56 (d, J=4.5 Hz, 1H), 7.94 (d, J=9.5 Hz, 1H), 8.72 (d, J=4.5 Hz, 1H).

Diastereoisomer B: $^1$H N.M.R. spectrum (300 MHz, d6-(CD$_3$)$_2$SO, δ in ppm): from 1.10 to 2.10 and from 2.30 to 2.80 (2 series of mts, 29H in all), 3.92 (s, 3H), 5.27 (broad dd, J=7.5 and 3 Hz, 1H), from 5.30 to 5.75 (broad unresolved peak, 1H), from 7.35 to 7.45 (mt, 2H), 7.54 (d, J=4.5 Hz, 1H), 7.94 (d, J=9.5 Hz, 1H), 8.71 (d, J=4.5 Hz, 1H).

(3R,4R)-1-[2-(Cyclohexylthio)ethyl]-4-[3-(R,S)-hydroxy-3-(6-methoxyquinolin-4-yl)propyl]piperidine-3-acetic acid 2.96 cm³ of 5N aqueous sodium hydroxide solution were added, with stirring at a temperature in the region of 20° C., to a solution of 1.9 g of methyl (3R,4R)-1-[2-(cyclohexylthio)ethyl]-4-[3-(R,S)-hydroxy-3-(6-methoxyquinolin-4-yl)propyl]piperidine-3-acetate in 35 cm³ of dioxane. The solution was heated for 16 hours at a temperature in the region of 60° C. The reaction mixture was evaporated under reduced pressure (5 kPa) at a temperature in the region of 50° C. and then the residue obtained was taken up in 50 cm³ of acetone and reevaporated as above. After having taken up the residue obtained in 50 cm³ of diethyl ether and having concentrated as under the above conditions, the yellow solid obtained had 20 cm³ of water added and was acidified with an amount of citric acid sufficient to obtain a pH in the region of 4–5. The mixture was extracted with 50 cm³ of dichloromethane. The organic extract was concentrated under reduced pressure (5 kPa) at a temperature in the region of 50° C. The evaporation residue was taken up in 2 times 100 cm³ of a dichloromethane/methanol (90/10 by volume) mixture, the insoluble material was filtered off each time after the residue had been taken up. The combined filtrates were concentrated as above and then the residue obtained was taken in 50 cm³ of diethyl ether and evaporated as under the above conditions. The crystals obtained were taken up in 50 cm³ of diethyl ether, filtered off, and washed with 2 times 50 cm³ of ether. The product was finally dried under reduced pressure, first under 5 kPa and then in an oven under 10 Pa at a temperature in the region of 60° C. 1.9 g of (3R,4R)-1-[2-(cyclohexylthio)ethyl]4-[3 -(R,S)-hydroxy-3-(6-methoxyquinolin-4-yl)propyl]piperidine-3-acetic acid were obtained in the form of a solid with a yellow color.

¹H N.M.R. spectrum (300 MHz, d6-(CD₃)₂SO, δ in ppm). A mixture of two diastereoisomers was observed: from 1.00 to 2.95 (mts, 29H), 3.92 (s, 3H), 5.27 (mt, 1H), 5.54 (unresolved peak, 1H), from 7.30 to 7.45 (mt, 2H), 7.55 (mt, 1H), 7.95 (d, J=9.5 Hz, 1H), 8.72 (d, J=4.5 Hz, 1H), from 10.80 to 11.90 (very broad unresolved peak, 1H).

EXAMPLE 52A

Methyl (3R,4R)-1-[2-(cyclohexylthio)ethyl]-4-[3-(R,S)-hydroxy-3-(6-methoxyquinolin-4-yl)propyl] piperidine-3-acetate dihydrochloride 0.42 g of sodium borohydride was added portionwise for approximately 1 hour with stirring and under an inert atmosphere, to a solution cooled to a temperature in the region of 15° C., of 3.5 g of methyl (3R,4R)-1-[2-(cyclohexylthio)ethyl]-4-[3-oxo-3-(6-methoxyquinolin-4-yl)propyl]piperidine-3-acetate in 50 cm³ of methanol to which had been added 1 drop of 5N sodium hydroxide solution. The mixture was stirred for 2 hours at this temperature and then cooled to approximately 10° C. 10 cm³ of water were then added dropwise. The mixture was concentrated under reduced pressure (5 kPa) at a temperature in the region of 45° C. After adding 100 cm³ of water to the residue obtained, the mixture was extracted with 2 times 100 cm³ of ethyl acetate. The combined extracts were dried over sodium sulfate, filtered, and concentrated as above. An oil was obtained, which product was purified by chromatography under a nitrogen pressure of 50 kPa on a column of silica gel (particle size 20–45 μm; diameter 3 cm; height 35 cm), elution was carried out with ethyl acetate, and 30-cm³ fractions were collected. Fractions 19 to 42 were combined and concentrated as under the above conditions 2.44 g of a product were obtained, the hydrochloride of which was prepared in the following way: 0.5 g of product was dissolved in 10 cm³ of diethyl ether and then the solution was poured into 5 cm³ of a 1 N solution of hydrochloric acid in ether. 10 cm³ of ether were added and then the mixture was left to act for 1 hour at a temperature in the region of 20° C. The mixture was filtered and the cake was washed with 2 times 10 cm³ of diethyl ether and dried under reduced pressure (5 kPa) at a temperature in the region of 20° C. and then in an oven under reduced pressure (10 Pa) at a temperature in the region of 60° C. 0.46 g of methyl (3R,4R)-1-[2-(cyclohexylthio)ethyl]-4-[3-(R,S)-hydroxy-3-(6-methoxyquinolin-4-yl)propyl]piperidine-3-acetate dihydrochloride was obtained in the form of a solid with a pale pink color melting at 80° C. while softening.

¹H N.M.R. spectrum (400 MHz, d6-(CD₃)₂SO at a temperature of 383 K, δ in ppm). A mixture of two diastereoisomers was observed: from 1.20 to 2.05 and from 2.30 to 2.65 (mts, 20H in all), 2.82 (mt, 1H), from 2.85 to 3.50 (broad unresolved peak, 4H), 2.96 (mt, 2H), 3.19 (mt, 2H), 3.62 and 3.63 (2s, 3H in all), 4.00 (s, 3H), 5.37 (mt, 1H), from 7.50 to 7.65 (mt, 2H), 7.73 (unresolved peak, 1H), 8.15 (broad d, J=9 Hz, 1H), 8.83 (d, J=4.5 Hz, 1H).

Methyl (3R,4R)-1-[2-(cyclohexylthio)ethyl]-4-[3-oxo-3-(6-methoxyquinolin-4-yl)propyl]piperidine-3-acetate 2.06 g of 2-chloroethyl cyclohexyl sulfide in 50 cm³ of acetonitrile, followed by 1.78 g of potassium iodide and 7.25 g of potassium carbonate, were added with stirring, at a temperature in the region of 20° C. and under an inert atmosphere, to a solution of 3.9 g of methyl (3R,4R)-4-[3-oxo-3-(6-methoxyquinolin-4-yl)propyl]piperidine-3-acetate in 50 cm³ of acetonitrile. The mixture was heated for 18 hours at a temperature in the region of 80° C. After cooling to approximately 20° C., the mixture had 100 cm³ of water and 100 cm³ of ethyl acetate added. The organic phase was separated by settling, while the aqueous phase was extracted with 200 cm³ of ethyl acetate. The organic extracts were combined, dried over sodium sulfate, filtered, and concentrated under reduced pressure (5 kPa) at a temperature in the region of 45° C. An oil was obtained, which product was purified by chromatography under a nitrogen pressure of 50 kPa on a column of silica gel (particle size 20–45 μ; diameter 3.5 cm; height 46 cm), elution was carried out with. a dichloromethane/methanol (95/5 by volume) mixture, and 50-cm³ fractions were collected. Fractions 18 to 37 were combined and concentrated as above. A product was obtained, which product was purified a second time by chromatography under a nitrogen pressure of 50 kPa on a column of silica gel (particle size 20–45 μ; diameter 4 cm; height 40 cm), elution was carried out with an ethyl acetate/cyclohexane (7/3 by volume) mixture, and 100-cm³ fractions were collected. Fractions 24 to 54 were combined and then concentrated under the same conditions as above. 3.7 g of methyl (3R,4R)-1-[2-(cyclohexylthio)ethyl]-4-[3-oxo-3-(6-methoxyquinolin-4-yl)propyl]piperidine-3-acetate were obtained in the form of an oil with a brown color.

Infrared spectrum (CH₂Cl₂): 2933, 2855, 1732, 1693, 1620, 105, 1244, 1029, and 853 cm⁻¹.

Methyl (3R,4R)-4-[3-oxo-3-(6-methoxyquinolin-4-yl) propylpiperidine-3-acetate was obtained in Example 48.

EXAMPLE 53

(3R,4R)-4-[3-Hydroxy-3-(6-methoxyquinolin-4-yl) propyl]-1-[3-(thien-2-yl)prop-2-ynyl]piperidine-3-acetic acid, diastereoisomer A, and (3R,4R)-4-[3-hydroxy-3-(6 -methoxyquinolin-4-yl)propyl]-1-[3-(thien-2-yl)prop-2-ynyl]piperidine-3-acetic acid, diastereoisomer B 1.2 g of (3R,4R)-4-[3-(R,S)-hydroxy-3-(6-methoxyquinolin-4-yl)propyl]-1-[3-(thien-2-yl)prop-2- ynyl]piperidine-3-acetic acid were chromatographed on a column with a length of 35 cm and a diameter of 6 cm packed with 700 g of Kromasil® silica (particle size 10 μm). Elution was carried out using a dichloromethane/-acetonitrile/methanol/triethylamine (70/15/15/0.05 by volume) mixture. The flow rate was 90 cm³/min. Detection was carried out using ultraviolet radiation at 265 nm. Two preparative injections led to the separation of the two diastereoisomers. The fractions corresponding to the first, diastereoisomer A, were concentrated under reduced pressure (5 kPa) at a temperature in the region of 40° C. The crystalline mass obtained was dried in an oven under reduced pressure (10 Pa) at a temperature in the region of 20° C. 0.408 g of (3R,4R)-4-[3-hydroxy-3-(6-methoxyquinolin-4-yl)propyl]-1-[3-(thien-2-yl)prop-2-ynyl]piperidine-3-acetic acid, diastereoisomer A, was obtained in the form of a solid with a yellow color ([α]$_D^{20}$=−62.9°+/−1.3, in methanol at 0.5%). The fractions corresponding to the second, diastereoisomer B, were concentrated under reduced pressure (5 kPa) at a temperature in the region of 40° C. The crystalline mass obtained was dried in an oven under reduced pressure (10 Pa) at a temperature in the region of 20° C. 0.376 g of (3R,4R)-4-[3-hydroxy-3-(6-methoxyquinolin-4-yl)propyl]-1-[3-(thien-2-yl)prop-2-ynyl]piperidine-3-acetic acid, diastereoisomer B, was obtained in the form of a solid with a yellow color ([α]$_D^{20}$=+46.9°+/−1.1, in methanol at 0.5%).

Diastereoisomer A: $^1$H N.M.R. spectrum (300 MHz, d6-(CD$_3$)$_2$SO with addition of a few drops of d4-CD$_3$COOD, δ in ppm): from 1.20 to 2.00 and from 2.05 to 2.50 (2 series of mts, 12H in all), from 2.60 to 2.85 (mt, 2H), 3.55 (limit AB, J=17 Hz, 2H), 3.90 (s, 3H), 5.27 (dd, J=8 and 3 Hz, 1H), 7.04 (mt, 1H), 7.26 (broad d, J=4 Hz, 1H), from 7.30 to 7.45 (mt, 2H), 7.52 (d, J=5.5 Hz, 1H), 7.56 (d, J=4.5 Hz, 1H), 7.93 (d, J=10 Hz, 1H), 8.70 (d, J=4.5 Hz, 1H).

Diastereoisomer B: $^1$H N.M.R. spectrum (300 MHz, d6-(CD$_3$)$_2$SO with addition of a few drops of d4-CD$_3$COOD, δ in ppm): from 1.20 to 1.90 and from 2.00 to 2.45 (2 series of mts, 12H in all), from 2.60 to 2.85 (mt, 2H), 3.50 (AB, J=17 Hz, 2H), 3.91 (s, 3H), 5.27 (dd, J=8 and 3.5 Hz, 1H), 7.05 (dd, J=5.5 and 4 Hz, 1H), 7.26 (broad d, J=4 Hz, 1H), from 7.35 to 7.45 (mt, 2H), from 7.50 to 7.60 (mt, 2H), 7.95 (d, J=10 Hz, 10 Hz, 1H), 8.71 (d, J=4.5 Hz, 1H).

(3R,4R)-4-[3-(R,S)-Hydroxy-3-(6-methoxyquinolin-4-yl)propyl]-1-[3-(thien-2-yl)prop-2-ynyl]piperidine-3-acetic acid A solution of 3 g of methyl (3R,4R)-4-[3-(R,S)-hydroxy-3-(6-methoxyquinolin-4-yl)propyl]-1-[3-(thien-2-yl)prop-2-ynyl]piperidine-3-acetate in 50 cm³ of dioxane to which had been added 5 cm³ of 5N aqueous sodium hydroxide solution was heated for 17 hours, with stirring and under an inert atmosphere, at a temperature in the region of 60° C. After cooling to approximately 20° C., the mixture was concentrated under reduced pressure (5 kPa) at a temperature in the region of 40° C. and then the residue was taken up in 100 cm³ of dichloromethane and 5 cm³ of water. The mixture was acidified with an amount of citric acid sufficient to obtain a pH in the region of 4–5 and then dried over magnesium sulfate, filtered, and concentrated as above. The residual water was entrained by azeotroping in chloroform. After concentrating as above, the residue obtained was purified by chromatography at atmospheric pressure on a column of silica gel (particle size 20–45 μm; diameter 3.5 cm; silica volume 200 cm³), elution was carried out with a chloroform/methanol/28% aqueous ammonia (12/2/0.5 by volume) mixture, and approximately 60-cm³ fractions were collected. The fractions comprising the expected product were combined and then concentrated under reduced pressure (5 kPa) at a temperature in the region of 40° C. The residue obtained was taken up in 40 cm³ of diethyl ether, filtered off, washed with 2 times 5 cm³ of ether, and dried under reduced pressure (5 kPa) at a temperature in the region of 20° C. and then in an oven under reduced pressure (10 Pa) at a temperature in the region of 40° C. 1.9 g of (3R,4R)-4-[3-(R,S)-hydroxy-3-(6-methoxyquinolin-4-yl)propyl]-1-[3-(thien-2-yl)prop-2-ynyl]piperidine-3-acetic acid were obtained in the form of a white solid.

$^1$H N.M.R. spectrum (300 MHz, d6-(CD$_3$)$_2$SO, δ in ppm). A mixture of two diastereoisomers was observed: from 1.20 to 2.45 (mts, 12H), from 2.60 to 2.85 (mt, 2H), 3.48 (mt, 2H), 3.92 (s, 3H), 5.28 (mt, 1H), 7.06 (dd, J=5.5 and 3.5 Hz, 1H), 7.27 (dd, J=3.5 and 1 Hz, 1H), from 7.30 to 7.45 (mt, 2H), from 7.50 to 7.60 (mt, 2H), 7.94 (d, J=9 Hz, 1H), 8.70 (d, J=4.5 Hz, 1H).

EXAMPLE 53A

Methyl (3R,4R)-4-[3-(R,S)-hydroxy-3-(6-methoxyquinolin-4-yl)propyl]-1-[3-(thien-2-yl)prop-2-ynyl]piperidine-3-acetate 0.317 g of sodium borohydride was added over approximately 40 minutes at a temperature of less than 30° C., with stirring and under an inert atmosphere, to a solution of 4.0 g of methyl (3R,4R)-4-[3-oxo-3-(6-methoxyquinolin-4-yl)propyl-1-[3-(thien-2-yl)prop-2-ynyl]piperidine-3-acetate in 65 cm³ of methanol to which had been added one drop of 5N aqueous sodium hydroxide solution. After stirring for 3 hours at a temperature in the region of 20° C., the mixture had 100 cm³ of water added and was then extracted with 4 times 50 cm³ of dichloromethane. The extracts were washed with 3 times 50 cm³ of water, dried over magnesium sulfate, filtered, and concentrated under reduced pressure (5 kPa) at a temperature in the region of 40° C. An oil was obtained, which product was purified by chromatography at atmospheric pressure on a column of silica gel (particle size 20–45 μm; diameter 3.2 cm; silica volume 300 cm³), elution was carried out with ethyl acetate, and approximately 100-cm³ fractions were collected. The fractions corresponding to the expected product were combined. These fractions were concentrated as above. 3.5 g of methyl (3R,4R)-4-[3-(R,S)-hydroxy-3-(6-methoxyquinolin-4-yl)propyl]-1-[3-(thien-2-yl)prop-2-ynyl]piperidine-3-acetate were obtained in the form of an oil with a yellow color.

Infrared spectrum (CCl$_4$): 2939, 1739, 1622, 1509, 1434, 1241, 850, and 696 cm$^{-1}$.

The hydrochloride was prepared in the following way: a solution of 0.5 g of methyl (3R,4R)-4-[3-(R,S)-hydroxy-3-(6-methoxyquinolin4-yl)propyl]-1-[3-(thien-2-yl)prop-2-ynyl]piperidine-3-acetate in 20 cm³ of dichloromethane was added with stirring to 30 cm³ of diethyl ether to which had been added 4 cm³ of a 1N solution of hydrochloric acid in ether. After 2 hours, the white solid formed was filtered off, washed with 2 times 5 cm³ of diethyl ether, and dried under partial pressure (5 kPa) and then, to constant weight, in an oven under reduced pressure (10 Pa) at a temperature in the region of 40° C. 0.35 g of methyl (3R,4R)-4-[3-(R,S)-hydroxy-3-(6-methoxyquinolin-4-yl)propyl]-1-[3-(thien-2-yl)prop-2-ynyl]piperidine-3-acetate dihydrochloride was obtained. in the form of a white solid.

Infrared spectrum (KBr): 3278, 2932, 2524, 1730, 1619, 1601, 1427, 1248, 1021, 849, and 714 cm$^{-1}$.

Methyl (3R,4R)-4-[3-oxo-3-(6-methoxyquinolin-4-yl)propyl]-1-[3-(thien-2-yl)prop-2-ynyl]piperidine-3-acetate 0.263 g of triphenylphosphine and then 0.85 g of tetrakis (triphenylphosphine)palladium, 0.4 g of cuprous iodide, and 1.75 cm³ of 2-iodothiophene were added with stirring, at a temperature in the region of 20° C. and under an inert atmosphere, to a solution of 4.3 g of methyl (3R,4R)-4-[3-oxo-3-(6-methoxyquinolin-4-yl)propyl]-1-[prop-2-ynyl]piperidine-3-acetate in 100 cm³ of acetonitrile. The mixture was stirred for 10 minutes and then 2.95 cm³ of triethylamine were added. After stirring for 48 hours at a temperature in the region of 20° C., the mixture was filtered through celite and the insoluble material was washed with 2 times 50 cm³ of acetonitrile. The filtrate was concentrated under reduced pressure (5 kPa) at a temperature in the region of 40° C. The evaporation residue was purified by chromatography at atmospheric pressure on a column of silica gel (particle size 20-45 μm; diameter 4.5 cm; silica volume 500 cm³), elution was carried out with pure ethyl acetate, and approximately 60-cm³ fractions were collected. The fractions corresponding to the expected product were combined. These fractions were concentrated under the above conditions. 4 g of methyl (3R,4R)-4-[3-oxo-3-(6-methoxyquinolin-4-yl)propyl]-1-[3-(thien-2-yl)prop-2-ynyl]piperidine-3-acetate were obtained in the form of an oil with a yellow color.

Infrared spectrum (CCl₄): 2935, 1740, 1692, 1431, 1242, 1032, 849, and 698 cm⁻¹.

Methyl (3R,4R)-4-[3-oxo-3-(6-methoxyquinolin-4-yl)propyl]-1-[prop-2-ynyl]piperidine-3-acetate 4.8 cm³ of triethylamine were added with stirring, at a temperature in the region of 20° C. and under an inert atmosphere, to a solution of 5 g of methyl (3R,4R)-4-[3-oxo-3-(6-methoxyquinolin-4-yl)propyl]piperidine-3-acetate in 60 cm³ of dimethylformamide. After stirring for 15 minutes at this temperature, 1.5 cm³ of propargyl bromide were added over approximately 15 minutes and then, after 15 minutes, the mixture was heated at a temperature in the region of 45° C. for 4 hours. After cooling to approximately 20° C., the reaction mixture was poured onto approximately 700 cm³ of water and then the mixture was extracted with 4 times 80 cm³ of diethyl ether. The combined extracts were washed with 3 times 80 cm³ of water, dried, filtered, and concentrated under reduced pressure (5 kPa) at a temperature in the region of 40° C. The evaporation residue was purified by chromatography at atmospheric pressure on a column of silica gel (particle size 20–45 μm; diameter 4 cm; silica volume 500 cm³), elution was carried out with pure ethyl acetate, and 60-cm³ fractions were collected. Fractions 9 to 20 were combined and then concentrated as under the above conditions. 4.3 g of methyl (3R,4R)-4-[3-oxo-3-(6-methoxyquinolin-4-yl)propyl]-1-[prop-2-ynyl]piperidine-3-acetate were obtained in the form of an oil with a yellow color.

Infrared spectrum (CCl₄): 3311, 2936, 1739, 1692, 1620, 1431, 1242, 1032, 849, 654, and 627 cm⁻¹.

Methyl (3R,4R)-4-[3-oxo-3-(6-methoxyquinolin-4-yl)propyl]piperidine-3-acetate was prepared in Example 48.

EXAMPLE 54

(3R,4R)-4-[3-Hydroxy-3-(6-methoxyquinolin-4-yl)propyl]-1-[2-(cyclopentylthio)ethyl]piperidine-3-acetic acid, diastereoisomer A, and (3R,4R)-4-[3-hydroxy-3-(6-methoxyquinolin-4-yl)propyl]-1-[2-(cyclopentyl-thio)ethyl]piperidine-3-acetic acid, diastereoisomer B, dihydrochloride By proceeding as described in Example 52, the two diastereoisomers of (3R,4R)-4-[3-(R,S)-hydroxy-3-(6-methoxyquinolin4-yl)propyl]-1-[2-(cyclopentyl-thio)ethyl]piperidine-3-acetic acid were separated. (3R,4R)-4-[3-Hydroxy-3-(6 -methoxyquinolin4-yl)propyl]-1-[2-(cyclopentylthio)ethyl]piperidine-3-acetic acid, diastereoisomer B, was thus isolated in the form of a solid with a white color, the dihydrochloride of which was prepared ($[\alpha]_D^{20}$=−89.6°+/−1.6, in methanol at 0.5%), and (3R,4R)-4-[3-hydroxy-3-(6-methoxyquinolin-4-yl)propyl]-1-[2-(cyclopentylthio)ethyl]piperidine-3-acetic acid, diastereoisomer A, was thus isolated in the form of a thick oil with a yellow color ($[\alpha]_D^{20}$=+57.4°+/−0.9, in methanol at 0.5%).

Diastereoisomer A: ¹H N.M.R. spectrum (300 MHz, d6-(CD₃)₂SO, δ in ppm): from 1.15 to 2.10. and from 2.25 to 2.60 (mts, 24H in all), 2.70 (mt, 2H), 3.11 (mt, 1H), 3.92 (s, 3H), 5.26 (dd, J=8 and 4 Hz, 1H), from 7.35 to 7.45 (mt, 2H), 7.54 (d, J=4.5 Hz, 1H), 7.94 (d, J=10 Hz, 1H), 8.71 (d, J=4.5 Hz, 1H).

Diastereoisomer B: ¹H N.M.R. spectrum (300 MHz, d6-(CD₃)₂SO, δ in ppm): from 1.30 to 2.10, from 2.15 to 2.40 and from 2.65 to 3.50 (mts, 27H in all), 4.00 and 4.01 (2s, 3H in all), 5.50 (mt, 1H), 7.54 and 7.58 (2d, J=2.5 Hz, 1H in all), 7.71 (very broad d, J=9 Hz, 1H), 7.96 (mt, 1H), 8.23 (very broad d, J=9 Hz, 1H), 9.00 (very broad d, J=4.5 Hz, 1H), from 9.70 to 9.85 and from 10.15 to 10.35 (2 unresolved peaks, 1H in all).

(3R,4R)-4-[3-(R,S)-Hydroxy-3-(6-methoxyquinolin-4-yl)propyl]-1-[2-(cyclopentylthio)ethyl]piperidine-3-acetic acid A solution of 1.6 g of methyl (3R,4R)-4-[3-(R,S)-hydroxy-3-(6-methoxyquinolin-4-yl)propyl]-1-[2-(cyclopentylthio)ethyl]piperidine-3-acetate dihydrochloride in 30 cm³ of dioxane, to which had been added 2.6 cm³ of 5N aqueous sodium hydroxide solution, was stirred for 6 hours at a temperature in the region of 65° C. After concentrating the reaction mixture under reduced pressure (5 kPa) at a temperature in the region of 40° C., a residue was obtained, which residue was taken up in 2 times 30 cm³ of chloroform and which was concentrated as under the above conditions. The residue was purified by chromatography at atmospheric pressure on a column of silica gel (particle size 20-45 μm; diameter 3 cm; silica volume 100 cm³), elution was carried out with a chloroform/methanol/28% aqueous ammonia (12/3/0.5 by volume) mixture, and 30-cm³ fractions were collected. The fractions comprising the expected product were combined and concentrated as above. 1.5 g of a colorless lacquer were obtained, which product was taken up in 20 cm³ of diethyl ether, filtered, and washed with 2 times 10 cm³ of diethyl ether. The product was dried under partial pressure (5 kPa) and then to constant weight in an oven under reduced pressure (10 Pa) at a temperature in the region of 40° C. 1.35 g of (3R,4R)-4-[3-(R,S)-hydroxy-3-(6-methoxyquinolin-4-yl)propyl]-1-[2-(cyclopentylthio)ethyl]piperidine-3-acetic acid were obtained in the form of a white solid.

¹H N.M.R. spectrum (300 MHz, d6-(CD₃)₂SO, δ in ppm). A mixture of two diastereoisomers was observed: from 1.00 to 2.20 and from 2.25 to 2.80 (mts, 25H in all), 3.10 (mt, 2H), 3.92 (broad s, 3H), 5.26 (unresolved peak, 1H), from 7.20 to 7.60 (mt, 3H), 7.93 (broad d, J=9 Hz, 1H), 8.71 (mt, 1H).

EXAMPLE 54A

Methyl (3R,4R)-4-[3-(R,S)-hydroxy-3-(6-methoxyquinolin-4-yl)propyl]-1-[2-(cyclopentylthio)ethyl]piperidine-3-acetate dihydrochloride 0.227 g of sodium borohydride was added portionwise over approximately 30 minutes at a temperature of less than 30° C., with stirring and under an inert atmosphere, to a mixture of 2.5 g of methyl (3R,4R)-4-[3-oxo-3-(6-methoxyquinolin-4-yl)propyl]-1-[2-(cyclopentylthio)ethyl]piperidine-3-acetate in 40 cm³ of methanol to which had been added one drop of 5N aqueous sodium hydroxide solution. After stirring the reaction mixture for 3 hours at a temperature in the region of 20° C., 100 cm³ of water were added and then the mixture was extracted with 4 times 50 cm³ of ethyl acetate. The combined extracts were washed with 3 times 50 cm³ of water, dried over magnesium sulfate, filtered, and concentrated under reduced pressure (5 kPa) at a temperature in the region of 40° C. The residual oil obtained was purified by chromatography at atmospheric pressure on a column of silica gel (particle size 20-45 μm; diameter 3.2 cm; silica volume 100 cm³), elution was carried out with pure ethyl acetate, and 25-cm³ fractions were collected. The fractions comprising the expected product were combined and then concentrated as above. 2.1 g of methyl (3R,4R)-4-[3-(R,S)-hydroxy-3-(6-methoxyquinolin4-yl)propyl]-1-[2-(cyclopentylthio)ethyl]piperidine-3-acetate were obtained in the form of an oil with a pale yellow color. The hydrochloride was prepared in the following way: a solution of 0.5 g of the oil obtained above, dissolved in 15 cm³ of dichloromethane, was poured with stirring into 4 cm³ of a 1N solution of hydrochloric acid in diethyl ether. A product precipitated and then crystallized by addition of 25 cm³ of diethyl ether. The solid was filtered off, washed with 2 times 10 cm³ of ether, and dried under vacuum over potassium hydroxide (5 kPa) and then, to constant weight, in an oven under reduced pressure (10 Pa) at a temperature in the region of 40° C. 0.35 g of methyl (3R,4R)-4-[3-(R,S)-hydroxy-3-(6-methoxyquinolin-4-yl)propyl]-1-[2-(cyclopentylthio)ethyl]piperidine-3-acetate dihydrochloride was obtained in the form of a solid with an off-white color.

Infrared spectrum (KBr): 3355, 2950, 2560, 2051, 1982, 1731, 1619, 1601, 1428, 1248, 1206, 1020, 849, and 714 cm$^{-1}$.

Methyl (3R,4R)-4-[3-oxo-3-(6-methoxyquinolin-4-yl)propyl]-1-[2-(cyclopentylthio)ethyl]piperidine-3-acetate A mixture of 4.9 g of methyl (3R,4R)-4-[3-oxo-3-(6-methoxyquinolin-4-yl)propyl]piperidine-3-acetate, 2.9 g of 2-chloroethyl cyclopentyl sulfide, 9 g of potassium carbonate, and 2.7 g of potassium iodide in 130 cm³ of acetonitrile was stirred for 17 hours at a temperature in the region of 65° C. After cooling to a temperature in the region of 20° C., the reaction mixture has 150 cm³ of water added and was extracted with 3 times 60 cm³ of ethyl acetate. The organic extracts were combined, washed with 2 times 50 cm³, dried over magnesium sulfate, filtered, and concentrated under reduced pressure (5 kPa) at a temperature in the region of 40° C. An oil was obtained, which product was purified by chromatography at atmospheric pressure on a column of silica gel (particle size 20–45 μm; diameter 4 cm; silica volume 300 cm³), elution was carried out with pure ethyl acetate, and approximately 70-cm³ fractions were collected. The fractions comprising the expected product were combined and then concentrated under the above conditions. 2.6 g of methyl (3R,4R)-4-(3-oxo-3-(6-methoxyquinolin-4-yl)propyl]-1-[2-(cyclopentylthio)ethyl]piperidine-3-acetate were obtained in the form of an oil with a yellow color.

Infrared spectrum (CCl$_4$): 2952, 2802, 1738, 1692, 1620, 1504, 1242, 1165, 1032, and 850 cm$^{-1}$.

Methyl (3R,4R)-4-[3-oxo-3-(6-methoxyquinolin-4-yl)propyl]piperidine-3-acetate was obtained in Example 48.

2-Chloroethyl cyclopentyl sulfide was prepared by application of the method disclosed in Patent Application FR 2,395,260, the disclosure of which is specifically incorporated by reference herein.

EXAMPLE 55

(3R,4R)-4-[3-(R,S)-Hydroxy-3-(6-methoxyquinolin-4-yl)propyl]-1-[3-(2,6-difluorophenyl)prop-2-ynyl]piperidine-3-carboxylic acid A solution of 0.531 g of methyl (3R,4R)-4-[3-(R,S)-hydroxy-3-(6-methoxyquinolin-4-yl)propyl]-1-[3-(2,6-difluorophenyl)prop-2-ynyl]piperidine-3-carboxylate in 5.3 cm³ of dioxane to which had been added 0.84 cm³ of 5N aqueous sodium hydroxide solution was stirred for 15 hours at a temperature in the region of 60° C. After cooling to a temperature in the region of 20° C., the reaction mixture was concentrated under reduced pressure (5 kPa) at a temperature in the region of 40° C. The residue obtained was purified by chromatography under a nitrogen pressure of 50 kPa on a column of silica gel (particle size 20–45 μm; diameter 3 cm; 20 g), elution was carried out with a dichloromethane/methanol (90/10 by volume) mixture, and first a fraction of 100 cm³ was collected, followed by 25-cm³ fractions. Fractions 1 to 12 were combined and then concentrated as above. A foam was obtained, which product was taken up with stirring in 15 cm³ of diisopropyl ether for 15 minutes. After adding 15 cm³ of pentane and stirring for an additional 10 minutes, the crystallized product formed was filtered off, washed with 2 times 10 cm³ of a diisopropyl ether/pentane (50/50 by volume) mixture, and then 3 times 20 cm³ of pentane, and dried in the air. 0.293 g of (3R,4R)-4-[3-(R,S)-hydroxy-3-(6-methoxyquinolin-4-yl)propyl]-1-[3-(2,6-difluorophenyl)prop-2-ynyl]piperidine-3-carboxylic acid was obtained in the form of a solid with a cream color melting at 107° C.

$^1$H N.M.R. spectrum (300 MHz, d6-(CD$_3$)$_2$SO, δ in ppm). A mixture of two diastereoisomers was observed: from 1.40 to 1.95 and from 2.30 to 3.00 (mts, 12H in all), 3.67 and 3.68 (2s, 2H in all), 3.88 and 3.92 (2s, 3H in all), 5.24 (mt, 1H), 5.55 (unresolved peak, 1H), 7.22 (mt, 2H), from 7.30 to 7.60 (mt, 4H), 7.39 (d, J=9 Hz, 1H), 8.70 (mt, 1H), from 12.20 to 12.80 (broad unresolved peak, 1H).

Methyl (3R,4R)-4-[3-(R,S)-hydroxy-3-(6-methoxyquinolin-4-yl)propyl]-1-[3-(2,6-difluorophenyl)prop-2-ynyl]piperidine-3-carboxylate A mixture of 1.07 g of methyl (3R,4R)-4-[3-(R,S)-hydroxy-3-(6-methoxyquinolin-4-yl)propyl]-1-(prop-2-ynyl)piperidine-3-carboxylate in 10 cm³ of triethylamine was stirred for 5 minutes under an inert atmosphere at a temperature in the region of 20° C. 0.156 g of tetrakis(triphenylphosphine)palladium, 0.051 gof cuprous iodide, and 0.78 g of 1-bromo-2,6-difluorobenzene were added. The mixture was stirred for 3 hours 30 minutes at a temperature in the region of 80° C. After cooling to approximately 20° C., the reaction mixture had 30 cm³ of ethyl acetate and 30 cm³ of water added. After stirring for 10 minutes, the mixture was separated by settling. After separating off the organic phase, the aqueous layer was extracted with 2 times 30 cm³ of ethyl acetate. The organic extracts were combined, washed with 3 times 30 cm³ of water, dried over sodium sulfate, filtered, and concentrated under reduced pressure (5 kPa) at a temperature in the region of 40° C. The residue obtained was purified by chromatography under a nitrogen pressure of 50 kPa on a column of silica gel (particle size 20–45 μm; diameter 3 cm; 50 g), elution was carried out with pure ethyl acetate, and first a fraction of 300 cm³ were collected, followed by 38-cm³ fractions. Fractions 6 to 16 were combined and concentrated as above. 0.55 g of methyl (3R,4R)-4-[3-(R,S)-hydroxy-3-(6-methoxyquinolin-4-yl)propyl]-1-[3-(2,6-difluorophenyl)prop-2-ynyl]piperidine-3-carboxylate was obtained in the form of a foam with a pale yellow color.

Infrared spectrum (CCl₄): 3615, 2950, 1738, 1622, 1470, 1241, 1007, 854, and 719 cm⁻¹.

Methyl (3R,4R)-4-[3-(R,S)-hydroxy-3-(6-methoxyquinolin-4-yl)propyl]-1-(prop-2-ynyl)piperidine-3-carboxylate was prepared as described in Example 32.

EXAMPLE 56

(3R,4R)-4-[3-(6-Methoxyquinolin-4-yl)propyl]-1-[3-(3,5-difluorophenyl)prop-2-ynyl]piperidine-3-acetic acid 0.83 cm³ of 5N aqueous sodium hydroxide solution was introduced with stirring, at a temperature in the region of 20° C., into a solution of 0.525 g of methyl (3R,4R)-4-[3-(6-methoxyquinolin-4-yl)propyl]-1-[3-(3,5-difluorophenyl)prop-2-ynyl]piperidine-3-acetate in 5 cm³ of dioxane and then the mixture was heated for 3 hours at a temperature in the region of 60° C. After cooling to approximately 20° C., the mixture was stirred for 3 days and then concentrated under reduced pressure (5 kPa) at a temperature in the region of 40° C. The residue obtained was taken up in 15 cm³ of water and then the solution was extracted with 5 cm³ of ethyl acetate. The aqueous phase was brought to a pH in the region of 5–6 by addition of 4.1 cm³ of 1N aqueous hydrochloric acid and then extracted, first with 30 cm³ of dichloromethane and then with 10 cm³ of the same solvent. The organic extracts were combined, washed with 2 times 5 cm³ of water, dried over magnesium sulfate, filtered, and concentrated under reduced pressure (5 kPa) at a temperature in the region of 40° C. The residue obtained was taken up in diethyl ether and then concentrated under the same conditions as above until a constant weight was obtained. 0.45 g of (3R,4R)-4-[3-(6-methoxyquinolin-4-yl)propyl]-1-[3-(3,5-difluorophenyl)prop-2-ynyl]piperidine-3-acetic acid was obtained in the form of a solid with a light beige color.

¹H N.M.R. spectrum (300 MHz, d6-(CD₃)₂SO, δ in ppm): from 1.20 to 1.80 (mt, 7H), from 2.10 to 2.35 (mt, 4H), 2.43 (dd, J=16.5 and 10.5 Hz, 1H), 2.75 (mt, 2H), 3.05 (mt, 2H), 3.47 (s, 2H), 3.93 (s, 3H), 7.18 (mt, 2H), from 7.25 to 7.35 (mt, 1H), 7.33 (d, J=4 Hz, 1H), from 7.35 to 7.45 (mt, 2H), 7.92 (d, J=9 Hz, 1H), 8.62 (d, J=4 Hz, 1H).

Methyl (3R,4R)-4-[3-(6-methoxyquinolin-4-yl)propyl]-1-[3-(3,5-difluorophenyl)prop-2-ynyl)piperidine-3-acetate 0.35 cm³ of 1-bromo-3,5-difluorobenzene and then 0.112 g of tetrakis(triphenylphosphine)palladium and 0.037 g of cuprous iodide were added at a temperature in the region of 20° C., under an inert atmosphere, to a stirred mixture of 0.77 g of methyl (3R,4R)-4-[3-(6-methoxyquinolin-4-yl)propyl]-1-(prop-2-ynyl)piperidine-3-acetate in 7.7 cm³ of triethylamine. The suspension obtained was heated at a temperature in the region of 80° C. for 3 hours and then concentrated under reduced pressure (5 kPa) at a temperature in the region of 40° C. The residue obtained was taken up in 50 cm³ of ethyl acetate in 20 cm³ of water. After stirring the mixture for 15 minutes, the remaining insoluble material was filtered through clarcel and then the filtrate was separated by settling: the organic phase was separated off, then washed with 3 times 3 cm³ of water and a saturated aqueous sodium chloride solution, dried over magnesium sulfate, filtered, and concentrated under reduced pressure (5 kPa) at a temperature in the region of 40° C. The oily residue obtained was purified by. chromatography under a nitrogen pressure of 50 kPa on a column of silica gel (particle size 40–63μ; diameter 3 cm; 45 g), elution was carried out with a dichloromethane/methanol (97/3 by volume) mixture. The fractions comprising the expected product were collected. These fractions were concentrated under reduced pressure (5 kPa) at a temperature in the region of 40° C. 0.345 g of methyl (3R,4R)-4 -[3-(6-methoxyquinolin-4-yl)propyl]-1-[3-(3,5-difluorophenyl)prop-2-ynyl]piperidine-3-acetate was obtained in the form of an oil with a pale yellow color. Mass spectrum (EI): m/z=506 M⁺.

Methyl (3R,4R)-4-[3-(6-methoxyquinolin-4-yl)propyl]-1-(prop-2-ynyl)piperidine-3-acetate was prepared according to the procedure described in Example 39.

EXAMPLE 57

(3R,4R)-1-[2-(3,5-Difluorophenylthio)ethyl]-4-[3-(R,S)-hydroxy-3-(6-methoxyquinolin-4-yl)propyl] piperidine-3-carboxylic acid dihydrochloride 1.6 cm³ of 5N aqueous sodium hydroxide solution were added at a temperature in the region of 20° C., with stirring and under an inert atmosphere, to a solution of 0.42 g of methyl (3R,4R)-1-[2-(3,5-difluorophenylthio)ethyl]-4-[3-(R,S)-hydroxy-3-(6-methoxyquinolin-4-yl)propyl] piperidine-3-carboxylate in 5.5 cm³ of methanol. The mixture was heated for 16 hours at a temperature in the region of 60° C. The solution obtained was evaporated under reduced pressure (5 kPa) at a temperature in the region of 40° C. and then 5 cm³ of distilled water and 2.66 cm³ of 6N aqueous hydrochloric acid were added to the residue obtained. The mixture was then heated in the region of 60° C. until a homogeneous solution was obtained, which solution was subsequently evaporated under the above conditions. The residue obtained was triturated in 10 cm³ of a dichloromethane/methanol (90/10 by volume) mixture and then the resulting insoluble material was filtered off and washed with 2 times 2.5 cm³ of the same mixture. The filtrate was concentrated under the same conditions as above. 0.465 g of (3R,4R)-1-[2-(3,5-difluorophenylthio) ethyl]-4-[3-(R,S)-hydroxy-3-(6-methoxyquinolin-4-yl) propyl]piperidine-3-carboxylic acid dihydrochloride was obtained in the form of a foam with a yellow color melting at 160° C. while decomposing.

¹H N.M.R. spectrum (300 MHz, d6-(CD₃)₂SO, δ in ppm). A mixture of two diastereoisomers was observed: from 1.35 to 2.35 and from 2.60 to 4.00 (mts, 16H in all), 4.01 and 4.02 (2s, 3H in all), from 5.45 to 5.65 (mt, 1H), 7.10 (mt, 1H), 7.21 (mt, 2H), from 7.50 to 7.70 (mt, 1H), 7.76 (mt, 1H), 8.00 (mt, 1H), 8.33 (mt, 1H), 9.04 (d, J=5.5 Hz, 1H), from 11.10 to 11.55 (2 unresolved peaks, 1H in all).

Methyl (3R,4R)-1-[2-(3,5-difluorophenylthio)ethyl]-4-[3-(R,S)-hydroxy-3-(6-methoxyquinolin-4-yl) propyl]piperidine-3-carboxylate 0.332 g of potassium carbonate, then 0.4 g of potassium iodide and, finally, 0.675 g of 1-[(2-bromoethyl)thio]-3,5-difluorobenzene, dissolved beforehand in 5 cm³ of acetonitrile, were added at a temperature in the region of 20° C., with stirring and under an inert atmosphere, to a solution of 0.717 g of methyl (3R,4R)-4-[3-(R,S)-hydroxy-3-(6- methoxyquinolin-4-yl)propyl]piperidine-3-carboxylate in 15 cm³ of acetonitrile and 1 cm³ of methanol. The mixture was heated for 3 hours at a temperature in the region of 80° C. After cooling to a temperature in the region of 20° C., the reaction mixture was filtered and the cake was washed with 2 times 5 cm³ of acetonitrile. The filtrate was evaporated under reduced pressure (5 kPa) at a temperature in the region of 40° C. The residue obtained was purified by chromatography under a nitrogen pressure of 50 kPa on a column of silica gel (particle size 40–63 μm; diameter 3.5 cm; height 35 cm), elution was carried out with a dichloromethane/methanol (95/5 by volume) mixture, and 35-cm³ fractions were collected. Fractions 18 to 21 were combined and then evaporated as above. 0.47 g of methyl (3R,4R)-1-[2-(3,5-difluorophenylthio)ethyl]-4-[3-(R,S)-hydroxy-3-(6-methoxyquinolin-4-yl)propyl]piperidine-3-carboxylate was obtained in the form of a viscous oil with an orange-yellow color.

Infrared spectrum (CH₂Cl₂): 3597, 2951, 2814, 1733, 1611, 1586, 1242, 1119, 985, 877, 840, and 667 cm⁻¹.

1-[(2-Bromoethyl)thio]-3,5-difluorobenzene

A solution of 2.59 g of sodium hydroxide pellets in 27 cm³ of distilled water and then 0.27 cm³ of aliquat 336 (tricaprylylmethylammonium chloride) were added, with stirring and under an inert atmosphere, to a mixture, maintained at a temperature in the region of 23° C., of 7.5 g of 3,5-difluorothiophenol in 9.01 cm³ of 1,2-dibromoethane. After stirring for 15 minutes at a temperature in the region of 20° C., 50 cm³ of dichloromethane were added to the mixture and then, after a few minutes, the organic phase was separated by settling, washed with 25 cm³ of water and 25 cm³ of a saturated 10% sodium chloride solution, dried over magnesium sulfate, filtered, and evaporated under reduced pressure (5 kPa) at a temperature in the region of 40° C. The evaporation residue was purified by chromatography under a nitrogen pressure of 50 kPa on a column of silica gel (particle size 40–63 μm; diameter 5 cm; height 30 cm), elution was carried out with cyclohexane, and first a fraction of 500 cm³ was collected, followed by 50-cm³ fractions. Fractions 9 to 26 were combined and then concentrated under reduced pressure (5 kPa) at a temperature in the region of 40° C. 5.9 g of 1-[(2-bromoethyl)thio]-3,5-difluorobenzene were obtained in the form of a colorless liquid. Infrared spectrum (CCl₄): 3094, 1607, 1587, 1429, 1192, 1122, 988, 876, 841, and 667 cm⁻¹.

3,5-Difluorothiophenol was prepared according to Dae-Kee Kim, Jongsik Gam et al., J. Med. Chem., 1997, p. 2371, the disclosure of which is specifically incorporated by reference herein.

EXAMPLE 58

(3R,4R)-4-[3-(R,S)-Hydroxy-3-(6-methoxyquinolin-4-yl)propyl]-1-[3-(2,3-difluorophenyl)prop-2-ynyl]piperidine-3-carboxylic acid A mixture of 0.810 g of methyl (3R,4R)-4-[3-(R,S)-hydroxy-3-(6-methoxyquinolin-4-yl)propyl]-1-[3-(2,3-difluorophenyl)prop-2-ynyl]piperidine-3-carboxylate in 8 cm³ of dioxane to which had been added 1.3 cm³ of 5N aqueous sodium hydroxide solution was stirred for 17 hours at a temperature in the region of 60° C. After cooling to approximately 20° C., the reaction mixture was evaporated under reduced pressure (5 kPa) at a temperature in the region of 50° C. The residue obtained was purified by chromatography under a nitrogen pressure of 50 kPa on a column of silica gel (particle size 20–45 μm; diameter 3 cm; mass 45 g), elution was carried out with a dichloromethane/methanol (92/8 by volume) mixture. A fraction of 275 cm³ was first collected, followed by 20-cm³ fractions. Fractions 12 to 46 were collected. These fractions were combined and concentrated under reduced pressure (5 kPa) at a temperature in the region of 35° C. The residue obtained was taken up in dichloromethane and filtered. The filtrate was evaporated as above and then the new residue obtained was triturated in 10 cm³ of diisopropyl ether. The mixture was stirred for 1 hour at a temperature in the region of 20° C. and then left for 16 hours. The solid precipitate was separated by filtration and washed with 2 times 10 cm³ of the same solvent and then with 2 times 10 cm³ of pentane. 0.47 g of (3R,4R)-4-[3-(R,S)-hydroxy-3-(6-methoxyquinolin-4-yl)propyl]-1-[3-(2,3-difluorophenyl)prop-2-ynyl]piperidine-3-carboxylic acid was obtained in the form of a solid with a white color melting at 92° C.

¹H N.M.R. spectrum (300 MHz, d6-(CD₃)₂SO, δ in ppm): a mixture of diastereoisomers was observed: from 1.40 to 1.95 and from 2.30 to 3.00 (2 series of mts, 12H in all), 3.64 and 3.65 (2s, 2H in all), 3.90 and 3.92 (2s, 3H in all), 5.25 (mt, 1H), 5.52 (unresolved peak, 1H), and 7.15 to 7.30 (mt, 1H), and 7.30 to 7.60 (mt, 5H), 7.93 (d, J=10 Hz, 1H), 8.70 (d, J=4.5 Hz, 1H), from 11.90 to 12.80 (very broad unresolved peak, 1H).

Methyl (3R,4R)-4-[3-(R,S)-hydroxy-3-(6-methoxyquinolin-4-yl)propyl]-1-[3-(2,3-difluorophenyl)prop-2-ynyl]piperidine-3-carboxylate 0.16 g of tetrakis(triphenylphosphine)palladium, 0.053 g of cuprous iodide, and 0.47 cm³ of 1-bromo-2,3-difluorobenzene were added to a mixture, stirred at a temperature in the region of 20° C. under an inert atmosphere, of 1.1 g of methyl (3R,4R)-4-[3-(R,S)-hydroxy-3-(6-methoxyquinolin-4-yl)propyl]-1-(prop-2-ynyl)piperidine-3-carboxylate in 11 cm³ of triethylamine. The mixture was heated at a temperature in the region of 80° C. for 3 hours 30 minutes. After cooling to approximately 20° C., the reaction mixture was taken up in 30 cm³ of ethyl acetate and 30 cm³ of water and stirred for 15 minutes. The organic phase was separated by settling, while the aqueous layer was extracted with 3 times 30 cm³ of ethyl acetate. The organic extracts were combined, washed with 3 times 30 cm³ of water, dried over sodium sulfate, filtered, and concentrated under reduced pressure (5 kPa) at a temperature in the region of 40° C. The residue obtained was purified by chromatography under a nitrogen pressure of 50 kPa on a column of silica gel (particle size 20–45 μm; diameter 3 cm; 50 g), elution was carried out with pure ethyl acetate. 1 fraction of 300 cm³ was first collected and then 30-cm³ fractions were obtained. Fractions 10 to 30 were combined and evaporated under the above conditions. 0.94 g of methyl (3R,4R)A-[3-(R,S)-hydroxy-3-(6-methoxyquinolin-4-yl)propyl]-1-[3-(2,3-difluorophenyl)prop-2-ynyl]piperidine-3-carboxylate was obtained in the form of a foam with an orange color.

Infrared spectrum (CH₂Cl₂): 3598, 2951, 1733, 1622, 1489, 1475, 1243, 1227, 1031, 856. and 831 cm⁻¹.

Methyl (3R,4R)-4-[3-(R,S)-hydroxy-3-(6-methoxyquinolin-4-yl)propyl]-1-(prop-2-ynyl)piperidine-3-carboxylate was prepared as described in Example 32.

EXAMPLE 59

(3R,4R)-4-[3-(R,S)-Hydroxy-3-(6-methoxyquinolin-4-yl)propyl]-1-[3-(2,3,5-trifluorophenyl)prop-2-ynyl]piperidine-3-carboxylic acid A solution of 1.7 g of methyl (³R,⁴R)-4-[3-(R,S)-hydroxy-3-(6-methoxyquinolin-4yl)propyl]-1-[3-(2,3,5- trifluorophenyl)prop-2-ynyl]piperidine-3-carboxylate in 17 cm³ of dioxane to which had been added 2.58 cm³ of 5N aqueous sodium hydroxide solution was stirred for 15 hours at a temperature in the region of 60° C. After cooling to a temperature in the region of 20° C., the reaction mixture was concentrated under reduced pressure (5 kPa) at a temperature in the region of 40° C. The residue obtained was purified by chromatography under a nitrogen pressure of 50 kPa on a column of silica gel (particle size 20–45 μm; diameter 3 cm; 50 g), elution was carried out with a dichloromethane/methanol (90/10 by volume) mixture, and first a fraction of 200 cm³ was collected, followed by 23-cm³ fractions. Fractions 3 to 21 were combined and then concentrated as above. A foam was obtained, which product was subjected to a second purification by chromatography under a nitrogen pressure of 50 kPa on a column of silica gel (particle size 20–45 μm; diameter 3 cm; 70 g), elution was carried out with a dichloromethane/methanol (95/5 by volume) mixture, and first a fraction of 250 cm³ was collected, then a fraction of 100 cm³ was collected, followed by 20-cm³ fractions. Fractions 1 to 17 were combined and then concentrated as above. A foam was obtained, which product was taken up in dichloromethane and then in 20 cm³ of a 50/50 mixture of diisopropyl ether and pentane. The crystallized product formed was filtered off, washed with 2 times 10 cm³ of a diisopropyl ether/pentane (50/50 by volume) mixture and then 2 times 10 cm³ of pentane, and dried in the air. 0.524 g of (3R,4R)-4-[3-(R,S)-hydroxy-3-(6-methoxyquinolin-4-yl)propyl]-1-[3-(2,3,5-trifluorophenyl)prop-2-ynyl] piperidine-3-carboxylic acid was obtained in the form of a solid with a cream color melting at approximately 97° C.

¹H N.M.R. spectrum (300 MHz, d6-(CD₃)₂SO, δ in ppm): a mixture of diastereoisomers in the proportions 50/50 was observed: from 1.40 to 2.00 (mt, 7H), from 2.35 to 3.00 (mt, 5H), 3.65 and 3.66 (2s, 2H in all), 3.90 and 3.92 (2s, 3H in all), 5.24 (mt, 1H), 5.54 (unresolved peak, 1H), from 7.25 to 7.45 (mt, 3H), from 7.50 to 7.70 (mt, 2H), 7.94 (d, J=9.5 Hz, 1H), 8.71 (d, J 4.5 Hz, 1H).

Methyl (3R,4R)-4-[3-(R,S)-hydroxy-3-(6-methoxyquinolin-4-yl)propyl]-1-[3-(2,3,5-trifluorophenyl)prop-2-ynyl]piperidine-3-carboxylate A mixture of 1.95 g of methyl (3R,4R)-4-[3-(R,S)-hydroxy-3-(6-methoxyquinolin-4-yl)propyl]-1-(prop-2-ynyl)piperidine-3-carboxylate in 20 cm³ of triethylamine was stirred for 5 minutes under an inert atmosphere at a temperature in the region of 20° C. 0.284 g of tetrakis (triphenylphosphine)palladium, 0.094 9 of cuprous iodide, and 1.56 g of 1-bromo-2,3,5-trifluorobenzene were added. The mixture was stirred for 2 hours 30 minutes at a temperature in the region of 80° C. After cooling to approximately 20° C., the reaction mixture had 60 cm³ of ethyl acetate and 60 cm³ of water added. After stirring for 30 minutes, the mixture was separated by settling. After separating off the organic phase, the aqueous layer was extracted with 3 times 30 cm³ of ethyl acetate. The organic extracts were combined, washed with 3 times 30 cm³ of water, dried over sodium sulfate, filtered, and concentrated under reduced pressure (5 kPa) at a temperature in the region of 40° C. The residue obtained was purified by chromatography under a nitrogen pressure of 50 kPa on a column of silica gel (particle size 20–45 μm, diameter 4 cm; 80 g), elution was carried out with pure ethyl acetate, and first a fraction of 100 cm³ was collected, followed by 20-cm³ fractions. Fractions 23 to 27 were combined and concentrated as above. 1.3 g of methyl (3R,4R)-4-[3-(R,S)-hydroxy-3-(6-methoxyquinolin-4-yl)propyl]-1-[3-(2,3,5-trifluorophenyl)prop-2-ynyl] piperidine-3-carboxylate were obtained in the form of a foam.

Infrared spectrum in CCl₄: 2950, 1740, 1624, 1496, 1231, 1133, 861, and 845 cm⁻¹.

Methyl (3R,4R)-4-[3-(R,S)-hydroxy-3-(6-methoxyquinolin-4-yl)propyl]-1-(prop-2-ynyl)piperidine-3-carboxylate was prepared as described in Example 32.

EXAMPLE 60

(3R,4R)-4-[3-(R,S)-Fluoro-3-(6-methoxyquinolin-4-yl)propyl]-1-[2-(2-thienylthio)ethyl]piperidine-3-acetic acid A mixture of 1.28 g of methyl (3R,4R)-4-[3-(R,S)-fluoro-3-(6-methoxyquinolin-4-yl)propyl]-1-[2-(2-thienylthio) ethyl]piperidine-3-acetate in 25 cm³ of dioxane to which had been added 2 cm³ of 5N aqueous sodium hydroxide solution was stirred for 18 hours at a temperature in the region of 60° C. After evaporating under reduced pressure (5 kPa) at a temperature in the region of 50° C., the residue was taken up in 50 cm³ of acetone. The acetone was evaporated under reduced pressure (5 kPa) at a temperature in the region of 50° C. The residue was taken up in 75 cm³ of water and 100 cm³ of dichloromethane. The organic phase was separated off. The aqueous phase was extracted twice with 100 cm³ of dichloromethane and then the organic extracts were combined, dried over sodium sulfate, filtered, and evaporated under reduced pressure (5 kPa) at a temperature in the region of 40° C. The solid obtained was taken up in 50 cm³ of diethyl ether and the suspension obtained was stirred for 48 hours at a temperature in the region of 20° C. The solid was filtered off, rinsed with a total of 75 cm³ of diethyl ether, and then dried under reduced pressure (5 kPa) at a temperature in the region of 40° C. 1 g of solid was obtained, which product was purified by chromatography under a nitrogen pressure of 100 kPa on a column of silica gel (particle size 60–200 μm; diameter 2 cm; silica height 15 cm), elution was carried out with a chloroform/methanol/aqueous ammonia (24/6/1 by volume) mixture, and 20-cm³ fractions were collected. The fractions comprising the product were combined and evaporated under reduced pressure (5 kPa) at a temperature in the region of 40° C. 0.97 g of (3R,4R)-4-[3-(R,S)-fluoro-3-(6-methoxyquinolin-4-yl)propyl]-1-[2-(2-thienylthio)ethyl]piperidine-3-acetic acid was obtained in the form of a white foam which was a mixture of two diastereoisomers.

¹H N.M.R. spectrum (400 MHz, d6-(CD₃)₂SO with addition of a few drops of d4-CD₃COOD, δ in ppm). A mixture of two diastereoisomers in the proportions 50/50 was observed: from 1.15 to 1.65 (mt, 5H), 1.90 to 2.60 (mt, 7H), 2.61 (mt, 2H), 2.78 (mt, 2H), 2.93 (broad t, J=7 Hz, 2H), 3.92 and 3.93 (2s, 3H in all), 6.36 (mt, J$_{HF}$=1H), 7.04 (dd, J=5.5 and 3.5 Hz, 1H), 7.18 (dd, J=3.5 and 1 Hz, 1H), 7.29 (mt, 1H), 7.44 (mt, 1H), 7.49 (broad d, J=4.5 Hz, 1H), 7.59 (dd, J=5.5 and 1 Hz, 1H), 7.98 (broad d, J=9 Hz, 1H), 8.77 (d, J=4.5 Hz, 1H).

Methyl (3R,4R)-4-[3-(R,S)-fluoro-3-(6-methoxyquinolin-4-yl)propyl]-1-[2-(2-thienylthio) ethyl]piperidine-3-acetate 0.62 cm³ of diethylaminosulfur trifluoride was added over approximately 15 minutes, under an inert atmosphere and at a temperature in the region of 20° C., to a stirred solution of 1.96 g of methyl (3R,4R)-4-[3-(R,S)-hydroxy-3-(6-methoxyquinolin-4 -yl)propyl]-1-[2-(2-thienylthio)ethyl] piperidine-3-acetate in 15 cm³ of dichloromethane. Stirring was maintained for 18 hours. After adding 30 cm³ of a saturated aqueous sodium hydrogen carbonate solution, the organic phase was separated by settling. The aqueous phase was extracted with 2 times 50 cm³ of dichloromethane and then the organic extracts were combined, washed with 2 times 50 cm³ of distilled water, dried over sodium sulfate, filtered, and evaporated under reduced pressure (5 kPa) at a temperature in the region of 40° C. 1.95 g of a yellow oil were obtained, which product was purified by chromatography under a nitrogen pressure of 100 kPa on a column of silica gel (particle size 20–45 µm; diameter 3 cm; silica height 40 cm), elution was carried out with a cyclohexane/ethyl acetate (3/2 by volume) mixture, and 80-cm³ fractions were collected. Fractions 32 to 64 were combined and were evaporated under reduced pressure (5 kPa) at a temperature in the region of 40° C. 1.28 g of methyl (3R,4R)-4-[3-(R,S)-fluoro-3-(6-methoxyquinolin-4-yl)propyl]-1-[2-(2-thienylthio)ethyl]piperidine-3-acetate were obtained in the form of a colorless oil.

¹H N.M.R. spectrum (300 MHz, d6-(CD₃)₂SO, δ in ppm). A mixture of two diastereoisomers in the proportions of 60/40 was observed: from 1.10 to 1.60 (mt, 5H), 1.85 to 2.15 (mt, 6H), from 2.20 to 2.80 (mt, 5H), 2.88 (broad t, J=7 Hz, 2H), 3.53 and 3.55 (2s, 3H in all), 3.93 and 3.94 (2s, 3H in all), 6.40 (mt, $J_{HF}$=48 Hz, 1H), 7.03 (dd, J=5.5 and 3.5 Hz, 1H), 7.15 (broad d, J=3.5 Hz, 1H), 7.30 (broad d, J=1.5 Hz, 1H), 7.46 (dd, J=9 and 1.5 Hz, 1H), 7.49 (broad d, J=4.5 Hz, 1H), 7.60 (dd, J=5.50 and 1 Hz, 1H), 7.99 (broad d, J=9 Hz, 1H), 8.79 (d, J=4.5 Hz, 1H).

Methyl (3R,4R)-4-[3-(R,S)-hydroxy-3-(6-methoxyquinolin-4-yl)propyl]-1-[2-(2-thienylthio)ethyl]piperidine-3-acetate was prepared as described in Example 48.

EXAMPLE 61

(3R,4R)-4-[3-Fluoro-3-(6-methoxyquinolin-4-yl)propyl]-1-[2-(2-thienylthio)ethyl]piperidine-3-acetic acid, diastereoisomer A 0.5 g of methyl (3R,4R)-4-[3[fluoro-3-(6-methoxyquinolin-4-yl)propyl]-1-[2-(2-thienylthio)ethyl]piperidine-3-acetate, diastereoisomer A ($[\alpha]_D^{20}$=−48±3 in methanol) in 10 cm³ of dioxane, to which 0.77 cm³ of 5N aqueous soda had been added, was agitated for 18 h at a temperature of about 60° C. After evaporating under reduced pressure (5 kPa) at a temperature of about 50° C., 0.6 g of solid was obtained which was purified by chromatography under a pressure of 100 kPa of nitrogen on a silica gel column (particle size 20–45µ, diameter 2 cm, silica height 30 cm), eluted with a mixture of chloroform-methanol-ammonia (24/6/1 by volume), and collected fractions of 20 cm³. The fractions containing the product were combined and evaporated under reduced pressure (5 kPa) at a temperature of about 40° C. 0.27 g of (3R,4R)-4-[3-fluoro-3-(6-methoxyquinolin-4-yl)propyl]-1-[2-(2-thienylthio)ethyl]piperidine-3-acetic acid, diastereoisomer A, in the form of a white meringue-like foam ($[\alpha]_D^{20}$=−66±1.2 in methanol).

¹H N.M.R. spectrum (300 MHz, d6-(CD₃)₂SO, δ in ppm): from 1.20 to 1.55 (mt, 5H), from 1.85 to 2.20, and from 2.35 to 2.60 (2 series of mts: 9H total), 2.68 (mt, 2H), 2.89 (broad t, J=7 Hz, 2H), 3.94 (s, 3H), 6.38 (mt, $J_{HF}$=48 Hz, 1H), 7.05 (dd, J=5.5 and 3.5 Hz, 1H), 7.17 (dd, J=3.5 and 1 Hz, 1H), 7.32 (d, J=2.5 Hz, 1H), 7.45 (dd, J=9 and 2.5 Hz, 1H), 7.51 (d, J=4.5 Hz, 1H), 7.60 (dd, J=5.5 and 1 Hz, 1H), 7.99 (d,J=9 Hz, 1H), 8.78 (d, J=4.5 Hz, 1H).

Methyl (3R,4R)-4-[3-fluoro-3-(6-methoxyquinolin-4-yl)propyl]-1-[2-(2-thienylthio)-ethyl]piperidine-3-acetate, diastereoisomer A Methyl (3R,4R)-4-[3-fluoro-3-(6-methoxyquinolin-4-yl)propyl]-1-[2-(2-thienylthio)-ethyl]piperidine-3-acetate, diastereoisomer B 3.2 g of methyl (3R,4R)-4-[3-(R,S)-fluoro-3-(6-methoxyquinolin-4-yl)propyl]-1-[2-(2-thienylthio)ethyl] piperidine-3-acetate were chromatographed on a column 30 cm long and 8 cm in diameter, treated with 1200 g of Chiralcel OD silica (particle size 20µ) The elution was carried out with a mixture of heptane-isopropanol (90/10 by volume). The flow rate was 140 cm³/min. Detection was done by ultraviolet at 265 nm. After several preparatory injections, fractions were collected that corresponded to diastereoisomers A and B. The fractions containing the diastereoisomer A were concentrated under reduced pressure (5 kPa) at a temperature of about 40° C. 1.6 g of methyl (3R,4R)-4-[3-fluoro-3-(6-methoxyquinolin-4-yl)propyl]-1-[2-(2-thienylthio)ethyl]-piperidine-3-acetate diastereoisomer A, were obtained in the form of a thick oil ($[\alpha]_D^{20}$=−48±3 in methanol at 0.1%). The fractions containing diastereoisomer B were concentrated under the same conditions as above. 1.17 g methyl (3R,4R)-4-[3fluoro-3-[6-methoxyquinolin-4-yl)propyl]-1-[2-(2-thienylthio)ethyl]-piperidine-3-acetate diastereoisomer B were obtained in the form of a thick oil ($[\alpha]_D^{20}$=+82±3 in methanol at 0.1%).

Diastereoisomer A: Infrared spectrum (KBr): 2936, 2861, 2805, 2768, 1731, 1623, 1594, 1508, 1475, 1435, 1359, 1229, 1217, 1167, 1108, 1084, 1030, 855, 847, and 830 cm⁻¹.

Diastereoisomer B: Infrared spectrum (KBr): 2932, 2861, 2805, 2768, 1731, 1623, 1594, 1509, 1475, 1435, 1359, 1229, 1217, 1168, 1108, 1083, 1030, 855, 847, and 830 cm⁻¹.

Methyl (3R,4R)-4-[3-(R,S)-fluoro-3-(6-methoxyquinolin-4-yl)propyl]-1-[2-(2-thienylthio)ethyl]piperidine-3-acetate was prepared as described previously, in Example 60.

EXAMPLE 62

(3R,4R)-4-[3-Fluoro-3-(6-methoxyquinolin-4-yl)propyl]-1-[2-(2-thienylthio)ethyl]piperidine-3-acetic acid, diastereoisomer B Operating as described in Example 60, but starting with 0.5 of (3R,4R)-4-[3-fluoro-3-(6-methoxyquinolin-4-yl)propyl]-1-[2-(2-thienylthio)ethyl]- piperidine-3-acetic acid, diastereoisomer B ($[\alpha]_D^{20}$=+82), 0.29 g of (3R,4R)-4-[3-fluoro-3-(6-methoxyquinolin-4-yl)propyl]-1-[2-(2-thienylthio)ethyl]- piperidine-3-acetic acid, diastereoisomer B, was obtained in the form of a white meringue-like foam ($[\alpha]_D^{20}$=+66.3±1.1).

hu 1H N.M.R. spectrum (300 MHz, d6-(CD₃)₂SO, δ in ppm): from 1.20 to 1.60 (mt, 5H), from 1.90 to 2.15, and from 2.30 to 2.60 (2 series of mts: 9H total), 2.68 (mt, 2H), 2.89 (broad t, J=7 Hz, 2H), 3.95 (s, 3H), 6.38 (mt, $J_{HF}$=48 Hz, 1H), 7.05 (dd, J=5.5 and 3.5 Hz, 1H), 7.18 (dd, J=3.5 and 1 Hz, 1H), 7.32 (d, J=2.5 Hz, 1H), 7.46 (dd, J=9 and 2.5 Hz, 1H), 7.51 (d, J=4.5 Hz, 1H), 7.61 (dd, J=5.5 and 1 Hz, 1H), 7.99 (d,J=9 Hz, 1H), 8.78 (d, J=4.5 Hz, 1H).

Methyl (3R,4R)-4-[3-fluoro-3-(6-methoxyquinolin-4-yl)propyl]-1-[2-(2-thienylthio)-ethyl]piperidine-3-acetate, diastereoisomer B, was prepared as described previously in Example 61.

EXAMPLE 63

(3R,4R)-4-[3-Hydroxy-3-(6-methoxyquinolin-4-yl)propyl]-1-[3-(2,3,5-trifluorophenyl)-prop-2-ynyl]piperidine-3-carboxylic acid, diastereoisomer A, and (3R,4R)-4-[3-Hydroxy-3-(6-methoxyquinolin4-yl)propyl]-1-[3-(2,3,5-trifluorophenyl)-prop-2-ynyl]piperidine-3-carboxylic acid, diastereoisomer B 1.50 g of (3R,4R)-4-[3-(R,S)-hydroxy-3-(6-methoxyquinolin-4-yl)propyl]-1-[3-(2,3,5-trifluorophenyl)

prop-2-ynyl]piperidine-3-carboxylic acid dissolved in 200 cm³ of dichloromethane was chromatographed on a column 30 cm long by 6 cm in diameter, prepared with 700 g of Kromasil® silica gel (particle size 10μ). The elution was carried out with a mixture of dichloromethane-acetonitrile-methanol in proportions of 90/5/5 by volume. The flow rate was 130 cm³ per min and the detection was done with ultraviolet at 265 nm. This operation led, after 4 preparatory injections, to the two diastereoisomers. The fractions corresponding to the first were concentrated dry under reduced pressure (5 kPa) at a temperature of about 40° C., then the resulting residue was oven dried under reduced pressure (13 Pa) at a temperature of about 40° C. 1.9 g of (3R,4R)-4-[3-hydroxy-3-(6-methoxyquinolin-4-yl)propyl]-1-[3-(2,3,5-trifluorophenyl)-prop-2-ynyl]piperidine-3-carboxylic acid, diastereoisomer A ($[\alpha]_D^{20}=-50.90\pm1.4$ in methanol at 0.5%), was obtained in the form of a meringue-like foam.

¹H N.M.R. spectrum (300 MHz, d6-$(CD_3)_2SO$, δ in ppm): from 1.40 to 2.00 (mt, 7H), from 2.35 to 3.00 (mt, 5H), 3.66 (s, 2H), 3.92 (s, 3H total), 5.24 (mt, 1H), 5.54 (mt, 1H), from 7.25 to 7.45 (mt, 3H), from 7.50 to 7.70 (mt, 2H), 7.94 (d, J=9.5 Hz, 1H), 8.71 (d, J=4.5 Hz, 1H).

The fractions corresponding to the second diastereoisomer were treated as previously. 2.17 g of (3R,4R)-4-[3-hydroxy-3-(6-methoxyquinolin-4-yl)propyl]-1-[3-(2,3,5-trifluorophenyl)prop-2-ynyl]piperidine-3-carboxylic acid, diastereoisomer B ($[\alpha]_D^{20}=+67.8°\pm1.2$ in methanol at 0.5%), was obtained in the form of a meringue-like foam.

hu 1H N.M.R. spectrum (300 MHz, d6-$(CD_3)_2SO$, δ in ppm): from 1.40 to 2.00 (mt, 7H), from 2.35 to 3.00 (mt, 5H), 3.65 (s, 2H), 3.90 (s, 3H total), 5.24 (mt, 1H), 5.54 (mt, 1H), from 7.25 to 7.45 (mt, 3H), from 7.50 to 7.70 (mt, 2H), 7.94 (d, J=9.5 Hz, 1H), 8.71 (d, J=4.5 Hz, 1H).

(3R,4R)-4-[3-(R,S)-hydroxy-3-(6-methoxyquinolin-4-yl) propyl]-1-[3-(2,3,5-trifluorophenyl)prop-2-ynyl]piperidine-3-carboxylic acid was prepared as described in Example 59.

The present invention also relates to pharmaceutical compositions comprising at least one quinolylpropylpiperidine derivative according to the invention, if appropriate in the form of a salt, in the pure state or in the form of a combination with one or more compatible and pharmaceutically acceptable diluents or adjuvants.

The compositions according to the invention can be used orally, parenterally, topically, rectally, or in aerosol form.

Use may be made, as solid compositions for oral administration, of tablets, pills, hard gelatin capsules, powders, or granules. In these compositions, the active product according to the invention is mixed with one or more inert diluents or adjuvants, such as sucrose, lactose, or starch. These compositions can comprise substances other than diluents, for example, a lubricant, such as magnesium stearate, or a coating intended for controlled release.

Use may be made, as liquid compositions for oral administration, of solutions which are pharmaceutically acceptable, suspensions, emulsions, syrups, and elixirs comprising inert diluents, such as water or liquid paraffin. These compositions can also comprise substances other than diluents, for example, wetting, sweetening, or flavoring products.

The compositions for parenteral administration are emulsions or sterile solutions. Use may be made, as solvent or vehicle, of water, propylene glycol, polyethylene glycol, vegetable oils, in particular olive oil, or injectable organic esters, for example, ethyl oleate. These compositions can also comprise adjuvants, in particular wetting, isotonizing, emulsifying, dispersing, and stabilizing agents.

Sterilization can be carried out in several ways, for example, using a bacteriological filter, by irradiation, or by heating. The compositions can also be prepared in the form of sterile solid compositions which are dissolved at the time of use in sterile water or any other injectable sterile medium.

The compositions for topical administration are, for example, creams, ointments, lotions, or aerosols.

The compositions for rectal administration are suppositories or rectal capsules which comprise, in addition to the active principle, excipients such as cocoa butter, semi-synthetic glycerides, or polyethylene glycols.

The compositions can also be aerosols. For use in the form of liquid aerosols, the compositions are stable sterile solutions or solid compositions dissolved at the time of use in apyrogenic sterile water, in saline, or any other pharmaceutically acceptable vehicle. For use in the form of dry aerosols intended to be directly inhaled, the active principle can be finely divided and combined with a water-soluble solid diluent or vehicle with a particle size of 30 to 80 μm, for example, dextran, mannitol, or lactose.

In human therapeutics, the novel quinolylpropylpiperidine derivatives according to the invention are of particular use in the treatment of infections of bacterial origin. The doses depend on the desired effect and on the duration of the treatment. The doctor will determine the dosage which he considers the most appropriate according to the treatment and according to the age, weight, stage of the infection, and other factors specific to the subject to be treated. The doses range generally between 750 mg and 3 g of active product, the taking of which doses can be spread over 2 or 3 occasions, per day orally or between 400 mg and 1.2 g intravenously for an adult.

The following examples illustrate the compositions according to the invention.

EXAMPLE 1

A liquid composition intended for parenteral use was prepared according to usual techniques comprising:

| | |
|---|---|
| (3R,4R)-4-[3-(R,S)-Hydroxy-3-(6-methoxyquinolin-4-yl)propyl]-1-[2-(2-thienylthio)ethyl]piperidine-3-carboxylic acid | 125 mg |
| Glucose | q.s. for 2.5% |
| Sodium hydroxide | q.s. for pH = 4–4.5 |
| Water for Injections | q.s. for 20 ml |

EXAMPLE 2

A liquid composition intended for parenteral use was prepared according to usual techniques comprising:

| | |
|---|---|
| (3R,4R)-4-[3-(R,S)-Hydroxy-3-(6-methoxyquinolin-4-yl)propyl]-1-[2-(2-thienylthio)ethyl]piperidine-3-acetic acid | 125 mg |
| Glucose | q.s. for 2.5% |
| Sodium hydroxide | q.s. for pH = 4–4.5 |
| Water for Injections | q.s. for 20 ml |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A quinolylpropylpiperidine derivative of formula:

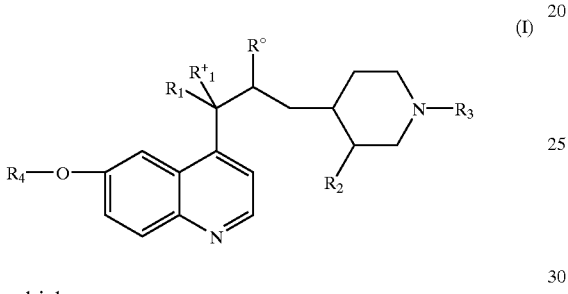

in which:
$R_1$ is a hydrogen atom, a halogen atom, or a hydroxyl radical;
$R'_1$ is a hydrogen atom or can represent a halogen atom when $R_1$ is a halogen atom; and
$R°$ is a hydrogen atom; or
$R_1$ and $R°$ together form a bond; and
$R'_1$ is a hydrogen atom; and either
$R_2$ represents a carboxyl, carboxymethyl, or 2-carboxyethyl radical; and
$R_3$ represents an alkyl radical having 1 to 6 carbon atoms substituted by 1 to 3 substituents chosen from hydroxyl, halogen, oxo, carboxyl. alkyloxycarbonyl, alkyloxy, and alkylthio;
or from phenyl, phenylthio, and phenylalkylthio radicals, which radicals are unsubstituted or substituted by 1 to 4 substituents chosen from halogen, hydroxyl, alkyl, alkyloxy, trifluoromethyl, trifluoromethoxy, carboxyl, alkyloxycarbonyl, cyano, acetamido having 1 to 4 carbon atoms, and amino;
or from cycloalkyl and cycloalkylthio radicals, the cyclic part of which comprises 3 to 7 members;
or from 5- to 6-membered aromatic heterocyclyl and heterocyclylthio radicals comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino;
or $R_3$ represents a propargyl radical substituted by a phenyl radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;
or said propargyl radical is substituted by a cycloalkyl radical comprising 3 to 7 members;

or said propargyl radical is substituted by a 5- to 6-membered aromatic heterocyclyl radical comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino;
or $R_3$ represents cinnamyl or 4-phenylbuten-3-yl; and
$R_4$ represents an alkenyl-$CH_2$— or an alkynyl-$CH_2$— radical, the alkenyl or alkynyl parts of which comprise from 2 to 6 carbon atoms; or
$R_2$ represents a carboxyl, carboxymethyl, or 2-carboxyethyl radical; and
$R_3$ represents an alkyl radical having 1 to 6 carbon atoms substituted by 1 to 3 substituents chosen from halogen, oxo, carboxyl, alkyloxycarbonyl, and alkylthio;
or from phenylthio and phenylalkylthio radicals, which radicals are unsubstituted or substituted by 1 to 4 substituents chosen from halogen, hydroxyl, alkyl, alkyloxy, trifluoromethyl, trifluoromethoxy, carboxyl, alkyloxycarbonyl, cyano, acetamido having 1 to 4 carbon atoms, and amino;
or from cycloalkylthio radicals, the cyclic part of which comprises 3 to 7 members;
or from 5- to 6-membered aromatic heterocyclylthio radicals comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino;
or $R_3$ represents a propargyl radical substituted by a phenyl radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;
or said propargyl radical is substituted by a cycloalkyl radical comprising 3 to 7 members;
or said propargyl radical is substituted by a 5- to 6-membered aromatic heterocyclyl radial comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxy, alkyloxycarbonyl, cyano, or amino; and
$R_4$ represents an alkyl radical comprising 1 to 6 carbon atoms;
or $R_2$ represents a hydroxymethyl, alkyloxycarbonyl, alkyloxycarbonylmethyl, or 2(alkyloxycarbonyl) ethyl radical, wherein the alkyl parts of said radicals comprise 1 to 6 carbon atoms; and
$R_3$ represents an alkyl radical having 1 to 6 carbon atoms substituted by a phenylthio radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or said alkyl radical is substituted by a cycloalkylthio radical, the cyclic part of which comprises 3 to 7 members;

or said alkyl radical is substituted by a 5- to 6-membered aromatic heterocyclylthio radical comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents a propargyl radical substituted by a phenyl radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or said propargyl radical is substituted by a cycloalkyl radical comprising 3 to 7 members;

or said propargyl radical is substituted by a 5- to 6-membered aromatic heterocyclyl radical comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino; and $R_4$ represents an alkyl radical comprising 1 to 6 carbon atoms, or an alkenyl-CH2— or an alkynyl-CH2— radical, the alkenyl or alkynyl parts of which comprise 2 to 6 carbon atoms;

it being understood that the alkyl radicals and alkyl portions of radicals are straight- or branched-chain radicals and portions of radicals and comprise, except when specifically mentioned, 1 to 4 carbon atoms;

a diastereoisomer thereof, a mixture of diastereoisomers thereof, or a salt thereof.

2. A quinolylpropylpiperidine derivative according to claim 1, in which:

$R_1$ is a hydrogen atom, a halogen atom, or a hydroxy radical;

$R'_1$ is a hydrogen atom or can represent a halogen atom when $R_1$ is a halogen atom; and $R°$ is a hydrogen atom; or $R_1$ and $R°$ together form a bond; and $R'_1$ is a hydrogen atom;

$R_2$ represents a carboxyl, carboxymethyl, or carboxy-2-ethyl radical; and $R_3$ represents an alkyl radical having 1 to 6 carbon atoms substituted by 1 to 3 substituents chosen from halogen, oxo, carboxyl, alkyloxycarbonyl, and alkylthio;

or from phenylthio and phenylalkylthio radicals, which are unsubstituted or substituted by 1 to 4 substituents chosen from halogen, hydroxyl, alkyl, alkyloxy, trifluoromethyl, trifluoromethoxy, carboxyl, alkyloxycarbonyl, cyano, acetamido having 1 to 4 carbon atoms, and amino;

or from a cycloalkylthio radical, the cyclic part of which comprises 3 to 7 members;

or from a 5- to 6-membered aromatic heterocyclylthio radical comprising 1 to 4 heteroatoms chosen from nitrogen, oxygen, and sulfur, and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents an alkyl radical having 1 to 6 carbon atoms, said alkyl radical being substituted by 2 or 3 substituents chosen from hydroxy and alkyloxy;

or from phenylthio and phenylalkylthio radicals, which are unsubstituted or substituted by 1 to 4 substituents chosen from halogen, hydroxyl, alkyl, alkyloxy, trifluoromethyl, trifluoromethoxy, carboxyl, alkyloxycarbonyl, cyano, acetamido having 1 to 4 carbon atoms, and amino;

or from a cycloalkylthio radical, the cyclic part of which comprises 3 to 7 members;

or from a 5- to 6-membered aromatic heterocyclylthio radical comprising 1 to 4 heteroatoms chosen from nitrogen, oxygen, and sulfur, and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents a propargyl radical substituted by a phenyl radical which is unsubstituted or substituted by 1 to 4 substituents chosen from halogen, hydroxy, alkyl, alkyloxy, trifluoromethyl, trifluoromethoxy, carboxy, alkyloxycarbonyl, cyano, and amino;

or said propargyl radical is substituted by a cycloalkyl radical comprising 3 to 7 members;

or said propargyl radical is substituted by a 5- to 6-membered aromatic heterocyclyl radical comprising 1 to 4 heteroatoms chosen from nitrogen, oxygen, and sulfur, and being unsubstituted or substituted by halogen, hydroxyl, alkyl, alkyloxy, trifluoromethyl, trifluoromethoxy, oxo, carboxyl, alkyloxycarbonyl, cyano or amino;

or $R_2$ represents a hydroxymethyl, alkyloxycarbonyl, alkyloxycarbonylmethyl, or alkyloxycarbonyl-2-ethyl radical, wherein the alkyl parts of said radicals comprise 1 to 6 carbon atoms; and $R_3$ represents an alkyl radical having 1 to 6 carbon atoms substituted by a phenylthio radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or said alkyl radical is substituted by a cycloalkylthio radical, the cyclic part of which comprises 3 to 7 members;

or said alkyl radical is substituted by a 5- to 6-membered aromatic heterocyclylthio radical comprising 1 to 4 heteroatoms chosen from nitrogen, oxygen, and sulfur, and being unsubstituted or substituted by halogen, hydroxyl, alkyl, alkyloxy, trifluoromethyl, trifluoromethoxy, oxo, carboxyl, alkyloxycarbonyl, cyano, or amino;

or $R_3$ represents a propargyl radical substituted by a phenyl radical which is unsubstituted or substituted by 1 to 4 substituents chosen from halogen, hydroxyl, alkyl, alkyloxy, trifluoromethyl, trifluoromethoxy, carboxyl, alkyloxycarbonyl, cyano, and amino;

or said propargyl radical is substituted by a cycloalkyl radical comprising 3 to 7 members;

or said propargyl radical is substituted by a 5- to 6-membered aromatic heterocyclyl radical comprising 1 to 4 heteroatoms chosen from nitrogen, oxygen, and sulfur and being unsubstituted or substituted by halogen, hydroxyl, alkyl, alkyloxy, trifluoromethyl, trifluoromethoxy, oxo, carboxyl, alkyloxycarbonyl, cyano, or amino; and $R_4$ represents an alkyl radical comprising 1 to 6 carbon atoms, or an alkenyl-CH$_2$— or alkynyl —CH$_2$— radical, the alkenyl or alkynyl parts of which comprise 2 to 6 carbon atoms;

it being understood that the alkyl radicals and alkyl portions of radicals are straight- or branched-chain radicals and portions of radicals and comprise, except when specifically mentioned, 1 to 4 carbon atoms;

a diastereoisomer thereof, a mixture of diastereoisomers thereof, or a salt thereof.

3. A quinolylpropylpiperidine derivative according to claim 1, in which:

$R_1$ is a hydrogen atom, a halogen atom, or a hydroxyl radical;

$R'_1$ is a hydrogen atom; and $R°$ is a hydrogen atom; or $R_1$ and $R°$ together form a bond; and $R'_1$ is a hydrogen atom;

$R_2$ represents a carboxyl or carboxymethyl radical; and $R_3$ represents an alkyl radical having 1 to 6 carbon atoms substituted by 1 to 3 substituents chosen from halogen, oxo, alkyloxy, and alkylthio;

or from phenyl and phenylthio radicals, which are unsubstituted or substituted by 1 to 4 halogen atoms;

or from cycloalkyl and cycloalkylthio radicals, the cyclic part of which comprises 3 to 7 members;

or from 5- to 6-membered aromatic heterocyclyl and heterocyclylthio radicals comprising 1 to 4 heteroatoms chosen from nitrogen, oxygen, and sulfur and being unsubstituted or substituted by halogen;

or $R_3$ represents a propargyl radical substituted by a phenyl radical which is unsubstituted or substituted by 1 to 3 halogen substituents;

or said propargyl radical is substituted by a 5- to 6-membered aromatic heterocyclyl radical comprising 1 to 4 heteroatoms chosen from nitrogen, oxygen, and sulfur;

or $R_3$ represents cinnamyl;

or $R_2$ represents a hydroxymethyl, alkyloxycarbonyl, or alkyloxycarbonylmethyl radical, the alkyl portions of said radicals comprising 1 to 6 carbon atoms; and $R_3$ represents an alkyl radical having 1 to 6 carbon atoms substituted by a 5- to 6-membered aromatic heterocyclylthio radical comprising 1 to 4 heteroatoms chosen from nitrogen, oxygen, and sulfur:

or $R_3$ represents a propargyl radical substituted by a 5- to 6-membered aromatic heterocyclyl radical comprising 1 to 4 heteroatoms chosen from nitrogen, oxygen, and sulfur; and $R_4$ represents an alkyl radical comprising 1 to 6 carbon atoms; it being understood that the alkyl radicals and alkyl portions of radicals are straight- or branched-chain radicals and portions of radicals;

a diastereoisomer thereof, a mixture of diastereoisomers thereof, or a salt thereof.

4. A quinolylpropylpiperidine derivative according to claim 1, which is (3R,4R)-4-[3-hydroxy-3-(6-methoxyquinolin-4-yl)propyl]-1-[2-(2-thienylthio)ethyl]piperidine-3-acetic acid, a diastereoisomer thereof, a mixture of diastereoisomers thereof, or a salt thereof.

5. A quinolylpropylpiperidine derivative according to claim 1, which is (3R,4R)-4-[3-(6-methoxyquinolin-4-yl)propyl]-1-[2-(2-thienylthio)ethyl]piperidine-3-acetic acid, or a salt thereof.

6. A quinolylpropylpiperidine derivative according to claim 1, which is (3R,4R)-4-[3-fluoro-3-(6-methoxyquinolin-4-yl)propyl]-1-[2-(2-thienylthio)ethyl]piperidine-3-acetic acid, a diastereoisomer thereof, a mixture of diastereoisomers thereof, or a salt thereof.

7. A quinolylpropylpiperidine derivative according to claim 1, which is (3R,4R)-1-[2-(3-fluorophenylthio)ethyl]-4-[3-hydroxy-3-(6-methoxyquinolin-4-yl)propyl]piperidine-3-acetic acid, a diastereoisomer thereof, a mixture of diastereoisomers thereof, or a salt thereof.

8. A quinolylpropylpiperidine derivative according to claim 1, which is (3R,4R)-4-[3-hydroxy-3-(6-methoxyquinolin-4-yl)propyl]-1-[3-(2,3,5-trifluorophenyl)prop-2-ynyl]piperidine-3-carboxylic acid, a diastereoisomer thereof, a mixture of diastereoisomers thereof, or a salt thereof.

9. A process for preparing a quinolylpropylpiperidine derivative of formula (I) according to claim 1, said process comprising condensing an $R_3$ chain as defined in claim 1 onto a quinolylpropylpiperidine derivative of formula:

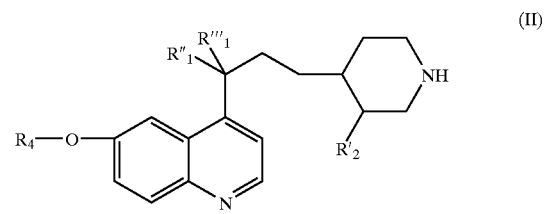

(II)

in which $R_4$ is defined as in claim 1, $R''_1$, and $R'''_1$ each independently represent a hydrogen atom or together form an oxo radical, and $R'_2$ represents a protected carboxyl, carboxymethyl, or 2-carboxyethyl radical, or an alkyloxycarbonyl, alkyloxycarbonylmethyl, or 2-(alkyloxycarbonyl)ethyl radical, to obtain a quinolylpropylpiperidine derivative of formula:

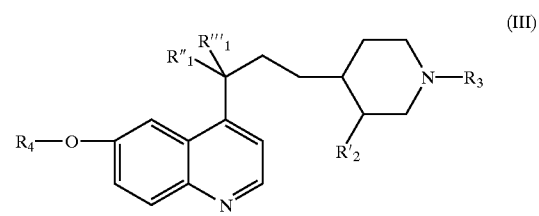

(III)

in which $R''_1$, $R'''_1$, $R'_2$, and $R_4$ are defined as above and $R_3$ is defined as in claim 1;

then, if appropriate, removing the acid-protecting radical, or, if appropriate, reducing the oxo radical represented by $R''_1$ and $R'''_1$ to an alcohol in which $R_1$ represents hydroxyl;

then, if appropriate, halogenating the quinolylpropylpiperidine derivative wherein $R_1$ is hydroxyl if it is desired to obtain a quinolylpropylpiperidine derivative in which $R_1$ is a halogen atom, and, if appropriate, dehydrohalogenating the halogenated derivative to obtain a quinolylpropylpiperidine derivative in which $R_1$ and $R°$ together form a bond, or, if appropriate, dihalogenating the product of formula (III) in which $R''_1$ and $R'''_1$ together form an oxo radical to obtain a quinolylpropylpiperidine derivative in which $R_1$ and $R'_1$ are halogen atoms;

and, if appropriate, reducing the acid, protected in the form of an $R'_2$ radical, in the 3-position of the piperidine to a hydroxymethyl radical.

10. A process according to claim 9, further comprising converting the reduced derivative to a carboxymethyl or 2-carboxyethyl radical.

11. A process according to claim 9, further comprising removing the acid-protecting radical.

12. A process according to claim 9, further comprising converting the product obtained from said reduction to a salt.

13. A process according to claim 10, further comprising converting the carboxyl product obtained to a salt.

14. A process according to claim 11, further comprising converting the product obtained from said removal to a salt.

15. A process according to claim 9, further comprising separating at least one diastereoisomer.

16. A process according to claim 9, in which the condensation of the $R_3$ chain onto the quinolylpropylpiperidine derivative of formula (II) is carried out by the action of a derivative of formula:

$$R_3\text{-}X$$

in which $R_3$ is defined as in claim 9 and X represents a halogen atom, a methylsulfonyloxy radical, a trifluoromethylsulfonyloxy radical, or a p-toluenesulfonyloxy radical.

17. A process according to claim 9, in which $R_3$ in formula (I) represents a propargyl radical substituted by a phenyl, cycloalkyl, or heterocyclyl radical, said process comprising condensing a propargyl halide onto said quinolylpropylpiperidine derivative of formula (II), and then substituting the chain with a phenyl, cycloalkyl, or heterocyclyl radical.

18. A process according to. claim 16, further comprising separating at least one diastereoisomer.

19. A process according to claim 17, further comprising separating at least one diastereoisomer.

20. A pharmaceutical composition, said composition comprising at least one quinolylpropylpiperidine derivative of formula (I) according to claim 1.

21. A pharmaceutical composition according to claim 20, said composition further comprising at least one compatible and pharmaceutically acceptable diluent or adjuvant.

22. A method for treating a bacterial infection, said method comprising administering to a host in desire or need thereof an effective amount of at least one quinolylpropylpiperidine derivative of formula (I) according to claim 1.

23. A method according to claim 22, wherein the quinolylpropylpiperidine derivative is orally administered in an amount ranging from 750 mg to 3 g.

24. A method according to claim 23, wherein the administration comprises two or three oral doses per day.

25. A method according to claim 22, wherein the quinolylpropylpiperidine derivative is administered intravenously in an amount ranging from 400 mg to 1.2 g.

26. A method for treating a bacterial infection, said method comprising administering to a host in desire or need thereof an effective amount of a pharmaceutical composition according to claim 20.

27. A method for treating a bacterial infection, said method comprising administering to a host in desire or need thereof an effective amount of a pharmaceutical composition according to claim 21.

\* \* \* \* \*

UNITED STATES PATENT AND TRADEMARK OFFICE
CERTIFICATE OF CORRECTION

PATENT NO.   : 6,403,610 B1
DATED        : June 11, 2002
INVENTOR(S)  : Jean-Luc Malleron et al.

It is certified that error appears in the above-identified patent and that said Letters Patent is hereby corrected as shown below:

Title page,
Item [57], ABSTRACT,
Replace Formula I with the following Formula I:

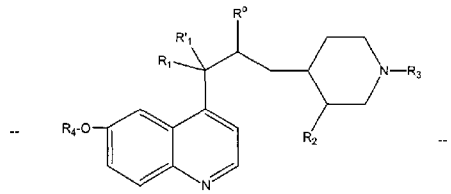

Column 215,
Lines 20-30, replace Formula I with the following Formula I:

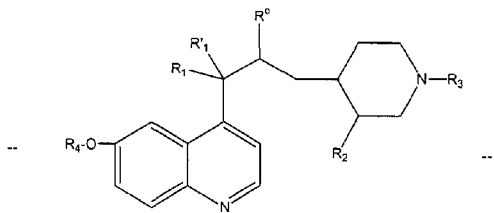

Line 42, delete the period after "carboxyl" and insert a -- , --.

Column 216,
Line 54, "carboxy" should read -- carboxyl --.

Column 217,
Line 26, "alkenyl-CH2" should read -- alkenyl-$CH_2$ --.
Line 26, "alkynyl-CH2" should read -- alkynyl-$CH_2$ --.

UNITED STATES PATENT AND TRADEMARK OFFICE
CERTIFICATE OF CORRECTION

PATENT NO.    : 6,403,610 B1
DATED         : June 11, 2002
INVENTOR(S)   : Jean-Luc Malleron et al.

It is certified that error appears in the above-identified patent and that said Letters Patent is hereby corrected as shown below:

Column 221,
Line 28, delete period after "to".

Signed and Sealed this

Seventh Day of January, 2003

JAMES E. ROGAN
*Director of the United States Patent and Trademark Office*